(12) United States Patent
Pedersen et al.

(10) Patent No.: US 11,668,705 B2
(45) Date of Patent: Jun. 6, 2023

(54) GENERAL DETECTION AND ISOLATION OF SPECIFIC CELLS BY BINDING OF LABELED MOLECULES

(71) Applicants: Immudex ApS, Virum (DK); Herlev Hospital, Herlev (DK)

(72) Inventors: Henrik Pedersen, Bagsværd (DK); Søren Jakobsen, Hellerup (DK); Sine Reker Hadrup, Virum (DK); Amalie Kai Bentzen, Frederiksberg C (DK); Kristoffer Haurum Johansen, Copenhagen N (DK)

(73) Assignees: Immudex Aps, Virum (DK); Herlev Hospital, Herlev (DK)

( * ) Notice: Subject to any disclaimer, the term of this patent is extended or adjusted under 35 U.S.C. 154(b) by 0 days.

(21) Appl. No.: 17/854,960

(22) Filed: Jun. 30, 2022

(65) Prior Publication Data

US 2022/0341921 A1    Oct. 27, 2022

Related U.S. Application Data

(63) Continuation of application No. 17/668,980, filed on Feb. 10, 2022, now Pat. No. 11,402,373, which is a (Continued)

(30) Foreign Application Priority Data

| Jun. 13, 2014 | (DK) | ............................ PA 2014 00311 |
| Jun. 18, 2014 | (DK) | ............................ PA 2014 00322 |
| Aug. 16, 2014 | (DK) | ............................ PA 2014 00453 |

(51) Int. Cl.
  *G01N 33/532* (2006.01)
  *G01N 33/533* (2006.01)
  *G01N 33/569* (2006.01)

(52) U.S. Cl.
  CPC ......... *G01N 33/532* (2013.01); *G01N 33/533* (2013.01); *G01N 33/56977* (2013.01)

(58) Field of Classification Search
  CPC ............... G01N 33/532; G01N 33/533; G01N 33/56977
  See application file for complete search history.

(56) References Cited

U.S. PATENT DOCUMENTS 4,485,045 A    11/1984    Regen
4,544,545 A    10/1985    Ryan et al.
(Continued)

FOREIGN PATENT DOCUMENTS

EP    0594772 B1    8/1996
EP    0525821 B1    3/2006
(Continued)

OTHER PUBLICATIONS

Degauque et al. (PLoS ONE, 2013, 8(12):e84273) (Year: 2013).*
(Continued)

*Primary Examiner* — Jeremy C Flinders
(74) *Attorney, Agent, or Firm* — Verrill Dana, LLP

(57) ABSTRACT

The present invention relates to detection molecules comprising at least one binding molecule, at least one linker and at least one label, and detection methods making use of same. The invention provides a high-throughput method for detection, isolation and/or identification of specific entities or cells.

19 Claims, 20 Drawing Sheets

Specification includes a Sequence Listing.

Related U.S. Application Data continuation of application No. 15/316,587, filed as application No. PCT/DK2015/050169 on Jun. 15, 2015.

(56) References Cited

U.S. PATENT DOCUMENTS

| | | | |
|---|---|---|---|
| 4,994,373 | A | 2/1991 | Stavrianopoulos |
| 5,543,332 | A | 8/1996 | Lihme et al. |
| 5,635,363 | A | 6/1997 | Altman et al. |
| 6,387,622 | B1 | 5/2002 | Siiman et al. |
| 6,413,934 | B1 | 7/2002 | Stayton et al. |
| 6,489,116 | B2 | 12/2002 | Wagner |
| 7,074,904 | B2 | 7/2006 | Wong et al. |
| 7,981,843 | B2 | 7/2011 | Flynn et al. |
| 2002/0119162 | A1 | 8/2002 | Nielsen et al. |
| 2004/0209295 | A1 | 10/2004 | Schwabe et al. |
| 2005/0019843 | A1 | 1/2005 | Chen et al. |
| 2005/0074848 | A1 | 4/2005 | Schwabe |
| 2008/0269068 | A1 | 10/2008 | Church et al. |
| 2010/0168390 | A1 | 7/2010 | Brix et al. |
| 2011/0166034 | A1 | 7/2011 | Kwong et al. |
| 2011/0236411 | A1 | 9/2011 | Scholler et al. |
| 2015/0337369 | A1 | 11/2015 | Davis et al. |
| 2017/0095544 | A1 | 4/2017 | Santamaria |

FOREIGN PATENT DOCUMENTS

| | | | |
|---|---|---|---|
| JP | 2001158800 | A | 6/2001 |
| WO | 1991008307 | A1 | 6/1991 |
| WO | 1993001498 | A1 | 1/1993 |
| WO | 1996026962 | A1 | 9/1996 |
| WO | 1998006749 | A2 | 2/1998 |
| WO | 1999024577 | A1 | 5/1999 |
| WO | 9942597 | A1 | 8/1999 |
| WO | 2000057183 | A1 | 9/2000 |
| WO | 2001027625 | A1 | 4/2001 |
| WO | WO 01/73443 | A2 | 10/2001 |
| WO | 2002072631 | A2 | 9/2002 |
| WO | 2002083903 | A2 | 10/2002 |
| WO | 2003016905 | A2 | 2/2003 |
| WO | 2003031591 | A2 | 4/2003 |
| WO | 2003072753 | A2 | 9/2003 |
| WO | 2003073097 | A2 | 9/2003 |
| WO | 2004033497 | A1 | 4/2004 |
| WO | 2005003394 | A2 | 1/2005 |
| WO | 2005054860 | A1 | 6/2005 |
| WO | 2005111624 | A2 | 11/2005 |
| WO | 2006009838 | A2 | 1/2006 |
| WO | 2006082387 | A1 | 8/2006 |
| WO | 2006130347 | A2 | 12/2006 |
| WO | 2007015168 | A2 | 2/2007 |
| WO | 2008015425 | A2 | 2/2008 |
| WO | 2008016680 | A1 | 2/2008 |
| WO | 2008116468 | A2 | 10/2008 |
| WO | 2008121836 | A1 | 10/2008 |
| WO | 2009003492 | A1 | 1/2009 |
| WO | 2009003493 | A2 | 1/2009 |
| WO | 2009039854 | A2 | 4/2009 |
| WO | 2009077173 | A2 | 6/2009 |
| WO | 2009106073 | A3 | 9/2009 |
| WO | 2009126828 | A2 | 10/2009 |
| WO | 2010009735 | A2 | 1/2010 |
| WO | 2010037395 | A2 | 4/2010 |
| WO | 2010037397 | A1 | 4/2010 |
| WO | 2010037402 | A1 | 4/2010 |
| WO | 2010060439 | A1 | 6/2010 |
| WO | 2012022975 | A1 | 2/2012 |
| WO | 2012044999 | A2 | 4/2012 |
| WO | 2012048341 | A1 | 4/2012 |
| WO | 2012094492 | A2 | 7/2012 |
| WO | 2013059725 | A1 | 4/2013 |
| WO | 2013137737 | A1 | 9/2013 |
| WO | 2014026032 | A3 | 2/2014 |
| WO | 2014080286 | A2 | 5/2014 |
| WO | 2014145047 | A1 | 9/2014 |
| WO | 2015153969 | A1 | 10/2015 |
| WO | 2015185067 | A1 | 12/2015 |
| WO | 2015188839 | A2 | 12/2015 |
| WO | 2016044227 | A1 | 3/2016 |
| WO | 2016069886 | A1 | 5/2016 |
| WO | 2016138122 | A1 | 9/2016 |
| WO | 2016161372 | A1 | 10/2016 |
| WO | 2016176322 | A1 | 11/2016 |
| WO | 2016196691 | A2 | 12/2016 |
| WO | 2017053905 | A1 | 3/2017 |
| WO | 2017201210 | A1 | 11/2017 |

OTHER PUBLICATIONS

U.S. Appl. No. 15/316,587, filed Dec. 6, 2016, Henrik Pedersen et al.

U.S. Appl. No. 17/668,980, filed Feb. 10, 2022, Henrik Pedersen et al.

Kwong, Gabriel Abner "DNA Encoded Biotechnologies for Informative Cancer Diagnostics", Thesis (Dissertation (Ph. D.)), California Institute of Technology, Sep. 26, 2015, 137 pages.

ProQuest index page for Kwong, Gabriel Abner "DNA Encoded Biotechnologies for Informative Cancer Diagnostics" in Opposition Proceedings to EP3152232B, May 6, 2021, (register.epo.org/application?documentId=E568YXAV7506DSU&number=EP15739508&Ing=en&npl=false).

Email correspondence between Mewbum Ellis LLP and ProQuest in Opposition Proceedings to EP3152232B, May 6, 2021, (register.epo.org/application?documentId=E568YXEG0498DSU&number=EP15739508&Ing=en&npl=false).

Declaration of Shirley Katherine Johnson in Opposition Proceedings to EP3152232B, May 6, 2021, (register.epo.org/application?documentId=E568YU303993DSU&number=EP15739508&Ing=en&npl=false).

European Patent Office Summons to Attend Oral Proceedings pursuant to Rule 115(1) EPC dated May 17, 2021 in Opposition Proceedings to EP3152232B, (register.epo.org/application?documentId=E57YNT6Y8402929&number=EP15739508&Ing=en&npl=false) and Annex to the Communication (register.epo.org/application?documentId=E57YN3AP6944DSU&number=EP15739508&Ing=en&npl=false).

Letter from the Opponent in Opposition Proceedings to EP3152232B, May 6, 2021, (register.epo.org/application?documentId=E568YU0G6403DSU&number=EP15739508&Ing=en&npl=false).

von Wintzingerode et al. Peptide nucleic acid-mediated PCR clamping as a useful supplement in the determination of microbial diversity. Applied and Environmental Microbiology, vol. 66 No. 2, pp. 549-557, 2000.

June et al. Adoptive T cell therapy for cancer in the clinic. J Clin Invest. 2007, 117(6), pp. 1466-1476.

Demaria et al. Combining radiotherapy and immunotherapy: a revived partnership. Int. J. Radiation Oncology Biol. 63,3, pp. 655-666, 2005.

Kalos and June. Adoptive T cell transfer for cancer immunotherapy in the era of synthetic biology. Immunity, 39, pp. 49-60, 2013.

Spranger S. Mechanisms of tumor escape in the context of the T-cell-inflamed and the non-T-cell inflamed tumor microenvironment. International Immunology, 28 (8), pp. 383-391, 2016.

Beatty and Gladney. Immune Escape mechanisms as a guide for cancer immunotherapy. Clin. Cancer Res. 2014, 21(4), pp. 687-692.

Kerkar et al. Cellular constituents of immune escape within the tumor microenvironment. Cancer Res. 2012, 72(13), pp. 3125-3130.

Le Doussal et al. Phage diplay of peptide/major histocompatibility complex. J. Immun. vol. 241, issues 1-2, 31, pp. 147-158, 2000.

Arlehamn, C. et al. Dissecting mechanisms of immunodominance to the common tuberculosis antigens ESAT-6, 2, CFP10, Rv2031c (hspX), Rv2654c (TB7.7), and Rv1038c (EsxJ). J. Immun. vol. 188, pp. 1-12, Apr. 13, 2012.

(56) References Cited

OTHER PUBLICATIONS

Mannocci, L. et al. High-throughput sequencing allows the identification of binding molecules isolated from DNA-encoded chemical libraries. PBAS vol. 105 No. 46, pp. 17670-17675, 2008.
Kozlov, I. et al. Efficient strategies for the conjugation of oligonucleotides to antibodies enabling highly sensitive protein detection. Biopolymers, vol. 73, No. 5, pp. 621-630, 2004.
Buller, F. et al. Discovery of TNF inhibitors from a DNA-encoded chemical library based on Diels-Alder cycloaddition. Chemistry and Biology 2009, pp. 1075-1086 plus Supplemental Data.
Newell, E. et al. Simultaneous detection of many T-cell specificities using combinatorial tetramer staining. Nature methods vol. 6 No. 7, pp. 497-500, 2009.
Nong, R. et al. DNA-assisted protein detection technologies. Expert Review of Proteomics vol. 9 No. 1, , pp. 22-32, 2012.
Nelms, B. et al. A predicted hairpin cluster correlates with barriers to PCR, sequencing and possibly BAC recombineering. Scientific Reports, vol. 1 No. 106, pp. 1-7, 2011.
Soria-Guerra et al. An overview of bioinformatics tools for epitope prediction: implications on vaccine development. J. of biomedical informatics, 2015, 53, pp. 405-414.
Klebanoff et al. Therapeutic cancer vaccines: are we there yet? Immunol. Reviews 239/2011, pp. 27-44.
Fournier and Schirmiacher. Randomised clinical studies of antitumor vaccination: state of the art in 2008. Expert Reviews Vaccines 8(1) 2009, pp. 51-66.
Kwong, G. et al. Modular nucleic acid assembled p/MHC microarrays for multiplexed sorting of antigen-specific T cells. J Am Chem Soc. vol. 131, No. 28, 2009, pp. 1-17 plus Supplementary Information.
Arlehamn, C. et al. Dissecting mechanisms of immunodominance to the common tuberculosis antigens ESAT-6, CFP10, Rv2031c (hspX), Rv2654c (TB7.7), and Rv1038c (EsxJ). J. Immun. vol. 188, Apr. 13, 2012.
Buller, F. et al. Drug discovery with DNA-encoded chemical libraries. Am Chem Soc 2010, vol. 21, No. 9, pp. 1571-1580.
Le Doussal et al. Phage diplay of peptide/major histocompatibility complex. J. Immun. vol. 241, issues 1-2, 31, 2000.
Mannocci, L. et al. 20 years of DNA-encoded chemical libraries. The Royal Society of Chemistry 2011, 47, 12747-12753.
Miannocci, L. et al. High-throughput sequencing allows the identification of binding molecules isolated from DNA-encoded chemical libraries. PBAS vol. 105 No. 46, 2008.
Kozlov, I. et al. Efficient strategies for the conjugation of oligonucleotides to antibodies enabling highly sensitive protein detection. Biopolymers, vol. 73, No. 5, 2004.
Knabel, M. et al., "Reversible MHC multimer staining for functional isolation of T-cell populations and effective adoptive transfer," Nature Medicine, Nature Publishing Group, pp. 631-637, Jun. 1, 2002 (Jun. 1, 2002), vol. 8, No. 6, New York, NY, USA.
Batard, P. et al., "Dextramers: New generation of fluorescent MHC class I/ peptide multimers for visualization of antigen-specific CD8 T cells," Journal of Immunological Methods, Elsevier Science Publishers, pp. 136-148, Mar. 20, 2006 (Mar. 20, 2006), vol. 310, No. 1-2, Amsterdam, NL.
Constantin, C. et al., "Major histocompatibility complex (MHC) tetramer technology: An evaluation," Biol. Res. Nursing, pp. 115-127, Oct. 2002, vol. 4.
Buller, F. et al. Discovery of TNF inhibitors from a DNA-encoded chemical library based on Diels-Alder cycloaddition. Chemistry and Biology 2009.
Newell, E. et al. Simultaneous detection of many T-cell specificities using combinatorial tetramer staining. Nature methods vol. 6 No. 7, 2009.
Nong, R. et al. DNA-assisted protein detection technologies. Expert Review of Proteomics vol. 9 No. 1, 2012.
Nelms, B. et al. A predicted hairpin cluster correlates with barriers to PCR, sequencing and possibly BAC recombineering. Scientific Reports, vol. 1 No. 106, 2011.

Kivioja et al. Counting absolute numbers of molecules using unique molecular identifiers. Nature Methods vol. 9 No. 1 2012.
Karin et al., "Reversal of experimental autoimmune encephalomyelitis by a soluble peptide variant of a myelin basic protein epitope: T cell receptor antagonism and reduction of interferon $\gamma$ and tumor necrosis factor $\alpha$ production", J. Exp. Med., 1994, 180, pp. 2227-2237.
Timmerman et al. Immunogenicity of a plasmid DNA vaccine encoding chimeric idiotype in patients with B-cell lymphoma Cancer Research 62, 5842-5852, 2002.
June et al. Adoptive T cell therapy for cancer in the clinic. J Clin Invest. 2007, 117(6).
Demaria et al. Combining radiotherapy and immunotherapy: a revived partnership. Int. J. Radiation Oncology Biol. 63,3,2005.
Nielsen et al. MHC class II epitope predictive algorithms, Immunology 2010, 130, 319-328.
Soria-Guerra et al. An overview of bioinformatics tools for epitope prediction: implications on vaccine development J. of biomedical informatics, 2015, 53.
Kalandadze, et al., "Expression of Recombinant HLA-DR2 molecules," J. Biol. Chem., pp. 20156-20162, Aug. 16, 1996, vol. 271.
Fournier and Schirrmacher. Randomised clinical studies of antitumor vaccination: state of the art in 2008. Expert Reviews Vaccines 8(1) 2009.
Schreiber et al. Tumor immunogenicity and responsiveness to cancer vaccine therapy: the state of the art. Seminars in Immun. 22(2010) 105-112.
Klebanoff et al. Therapeutic cancer vaccines: are we there yet? Immunol. Reviews 239/2011.
Berger, et al., "Circulation and homing of melanoma-reactive T cells to both cutaneous and visceral metastases after vaccinnation with monocyte-derived dendritic cells," Int. J Cancer, pp. 229-237, 2004, vol. 111.
Kalos and June. Adoptive T cell transfer for cancer immunotherapy in the era of synthetic biology. Immunity, 39, 2013.
Spranger S. Mechanisms of tumor escape in the context of the T-cell-inflamed and the non-T-cell inflamed tumor microenvironment. International Immunology, 28 (8), 2016.
Beatty and Gladney. Immune Escape mechanisms as a guide for cancer immunotherapy. Clin. Cancer Res. 2014, 21(4).
Kerkar et al. Cellular constituents of immune escape within the tumor microenvironment. Cancer Res. 2012, 72(13).
von Wintzingerode et al. Peptide nucleic acid-mediated PCR clamping as a useful supplement in the determination of microbial diversity. Applied and Environmental Microbiology, vol. 66 No. 2, 2000.
Seneci, Pierfausto, "Encoding Techniques for Pool Libraries of Small Organic Molecules", Journal of Receptors and Signal Transduction, vol. 21, 2001—Issue 4. pp. 409-445. doi.org/10.1081/RRS-100107925.
Seneci, "Encoding techniques for pool libraries of small organic molecules". Journal of Receptor and Signal Transduction Research, vol. 21, No. 4, Nov. 1, 2001, p. 409-445.
Bentzen et al., "Large-scale detection of antigen-specific T cells using peptide-MHC-1 multimers labeled with DNA barcodes", Nature Biotechnology, Aug. 29, 2016.
Bentzen & Reker Hadrup, "Evolution of MHC-based technologies used for detection of antigen-responsive T cells" Cancer Immunol Immunother (2017) 66:657-666.
Hendrickson et al., "High sensitivity multianalyte immunoassay using covalent DNA-labeled antibodies and polymerase chain reaction", Nucleic Acid Res. 1995, vol. 23, No. 3.
Joerger et al., "Analyte detection with DNA-labeled antibodies and polymerase chain reaction", Clin. Chem. 41/9, 1371-1377 (1995).
Kazane et al. "Site-specific DNA-antibody conjugates for specific and sensitive immune-PCR", PNAS 2012 vol. 109 No. 10, 3731-3736.
Kwong et al., "Modular nucleic acid assembled p/MHC microanays for multiplexed sorting of antigen-specific T cells" J Am Chem Soc. 2009 131(28): 9695-9703.
McCluskey et al., "T cell activation by purified, soluble, Class I MHC molecules—requirement for polyvalency", J Immunology 1988, vol. 141, 1451-1455.

(56) References Cited

OTHER PUBLICATIONS

Siiman et. al., "Fluorescent neoglycoproteins: Antibody-aminodextran-phycobiliprotein conjugates", Bioconjugate Chem. 1999, 10, 1090-1106.

Xu et. al., "Design of 240,000 orthogonal 25mer DNA barcode probes". PNAS, Feb. 17, 2009, vol. 106 No. 7 2289-2294.

Altman JD, Moss PA, Goulder PJ, Barouch DH, McHeyzer-Williams MG, Bell JI, et al. Phenotypic analysis of antigen-specific T lymphocytes. Science. 1996;274:94-6.

Andersen RS, Kvistborg P, Mørch IF, Pedersen NW, Lyngaa R, Bakker AH, et al. Parallel detection of antigen-specific T-cell responses by combinatorial encoding of MHC multimers NatProtoc. 2012; vol. 7 No. 5; 891-902.

Cameron BJ, Gerry AB, Dukes J, Harper J V, Kannan V, Bianchi FC, et al. Identification of a Titin-derived HLA-A1-presented peptide as a cross-reactive target for engineered MAGE A3-directed T cells. Sci Transl Med. 2013;5:197ra103.

Cha E, Klinger M, Hou Y, Cummings C, Ribas A, Faham M, et al. Improved Survival with T Cell Clonotype Stability After Anti-CTLA-4 Treatment in Cancer Patients. Sci Transl Med. 2014;6:238ra70.

Davis MM, Bjorkman PJ. T-cell antigen receptor genes and T-cell recognition. Nature. 1988;334:395-402.

Dössinger G, Bunse M, Bet J, Albrecht J, Paszkiewicz PJ, Weißbrich B, et al. MHC multimer-guided and cell culture-independent isolation of functional T cell receptors from single cells facilitates TCR identification for immunotherapy. PLoS One. 2013;8:e61384.

Epstein et al., Biological activity of liposome-encapsulated murine interferon gamma is mediated by a cell membrane receptor. Proc Natl. Acad. Sci USA 82: 3688 (1985).

Hadrup SR, Bakker AH, Shu CJ, Andersen RS, van VJ, Hombrink P, et al. Parallel detection of antigen-specific T-cell responses by multidimensional encoding of MHC multimers. Nature Methods. 2009;6:520-6.

Hansen et al. Phage display of peptide/major histocompatibility class I complexes. European Journal of Immunology, vol. 31, pp. 32-38, 2001.

Hwang et al. Hepatic uptake and degradation of unilamellar sphingomyelin/cholesterol liposomes: A kinetic study. Proc. Natl. Acad. Sci USA 77: 4030 (1980).

Khurana A, et.al. A Method for Production of Recombinant mCD1d Protein in Insect Cells.J Vis Exp. 2007; (10): 556.

Le Doussal et al. Phage display of peptide/major histocompatibility complex. Journal of Immunological Methods, vol. 241, issues 1-2, 31, pp. 147-158, 2000.

Linette GP, Stadtmauer E a, Maus M V, Rapoport AP, Levine BL, Emery L, et al. Cardiovascular toxicity and titin cross-reactivity of affinity-enhanced T cells in myeloma and melanoma. Blood. 2013;122:863-71.

Lissina A, Ladell K, Skowera A, Clement M, Edwards E, Seggewiss R, van den Berg HA, Gostick E, Gallagher K, Jones E, Melenhorst JJ, Godkin AJ, Peakman M, Price DA, Sewell AK, Wooldridge L. Protein kinase inhibitors substantially improve the physical detection of T-cells with peptide-MHC tetramers. J Immunol Methods. 2009;340:11-24.

Manz R. et al. Analysis and sorting of live cells according to secreted molecules, relocated to a cell-surface affinity matrixProc. Natl. Acad. Sci. USA 92:1921 (1995).

Morgan RA, Dudley ME, Wunderlich JR, Hughes MS, Yang JC, Sherry RM, et al. Cancer Regression in Patients After Transfer of Genetically Engineered Lymphocytes. Science. 2006. 314(5796): 126-129.

Newell EW, Sigal N, Nair N, Kidd B a, Greenberg HB, Davis MM. Combinatorial tetramer staining and mass cytometry analysis facilitate T-cell epitope mapping and characterization. Nat Biotechnol. 2013;31(7)623-629.

Newell EW, Davis MM. Beyond model antigens: high-dimensional methods for the analysis of antigen-specific T cells. Nat Biotechnol. 2014;32, pp. 149-157.

Pannetier C, Even J, Kourilsky P. T-cell repertoire diversity and clonal expansions in normal and clinical samples. ImmunolToday. 1995;16:176-81.

Robert L, Tsoi J, Wang X, Emerson RO, Hornet B, Chodon T, et al. CTLA4 blockade broadens the peripheral T cell receptor repertoire. Clin Cancer Res. 20(9), 2014, pp. 2424-2432.

Robins HS, Campregher P V, Srivastava SK, Wacher A, Turtle CJ, Kahsai O, et al. Comprehensive assessment of T-cell receptor beta-chain diversity in alphabeta T cells. Blood. 2009;114:4099-107.

Sano et al. Immuno-PCR: very sensitive antigen detection by means of specific antibody-DNA conjugates. Science 258(Oct. 2, 1992), No. 5079, p. 120-122.

Soen Y, Chen DS, Kraft DL, Davis MM, Brown PO. Detection and characterization of cellular immune responses using peptide-MHC microarrays. PLoSBiol. 2003;1:429-38.

Stoeva et al. Multiplexed detection of protein cancer markers with biobarcoded nanoparticle probes. J Am Chem Soc 2006, 128, 8378-8379.

Stone JD, Demkowicz Jr. WE, Stern LJ. HLA-restricted epitope identification and detection of functional T cell responses by using MHC-peptide and costimulatory microarrays. ProcNatlAcadSciUSA. 2005;102:3744-9.

Andersen et al. Dissection of T-cell Antigen Specificity in Human Melanoma. Cancer Res 2012;72:1642-1650.

Bystrykh, Leonid V., "Generalized DNA Barcode Design Based on Hamming Codes", PLoS ONE, vol. 7, Issue 5, May 2012, 8 pg.

Lundberg et al., "Practical innovations for high-throughput amplicon sequencing", Nature Methods, vol. 10, No. 10, Oct. 2013, 9 pages.

Kivioja et al., "Counting absolute numbers of molecules using unique molecular identifiers", Nature Methods, vol. 9, No. 1,2012 pp. 72-76) (Year: 2012).

Harvey et al., "Cracking the code of human T-cell immunity", Nature Biotechnology, 2013, 31(7):609-610 (Year 2013).

Reznik et al., "A Streptavidin Mutant Useful for Directed Immobilization on Solid Surfaces", Bioconjugate Chemistry 2001, 12, 1000-1004.

Day et al., "Ex vivo analysis of human memory CD4 T cells specific for hepatitis C virus using MHC class II tetramers", J Clin Invest. 112: 831-842 (2003).

Moon et al., "Naive CD4+ T Cell Frequency Varies for Different Epitopes and Predicts Repertoire Diversity and Response Magnitude", Immunity, 27, 203-213 (2007).

Scriba et al., "Ultrasensitive Detection and Phenotyping of CD4+ T Cells with Optimized HLA Class II Tetramer Staining", Journal of Immunology, 2005, 175: 6334-6343.

Davis et al., "Interrogating the repertoire: broadening the scope of peptide-MHC multimer analysis", Nature Reviews Immunology, vol. 11, (2011), pp. 551-558.

Donolato et al., "On-Chip Manipulation of Protein-Coated Magnetic Beads via Domain-Wall Conduits", Adv. Mater. 2010, 22, 2706-2710.

* cited by examiner

A
Barcode#  MHC Complex#

B

Mix barcode labeled peptide-MHC multimer library in one tube. Possible complexity up to 1000-10.000 different MHC multimers

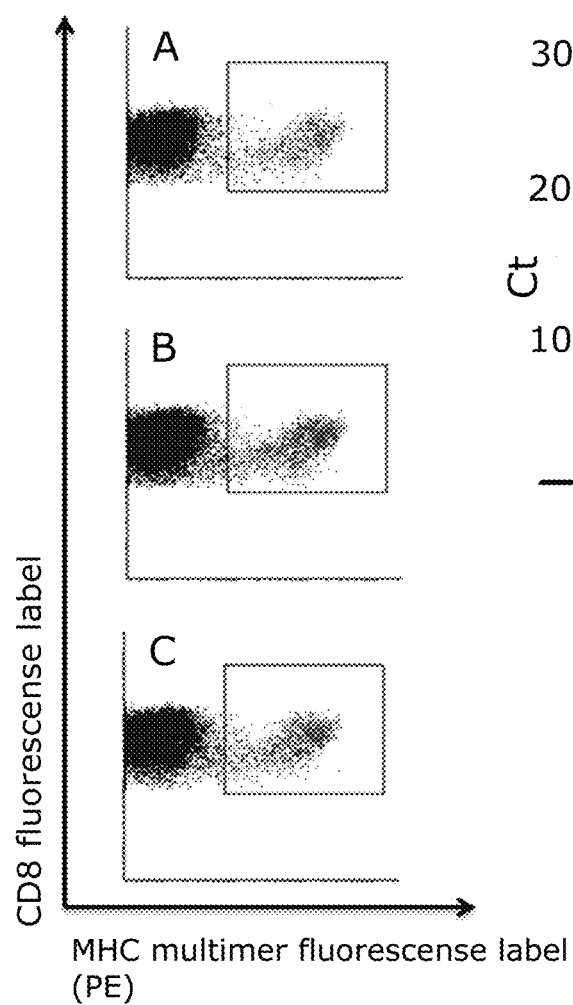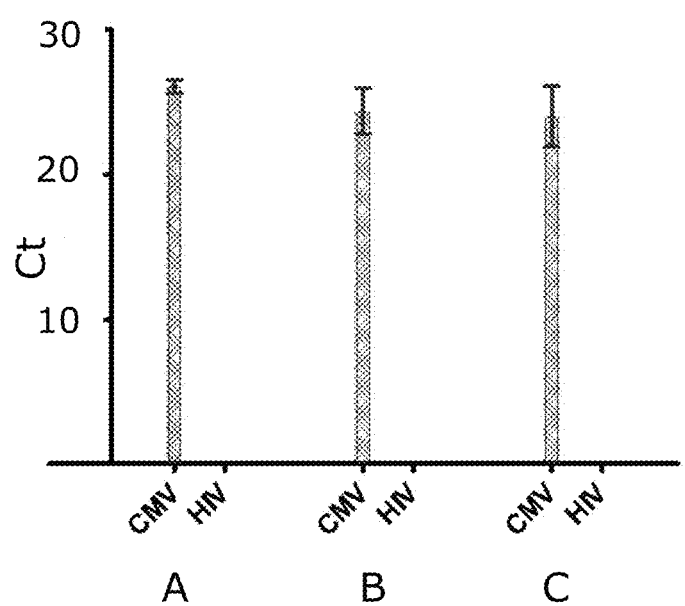
Fig. 7A
Fig. 7B

DNA barcode design

\* Did not reach threshold within 40 cycles

* Did not reach threshold within 40 cycles

Fig. 16

GENERAL DETECTION AND ISOLATION OF SPECIFIC CELLS BY BINDING OF LABELED MOLECULES

CROSS REFERENCE TO RELATED APPLICATIONS

This application is a continuation of U.S. application Ser. No. 17/668,980, filed 10 Feb. 2022, which is a continuation of U.S. application Ser. No. 15/316,587, filed 6 Dec. 2016, which is the U.S. national phase of PCT/DK2015/050169, filed 15 Jun. 2015, which claims priority of Danish applications PA 2014 00311, filed 13 Jun. 2014, PA 2014 00322, filed 18 Jun. 2014, and PA 2014 00453 filed 16 Aug. 2014. Each of the aforementioned applications is hereby incorporated by reference in its entirety.

FIELD OF INVENTION

The present invention relates to detection molecules comprising at least one binding molecule, at least one linker and at least one label, and detection methods making use of same. The invention provides a high-throughput method for detection, isolation and/or identification of specific entities or cells.

BACKGROUND

The adaptive immune system is directed through specific interactions between immune cells and antigen-presenting cells (e.g. dendritic cells, B-cells, monocytes and macrophages) or target cells (e.g. virus infected cells, bacteria infected cells or cancer cells). In important field in immunology relates to the understanding of the molecular interaction between an immune cell and the target cell.

Specifically for T-lymphocytes (T-cells), this interaction is mediated through binding between the T-cell receptor (TCR) and the Major Histocompatibility Complex (MHC) class I or class II. The MHC molecules carries a peptide cargo, and this peptide in decisive for T-cell recognition. The understanding of T-cell recognition experienced a dramatic technological breakthrough when Atman et al. (1) in 1996 discovered that multimerization of single peptide-MHC molecules would allow sufficient binding-strength (avidity) between the peptide-MHC molecules and the TCR to determine this interaction through a fluorescence label attached to the MHC-multimer. Such fluorescent-labelled MHC multimers (of both class I and class II molecules) are now widely used for determining the T-cell specificity. The MHC multimer associated fluorescence can be determined by e.g. flow cytometry or microscopy, or T-cells can be selected based on this fluorescence label through e.g. flow cytometry or bead-based sorting. However, a limitation to this approach relates to the number of different fluorescence labels available, as each fluorescence label serve as a specific signature for the peptide-MHC in question.

Thus, this strategy is poorly matching the enormous diversity in T-cell recognition. For the most predominant subset of T-cells (the αβ TCR T-cells), the number of possible distinct αβ TCRs has been estimated at ~1015 (2) although the number of distinct TCRs in an individual human is probably closer to 107(3). Therefore, much effort has attempted to expand the complexity of the T-cell determination, with the aim to enable detection of multiple different T-cell specificities in a single sample. A more recent invention relates to multiplex detection of antigen specific T-cells is the use of combinatorial encoded MHC multimers. This technique uses a combinatorial fluorescence labelling approach that allows for the detection of 28 different T-cell populations in a single sample when first published (4,5), but has later been extended through combination with novel instrumentation and heavy metal labels to allow detection of around 100 different T-cell populations in a single sample (6).

The requirement for new of technologies that allow a more comprehensive analysis of antigen-specific T-cell responses is underscored by the fact that several groups have tried to develop so-called MHC microarrays. In these systems, T-cell specificity is not encoded by fluorochromes, but is spatially encoded (7,8). In spite of their promise, MHC microarrays have not become widely adopted, and no documented examples for its value in the multiplexed measurement of T-cell responses, for instance epitope identification, are available.

Considering the above, there remains a need for a high-throughput method in the art of detection, isolation and/or identification of specific antigen responsive cells, such as antigen specific T-cells.

Further, there remains a need for a high-throughput method in the art of detection, isolation and/or identification of specific entities or cells, which cells can be detected via a binding molecule specific for said entity or cell.

Further, there remains a need in the art, considering the often limited amounts of sample available, for methods allowing detection, isolation and/or identification of multiple species of specific entities or cells, such as specific antigen responsive cells, such as T-cells, in a single sample.

SUMMARY

The present invention provides a detection molecule comprising a binding molecule (BM), a linker (Li) and a label (La). Said detection molecule can be used in various methods, such as methods comprising one or more steps of recognizing at least one entity or cell, binding at least one entity or cell, detecting at least one entity/cell-detection molecule complex, isolating at least one entity/cell-detection molecule complex and/or identifying one or more detection molecules bound to at least one entity/cell.

It is an aspect of the invention to provide a detection method comprising the steps of
1. Combining a sample with at least one detection molecule; wherein the detection molecule comprises a binding molecule (BM), a linker (Li), and a label (La); and wherein said sample comprises at least one cell and/or entity,
2. Incubating the at least one detection molecule and the sample;
3. Isolating and/or detecting the at least one detection molecule of step b), and
4. Optionally determining the identity of the at least one detection molecule of step c).

A binding molecule is a molecule that specifically associates covalently or non-covalently with a structure belonging to or associated with an entity in a sample. The defined structure in sample bound by a binding molecule is also called the target structure or target of the binding molecule.

The label comprised in the detection molecule of the present invention is any molecule, atom or signal the identity of which can be found or determined by any means. The label is unique and specific for a certain detection molecule, or set of detection molecules, and enables the isolation, detection and/or identification of the identity of said detection molecules (or cell-detection molecule complexes). In a particular embodiment the label is a nucleic acid label, such as a DNA label, The linker comprised in the detection molecule of the present invention is a molecular entity and/or bond that connect the binding molecule and the label of the detection molecule.

The present invention describes the use of labels, preferably nucleic acid labels (comprising a barcode sequence) as specific labels for binding molecules such as MHC multimers to determine e.g. the antigen responsiveness in biological samples. After cellular selection the barcode sequence of the label can be revealed by e.g. sequencing. This technology allows for detection of multiple (potentially >1000) different antigen-specific cells in a single sample.

BRIEF DESCRIPTION OF DRAWINGS

FIG. 3 describes how peptide-MHC molecules, nucleic acid (DNA)-barcodes and (optional) fluorescent labels are assembled to form a library of MHC multimers each holding a DNA-barcode specific for the given peptide-MHC molecule involved. Structure A: The barcode is designed to have a unique sequence that can be determined through DNA sequencing. Also the barcode have shared amplification ends, enabling amplification of all DNA-barcodes simultaneously in a PCR reaction. DNA-barcodes are attached to the MHC-multimerization backbone (e.g. via a biotin linker binding to streptavidin on the multimer backbone). Structure B: Represents the multimer backbone. This may be any backbone that allow multimerization of macro-molecules. The backbone may (optionally) hold a fluorescence label (illustrated by the asterisk) to track the total pool of MHC multimer binding cells irrespectively of the peptide-MHC multimer specificity. Structure C: Represents the peptide-MHC molecule of interest, carrying a specific peptide cargo (horizontal line). Structure D: Represents the assembled peptide-MHC multimers carrying the DNA barcode.

FIG. 4 illustrates the generation of a full barcode library. Library components (A): This library is composed of multiple, potentially more than 1000 different peptide-MHC multimers, each with a specific DNA-barcode. Such that barcode #1 codes for peptide-MHC complex #1, barcode #2 codes for peptide-MHC complex #2, barcode #3 codes for peptide-MHC complex #3, and so on until the possible mixture of thousands different specificities each with a specific barcode. Completed library (B): Represents the final reagent, which is a mixture of numerous different MHC-multimers each carrying a specific DNA barcode as a label for each peptide-MHC specificity.

Method for detecting antigen responsive cells in a sample. In FIG. 5 it is illustrated how this library can be used for staining of antigen responsive cells in a single sample. Step A: Cells in single cell suspension (may e.g., but not exclusive, originate from peripheral blood, tissue biopsies or other body fluids) are mixed with the peptide-library represented in Step B. Step B: After staining, cells are sequentially washed and spun to remove residual MHC multimers that are not bound to a cellular surface. Specific cell populations, e.g. T-cells (CD8 or CD4 restricted), other immune cells or specifically MHC multimer binding T-cells may be sorted by flow cytometry or others means of cell sorting/selection. Step C: The DNA-barcode oligonucleotide sequences isolated from the cell population is amplified by PCR. Step D: This amplification product is sequenced by deep sequencing (providing 10-100.000 s of reads). The sequencing will reveal the specific barcode sequence of DNA barcodes attached to cells in the specimen after selection, as these will appear more frequent than sequences associated to the background of non-specific attachment of MHC multimers. The "signal-to-noise" is counteracted by the fact that any unspecific MHC multimer event will have a random association of 1/1000 different barcodes (dependent of the size of the library), making it even more sensitive than normal multimer staining.

In FIG. 6, it is illustrated how this technology can be used to link different properties to the antigen specificity of a cell population.

Figure 1:
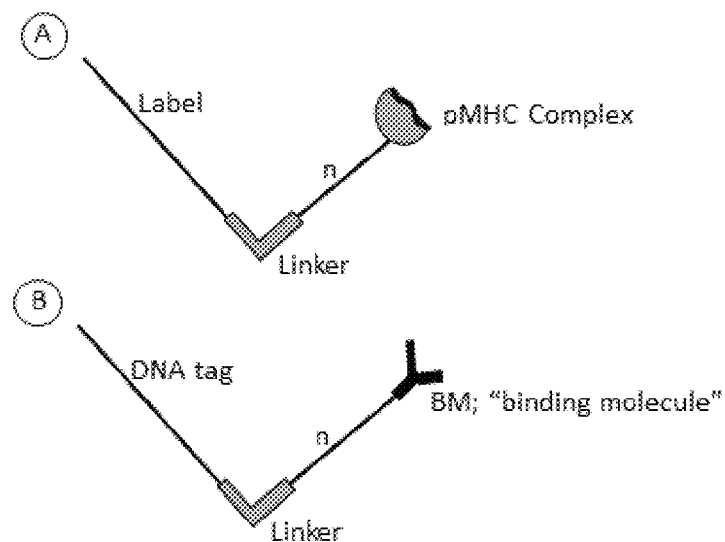
FIG. 1. Structure of detection molecules. (Detection Molecule A) Structure of a detection molecule, in which the "binding molecule" comprises n pMHC complexes, where n can be any integer between 1 and 1000. (Detection Molecule B) Structure of a detection molecule, comprising "binding molecule", label and the linker connecting the binding molecule and the label. The lower half of the figure shows the symbols representing the DNA tag (also called the oligonucleotide or oligonucleotide tag), the linker connecting binding molecule and label, MHC (major histocompatibility complex), peptide or other molecule (that binds to the MHC complex), pMHC (peptide-major histocompatibility complex), and the binding molecule (BM).

Functional Readout (A): Illustrates how cells after binding to a barcode labeled MHC multimer library may be exposed to a certain stimuli. Cell populations can be selected based on the functional response to this stimuli (e.g., but not exclusive, cytokine secretion, phosphorylation, calcium release or numerous other measures). After selecting the responsive or non-responsive population (following the steps of FIG. 5), the DNA barcodes can be sequenced to decode the antigen responsiveness, and thereby determining the antigen-specificities involved in a given response.

Phenotype Readout (B): Illustrates how cells can be selected based on phenotype, to link a certain set of phenotypic characteristics to the antigen-responsiveness.

Cell Sorting and Sequencing (C): Represents the possibility for single-cell sorting of MHC-multimer binding cells based on the co-attached fluorescence label on the MHC multimer. Through single-cell sorting the antigen-specificity of the given cell can be determined on a single cell level through sequencing of the associated barcode label. This can be linked to the TCR that can also be sequenced on a single cell level, as recently described (10). Hereby, this invention will provide a link between the TCR sequence, or other single-cell properties and the antigen specificity, and may through the use of barcode labeled MHC multimer libraries enable definition of antigen-specific TCRs in a mixture of thousands different specificities.

Quantitative Assessment (D): Illustrates the use of barcode labeled MHC multimer libraries for the quantitative assessment of MHC multimer binding to a given T-cell clone or TCR transduced/transfected cells. Since sequencing of the barcode label allow several different labels to be determined simultaneously on the same cell population, this strategy can be used to determine the avidity of a given TCR relative to a library of related peptide-MHC multimers. The relative contribution of the different DNA-barcode sequences in the final readout is determined based on the quantitative contribution of the TCR binding for each of the different peptide-MHC multimers in the library. Via titration based analyses it is possible to determine the quantitative binding properties of a TCR in relation to a large library of peptide-MHC multimers. All merged into a single sample. For this particular purpose the MHC multimer library may specifically hold related peptide sequences or alanine-substitution peptide libraries.

FIGS. 7A and 7B. Experimental data for attaching a DNA-barcode to a MHC multimer and amplify the specific sequences following T-cell staining. FIG. 7A: Shows the staining of cytomegalovirus (CMV) specific T-cells in a peripheral blood samples. The specific CMV-derived peptide-MHC multimers was labeled with a barcode (barcode #1) and mixed with an irrelevant/non-specific peptide-MHC multimer (HIV) labeled with barcode (barcode #2) and mixed with 998 other non-barcode labeled non-specific MHC multimers. Data here shows the feasibility for staining of CMV-specific T-cells in a mixture of 1000 other MHC multimers. Data is shown for three different staining protocols (A, B, C). FIG. 7B: Shows the readout of the specific barcode sequences by quantitative PCR. Barcode #1 (CMV) determining the CMV specific T-cell in detected for all three staining protocols, whereas the irrelevant/non-specific barcode signal, barcode #2 (HIV) is undetectable.

Figure 8:
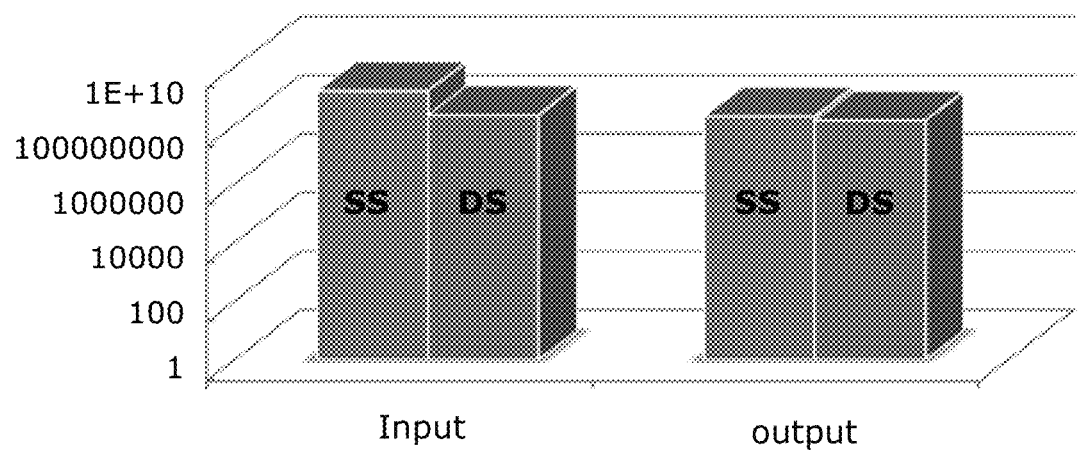

FIG. 8: Stability of single-stranded and double-stranded oligonucleotides in blood preparations, cf. Example A.

Figure 9A:
Figure 9A:
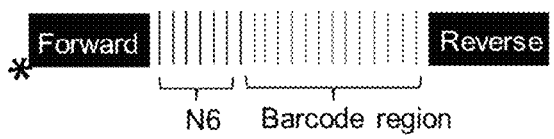
Figure 9B:
Figure 9C:
Figure 9C:
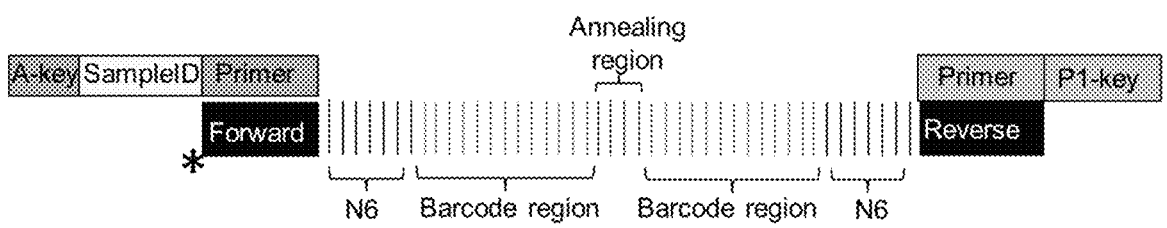

FIGS. 9A-9C: A schematic presentation of the Label systems applied; the 1OS and 2OS DNA-barcode systems. FIG. 9A. The 1OS system comprised of single stranded oligonucleotides which were applied as a DNA barcodes. 1OS structure: A ~80 nucleotide sequence. Biotin is attached at the 5'end where it accommodates easy attachment via a streptavidin binding site. The nucleotide sequence consists of a 20-25 nt forward primer followed by a random incorporation of 6 nt (N6), a short 3 nt linker and 25 nt that comprise the diverse barcode-identity. This is followed by 20-25 nt reverse primer region. FIG. 9B. The 2OS system are generated from annealing and elongation of two partially complementary oligonucleotides-nucleotide sequences, Oligo A and Oligo B, producing a fully double-stranded unique DNA sequences, which are used as DNA-barcodes. Oligo A corresponds largely to the 1OS DNA-barcodes, i.e. biotin is coupled to the 5'-end which begins with a forward primer region that is followed by a N6 segment and the unique oligonucleotide-sequence that will constitute one half of the barcode identity. After the unique sequence the reverse primer region of the 1OS system is replaced by a 16 nt sequence that is complementary to the 3'-end of Oligo B. Oligo B is described from the 3'-end where it anneals with Oligo A with a 16 nt complementary binding region followed by the unique oligonucleotide-sequence that will constitute the other half of the barcode identity. Hereafter comes a N6 region, which is followed by what is actually a forward primer region (since it lies in the 5'-end) but its complementary region will constitute the reverse priming region of the 2OS-DNA barcodes. Thus the primary differences between 1OS and 2OS barcodes are revealed in a greater length of the 2OS barcode, which is required to encompass two unique barcode regions, an annealing-site and an additional N6 region nearest the 3'-end. This adds up to ~130 nts. FIG. 9C. Through PCR amplification of enriched DNA-barcode Labels these are appointed a sample identification barcode (6-8 nt), which is part of the forward primer design. Additionally both the forward and reverse primers hold adaptors for the Ion Torrent sequencing (A-key and P1-key respectively). Primers and keys for the 1OS and the 2OS barcode were of a similar design (here showing a 2OS barcode). Asterisk=biotin, nt=nucleotide.

Figure 10A:
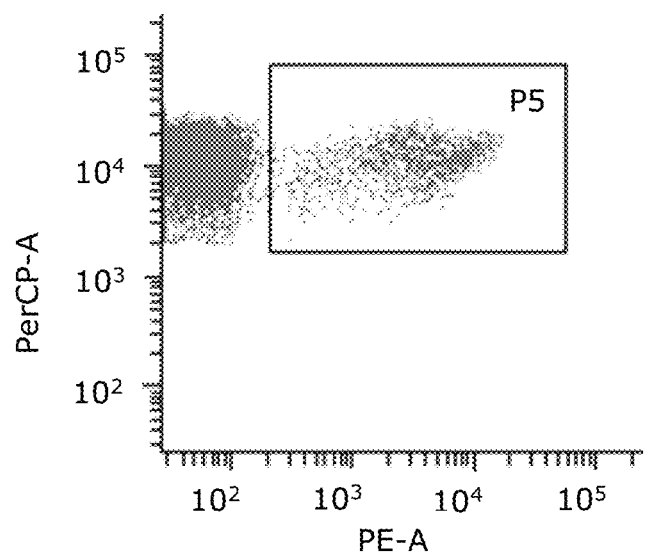
Figure 10B:
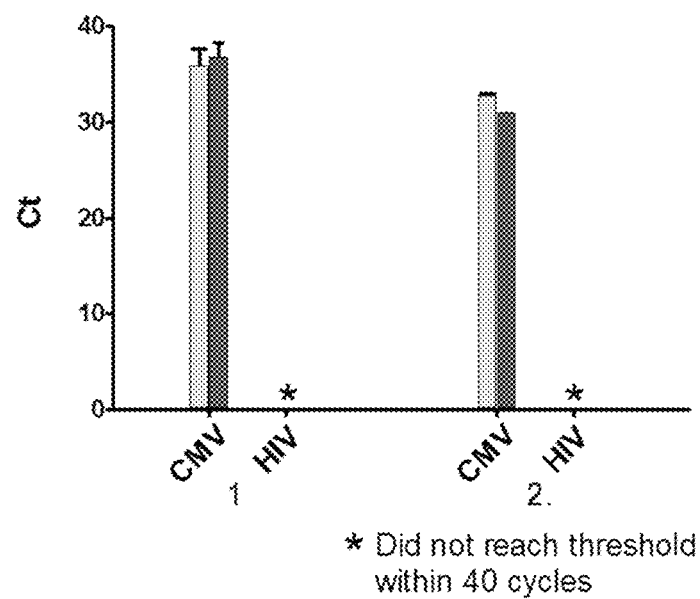

FIGS. 10A-10B: Detection of a CMV specificity amongst negative control Detection Molecules (cf Example 1). A unique 2OS DNA-barcode was associated with the CMV positive Detection Molecules in 1, while another unique 2OS DNA-barcode was associated with the CMV positive control Detection Molecules in 2. The spare DNA-barcode in each sample incubation was associated with the HIV negative control Detection Molecule. FIG. 10A. Representative dot plot showing the PE positive population after staining with CMV and HIV Detection Molecules carrying separate 2OS DNA-barcodes. FIG. 10B. Ct values from multiplex qPCR of the sorted PE-pMHC-dextramer positive cells. Cells were stained with 1. and 2. respectively. Detection Molecules associated with a positive control (CMV) 2OS barcode and a negative control (HIV) 2OS barcode were present during staining, but the negative control (HIV) Detection Molecule was evidently washed out. The results obtained from two individual experiments are presented in separate bars. Approximately 200 cells were applied in each PCR. QPCR was run in duplicates and Ct values are shown as mean±range of duplicates.

Figure 11A:
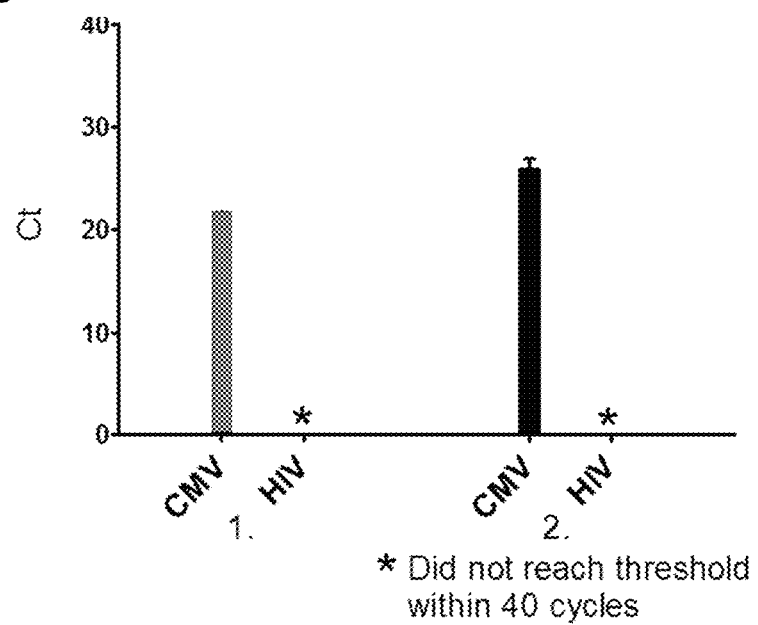
Figure 11B:
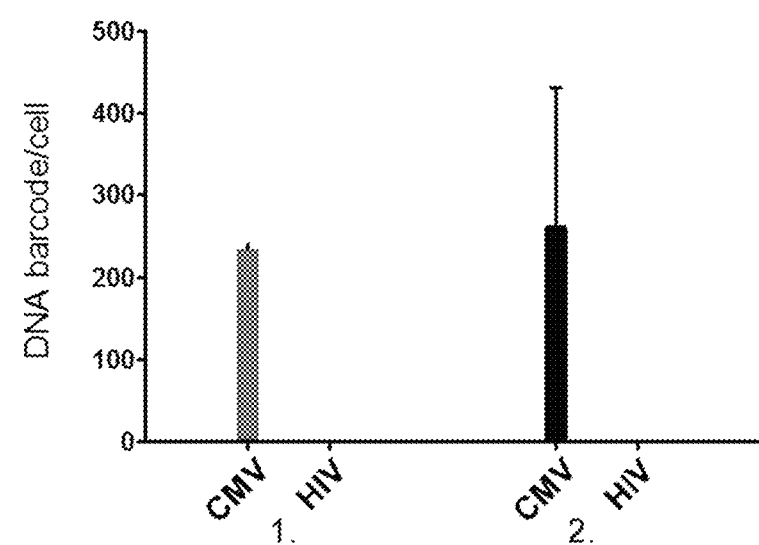

FIGS. 11A-11B: Detection of a CMV specificity amongst negative control Detection Molecules (cf. Example 2). A unique 1OS DNA-barcode was associated with the positive control Detection Molecules in 1, while another unique barcode was associated with the positive control reagents in 2. The spare barcode in each experiment was associated with a HIV negative Detection Molecules. In addition 998× unlabeled (i.e. lacking a DNA-barcode) negative control Detection Molecules were present in both 1. and 2. FIG. 11A, Ct values from multiplex qPCR of the sorted PE-pMHC-dextramer positive cells. Cells were stained with 1. and 2. respectively. Detection Molecules associated with a positive control (CMV) 1OS barcode and a negative control (HIV) 1OS barcode were present during staining, but the negative control (HIV) Detection Molecules were evidently washed out. Approximately 575 cells were analyzed in each qPCR. FIG. 11B. The estimated number of barcodes bound per cell relative to the obtained Ct-values (as calculated from a standard curve of 1OS barcode). It is evident that there were some differences in the Ct values shown in B, even though the same number of cells was present in all qPCRs. This is however leveled when the values are normalized in respect to their specific probes. QPCR was run in duplicates, here showing mean±range of duplicates.

Figure 12:
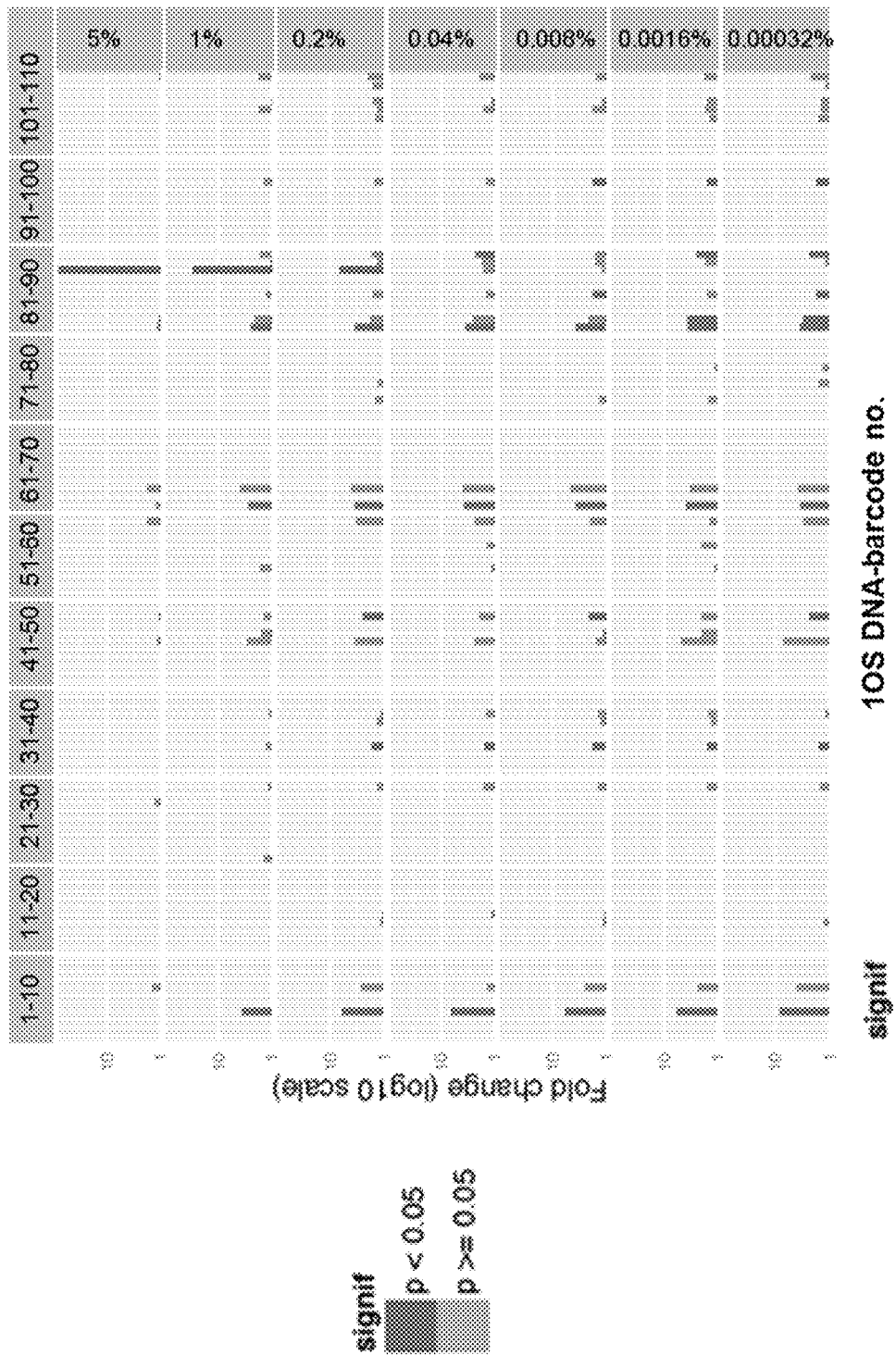

FIG. 12: Schematic presentations of the number of specific 1OS DNA-barcode reads mapped to seven different samples as identified by their respective sample-ID barcodes (cf. Example 3). A BC sample containing a 5% HLA-B0702 CMV pp65 TPR T cell response (corresponding Detection Molecule encoded by barcode 88) were spiked into a HLA-B0702 negative BC in fivefold dilutions, creating seven samples with theoretic frequencies of 5%, 1%, 0.2%, 0.04%, 0.008%, 0.0016% and 0.00032% of these T cells. The BC that these cells were spiked into contained ~0.1% HLA-A1101 EBV-EBNA4 specific T cells (corresponding Detection Molecule encoded by barcode 4). Samples were stained with the same library comprised of 110 different 1OS-labeled Detection Molecules. Each panel, named according to the theoretic frequency of the HLA-B0702 CMV response, represents the respective reads mapped to that given sample-ID barcode. The bars indicate reads mapped to a given 1OS barcode (vertical lines) after normalization in respect to the Detection Molecule-input reads mapped to that same 1OS barcode. Experiments were performed in duplicate. Here showing mean.

Figure 13:
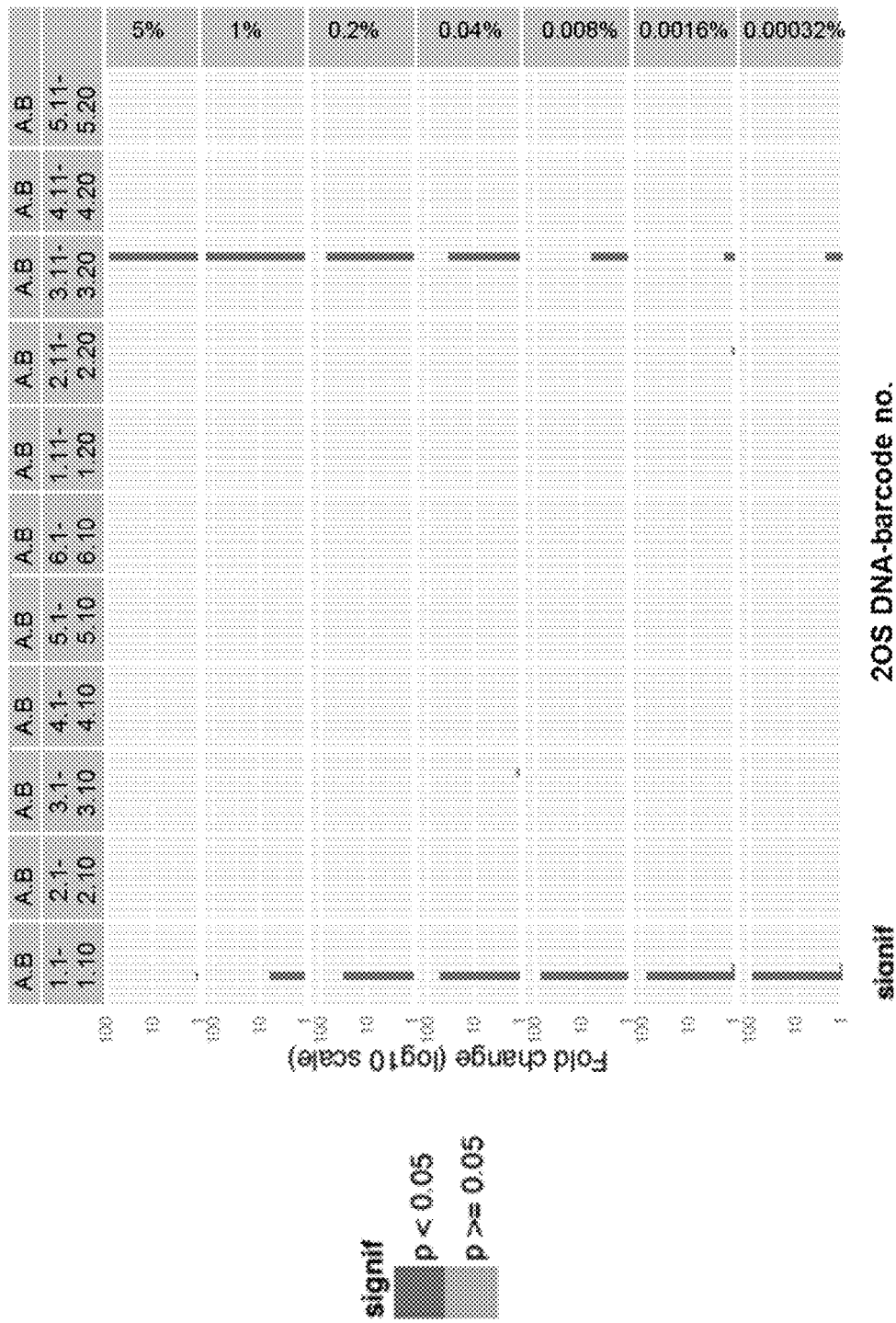

FIG. 13: Schematic presentations of the number of specific 2OS DNA-barcode reads mapped to seven different samples as identified by their respective sample-ID barcodes (cf. Example 4). A BC sample containing a 5% HLA-B0702 CMV pp65 TPR T cell response (corresponding Detection Molecule encoded by barcode A3B18) were spiked into a HLA-B0702 negative BC in fivefold dilutions, creating seven samples with theoretic frequencies of 5%, 1%, 0.2%, 0.04%, 0.008%, 0.0016% and 0.00032% of these T cells. The BC that these cells were spiked into contained ~1% HLA-A1101 EBV-EBNA4 specific T cells (corresponding Detection Molecule encoded by barcode A1B4). Samples were stained with the same library comprised of 110 different 2OS-labeled Detection Molecules. Each panel, named according to the theoretic frequency of the HLA-B0702 CMV response, represents the respective reads mapped to that given sample-ID barcode. The bars indicate reads mapped to a given 2OS barcode (vertical lines) after normalization in respect to the Detection Molecule-input reads mapped to that same 2OS barcode. Experiments were performed in duplicate. Here showing mean.

Figure 14:
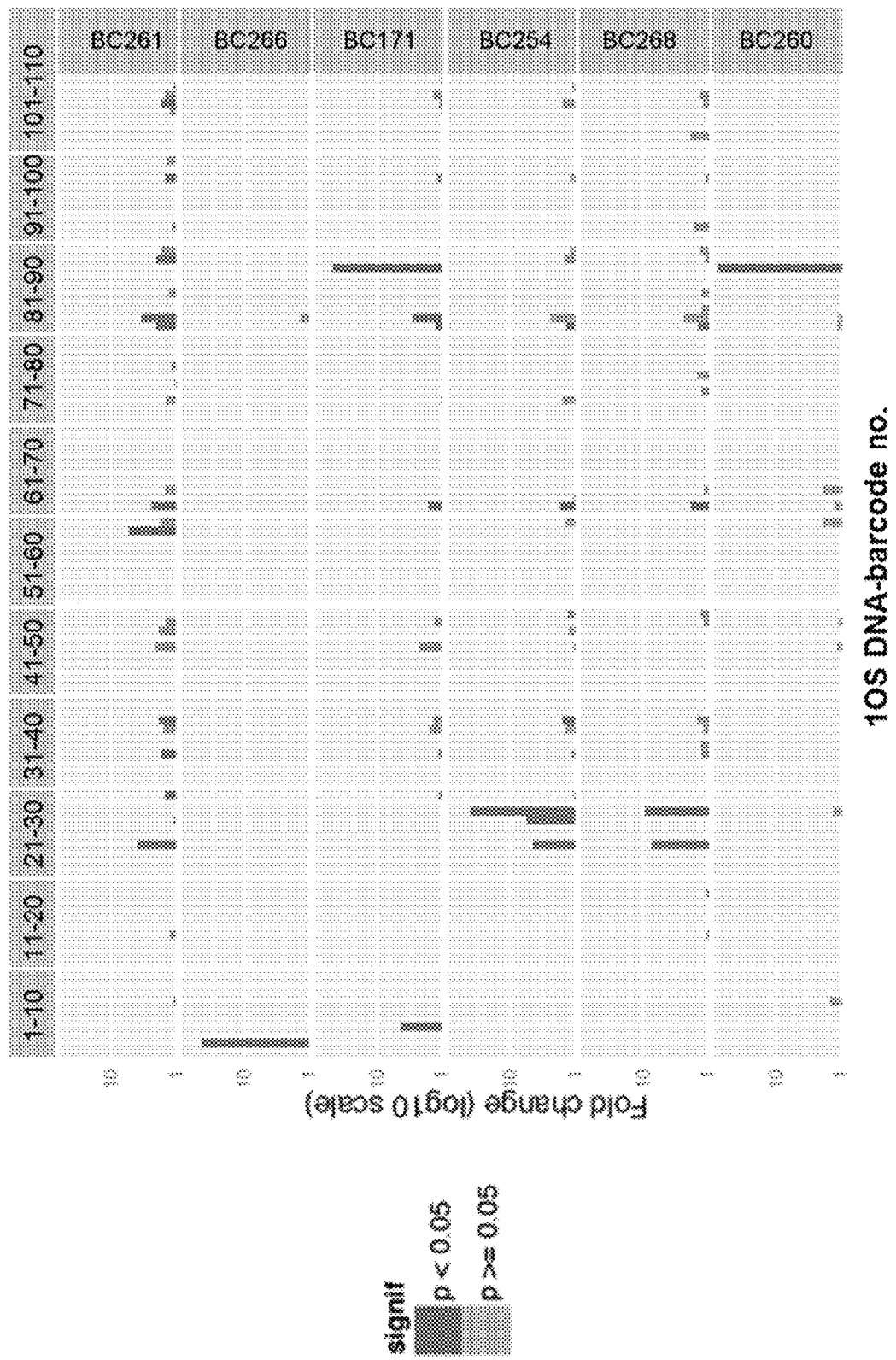

FIG. 14: Schematic presentations of the number of specific 1OS barcode reads mapped to six different samples as identified by their respective sample-ID barcodes (cf. Example 5). Six BCs were stained with the same library comprised of 110 different 1OS-labeled Detection Molecules. Each panel, named according to the donor BC number, represents the respective reads mapped to that given sample-ID barcode. The bars indicate reads mapped to a given 1OS barcode (vertical lines) after normalization in respect to the Detection Molecule-input reads mapped to that same 1OS barcode.

Figure 15:
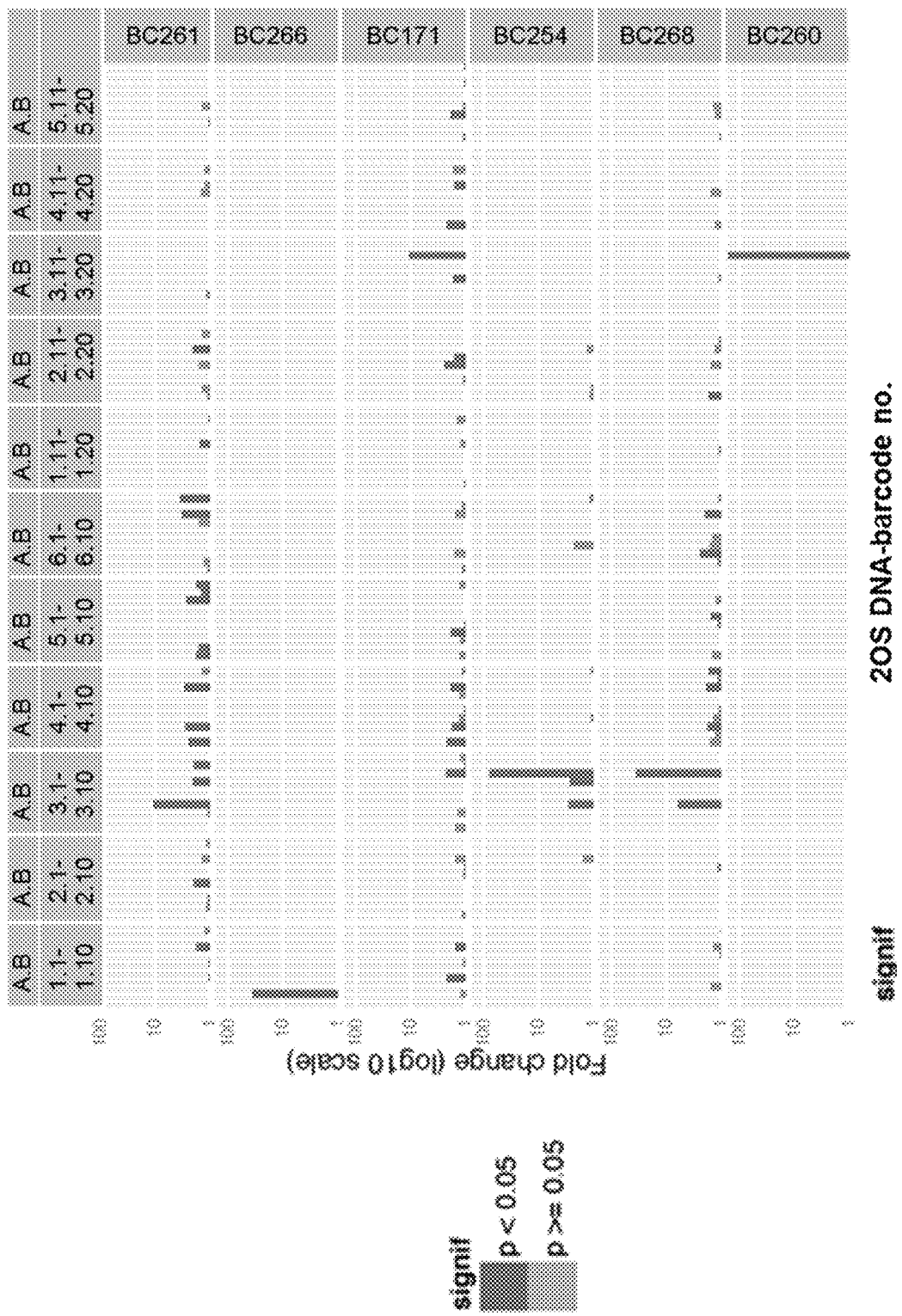

FIG. 15: Schematic presentations of the number of specific 2OS barcode reads mapped to six different samples as identified by their respective sample-ID barcodes (cf. Example 6). Six BCs were stained with the same library comprised of 110 different 2OS-labeled Detection Molecules. Each panel, named according to the donor BC number, represents the respective reads mapped to that given sample-ID barcode. The bars indicate reads mapped to a given 2OS barcode (vertical lines) after normalization in respect to the Detection Molecule-input reads mapped to that same 2OS barcode.

Figure 16:
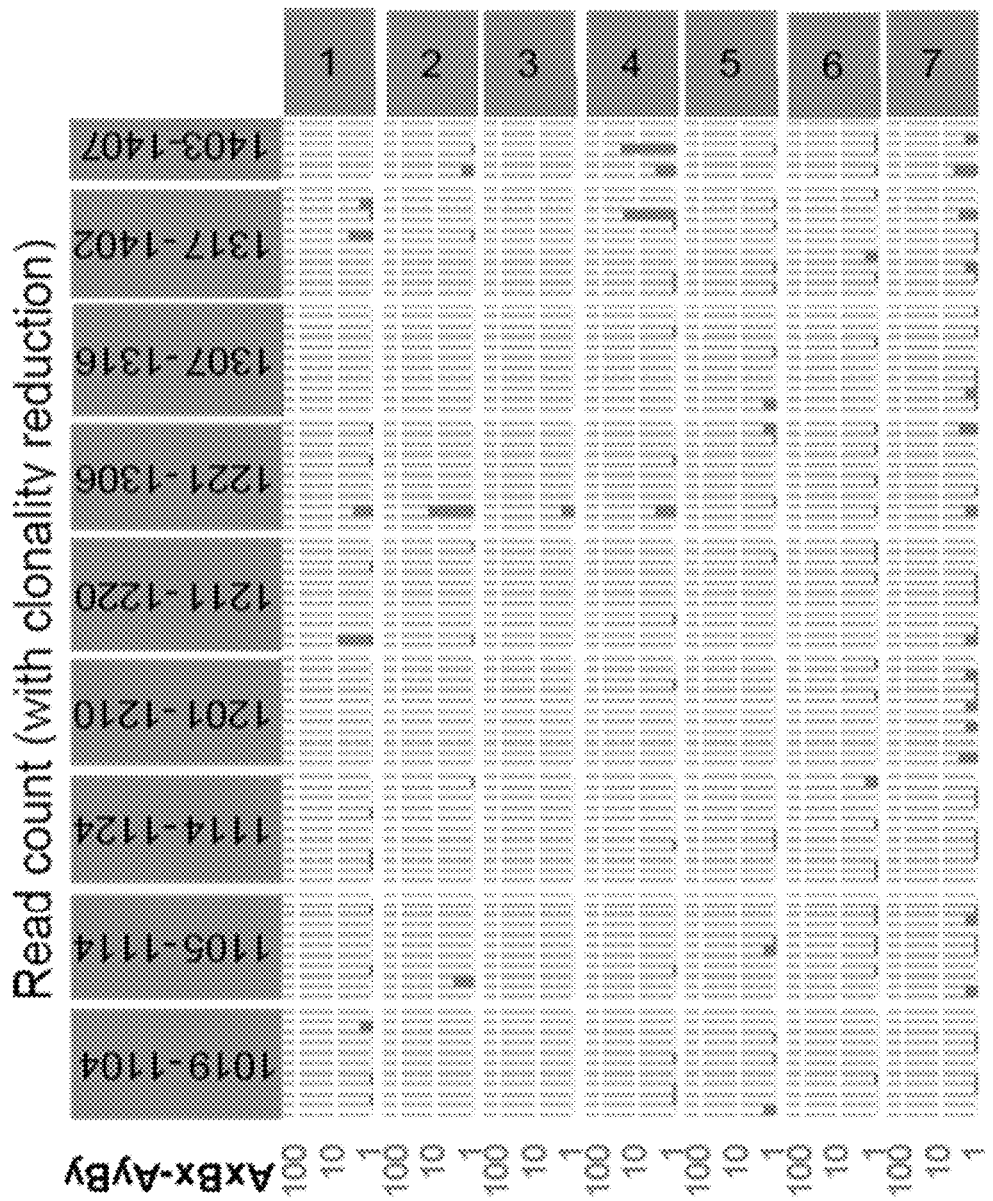
Figure 16:
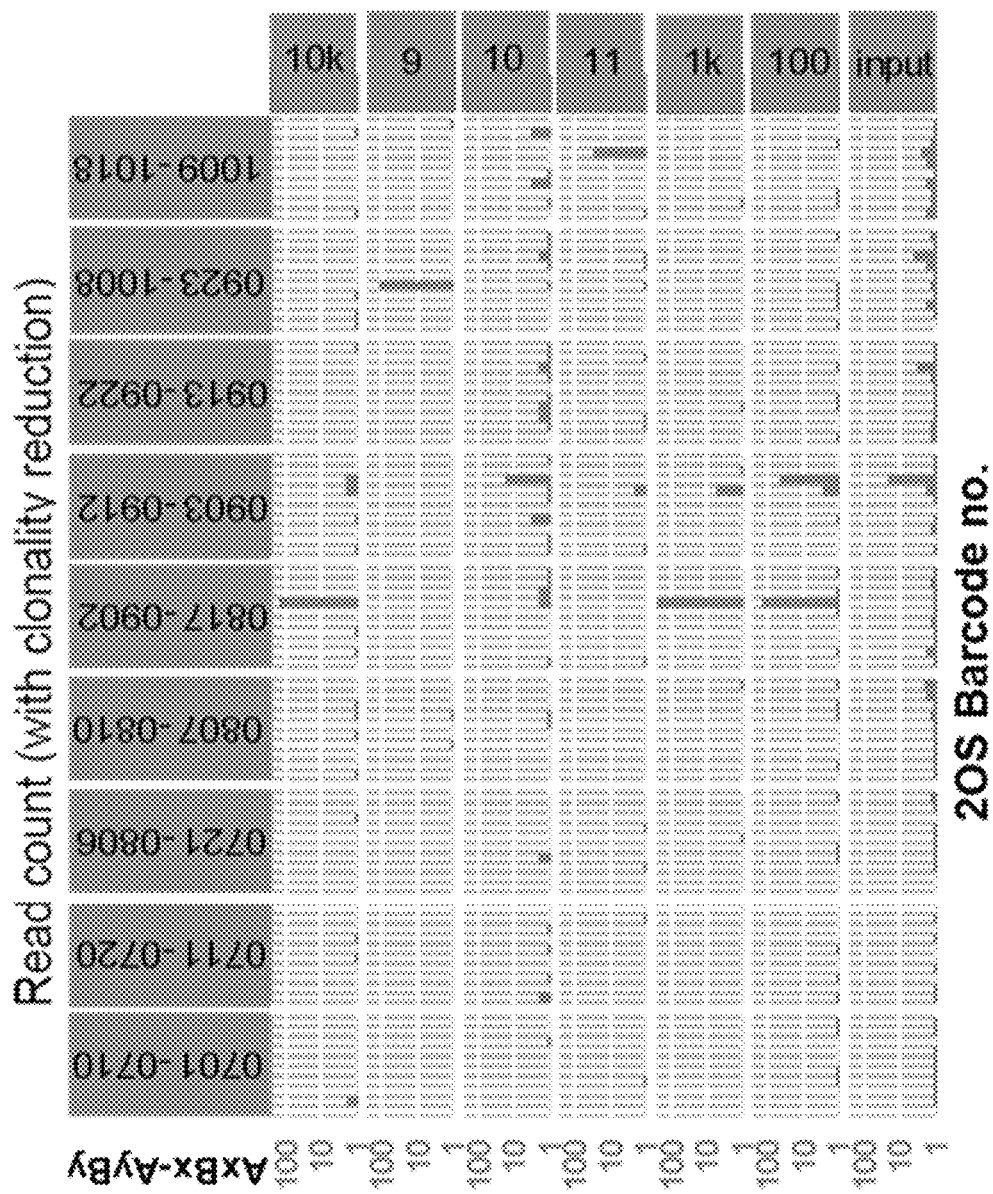
Figure 16:
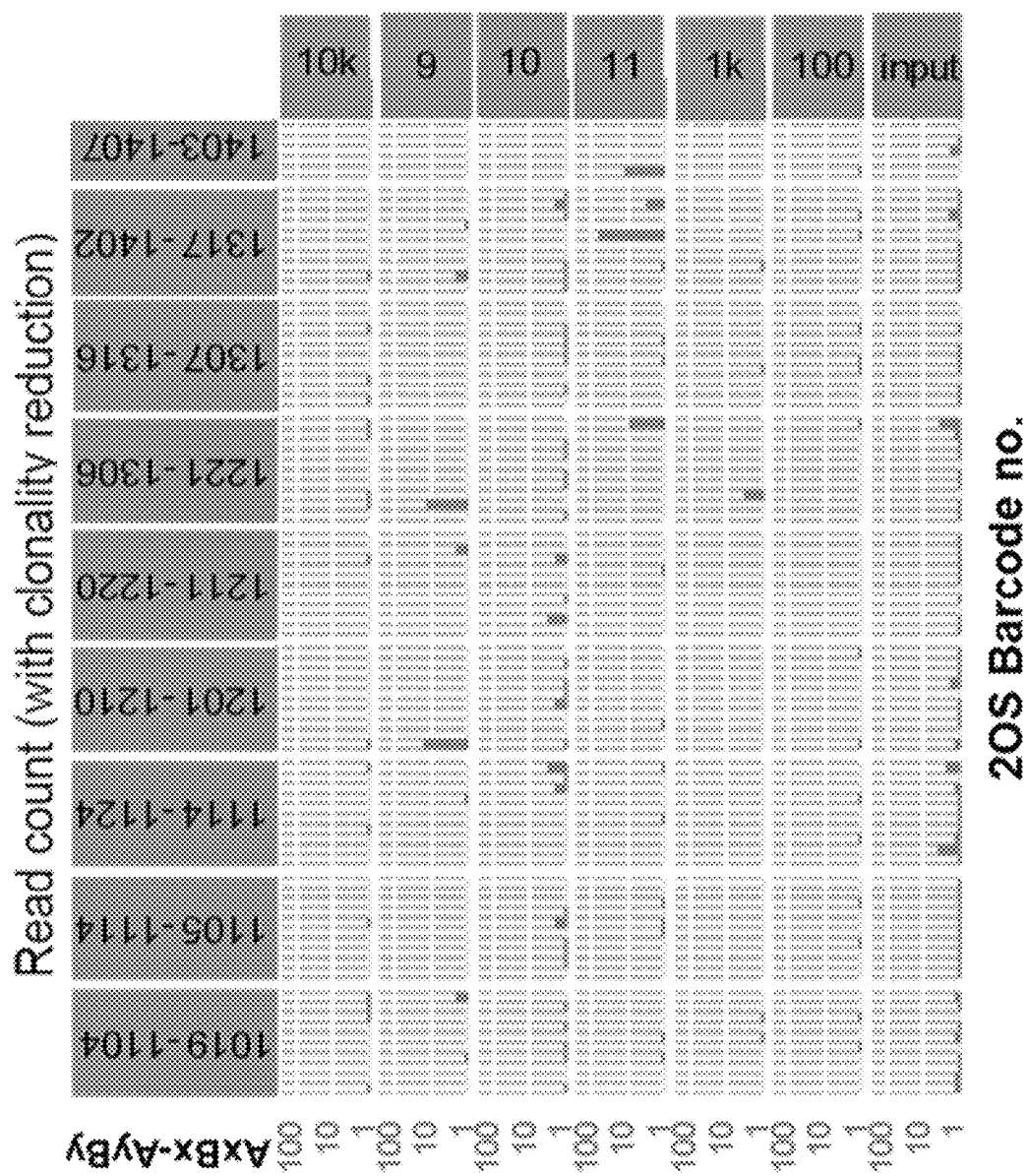

FIG. 16: Schematic presentations of the number of specific 2OS barcode reads mapped to 13 different TIL samples as identified by their respective sample-ID barcodes along with the reads mapped to the Detection Molecule-input sample (lower panel) (cf. Example 7). 11 TIL samples were stained with the same library comprised of 175 different 2OS-labeled Detection Molecules. Each panel represents the respective reads mapped to that given sample-ID barcode, which corresponds to TILs from resected tumor of a given malignant melanoma patient or to the Detection Molecule-input sample. Panel 1-7 and 9-11 represents the reads obtained from a singular amplification and sequencing of enriched Detection Molecules, i.e. 2OS barcodes, with individual patient samples. Panel 10$k$ corresponds to the mean reads obtained from three separate amplification-rounds (with individual sample-IDs) of equivalent to 10.000 sorted cells (enriched Detection Molecule) from the same patient-sample (TIL sample 8). Panel 1K corresponds to the reads obtained from amplification of equivalent to 1000 sorted cells (enriched Detection Molecule) and panel 100 corresponds to the mean reads obtained from three separate amplification-rounds (with individual sample-IDs) of equivalent to 100 sorted cells (enriched Detection Molecule) from the same patient-sample (TIL sample 8). The bars indicate reads mapped to a given 2OS barcode (vertical lines). The reads were not normalized in respect to the input sample (here mean of triplicate PCRs with unique sample-IDs), since only a total of ~5600 reads were obtained in the sequencing reaction (samples are being resequenced). Even so, the results are encouraging, with 2OS sequences mapping to most of the barcode identities present in the Detection Molecule library (input) and a trend showing preferential enrichment of certain, but different, 2OS barcodes across the patient samples. Furthermore, the replicates of sample 8, based on different cell numbers, shows comparable results. The number of reads of each barcode is reduced in clonality in respect to their N6 sequence.

DEFINITIONS AND ABBREVIATIONS

As used everywhere herein, the term "a", "an" or "the" is meant to be one or more, i. e. at least one.

'Aff.' is an abbreviation for affinity.

An "amino acid residue" can be a natural or non-natural amino acid residue linked peptide bonds or bonds different from peptide bonds. The amino acid residues can be in D-configuration or L-configuration. An amino acid residue comprises an amino terminal part ($NH_2$) and a carboxy terminal part (COOH) separated by a central part comprising a carbon atom, or a chain of carbon atoms, at least one of which comprises at least one side chain or functional group. $NH_2$ refers to the amino group present at the amino terminal end of an amino acid or peptide, and COOH refers to the carboxy group present at the carboxy terminal end of an amino acid or peptide. The generic term amino acid comprises both natural and non-natural amino acids. Natural amino acids of standard nomenclature as listed in J. Biol. Chem., 243:3552-59 (1969) and adopted in 37 C.F.R., section 1.822(b)(2) belong to the group of amino acids listed in the table herein below. Non-natural amino acids are those not listed in the Table below. Examples of non-natural amino acids are those listed e.g. in 37 C.F.R. section 1.822(b)(4), all of which are incorporated herein by reference. Also, non-natural amino acid residues include, but are not limited to, modified amino acid residues, L-amino acid residues, and stereoisomers of D-amino acid residues.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

Adjuvant: adjuvants are drugs that have few or no pharmacological effects by themselves, but can increase the efficacy or potency of other drugs when given at the same time. In another embodiment, an adjuvant is an agent which, while not having any specific antigenic effect in itself, can stimulate the immune system, increasing the response to a vaccine.

Agonist: agonist as used herein is a substance that binds to a specific receptor and triggers a response in the cell. It mimics the action of an endogenous ligand that binds to the same receptor.

Antagonist: antagonist as used herein is a substance that binds to a specific receptor and blocks the response in the cell. It blocks the action of an endogenous ligand that binds to the same receptor.

Antibodies: As used herein, the term "antibody" means an isolated or recombinant binding agent that comprises the necessary variable region sequences to specifically bind an antigenic epitope. Therefore, an antibody is any form of antibody or fragment thereof that exhibits the desired biological activity, e.g., binding the specific target antigen. Antibodies can derive from multiple species. For example, antibodies include rodent (such as mouse and rat), rabbit, sheep, camel, and human antibodies. Antibodies can also include chimeric antibodies, which join variable regions from one species to constant regions from another species. Likewise, antibodies can be humanized, that is constructed by recombinant DNA technology to produce immunoglobulins which have human framework regions from one species combined with complementary determining regions (CDR's) from a another species' immunoglobulin. The antibody can be monoclonal or polyclonal. Antibodies can be divided into isotypes (IgA, IgG, IgM, IgD, IgE, IgG1, IgG2, IgG3, IgG4, IgA1, IgA2, IgM1, IgM2)

Antibodies: In another embodiment the term "antibody" refers to an intact antibody, or a fragment of an antibody that competes with the intact antibody for antigen binding. In certain embodiments, antibody fragments are produced by recombinant DNA techniques. In certain embodiments, antibody fragments are produced by enzymatic or chemical cleavage of intact antibodies. Exemplary antibody fragments include, but are not limited to, Fab, Fab', F(ab')2, Fv, and scFv. Exemplary antibody fragments also include, but are not limited to, domain antibodies, nanobodies, minibodies ((scFv-C.sub.H3).sub.2), maxibodies ((scFv-C.sub.H2-C.sub.H3).sub.2), diabodies (noncovalent dimer of scFv).

Antigen presenting cell: An antigen-presenting cell (APC) as used herein is a cell that displays foreign antigen complexed with MHC on its surface.

Antigenic peptide: Used interchangeably with binding peptide. Any peptide molecule that is bound or able to bind into the binding groove of either MHC class 1 or MHC class 2 molecules.

Antigenic polypeptide: Polypeptide that contains one or more antigenic peptide sequences.

APC: Antigen presenting cell

Aptamer: the term aptamer as used herein is defined as oligonucleic acid or peptide molecules that bind a specific target molecule. Aptamers are usually created by selecting them from a large random sequence pool, but natural aptamers also exist. Aptamers can be divided into DNA aptamers, RNA aptamers and peptide aptamers.

Avidin: Avidin as used herein is a glycoprotein found in the egg white and tissues of birds, reptiles and amphibians. It contains four identical subunits having a combined mass of 67,000-68,000 daltons. Each subunit consists of 128 amino acids and binds one molecule of biotin.

Binding molecule (BM): The binding molecule comprised in the detection molecule of the present invention is any molecule that can specifically associate with, recognize and/or bind to a cell or any other entity, such as another molecule, a surface or a biological cell or other type of cellular entity (e.g. micelle). Example binding molecules are antibodies, MHC- and MHC-peptide complexes, peptides, small organic molecules, oligonucleotides, any kind of aptamer, proteins, multicomponent complexes comprising 2, 3, 4, 5, 6, 7, 8, or more subunits, and supramolecular structures.

Biologically active molecule: A biologically active molecule is a molecule having itself a biological activity/effect or is able to induce a biological activity/effect when administered to a biological system. Biologically active molecules include adjuvants, immune targets (e.g. antigens), enzymes, regulators of receptor activity, receptor ligands, immune potentiators, drugs, toxins, cytotoxic molecules, co-receptors, proteins and peptides in general, sugar moieties, lipid groups, nucleic acids including siRNA, nanoparticles, small molecules.

Bioluminescent: Bioluminescence, as used herein, is the production and emission of light by a living organism as the result of a chemical reaction during which chemical energy is converted to light energy.

Biotin: Biotin, as used herein, is also known as vitamin H or $B_7$. Niotin has the chemical formula $C_{10}H_{16}N_2O_3S$.

Bispecific antibodies: The term bispecific antibodies as used herein is defined as antibodies that have binding specificities for at least two different antigens. The antibody can also be trispecific or multispecific.

Bispecific capture molecule: Molecule that have binding specificities for at least two different antigens. The molecule can also be trispecific or multispecific.

Carrier/linker (Li): Carrier and linker may be used interchangeably herein, whereby a carrier is one type of a linker according to the present invention. A carrier as used herein can be any type of molecule that is directly or indirectly associated with the binding molecule such as a MHC peptide complex. In this invention, a carrier will typically refer to a functionalized polymer (e.g. dextran) that is capable of reacting with a binding molecule such as MHC-peptide complexes, thus covalently attaching the binding molecule to the carrier, or that is capable of reacting with scaffold molecules (e.g. streptavidin), thus covalently attaching streptavidin to the carrier; the streptavidin then may bind MHC-peptide complexes. Carrier and scaffold may also be used interchangeably herein where scaffold typically refers to smaller molecules of a linker or multimerization domain and carrier typically refers to larger molecule and/or cell like structures.

Cell-detection molecule complex: A complex comprising at least one detection molecule according to the invention and at least one cell.

Chelating chemical compound: Chelating chemical compound, as used herein, is the process of reversible binding of a ligand to a metal ion, forming a metal complex.

Chemiluminescent: Chemiluminescence, as used herein, is the emission of light (luminescence) without emission of heat as the result of a chemical reaction.

Chromophore: A chromophore, as used herein, is the part of a visibly coloured molecule responsible for light absorption over a range of wavelengths thus giving rise to the colour. By extension the term can be applied to uv or it absorbing parts of molecules.

Coiled-coil polypeptide: Used interchangeably with coiled-coil peptide and coiled-coil structure. The term coiled-coil polypeptide as used herein is a structural motif in proteins, in which 2-7 alpha-helices are coiled together like the strands of a rope Complement protein: Protein of the complement system.

Counting beads: Beads or particles countable in a flow cytometry experiment. They can be used as internal control beads enabling absolute cell count in a sample.

Covalent binding: The term covalent binding is used herein to describe a form of chemical bonding that is characterized by the sharing of pairs of electrons between atoms. Attraction-to-repulsion stability that forms between atoms when they share electrons is known as covalent bonding.

Crosslinking is the process of chemically joining two or more molecules by a covalent bond. Crosslinking reagents contain reactive ends to specific functional groups (primary amines, sulfhydryls, etc.) on proteins or other molecules.

Detection molecule: A molecule comprising a binding molecule (BM), a label (La) and a linker (Li), wherein 'a' is meant to comprise at least one, or one or more.

Diagnosis: The act or process of identifying or determining the nature and cause of a disease or injury through evaluation Diabodies: The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

Dendritic cell: The term dendritic cell as used herein is a type of immune cells. Their main function is to process antigen material and present it on the surface to other cells of the immune system, thus functioning as antigen-presenting cells.

Detection: In this invention detection means any method capable of measuring, or determining the presence of, one molecule alone or bound to another molecule.

Dextran: the term dextran as used herein is a complex, branched polysaccharide made of many glucose molecules joined into chains of varying lengths. The straight chain consists of $\alpha 1 \rightarrow 6$ glycosidic linkages between glucose molecules, while branches begin from $\alpha 1 \rightarrow 3$ linkages (and in some cases, $\alpha 1 \rightarrow 2$ and $\alpha 1 \rightarrow 4$ linkages as well).

Diabodies: The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

Direct detection of T cells: Direct detection of T cells is used herein interchangeably with direct detection of TCR and direct detection of T cell receptor. As used herein direct detection of T cells is detection directly of the binding interaction between a specific T cell receptor and a MHC multimer.

DNA: The term DNA (Deoxyribonucleic acid) duplex as used herein is a polymer of simple units called nucleotides, with a backbone made of sugars and phosphate atoms joined by ester bonds. Attached to each sugar is one of four types of molecules called bases.

DNA duplex: In living organisms, DNA does not usually exist as a single molecule, but instead as a tightly-associated pair of molecules. These two long strands entwine like vines, in the shape of a double helix.

Electrophilic: electrophile, as used herein, is a reagent attracted to electrons that participates in a chemical reaction by accepting an electron pair in order to bond to a nucleophile.

Entity-detection molecule complexes: A complex comprising at least one detection molecule according to the invention and at least one entity.

Enzyme label: enzyme labelling, as used herein, involves a detection method comprising a reaction catalysed by an enzyme.

Entity: An entity according to the present invention is capable of being recognized and/or bound by a detection molecule comprising a binding molecule as defined herein, to form a complex comprising the entity and the detection molecule.

Epitope-focused antibody: Antibodies also include epitope-focused antibodies, which have at least one minimal essential binding specificity determinant from a heavy chain or light chain CDR3 from a reference antibody, methods for making such epitope-focused antibodies are described in U.S. patent application Ser. No. 11/040,159, which is incorporated herein by reference in its entirety.

Flow cytometry: The analysis and/or sorting of single cells using a flow cytometer.

Flow cytometer: Instrument that measures cell size, granularity and flourescence due to bound fluorescent molecules as single cells pass in a stream past photodectors. A flow cytometer carry out the measurements and/or sorting of individual cells.

Fluorescent: the term fluorescent as used herein is to have the ability to emit light of a certain wavelength when activated by light of another wavelength.

Fluorochromes: Fluorochrome, as used herein, is any fluorescent compound used as a dye to mark e.g. protein with a fluorescent label.

Fluorophore: A fluorophore, as used herein, is a component of a molecule which causes a molecule to be fluorescent.

Folding: In this invention folding means in vitro or in vivo folding of proteins in a tertiary structure.

Fusion antibody: As used herein, the term "fusion antibody" refers to a molecule in which an antibody is fused to a non-antibody polypeptide at the N- or C-terminus of the antibody polypeptide.

Glycosylated: Glycosylation, as used herein, is the process or result of addition of saccharides to proteins and lipids.

Hapten: A residue on a molecule for which there is a specific molecule that can bind, e.g. an antibody.

Heteroconjugate antibodies are composed of two covalently joined antibodies. Such antibodies have, for example, been proposed to target immune system cells to unwanted cells.

IgG: IgG as used herein is a monomeric immunoglobulin, built of two heavy chains and two light chains. Each molecule has two antigen binding sites.

Isolated antibody: The term "isolated" antibody as used herein is an antibody which has been identified and separated and/or recovered from a component of its natural environment.

Immunoconjugates: The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate). Enzymatically active toxins and fragments thereof that can be used include diphtheria A chain, nonbinding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, Phytolaca americana proteins (PAPI, PAPII, and PAP-S), Momordica charantia inhibitor, curcin, crotin, Sapaonaria officinalis inhibitor, gelonin, mitogellin, restrictocin, phenomycin, enomycin, and the tricothecenes. A variety of radionuclides are available for the production of radioconjugated antibodies. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene).

Immune monitoring: Immune monitoring of the present invention refers to testing of immune status in the diagnosis and therapy of diseases like but not limited to cancer, immunoproliferative and immunodeficiency disorders, autoimmune abnormalities, and infectious disease. It also refers to testing of immune status before, during and after vaccination and transplantation procedures.

Immune monitoring process: a series of one or more immune monitoring analyses

Indirect detection of T cells: Indirect detection of T cells is used interchangeably herein with indirect detection of TCR and indirect detection of T cell receptor. As used herein indirect detection of T cells is detection of the binding interaction between a specific T cell receptor and a MHC multimer by measurement of the effect of the binding interaction.

Ionophore: ionophore, as used herein, is a lipid-soluble molecule usually synthesized by microorganisms capable of transporting ions.

Label (La). The label comprised in the detection molecule of the present invention is any molecule, atom or signal the identity of which can be found or determined by any means. The label of a detection molecule specifies the binding molecule that is linked to the label. Example labels are nucleic acid labels including oligonucleotides such as DNA, RNA, PNA, LNA; antibodies; any of the elements such as zinc, iron, magnesium, any of the lanthanides; peptides; proteins; and any type of organic molecules. The identity of the label can be determined by any appropriate method for the specific type of label, including but not limited to mass spectrometry, sequencing (e.g. DNA sequencing, peptide sequencing), gel electrophoresis, gel filtration, and many other methods.

Labelling: Labelling herein means attachment of a label to a molecule.

Lanthanide: lanthanide, as used herein, series comprises the 15 elements with atomic numbers 57 through 71, from lanthanum to lutetium.

LDA: limiting dilution assay

A ligand is a molecule capable of binding to and forming a complex with a biomolecule to serve a biological purpose.

Linker (Li). The linker comprised in the detection molecule of the present invention is a molecular entity and/or bond that connect the binding molecule and the label of the detection molecule. The linker can be of any length, such as length 1-10.000 Å (Angstrom), and can have any composition, including for example an oligonucleotide, peptide, organic molecule, and more. A linker according to the present invention comprises, or is identical to, a carrier molecule (or carrier), a multimerization domain, a scaffold, a connector and/or a backbone, and may equally be referred to as such herein. The linker in one embodiment comprises any linker, carrier or carrier molecule, multimerization domain or backbone, to which the binding molecule and the label are attached. The attachment may be direct or indirect, and may comprise a covalent or non-covalent binding.

Liposomes: The term liposome as used herein is defined as a spherical vesicle with a membrane composed of a phospholipid and cholesterol bilayer. Liposomes, usually but not by definition, contain a core of aqueous solution; lipid spheres that contain no aqueous material are called micelles.

Immunoliposomes: The antibodies disclosed herein can also be formulated as immunoliposomes. Liposomes comprising the antibody are prepared by methods known in the art, such as described in Epstein et al., Proc. Natl. Acad. Sci. USA 82: 3688 (1985); Hwang et al., Proc. Natl. Acad. Sci. USA 77: 4030 (1980); and U.S. Pat. Nos. 4,485,045 and 4,544,545. Particularly useful liposomes can be generated by the reverse-phase evaporation method with a lipid composition comprising phosphatidylcholine, cholesterol, and PEG-derivatized phosphatidylethanolamine (PEG-PE).

Immuno-profiling: Immuno profiling as used herein defines the profiling of an individual's antigen-specific T-cell repertoire MHC: Major histocompatibility complex.

MHC I is used interchangeably herein with MHC class I and denotes the major histocompatibility complex class I.

MHC II is used interchangeably herein with MHC class II and denotes the major histocompatibility complex class I.

MHC molecule: a MHC molecule as used everywhere herein is defined as any MHC class I molecule or MHC class II molecule as defined herein.

A "MHC Class I molecule" as used everywhere herein is used interchangeably with MHC I molecule and is defined as a molecule which comprises 1-3 subunits, including a MHC I heavy chain, a MHC I heavy chain combined with a MHC I beta2microglobulin chain, a MHC I heavy chain combined with MHC I beta2microglobulin chain through a flexible linker, a MHC I heavy chain combined with an antigenic peptide, a MHC I heavy chain combined with an antigenic peptide through a linker, a MHC I heavy chain/MHC I beta2microglobulin dimer combined with an antigenic peptide, and a MHC I heavy chain/MHC I beta2microglobulin dimer combined with an antigenic peptide through a flexible linker to the heavy chain or beta2microglobulin. The MHC I molecule chains can be changed by substitution of single or by cohorts of native amino acids, or by inserts, or deletions to enhance or impair the functions attributed to said molecule.

MHC Class I like molecules (including non-classical MHC Class I molecules) include CD1d, HLA E, HLA G, HLA F, HLA H, MICA, MIC B, ULBP-1, ULBP-2, and ULBP-3.

A "MHC Class II molecule" as used everywhere herein is used interchangeably with MHC II molecule and is defined as a molecule which comprises 2-3 subunits including a MHC II alpha-chain and a MHC II beta-chain (i.e. a MHC II alpha/beta-dimer), an MHC II alpha/beta dimer with an antigenic peptide, and an MHC II alpha/beta dimer combined with an antigenic peptide through a flexible linker to the MHC II alpha or MHC II beta chain, a MHC II alpha/beta dimer combined through an interaction by affinity tags e.g. jun-fos, a MHC II alpha/beta dimer combined through an interaction by affinity tags e.g. jun-fos and further combined with an antigenic peptide through a flexible linker to the MHC II alpha or MHC II beta chain. The MHC II molecule chains can be changed by substitution of single or by cohorts of native amino acids, or by inserts, or deletions to enhance or impair the functions attributed to said molecule. Under circumstances where the MHC II alpha-chain and MHC II beta-chain have been fused, to form one subunit, the "MHC Class II molecule" can comprise only 1 subunit or 2 subunits if antigenic peptide is also included.

MHC Class II like molecules (including non-classical MHC Class II molecules) include HLA DM, HLA DO, I-A beta2, and I-E beta2.

"MHC complexes", "MHC molecules" and "MHC constructs" are used interchangeably herein, and—if not further specified—comprises MHCs loaded with or bound to peptides as well as empty MHCs (not loaded with peptides).

MHC-peptide complex defines any MHC I and/or MHC II molecule combined with antigenic peptide.

A "peptide free MHC Class I molecule" is used interchangeably herein with "peptide free MHC I molecule" and as used everywhere herein is meant to be a MHC Class I molecule as defined above with no peptide.

A "peptide free MHC Class II molecule" is used interchangeably herein with "peptide free MHC II molecule" and as used everywhere herein is meant to be a MHC Class II molecule as defined above with no peptide.

Such peptide free MHC Class I and II molecules are also called "empty" MHC Class I and II molecules.

The MHC molecule may suitably be a vertebrate MHC molecule such as a human, a mouse, a rat, a porcine, a bovine or an avian MHC molecule. Such MHC complexes from different species have different names. E.g. in humans, MHC complexes are denoted HLA. The person skilled in the art will readily know the name of the MHC complexes from various species.

In general, the term "MHC molecule" is intended to include all alleles. By way of example, in humans e.g. HLA A, HLA B, HLA C, HLA D, HLA E, HLA F, HLA G, HLA H, HLA DR, HLA DQ and HLA DP alleles are of interest shall be included, and in the mouse system, H-2 alleles are of interest shall be included. Likewise, in the rat system RT1-alleles, in the porcine system SLA-alleles, in the bovine system BoLA, in the avian system e.g. chicken-B alleles, are of interest shall be included.

By the terms "MHC complexes" and "MHC multimers" as used herein are meant such complexes and multimers thereof, which are capable of performing at least one of the functions attributed to said complex or multimer. The terms include both classical and non-classical MHC complexes. The meaning of "classical" and "non-classical" in connection with MHC complexes is well known to the person skilled in the art. Non-classical MHC complexes are subgroups of MHC-like complexes. The term "MHC complex" includes MHC Class I molecules, MHC Class II molecules, as well as MHC-like molecules (both Class I and Class II), including the subgroup non-classical MHC Class I and Class II molecules.

MHC multimer: The terms MHC multimer, MHC-multimer, MHCmer and MHC'mer herein are used interchangeably, to denote a complex comprising more than one MHC-complex and/or MHC-peptide complex, held together by covalent or non-covalent bonds. In one embodiment a MHC multimer comprises 2 copies (dimer), 3 copies (trimer), 4 copies (tetramer), 5 copies, (pentamer), 6 copies (hexamer), 7 copies (heptamer), 8 copies (octamer), 9 copies (nonamer), 10 copies (decamer), 11 copies, 12 copies, 13 copies, 14 copies, 15 copies, 16 copies, 17 copies, 18 copies, 19 copies or 20 copies, Monoclonal antibodies: Monoclonal antibodies, as used herein, are antibodies that are identical because they were produced by one type of immune cell and are all clones of a single parent cell.

Monovalent antibodies: The antibodies in the present invention can be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking. In vitro methods are also suitable for preparing monovalent antibodies. Digestion of antibodies to produce fragments thereof, particularly, Fab fragments, can be accomplished using routine techniques known in the art.

Multimerization domain: A multimerization domain is a type of linker according to the present invention. It may also be used as a synonym to linker. It defines a molecule, a complex of molecules, or a solid support, to which one or more binding molecules, such as MHC or MHC-peptide complexes, can be attached. A multimerization domain consist of one or more carriers and/or one or more scaffolds and may also contain one or more scaffold molecules (or connectors) connecting carrier to scaffold, carrier to carrier, scaffold to scaffold. The multimerization domain may also contain one or more scaffold molecules that can be used for attachment of binding molecules and/or other molecules to the multimerization domain. Multimerization domains thus comprises IgG, streptavidin, streptactin, micelles, cells, polymers, beads and other types of solid support, and small organic molecules carrying reactive groups or carrying chemical motifs that can bind binding molecules such as MHC complexes and other molecules.

Nanobodies: Nanobodies as used herein is a type of antibodies derived from camels, and are much smaller than traditional antibodies.

Neutralizing antibodies: neutralizing antibodies as used herein is an antibody which, on mixture with the homologous infectious agent, reduces the infectious titer.

NMR: NMR (Nuclear magnetic resonance), as used herein, is a physical phenomenon based upon the quantum mechanical magnetic properties of an atom's nucleus. NMR refers to a family of scientific methods that exploit nuclear magnetic resonance to study molecules.

Non-covalent: The term non-covalent bond as used herein is a type of chemical bond that does not involve the sharing of pairs of electrons, but rather involves more dispersed variations of electromagnetic interactions.

Nucleic acid duplex: A nucleic acid is a complex, high-molecular-weight biochemical macromolecule composed of nucleotide chains that convey genetic information. The most common nucleic acids are deoxyribonucleic acid (DNA) and ribonucleic acid (RNA).

Nucleophilic: a nucleophile, as used herein, is a reagent that forms a chemical bond to its reaction partner (the electrophile) by donating both bonding electrons.

"One or more" as used everywhere herein is intended to include one and a plurality i.e. more than one.

Pegylated: pegylated, as used herein, is conjugation of Polyethylene glycol (PEG) to proteins.

Peptide or protein: Any molecule composed of at least two amino acids. Peptide normally refers to smaller molecules of up to around 30 amino acids and protein to larger molecules containing more amino acids.

Phosphorylated; phosphorylated, as used herein, is the addition of a phosphate ($PO_4$) group to a protein molecule or a small molecule.

PNA: PNA (Peptide nucleic acid) as used herein is a chemical similar to DNA or RNA. DNA and RNA have a deoxyribose and ribose sugar backbone, respectively, whereas PNA's backbone is composed of repeating N-(2-aminoethyl)-glycine units linked by peptide bonds. The various purine and pyrimidine bases are linked to the backbone by methylene carbonyl bonds. PNAs are depicted like peptides, with the N-terminus at the first (left) position and the C-terminus at the right.

"A plurality" as used everywhere herein should be interpreted as two or more.

This applies i.a. to the MHC complex and the binding entity. When a plurality of MHC complexes is attached to the multimerization domain, such as a scaffold or a carrier molecule, the number of MHC complexes need only be limited by the capacity of the multimerization domain.

Polyclonal antibodies: a polyclonal antibody as used herein is an antibody that is derived from different B-cell lines. They are a mixture of immunoglobulin molecules secreted against a specific antigen, each recognising a different epitope.

Polymer: the term polymer as used herein is defined as a compound composed of repeating structural units, or monomers, connected by covalent chemical bonds.

Polypeptide: Peptides are the family of short molecules formed from the linking, in a defined order, of various α-amino acids. The link between one amino acid residue and the next is an amide bond and is sometimes referred to as a peptide bond. Longer peptides are referred to as proteins or polypeptide.

Polysaccharide: The term polysaccharide as used herein is defined as polymers made up of many monosaccharides joined together by glycosidic linkages.

Radicals: radicals, as used herein, are atomic or molecular species with unpaired electrons on an otherwise open shell configuration. These unpaired electrons are usually highly reactive, so radicals are likely to take part in chemical reactions.

Radioactivity: Radioactive decay is the process in which an unstable atomic nucleus loses energy by emitting radiation in the form of particles or electromagnetic waves. RNA: RNA (Ribonucleic acid) as used herein is a nucleic acid polymer consisting of nucleotide monomers that plays several important roles in the processes that translate genetic information from deoxyribonucleic acid (DNA) into protein products.

RNA: RNA (Ribonucleic acid) as used herein is a nucleic acid polymer consisting of nucleotide monomers that plays several important roles in the processes that translate genetic information from deoxyribonucleic acid (DNA) into protein products Scaffold: A scaffold is typically an organic molecule carrying reactive groups, capable of reacting with reactive groups on a MHC- or MHC-peptide complex. Particularly small organic molecules of cyclic structure (e.g. functionalized cycloalkanes or functionalized aromatic ring structures) are termed scaffolds. Scaffold and carrier are used interchangeably herein where scaffold typically refers to smaller molecules of a multimerization domain and carrier typically refers to larger molecule and/or cell like structures. Both scaffold, carrier and multimerization domain are types of linkers according to the present invention.

Sequencing. In the present aspect it is understood that sequencing encompasses all types of sequencing of a given nucleic acid sequence, including also e.g. deep-sequencing or next-generation sequencing, in which amplified barcode sequences of a nucleic acid label (the PCR product) is sequenced a large number of repetitive time (number of total reads, e.g. 100.000 s of reads). The number of reads for the individual barcode sequence will relate to their quantitative presence in the amplification product, which again represents their quantitative presence before amplification, since all DNA-barcodes have similar amplification properties. Thus, the number of reads for a specific barcode sequence compared to the total number of reads will correlate to the presence of antigen responsive cells in the test-sample.

Staining: In this invention staining means specific or unspecific labelling of cells by binding labeled molecules to defined proteins or other structures on the surface of cells or inside cells. The cells are either in suspension or part of a tissue. The labeled molecules can be MHC multimers, antibodies or similar molecules capable of binding specific structures on the surface of cells.

Streptavidin: Streptavidin as used herein is a tetrameric protein purified from the bacterium Streptomyces avidinii. Streptavidin is widely use in molecular biology through its extraordinarily strong affinity for biotin.

Sugar: Sugars as used herein include monosaccharides, disaccharides, trisaccharides and the oligosaccharides—comprising 1, 2, 3, and 4 or more monosaccharide units respectively.

TCR: T-cell receptor

Therapy: Treatment of illness or disability

Vaccine: A vaccine is an antigenic preparation used to establish immunity to a disease or illness and thereby protect or cure the body from a specific disease or illness. Vaccines are either prophylactic and prevent disease or therapeutic and treat disease. Vaccines may contain more than one type of antigen and is then called a combined vaccine.

Vaccination: The introduction of vaccine into the body of human or animals for the purpose of inducing immunity.

DETAILED DESCRIPTION

The present invention provides a detection molecule comprising a binding molecule (BM), a linker (Li) and a label (La). Said detection molecule can be used in various methods, such as detection methods as outlined herein.

The binding molecules of the invention are capable of specifically associating with, such as recognizing and/or binding to, a target entity or cell.

The present invention provides a means for detecting detection molecules capable of binding to—and/or bound to—individual cells or to a subset of cells. Alternatively, the present invention provides a means for detecting the presence and/or abundance of cells capable of binding to detection molecules.

The present invention is in one embodiment used for epitope discovery, analytical studies, diagnosis, and therapy, and may be used in vivo (e.g. in animals) or in vitro (e.g. in any kind of cell samples such as blood, synovial fluid or bone marrow).

The present invention is in one embodiment used to characterize cells for their ability to bind certain detection molecules. The present invention is in one embodiment used to detect the presence of certain cell types, identified by their detection molecule-binding pattern.

In another embodiment, the technology is used for T-cell epitope mapping, immune-recognition discovery, or measuring immune reactivity after vaccination or immune-related therapies.

Composition

It is an aspect of the present invention to provide a detection molecule comprising
 a. a binding molecule (BM),
 b. a linker (Li), and
 c. a label (La).

The components of the detection molecule namely binding molecule, linker and label are defined herein elsewhere. It is understood that 'a' in the present context include at least one, or one or more, of each of said components. A binding molecule can thus be a monomeric or a multimeric binding molecule.

The present invention thus provides a detection molecule comprising at least one binding molecule (BM), at least one linker (Li) and at least one label (La).

It is understood that each component of the detection molecule, namely the binding molecule, the linker and the label, individually can be selected from any of the binding molecules, linkers and labels disclosed herein throughout. Thus, any combination of binding molecules, linkers and labels are encompassed within the present disclosure and invention.

It is also an aspect of the present invention to provide an entity-detection molecule complex, wherein said complex comprises
 a. at least one detection molecule comprising a binding molecule (BM), a linker (Li) and a label (La), and
 b. at least one entity.

It is also an aspect of the present invention to provide a cell-detection molecule complex, wherein said complex comprises
 c. at least one detection molecule comprising a binding molecule (BM), a linker (Li) and a label (La), and
 d. at least one cell.

In one embodiment the cell-detection molecule complexes comprises a cell, such as an immune cell, associated with or bound to a detection molecule having a binding molecule specific for the immune cell.

In one embodiment one or more components of the detection molecule; that is one or more of the binding molecule, the linker and the label are each as described in WO 2002/072631, WO 2009/106073 or WO 2009/003492, which are hereby incorporated by reference in their entirety.

In a particular embodiment the detection molecule has one or more characteristics as the detection molecules described in, and/or is prepared as described in, WO 2009/003492; European Journal of Immunology, vol. 31, pp 32-38, January 2001 (Hansen et al); or Journal of Immunological Methods, vol. 241, issues 1-2, 31 Jul. 2000 (Le Doussal et al).

In an aspect of the present invention the label will serve as a specific label for identifying a given binding molecule.

In an aspect of the present invention the label, such as a nucleic acid label, will serve as a specific label for a given binding molecule, such as a MHC molecule or peptide-MHC molecule that is multimerized to form a MHC multimer.

In one embodiment the present invention provides a detection molecule comprising
 a. a monomeric or a multimeric major histocompatibility complex (MHC) molecule, such as a monomeric or multimeric peptide MHC complex,
 b. a linker comprising a multimerization domain and optionally one or more connectors, and
 c. a nucleic acid label.

In one embodiment the present invention provides a detection molecule comprising
 a. a monomeric or a multimeric major histocompatibility complex (MHC) molecule, such as a monomeric or multimeric peptide MHC complex,
 b. a linker comprising a multimerization domain and optionally one or more connectors, and
 c. a peptide label.

In one embodiment the present invention provides a detection molecule comprising
 a. an anti-target molecule capable of associating with, recognizing and/or binding to a predetermined marker molecule (or target) on a cell type, wherein said marker molecule is specific for a certain cell type
 b. a linker (Li) comprising a multimerization domain and optionally one or more connectors, and
 c. a nucleic acid label.

Anti-target molecules are defined in more detail herein below.

In one embodiment the present invention provides a detection molecule comprising
 a. CD1, wherein said CD1 is selected from the group consisting of CD1 CD1a, CD1b, CD1c, CD1d and CD1e,
 b. a linker comprising a multimerization domain and optionally one or more connectors, and
 c. a nucleic acid label.

In one the linker of the detection molecule comprises a multimerization domain, such as a polysaccharide such as dextran, and optionally further comprises streptavidin or avidin whereby the binding molecule and/or the label comprises biotin.

In one embodiment the invention relates to a multimeric major histocompatibility complex (MHC) comprising
 a. two or more MHC molecules linked by a backbone molecule (linker); and
 b. at least one nucleic acid molecule (label) linked to said backbone, wherein said nucleic acid molecule comprises a central stretch of nucleic acids (barcode region) designed to be amplified by e.g. PCR.

In one embodiment the invention relates to a major histocompatibility complex (MHC) comprising
 a. one MHC molecule
 b. a backbone molecule (linker); and c. at least one nucleic acid molecule (label) linked to said backbone, wherein said nucleic acid molecule comprises a central stretch of nucleic acids (barcode region) designed to be amplified by e.g. PCR.

The invention provides a composition comprising one detection molecule, or one set of identical detection molecules.

Also provided is a composition comprising two or more different detection molecules, or two or more sets of different detection molecules, each detection molecule comprising at least one binding molecule (BM), at least one linker (Li) and at least one label (La) as defined herein, wherein each of the two or more detection molecules, or two or more sets of detection molecules, comprises a label which is unique to and specific for the binding molecule of each of said two or more different detection molecules.

In one embodiment said composition comprising two or more different detection molecules, or two or more sets of different detection molecules, comprises 2 to 1,000,000 different detection molecules, such as 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 different detection molecules; for example 1-3, 3-5, 5-10, 10-15, 15-20, 20-25, 25-30, 30-35, 35-40, 40-50, 50-60, 60-70, 70-80, 80-90, 90-100, 100-110, 110-120, 120-130, 130-140, 140-150, 150-175, 175-200, 200-250, 250-300, 300-400, 400-500, 500-600, 600-700, 700-800, 800-900, 900-1000, 1000-1500, 1500-2000, 2000-3000, 3000-4000, 4000-5000, 5000-7500, 7500-10,000, 10,000-20,000, 20,000-50,000, 50,000-100,000, 100,000-200,000, 200,000-500,000, 500,000-1,000,000 different detection molecules, or sets of different detection molecules.

The term 'different detection molecules' as used herein means that one or more of the binding molecule and/or label of each of the two or more detection molecules, or two or more sets of detection molecules, are different. Thus, the different detection molecules have different binding specificities (targets) and/or have different labels.

Another embodiment of the present invention relates to a composition comprising a subset of multimeric major histocompatibility complexes (MHC's) according to the invention, wherein each set of MHC's has a different peptide decisive for T cell recognition and a unique "barcode" region in the nucleic acid label (such as a DNA molecule).

Ratio of Binding Molecule/Label

In one embodiment there is a one-to-one relation between the label and the binding molecule, i.e. only one specific label (e.g. a specific oligonucleotide sequence) is attached to a specific binding molecule (e.g. a specific antibody). In other words, identifying the label (e.g. by sequencing an oligonucleotide label) will unambiguously identify the binding molecule attached to the label.

In another embodiment there is a one-to-one relation between the label and a group of binding molecules, i.e. only one specific label (e.g. a specific oligonucleotide sequence) is attached to a specific set of binding molecules (e.g. twenty different antibodies). In other words, identifying the label (e.g. by sequencing an oligonucleotide label) will unambiguously identify the group of binding molecule that may be attached to the label; identifying the label, however, will not identify the specific binding molecule that is attached to this particular copy of the label.

In yet another embodiment there is a one-to-one relation between a group of labels and a group of binding molecules, i.e. the label chosen for a specific detection molecule is chosen from a set of labels (e.g. twenty different oligonucleotide sequences) and the binding molecule chosen for a specific detection molecule is chosen from a set of binding molecules (e.g. twenty different antibodies). In other words, identifying the label of a detection molecule (e.g. by sequencing an oligonucleotide label) will unambiguously identify the group of binding molecule that may be attached to the label; identifying the label, however, will not identify the specific binding molecule that is attached to this particular copy of the label.

In another embodiment there is a one-to-one relation between a group of labels and a binding molecule, i.e. the label chosen for a specific detection molecule is chosen from a set of labels (e.g. twenty different oligonucleotide sequences). In other words, identifying the label of a detection molecule (e.g. by sequencing an oligonucleotide label) will unambiguously identify the binding molecule attached to the label; identifying the binding molecule, however, will not identify the specific label that is attached to this particular copy of the label. In cases where a certain label itself binds to the cells (and thus might lead to the wrong conclusion that the attached binding molecule binds to the cell), using several labels to encode the same binding molecule will allow the operator to distinguish binding of the binding molecule from binding of the label to the cell. Using several labels for the same binding molecule, or using several binding molecules for the same label can thus be used as internal controls.

Label

The label comprised in the detection molecule of the present invention is any molecule, atom or signal the identity of which can be found or determined by any means. The label of a detection molecule specifies the identity of the binding molecule that is linked to the label. The identity of the label can be determined by any appropriate method for the specific type of label.

In one embodiment there is provided a detection molecule comprising one or more binding molecules, one or more linkers, and one or more labels. The one or more labels may be connected with the other components of the detection molecule in any manner. In one embodiment, one or more labels are connected to the linker (or one of the linkers, or both or all of the multiple linkers) of the detection molecule. In one embodiment one or more labels are connected to the binding molecule (or one of the binding molecules, or both or all of the multiple binding molecules) of the detection molecule.

In one embodiment each detection molecule comprises one label. In another embodiment the detection molecule comprises two or more labels, such as 3, 4, 5, 6, 7, 8, 9, 10, 11, 12, 13, 14, 15, 16, 17, 18, 19, 20 labels. In one embodiment the detection molecule comprises 1-2, 2-3, 3-4, 4-5, 5-6, 6-7, 7-8, 8-9, 9-10, 10-15, 15-20, 20-25, 25-30, 30-40, 40-50, 50-75, 75-100, 100-150, 150-200, 200-250, 250-500, 500-750, 750-1000 labels.

In one embodiment each of said labels are identical to each other. In another embodiment each of said labels are different from each other. In yet another embodiment two or more of said labels are different with respect to each other.

In one embodiment the label linked to a given detection molecule is different from the label linked to other detection molecules used in the same assay.

In another embodiment the detection molecule comprises two different types of labels, such as 3, 4, 5, 6, 7, 8, 9, 10, 11, 12, 13, 14, 15, 16, 17, 18, 19, 20 different types of labels.

Labeling Molecules

Labelling molecules are molecules that can be detected in a certain analysis, i.e. the labelling molecules provide a signal detectable by the used method. Label and labelling molecules are used interchangeably herein.

The labelling molecule may be any labelling molecule suitable for direct or indirect detection. By the term "direct" is meant that the labelling molecule can be detected per se without the need for a secondary molecule, i.e. is a "primary" labelling molecule. By the term "indirect" is meant that the labelling molecule can be detected by using one or more "secondary" molecules, i.e. the detection is performed by the detection of the binding of the secondary molecule(s) to the primary molecule.

In one embodiment the labelling molecule is attached to the linker In one embodiment the labelling molecule is attached to the binding molecule.

The labelling molecule in one embodiment comprises a suitable linker or 'connector molecule' for attachment to the linker. Linkers suitable for attachment to labelling molecules would be readily known by the person skilled in the art and as described elsewhere herein.

A label of the present invention is in one embodiment selected from the group consisting of polymers, nucleic acids, oligonucleotides, peptides, fluorescent labels, phosphorescent labels, enzyme labels, chemiluminescent labels, bioluminescent labels, haptens, antibodies, dyes, nanoparticle labels, elements, metal particles, heavy metal labels, isotope labels, radioisotopes, stable isotopes, chains of isotopes and single atoms.

Labels may be organic or inorganic molecules or particles.

Organic molecules labels include ribonucleic acids (e.g. RNA, DNA or unnatural DNA, RNA, and XNA (e.g. PNA, LNA, GNA, TNA) and mononucleotides, peptides and other polyamides (e.g. peptides comprising β-amino acid residues), lipids, carbohydrates, amino acids, and many other molecules.

Inorganic molecule labels include the elements (e.g. Lanthanum, Cerium, Praseodymium, Neodymium, Promethium, Samarium, Europium, Gadolinium, Terbium, Dysprosium, and the rest of the elements known). The elements may coupled to the linker by way of chelates that coordinate the ions (interact non-covalently with the ions), where the chelates are then linked to the linker (in cases such as Gadolinium where the element can exist on ionic form), or the element may be contained in micelles. For some applications, rare elements are particularly favorable. For other applications heavy metals are particularly favorable.

Isotopes may also be used as labels (e.g. Carbon isotopes $^{12}C$, $^{13}C$ and $^{14}C$). Furthermore, label molecules comprising combinations of different isotopes and elements may also be used.

Particle labels include quantum dots, nanoparticles, micelles (e.g. comprising different fluorophores internally or in its membrane) and other particulate structures.

A molecule label may have a molecular weight of between 1 Da and several million Da. In some instances a very low molecular weight is preferred, such as a molecular weight of 1-10 Da, 11-50 Da, 50-250 Da, or 251-500 Da. This may for example be the case when mass spectrometry is used to detect the identity of element labels (e.g. Gadolinium, Gd). In other cases a low molecular weight, e.g. 501-2000 Da, 2001-5000 Da, or 5001-10000 Da may be preferred. This may be the case when e.g. peptide labels are used, where the peptide label comprises around 10-40 amino acid residues. In yet other cases, a high molecular weight of the molecule label is practical, and the molecular weight of the molecule label may be 10001-50000 Da, 50001-200000 Da, or 200000-1000000 Da. This may be the case e.g. in cases where a ribonucleic acid label is used, where the coding region (also called the barcode region or barcode sequence) is of significant length (e.g. 10-20 nucleotides) and where it is practical to have flanking primer binding regions of each 10-20 nucleotides, plus other sequences of different practical use. The resulting oligonucleotide label may in these cases be 30-1000 nt long, corresponding to molecular weights of about 10000-600000 Da. Finally, multi-molecule structures, such as in cases where a number of different fluorescent proteins are ordered in an array by binding to specific regions in a template DNA, where the total label thus comprises a long oligonucleotide to which is bound a number of proteins, and the total molecular weight of the label may thus be 50000-200000 Da, 200001-100000, or 1000001-10000000 Da.

In one embodiment the labels are fluorophores and other molecules that emit or absorb radiation. The fluorophores and other molecules emitting or absorbing radiation may be of organic or inorganic nature, and can be e.g. small molecules as well as large proteins. In one embodiment, it is particularly favorable if all the fluorophores and other molecules that emit or absorb radiation are within the same narrow range of emission wavelength optimum, such as having wavelength optima in the range 1-10 nm, 11-30 nm, 31-100 nm, 101-200 nm, 201-300 nm, 301-400 nm, 401-500 nm, 501-600 nm, 601-700 nm, 701-800 nm, 800-900 nm, 901-1200 nm, 1201-1500 nm, or larger than 1500 nm. As an example, if the instrument has a narrow range of wavelengths that can be detected, it is advantageous that all labels fall within this range of detection. On the other hand, if the instrument used to detect the radiation emitted by the labels has a wide span of detectable wavelengths, it is desirable that the different labels used in an experiment fall in several of the above-mentioned ranges, as this will result in little overlap between emission of different labels, and therefore more accurate detection of relative abundance of the different labels of an experiment. Emitted radiation may be phosphorescence, luminescence, fluorescence and more.

The labelling compound may suitably be selected:

from fluorescent labels such as 5-(and 6)-carboxyfluorescein, 5- or 6-carboxyfluorescein, 6-(fluorescein)-5-(and 6)-carboxamido hexanoic acid, fluorescein isothiocyanate (FITC), rhodamine, tetramethylrhodamine, and dyes such as Cy2, Cy3, and Cy5, optionally substituted coumarin including AMCA, PerCP, phycobiliproteins including R-phycoerythrin (RPE) and allophycoerythrin (APC), Texas Red, Princeston Red, Green fluorescent protein (GFP) and analogues thereof, and conjugates of R-phycoerythrin or allophycoerythrin and e.g. Cy5 or Texas Red, and inorganic fluorescent labels based on semiconductor nanocrystals (like quantum dot and Qdot™ nanocrystals), and time-resolved fluorescent labels based on lanthanides like Eu3+ and Sm3+, from haptens such as DNP, biotin, and digoxiginin, from enzymatic labels such as horse radish peroxidase (HRP), alkaline phosphatase (AP), beta-galactosidase (GAL), glucose-6-phosphate dehydrogenase, beta-N-acetylglucosaminidase, ß-glucuronidase, invertase, Xanthine Oxidase, firefly luciferase and glucose oxidase (GO), from luminiscence labels such as luminol, isoluminol, acridinium esters, 1,2-dioxetanes and pyridopyridazines, from radioactivity labels such as incorporated isotopes of iodide, cobalt, selenium, tritium, and phosphor, and from single atoms such as zinc (Zn), iron (Fe), magnesium (Mg), any of the lanthanides (Ln) including La, Ce, Pr, Nd, Pm, Sm, Eu, Gd, Tb, Dy, Ho, Er, Tm, Yb and Lu; scandium (Sc) and yttrium (Y).

Different principles of labelling and detection exist, based on the specific property of the labelling molecule. Examples of different types of labelling are emission of radioactive radiation (radionuclide, isotopes), absorption of light (e.g. dyes, chromophores), emission of light after excitation (fluorescence from fluorochromes), NMR (nuclear magnetic resonance form paramagnetic molecules) and reflection of light (scatter from e.g. such as gold-, plastic- or glass-beads/particles of various sizes and shapes).

Alternatively, the labelling molecules can have an enzymatic activity, by which they catalyze a reaction between chemicals in the near environment of the labelling molecules, producing a signal, which include production of light (chemi-luminescence), precipitation of chromophor dyes, or precipitates that can be detected by an additional layer of detection molecules. The enzymatic product can deposit at the location of the enzyme or, in a cell based analysis system, react with the membrane of the cell or diffuse into the cell to which it is attached. Examples of labelling molecules and associated detection principles are shown in the table below.

| Labelling substance | Effect | Assay-principle |
| --- | --- | --- |
| Fluorochromes | emission of light having a specific spectra | ▫Photometry, Microscopy, spectroscopy PMT, photographic film, CCD's (Color-Capture Device or Charge-coupled device). |
| Radionuclide | irradiation, α, β or gamma ▫rays | Scintillation counting, GM-tube, photographic film, excitation of phosphor-imager screen |
| Enzyme; HRP, (horse reddish peroxidase), peroxidases in general | catalysis of $H_2O_2$ reduction using luminol as Oxygen acceptor, resulting in oxidized luminal + light catalysis of $H_2O_2$ reduction using a soluble dye, or molecule containing a hapten, such as a biotin residue as Oxygen acceptor, resulting in precipitation. The habten can be recognized by a detection molecule. | ▫Photometry, Microscopy, spectroscopy PMT, photographic film, CCD's (Colour-Capture Device or Charge-coupled device), Secondary label linked antibody |
| Particles; gold, polystyrene beads, pollen and other particles | Change of scatter, reflection and transparency of the associated entity | Microscopy, cytometry, electron microscopy PMT's, light detecting devices, flowcytometry scatter |
| AP (Alkaline Phosphatase) | Catalyze a chemical conversion of a non-detectable to a precipitated detectable molecule, such as a dye or a hapten | ▫Photometry, Microscopy, spectroscopy Secondary label linked antibody |
| Ionophores or chelating chemical compounds binding to specific ions, e.g. $Ca^{2+}$ | Change in absorption and emission spectrums when binding. Change in intensity | ▫Photometry, Cytometry, spectroscopy |
| Lanthanides | Fluorescence Phosphorescence Paramagnetic | ▫photometry, cytometry, spectroscopy NMR (Nuclear magnetic resonance) |
| DNA fluorescing stains | Propidium iodide Hoechst stain DAPI AMC DraQ5 ™ Acridine orange 7-AAD | ▫Photometry, cytometry, spectroscopy |
| Nucleic acid label | Sequence, mass | PCR amplification, sequening Mass spec Gel electrophoresis, PAGE QPCR |
| Peptide label | Sequence, mass | Sequencing Mass spec Gel electrophoresis, PAGE |

Labelling molecules can be attached to a given binding molecule by covalent linkage as described for attachment of binding molecules to multimerization domains elsewhere herein. The attachment can be directly between reactive groups in the labelling molecule and reactive groups in the binding molecule or the attachment can be through a linker covalently attached to labelling molecule and binding molecule. When labelling MHC multimers the label can be attached either to the MHC complex (heavy chain, β2m or peptide) or to the multimerization domain.

In particular,
one or more labelling molecules may be attached to the carrier molecule, or one or more labelling molecules may be attached to one or more of the scaffolds, or one or more labelling compounds may be attached to one or more of the binding molecules, or one or more labelling compounds may be attached to the carrier molecule and/or one or more of the scaffolds and/or one or more of the binding molecules.

A single labelling molecule does not always generate sufficient signal intensity. The signal intensity can be improved by assembling single label molecules into large multi-labelling compounds, containing two or more label residues. Generation of multi-label compounds can be achieved by covalent or non-covalent, association of labelling molecules with a major structural molecule. Examples of such structures are synthetic or natural polymers (e.g. dextramers), proteins (e.g. streptavidin), or polymers. The labelling molecules in a multi-labelling compound can all be of the same type or can be a mixture of different labelling molecules.

Detection principles can be applied to flow cytometry, stationary cytometry, and batch-based analysis. Most batch-based approaches can use any of the labelling substances depending on the purpose of the assay. Flow cytometry primarily employs fluorescence, whereas stationary cytometry primarily employs light absorption, e.g. dyes or chromophore deposit from enzymatic activity.

In flow cytometry the typical label is detected by its fluorescence. Most often a positive detection is based on the presence of light from a single fluorochrome, but in other techniques the signal is detected by a shift in wavelength of emitted light; as in FRET based techniques, where the exited fluorochrome transfer its energy to an adjacent bound fluorochrome that emits light, or when using $Ca^{2+}$ chelating fluorescent props, which change the emission (and absorption) spectra upon binding to calcium. Preferable labelling molecules employed in flow cytometry are illustrated in the tables and described in the following.

Simple fluorescent labels:
Fluor dyes, Pacific Blue™, Pacific Orange™, Cascade Yellow™,
AlexaFluor® (AF);
AF405, AF488, AF500, AF514, AF532, AF546, AF555, AF568, AF594, AF610, AF633, AF635, AF647, AF680, AF700, AF710, AF750, AF800
Quantum Dot based dyes, QDot® Nanocrystals (Invitrogen, MolecularProbs)
Qdot®525, Qdot®565, Qdot®585, Qdot®605, Qdot®655, Qdot®705, Qdot®800
DyLight™ Dyes (Pierce) (DL);
DL549, DL649, DL680, DL800
Fluorescein (Flu) or any derivate of that, ex. FITC
Cy-Dyes
Cy2, Cy3, Cy3.5, Cy5, Cy5.5, Cy7
Fluorescent Proteins;
RPE, PerCp, APC
Green fluorescent proteins;
GFP and GFP-derived mutant proteins; BFP, CFP, YFP, DsRed, T1, Dimer2, mRFP1, MBanana, mOrange, dTomato, tdTomato, mTangerine, mStrawberry, mCherry Tandem dyes:
RPE-Cy5, RPE-Cy5.5, RPE-Cy7, RPE-AlexaFluor® tandem conjugates; RPE-Alexa610, RPE-TxRed
APC-Aleca600, APC-Alexa610, APC-Alexa750, APC-Cy5, APC-Cy5.5

Ionophors; ion chelating fluorescent props
Props that change wavelength when binding a specific ion, such as Calcium
Props that change intensity when binding to a specific ion, such as Calcium Combinations of fluorochromes on the same marker. Thus, the marker is not identified by a single fluorochrome but by a code of identification being a specific combination of fluorochromes, as well as inter related ratio of intensities.

Example: Antibody Ab1 and Ab2, are conjugated to both. FITC and BP but Ab1 have 1 FITC to 1 BP whereas Ab2 have 2 FITC to 1 BP. Each antibody may then be identified individually by the relative intensity of each fluorochrome. Any such combinations of n fluorochromes with m different ratios can be generated.

Examples of preferable fluorochromes:

| Fluorofor/Fluorochrome | Excitation nm | Emission nm |
| --- | --- | --- |
| 2-(4'-maleimidylanilino)naphthalene-6-sulfonic acid, sodium salt | 322 | 417 |
| 5-((((2-iodoacetyl)amino)ethyl)amino)naphthalene-1-sulfonic acid | 336 | 490 |
| Pyrene-1-butanoic acid | 340 | 376 |
| AlexaFluor 350 (7-amino-6-sulfonic acid-4-methyl coumarin-3-acetic acid) | 346 | 442 |
| AMCA (7-amino-4-methyl coumarin-3-acetic acid) | 353 | 442 |
| 7-hydroxy-4-methyl coumarin-3-acetic acid | 360 | 455 |
| Marina Blue (6,8-difluoro-7-hydroxy-4-methyl coumarin-3-acetic acid) | 362 | 459 |
| 7-dimethylamino-coumarin-4-acetic acid | 370 | 459 |
| Fluorescamin-N-butyl amine adduct | 380 | 464 |
| 7-hydroxy-coumarine-3-carboxylic acid | 386 | 448 |
| CascadeBlue (pyrene-trisulphonic acid acetyl azide) | 396 | 410 |
| Cascade Yellow | 409 | 558 |
| Pacific Blue (6,8 difluoro-7-hydroxy coumarin-3-carboxylic acid) | 416 | 451 |
| 7-diethylamino-coumarin-3-carboxylic acid | 420 | 468 |
| N-(((4-azidobenzoyl)amino)ethyl)-4-amino-3,6-disulfo-1,8-naphthalimide, dipotassium salt | 426 | 534 |
| Alexa Fluor 430 | 434 | 539 |
| 3-perylenedodecanoic acid | 440 | 448 |
| 8-hydroxypyrene-1,3,6-trisulfonic acid, trisodium salt | 454 | 511 |
| 12-(N-(7-nitrobenz-2-oxa-1,3-diazol-4-yl)amino)dodecanoic acid | 467 | 536 |
| N,N'-dimethyl-N-(iodoacetyl)-N'-(7-nitrobenz-2-oxa-1,3-diazol-4-yl)ethylenediamine | 478 | 541 |
| Oregon Green 488 (difluoro carboxy fluorescein) | 488 | 518 |
| 5-iodoacetamidofluorescein | 492 | 515 |
| Propidium iodide-DNA adduct | 493 | 636 |
| Carboxy fluorescein | 495 | 519 |

Examples of preferable fluorochrome families:

| Fluorochrome family | Example fluorochrome |
|---|---|
| AlexaFluor ®(AF) | AF ®350, AF405, AF430, AF488, AF500, AF514, AF532, AF546, AF555, AF568, AF594, AF610, AF633, AF635, AF647, AF680, AF700, AF710, AF750, AF800 |
| Quantum Dot (Qdot ®) based dyes | Qdot ®525, Qdot ®565, Qdot ®585, Qdot ®605, Qdot ®655, Qdot ®705, Qdot ®800 |
| DyLight ™ Dyes (DL) | DL549, DL649, DL680, DL800 |
| Small fluorescing dyes | FITC, Pacific Blue ™, Pacific Orange ™, Cascade Yellow ™, Marina blue ™, DSred, DSred-2, 7-AAD, TO-Pro-3, |
| Cy-Dyes | Cy2, Cy3, Cy3.5, Cy5, Cy5.5, Cy7 |
| Phycobili Proteins: | R-Phycoerythrin (RPE), PerCP, Allophycocyanin (APC), B-Phycoerythrin, C-Phycocyanin |
| Fluorescent Proteins | (E)GFP and GFP ((enhanced) green fluorescent protein) derived mutant proteins; BFP, CFP, YFP, DsRed, T1, Dimer2, mRFP1, MBanana, mOrange, dTomato, tdTomato, mTangerine, mStrawberry, mCherry |
| Tandem dyes with RPE | RPE-Cy5, RPE-Cy5.5, RPE-Cy7, RPE-AlexaFluor ® tandem conjugates; RPE-Alexa610, RPE-TxRed |
| Tandem dyes with APC | APC-Aleca600, APC-Alexa610, APC-Alexa750, APC-Cy5, APC-Cy5.5 |
| Calcium dyes | Indo-1-Ca2+ Indo-2-Ca2+ |

Preferable labelling molecules employed in stationary cytometry and IHC:
  Enzymatic labelling:
    Horse radish peroxidase; reduces peroxides ($H_2O_2$), and the signal is generated by the Oxygen acceptor when being oxidized.
      Precipitating dyes; Dyes that when they are reduced they are soluble, and precipitate when oxidized, generating a coloured deposit at the site of the reaction.
      Precipitating agent, carrying a chemical residue, a hapten, for second layer binding of binding molecules, for amplification of the primary signal.
      Luminol reaction, generating a light signal at the site of reaction.
    Other enzymes, such as Alkaline Phosphatase, capable of converting a chemical compound from a non-detectable molecule to a precipitated detectable molecule, which can be coloured, or carries a hapten as described above.
  Fluorescent labels; as those described for Flow cytometry are likewise important for used in stationary cytometry, such as in fluorescent microscopy.

Examples of preferable labels for stationary cytometry:

| Label | Enzyme substrate, Oxygen acceptor Chromogen/ precipitating agent | Precipitate or Residue, hapten* for secondary detection layer | Binding partner to hapten |
|---|---|---|---|
| HRP | diaminobenzidine (DAB) | Colored precipitate | — |
| HRP | 3-amino-9-ethyl-carbazole (AEC+) | Colored precipitate | — |
| AP | Fast red dye | Red precipitate | — |
| HRP | biotinyl tyramide | Exposed Biotin residue | Streptavidin, avidine |
| HRP | fluorescein tyramide | Exposed Fluorescein residue | Anti-Fluorecein Antibody |

| Label | Enzyme substrate, Oxygen acceptor Chromogen/ precipitating agent | Precipitate or Residue, hapten* for secondary detection layer | Binding partner to hapten |
|---|---|---|---|
| "Enzyme" | Substrate that when reacted precipitate | Primary label; being a dye, chemiluminescence's, or exposure of a hapten | Secondary label in case the primary label is a hapten |

In one embodiment the label comprises a connector molecule, which connector molecule is able to interact with a component on the linker and/or binding molecule of the detection molecule. In one embodiment the connector molecule is biotin or avidin. In one embodiment the linker comprises streptavidin to which the label binds via its biotin or avidin connector molecule.

Nucleic Acid Label

In one embodiment the detection molecule comprises at least one nucleic acid label, such as a nucleotide label, for example an oligonucleotide label.

In a preferred embodiment the label is an oligonucleotide. In a preferred embodiment, the label of the detection molecule is a DNA oligonucleotide (DNA label).

The terms nucleic acid label, nucleic acid molecule, nucleotide label, oligonucleotide label, DNA molecule, DNA label, DNA tag, DNA oligonucleotides and nucleic acid component may be used interchangeably herein.

In one embodiment the nucleic acid label comprises one or more of the following components:
  barcode region,
  5' first primer region (forward)
  3' second primer region (reverse),
  random nucleotide region,
  connector molecule
  stability-increasing components
  short nucleotide linkers in between any of the above-mentioned components
  adaptors for sequencing
  annealing region Preferably the nucleic acid label comprises at least a barcode region (i.e. barcode sequence). A barcode region comprises a sequence of consecutive nucleic acids.

A nucleic acid label of the present invention comprises a number of consecutive nucleic acids. The nucleic acid can be any type of nucleic acid or modifications thereof, naturally occurring or synthetically made (artificial nucleic acids).

In one embodiment the nucleic acid label comprises or consists of DNA.

In another embodiment the nucleic acid label comprises or consists of RNA.

In yet another embodiment the nucleic acid label comprises or consists of artificial nucleic acids or Xeno nucleic acid (XNA).

Artificial nucleic acid analogs have been designed and synthesized by chemists, and include peptide nucleic acid (PNA), morpholino- and locked nucleic acid (LNA), as well as glycol nucleic acid (GNA), threose nucleic acid (TNA), HNA and CeNA. Each of these is distinguished from naturally occurring DNA or RNA by changes to the backbone of the molecule.

In yet another embodiment the nucleic acid label comprises or consists of one or more of XNA, PNA, LNA, TNA, GNA, HNA and CeNA, In a further embodiment the at least one nucleic acid molecule comprises or consists of DNA, RNA, and/or artificial nucleotides such as PLA or LNA. Preferably DNA, but other nucleotides may be included to e.g. increase stability.

In a preferred embodiment the oligonucleotide used in the invention is a natural oligonucleotide such as DNA or RNA, or it may be PNA, LNA, or another type of unnatural oligonucleotide. The oligonucleotides may be modified on the base entity, the sugar entity, or in the linker connecting the individual nucleotides.

The length of the nucleic acid molecule may also vary. Thus, in one embodiment the at least one nucleic acid molecule has a length in the range 20-100 nucleotides, such as 30-100, such as 30-80, such as 30-50 nucleotides.

In one embodiment the label is an oligonucleotide of length 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31-35, 36-50, 51-100, or more than 100 nucleotides.

In one embodiment the nucleic acid label comprises 1 to 1,000,000 nucleic acids, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleic acids; for example 1-3, 3-5, 5-10, 10-15, 15-20, 20-25, 25-30, 30-35, 35-40, 40-50, 50-60, 60-70, 70-80, 80-90, 90-100, 100-110, 110-120, 120-130, 130-140, 140-150, 150-175, 175-200, 200-250, 250-300, 300-400, 400-500, 500-600, 600-700, 700-800, 800-900, 900-1000, 1000-1500, 1500-2000, 2000-3000, 3000-4000, 4000-5000, 5000-7500, 7500-10,000, 10,000-100,000, 100,000-1,000,000 nucleic acids.

A nucleic acid label of the present invention as minimum comprises a number of consecutive nucleic acids. The sequence of the nucleic acids serves as a code that can be identified, such as amplified and/or sequenced.

The identifiable consecutive nucleic acids, or the identifiable sequence, of the nucleic acid label are denoted a 'barcode', 'barcode region', 'nucleic acid barcode', 'unique sequence', 'unique nucleotide sequence' and 'coding sequence' herein (used interchangeably). The barcode region comprises of a number of consecutive nucleic acids making up a nucleic acid sequence.

In one embodiment the nucleic acid label comprises a central stretch of nucleic acids (barcode region) designed to be amplified by e.g. PCR.

In one embodiment, a nucleic acid barcode is a unique oligo-nucleotide sequence ranging for 10 to more than 50 nucleotides. In this embodiment, the barcode has shared amplification sequences in the 3' and 5' ends, and a unique sequence in the middle. This unique sequence can be revealed by sequencing and can serve as a specific barcode for a given binding molecule.

The unique sequence, the barcode, is composed of a series of nucleotides that together forms a sequence (series of nucleotides) that can be specifically identified based on its composition. This sequence composition enables barcode #1 to be distinguishable from barcode #2, #3, #4 etc, up to more than 100.000 barcodes, based solely on the unique sequence of each barcode. The complete nucleotide barcode may also be composed of a combination of series of unique nucleotide sequences linked to each other. The series of unique sequences will together assign the barcode.

In one embodiment, each unique nucleotide sequence (barcode) holds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31-35, 36-50, 51-100, or more than 100 nucleotides (nucleic acids).

In a preferred embodiment the label is an oligonucleotide, where the unique sequence has a length of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31-35, 36-50, 51-100, or more than 100 nucleotides. In one embodiment the unique sequence is shorter than the total length of the label.

In one embodiment the barcode region comprises or consists of 2-5, 5-10, 10-15, 15-20, 20-25, 25-30, 30-40, 40-45, 45-50, 50-60, 60-70, 70-80, 80-90, 90-100, 100-110, 110-120, 120-130, 130-140, 140-150, 150-175, 175-200, 200-250, 250-300, 300-400, 400-500 nucleic acids.

The unique nucleotide sequence (barcode) is solely used as an identification tag for the molecular interaction between the binding molecule and its target. The unique nucleotide sequences preferably are not identical to any natural occurring DNA sequence, although sequence similarities or identities may occur.

Each nucleic acid barcode should hold sufficient difference from the additional barcodes in a given experiment to allow specific identification of a given barcode, distinguishable from the others.

The nucleic acid component (preferably DNA) has a special structure. Thus, in an embodiment the at least one nucleic acid molecule (label) is composed of at least a 5' first primer region, a central region (barcode region), and a 3' second primer region. In this way the central region (the barcode region) can be amplified by a primer set.

The coupling of the nucleic acid molecule to the backbone may also vary. Thus, in one embodiment the at least one nucleic acid molecule is linked to said backbone via a streptavidin-biotin binding and/or streptavidin-avidin binding. Other coupling moieties may also be used.

In one embodiment the nucleic acid label comprises a connector molecule, which connector molecule is able to interact with a component on the linker and/or binding molecule of the detection molecule. In one embodiment the connector molecule is biotin or avidin. In one embodiment the linker comprises streptavidin to which the label binds via its biotin or avidin connector molecule.

In one embodiment the nucleic acid label comprises a random nucleotide region. This random nt region is a potential tool for detecting label contaminants. A random nt region of the invention in one embodiment comprises from 3-20 nucleotides, such as 3, 4, 5, 6, 7, 8, 9, 10, 11, 12, 13, 1 4, 1 5, 16, 17, 18, 19 or 20 nt.

In some embodiments, the different labels used in an experiment possess the same amplification properties and share common primer regions: Common primer regions together with shared amplification properties will ensure that all labels that are present after cellular interaction and sorting are amplified equally whereby no sequences will be biased due to the sequencing reaction.

With identical primer regions on differing labels there is an inherent risk of contaminating one label with another— especially following amplification reactions. To be able to trace potential contaminants a short 'random nucleotide region' can be included in the nucleic acid label. Since the random nucleotide region is unique for each label, it will be possible to inspect the sequencing data and see whether numerous reads of a given label is present. I.e. the random nucleotide region is a clonality control region. In one embodiment the random nucleotide region consist of 2-20 nucleic acids; such as 2, 3, 4, 5, 6, 7, 8, 9, 10, 11, 12, 13, 14, 15, 16, 17, 18, 19 or 20 nucleic acids. A random nucleotide region consisting of 6 nucleotides may be denoted 'N6' herein, and so forth.

In one embodiment the nucleic acid label comprises one or more stability-increasing components (such as HEG or TEG)

The label is preferably stable when mixing with cells: as this may expose the label to nuclease digestion. A measure to minimize this may be to add modifications in the form of hexaethylene glycol (HEG) or TEG at one or both ends of the oligonucleotide label.

Additionally stability can be accounted for in the buffers applied by adding constituents that exert a protective effect towards the oligo-nucleotides, e.g herring DNA and EDTA In one embodiment the nucleic acid label comprises a sample identifying sequence. To be able to analyze more than a single sample in each sequencing reaction the nucleic acid labels may be appointed an additional recognition feature, namely a sample identifying sequence. The sample identifying sequence is not a part of the initial design of the label, but will be appointed after cellular interaction and sorting via primers in a PCR—thus all cells originating from the same sample, will have the same sample identification sequence. In one embodiment the sample identifying sequence is a short sequence, consisting of 2-20 nucleic acids; such as 2, 3, 4, 5, 6, 7, 8, 9, 10, 11, 12, 13, 14, 15, 16, 17, 18, 19 or 20 nucleic acids. The sample identifying sequence may be attached to a primer, such as the forward primer.

The nucleic acid label is in one embodiment '1 oligo system' comprising a forward primer, a barcode region and a reverse primer.

The nucleic acid label is in one embodiment a '2 oligo system' with two sequences, the first comprising a forward primer, a barcode region and a annealing region; and the second comprising an annealing region, a barcode region and a reverse primer.

Peptide Label

In one embodiment the label, or the coding label, is a peptide label comprising a stretch of consecutive amino acid residues. This is the 'coding region' the identity of which can be determined.

In one embodiment the peptide label comprises or consists of a defined number of consecutive amino acids. It follows that the nucleic acid label in one embodiment comprises 2 or more consecutive amino acids, such as 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, 20-21, 21-22, 22-23, 23-24, 24-25, 25-26, 26-27, 27-28, 28-29, 29-30, 30-31, 31-32, 32-33, 33-34, 34-35, 35-36, 36-37, 37-38, 38-39, 39-40, 40-45, 45-50, 50-55, 55-60, 60-65, 65-70, 70-75, 75-80, 80-85, 85-90, 90-95, 95-100, 100-110, 110-120, 120-130, 130-140, 140-150, 150-160, 160-170, 170-180, 180-190, 190-200, 200-225, 225-250, 250-275, 275-300, 300-350, 350-400, 400-450, 450-500, 500-600, 600-700, 700-800, 800-900, 900-1000, 1000-1500, 1500-2000, or more than 2000, consecutive amino acids.

In one embodiment the peptide label comprises a stretch of consecutive amino acid residues (coding region) and a protease cleavage site. The protease cleavage site is preferably located proximal to the linker that connects the label to the binding molecule.

When the detection molecule is brought into proximity of a protease, the peptide label is cleaved and the coding region released from the detection molecule. The sample cells may be precipitated and the supernatant can be analysed by mass spectrometry to determine the identity and amount of the labels that was released.

Proteases capable of cleaving the peptide labels may be coated on the surface of sample cells, for example by adding antibody-protease conjugates where the antibody recognizes a particular cell surface structure.

In one embodiment the peptide label comprises natural (or standard) amino acids. In another embodiment the peptide label comprises non-naturally occurring amino acids (non-proteinogenic or non-standard). In one embodiment the peptide label comprises standard and non-standard amino acids.

A natural amino acid is a naturally occurring amino acid existing in nature and being naturally incorporated into polypeptides (proteinogenic). They consist of the 20 genetically encoded amino acids Ala, Arg, Asn, Asp, Cys, Gln, Glu, Gly, His, Ile, Leu, Lys, Met, Phe, Pro, Ser, Tyr, Thr, Trp, Val, and 2 which are incorporated into proteins by unique synthetic mechanisms: Sec (selenocysteine, or U) and Pyl (pyrrolysine, O). These are all L-stereoisomers.

Aside from the 22 natural or standard amino acids, there are many other non-naturally occurring amino acids (non-proteinogenic or non-standard). They are either not found in proteins, or are not produced directly and in isolation by standard cellular machinery. Non-standard amino acids are usually formed through modifications to standard amino acids, such as post-translational modifications.

Any amino acids according to the present invention may be in the L- or D-configuration.

The standard and/or non-standard amino acids may be linked by peptide bonds to form a linear peptide chain.

The term peptide also embraces post-translational modifications introduced by chemical or enzyme-catalyzed reactions, as are known in the art. Also, functional equivalents may comprise chemical modifications such as ubiquitination, labeling (e.g., with radionuclides, various enzymes, etc.), pegylation (derivatization with polyethylene glycol), or by insertion (or substitution by chemical synthesis) of amino acids (amino acids) which do not normally occur in human proteins.

Protein post-translational modification (PTM) increases the functional diversity of the proteome by the covalent addition of functional groups or proteins, proteolytic cleavage of regulatory subunits or degradation of entire proteins. These modifications include phosphorylation, glycosylation, ubiquitination, nitrosylation, methylation, acetylation, lipidation (C-terminal glycosyl phosphatidylinositol (GPI) anchor, N-terminal myristoylation, S-myristoylation, S-prenylation), amidation, and proteolysis and influence almost all aspects of normal cell biology and pathogenesis.

Sterically similar compounds may be formulated to mimic the key portions of the peptide structure and that such compounds may also be used in the same manner as the peptides of the invention. This may be achieved by techniques of modelling and chemical designing known to those of skill in the art. For example, esterification and other alkylations may be employed to modify the amino terminus of e.g a di-arginine peptide backbone, to mimic a tetra peptide structure. It will be understood that all such sterically similar constructs fall within the scope of the present invention.

Peptides with N-terminal alkylations and C-terminal esterifications are also encompassed within the present invention. Functional equivalents also comprise glycosylated and covalent or aggregative conjugates formed with the same molecules, including dimers or unrelated chemical moieties. Such functional equivalents are prepared by linkage of functionalities to groups which are found in fragment including at any one or both of the N- and C-termini, by means known in the art.

Binding Molecules

A binding molecule is a molecule that specifically associates covalently or non-covalently with a structure belonging to or associated with an entity in a sample. The defined structure in sample bound by a binding molecule is also called the target structure or target of the binding molecule. A typical target for a binding molecule is a 'marker molecule', which marker molecule is specific for a given cell or cell type.

Example binding molecule include but is not limited to proteins, antibodies (monoclonal or polyclonal, derived from any species e.g. man, mouse, rat, rabbit, pig or camel, monkey or may be recombinant antibodies), antibody fragments, MHC multimers (including but not limited to MHC dextramers, MHC tetramers, MHC Pentamers, cells expressing MHC molecules, MHC-peptide molecules covalently or non-covalently attached to beads, streptactin or other molecule structures), scaffold molecules, ligands, small organic molecules, nucleic acids (e.g. DNA, RNA, PNA), polysaccharides, other polymers, Aptamers including nucleic acid aptamers and peptide aptamers, affimers, beads, cells, living cells, dead cells, naturally occurring cells, genetic modified cells, hybridoma cells, gene transfected cells, cell like structures (e.g. liposomes, micelles), multicomponent complexes comprising 2, 3, 4, 5, 6, 7, 8, or more binding molecule subunits, and supramolecular structures, or other molecules, cells or substances able to bind defined structure in sample.

A binding molecule is useful for detection of a given defined structure in sample if the binding molecule binds the defined structure with a certain affinity. In order to be specific the binding molecule has to have a binding affinity that is higher than the binding molecules binding affinity for other structures in sample.

When the detection molecule comprises two or more binding molecules, the binding molecule may be referred to as a binding molecule multimer. When the detection molecule comprises two or more binding molecules, wherein the binding molecules are MHC molecules or MHC complexes, the MHC complexes may be referred to as a MHC multimer.

Typical defined structures or targets to which the binding molecule associate include but is not limited to: surface receptors on cells (e.g. TCR, CD molecules, growth receptors, MHC complexes, mannose binding receptor, transporter proteins), other structures on the surface of cells (e.g. lipids, sugars, proteins), intracellular substances in cells (e.g. DNA, RNA, ribosomes, organelles, cytokines, transcription factors, cytoskeleton components, intracellular proteins, sugars), components in fluidics (e.g. antibodies, blood plates, serum proteins, sugars), structures in interstitial space in tissues ect.

A binding molecule may have a molecular weight of between 50 Da and several million Da. In some instances a very low molecular weight is preferred, such as a molecular weight of 50-250 Da, or 251-500 Da. In other cases a low molecular weight, e.g. 501-2000 Da, 2001-5000 Da, or 5001-10000 Da may be preferred. In yet other cases, a high molecular weight of the binding molecule is practical, and the molecular weight of the binding molecule may be 10001-50000 Da, 50001-200000 Da, or 200000-1000000 Da. Finally, multi-molecule structures, such as in cases where a number of different fluorescent proteins are ordered in an array by binding to specific regions in a template DNA, where the total binding molecule thus is 50000-200000 Da, 200001-100000, or 1000001-10000000 Da.

Examples of binding molecules and corresponding target molecules are given below:
I. Antibodies binding to membrane components on, or within cells; e.g. Polysaccharides, proteins, or lipid residues.
II. MHC multimers (e.g. MHC dextramers, MHC tetramers, MHC pentamers), optionally complexed with a specific peptide, binds to the T-cell receptor (TCR) on T-cells.
III. MHC multimers (e.g. MHC dextramers, MHC tetramers, MHC pentamers), complexed with a so-called nonsense peptide (i.e. a peptide that binds the MHC protein but expectably does not mediate efficient MHC complex-TCR interaction with any T-cell), are used as negative control for the specific binding of a specific MHC multimers to the cell.
IV. Binding molecules such as Propidium Iodide (PI) that stain DNA in cells, here the binding molecule and the label can optionally be the same molecule.
V. Binding molecules that stain DNA, and that is used to characterize the state of a cell (e.g. state of cell cycle), e.g. Draq 5, PI, or other DNA binding molecules.
VI. Binding molecules that bind specifically to incorporated molecules. An example is BrdU, which may be added to a cell which will incorporate BrdU into its DNA; by using anti-BrdU antibody, cells that have incorporated BrdU will be detected.
VII. Binding molecules such as hormones, or growth factors, that specifically interacts with a cellular component, such as the estrogen receptor with estrogen or the EGF receptor with EGF.
VIII. Introduction of modified nucleotides, amino acids, or vitamins into cells which incorporate these into cellular components that subsequently can be detected, by themselves (e.g. if they are radioactive, or fluoresce) or by their association with a detection molecule.

In one embodiment the binding molecule is an MHC or MHC like complex, such as CD1a, CD1b, CD1c, or CD1d in complex with a peptide, lipid, glycolipid or any other molecule that binds to CD1a, CD1b, CD1c, or CD1d, or such as MR1 in complex with any epitope that binds to the MR1 complex, or such as an empty CD1a, CD1b, CD1c, CD1d or MR1, i.e. without epitope bound.

In one embodiment the detection molecule is CD1, such as CD1 selected from the group consisting of CD1 CD1a, CD1b, CD1c, CD1d and CD1e.

CD1 (cluster of differentiation 1) is a family of glycoproteins expressed on the surface of various human antigen-presenting cells. They are related to the class I MHC molecules, and are involved in the presentation of lipid antigens to T cells.

In one embodiment the detection molecule is a MHC Class I-like proteins; such as MIC A, MIC B, CD1d, HLA E, HLA F, HLA G, HLA H, ULBP-1, ULBP-2, and ULBP-3.

In one embodiment the binding molecule of the invention comprises one peptide-major histocompatibility complex (pMHC) or MHC complex. In another embodiment the binding molecule of the invention comprises 2, 3, 4, 5, 6, 7, 8, 9, 10, 11, 12, 13, 14, 15, 16, 17, 18, 19, 20, such as 1-2, 2-3, 3-4, 4-5, 5-6, 6-7, 7-8, 8-9, 9-10, 10-11, 11-12, 12-13, 13-15, 15-16, 16-20, 20-21, 21-50, 50-100, 51-100, or more than 100 MHC complexes, such as peptide-MHC complexes.

In a particular embodiment the binding molecule of the detection molecule is an oligonucleotide, wherein said oligonucleotide preferably binds to DNA or RNA molecules inside a cell. Optionally, the identity of the detection molecule within a cell is determined by extending the oligonucleotide-binding molecule using a polymerase, in this way identifying the detection molecule as well as the RNA or DNA template to which it is attached.

The MHC multimer can be composed of MHC class I, class II, CD1 or other MHC-like molecules. Thus, when the term MHC multimers is used herein this includes all MHC-like molecules. The MHC multimer is formed through multimerization of peptide-MHC molecules via different backbones.

An aspect of the invention relates to a multimeric major histocompatibility complex (MHC) comprising
two or more MHC's linked by a backbone molecule; and
at least one nucleic acid molecule linked to said backbone, wherein said nucleic acid molecule comprises a central stretch of nucleic acids (barcode region) designed to be amplified by e.g. PCR.

Different types of backbones may be used. Thus, in an embodiment the backbone molecule is selected from the group consisting of polysaccharides, such as glucans such as dextran, a streptavidin or a streptavidin multimer. The skilled artisan may find other alternative backbones.

The MHC's may be coupled to the backbone by different means. Thus, in an embodiment the MHC's are coupled to the backbone through a streptavidin-biotin binding or a streptavidin-avidin binding. Again other binding moieties may be used. The specific binding may use specific couplings points. In another embodiment the MHC's are linked to the backbone via the MHC heavy chain.

The MHC consists of different elements, which may partly be expressed and purified from cell systems (such as the MHC heavy chain and the Beta-2-microglobulin element). Alternatively, the elements may be chemically synthesized. The specific peptide is preferably chemically synthesized.

All three elements are required for the generation of a stable MHC (complex). Thus, in an embodiment the MHC is artificially assembled.

The multimeric MHC may comprise different numbers of MHC's. Thus, in yet an embodiment the multimeric major histocompatibility complex (MHC) is composed of at least four MHC's, such as at least eight, such as at least ten, 2-30, 2-20, such as 2-10 or such as 4-10 MHC's.

In one embodiment there is provided a detection molecule comprising two or more MHC complexes and a multimerization domain, such as comprising 2 MHC complexes, such as 3 MHC complexes, for example 4 MHC complexes, such as 5 MHC complexes, for example 6 MHC complexes, such as 7 MHC complexes, for example 8 MHC complexes, such as 9 MHC complexes, for example 10 MHC complexes, such as 11 MHC complexes, for example 12 MHC complexes, such as 13 MHC complexes, for example 14 MHC complexes, such as 15 MHC complexes, for example 16 MHC complexes, such as 17 MHC complexes, for example 18 MHC complexes, such as 19 MHC complexes, for example 20 MHC complexes, such as 21 MHC complexes, for example 22 MHC complexes, such as 23 MHC complexes, for example 24 MHC complexes, such as 25 MHC complexes, for example 26 MHC complexes, such as 27 MHC complexes, for example 28 MHC complexes, such as 29 MHC complexes, for example 30 MHC complexes, such as more than 30 MHC complexes.

In one embodiment there is provided a detection molecule comprising two or more MHC complexes and a multimerization domain, such as 2-3 MHC complexes, for example 3-4 MHC complexes, such as 4-5 MHC complexes, for example 5-6 MHC complexes, such as 6-7 MHC complexes, for example 7-8 MHC complexes, such as 8-9 MHC complexes, for example 9-10 MHC complexes, such as 10-11 MHC complexes, for example 11-12 MHC complexes, such as 12-13 MHC complexes, for example 13-14 MHC complexes, such as 14-15 MHC complexes, for example 15-16 MHC complexes, such as 16-17 MHC complexes, for example 17-18 MHC complexes, such as 18-19 MHC complexes, for example 19-20 MHC complexes, such as 20-25 MHC complexes, for example 25-30 MHC complexes, such as 30-35 MHC complexes, for example 35-40 MHC complexes, such as 40-45 MHC complexes, for example 45-50 MHC complexes, such as 50-55 MHC complexes, for example 55-60 MHC complexes, such as 60-65 MHC complexes, for example 65-70 MHC complexes, such as 70-75 MHC complexes, for example 75-80 MHC complexes, such as 80-85 MHC complexes, for example 85-90 MHC complexes, such as 90-95 MHC complexes, for example 95-100 MHC complexes, such as 100-125 MHC complexes, for example 125-150 MHC complexes, such as 150-175 MHC complexes, for example 175-200 MHC complexes, such as more than 200 MHC complexes.

In one embodiment the detection molecule comprises 2-20 MHC complexes, for example 2-10 MHC complexes, such as 4-20 MHC complexes, for example 4-10 MHC complexes, such as 5-10 MHC complexes, for example 5-20 MHC complexes, such as 5-25 MHC complexes.

In one embodiment there is provided a detection molecule comprising two or more MHC complexes and a multimerization domain, and comprising one or more labels, such as DNA labels, as defined herein elsewhere.

Different types of MHC's may form part of the multimer. Thus, in an embodiment the MHC is selected from the group consisting of class I MHC, a class II MHC, a CD1, or a MHC-like molecule. For MHC class I the presenting peptide is a 9-11 mer peptide; for MHC class II, the presenting peptide is 12-18 mer peptides. For alternative MHC-molecules it may be fragments from lipids or gluco-molecules which are presented.

In one embodiment the binding molecule comprises a connector molecule, which connector molecule is able to interact with a component on the linker and/or label of the detection molecule. In one embodiment the connector molecule is biotin or avidin. In one embodiment the linker comprises streptavidin to which the binding molecule binds via its biotin or avidin connector molecule.

BM: MHC Complexes

In a preferred embodiment the binding molecule of the detection molecule of the present invention comprises one or more MHC complexes (or MHC molecules).

The present invention in one embodiment provides a detection molecule comprising a binding molecule (BM), a linker (Li) and a label (La), wherein the binding molecule comprises one or more MHC complexes.

The present invention in one embodiment provides a detection molecule comprising a binding molecule (BM), a linker (Li) and a label (La), wherein the binding molecule comprises one or more MHC complexes, and the label is a nucleic acid label, such as a DNA label.

The present invention in one embodiment provides a detection molecule comprising a binding molecule (BM), a linker (Li) and a label (La), wherein the binding molecule comprises one or more MHC complexes, the label is a nucleic acid label, such as a DNA label, and the linker is a multimerization domain (or carrier molecule, or backbone).

The present invention in one embodiment provides a detection molecule comprising a binding molecule (BM), a linker (Li) and a label (La), wherein the binding molecule comprises two or more MHC complexes, the linker is a dextran multimerization domain (also known as 'MHC dextramers'), and the label is a nucleic acid label, such as a DNA label.

The MHC as a binding molecule (MHC-BM) according to the present invention is described in more detail herein below. The MHC as a binding molecule according to the present invention in combination with some linkers is also disclosed in detail herein below.

Each embodiment wherein the binding molecule is a MHC complex can be combined individually with any of the herein disclosed further components of the detection molecules namely linker and label.

The present invention in one aspect refers to a detection molecule comprising a MHC monomer comprising a-b-P, or a MHC multimer comprising $(a-b-P)_n$, wherein $n>1$, wherein a and b together form a functional MHC protein capable of binding an antigenic peptide P, wherein (a-b-P) is a MHC-peptide complex formed when the antigenic peptide P binds to the functional MHC protein.

The present invention in another aspect refers to a MHC monomer comprising a-b-P, or a MHC multimer comprising $(a-b-P)_n$, wherein $n>1$, wherein a and b together form a functional MHC protein capable of binding an antigenic peptide P, wherein (a-b-P) is a MHC-peptide complex formed when the antigenic peptide P binds to the functional MHC protein, and wherein each MHC complex or MHC peptide complex of a MHC multimer is associated with one or more multimerization domains.

MHC monomers and MHC multimers comprising two or more MHC complexes and/or MHC peptide complexes of class 1 or class 2 MHC are covered by the present invention.

In another aspect the present invention is directed to a composition comprising a plurality of MHC monomers and/or MHC multimers according to the present invention, wherein the MHCs of the MHC multimers individually are identical or different, and a linker such as a carrier.

The present invention further relates to a method for detection of antigen-specific T cells, said method comprising the steps of 1) providing a detection molecule comprising a MHC multimer, 2) providing a population of antigen-specific T cells, and 3) detecting antigen-specific T cells specific for the peptide P of the MHC multimer.

In a further embodiment the present invention relates to a method for counting of antigen-specific T cells, said method comprising the steps of 1) providing a detection molecule comprising a MHC multimer, 2) providing a population of antigen-specific T cells, and 3) counting antigen-specific T cells specific for the peptide P of the MHC multimer.

The present invention also relates to a method for sorting of antigen-specific T cells, said method comprising the steps of 1) providing a detection molecule comprising a MHC multimer, 2) providing a population of antigen-specific T cells, and 3) sorting antigen-specific T cells specific for the peptide P of the MHC multimer.

In yet another embodiment the present invention relates to a method for isolation of antigen-specific T cells, said method comprising the steps of 1) providing a detection molecule comprising a MHC multimer, 2) providing a population of antigen-specific T cells, and 3) isolating antigen-specific T cells specific for the peptide P of the MHC multimer.

In a still further aspect there is provided a method for immune monitoring of one or more diseases comprising monitoring of antigen-specific T cells, said method comprising the steps of i) providing a detection molecule comprising a MHC monomer or MHC multimer or individual components thereof according to the present invention, ii) providing a population of antigen-specific T cells or individual antigen-specific T cells, and iii) measuring the number, activity or state and/or presence of antigen-specific of T cells specific for the peptide P of the said MHC monomer or MHC multimer, thereby immune monitoring said one or more diseases.

In one aspect, the present invention is directed to MHC complexes comprising a linker which is a multimerization domain, preferably comprising a carrier molecule and/or a scaffold.

There is also provided a MHC multimer comprising 2 or more MHC-peptide complexes and a multimerization domain to which the 2 or more MHC-peptide complexes are associated. The MHC multimer can generally be formed by association of the 2 or more MHC complexes with the multimerization domain to which the 2 or more MHC complexes are capable of associating.

The multimerization domain can be a scaffold associated with one or more MHC complexes, or a carrier associated with one or more, preferably more than one, MHC complex(es), or a carrier associated with a plurality of scaffolds each associated with one or more MHC complexes, such as 2 MHC complexes, 3 MHC complexes, 4 MHC complexes, 5 MHC complexes or more than 5 MHC complexes. Accordingly, multimerization domain collectively refers to each and every of the above. It will be clear from the detailed description of the invention provided herein below when the multimerization domain refers to a scaffold or a carrier or a carrier comprising one or more scaffolds. It is understood that MHC complexes of the invention may or may not be loaded with antigenic peptides; when they are this may be referred to as a MHC-peptide complex.

Generally, when a multimerization domain comprising a carrier and/or a scaffold is present, the MHC complexes can be associated with this domain either directly or via one or more binding entities. The association can be covalent or non-covalent.

Accordingly, there is provided in one embodiment a MHC complex comprising one or more entities $(a-b-P)_n$, wherein a and b together form a functional MHC protein capable of binding a peptide P, and wherein (a-b-P) is the MHC-peptide complex formed when the peptide P binds to the functional MHC protein, said MHC complex optionally further comprising a multimerization domain comprising a carrier molecule and/or a scaffold. "MHC complex" refers to any MHC complex, including MHC monomers in the form of a single MHC complex and MHC multimers comprising a multimerization domain to which more than one MHC complex is associated. MHC complexes can be with or without peptide P included in the binding groove of the MHC.

When the invention is directed to complexes comprising a MHC multimer, i.e. a plurality of MHC complexes of the general composition $(a-b-P)_n$ associated with a multimerization domain, n is by definition more than 1, i.e. at least 2 or more. Accordingly, the term "MHC multimer" is used herein specifically to indicate that more than one MHC complex is associated with a multimerization domain, such as a scaffold or carrier or carrier comprising one or more scaffolds. Accordingly, a single MHC complex can be associated with a scaffold or a carrier or a carrier comprising a scaffold and a MHC-multimer comprising 2 or more MHC complexes can be formed by association of the individual MHC complexes with a scaffold or a carrier or a carrier comprising one or more scaffolds each associated with one or more MHC complexes.

When the MHC complex comprises a multimerization domain to which the n MHC complexes are associated, the association can be a covalent linkage so that each or at least some of the n MHC complexes is covalently linked to the multimerization domain, or the association can be a non-covalent association so that each or at least some of the n MHC complexes are non-covalently associated with the multimerization domain.

The MHC complexes of the invention may be provided in non-soluble or soluble form, depending on the intended application.

Effective methods to produce a variety of MHC complexes comprising highly polymorphic human HLA encoded proteins makes it possible to perform advanced analyses of complex immune responses, which may comprise a variety of peptide epitope specific T-cell clones.

One of the benefits of the MHC complexes of the present invention is that the MHC complexes overcome low intrinsic affinities of monomer ligands and counter receptors. The MHC complexes have a large variety of applications that include targeting of high affinity receptors (e.g. hormone peptide receptors for insulin) on target cells. Taken together poly-ligand binding to target cells has numerous practical, clinical and scientifically uses.

Thus, the present invention provides MHC complexes which present mono-valent or multi-valent binding sites for MHC-peptide recognising cells, such as MHC complexes optionally comprising a multimerization domain, such as a scaffold or a carrier molecule, which multimerization domain have attached thereto, directly or indirectly via one or more connectors, covalently or non-covalently, one or more MHC complexes. "One or more" as used herein is intended to include one as well as a plurality, such as at least 2. This applies i.a. to the MHC complexes and to the binding entities of the multimerization domain. The scaffold or carrier molecule may thus have attached thereto a MHC complex or a plurality of such MHC complexes, and/or a connector or a plurality of connectors.

In one preferred embodiment the MHC multimer is between 50,000 Da and 1,000,000 Da, such as from 50,000 Da to 980,000; for example from 50,000 Da to 960,000; such as from 50,000 Da to 940,000; for example from 50,000 Da to 920,000; such as from 50,000 Da to 900,000; for example from 50,000 Da to 880,000; such as from 50,000 Da to 860,000; for example from 50,000 Da to 840,000; such as from 50,000 Da to 820,000; for example from 50,000 Da to 800,000; such as from 50,000 Da to 780,000; for example from 50,000 Da to 760,000; such as from 50,000 Da to 740,000; for example from 50,000 Da to 720,000; such as from 50,000 Da to 700,000; for example from 50,000 Da to 680,000; such as from 50,000 Da to 660,000; for example from 50,000 Da to 640,000; such as from 50,000 Da to 620,000; for example from 50,000 Da to 600,000; such as from 50,000 Da to 580,000; for example from 50,000 Da to 560,000; such as from 50,000 Da to 540,000; for example from 50,000 Da to 520,000; such as from 50,000 Da to 500,000; for example from 50,000 Da to 480,000; such as from 50,000 Da to 460,000; for example from 50,000 Da to 440,000; such as from 50,000 Da to 420,000; for example from 50,000 Da to 400,000; such as from 50,000 Da to 380,000; for example from 50,000 Da to 360,000; such as from 50,000 Da to 340,000; for example from 50,000 Da to 320,000; such as from 50,000 Da to 300,000; for example from 50,000 Da to 280,000; such as from 50,000 Da to 260,000; for example from 50,000 Da to 240,000; such as from 50,000 Da to 220,000; for example from 50,000 Da to 200,000; such as from 50,000 Da to 180,000; for example from 50,000 Da to 160,000; such as from 50,000 Da to 140,000; for example from 50,000 Da to 120,000; such as from 50,000 Da to 100,000; for example from 50,000 Da to 80,000; such as from 50,000 Da to 60,000; such as from 100,000 Da to 980,000; for example from 100,000 Da to 960,000; such as from 100,000 Da to 940,000; for example from 100,000 Da to 920,000; such as from 100,000 Da to 900,000; for example from 100,000 Da to 880,000; such as from 100,000 Da to 860,000; for example from 100,000 Da to 840,000; such as from 100,000 Da to 820,000; for example from 100,000 Da to 800,000; such as from 100,000 Da to 780,000; for example from 100,000 Da to 760,000; such as from 100,000 Da to 740,000; for example from 100,000 Da to 720,000; such as from 100,000 Da to 700,000; for example from 100,000 Da to 680,000; such as from 100,000 Da to 660,000; for example from 100,000 Da to 640,000; such as from 100,000 Da to 620,000; for example from 100,000 Da to 600,000; such as from 100,000 Da to 580,000; for example from 100,000 Da to 560,000; such as from 100,000 Da to 540,000; for example from 100,000 Da to 520,000; such as from 100,000 Da to 500,000; for example from 100,000 Da to 480,000; such as from 100,000 Da to 460,000; for example from 100,000 Da to 440,000; such as from 100,000 Da to 420,000; for example from 100,000 Da to 400,000; such as from 100,000 Da to 380,000; for example from 100,000 Da to 360,000; such as from 100,000 Da to 340,000; for example from 100,000 Da to 320,000; such as from 100,000 Da to 300,000; for example from 100,000 Da to 280,000; such as from 100,000 Da to 260,000; for example from 100,000 Da to 240,000; such as from 100,000 Da to 220,000; for example from 100,000 Da to 200,000; such as from 100,000 Da to 180,000; for example from 100,000 Da to 160,000; such as from 100,000 Da to 140,000; for example from 100,000 Da to 120,000; such as from 150,000 Da to 980,000; for example from 150,000 Da to 960,000; such as from 150,000 Da to 940,000; for example from 150,000 Da to 920,000; such as from 150,000 Da to 900,000; for example from 150,000 Da to 880,000; such as from 150,000 Da to 860,000; for example from 150,000 Da to 840,000; such as from 150,000 Da to 820,000; for example from 150,000 Da to 800,000; such as from 150,000 Da to 780,000; for example from 150,000 Da to 760,000; such as from 150,000 Da to 740,000; for example from 150,000 Da to 720,000; such as from 150,000 Da to 700,000; for example from 150,000 Da to 680,000; such as from 150,000 Da to 660,000; for example from 150,000 Da to 640,000; such as from 150,000 Da to 620,000; for example from 150,000 Da to 600,000; such as from 150,000 Da to 580,000; for example from 150,000 Da to 560,000; such as from 150,000 Da to 540,000; for example from 150,000 Da to 520,000; such as from 150,000 Da to 500,000; for example from 150,000 Da to 480,000; such as from 150,000 Da to 460,000; for example from 150,000 Da to 440,000; such as from 150,000 Da to 420,000; for example from 150,000 Da to 400,000; such as from 150,000 Da to 380,000; for example from 150,000 Da to 360,000; such as from 150,000 Da to 340,000; for example from 150,000 Da to 320,000; such as from 150,000 Da to 300,000; for example from 150,000 Da to 280,000; such as from 150,000 Da to 260,000; for example from 150,000 Da to 240,000; such as from 150,000 Da to 220,000; for example from 150,000 Da to 200,000; such as from 150,000 Da to 180,000; for example from 150,000 Da to 160,000.

In another preferred embodiment the MHC multimer is between 1,000,000 Da and 3,000,000 Da, such as from 1,000,000 Da to 2,800,000; for example from 1,000,000 Da to 2,600,000; such as from 1,000,000 Da to 2,400,000; for example from 1,000,000 Da to 2,200,000; such as from 1,000,000 Da to 2,000,000; for example from 1,000,000 Da to 1,800,000; such as from 1,000,000 Da to 1,600,000; for example from 1,000,000 Da to 1,400,000.

Number of MHC Complexes Per Multimer

A non-exhaustive list of possible MHC mono- and multimers illustrates the possibilities. 'n' indicates the number of MHC complexes comprised in the multimer:
- a) n=1, Monomers
- b) n=2, Dimers, multimerization can be based on IgG scaffold, streptavidin with two MHC's, coiled-coil dimerization e.g. Fos.Jun dimerization
- c) n=3, Trimers, multimerization can be based on streptavidin as scaffold with three MHC's, TNFalpha-MHC hybrids, triplex DNA-MHC konjugates or other trimer structures
- d) n=4, Tetramers, multimerization can be based on streptavidin with all four binding sites occupied by MHC molecules or based on dimeric IgA
- e) n=5, Pentamers, multimerization can take place around a pentameric coil-coil structure
- f) n=6, Hexamers
- g) n=7, Heptamers
- h) n=8-12, Octa-dodecamers, multimerization can take place using Streptactin
- i) n=10, Decamers, multimerization can take place using IgM
- j) 1<n<100, Dextramers, as multimerization domain polymers such as polypeptide, polysaccharides and Dextrans can be used.
- k) 1<n<1000, Multimerization can make use of dendritic cells (DC), antigen-presenting cells (APC), micelles, liposomes, beads, surfaces e.g. microtiterplate, tubes, microarray devices, micro-fluidic systems
- l) 1<n, n in billions or trillions or higher, multimerization take place on beads, and surfaces e.g. microtiterplate, tubes, microarray devices, micro-fluidic systems MHC multimers thus include MHC-dimers, MHC-trimers, MHC-tetramers, MHC-pentamers, MHC-hexamers, as well as organic molecules, cells, membranes, polymers and particles that comprise two or more MHC-peptide complexes. Example organic molecule-based multimers include functionalized cyclic structures such as benzene rings where e.g. a benzene ring is functionalized and covalently linked to e.g. three MHC complexes; example cell-based MHC multimers include dendritic cells and antigen presenting cells (APCs); example membrane-based MHC multimers include liposomes and micelles carrying MHC-peptide complexes in their membranes; example polymer-based MHC multimers include MHC-dextramers (dextran to which a number of MHC-peptide complexes are covalently or non-covalently attached) and example particles include beads or other solid supports with MHC complexes immobilized on the surface. Obviously, any kind of multimerization domain can be used, including any kind of cell, polymer, protein or other molecular structure, or particles and solid supports.

More than 600 MHC alleles (class 1 and 2) are known in humans; for many of these, the peptide binding characteristics are known. The frequency of the different HLA alleles varies considerably, also between different ethnic groups. Thus it is of outmost importance to carefully select the MHC alleles that corresponds to the population that one wish to study.

Any of the components of a MHC complex can be of any of the below mentioned origins. The list is non-exhaustive. A complete list would encompass all Chordate species. By origin is meant that the sequence is identical or highly homologous to a naturally occurring sequence of the specific species.

List of origins: Human, Mouse, Primate (Chimpanzee, Gorilla, Orang Utan), Monkey (Macaques), Porcine (Swine/Pig), Bovine (Cattle/Antelopes), Equine (Horse), Camelides (Camels), Ruminants (Deears), Canine (Dog), Feline (Cat), Bird (Chicken, Turkey), Fish, Reptiles, Amphibians.

In one embodiment the binding molecule is a MHC class I complex of HLA-type A.

In one embodiment the binding molecule is a MHC class I complex of HLA-type B.

In one embodiment the binding molecule is a MHC class I complex of HLA-type C.

In one embodiment the binding molecules is a MHC class I complex, of supertype HLA-A1 (eg. HLA-A*0101, HLA-A*2601, HLA-A*2602, HLA-A2603, HLA-A*3002, HLA-A*3003, HLA-A*3004, HLA-A*3201).

In one embodiment the binding molecules is a MHC class I complex, of supertype HLA-A01 A03 (eg. HLA-A*3001).

In one embodiment the binding molecules is a MHC class I complex, of supertype HLA-A01 A024 (eg. HLA-A*2902).

In one embodiment the binding molecules is a MHC class I complex, of supertype HLA-A2 (eg. HLA-A*0201, HLA-A*0202, HLA-A*0203, HLA-A*0204, HLA-A*0205, HLA-A*0206, HLA-A*0207, HLA-A*0214, HLA-A*0217, HLA-A*6802, HLA-A*6901).

In one embodiment the binding molecules is a MHC class I complex, of supertype HLA-A3 (eg. HLA-A*0301, HLA-A*1101, HLA-A*3101, HLA-A*3301, HLA-A*3303, HLA-A*6601, HLA-A*6801, HLA-A*7401).

In one embodiment the binding molecules is a MHC class I complex, of supertype HLA-A24 (eg. HLA-A*2301, HLA-A*2402).

In one embodiment the binding molecules is a MHC class I complex, of supertype HLA-B7 (eg. HLA-B*0702, HLA-B*0703, HLA-B*0705, HLA B*1508, HLA-B*3501, HLA-B*3503, HLA-B*4201, HLA-B*5101, HLA-B*5102, HLA-B*5103, HLA-B*5301, HLA-B*5401, HLA-B*5501, HLA-B*5502, HLA-B*5601, HLA-B*6701, HLA-B*7801).

In one embodiment the binding molecules is a MHC class I complex, of supertype HLA-B8 (eg. HLA-B*0801, HLA-B*0802).

In one embodiment the binding molecules is a MHC class I complex, of supertype HLA-B27 (eg. HLA-B*1402, HLA-B*1503, HLA-B*1509, HLA-B*1510, HLA-B*1518, HLA-B*2702, HLA-B*2703, HLA-B*2704, HLA-B*2705, HLA-B*2706, HLA-B*2707, HLA-B*2708, HLA-B*2709, HLA-B*3801, HLA-B*3901, HLA-B*3902, HLA-B*3909, HLA-B*4801, HLA-B*7301).

In one embodiment the binding molecules is a MHC class I complex, of supertype HLA-B44 (eg. HLA-B*1801, HLA-B*3701, HLA-B*4001, HLA-B*4002, HLA-B*4006, HLA-B*4402, HLA-B*4403, HLA-B*4501).

In one embodiment the binding molecules is a MHC class I complex, of supertype HLA-B58 (eg. HLA-B*1516, HLA-B*1517, HLA-B*5701, HLA-B*5702, HLA-B*5801, HLA-B*5802).

In one embodiment the binding molecules is a MHC class I complex, of supertype HLA-B62 (eg. HLA-B*1501, HLA-B*1502, HLA-B*1512, HLA-B*1513, HLA-B*4601, HLA-B*5201).

In one embodiment the binding molecules is a MHC class I complex, of supertype HLA Cw 1-8 (eg. HLA-C*01, HLA-C*02, HLA-C*03, HLA-C*04, HLA-C*05, HLA-C*06, HLA-C*07, HLA-C*08).

In one embodiment the binding molecule is a MHC class I complex, which binds peptides with an acidic amino acid on $3^{rd}$ position (eg. HLA-A*0101, HLA-A*2601, HLA-A*2602, HLA-A*2603, HLA-A*3002, HLA-A*3003, HLA-A*3004, HLA-A*3201).

In one embodiment the binding molecule is a MHC class I complex, which binds peptides with a hydrophobic amino acid on $9^{th}$ position (eg. HLA-A*0201 . . . 0207, A*0214, A*0217, A*6802, A*6901, HLA-B*1516, B*1517, B*5701, B*5702, B*5801, B*5802).

In one embodiment the binding molecule is a MHC class I complex, which binds peptides with a Basic amino acid on $9^{th}$ position (eg. HLA-A*0301, HLA-A*1101, HLA-A*3101, HLA-A*3301, HLA-A*3303, HLA-A*6601, HLA-A*6801, HLA-A*7401).

In one embodiment the binding molecule is a MHC class I complex, which binds peptides with a Tyrosine amino acid on $2^{nd}$ position (eg. HLA-A*2301, HLA-A*2402).

In one embodiment the binding molecule is a MHC class I complex, which binds peptides with a Proline amino acid on $2^{nd}$ position (eg. HLA-B*0702, HLA-B*0703, HLA-B*0705, HLA-B*1508, HLA-B*3501, HLA-B*3503, HLA-B*4201, HLA-B*5101, HLA-B*5102, HLA-B*5103, HLA-B*5301, HLA-B*5401, HLA-B*5501, HLA-B*5502, HLA-B*5601, HLA-B*6701, HLA-B*7801).

In one embodiment the binding molecule is a MHC class I complex, which binds peptides with a Lysine amino acid on $3^{rd}$ and $5^{th}$ position (eg. HLA-B*0801, B*0802).

In one embodiment the binding molecule is a MHC class I complex, which binds peptides with a Arginine amino acid on $2^{nd}$ position (eg. HLA-B*1402, HLA-B*1503, HLA-B*1509, HLA-B*1510, HLA-B*1518, HLA-B*2702, HLA-B*2703, HLA-B*2704, HLA-B*2705, HLA-B*2706, HLA-B*2707, HLA-B*2708, HLA-B*2709, HLA-B*3801, HLA-B*3901, HLA-B*3902, HLA-B*3909, HLA-B*4801, HLA-B*7301).

In one embodiment the binding molecule is a MHC class I complex, which binds peptides with a Glutamic acid amino acid on $2^{nd}$ position (eg. HLA-B*1801, HLA-B*3701, HLA-B*4001, HLA-B*4002, HLA-B*4006, HLA-B*4402, HLA-B*4403, HLA-B*4501).

In one embodiment the binding molecule is a MHC class I complex, which binds peptides with a Tyrosine amino acid on $9^{th}$ position (eg. HLA-B*1501, HLA-B*1502, HLA-B*1512, HLA-B*1513, HLA-B*4601, HLA-B*5201).

In one embodiment the binding molecule is a MHC class I complex, which in the B pocket selectively binds small or aliphatic peptides (eg. HLA-A*0101, HLA-A*2601, HLA-A*2602, HLA-A*2603, HLA-A*3002, HLA-A*3003, HLA-A*3004, HLA-A*3201, HLA-A*0201, HLA-A*0202, HLA-A*0203, HLA-A*0204, HLA-A*0205, HLA-A*0206, HLA-A*0207, HLA-A*0214, HLA-A*0217, HLA-A*6802, HLA-A*6901, HLA-A*0301, HLA-A*1101, HLA-A*3101, HLA-A*3301, HLA-A*3303, HLA-A*6601, HLA-A*6801, HLA-A*7401).

In one embodiment the binding molecule is a MHC class I complex, which in the F pocket selectively binds aliphatic peptides (eg. HLA-A*0101, HLA-A*2601 . . . 2603, HLA-A*3002, HLA-A*3003, HLA-A*3004, HLA-A*3201, HLA-A*0201, HLA-A*0202, HLA-A*0203, HLA-A*0204, HLA-A*0205, HLA-A*0206, HLA-A*0207, HLA-A*0214, HLA-A*0217, HLA-A*6802, HLA-A*6901, HLA-A*0301, HLA-A*1101, HLA-A*3101, HLA-A*3301, HLA-A*3303, HLA-A*6601, HLA-A*6801, HLA-A*7401, HLA-B*1501, HLA-B*1502, HLA-B*1512, HLA-B*1513, HLA-B*4601, HLA-B*5201).

In one embodiment the binding molecule is a MHC class II complex, of HLA-type DP.

In one embodiment the binding molecule is a MHC class II complex, of HLA-type DQ.

In one embodiment the binding molecule is a MHC class II complex, of HLA-type DR.

In one embodiment the binding molecule is a MHC class II complex of HLA supertype DR1 (eg. HLA-DR1*0101, HLA-DR*0102).

In one embodiment the binding molecule is a MHC class II complex of HLA supertype DR3 (eg. HLA-DR1*1107, HLA-DR*0301, HLA-DR*0305, HLA-DR*0306, HLA-DR*0309).

In one embodiment the binding molecule is a MHC class II complex of HLA supertype DR4 (eg. HLA-DR1*0401, HLA-DR*0402, HLA-DR*0404, HLA-DR*0405, HLA-DR*0408, HLA-DR*0410, HLA-DR*0426).

In one embodiment the binding molecule is a MHC class II complex of HLA supertype DR7 (eg. HLA-DR1*0701).

In one embodiment the binding molecule is a MHC class II complex of HLA supertype DR8 (eg. HLA-DR1*0801, HLA-DR*0802, HLA-DR*0804, HLA-DR*0806, HLA-DR*0813, HLA-DR*0817).

In one embodiment the binding molecule is a MHC class II complex of HLA supertype DR11 (eg. HLA-DR1*1101, HLA-DR*1104, HLA-DR*1128, HLA-DR*1307, HLA-DR*1321).

In one embodiment the binding molecule is a MHC class II complex of HLA supertype DR13 (eg. HLA-DR1*1102, HLA-DR*1114, HLA-DR*1120, HLA-DR*1301, HLA-DR*1304, HLA-DR*1322).

In one embodiment the binding molecule is a MHC class II complex of HLA supertype DR15 (eg. HLA-DR1*1501, HLA-DR*1502).

In one embodiment the binding molecule is a MHC class II complex of HLA supertype DR51 (eg. HLA-DR5*0101).

Generation of MHC Multimers

Different approaches to the generation of various types of MHC multimers are described in U.S. Pat. No. 5,635,363 (Altmann et al.), patent application WO 02/072631 A2 (Winther et al.), patent application WO 99/42597, US patent 2004209295, U.S. Pat. No. 5,635,363.In brief, MHC multimers can be generated by first expressing and purifying the individual protein components of the MHC protein, and then combining the MHC protein components and the peptide, to form the MHC-peptide complex. Then an appropriate number of MHC-peptide complexes are linked together by covalent or non-covalent bonds to a multimerization domain. This can be done by chemical reactions between reactive groups of the multimerization domain (e.g. vinyl sulfone functionalities on a dextran polymer) and reactive groups on the MHC protein (e.g. amino groups on the protein surface), or by non-covalent interaction between a part of the MHC protein (e.g. a biotinylated peptide component) and the multimerization domain (e.g. four binding sites for biotin on the strepavidin tetrameric protein). As an alternative, the MHC multimer can be formed by the non-covalent association of amino acid helices fused to one component of the MHC protein, to form a pentameric MHC multimer, held together by five helices in a coiled-coil structure making up the multimerization domain.

Appropriate chemical reactions for the covalent coupling of MHC and the multimerization domain include nucleophilic substitution by activation of electrophiles (e.g. acylation such as amide formation, pyrazolone formation, isoxazolone formation; alkylation; vinylation; disulfide formation), addition to carbon-hetero multiple bonds (e.g. alkene formation by reaction of phosphonates with aldehydes or ketones; arylation; alkylation of arenes/hetarenes by reaction with alkyl boronates or enolethers), nucleophilic substitution using activation of nucleophiles (e.g. condensations; alkylation of aliphatic halides or tosylates with enolethers or enamines), and cycloadditions.

Appropriate molecules, capable of providing non-covalent interactions between the multimerization domain and the MHC-peptide complex, involve the following molecule pairs and molecules: streptavidin/biotin, avidin/biotin, antibody/antigen, DNA/DNA, DNA/PNA, DNA/RNA, PNA/PNA, LNA/DNA, leucine zipper e.g. Fos/Jun, IgG dimeric protein, IgM multivalent protein, acid/base coiled-coil helices, chelate/metal ion-bound chelate, streptavidin (SA) and avidin and derivatives thereof, biotin, immunoglobulins, antibodies (monoclonal, polyclonal, and recombinant), antibody fragments and derivatives thereof, leucine zipper domain of AP-1 (jun and fos), hexa-his (metal chelate moiety), hexa-hat GST (glutathione S-transferase) gluta-thione affinity, Calmodulin-binding peptide (CBP), Strep-tag, Cellulose Binding Domain, Maltose Binding Protein, S-Peptide Tag, Chitin Binding Tag, Immuno-reactive Epitopes, Epitope Tags, E2Tag, HA Epitope Tag, Myc Epitope, FLAG Epitope, AU1 and AU5 Epitopes, Glu-Glu Epitope, KT3 Epitope, IRS Epitope, Btag Epitope, Protein Kinase-C Epitope, VSV Epitope, lectins that mediate binding to a diversity of compounds, including carbohydrates, lipids and proteins, e.g. Con A (*Canavalia ensiformis*) or WGA (wheat germ agglutinin) and tetranectin or Protein A or G (antibody affinity). Combinations of such binding entities are also comprised. In particular, when the MHC complex is tagged, the binding entity can be an "anti-tag". By "anti-tag" is meant an antibody binding to the tag and any other molecule capable of binding to such tag.

Generation of Components of MHC

When employing MHC multimers for diagnostic purposes, it is preferable to use a MHC allele that corresponds to the tissue type of the person or animal to be diagnosed. Once the MHC allele has been chosen, a peptide derived from the antigenic protein may be chosen. The choice will depend on factors such as known or expected binding affinity of the MHC protein and the various possible peptide fragments that may be derived from the full sequence of the antigenic peptide, and will depend on the expected or known binding affinity and specificity of the MHC-peptide complex for the TCR. Preferably, the affinity of the peptide for the MHC molecule, and the affinity and specificity of the MHC-peptide complex for the TCR, should be high.

Similar considerations apply to the choice of MHC allele and peptide for therapeutic and vaccine purposes. In addition, for some of these applications the effect of binding the MHC multimer to the TCR is also important. Thus, in these cases the effect on the T-cell's general state must be considered, e.g. it must be decided whether the desired end result is apoptosis or proliferation of the T-cell.

Likewise, it must be decided whether stability is important. For some applications low stability may be an advantage, e.g. when a short-term effect is desired; in other instances, a long-term effect is desired and MHC multimers of high stability is desired. Stabilities of the MHC protein and of the MHC-peptide complex may be modified as described elsewhere herein.

Finally, modifications to the protein structure may be advantageous for some diagnostics purposes, because of e.g. increased stability, while in for vaccine purposes modifications to the MHC protein structure may induce undesired allergenic responses.

The generation of protein chains of MHC as well as the Stabilization of MHC complexes is thoroughly explained in WO 2009/106073, which is incorporated herein by reference in its entirety.

Other TCR Binding Molecules

MHC I and MHC II complexes bind to TCRs. However, other molecules also bind TCR. Some TCR-binding molecules are described in the following.

In one embodiment the binding molecule is an anti-target-molecule capable of binding TCR.

In one embodiment the anti-target-molecule capable of binding TCR is a molecule that has homology to the classical MHC molecules and therefore potentially could be TCR binding molecules. These other TCR binding or MHC like molecules include:

Non-Classical MHC Complexes and Other MHC-Like Molecules

Non-classical MHC complexes include protein products of MHC Ib and MHC IIb genes. MHC Ib genes encode β2m-associated cell-surface molecules but show little polymorphism in contrast to classical MHC class I genes. Protein products of MHC class Ib genes include HLA-E, HLA-G, HLA-F, HLA-H, MIC A, MIC B, ULBP-1, ULBP-2, ULBP-3 in humans and H2-M, H2-Q, H2-T and Rae1 in mice.

Non-classical MHC II molecules (protein products of MHC IIb genes) include HLA-DM, HLA-DO in humans and H2-DM and H2-DO in mice that are involved in regulation of peptide loading into MHC II molecules.

Another MHC-like molecule of special interest is the MHC I-like molecule CD1. CD1 is similar to MHC I molecules in its organization of subunits and association with β2m but presents glycolipids and lipids instead of peptides.

Artificial Molecules Capable of Binding Specific TCRs

Of special interest are antibodies that bind TCRs. Antibodies herein include full length antibodies of isotype IgG, IgM, IgE, IgA and truncated versions of these, antibody fragments like Fab fragments and scFv. Antibodies also include antibodies of antibody fragments displayed on various supramolecular structures or solid supports, including filamentous phages, yeast, mammalian cells, fungi, artificial cells or micelles, and beads with various surface chemistries.

Peptide Binding TCR

Another embodiment of special interest is peptides that bind TCRs. Peptides herein include peptides composed of natural, non-natural and/or chemically modified amino acids with a length of 8-20 amino acid. The peptides could also be longer than 20 amino acids or shorter than 8 amino acids. The peptides can or cannot have a defined tertiary structure.

Aptamers

Aptamers are another preferred group of TCR ligands. Aptamers are herein understood as natural nucleic acids (e.g. RNA and DNA) or unnatural nucleic acids (e.g. PNA, LNA, morpholinos) capable of binding TCR. The aptamer molecules consist of natural or modified nucleotides in various lengths.

Other TCR-binding molecules can be ankyrin repeat proteins or other repeat proteins, Avimers, or small chemical molecules, as long as they are capable of binding TCR with a dissociation constant smaller than $10^{-3}$ M.

BM: Anti-Target Molecules

In one embodiment the binding molecule is an anti-target-molecule capable of associating with, recognizing and/or binding to a predetermined target structure belonging to or associated with an entity/cell, e.g. in a sample. A typical target for a binding molecule is a 'marker molecule', which marker molecule is specific for a given cell or cell type.

Any binding molecule that is capable of specifically associating with, recognizing and/or binding to a predetermined target structure is encompassed within the present invention.

In one embodiment the binding molecule is an anti-target-molecule capable of binding a specific cell type.

In one embodiment the binding molecule is an anti-target-molecule capable of binding a specific cell type selected from the group consisting of immune cells, lymphocytes, monocytes, dendritic cells, T-cells, B-cells and NK cells.

In one embodiment the binding molecule is an anti-target-molecule capable of binding a specific cell type selected from the group consisting CD4+ T cells, CD8+ T cells, αβ T cells, invariant γδ T cells and antigen-specific T-cells.

In one embodiment the binding molecule is an anti-target-molecule capable of binding a cell comprising TCRs. In one embodiment the binding molecule is an anti-target-molecule capable of binding a cell comprising BCRs.

In one embodiment the binding molecule is an anti-target-molecule capable of binding a specific cancer cell.

In one embodiment the binding molecule is an anti-target-molecule capable of binding a target specifically associated with an organ selected from the group consisting of lymph nodes, kidney, liver, skin, brain, heart, muscles, bone marrow, skin, skeleton, lungs, the respiratory tract, spleen, thymus, pancreas, exocrine glands, bladder, endocrine glands, reproduction organs including the fallopian tubes, eye, ear, vascular system, the gastroinstestinal tract including small intestines, colon, rectum, canalis analis and prostate gland.

Anti-target-molecule is in one embodiment selected from antibodies, antibody mimetics, natural ligands, variants or fragments of natural ligands, synthetic ligands, agonists, antagonists, aptamers (including DNA aptamers, RNA aptamers and peptide aptamers), peptides, and artificial molecules capable of binding a specific target.

Peptide Aptamer

In one embodiment the binding molecule is an anti-target-molecule. In one embodiment the anti-target-molecule is a peptide aptamer, such as a peptide that bind a target. Peptides herein include peptides composed of natural, non-natural and/or chemically modified amino acids, in one embodiment with a length of 8-20 amino acid, such as 5-25 amino acids, for example 5-40 amino acids. The peptides can or cannot have a defined tertiary structure.

In one embodiment the binding molecule is a peptide of 1-100 amino acid residues without tertiary structure.

Nucleic Acid Aptamer

In one embodiment the binding molecule is an anti-target-molecule. In one embodiment the anti-target-molecule is a nucleic acid aptamer (or oligonucleotide aptamer, or simply 'oligonucleotide'). Nucleic acid aptamers are herein understood as natural nucleic acids (e.g. RNA and DNA) or artificial nucleic acids (e.g. PNA, LNA, morpholinos) capable of binding a target. The aptamer molecules consist of natural or modified nucleotides in various lengths.

Other target-binding molecules include ankyrin repeat proteins or other repeat proteins, Avimers, or small chemical molecules, as long as they are capable of binding the target with an acceptable dissociation constant such as smaller than $10^{-3}$ M.

Ligand

In one embodiment the binding molecule is an anti-target-molecule. In one embodiment the anti-target-molecule is a ligand capable of binding a target.

Antibodies

In one embodiment the binding molecule is an anti-target-molecule. In one embodiment anti-target-molecule is an antibody. In a preferred embodiment the anti-target-molecule is an antibody that selectively associates with, recognizes and/or binds to a predetermined target structure belonging to or associated with an entity/cell in a sample.

Immunoglobulins are a class of structurally related glycoproteins consisting of two pairs of polypeptide chains, one pair of light (L) low molecular weight chains and one pair of heavy (H) chains, all four inter-connected by disulfide bonds. The structure of immunoglobulins has been well characterized. Briefly, each heavy chain typically is comprised of a heavy chain variable region (VH) and a heavy chain constant region (CH) typically comprised of three domains, CH1, CH2, and CH3. Each light chain typically is comprised of a light chain variable region (VL) and a light chain constant region, typically comprised of one domain (CL). The VH and VL regions may be further subdivided into regions of hypervariability also termed complementarity determining regions (CDRs), interspersed with regions that are more conserved, termed framework regions (FRs).

The term "antibody" or "Ab" in the context of the present invention refers to an immunoglobulin molecule, a fragment of an immunoglobulin molecule, or a derivative of either thereof, which has the ability to specifically bind to an antigen under typical physiological conditions. The variable regions of the heavy and light chains of the immunoglobulin molecule contain a binding domain that interacts with an antigen. An antibody may also be multispecific, having specificities for two or more different epitopes, typically non-overlapping. Examples of multispecific antibodies include bispecific antibodies, diabodies, and similar antibody molecules. As indicated above, the term antibody herein, unless otherwise stated, includes fragments of an antibody that retain the ability to specifically bind to the antigen. The antigen-binding function of an antibody may be performed by fragments of a full-length antibody, e.g., Fab and F(ab')2 fragments. In the context of the present invention the term antibody, unless specified otherwise, includes polyclonal antibodies, monoclonal antibodies (mAbs), antibody-like polypeptides such as chimeric antibodies and humanized antibodies. An antibody as generated can possess any isotype. The term "epitope" means a protein determinant capable of specific binding to an antibody.

The terms "human antibody" include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The terms "monoclonal antibody" (mAb), refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. The human monoclonal antibodies may be produced by a hybridoma which includes a B cell obtained from a transgenic or transchromosomal non-human animal, such as a transgenic mouse, having a genome comprising a human heavy chain transgene and a light chain transgene, fused to an immortalized cell.

As used herein, "isotype" refers to the immunoglobulin class (for instance IgG1, IgG2, IgG3, IgG4, IgD, IgA, IgE, or IgM) that is encoded by heavy chain constant region genes. The term "full-length antibody" when used herein, refers to an antibody which contains all heavy and light chain constant and variable domains that are normally found in an antibody of that isotype.

Antibody Mimetics

In one embodiment the binding molecule is an anti-target-molecule. In one embodiment anti-target-molecule is an antibody mimetic. Antibody mimetics are organic compounds that, like antibodies, can specifically bind antigens, but that are not structurally related to antibodies.

Antibody mimetics include, but is not limited to, affibody molecules, affilins, affimers, affitins, alphabodies, anticalins, avimers, DARPins, fynomers, Kunitz domain peptides and monobodies.

Avimers (short for avidity multimers) are artificial proteins that are able to specifically bind to certain antigens via multiple binding sites. Avimers consist of two or more peptide sequences of 30 to 35 amino acids each, connected by linker peptides.

Targets of Binding Molecules

In one embodiment the binding molecule is an anti-target-molecule capable of associating with, recognizing and/or binding to a predetermined target structure belonging to or associated with an entity/cell in a sample.

In one embodiment the target for a binding molecule is a 'marker molecule', which marker molecule is specific for a given cell or cell type.

In one embodiment the target is an intracellular target.

In one embodiment the target is a cell-surface target.

In one embodiment the target is a membrane-associated target.

In one embodiment the target is a receptor.

In one embodiment the receptor is an intracellular receptor.

In one embodiment the receptor is a cell-surface receptor or membrane-associated receptor.

In one embodiment the target is a soluble receptor.

In one embodiment the target is a extracellular receptor.

In one embodiment the binding molecule is an anti-target-molecule capable of binding a target selected from the group consisting of CD1, CD1a, CD1b, CD1c, CD1d, and MR1.

In one embodiment the target is a T cell receptor.

In one embodiment the target is a B cell receptor.

In one embodiment the target is CD4.

In one embodiment the target is CD8.

In one embodiment the target is CD20.

In one embodiment the target of the binding molecule (anti-target molecule) binds a target selected from the group consisting of cancer cell markers, developmental markers, stem cell markers, cell cycle markers, proliferation markers, activation markers, hormones, hormone receptors, cluster of differentiation (CD), cytokines and cytokine receptors.

In one embodiment the cluster of differentiation is selected from a group consisting of CD1-10, CD10-20, CD20-30, CD30-40, CD40-50, CD50-100, CD100-200, CD200-300 and CD300-364.

In one embodiment the cancer cell marker is selected from a group consisting of HER2, CA125, Tyrosinase, Melanoma-associated antigen (MAGE), abnormal products of Ras or p53, Carcinoembryonic antigen, Muc-1, Epithelial tumor antigen, Carbonic Anhydrase, VEGFR, EGFR, TRAI and RANKL.

In one embodiment the stem cell marker is selected from a group consisting of Stro-1, CD146, CD105, CD44, c-kit, Oct4, Sox-2, Klf4, EphB, Nestin and TWIST-1.

In one embodiment the developmental cell marker is selected from a group consisting of Nanog, Oct4, Sox2, TEKT-1, NANOS, c-kit, Sox9, Notch, Msx1, Msx2 and Col1.

In one embodiment the cytokine is selected from a group consisting of TNFα, TNFβ, TNF, IFNα, IFNβ, IFNγ, IL-1, IL-2, IL-3, IL-4, IL-5, IL-6, IL-7, IL-8, IL-9, IL-10, IL-10-20, IL-20-30, IL-30, IL-31, IL-32, IL-33, IL-34, IL-35, IL-36, IL-37, IL-38, IL-39, IL-40, NFηB, chemokines including CC chemokines (CCL1-CCL-28), CXC chemokines (CXCL1-CXCL17) C chemokines (XCL-1 and -2) and CX3X chemokines (CX3CL1).

In one embodiment the proliferation marker is selected from a group consisting of CyclinA, CyclinB, PCNA, PC10, p53, Mdm2, Cyclin D, Cyclin E, Rb, ARF and HDM2.

In one embodiment the activation marker is selected from a group consisting of CD28, Tbet, Eomes, Blimp, Bcl-6, CD27, MHC-II, TNF, IFN, Fizz1, ARG1 and CCL22R.

In one embodiment the hormone is selected from a group consisting of estrogen, PTH, ADH, T3, ANP, Epinephrine, Norepinephrine, Cortisol, Corticosterone, Aldosterone, Progestin, EPO, Leptin, Insulin, Glucagon, T4, ACTH, FSH, oxytocin and Calcitriol.

In one embodiment the hormone receptor is selected from a group consisting of EstrogenR (ER), GLP-1R, Thyroid receptor, Leptin receptor, Epinephrine receptor, Insulin receptor and Glucagon receptor.

In one embodiment the intracellular marker is selected from a group consisting of Cyclins, Cytokines and organelle markers (for example Apg12, Syntaxin, PAF-46, Histones, Early endosome antigen, clathrin, tubulins, PAF49, FTCD).

In one embodiment the target of the binding molecule is selected from the group consisting of CD2, CD3, CD4, CD5, CD8, CD9, CD27, CD28, CD30, CD69, CD134 (OX40), CD137 (4-1BB), CD147, CDw150 (SLAM), CD152 (CTLA-4), CD153 (CD30L), CD40L (CD154), NKG2D, ICOS, HVEM, HLA Class II, PD-1, Fas (CD95), FasL, CD40, CD48, CD58, CD70, CD72, B7.1 (CD80), B7.2 (CD86), B7RP-1, B7-H3, PD-L1, PD-L2, CD134L, CD137L, ICOSL, LIGHT CD16, NKp30, NKp44, NKp46, NKp80, 2B4, KIR, LIR, CD94/NKG2A, CD94/NKG2C, LFA-1, CD11a/18, CD54 (ICAM-1), CD106 (VCAM), CD49a,b,c,d,e,f/CD29 (VLA-4), CD11a, CD14, CD15, CD19, CD25, CD30, CD37, CD49a, CD49e, CD56, CD27, CD28, CD45, CD45RA, CD45RO, CD45RB, CCR7, CCR5, CD62L, CD75, CD94, CD99, CD107b, CD109, CD152, CD153, CD154, CD160, CD161, CD178, CDw197, CDw217, Cd229, CD245, CD247 and Foxp3.

Additional Components of Detection Molecule

Additional components or substituents may be coupled to the detection molecule, either coupled to carrier or added as individual components not coupled to carrier.

In one embodiment the detection molecule further comprises an enzyme capable of catalysing the transfer of a cell surface moiety from a cell surface entity to the binding molecule of the detection molecule, wherein said cell surface moiety binds to (or associates with) the binding molecule.

In one embodiment the cell surface entity is a cell surface protein.

In one embodiment the cell surface moiety is a peptide fragment or 'peptide tag'.

The peptide tag added to the binding molecule can be used as a means of isolating the detection molecules that have been in contact with said cell surface entity.

Attachment of Biologically Active Molecules to Binding Molecules

Engagement of MHC complex to the specific T cell receptor leads to a signaling cascade in the T cell. However, T-cells normally respond to a single signal stimulus by going into apoptosis. T cells needs a second signal in order to become activated and start development into a specific activation state e.g. become an active cytotoxic T cell, helper T cell or regulatory T cell.

It is to be understood that the binding molecule such as MHC complex or MHC multimer of the invention may further comprise one or more additional substituents, such as biologically active molecules. The definition of the terms "one or more", "a plurality", "a", "an", and "the" also apply here. Such biologically active molecules may be attached to the construct in order to affect the characteristics of the constructs, e.g. with respect to binding properties, effects, MHC molecule specificities, solubility, stability, or detectability. For instance, spacing could be provided between the two or more binding molecules such as two or more MHC complexes, one or both chromophores of a Fluorescence Resonance Energy Transfer (FRET) donor/acceptor pair could be inserted, functional groups could be attached, or groups having a biological activity could be attached.

Binding molecules such as MHC multimers can be covalently or non-covalently associated with various molecules: having adjuvant effects; being immune targets e.g. antigens; having biological activity e.g. enzymes, regulators of receptor activity, receptor ligands, immune potentiators, drugs, toxins, co-receptors, proteins and peptides in general; sugar moieties; lipid groups; nucleic acids including siRNA; nano particles; small molecules. In the following these molecules are collectively called biologically active molecules. Such molecules can be attached to the binding molecule such as MHC multimer using the same principles as those described for attachment of binding molecule such as MHC complexes to multimerisation domains as described elsewhere herein. In brief, attachment can be done by chemical reactions between reactive groups on the biologically active molecule and reactive groups of the multimerisation domain and/or between reactive groups on the biologically active molecule and reactive groups of the binding molecule such as MHC-peptide complex. Alternatively, attachment is done by non-covalent interaction between part of the multimerisation domain and part of the biological active molecule or between part of the binding molecule such as MHC-peptide complex and part of the biological active molecule. In both covalent and non-covalent attachment of the biologically molecule to the multimerisation domain a connector molecule can connect the two. The connector molecule can be covalent or non-covalent attached to both molecules. Examples of connector molecules are described elsewhere herein. Some of the binding molecules such as MHCmer structures better allow these kinds of modifications than others. Biological active molecules can be attached repetitively aiding to recognition by and stimulation of the innate immune system via Toll or other receptors.

Binding molecules such as MHC multimers carrying one or more additional groups can be used as therapeutic or vaccine reagents.

In particular, the biologically active molecule may be selected from:

proteins such as MHC Class I-like proteins like MICA, MIC B, CD1d, HLA E, HLA F, HLA G, HLA H, ULBP-1, ULBP-2, and ULBP-3, co-stimulatory molecules such as CD2, CD3, CD4, CD5, CD8, CD9, CD27, CD28, CD30, CD69, CD134 (OX40), CD137 (4-1BB), CD147, CDw150 (SLAM), CD152 (CTLA-4), CD153 (CD30L), CD40L (CD154), NKG2D, ICOS, HVEM, HLA Class II, PD-1, Fas (CD95), FasL expressed on T and/or NK cells, CD40, CD48, CD58, CD70, CD72, B7.1 (CD80), B7.2 (CD86), B7RP-1, B7-H3, PD-L1, PD-L2, CD134L, CD137L, ICOSL, LIGHT expressed on APC and/or tumour cells, cell modulating molecules such as CD16, NKp30, NKp44, NKp46, NKp80, 2B4, KIR, LIR, CD94/ NKG2A, CD94/NKG2C expressed on NK cells, IFN-alpha, IFN-beta, IFN-gamma, IL-1, IL-2, IL-3, IL-4, IL-6, IL-7, IL-8, IL-10, IL-11, IL-12, IL-15, CSFs (colony-stimulating factors), vitamin D3, IL-2 toxins, cyclosporin, FK-506, rapamycin, TGF-beta, clotrimazole, nitrendipine, and charybdotoxin, accessory molecules such as LFA-1, CD11a/18, CD54 (ICAM-1), CD106 (VCAM), and CD49a,b,c,d,e,f/ CD29 (VLA-4), adhesion molecules such as ICAM-1, ICAM-2, GlyCAM-1, CD34, anti-LFA-1, anti-CD44, anti-beta7, chemokines, CXCR4, CCR5, anti-selectin L, anti-selectin E, and anti-selectin P, toxic molecules selected from toxins, enzymes, antibodies, radioisotopes, chemiluminescent substances, bioluminescent substances, polymers, metal particles, and haptens, such as cyclophosphamide, methrotrexate, Azathioprine, mizoribine, 15-deoxuspergualin, neomycin, staurosporine, genestein, herbimycin A, Pseudomonas exotoxin A, saporin, Rituxan, Ricin, gemtuzumab ozogamicin, Shiga toxin, heavy metals like inorganic and organic mercurials, and FN18-CRM9, radioisotopes such as incorporated isotopes of iodide, cobalt, selenium, tritium, and phosphor, and haptens such as DNP, and digoxiginin, and combinations of any of the foregoing, as well as antibodies (monoclonal, polyclonal, and recombinant) to the foregoing, where relevant. Antibody derivatives or fragments thereof may also be used.

Biological active molecules as described above may also be attached to antigenic peptide products or antigenic polypeptide products using same principles for attachment.

Linker

The linker comprised in the detection molecule of the present invention is a molecular entity and/or bond that connect the binding molecule and the label of the detection molecule. The connection may be direct or indirect, and may comprise a covalent or non-covalent binding. A linker according to the present invention comprises, or is identical to, a carrier molecule (or carrier), a multimerization domain and/or a backbone, and may equally be referred to as such herein.

In a preferred embodiment the linker consist of or comprises one or more molecules chosen from the group of dextran, streptavidin, peptide, or antibody.

In a preferred embodiment the linker connecting the binding molecule and the label has a length of 1-2 Å, 3-4 Å, 5-8 Å, 9-15 Å, 16-30 Å, 31-50 Å, 51-100 Å, 101-200 Å, 201-500 Å, 501-2000 Å, or longer than 2000 Å.

In one embodiment the linker of the invention, connecting the binding molecule and the label, consists or comprises one or more of the following entities: a short peptide, a modified or non-modified alkane, alkene or alkyne, a polyamide, ethylenglycol or polyethylenglycol, a small chemical entity such as an amide bond or other chemical bond, an oligonucleotide, biotin, the bond formed after reaction of a thiol with an NHS-ester or a maleimide.

Multimerisation Domain

In a preferred aspect of the invention one or multiple binding molecules (BM), as well as one or more labels, associate with a multimerization domain to form a detection molecule, Wherein at least two binding molecules are associated via a multimerization domain this constitutes a binding molecule multimer (BM multimer).

The term 'multimerization domain' is used to refer to a type of linker in the below; namely any molecular entity and/or bond that connect the binding molecule and the label of the detection molecule; alone or via a connector.

A number of binding molecules associate with one or more multimerization domains to form a detection molecule comprising one or more binding molecules and one or more labels. In one embodiment a number of MHC complexes (binding molecules) associate with a multimerization domain to form a MHC multimer.

The size of the multimerization domain spans a wide range, from multimerisation domains based on small organic molecule scaffolds to large multimers based on a cellular structure or solid support. The multimerization domain may thus be based on different types of carriers or scaffolds, and likewise, the attachment of binding molecules, such as MHC complexes, to the multimerization domain may involve covalent or non-covalent connectors. Characteristics of different kinds of multimerization domains are described below.

Molecular Weight of Multimerization Domain

In one embodiment the multimerization domain(s) in the present invention is preferably less than 1,000 Da (small molecule scaffold). Examples include short peptides (e.g. comprising 10 amino acids), and various small molecule scaffolds (e.g. aromatic ring structures).

In another embodiment the multimerization domain(s) is preferably between 1,000 Da and 10,000 Da (small molecule scaffold, small peptides, small polymers). Examples include polycyclic structures of both aliphatic and aromatic compounds, peptides comprising e.g. 10-100 amino acids, and other polymers such as dextran, polyethylenglycol, and polyureas.

In another embodiment the multimerization domain(s) is between 10,000 Da and 100,000 Da (Small molecule scaffold, polymers e.g. dextran, streptavidin, IgG, pentamer structure). Examples include proteins and large polypeptides, small molecule scaffolds such as steroids, dextran, dimeric streptavidin, and multi-subunit proteins such as used in Pentamers.

In another embodiment the multimerization domain(s) is preferably between 100,000 Da and 1,000,000 Da (Small molecule scaffold, polymers e.g. dextran, streptavidin, IgG, pentamer structure). Typical examples include larger polymers such as dextran (used in e.g. Dextramers), and streptavidin tetramers.

In another embodiment the multimerization domain(s) is preferably larger than 1,000,000 Da (Small molecule scaffold, polymers e.g. dextran, streptavidin, IgG, pentamer structure, cells, liposomes, artificial lipid bilayers, polystyrene beads and other beads. Most examples of this size involve cells or cell-based structures such as micelles and liposomes, as well as beads and other solid supports.

As mentioned elsewhere herein multimerisation domains can comprise carrier molecules (connectors), scaffolds or combinations of the two.

Type of Multimerization Domain.

In principle any kind of carrier or scaffold can be used as multimerization domain, including any kind of cell, polymer, protein or other molecular structure, or particles and solid supports. Below different types and specific examples of multimerization domains are listed.

Cell. Cells can be used as carriers. Cells can be either alive and mitotic active, alive and mitotic inactive as a result of irradiation or chemically treatment, or the cells may be dead. The MHC expression may be natural (i.e. not stimulated) or may be induced/stimulated by e.g. Inf-γ. Of special interest are natural antigen presenting cells (APCs) such as dendritic cells, macrophages, Kupfer cells, Langerhans cells, B-cells and any MHC expressing cell either naturally expressing, being transfected or being a hybridoma.

Cell-like structures. Cell-like carriers include membrane-based structures carrying MHC-peptide complexes in their membranes such as micelles, liposomes, and other structures of membranes, and phages such as filamentous phages.

Solid support. Solid support includes beads, particulate matters and other surfaces. A preferred embodiment include beads (magnetic or non-magnetic beads) that carry electrophilic groups e.g. divinyl sulfone activated polysaccharide, polystyrene beads that have been functionalized with tosyl-activated esters, magnetic polystyrene beads functionalized with tosyl-activated esters), and where binding molecules such as MHC complexes may be covalently immobilized to these by reaction of nucleophiles comprised within the BM such as the MHC complex with the electrophiles of the beads. Beads may be made of sepharose, sephacryl, polystyrene, agarose, polysaccharide, polycarbamate or any other kind of beads that can be suspended in aqueous buffer.

Another embodiment includes surfaces, i.e. solid supports and particles carrying immobilized binding molecules such as MHC complexes on the surface. Of special interest are wells of a microtiter plate or other plate formats, reagent tubes, glass slides or other supports for use in microarray analysis, tubings or channels of micro fluidic chambers or devices, Biacore chips and beads Molecule. Multimerization domains may also be molecules or complexes of molecules held together by non-covalent bonds. The molecules constituting the multimerization domain can be small organic molecules or large polymers, and may be flexible linear molecules or rigid, globular structures such as e.g. proteins. Different kinds of molecules used in multimerization domains are described below.

Small organic molecules. Small organic molecules here includes steroids, peptides, linear or cyclic structures, and aromatic or aliphatic structures, and many others. The prototypical small organic scaffold is a functionalized benzene ring, i.e. a benzene ring functionalized with a number of reactive groups such as amines, to which a number of binding molecules such as MHC molecules may be covalently linked. However, the types of reactive groups constituting the connector connecting the binding molecules such as MHC complex and the multimerization domain, as well as the type of scaffold structure, can be chosen from a long list of chemical structures. A non-comprehensive list of scaffold structures are listed below.

Typical scaffolds include aromatic structures, benzodiazepines, hydantoins, piperazines, indoles, furans, thiazoles, steroids, diketopiperazines, morpholines, tropanes, coumarines, qinolines, pyrroles, oxazoles, amino acid precursors, cyclic or aromatic ring structures, and many others.

Typical carriers include linear and branched polymers such as peptides, polysaccharides, nucleic acids, and many others. Multimerization domains based on small organic or polymer molecules thus include a wealth of different structures, including small compact molecules, linear structures, polymers, polypeptides, polyureas, polycarbamates, cyclic structures, natural compound derivatives, alpha-, beta-, gamma-, and omega-peptides, mono-, di- and tri-substituted peptides, L- and D-form peptides, cyclohexane- and cyclopentane-backbone modified beta-peptides, vinylogous polypeptides, glycopolypeptides, polyamides, vinylogous sulfonamide peptide, Polysulfonamide-conjugated peptide (i.e., having prosthetic groups), Polyesters, Polysaccharides such as dextran and aminodextran, polycarbamates, polycarbonates, polyureas, poly-peptidylphosphonates, Azatides, peptoids (oligo N-substituted glycines), Polyethers, ethoxyformacetal oligomers, poly-thioethers, polyethylene, glycols (PEG), polyethylenes, polydisulfides, polyarylene sulfides, Polynucleotides, PNAs, LNAs, Morpholinos, oligo pyrrolinone, polyoximes, Poly-imines, Polyethyleneimine, Polyacetates, Polystyrenes, Polyacetylene, Polyvinyl, Lipids, Phospholipids, Glycolipids, polycycles, (aliphatic), polycycles (aromatic), polyheterocycles, Proteoglycan, Polysiloxanes, Polyisocyanides, Polyisocyanates, polymethacrylates, Monofunctional, Difunctional, Trifunctional and Oligofunctional open-chain hydrocarbons, Monofunctional, Difunctional, Trifunctional and Oligofunctional Nonaromat Carbocycles, Monocyclic, Bicyclic, Tricyclic and Polycyclic Hydrocarbons, Bridged Polycyclic Hydrocarbones, Monofunctional, Difunctional, Trifunctional and Oligofunctional Nonaromatic, Heterocycles, Monocyclic, Bicyclic, Tricyclic and Polycyclic Heterocycles, bridged Polycyclic Heterocycles, Monofunctional, Difunctional, Trifunctional and Oligofunctional Aromatic Carbocycles, Monocyclic, Bicyclic, Tricyclic and Polycyclic Aromatic Carbocycles, Monofunctional, Difunctional, Trifunctional and Oligofunctional Aromatic Hetero-cycles. Monocyclic, Bicyclic, Tricyclic and Polycyclic Heterocycles. Chelates, fullerenes, and any combination of the above and many others.

Biological polymers. Biological molecules here include peptides, proteins (including antibodies, coiled-coil helices, streptavidin and many others), nucleic acids such as DNA and RNA, and polysaccharides such as dextran. The biological polymers may be reacted with MHC complexes (e.g. a number of MHC complexes chemically coupled to e.g. the amino groups of a protein), or may be linked through e.g. DNA duplex formation between a carrier DNA molecule and a number of DNA oligonucleotides each coupled to a MHC complex. Another type of multimerization domain based on a biological polymer is the streptavidin-based tetramer, where a streptavidin binds up to four biotinylated MHC complexes, as described above (see Background of the invention).

Self-assembling multimeric structures. Several examples of commercial MHC multimers exist where the multimer is formed through self-assembling. Thus, the Pentamers are formed through formation of a coiled-coil structure that holds together 5 MHC complexes in an apparently planar structure. In a similar way, the Streptamers are based on the Streptactin protein which oligomerizes to form a MHC multimer comprising several MHC complexes.

In the following, alternative ways to make binding molecules such as MHC multimers based on a molecule multimerization domain are described. They involve one or more of the above-mentioned types of multimerization domains.

MHC dextramers can be made by coupling MHC complexes to dextran via a streptavidin-biotin interaction. In principle, biotin-streptavdin can be replaced by any dimerization domain, where one half of the dimerization domain is coupled to the MHC complex and the other half is coupled to dextran. For example, an acidic helix (one half of a coiled-coil dimer) is coupled or fused to MHC, and a basic helix (other half of a coiled-coil dimmer) is coupled to dextran. Mixing the two results in MHC binding to dextran by forming the acid/base coiled-coil structure.

Binding molecule dextramers can be made by coupling binding molecules to dextran via a streptavidin-biotin interaction. In principle, biotin-streptavdin can be replaced by any dimerization domain, where one half of the dimerization domain is coupled to the binding molecule and the other half is coupled to dextran. For example, an acidic helix (one half of a coiled-coil dimer) is coupled or fused to the BM, and a basic helix (other half of a coiled-coil dimmer) is coupled to dextran. Mixing the two results in the BM binding to dextran by forming the acid/base coiled-coil structure.

Antibodies can be used as scaffolds by using their capacity to bind to a carefully selected antigen found naturally or added as a tag to a part of the binding molecule such as the MHC molecule not involved in peptide binding. For example, IgG and IgE will be able to bind two binding molecules such as two MHC molecules, and IgM having a pentameric structure will be able to bind 10 binding molecules such as 10 MHC molecules. The antibodies can be full-length or truncated; a standard antibody-fragment includes the Fab2 fragment.

Peptides involved in coiled-coil structures can act as scaffold by making stable dimeric, trimeric, tetrameric and pentameric interactions. Examples hereof are the Fos-Jun heterodimeric coiled coil, the *E. coli* homo-trimeric coiled-coil domain Lpp-56, the engineered Trp-zipper protein forming a discrete, stable, α-helical pentamer in water at physiological pH.

Further examples of suitable scaffolds, carriers and connectors are streptavidin (SA) and avidin and derivatives thereof, biotin, immunoglobulins, antibodies (monoclonal, polyclonal, and recombinant), antibody fragments and derivatives thereof, leucine zipper domain of AP-1 (Jun and fos), hexa-his (metal chelate moiety), hexa-hat GST (glutathione S-tranferase), glutathione, Calmodulin-binding peptide (CBP), Strep-tag, Cellulose Binding Domain, Maltose Binding Protein, S-Peptide Tag, Chitin Binding Tag, Immuno-reactive Epitopes, Epitope Tags, E2Tag, HA Epitope Tag, Myc Epitope, FLAG Epitope, AU1 and AU5 Epitopes, Glu-Glu Epitope, KT3 Epitope, IRS Epitope, Btag Epitope, Protein Kinase-C Epitope, VSV Epitope, lectins that mediate binding to a diversity of compounds, including carbohydrates, lipids and proteins, e.g. Con A (*Canavalia ensiformis*) or WGA (wheat germ agglutinin) and tetranectin or Protein A or G (antibody affinity). Combinations of such binding entities are also comprised. Non-limiting examples are streptavidin-biotin and jun-fos. In particular, when the MHC molecule is tagged, the binding entity may be an "anti-tag". By "anti-tag" is meant an antibody binding to the tag, or any other molecule capable of binding to such tag.

Wherein the binding molecule comprise MHC complexes, these can be multimerized by other means than coupling or binding to a multimerization domain. Thus, the multimerization domain may be formed during the multimerization of MHCs. One such method is to extend the bound antigenic peptide with dimerization domains. One end of the antigenic peptide is extended with dimerization domain A (e.g. acidic helix, half of a coiled-coil dimer) and the other end is extended with dimerization domain B (e.g. basic helix, other half of a coiled-coil dimer). When MHC complexes are loaded/mixed with these extended peptides the following multimer structure will be formed: A-MHC-BA-MHC-BA-MHC-B etc. The antigenic peptides in the mixture can either be identical or a mixture of peptides with comparable extended dimerization domains. Alternatively both ends of a peptide are extended with the same dimerization domain A and another peptide (same amino acid sequence or a different amino acid sequence) is extended with dimerization domain B. When MHC and peptides are mixed the following structures are formed: A-MHC-AB-MHC-BA-MHC-AB-MHC-B etc. Multimerization of MHC complexes by extension of peptides are restricted to MHC II molecules since the peptide binding groove of MHC I molecules is typically closed in both ends thereby limiting the size of peptide that can be embedded in the groove, and therefore preventing the peptide from extending out of the groove.

Another multimerization approach applicable to both MHC I and MHC II complexes is based on extension of N- and C-terminal of the MHC complex. For example the N-terminal of the MHC complex is extended with dimerization domain A and the C-terminal is extended with dimerization domain B. When MHC complexes are incubated together they pair with each other and form multimers like: A-MHC-BA-MHC-BA-MHC-BA-MHC-B etc. Alternatively the N-terminal and the C-terminal of a MHC complex are both extended with dimerization domain A and the N-terminal and C-terminal of another preparation of MHC complex (either the same or a different MHC) are extended with dimerization domain B. When these two types of MHC complexes are incubated together multimers will be formed: A-MHC-AB-MHC-BA-MHC-AB-MHC-B etc.

In all the above-described examples the extension can be either chemically coupled to the peptide/MHC complex or introduced as extension by gene fusion. Dimerization domain AB can be any molecule pair able to bind to each other, such as acid/base coiled-coil helices, antibody-antigen, DNA-DNA, PNA-PNA, DNA-PNA, DNA-RNA, LNA-DNA, leucine zipper e.g. Fos/Jun, streptavidin-biotin and other molecule pairs as described elsewhere herein.

In one embodiment the one or more multimerization domains each have a molecular weight of from 50,000 Da to preferably less than 1,000,000 Da, such as from 50,000 Da to 980,000; for example from 50,000 Da to 960,000; such as from 50,000 Da to 940,000; for example from 50,000 Da to 920,000; such as from 50,000 Da to 900,000; for example from 50,000 Da to 880,000; such as from 50,000 Da to 860,000; for example from 50,000 Da to 840,000; such as from 50,000 Da to 820,000; for example from 50,000 Da to 800,000; such as from 50,000 Da to 780,000; for example from 50,000 Da to 760,000; such as from 50,000 Da to 740,000; for example from 50,000 Da to 720,000; such as from 50,000 Da to 700,000; for example from 50,000 Da to 680,000; such as from 50,000 Da to 660,000; for example from 50,000 Da to 640,000; such as from 50,000 Da to 620,000; for example from 50,000 Da to 600,000; such as from 50,000 Da to 580,000; for example from 50,000 Da to 560,000; such as from 50,000 Da to 540,000; for example from 50,000 Da to 520,000; such as from 50,000 Da to 500,000; for example from 50,000 Da to 480,000; such as from 50,000 Da to 460,000; for example from 50,000 Da to 440,000; such as from 50,000 Da to 420,000; for example from 50,000 Da to 400,000; such as from 50,000 Da to 380,000; for example from 50,000 Da to 360,000; such as from 50,000 Da to 340,000; for example from 50,000 Da to 320,000; such as from 50,000 Da to 300,000; for example from 50,000 Da to 280,000; such as from 50,000 Da to 260,000; for example from 50,000 Da to 240,000; such as from 50,000 Da to 220,000; for example from 50,000 Da to 200,000; such as from 50,000 Da to 180,000; for example from 50,000 Da to 160,000; such as from 50,000 Da to 140,000; for example from 50,000 Da to 120,000; such as from 50,000 Da to 100,000; for example from 50,000 Da to 80,000; such as from 50,000 Da to 60,000; for example from 100,000 Da to 1,000,000; such as from 100,000 Da to 980,000; for example from 100,000 Da to 960,000; such as from 100,000 Da to 940,000; for example from 100,000 Da to 920,000; such as from 100,000 Da to 900,000; for example from 100,000 Da to 880,000; such as from 100,000 Da to 860,000; for example from 100,000 Da to 840,000; such as from 100,000 Da to 820,000; for example from 100,000 Da to 800,000; such as from 100,000 Da to 780,000; for example from 100,000 Da to 760,000; such as from 100,000 Da to 740,000; for example from 100,000 Da to 720,000; such as from 100,000 Da to 700,000; for example from 100,000 Da to 680,000; such as from 100,000 Da to 660,000; for example from 100,000 Da to 640,000; such as from 100,000 Da to 620,000; for example from 100,000 Da to 600,000; such as from 100,000 Da to 580,000; for example from 100,000 Da to 560,000; such as from 100,000 Da to 540,000; for example from 100,000 Da to 520,000; such as from 100,000 Da to 500,000; for example from 100,000 Da to 480,000; such as from 100,000 Da to 460,000; for example from 100,000 Da to 440,000; such as from 100,000 Da to 420,000; for example from 100,000 Da to 400,000; such as from 100,000 Da to 380,000; for example from 100,000 Da to 360,000; such as from 100,000 Da to 340,000; for example from 100,000 Da to 320,000; such as from 100,000 Da to 300,000; for example from 100,000 Da to 280,000; such as from 100,000 Da to 260,000; for example from 100,000 Da to 240,000; such as from 100,000 Da to 220,000; for example from 100,000 Da to 200,000; such as from 100,000 Da to 180,000; for example from 100,000 Da to 160,000; such as from 100,000 Da to 140,000; for example from 100,000 Da to 120,000; such as from 150,000 Da to 1,000,000; for example from 150,000 Da to 960,000; such as from 150,000 Da to 940,000; for example from 150,000 Da to 920,000; such as from 150,000 Da to 900,000; for example from 150,000 Da to 880,000; such as from 150,000 Da to 860,000; for example from 150,000 Da to 840,000; such as from 150,000 Da to 820,000; for example from 150,000 Da to 800,000; such as from 150,000 Da to 780,000; for example from 150,000 Da to 760,000; such as from 150,000 Da to 740,000; for example from 150,000 Da to 720,000; such as from 150,000 Da to 700,000; for example from 150,000 Da to 680,000; such as from 150,000 Da to 660,000; for example from 150,000 Da to 640,000; such as from 150,000 Da to 620,000; for example from 150,000 Da to 600,000; such as from 150,000 Da to 580,000; for example from 150,000 Da to 560,000; such as from 150,000 Da to 540,000; for example from 150,000 Da to 520,000; such as from 150,000 Da to 500,000; for example from 150,000 Da to 480,000; such as from 150,000 Da to 460,000; for example from 150,000 Da to 440,000; such as from 150,000 Da to 420,000; for example from 150,000 Da to 400,000; such as from 150,000 Da to 380,000; for example from 150,000 Da to 360,000; such as from 150,000 Da to 340,000; for example from 150,000 Da to 320,000; such as from 150,000 Da to 300,000; for example from 150,000 Da to 280,000; such as from 150,000 Da to 260,000; for example from 150,000 Da to 240,000; such as from 150,000 Da to 220,000; for example from 150,000 Da to 200,000; such as from 150,000 Da to 180,000; for example from 150,000 Da to 160,000.

Connector

In one embodiment a number of binding molecules (BM) associate with a multimerization domain to form a binding molecule multimer (BM multimer). The association may be direct—between the binding molecule and the multimerization domain, or may be via an association with a connector, such as a connector molecule, which interconnects the binding molecule and the multimerization domain. A multimerization domain with a connector is an example of linkers according to the present invention, In another embodiment the linker of the detection molecule comprises or consists of one or more connectors and/or connector molecules. Connectors may be formed of chemical bonds and/or molecules.

The attachment of binding molecules to the multimerization domain may involve covalent or non-covalent connectors, and may involve small reactive groups as well as large protein-protein interactions. The coupling of multimerization domains and binding molecules involve the association of an entity X (attached to or part of the multimerization domain) and an entity Y (attached to or part of the binding molecule and/or label). Thus, the connector that connects the multimerization domain and the binding molecule comprises an XY portion.

A connector according to the invention in on one embodiment comprises one or more chemical bond formed between the linker/multimerization domain, and each of the binding molecules and labels.

A connector according to the invention in on one embodiment comprises one or more connector molecules associated with the linker/multimerization domain, and each of the binding molecules and labels.

In one embodiment, a number of MHC complexes associate with a multimerization domain to form a MHC multimer. The attachment of MHC complexes to the multimerization domain may involve covalent or non-covalent connectors, and may involve small reactive groups as well as large protein-protein interactions.

The coupling of multimerization domains and MHC complexes involve the association of an entity X (attached to or part of the multimerization domain) and an entity Y (attached to or part of the MHC complex and/or label). Thus, the connector that connects the multimerization domain and the MHC complex comprises an XY portion.

Covalent connector. The XY linkage can be covalent, in which case X and Y are reactive groups. In this case, X can be a nucleophilic group (such as —$NH_2$, —OH, —SH, —NH—$NH_2$), and Y an electrophilic group (such as CHO, COOH, CO) that react to form a covalent bond XY; or Y can be a nucleophilic group and X an electrophilic group that react to form a covalent bond XY. Other possibilities exist, e.g either of the reactive groups can be a radical, capable of reacting with the other reactive group.

X and Y can be reactive groups naturally comprised within the multimerization domain and/or the binding molecule such as MHC complex, or they can be artificially added reactive groups. Thus, connectors containing reactive groups can be linked to either of the multimerization domain and binding molecule such as MHC complex; subsequently the introduced reactive group(s) can be used to covalently link the multimerization domain and binding molecule such as MHC complex.

Example natural reactive groups of binding molecule such as MHC complexes include amino acid side chains comprising —$NH_2$, —OH, —SH, and —NH—. Example natural reactive groups of multimerization domains include hydroxyls of polysaccharides such as dextrans, but also include amino acid side chains comprising —$NH_2$, —OH, —SH, and —NH— of polypeptides, when the polypeptide is used as a multimerization domain.

In some MHC multimers, one of the polypeptides of the MHC complex (i.e. the β2M, heavy chain or the antigenic peptide) is linked by a protein fusion to the multimerization domain. Thus, during the translation of the fusion protein, an acyl group (reactive group X or Y) and an amino group (reactive group Y or X) react to form an amide bond. Example MHC multimers where the bond between the multimerization domain and the MHC complex is covalent and results from reaction between natural reactive groups, include MHC-pentamers (described in US patent 2004209295) and MHC-dimers, where the linkage between multimerization domain and MHC complex is in both cases generated during the translation of the fusion protein.

Example artificial reactive groups include reactive groups that are attached to the multimerization domain or the binding molecule such as MHC complex, through association of a connector molecule comprising the reactive group. The activation of dextran by reaction of the dextran hydroxyls with divinyl sulfone, introduces a reactive vinyl group that can react with e.g. amines of the binding molecule such as MHC complex, to form an amine that now links the multimerization domain (the dextran polymer) and the binding molecule such as MHC complex. An alternative activation of the dextran multimerization domain involves a multistep reaction that results in the decoration of the dextran with maleimide groups, as described in the patent Siiman et al. U.S. Pat. No. 6,387,622. In this approach, the amino groups of MHC complexes are converted to —SH groups, capable of reacting with the maleimide groups of the activated dextran. Thus, in the latter example, both the reactive group of the multimerization domain (the maleimide) and the reactive group of the MHC complex (the thiol) are artificially introduced.

Sometimes activating reagents are used in order to make the reactive groups more reactive. For example, acids such as glutamate or aspartate can be converted to activated esters by addition of e.g. carbodiimid and NHS or nitrophenol, or by converting the acid moiety to a tosyl-activated ester. The activated ester reacts efficiently with a nucleophile such as —NH$_2$, —SH, —OH, etc.

For the purpose of this invention, the multimerization domains (including small organic scaffold molecules, proteins, protein complexes, polymers, beads, liposomes, micelles, cells) that form a covalent bond with the binding molecules such as MHC complexes can be divided into separate groups, depending on the nature of the reactive group that the multimerization domain contains. One group comprise multimerization domains that carry nucleophilic groups (e.g. —NH$_2$, —OH, —SH, —CN, —NH—NH$_2$), exemplified by polysaccharides, polypeptides containing e.g. lysine, serine, and cysteine; another group of multimerization domains carry electrophilic groups (e.g. —COOH, —CHO, —CO, NHS-ester, tosyl-activated ester, and other activated esters, acid-anhydrides), exemplified by polypeptides containing e.g. glutamate and aspartate, or vinyl sulfone activated dextran; yet another group of multimerization domains carry radicals or conjugated double bonds.

Likewise, binding molecules such as MHC complexes can be divided into separate groups, depending on the nature of the reactive group comprised within the binding molecule. One group comprise binding molecules such as MHCs that carry nucleophilic groups (e.g. —NH$_2$, —OH, —SH, —CN, —NH—NH$_2$), e.g. lysine, serine, and cysteine; another group of binding molecules such as MHCs carry electrophilic groups (e.g. —COOH, —CHO, —CO, NHS-ester, tosyl-activated ester, and other activated esters, acid-anhydrides), exemplified by e.g. glutamate and aspartate; yet another group of binding molecules such as MHCs carry radicals or conjugated double bonds.

The reactive groups of the binding molecule such as MHC complex are either carried by the amino acids of the binding molecule such as MHC-peptide complex (and may be comprised by any of the peptides of the MHC-peptide complex, including the antigenic peptide), or alternatively, the reactive group of the binding molecule such as MHC complex has been introduced by covalent or non-covalent attachment of a molecule containing the appropriate reactive group.

Preferred reactive groups in this regard include —CSO$_2$OH, phenylchloride, —SH, —SS, aldehydes, hydroxyls, isocyanate, thiols, amines, esters, thioesters, carboxylic acids, triple bonds, double bonds, ethers, acid chlorides, phosphates, imidazoles, halogenated aromatic rings, any precursors thereof, or any protected reactive groups, and many others.

Reactions that may be employed include acylation (formation of amide, pyrazolone, isoxazolone, pyrimidine, comarine, quinolinon, phthalhydrazide, diketopiperazine, benzodiazepinone, and hydantoin), alkylation, vinylation, disulfide formation, Wittig reaction, Horner-Wittig-Emmans reaction, arylation (formation of biaryl or vinylarene), condensation reactions, cycloadditions ((2+4), (3+2)), addition to carbon-carbon multiplebonds, cycloaddition to multiple bonds, addition to carbon-hetero multiple bonds, nucleophilic aromatic substitution, transition metal catalyzed reactions, and may involve formation of ethers, thioethers, secondary amines, tertiary amines, beta-hydroxy ethers, beta-hydroxy thioethers, beta-hydroxy amines, beta-amino ethers, amides, thioamides, oximes, sulfonamides, di- and tri-functional compounds, substituted aromatic compounds, vinyl substituted aromatic compounds, alkyn substituted aromatic compounds, biaryl compounds, hydrazines, hydroxylamine ethers, substituted cycloalkenes, substituted cyclodienes, substituted 1, 2, 3 triazoles, substituted cycloalkenes, beta-hydroxy ketones, beta-hydroxy aldehydes, vinyl ketones, vinyl aldehydes, substituted alkenes, substituted alkenes, substituted amines, and many others.

Binding molecule dextramers, preferably MHC dextramers, can be made by covalent coupling of binding molecules such as MHC complexes to the dextran backbone, e.g. by chemical coupling of binding molecules such as MHC complexes to dextran backbones.

The MHC complexes can be coupled through either heavy chain or β2-microglobulin if the MHC complexes are MHC I or through α-chain or β-chain if the MHC complexes are MHC II. MHC complexes can be coupled as folded complexes comprising heavy chain/beta2microglobulin or α-chain/β-chain or either combination together with peptide in the peptide-binding cleft.

Alternatively either of the protein chains can be coupled to dextran and then folded in vitro together with the other chain of the MHC complex not coupled to dextran and together with peptide.

Direct coupling of binding molecules such as MHC complexes to dextran multimerization domain can be via an amino group or via a sulphide group. Either group can be a natural component of the binding molecule such as MHC complex or attached to the binding molecules such as MHC complex chemically. Alternatively, a cysteine may be introduced into the genes of the binding molecules such as either chain of the MHC complex.

Another way to covalently link binding molecules such as MHC complexes to dextran multimerization domains is to use the antigenic peptide as a connector between MHC and dextran. Connectors containing antigenic peptide at one end is coupled to dextran. Antigenic peptide here means a peptide able to bind MHC complexes in the peptide-binding cleft. As an example, 10 or more antigenic peptides may be coupled to one dextran molecule. When MHC complexes are added to such peptide-dextran construct the MHC complexes will bind the antigenic peptides and thereby MHC-peptide complexes are displayed around the dextran multimerization domain. The antigenic peptides can be identical or different from each other. Similarly MHC complexes can be either identical or different from each other as long as they are capable of binding one or more of the peptides on the dextran multimerization domain.

Non-covalent connector. The linkage molecule that connects the multimerization domain and the binding molecule such as MHC complex comprises an XY portion. Above different kinds of covalent linkages XY were described. However, the XY linkage can also be non-covalent. Non-covalent XY linkages can comprise natural dimerization pairs such as antigen-antibody pairs, DNA-DNA interactions, or can include natural interactions between small molecules and proteins, e.g. between biotin and streptavidin. Artificial XY examples include XY pairs such as His$_6$ tag (X) interacting with Ni-NTA (Y) and PNA-PNA interactions.

Protein-protein interactions. The non-covalent connector may comprise a complex of two or more polypeptides or proteins, held together by non-covalent interactions. Example polypeptides and proteins belonging to this group include Fos/Jun, Acid/Base coiled coil structure, antibody/antigen (where the antigen is a peptide), and many others.

A preferred embodiment involving non-covalent interactions between polypeptides and/or proteins are represented by the Pentamer structure described in US patent 2004209295.

Another preferred embodiment involves the use of antibodies, with affinity for the surface of the binding molecule (BM). Thus, an anti-BM antibody, with its two binding sites, will bind two binding molecules and in this way generate a bivalent BM multimer. In addition, the antibody can stabilize the BM through the binding interactions.

Another preferred embodiment involves the use of antibodies, with affinity for the surface of MHC opposite to the peptide-binding groove. Thus, an anti-MHC antibody, with its two binding sites, will bind two MHC complexes and in this way generate a bivalent MHC multimer. In addition, the antibody can stabilize the MHC complex through the binding interactions. This is particularly relevant for MHC class II complexes, as these are less stable than class I MHC complexes.

Polynucleotide-polynucleotide interactions. The non-covalent connector may comprise nucleotides that interact non-covalently. Example interactions include PNA/PNA, DNA/DNA, RNA/RNA, LNA/DNA, and any other nucleic acid duplex structure, and any combination of such natural and unnatural polynucleotides such as DNA/PNA, RNA/DNA, and PNA/LNA.

Protein-small molecule interactions. The non-covalent connector may comprise a macromolecule (e.g. protein, polynucleotide) and a small molecule ligand of the macromolecule. The interaction may be natural (i.e., found in Nature, such as the Streptavidin/biotin interaction) or non-natural (e.g. His-tag peptide/Ni-NTA interaction). Example interactions include Streptavidin/biotin and anti-biotin antibody/biotin.

Combinations—non-covalent connector molecules. Other combinations of proteins, polynucleotides, small organic molecules, and other molecules, may be used to link the MHC to the multimerization domain. These other combinations include protein-DNA interactions (e.g. DNA binding protein such as the gene regulatory protein CRP interacting with its DNA recognition sequence), RNA aptamer-protein interactions (e.g. RNA aptamer specific for growth hormone interacting with growth hormone)

Synthetic molecule-synthetic molecule interaction. The non-covalent connector may comprise a complex of two or more organic molecules, held together by non-covalent interactions. Example interactions are two chelate molecules binding to the same metal ion (e.g. EDTA-Ni$^{++}$-NTA), or a short polyhistidine peptide (e.g. His$_6$) bound to NTA-Ni$^{++}$.

In another preferred embodiment the multimerization domain is a bead. The bead is covalently or non-covalently coated with binding molecules, such as BM multimers or BM monomers, for example MHC multimers or single MHC complexes, through non-cleavable or cleavable connectors. As an example, the bead can be coated with streptavidin monomers, which in turn are associated with biotinylated binding molecules such as MHC complexes; or the bead can be coated with streptavidin tetramers, each of which are associated with 0, 1, 2, 3, or 4 biotinylated binding molecules such as MHC complexes; or the bead can be coated with BM-dextramers such as MHC-dextramers where e.g. the reactive groups of the BM- or MHC-dextramer (e.g. the divinyl sulfone-activated dextran backbone) has reacted with nucleophilic groups on the bead, to form a covalent linkage between the dextran of the dextramer and the beads.

In another preferred embodiment, the binding molecule multimers such as MHC multimers described above (e.g. where the multimerization domain is a bead) further contains a flexible or rigid, and water soluble, connector that allows for the immobilized binding molecules such as MHC complexes to interact efficiently with cells; such as T-cells with affinity for the MHC complexes. In yet another embodiment, the connector is cleavable, allowing for release of the binding molecules such as MHC complexes from the bead. If T-cells have been immobilized, by binding to the BMs such as MHC complexes, the T-cells can very gently be released by cleavage of this cleavable connector. Most preferably, the connector is cleaved at physiological conditions, allowing for the integrity of the isolated cells.

Further examples of connector molecules that may be employed in the present invention include Calmodulin-binding peptide (CBP), 6×HIS, Protein A, Protein G, biotin, Avidine, Streptavidine, Strep-tag, Cellulose Binding Domain, Maltose Binding Protein, S-Peptide Tag, Chitin Binding Tag, Immuno-reactive Epitopes, Epitope Tags, GST tagged proteins, E2Tag, HA Epitope Tag, Myc Epitope, FLAG Epitope, AU1 and AU5 Epitopes, Glu-Glu Epitope, KT3 Epitope, IRS Epitope, Btag Epitope, Protein Kinase-C Epitope, VSV Epitope.

The list of dimerization- and multimerization domains, described elsewhere in this document, define alternative non-covalent connectors between the multimerization domain and the binding molecule such as the MHC complex.

The abovementioned dimerization- and multimerization domains represent specific binding interactions. Another type of non-covalent interactions involves the non-specific adsorption of e.g. proteins onto surfaces. As an example, the non-covalent adsorption of proteins onto glass beads represents this class of XY interactions. Likewise, the interaction of binding molecules such as MHC complexes (comprising full-length polypeptide chains, including the transmembrane portion) with the cell membrane of for example dendritic cells is an example of a non-covalent, primarily non-specific XY interaction.

In some of the abovementioned embodiments, several multimerization domains (e.g. streptavidin tetramers bound to biotinylated MHC complexes) are linked to another multimerization domain (e.g. the bead). For the purpose of this invention we shall call both the smaller and the bigger multimerization domain, as well as the combined multimerization domain, for multimerization domain.

Kit of Parts

The composition of the invention may form part of a kit. Thus, yet an aspect of the invention relates to a kit of parts comprising
  a. one or more detection molecules, wherein each detection molecule or set of detection molecules are as disclosed herein throughout, and b. one or more additional components.

In one embodiment the kit of parts comprises
- a composition comprising a detection molecule, wherein said detection molecule comprises a DNA molecule label, according to the invention; and
- one or more sets of primers for amplifying the nucleic acid molecule label, such as DNA molecule label.

In one embodiment said additional components comprise reagents for detecting and/or amplifying the label of the detection molecule.

In one embodiment said additional components comprise reagents for detecting and/or amplifying the nucleic acid label of the detection molecule.

In one embodiment said additional components comprise one or more primer sets capable of amplifying the label of the nucleic acid label, such as amplifying the barcode region of the nucleic acid label via hybridization to the primer regions of the nucleic acid label.

DETECTION METHOD

It is an aspect of the invention to provide a detection method comprising one or more steps of:
a. Combining a sample with at least one detection molecule; wherein the detection molecule comprises a binding molecule (BM), a linker (Li), and a label (La), each as defined according to the present invention; and wherein said sample comprises at least one cell and/or entity,
b. Incubating the at least one detection molecule and the sample;
c. Isolating and/or detecting the at least one detection molecule of step b), and
d. Optionally determining the identity of the at least one detection molecule of step c).

It is understood that each step of the detection method, namely the sample, the isolation and/or detection and the determination of label, individually can be selected from any of the samples, isolation and/or detection steps and determination of label steps disclosed herein throughout. Thus, any combination of sample, isolation and/or detection and determination of label are encompassed within the present disclosure and invention.

In one embodiment there is provided a method comprising the following steps:
a. Combining at least one cell with at least one detection molecule, wherein the detection molecule comprises a binding molecule (BM), a linker (Li), and a label (La);
b. Allowing the detection molecules to recognize and bind cells through their binding molecule (BM);
c. Detecting and/or isolating cell-detection molecule complexes formed in step (b); and
d. Identifying detection molecules capable of binding to a cell in step (b)

Also provided is a method for detecting antigen-responsive cells in a sample comprising:
a. providing one or more multimeric major histocompatibility complexes (MHC's) according to the invention or a composition according to the invention;
b. contacting said multimeric MHC's with said sample; and
c. detecting binding of the multimeric MHC's to said antigen responsive cells, thereby detecting cells responsive to an antigen present in a set of MHC's; wherein said binding is detected by amplifying the barcode region of said nucleic acid molecule linked to the one or more MHC's.

It is understood that the detection molecule and each of the components of the detection molecule (BM, Li and La) referred to in the detection methods of the invention can individual be as outlined herein elsewhere.

The detection molecules and methods (e.g. detection methods) of the present invention can be used for or applied in a number of methods and assays. The assays for which the detection molecules and the methods of using same can be employed include assays for recognizing or detecting well-known targets or epitopes (such as diagnosis, detection of antigen-specific T-cells), and assays for investigating novel or unknown targets or epitopes (such as epitope discovery, whereby the binding properties of the detection molecule are unknown).

Methods include, but are not limited to one or more of: epitope discovery, analytical studies, diagnosis, therapy/treatment, detection of antigen-responsive cells, detection of antigen-specific T-cells, characterization of cells of their detection molecule-binding properties, T-cell epitope mapping, immune-related therapies, immune-recognition discovery and measuring immune reactivity after vaccination.

In one embodiment the present invention allows for detection of multiple antigen-responsive cells present in the same sample, wherein said antigen-responsive cells have different specificities and detect different antigens and/or epitopes. This can be achieved since each detection molecule has a unique and detectable label (La) associated with a specific binding molecule (BM) for the antigen-responsive cell.

In one embodiment the detection method further comprises one or more steps of providing a sample, preferably a sample comprising at least one entity and/or at least one cell.

In one embodiment the detection method further comprises one or more steps of pre-treatment of the sample, and/or pre-treatment of cells of the sample.

The method thus in one embodiment involves first the mixing of one or more detection molecules capable of binding certain cells with a sample comprising cells, followed by complex formation between some or all of the detection molecules and some or all of the cells, and finally detection and/or isolation of the cell-detection molecule complexes formed.

It follows that in step b) the one or more detection molecules are allowed to associate with, recognize, and/or bind to said at least one cell and/or entity through their binding molecule.

The detection method in some embodiment further comprises one or more steps of separating unbound detection molecules from cell- or entity-detection molecule complexes.

The detection method in some embodiment further comprises one or more steps of removing unbound detection molecules by washing and/or centrifuging.

In one embodiment in step c) and d) said detection molecule is comprised in a cell-detection molecule complex or an entity-detection molecule complex.

In another embodiment in step c) and d) said detection molecule is not comprised in a cell-detection molecule complex or an entity-detection molecule complex.

In one embodiment in step c) and d) said detection molecule is no longer comprised in a cell-detection molecule complex or an entity-detection molecule complex, wherein said detection molecule has previously interacted with a cell-detection molecule complex or an entity-detection molecule complex.

In steps c) and/or d) of the detection method the sorting and/or detecting thus ensues on the detection molecule per se, or the cell-detection molecule complex (or entity-detection molecule complex).

In one embodiment step c) comprises isolating and detecting the at least one detection molecule.

In one embodiment step c) comprises first isolating and then detecting the at least one detection molecule.

In one embodiment step c) comprises detecting the at least one detection molecule.

In one embodiment step c) comprises isolating the at least one detection molecule.

In one embodiment step c) comprises first detecting and then isolating the at least one detection molecule.

The isolation in step c) may be performed by any method known to the skilled person. Isolation is used interchangeably with enrichment and cell sorting herein.

In a particular embodiment the detection molecule further comprises one or more fluorescent labels, which are useful in the sorting of specific cell populations. Examples of specific cell populations include T-cells (CD8 or CD4 restricted), other immune cells or specifically MHC multimer binding T-cells In one embodiment, specific cell populations are sorted by methods comprising one or more of flow cytometry, FACS sorting, centrifugation, washing, precipitation, filtration and affinity column sorting, or any other means of cell sorting/selection.

In one embodiment in step c) isolating comprises sorting of cell populations based on the functional response to a stimuli (responsive or non-responsive population), such as cytokine secretion, phosphorylation, calcium release.

In one embodiment in step c) isolating comprises sorting of cell populations based on phenotype, such as by linking a certain set of phenotypic characteristics to the antigen-responsiveness.

In one embodiment in step c) isolating comprises immobilization of the detection molecule and/or cell-detection molecule complexes, such as by precipitating cells, such as by centrifugation, by immunoprecipitation, or any other means that precipitates the cells.or by binding the cell-detection molecule complexes to a bead, a particle, another surface, an antibody or an MHC complex.

In one embodiment said immobilization of the detection molecule and/or cell-detection molecule complexes comprises hybridization onto an array.

In one embodiment said immobilization of the detection molecule and/or cell-detection molecule complexes by hybridization onto an array comprises a nucleic acid/nucleic acid-interaction between the nucleic acid label of the detection molecule and an antisense nucleic acid sequence in the array.

In one embodiment said immobilization of the detection molecule and/or cell-detection molecule complexes by hybridization onto an array comprises a DNA/DNA-interaction between the DNA label of the detection molecule and an antisense DNA in the array.

In one embodiment said detecting in step c) and/or determining the identity in step d) comprises one or more steps of adding primary antibodies that bind to the immobilized detection molecule and/or cell-detection molecule complexes and detecting said primary antibodies directly wherein the primary antibody is labelled, or indirectly by adding labelled secondary antibodies.

In one embodiment said detecting in step c) and/or determining the identity in step d) comprises one or more steps of detecting the immobilized detection molecule and/or cell-detection molecule complexes by monitoring readout from a second label such as a fluorophore.

In one embodiment detecting in step c) and/or determining the identity in step d) comprises interaction between 'coating DNA' on the cell surface and the DNA label of the detection molecule.

In one embodiment detecting in step c) and/or determining the identity in step d) comprises protease cleavage of the peptide label of the detection molecule.

In one embodiment detecting in step c) and/or determining the identity in step d) comprises transfer of a cell surface moiety to the detection molecule (e.g. a 'peptide tag').

In one embodiment detecting in step c) and/or determining the identity in step d) comprises detection of the label based on the physical characteristics of the label, including mass, sequence, charge, volume, size, dimensions, fluorescence, absorption, emission, NMR spectra and others.

In one embodiment detecting in step c) and/or determining the identity in step d) comprises amplification of the label.

In one embodiment detecting in step c) and/or determining the identity in step d) comprises sequencing of the label (e.g. DNA sequencing, peptide sequencing).

In one embodiment detecting in step c) and/or determining the identity in step d) comprises amplification of the barcode sequence of a nucleic acid label by PCR and/or sequencing of the barcode sequence.

In one embodiment sequencing comprises deep sequencing or next generation sequencing.

In one embodiment detecting in step c) and/or determining the identity in step d) comprises mass spectrometry.

In one embodiment detecting in step c) and/or determining the identity in step d) comprises one or more of gel electrophoresis, gel filtration, PAGE, column fractionation, PCR and QPCR.

The detection method in some embodiments further comprises one or more steps of single-cell sorting and sequencing, such as single-cell T cell sorting of and single-cell TCR sequencing.

In an aspect of the present invention a nucleic acid label comprising a barcode will serve as a specific label for a given binding molecule, such as a peptide-MHC molecule that is multimerized to form a MHC multimer. The multimer can be composed of MHC class I, class II, CD1 or other MHC-like molecules. Thus, when the term MHC multimers is used this includes all MHC-like molecules. The MHC multimer is formed through multimerization of peptide-MHC molecules via different backbones. The barcode will be co-attached to the multimer and serve as a specific label for a particular peptide-MHC complex. In this way up to 1000 to 10.000 (or potentially even more) different peptide-MHC multimers can be mixed, allow specific interaction with T-cells from blood or other biological specimens, wash-out unbound MHC-multimers and determine the sequence of the DNA-barcodes. When selecting a cell population of interest, the sequence of barcodes present above background level, will provide a fingerprint for identification of the antigen responsive cells present in the given cell-population. The number of sequence-reads for each specific barcode will correlate with the frequency of specific T-cells, and the frequency can be estimated by comparing the frequency of reads to the input-frequency of T-cells. This strategy may expand our understanding of T-cell recognition.

In one embodiment a nucleic acid-label, DNA-label or DNA-barcode serves as a specific label for certain antigen specific T-cells and can be used to determine the specificity of a T-cell after e.g. single-cell sorting, functional analyses or phenotypical assessments. In this way antigen specificity can be linked to both the T-cell receptor sequence (that can be revealed by single-cell sequencing methods) and functional and phenotypical characteristics of the antigen specific cells.

Furthermore, this strategy may allow for attachment of several different (sequence related) peptide-MHC multimers to a given T-cell—with the binding avidity of the given peptide-MHC multimer determining the relative contribution of each peptide-MHC multimer to the binding of cell-surface TCRs. By applying this feature it is possible to allow the determination of the fine-specificity/consensus recognition sequence of a given TCR by use of overlapping peptide libraries or alanine substitution peptide libraries. Such determination is not possible with current MHC multimer-based technologies.

As previously described a pool (library) of different sets of multimeric major histocompatibility complexes (MHC's) may be used to analyze an overall cell population for its specificity for peptides. Thus, another aspect of the invention relates to a composition comprising a subset of multimeric major histocompatibility complexes (MHC's) according to the invention, wherein each set of MHC's has a different peptide, decisive for T cell recognition and a unique "barcode" region in the DNA molecule. In the present context, it is to be understood that each specific multimeric major histocompatibility complex is present in the composition with a certain number and that there is subset of different multimeric major histocompatibility complexes present in the composition.

Preferably all specific region for each multimeric MHC can be determined with only a few primer sets, preferably only one primer set. Thus, in an embodiment the primer regions in the DNA molecule are identical for each set of MHC's. In this way only one primer set is required. In an alternative embodiment, the multimeric MHC's are grouped by different primer sets, thereby allowing multiplication of different sets of the multimeric MHCs. In this way background noise may be limited, while also retrieving information of specific bindings. Thus, different primer set for different sets of MHC's may be used.

The number of individual sets of multimeric MHC's may vary. Thus, in an embodiment the composition comprises at least 10 different sets of multimeric MHC's such as at least 100, such as at least 500, at least 1000, at least 5000, such as in the range 10-50000, such as 10-1000 or such as 50-500 sets of MHC's.

Through analyses of barcode-sequence data, the antigen specificity of cells in the specimen can be determined. When DNA-barcode #1 is detected above background level of reads it means that peptide-MHC multimer #1 was preferentially bound to the selected cell type. Same goes for barcode no. 2, 3, 4, 5, . . . etc. up to the potential combination of more than 1000 (but not restricted to this particular number). When the number of input cells are known, e.g. when cell populations of interest is captured via a fluorescence signal also attached to the multimer by flow cytometry-based sorting or other means of capturing/sorting, the specific T-cell frequency can be calculated comparing the frequency of barcode-reads to the number of sorted T-cells.

In a particular embodiment the cells have not been permeabilized or lysed and therefore the detection molecules bind predominantly to the outer surface of the cells. In one embodiment the cells are intact, the cell membrane of the cells are intact.

In a particular embodiment the cells are permeable to the detection molecules wherefore the detection molecules bind to the outer surface of the cell as well as one or more components of the interior of the cell.

In a preferred embodiment, the combining of one or more cells (step a), followed by incubation to allow binding (step b), is performed in a buffer, such as a buffer selected from the group consisting of a PBS buffer, a Tris buffer, a phosphate buffer and any other buffer with appropriate ionic strength and pH, suitable for formation of the cell-detection molecule complexes.

In a preferred embodiment the detecting of the cell-detection molecule complexes is done by first spinning down the cells (and the detection molecules attached to the cells), removing the supernatant, optionally washing one or more times, and optionally amplifying the DNA oligonucleotide labels e.g. by PCR, then identifying the DNA label of the detection molecules still bound to the cells by e.g. sequencing of the DNA or by running polyacrylamide gel electrophoresis to identify different DNA oligonucleotides based on their differential migration in the gel, thereby identifying the detection molecules capable of binding cells.

As known to the skilled person, unbound molecules should preferably be removed. Thus, in an embodiment unbound (multimeric) MHC's are removed before amplification, e.g. by washing and/or spinning e.g. followed by removing of the supernatant.

The detection of the barcode in one embodiment includes sequencing of the amplified barcode regions. Thus, in an embodiment the detection of barcode regions includes sequencing of said barcode region, such as by deep sequencing or next generation sequencing.

In a preferred embodiment the isolation of cell-detection molecule complexes of step c. is done by immobilization of a population of cells by binding to a marker molecule attached to a surface such as the bottom of a well of a microtiter plate, a bead such as a magnetic polystyrene bead, or a glass plate, where the marker molecule binds to all or a subset of the cells.

In a preferred embodiment the marker molecule is an antibody against the CD8 or CD4 receptor of T cells, and the binding molecule of the detection molecule is a pMHC complex or a number of pMHC complexes, where the pMHC are of class I or class II, respectively.

In a preferred embodiment the cell-detection molecule complexes are first isolated, and then diluted and aliquoted into separate wells, under conditions where the majority of wells as a result will contain zero or one cell, and wherefore the detection molecules bound to each individual cell may be determined.

It may also be advantageously to be able to sort the cells. Thus, in an embodiment the method further comprises cell sorting by e.g. flow cytometry such as FACS. This may e.g. be done if the backbone is equipped with a fluorescent marker. Thus, unbound cells may also be removed/sorted.

In a preferred embodiment, the method is performed on known negative control cell samples (i.e. cell samples that are known to not contain cells that can bind to the detection molecules used in the method) to ensure that non-specific ("faulty") binding events occur. The method will typically be performed in parallel using two cell samples: one that contain cells that may comprise cells with binding affinity for one or more of the detection molecules; and one cell sample that does not contain cells with significant affinity for one or more detection molecules.

In a preferred embodiment, the method is performed including a negative control detection molecule (i.e. a detection molecule that is expected to not bind any of the cells).

In a preferred embodiment, the method is performed including a positive control detection molecule (i.e. a detection molecule that is expected to bind one or some of the cells).

As also known to the skilled person, the measured values are preferably compared to a reference level. Thus, in an embodiment said binding detection includes comparing measured values to a reference level, e.g. a negative control and/or total level of response in the sample. In a further embodiment, said amplification is PCR such as QPCR.

Isolating and/or Detecting Detection Molecules

Isolating detection molecules that are complexes with a certain cell, or that have been in contact with a certain cell, can be done in many ways.

In one embodiment, the detection molecules that are in contact with the cells are enriched by removing detection molecules that are not in contact with cells. This can for example be done by centrifugation of the mixture of detection molecules and cell, whereby cells are precipitated along with the detection molecules that bind them. When the supernatant is then removed, the detection molecules that do not bind the cells are removed. As a result, the detection molecules that bind the cells are enriched for.

In one embodiment the incubation mixture of detection molecules and cells is centrifuged, in order to precipitate the cells, and thereby the detection molecules bound to the cells. When the supernatant is the removed, the detection molecules that did not bind to cells are removed as well. Optionally, one may repeat centrifugation and resuspension one or more times, and then finally the enriched pool of detection molecules can be examined, e.g. the identity and quantity of the recovered detection molecules may be determined.

In one embodiment the incubation mixture of detection molecules and cells is centrifuged, in order to precipitate the cells, and thereby the detection molecules bound to the cells. When the supernatant is then removed, the detection molecules that did not bind to cells are removed as well. Optionally, one may repeat centrifugation and resuspension one or more times, and then finally the enriched pool of detection molecules can be examined, e.g. the identity and quantity of the recovered detection molecules may be determined. In one embodiment the resulting detection molecules, still bound to cells, may be released from the cells, by e.g. mild acid or mild base treatment or protease treatment if the binding molecule or linker is a peptide. Once released, the detection molecules may be examined by hybridization to an array of anti-sense molecules. For example, if the labels of e.g. 100 detection molecules are oligonucleotide labels of different sequence, the array can comprise the corresponding 100 complementary sequences, positioned in a way so that a given position or area of the array comprises only oligonucleotides of a given sequence. The identity of the oligonucleotide label and hence the detection molecule to which it is bound, can then be determined when examining to which position in the array that it anneals.

In another embodiment of the above embodiment, the cells and detection molecules are not separated before applying the cell-detection molecule complexes to the array. As a result, the cells will become immobilized on the array at those positions where the sequence of the oligonucleotide label of the detection molecule bound to said cell is complementary to the oligonucleotide of the array. This way, both the identity of the recovered detection molecules, as well as the number of cells capable of binding said detection molecules, can be deduced from the array.

In the two embodiments immediately above, the binding of detection molecules to the array is detected for example by adding antibodies that bind the binding molecule, and then staining these antibodies using secondary antibodies and e.g. chromophores or fluorophores as a readout, using standard procedures. Alternatively, the detection molecule can simply carry a signal molecule, such as a fluorophore.

In one embodiment the incubation mixture of detection molecules and cells is centrifuged, under conditions and buffer choice where a gradient develops in the centrifugation vial. As a result of the gradient being established in the centrifugation vial, the cells and detetion molecules and cell-detection molecule complexes will be distributed along the gradient according to their weight and volume. Different cell types with different characteristics will locate to different positions in the gradient. Therefore, cells of different kinds, along with the detection molecules that bind to them, can be recovered from specific positions along the gradient. Unbound detection molecules will locate far from the cells. After collecting the cells and detection molecules bound to these cells, from a given position in the gradient, the identity and quantity of the recovered detection molecules may be determined.

In one embodiment the incubation mixture of detection molecules and cells is applied to a filter that retains structures of same or larger size than cells, and let smaller structures and molecules pass through. The retained cells may be resuspended and applied to the filter one or more times. Finally, the identity and quantity of the recovered detection molecules, i.e. the detection molecules that bound to the cells, may be determined.

In one embodiment the detection molecules are incubated with a solid sample comprising cells, such as a tissue section or biopsy. After incubation, the solid tissue or biopsy is washed one or more times, to remove unbound detection molecules. Finally, the remaining detection molecules, bound to cells of the solid tissue, can be identified and quantified by determining the identity and amount of label remaining on the solid tissue.

In one embodiment, the detection molecules that are capable of binding certain cells are isolated by immobilizing said cells on e.g. beads, for example coated with an antibody specific for said cells (e.g. beads coated with anti-CD4 antibodies to specifically examine binding of detection molecules to CD4 T cells). When the cells have been immobilized on the beads, the beads are washed a couple of times to remove unbound or weakly bound detection molecules. The enriched pool of detection molecules, each of which are capable of binding the immobilized cells, can then be identified and quantified by identification and quantification of their respective labels.

In one embodiment, both the ability to secrete certain molecules, as well as the ability to bind specific detection molecules, is used as a means of enrichment of certain detection molecules. For example, if certain T cells of a cell sample are stimulated to secrete INF-γ (e.g by addition of free peptides to the cell suspension, or by binding of MHC multimers such as Dextramers or tetramers), and if bi-specific antibodies, recognizing both a T cell-specific protein on the cell surface, and INF-γ, are added, the secreted INF-γ will be captured by the bi-specific antibody and become immobilized on the cell surface. If then beads, coated with anti-INF-γ antibody recognizing another face of INF-γ are added, the cells that secrete INF-γ will become immobilized on the beads. If then detection molecules comprising pMHC binding molecules are added to the cell/bead suspension, detection molecules capable of binding T cells will become immobilized on the beads as well. After washing to remove unbound detection molecules, the detection molecules binding to T cells that were secreting INF-γ, can be recovered. Finally, the identity and amount of the recovered detection molecules can be determined by identifying the label of the recovered detection molecules. Thus, in this approach, the detection molecules are identified that bind to T cells, where said T cells are known to secrete INF-γ.

In one embodiment, the detection molecules carry both binding molecules (e.g. pMHC complexes) and anti-INF-γ antibody. INF-γ will be secreted from certain cells as a result of the stimulation brought about by the binding of the detection molecule (i.e. brought about by the binding of the pMHC binding molecule), and the secreted INF-γ will be captured on detection molecules bound to the same cell. These cells may be immobilized on beads carrying anti-INF-γ antibodies. After washing to remove unbound detection molecules, the detection molecules binding to T cells that were secreting INF-γ, can be recovered. Finally, the identity and amount of the recovered detection molecules can be determined by identifying the label of the recovered detection molecules. Thus, in this approach, the detection molecules are identified that bind to T cells, where said T cells are known to secrete INF-γ.

In one embodiment, the detection molecules that are capable of binding certain cells are isolated by applying the incubation mixture of cells and detection molecules to an affinity column, e.g. carrying antibodies or other proteins that bind to a certain cell membrane protein of said cells (where the cell membrane protein is indicative of the cell being e.g. in a certain development stage, a certain stage in the mitotic cycle, or indicative of the cell being of a certain kind). It is of course important that the column material allows the cells to migrate relatively unhindered through the column unless they bind to the affinity target (e.g. antibody) on the column. The cells that bind to the affinity column will migrate slower through the column and can be recovered from the later column fractions. The detection molecules that do not bind cells will flow through much faster than the cells, and can be recovered in early fractions. The enriched pool of detection molecules, each of which are capable of binding the immobilized cells, can then be identified and quantified from the later fractions, by identification and quantification of their respective labels.

In one embodiment, the detection molecules that are capable of binding certain cells are isolated by immobilizing all the detection molecules recovered after washing cells. Thus, in this embodiment, the detection molecules that are not bound to a cell are removed, by recovering the cell (e.g. by centrifugation, filtration through a filter that allows molecules but not cells to pass through, or any other means that recovers the cells (and the detection molecules bound to them) but does not recover the unbound detection molecules. The recovered cells may be re-suspended and the centrifugation/filtration process repeated, and then the recovered cells with detection molecules bound are immobilized on a surface (e.g. a microtiter-plate well coated with antibodies that recognize and bind detection molecules) or a bead (e.g. a bead coated with antibodies that recognize and bind detection molecules), or are precipitated by adding primary antibodies that bind detection molecules, and secondary antibodies that bind the primary antibodies, thus resulting in the formation of large aggregates of cells, detection molecules, and primary and secondary antibodies, which can easily be precipitated. Finally, the identity and quantity of each kind of recovered detection molecule is determined.

In one embodiment involving the isolation of detection molecules that are capable of binding to certain cells, flow-activated cell sorting (FACS) is used. For example, the detection molecule may, in addition to a linker, binding molecule and label, comprise a fluorescent moiety (i.e. a fluorophore). Detection molecules and cells are incubated, and those cells that are bound by a (fluorescent) detection molecule can be identified and collected by a flow activated cell sorter (FACS). Thus, after sorting, the detection molecules that were capable of binding to cells, are collected together with the cells they bind to. The identity and amount of the recovered binding molecules can then be identified by identification and quantification of the corresponding labels.

In one embodiment, the invention is used to perform single-cell phenotyping and/or analysis. Thus, most of the abovementioned isolation procedures, in which (a subset of) cells are isolated, e.g. by centrifugation, FACS sorting, or bead immobilization, the cells may (following their enrichment) be diluted and placed in separate containers (e.g. separate wells of a microtiter-plate well), at a dilution where there is on average significantly less than one cell per well. Consequently, those wells comprising one cell can be used to do single-cell phenotyping, by identifying the labels (and hence the detection molecules) associated with the one cell present in the well.

In one embodiment, the binding molecule binds to an intracellular target, e.g. a protein or a mRNA. For such cases, the detection molecule needs to become intracellularized, either as a means of active or passive transport across the fully functional membrane, or as a result of the cells having been mildly permeabilized. The cells may be permeabilized using standard methods such as those used routinely in intracellular staining (ICS) procedures.

Detecting detection molecules that are complexed with a certain cell, or that have been in contact with a certain cell, can be done in many ways.

In one embodiment, the detection molecules that are or have been in contact with the cells are marked specifically. In one embodiment the detection molecules carry DNA oligonucleotide labels ("label DNA") of different lengths, i.e. the length of the DNA label identifies the detection molecule. The surface of the sample cells is coated with DNA oligonucleotides ("coating DNA"), for example by adding antibody-DNA conjugates where the antibody recognizes a particular cell surface structure.

The "label DNA" and "coating DNA" have complementary regions in their 3'-ends but the 3'-end of "label DNA" is blocked and cannot serve as primer for an extension reaction. When a detection molecule binds the DNA coated cells, the "label DNA" is brought into proximity of the "coating DNA", allowing the complementary 3'ends to anneal. When a polymerase and radioactive nucleosides are added, the strand complementary to the "label DNA" is generated by extension from the 3'end of "coating DNA". DNA is then purified from the mixture and applied to an appropriate gel, allowing separation of the radioactive DNA fragments. The identity and amount of the labels (and hence the corresponding detection molecules) can be determined from the position and intensity of the band on the gel.

In one embodiment, the detection molecules that have been in contact with cells are marked specifically. In one embodiment the detection molecules carry peptide labels.

The peptide label consists of a coding region and a protease cleavage site proximal to the linker that connects the label to the binding molecule. The surface of the sample cells is coated with proteases capable of cleaving the peptide labels, for example by adding antibody-protease conjugates where the antibody recognizes a particular cell surface structure. Thus, when the detection molecules bind to the sample cells, they are brought into proximity of the protease, which results in cleavage of the label and release of the coding region from the detection molecule and hence, release from the cells. After centrifugation to precipitate the cells, the supernatant can be analysed by mass spectrometry to determine the identity and amount of the labels that were released from the cells, and hence, the identity and amount of detection molecules that bound to the cells in question.

In one embodiment, the detection molecules that have been in contact with cells are marked, allowing their enrichment and analysis. For example, if the detection molecule carries—in addition to the binding molecule, linker and label—an enzyme catalyzing the transfer of a cell surface moiety (e.g. a peptide fragment) from a cell surface protein to the binding molecule of the detection molecule, when said surface protein binds to the binding molecule. This peptide tag that has been added to the binding molecule, can then be used as a means of isolating all the detection molecules that have been in contact with said cell surface protein (e.g. by purifying the tagged detection molecules by applying the incubation mixture to beads coated with anti-peptide tag antibodies). Finally, the isolated detection molecules can be identified by identification and quantification of their labels.

Determining the Identity of the Label

The identity of the label and thereby the identity of the binding molecule, may be determined from the label's physical characteristics, such as its mass, composition or sequence, charge, volume, size and dimensions, fluorescence, absorption, emission, NMR spectrum, and many other physical characteristics.

The mass of a label can be determined by e.g. mass spectrometry.

The composition of a label can be determined by degradation to its components (e.g a peptide being degraded to its amino acid residues), and the amounts of each of its components be determined by e.g. chemical methods (e.g. specific reactions), whereby the composition can be determined.

The sequence of a polymer can be determined by appropriate sequencing methods. Thus, for peptides the sequence can be deduced by standard peptide sequencing methods (e.g. Edman degradation). Likewise, for natural oligonucleotides the sequence can be determined using standard sequencing reactions, involving chemical or enzymatic procedures. Oligonucleotides comprising certain unnatural nucleotides may also be sequenced by some of these methodologies.

The sequence and amount of an oligonucleotide can also be determined by measuring its ability to anneal to complementary oligonucleotide sequences. This principle is applied in Q-PCR, where a polymerase chain reaction is performed. Here, forward and reverse primers are added to the composition of labels, whereafter the amount corresponding (complementary) oligonucleotide template (label) can be determined by determining the amount of double-stranded PCR product generated at different stages (number of cycles) of the PCR reaction.

Where a composition of detection molecules carry labels of similar size and/or mass, but different charge, these may be separated and identified and their relative amounts determined by e.g. running them on a gel. If the labels are of similar size and dimension, and if the labels migrate from the negative to positive electrode, the labels with the highest negative charge will migrate the fastest through the gel. The relative amounts of the different labels are reflected in the density, optionally staining density if the gel is stained after electrophoresis, of the different bands on the gel.

The volume, size and dimensions of a label molecule determines how fast it will flow through a column. For some column types, the largest molecules flow through the column the fastest (e.g. gel filtration columns). For other column types, the largest molecules flow through the slowest. Both column types can be used to separate and identify and determine the relative amounts of different labels, by applying the composition of labels to the top of the column, and measuring the flow-through time for each of the labels, as well as the amount of label detected in a given fraction.

Labels emitting any kind of radiation can be identified and quantified from its spectrum of emission and intensity of radiation. Detection of radiation is used in e.g. flow cytometers and spectrophotometers.

Labels can also be identified and quantified from their NMR signal.

Binding of Detection Molecules can be Detected using Various Principles:

Fluidic samples are one embodiment of the present invention where binding and detection of binding molecules can be used to make a diagnostic analysis. One or more defined structures may be measured.

Often entities like cells or other particles in a sample are detected by binding molecules associated to surface receptors or intracellular structures of the cell or binding structures exposed on the bead One way to analyse fluidic samples is using flow cytometry. In flow cytometry, the sample is a suspension of entities, which are moved to and centered in the flow cell (interrogation point) by co-flow with sheath fluid, or is directly injected into the instrument.

Liquid cell samples can be analyzed using a flow cytometer, able to detect and count individual cells passing in a stream through a laser beam. For identification of specific cells in a sample, cells are tagged with fluorescent labeled detection molecules by incubating cells with labelled detection molecule and then force the cells with a large volume of liquid through a nozzle creating a stream of individually spaced cells. Each cell passes through a laser beam and during the passage the laser light is scattered and any fluorochrome bound to the cell is excited and thereby fluoresce. Sensitive photomultipliers detect emitted fluorescence and thereby gives information of binding detection molecules to the surface of a given cell. By this method labelled detection molecules can be used to identify specific cell populations in cell samples of any individual. In here the term "labeling" of cells with labelled detection molecules is used interchangeably with the term "staining".

Flow cytometry allows detection of a single entity with a specified set of characteristics, within a population of entities with other sets of characteristics. A major advantage of flow cytometry is that it allows rapid analysis of multiple parameters for each individual entity, simultaneously.

Another example of a method measuring binding of labeled binding molecules (detection molecules) to structures in fluidic samples is detection of cells or particles in the sample by binding labeled binding molecule followed by identification of labeled structures using microscopy include light microscopy, immunofluorescence microscopy, confocal microscopy or other forms of microscopy. Basically the fluidic sample is stained with labeled binding molecule and non-binding binding molecule removed by washing. Then the sample is spread out on a slide or similar in a thin layer and labelled cells identified using a microscope.

Measurement of detection molecule can also be used on solid samples. Example solid sample include but is not limited to solid tissue, blocks of solid tissue, slices of solid tissue, cells or particles embedded in a solid matrix or any other solid or semisolid sample.

Solid samples are typically analysed by placing them in instruments as blocks or in the form of thin slide of material on e.g. a glass plate. Solid material can then be labeled by binding detection molecule and the amount of bound detection molecule measured.

An example of a method measuring binding of detection molecule to solid sample is immunohistochemistry. This assay technique involves immobilization of the tissue slice on a glass slice, carrying the sample through the assay steps to the final analysis.

The means of detection typically involve photometric methods, microcopy and/or digital scanning of the sample. It may be simple light or fluorescence microscopy, for determination of chemiluminescence, morphology, shape, and fluorescence. Also, laser scanning techniques may be employed, where confocal microscopy or standard light microscopy is employed to give a 3- and 2-dimensional picture, respectively, of the sample. A digital image may be acquired, whereby the individual features e.g. light intensity at a given area of the sample can be determined.

Another example of a method measuring binding of detection molecule to solid sample is immunoelectron microscopy. In this technique detection molecules labeled with gold particle are applied to thin section of sample which are then examined in a transmission electron microscope. This method is used to detect intracellular location of structures or particular matter in a sample at high resolution.

Samples can also be attached to solid support and then incubated with detection molecule and bound detection molecule measured. Alternatively detection molecule of interest is bound to structure in sample before immobilization of sample to solid support. This principle is especially useful for binding detection molecules in solution to its binding partner in fluidic samples but can also be used on solid samples.

Below different principles for measurement of binding detection molecule to sample immobilized to solid support is listed.

Molecule of interest is immobilized on solid support and detected using labeled marker. Alternatively the sample is first labeled and then immobilized on solid support. An example is ELISA based and Radioimmuno based assays. In both assays the immobilized sample is incubated with detection molecule (or the sample is incubated with detection molecule and then immobilized on solid support), then non-binding detection molecule is removed by washing. Bound detection molecule is measured. The detection molecule may be labeled directly or indirectly. In ELISA the label is most often an enzyme while in radioimmuno assays the label is a radioactive molecule. Other labeling molecules may also be used like fluorochromes, chromophores or other molecules that can be measured. Useful labeling molecules are described elsewhere herein.

Structure of interest in sample is catched by its partner; the specific detection molecule that is immobilized on solid support. Bound sample or part of sample is then detected using a labeled marker specific for the same or a different structure in the bound sample.

Different detection molecules to two or more structures of interest in same sample are immobilized on solid support in a defined pattern. Structures of interest in sample are bound to the defined areas of the support and are detected by a labeled marker. Each individual structure binds to different partners immobilized in different positions on the solid support. Thereby the sample may be phenotyped.

Two or more solid supports (e.g. beads) with different characteristics (e.g. size, fluorescence, fluorescence intensities, labels), where each kind of bead has a specific detection molecule immobilized. Structures of interest in sample are bound to specific populations of beads, where each bead population is defined by the detection molecule they have immobilized. The different populations of beads are detected through their special characteristics.

The sample analysed by the above described methods may first be subjected to another analysis e.g. separation according to size. An example is Blotting techniques were molecular structures of a sample are first separated according to size and then transferred to a solid support followed by detection with labeled detection molecule. Depending on the structure to be analysed different forms of blotting exist, e.g. Western blotting for analysis of proteins, Northern blotting for analysis of RNA and Southern blotting for analysis of DNA.

Binding may also be measured without using labeled detection molecules for detection. A sample may be captured by immobilized binding molecule, then eluted and quantified. Usually the starting point is a sample in solution, such as a cell lysate, growth medium or blood. The molecule or structure of interest will have a well known and defined property which can be exploited during the binding process. The process itself can be thought of as an entrapment, with the target molecule becoming trapped on a solid or stationary phase or medium. The other molecules in solution will not become trapped as they do not possess this property. The solid medium can then be removed from the mixture, washed and the target molecule released from the entrapment in a process known as elution. Binding to the solid phase may be achieved by column chromatography, whereby the solid medium is packed onto a chromatography column, the initial mixture run through the column to allow binding, a wash buffer run through the column and the elution buffer subsequently applied to the column and collected. These steps are usually done at ambient pressure (as opposed to HPLC or FPLC).

Alternatively binding may be achieved using a batch treatment, by adding the initial mixture to the solid phase in a vessel, mixing, separating the solid phase (by centrifugation for example), removing the liquid phase, washing, re-centrifuging, adding the elution buffer, re-centrifuging and removing the eluate.

Sometimes a hybrid method is employed, the binding is done by the batch method, then the solid phase with the target molecule bound is packed onto a column and washing and elution are done on the column.

A third method, expanded bed adsorption, which combines the advantages of the two methods mentioned above, has also been developed. The solid phase particles are placed in a column where liquid phase is pumped in from the bottom and exits at the top. The gravity of the particles ensures that the solid phase does not exit the column with the liquid phase.

Following elution the purified or enriched molecule or structure can be quantitated, enriched further or used in new analytical processes or treatment processes.

Measurement of alteration of physical state of sample or structure in sample upon binding molecule. For example addition of binding molecule to a fluidic sample may induce cross-linking of structures, clumping and/or aggregation of sample. E.g. antibodies or other binding molecules can bind large particles and make the particle to clump or agglutinate. The antibody or other molecule binds multiple particles and joins them, creating a large complex.

Similar addition of binding molecule to solid sample may make the solid sample becoming semi solid, fluidic or in another way change texture.

Other physical characteristics may be changed as a consequence of addition of binding molecule to sample and if measureable they can be used for analysis of sample.

An example of a specific assay measuring alteration in the physical state of a sample upon addition of binding molecule is turbidimetry. This is a method for determining the concentration of a substance in a solution by the degree of cloudiness or turbidity it causes or by the degree of clarification it induces in a turbid solution.

Indirect measurement of binding is measurement of the result of the interaction between binding molecule and structure in sample in contrast to direct measurement of the binding molecule bound in sample. The result of interaction between binding molecule and structure in sample can be measured in several ways indirect ways.

Measurement of produced substance. Upon binding of binding molecule to structure in sample the sample may release and/or produce a substance that can be measured. Depending on the nature of the sample different principles exists The produced substance may be measured in solution either directly or by detection with a labeled detection molecule. The produced substance may be easily accessible for detection or alternatively need to be extracted from sample before measurement is possible.

One example of measurement of produced substance in solution is Polymerase Chain reaction (PCR). In this method fragments of DNA in solution are amplified by binding DNA primers (binding molecules) to defined areas of the DNA in sample. The amount of amplified DNA is then measured.

Another example is measurement of produced soluble substance inside cells using intracellular flow cytometry. This can be done using block of secretion of soluble substance (e.g. by monensin), permeabilization of cell (by e.g. saponine) followed by immunofluorescent staining. The method involves the following steps: 1) An reagent able to block extracellular secretion of cytokine is added, e.g. monensin that interrupt intracellular transport processes leading to accumulation of produced soluble factor, e.g. cytokine in the Golgi complex. 2) Fixation of cell membrane using mild fixator followed by permeabilization of cell membrane by. e.g. saponine. 3) Addition of labelled detection molecule specific for the produced soluble substance to be determined. 5) Measurement of labelled cells using a flow cytometer. Optionally this analysis can be combined with labeling with detection molecules specific for surface exposed structures. If so these detection molecules are added before step 2.

An alternative to this procedure is to trap secreted soluble factors on the surface of the secreting cells followed by detection with specific detection molecules as described by Manz, R. et al., Proc. Natl. Acad. Sci. USA 92:1921 (1995).

The produced substance may be immobilized to solid support followed by detection using labeled marker. Principles for immobilization and detection are as described elsewhere herein for immobilization of samples and direct detection An example of indirect detection of produced substance immobilized on solid support is measurement of substances secreted from stimulated cells by capture of the secreted substance on solid support followed by detection with labeled detection molecule. Secreted soluble substance in the supernatant is immobilized on solid support either directly or through a linker molecule. The cells may be stimulated by addition of other cells to the sample, addition of antigens (peptides/proteins) to the sample, addition of stimulatory proteins or other molecules or stimulated by other means. The amount of secreted substance can be measured in different ways:

Soluble substances secreted from individual cells can be detected by capturing of the secreted soluble substances locally by detection molecules, e.g. antibody specific for the soluble substance. Soluble substance recognizing detection molecules are then immobilised on a solid support together with cells and soluble substances secreted by individual cells are thereby captured in the proximity of each cell. Bound soluble substance can be measured using labelled detection molecule specific for the captured soluble substance. The number of cells that has given rise to labelled spots on solid support can then be enumerated and these spots indicate the presence of specific cells that have been stimulated with particular stimulator.

Soluble substances secreted from a population of cells are detected by capture and detection of soluble substance secreted from the entire population of specific cells. In this case soluble substance do not have to be captured locally close to each cell but the secreted soluble substances may be captured and detected in the same well as where the cells are or transferred to another solid support with detection molecules for capture and detection e.g. beads or wells of ELISA plate.

The produced substance is measured directly in solid sample using principles as described for solid samples elsewhere herein.

Measurement of effector function in sample. Binding of binding molecule may also result in changes in effector function of sample. Effector function is inhere any function of sample or produced in sample. This type of measurement is only relevant for samples comprising living cells, living organisms or other living material. Examples of effector function of/in a sample include but are not limited to cytolytic activity, catalytic activity, ability to stimulate other cells or samples or ability to induce apoptosis in sample itself or in other samples.

An example is measurement of activation of T cells in a sample by measurement of cytolytic activity of the T cell in a cytolytic assay, e.g. a chromium release assay.

Measurement of growth. Binding of binding molecule may induce or inhibit growth in a sample. This type of measurement is only relevant for samples comprising living cells, living organisms or other living material. In cell samples growth can be measured as proliferation of cells in the sample.

Examples of methods useful for measuring proliferation include but are not limited to:

Detection of mRNA. Proliferation of T cells can be detected by measurement of mRNA inside cell. Cell division and proliferation requires production of new protein in each cell which as an initial step requires production of mRNA encoding the proteins to be synthesized.

Detection of incorporation of thymidine. The proliferative capacity of T cells in response to stimulation by MHC multimer can be determined by a radioactive assay based on incorporation of [3H]thymidine ([3H]TdR) into newly generated DNA followed by measurement of radioactive signal.

Detection of incorporation of BrdU. Cell proliferation can also be detected by of incorporation of bromo-2'-deoxyuridine (BrdU) followed by measurement of incorporated BrdU using a labeled anti-BrdU antibody in an ELISA based analysis.

Viability of cells may be measured by measurement ATP in a cell culture.

Separation According to Size, Structure or Other Physical Characteristics

Properties of a sample can also be determined by measuring size and/or structure of sample. Below different methods based on different principles are listed.

Gel Electrophoresis

Gel electrophoresis is a technique used for the separation of deoxyribonucleic acid, ribonucleic acid, or protein molecules using an electric current applied to a gel matrix. The term "gel" in this instance refers to the matrix used to contain and separate the target molecules. In most cases the gel is a crosslinked polymer whose composition and porosity is chosen based on the specific weight and composition of the target to be analyzed. When separating proteins or small nucleic acids (DNA, RNA, or oligonucleotides) the gel is usually composed of different concentrations of acrylamide and a cross-linker, producing different sized mesh networks of polyacrylamide. When separating larger nucleic acids (greater than a few hundred bases), the preferred matrix is purified agarose. In both cases, the gel forms a solid, yet porous matrix. Acrylamide, in contrast to polyacrylamide, is a neurotoxin and must be handled using appropriate safety precautions to avoid poisoning.

"Electrophoresis" refers to the electromotive force (EMF) that is used to move the molecules through the gel matrix. By placing the molecules in wells in the gel and applying an electric current, the molecules will move through the matrix at different rates, usually determined by mass, toward the positive anode if negatively charged or toward the negative cathode if positively charged.

After the electrophoresis is complete, the molecules in the gel can be stained to make them visible. Ethidium bromide, silver, or coomassie blue dye may be used for this process. Other methods may also be used to visualize the separation of the mixture's components on the gel. If the analyte molecules fluoresce under ultraviolet light, a photograph can be taken of the gel under ultraviolet lighting conditions. If the molecules to be separated contain radioactivity added for visibility, an autoradiogram can be recorded of the gel.

If several mixtures have initially been injected next to each other, they will run parallel in individual lanes. Depending on the number of different molecules, each lane shows separation of the components from the original mixture as one or more distinct bands, one band per component. Incomplete separation of the components can lead to overlapping bands, or to indistinguishable smears representing multiple unresolved components.

Bands in different lanes that end up at the same distance from the top contain molecules that passed through the gel with the same speed, which usually means they are approximately the same size. There are molecular weight size markers available that contain a mixture of molecules of known sizes. If such a marker was run on one lane in the gel parallel to the unknown samples, the bands observed can be compared to those of the unknown in order to determine their size. The distance a band travels is approximately inversely proportional to the logarithm of the size of the molecule.

Gel electrophoresis is usually performed for analytical purposes, but may be used as a preparative technique prior to use of other methods such as mass spectrometry, RFLP, PCR, cloning, DNA sequencing, or Southern blotting for further characterization.

Depending on the type of material to be separated different techniques may be used some of these are listed below:

Polypeptide length can be determined by SDS PAGE. The solution of proteins to be analyzed is first mixed with SDS, an anionic detergent which denatures secondary and non-disulfide-linked tertiary structures, and applies a negative charge to each protein in proportion to its mass. Without SDS, different proteins with similar molecular weights would migrate differently due to differences in mass charge ratio, as each protein has an isoelectric point and molecular weight particular to its primary structure. This is known as Native PAGE. Adding SDS solves this problem, as it binds to and unfolds the protein, giving a near uniform negative charge along the length of the polypeptide.

SDS binds in a ratio of approximately 1.4 g SDS per 1.0 g protein (although binding ratios can vary from 1.1-2.2 g SDS/g protein), giving an approximately uniform mass:charge ratio for most proteins, so that the distance of migration through the gel can be assumed to be directly related to only the size of the protein. A tracking dye may be added to the protein solution to allow the experimenter to track the progress of the protein solution through the gel during the electrophoretic run.

Native Gel Electrophoresis is a technique used mainly in protein electrophoresis where the proteins are not denatured and therefore separated based on their charge-to-mass ratio. The two main types of native gels used in protein electrophoresis are polyacrylamide gels and agarose gels.

Polyacrylamide gel electrophoresis (PAGE) is used for separating proteins ranging in size from 5 to 2,000 kDa due to the uniform pore size provided by the polyacrylamide gel. Pore size is controlled by controlling the concentrations of acrylamide and bis-acrylamide powder used in creating a gel. Care must be used when creating this type of gel, as acrylamide is a potent neurotoxin in its liquid and powdered form. The other type of gel used is agarose gel. Agarose gels can also be used to separate native protein. They do not have a uniform pore size, but are optimal for electrophoresis of proteins that are larger than 200 kDa.

Unlike SDS-PAGE type electrophoreses, Native gel electrophoresis does not use a charged denaturing agent. The molecules being separated (usually proteins) therefore differ in Molecular mass and intrinsic charge and experience different electrophoretic forces dependent on the ration of the two. Since the proteins remain in the native state they may be visualised not only by general protein staining reagents but also by specific enzyme-linked staining.

QPNC-PAGE, or quantitative preparative native continuous polyacrylamide gel electrophoresis, is a high-resolution technique applied in biochemistry and bioinorganic chemistry to separate proteins by isoelectric point. This variant of gel electrophoresis is used by biologists to isolate active or native metalloproteins in biological samples and to resolve properly and improperly folded metal cofactor-containing proteins in complex protein mixtures Determination of size of DNA or RNA fragments, e.g. agarose gel electrophoresis Separation of proteins according to mass and isoelectric point, e.g. 2D gel electrophoresis. Two-dimensional gel electrophoresis, abbreviated as 2-DE or 2-D electrophoresis, is a form of gel electrophoresis where mixtures of proteins are separated by two properties in two dimensions on 2D gels.

2-D electrophoresis begins with 1-D electrophoresis but then separates the molecules by a second property in a direction 90 degree from the first. In 1-D electrophoresis, proteins (or other molecules) are separated in one dimension, so that all the proteins/molecules will lie along a lane but be separated from each other by a property (e.g. isoelectric point). The result is that the molecules are spread out across a 2-D gel. Because it is unlikely that two molecules will be similar in two distinct properties, molecules are more effectively separated in 2-D electrophoresis than in 1-D electrophoresis.

The two dimensions that proteins are separated into using this technique can be isoelectric point, protein complex mass in the native state, and protein mass.

Chromatography

Chromatography is another method to separate structures according to size, structure or other physical characteristics. In principle a sample dissolved in a "mobile phase" is passed through a stationary phase, which separates the analyte to be measured from other molecules in the mixture and allows it to be isolated.

Below different types of chromatography is listed
Column chromatography
Ion exchange chromatography
Size exclusion chromatography
Liquid chromatography (LC, HPLC)
Gas chromatography
Planar chromatography
Paper chromatography
Thin layer chromatography
Separation Based on Chemical Properties Samples can also be analysed be analyzing their chemical composition. The chemical composition of the whole sample med be determined, alternatively the chemical composition of fragments or individual structures of the sample is identified. Often this type of analysis are preceded by one or more other diagnostic or analytical methods e.g. separation according to size.

An example of this type of analysis is mass spectrometry. Mass spectrometry is an analytical technique that identifies the chemical composition of a compound or sample on the basis of the mass-to-charge ratio of charged particles. The method employs chemical fragmentation of a sample into charged particles (ions) and measurements of two properties, charge and mass, of the resulting particles, the ratio of which is deduced by passing the particles through electric and magnetic fields in a mass spectrometer. The design of a mass spectrometer has three essential modules: an ion source, which transforms the molecules in a sample into ionized fragments; a mass analyzer, which sorts the ions by their masses by applying electric and magnetic fields; and a detector, which measures the value of some indicator quantity and thus provides data for calculating the abundances each ion fragment present. The technique has both qualitative and quantitative uses, such as identifying unknown compounds, determining the isotopic composition of elements in a compound, determining the structure of a compound by observing its fragmentation, quantifying the amount of a compound in a sample using carefully designed methods (e.g., by comparison with known quantities of heavy isotopes), studying the fundamentals of gas phase ion chemistry (the chemistry of ions and neutrals in vacuum), and determining other physical, chemical, or biological properties of compounds.

Measurement of Catalysis

Catalysis is the process in which the rate of a chemical reaction is increased by means of a chemical substance known as a catalyst. Unlike other reagents that participate in the chemical reaction, a catalyst is not consumed. Thus, the catalyst may participate in multiple chemical transformations, although in practice catalysts are sometimes consumed in secondary processes. Examples of catalysis include but are not limited to:

Measurement of enzymatic activity
Measurement of induction of enzymatic activity
Measurement of inhibition of enzymatic activity
Measurement of substrate for enzyme in a sample
Measurement of Growth Growth is another parameter that can be measured in a sample. It can be natural growth in sample, the samples impact of growth on another sample or analysis system and/or the growth in sample after the sample has been added stimulus, inhibitor or other substance influencing growth.

Examples of measurement of growth in sample include but are not limited to:
Measurement of proliferation
Measurement of viability
Measurement of volume
Measurement of density The above described chemical assays may be combined with one or more other chemical assays in order to make the final diagnosis of the unit. The chemical assays may be applied to the sample of the unit or to different samples from the same unit.

Further Aspects Relates to Different Uses

Overall, the multimeric MHC's or compositions comprising such sets of MHC's may find different uses. Thus, an aspect relates to the use of a multimeric major histocompatibility complex (MHC) or a composition according to the invention for the detection of antigen-responsive cells in a sample.

Another aspect relates to the use of a multimeric major histocompatibility complex (MHC) or a composition according to the invention in the diagnosis of diseases or conditions, preferably cancer and/or infectious diseases.

A further aspect relates to the use of a multimeric major histocompatibility complex (MHC) or a composition according to the invention in the development of immune-therapeutics.

Yet a further aspect relates to the use of a multimeric major histocompatibility complex (MHC) or a composition according to the invention in the development of vaccines.

Another aspect relates to the use of a multimeric major histocompatibility complex (MHC) or a composition according to the invention for the identification of epitopes.

In sum, the advantages of the present invention include, without limitation, the possibility for detection of multiple (potentially, but exclusively, >1000) different antigen-responsive cells in a single sample. The technology can be used, but is not restricted, for T-cell epitope mapping, immune-recognition discovery, diagnostics tests and measuring immune reactivity after vaccination or immune-related therapies.

This level of complexity allow us to move from model antigens to determination of epitope-specific immune reactivity covering full organisms, viral genomes, cancer genomes, all vaccine components etc. It can be modified in a personalized fashion dependent of the individuals MHC expression and it can be used to follow immune related diseases, such as diabetes, rheumatoid arthritis or similar.

Biological materials are for instance analyzed to monitor naturally occurring immune responses, such as those that can occur upon infection or cancer. In addition, biological materials are analyzed for the effect of immunotherapeutics including vaccines on immune responses. Immunotherapeutics as used here is defined as active components in medical interventions that aim to enhance, suppress or modify immune responses, including vaccines, non-specific immune stimulants, immunosuppressives, cell-based immunotherapeutics and combinations thereof.

The invention can be used for, but is not restricted to, the development of diagnostic kits, where a fingerprint of immune response associated to the given disease can be determined in any biological specimen. Such diagnostic kits can be used to determining exposure to bacterial or viral infections or autoimmune diseases, e.g., but not exclusively related to tuberculosis, influenza and diabetes. Similar approach can be used for immune-therapeutics where immune-responsiveness may serve as a biomarker for therapeutic response. Analyses with a barcode labelled MHC multimer library allow for high-throughput assessment of large numbers of antigen responsive cells in a single sample.

Furthermore, barcode labelled MHC-multimers can be used in combination with single-cell sorting and TCR sequencing, where the specificity of the TCR can be determined by the co-attached barcode. This will enable us to identify TCR specificity for potentially 1000+ different antigen-responsive T-cells in parallel from the same sample, and match the TCR sequence to the antigen specificity. The future potential of this technology relates to the ability to predict antigen responsiveness based on the TCR sequence. This would be highly interesting as changes in TCR usage has been associated to immune therapy (11,12).

Further, there is a growing need for the identification of TCRs responsible for target-cell recognition (e.g., but not exclusive, in relation of cancer recognition). TCRs have been successfully used in the treatment of cancer (13), and this line of clinical initiatives will be further expanded in the future. The complexity of the barcode labeled MHC multimer libraries will allow for personalized selection of relevant TCRs in a given individual.

Due to the barcode-sequence readout, the barcode labeled MHC multimer technology allow for the interaction of several different peptide-MHC complexes on a single cell surface, while still maintaining a useful readout. When one T-cell binds multiple different peptide-MHC complexes in the library, their relative contribution to T-cell binding can be determined by the number of reads of the given sequences. Based on this feature it is possible to determine the fine-specificity/consensus sequences of a TCR. Each TCR can potential recognize large numbers of different peptide-MHC complexes, each with different affinity (14). The importance of such quantitative assessment has increased with clinical used of TCRs and lack of knowledge may have fatal consequences as recently exemplified in a clinical study where cross recognition of a sequence related peptide resulted in fatal heart failure in two cases (15,16). Thus, this particular feature for quantitative assessment of TCR binding of peptide-MHC molecules related to the present invention can provide an efficient solution for preclinical testing of TCRs aimed for clinical use.

Also related to the above, this allows for determination of antigen responsiveness to libraries of overlapping or to very similar peptides. Something that is not possible with present multiplexing technologies, like the combinatorial encoding principle. This allows for mapping of immune reactivity e.g. to mutation variant of viruses, such as, but not exclusive, HIV.

In broad embodiment, the present invention is the use of barcode labelled MHC multimers for high-throughput assessment of large numbers of antigen responsive cells in a single sample, the coupling of antigen responsiveness to functional and phenotypical characteristic, to TCR specificity and to determine the quantitative binding of large peptide-MHC libraries to a given TCR.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

It is as aspect of the invention to provide the use of barcode labelled MHC multimers for multiplex detection of different T-cell specificities in a single sample, enabling simultaneous detection of potentially more than 1000 different T-cell specificities where the specificity is revealed through sequencing of the barcode label.

It is as aspect of the invention to provide the use of barcode labelled MHC multimers in combination with single-cell sorting and TCR sequencing, where the specificity of the TCR can be determined by the co-attached barcode. This will enable identification of TCRs specific for a mixture of numerous (potentially, but not restricted to >1000) different peptide-MHC multimers, and match the TCR sequence to the antigen specificity.

It is as aspect of the invention to provide the use of barcode labelled MHC multimers for determining the affinity and binding motif of a given TCR. The barcode labelling strategy will allow for attachment of several different (sequence related) peptide-MHC multimers to a given T-cell—with the binding affinity determining the relative contribution by each peptide-MHC multimer. Thereby it is possible to map the fine-specificity/consensus recognition sequence of a given TCR by use of overlapping peptide libraries or e.g. alanine substitution libraries.

It is as aspect of the invention to provide the use of barcode labelled MHC multimers to map antigen responsiveness against sequence related/similar peptides in the same libraries, e.g. mutational changes in HIV infection. This has not been possible with previous MHC multimer based techniques.

It is as aspect of the invention to provide the use of barcode-labelled MHC multimers to couple any functional feature of a specific T-cell or pool of specific T-cells to the antigen (peptide-MHC) recognition. E.g. determine which T-cell specificities in a large pool secrete cytokines, releases Calcium or other functional measurement after a certain stimuli.

Sample

A binding molecule is a molecule that specifically associates covalently or non-covalently with a structure belonging to or associated with an entity in a sample. In one embodiment said entity is selected from the group consisting of a cell, a cell population, a sample comprising one or more cells, a molecule, a marker molecule, a surface of a biological cell, a cellular entity, and a cellular component (e.g. micelle), In an embodiment the methods of the present invention includes providing a sample such as a biological sample.

The type of sample may vary. In an embodiment the sample is a biological sample. In an embodiment the sample is a blood sample, such as an peripheral blood sample, a blood derived sample, a tissue biopsy or another body fluid, such as spinal fluid, or saliva.

The source of the sample may also vary. Thus, in a further embodiment said sample has been obtained from a mammal, such as a human, mouse, pigs, and/or horses.

In a preferred embodiment one cell may bind 1, 2-5, 6-20, 21-100, 101-1000, 1001-50000, 50000-200000, or more than 200000 detection molecules.

Each individual cell to be combined with at least one detection molecule has the capacity to bind a single or a number of detection molecules. It follows that one cell in one embodiment binds 1 detection molecule according to the invention, such as 2, 3, 4, 5, 6, 7, 8, 9, 10 detection molecules, such as binds 1-2, 2-3, 3-4, 4-5, 5-6, 6-7, 7-8, 8-9, 9-10, 10-15, 15-20, 20-25, 25-30, 30-40, 40-50, 50-75, 75-100, 100-150, 150-200, 200-250, 250-500, 500-750, 750-1000, 1000-2000, 2000-5000, 5000-10.000, 10.000-25.000, 25.000-50.000, 50.000-100.000, 100.000-250.000, 250.000-500.000, 500.000-1.000.000, or more than 1.000.000 detection molecules.

In a preferred embodiment the binding molecule specifically associates covalently or non-covalently with a structure belonging to or associated with a cell in a sample.

The sample in one embodiment is selected from the group consisting of a solid sample, a fluid sample, a semifluid sample, a liquid sample, a solubilised sample and a sample comprising dissociated cells of a solid sample.

The sample in one embodiment is selected from the group consisting of a biofilm, a biopsy, a surgical sample, a tissue sample, a microarray-fixed sample, solid tissue section such as a fresh section, a frozen section and a FFPE section.

Cell samples capable of being analyzed by detection molecules and then analysed using flow cytometry include but is not limited to blood, CSF, lymph, cell lines (e.g. hybridomas, transfected cells), semen, suspension of bacteria, suspension of viral particles, suspension of beads or other particles or supra molecular structures, homogenized tissues or any other fluidic sample from a given sample.

In one embodiment the sample is selected from the group consisting of blood, whole blood, plasma, serum, Peripheral blood mononuclear cells (PBMC), human PBMN (HPBMC), buffy coat, synovial fluid, bone marrow, cerebrospinal fluid, saliva, lymph fluid, seminal fluid, urine, stool, exudate, transdermal exudates, pharyngeal exudates, nasal secretions, sputum, sweat, bronchoalveolar lavage, tracheal aspirations, fluid from joints, vitreous fluid, vaginal or urethral secretions or semen.

Herein, disaggregated cellular tissues such as, for example, hair, skin, synovial tissue, tissue biopsies and nail scrapings are also considered as biological samples.

IN one embodiment the sample comprises one or more cells is selected from the group consisting of immune cells, lymphocytes, monocytes, dendritic cells, T-cells, B-cells and NK cells.

In one embodiment said sample comprises one or more cells selected from the group consisting of CD4+ T cells, CD8+ T cells, αβ T cells, invariant γδ T cells, an antigen-specific T-cell, antigen-responsive T cell and cells comprises T-cell receptors.

Many of the assays and methods described in the present invention are particularly useful for assaying T-cells in blood samples. Blood samples includes but is not limited to whole blood samples or blood processed to remove erythrocytes and platelets (e.g., by Ficoll density centrifugation or other such methods known to one of skill in the art) and the remaining PBMC sample, which includes the T-cells of interest, as well as B-cells, macrophages and dendritic cells, is used directly. Also included are blood samples processed in other ways e.g. isolating various subsets of blood cells by selecting or deselecting cells or entities in blood.

In one embodiment said cell is a cancer cell.

In one embodiment said sample is derived from an organ selected from the group consisting of lymph nodes, kidney, liver, skin, brain, heart, muscles, bone marrow, skin, skeleton, lungs, the respiratory tract, spleen, thymus, pancreas, exocrine glands, bladder, endocrine glands, reproduction organs including the fallopian tubes, eye, ear, vascular system, the gastrointestinal tract including small intestines, colon, rectum, canalis analis and prostate gland; normal, diseased and/or cancerous.

In one embodiment the surface of sample cells is coated with proteases capable of cleaving a peptide label, for example by adding antibody-protease conjugates where the antibody recognizes a particular cell surface structure.

In one embodiment the surface of sample cells is coated with DNA oligonucleotides ("coating DNA"), for example by adding antibody-DNA conjugates where the antibody recognizes a particular cell surface structure.

Diseases

Detection molecules of the present invention can be used in immune monitoring, diagnostics, prognostics, therapy and vaccines for many different diseases, including but not limited to the diseases listed in the following.

a) Infectious diseases caused by virus such as,

Adenovirus (subgroups A-F), BK-virus, CMV (Cytomegalo virus, HHV-5), EBV (Epstein Barr Virus, HHV-4), HBV (Hepatitis B Virus), HCV (Hepatitis C virus), HHV-6a and b (Human Herpes Virus-6a and b), HHV-7, HHV-8, HSV-1 (Herpes simplex virus-1, HHV-1), HSV-2 (HHV-2), JC-virus, SV-40 (Simian virus 40), VZV (Varizella-Zoster-Virus, HHV-3), Parvovirus B19, Haemophilus influenza, HIV-1 (Human immunodeficiency Virus-1), HTLV-1 (Human T-lymphotrophic virus-1), HPV (Human Papillomavirus giving rise to clinical manifestations such as Hepatitis, AIDS, Measles, Pox, Chicken pox, Rubella, Herpes and others.

b) Infectious diseases caused by bacteria such as,

Gram positive bacteria, gram negative bacteria, intracellular bacterium, extracellular bacterium, *Mycobacterium tuberculosis, Mycobacterium bovis, Mycobacterium avium* subsp. *Paratuberculosis, Borrelia burgdorferi, Borrelia Garinii, Borrelia Afzelii*, other spirochetes, *Helicobacter*

*pylori, Streptococcus pneumoniae, Listeria monocytogenes, Histoplasma capsulatum, Bartonella henselae, Bartonella quintana* giving rise to clinical manifestations such as Tuberculosis, Pneumonia, Stomach ulcers, Paratuberculosis and others.

c) Infectious diseases caused by fungus such as,

*Aspergillus fumigatus, Candida albicans, Cryptococcus neoformans, Pneumocystis carinii* giving rise to clinical manifestations such as skin-, nail-, and mucosal infections, Meningitis, Sepsis and others.

d) Parasitic diseases caused by parasites such as,

*Plasmodium falciparum, Plasmodium vivax, Plasmodium malariae, Schistosoma mansoni, Schistosoma japonicum, Schistosoma haematobium, Trypanosoma cruzi, Trypanosoma rhodesiense, Trypanosoma gambiense, Leishmania donovani,* and *Leishmania tropica.* e) Allergic diseases caused by allergens such as,

Birch, Hazel, Elm, Ragweed, Wormwood, Grass, Mould, Dust Mite giving rise to clinical manifestations such as Asthma.

f) Transplantation-related diseases caused by reactions to minor histocompatibility antigens such as HA-1, HA-8, USP9Y, SMCY, TPR-protein, HB-1Y and other antigens in relation to, Graft-versus-host-related disease, allo- or xenogene reactions i.e. graft-versus-host and host-versus-graft disease.

g) Cancerous diseases associated with antigens such as

Survivin, Survivin-2B, Livin/ML-IAP, Bcl-2, Mcl-1, Bcl-X(L), Mucin-1, NY-ESO-1, Telomerase, CEA, MART-1, HER-2/neu, bcr-abl, PSA, PSCA, Tyrosinase, p53, hTRT, Leukocyte Proteinase-3, hTRT, gp100, MAGE antigens, GASC, JMJD2C, JARD2 (JMJ), JHDM3a, WT-1,CA 9, Protein kinases, where the cancerous diseases include malignant melanoma, renal carcinoma, breast cancer, lung cancer, cancer of the uterus, cervical cancer, prostatic cancer, pancreatic cancer, brain cancer, head and neck cancer, leukemia, cutaneous lymphoma, hepatic carcinoma, colorectal cancer, bladder cancer.

h) Autoimmune and inflammatory diseases, associated with antigens such as GAD64, Collagen, human cartilage glycoprotein 39, β-amyloid, Aβ42, APP, Presenilin 1, where the autoimmune and inflammatory diseases include Diabetes type 1, Rheumatoid arthritis, Alzheimer, chronic inflammatory bowel disease, Crohn's disease, ulcerative colitis uterosa, Multiple Sclerosis, Psoriasis

EXAMPLES

Example A

This example relates to i) the stability of DNA oligonucleotides (DNA tag/label), used in one embodiment of the invention, in blood preparations, and ii) an embodiment of the invention, in which certain tagged Dextramers (detection molecules in which the binding molecule is a number of peptide-MHC complexes, and the label is a DNA oligonucleotide) are enriched for. Allowing identification of the Dextramers with binding specificity for certain (subpopulations of) cells in the cell sample tested.

In i) it is shown that DNA oligos are stable during handling in PBMC's and in blood for a time that will allow staining, washing and isolation of T cells and subsequent amplification of DNA tags.

In ii) Show that a model system consisting of DNA-tagged Dextramers with MHC specificities for CMV, Flu and negative control peptide will locate to and can be captured/sorted with relevant T cell specificities and can be identified by PCR amplification and/or sequencing.

Stability of Single-Stranded and Double-Stranded Oligonucleotides in Blood Preparations DNA tag oligo design. 69-nucleotide long, biotinylated TestOligo was prepared, consisting of 5'primer region (22 nt italic type, left)— random region (6×N-nt)—barcode region (21 nt underlined)—

3'primer region (20 nt italic type, right):

```
Forward-01 primer
GAGATACGTTGACCTCGTTG

Reverse-01 primer
ATGCAACCAAGAGCTTAAGT

TestOligo-01
bGAGATACGTTGACCTCGTTGAANNNNNNTCTATCCATTCCATCCAGCT
CACTTAAGCTCTTGGTTGCAT TestOligo-02
bhGAGATACGTTGACCTCGTTGAANNNNNNTCTATCCATTCCATCCAGC
TCACTTAAGCTCTTGGTTGCAT TestOligo-03
bhGAGATACGTTGACCTCGTTGAANNNNNNTCTATCCATTCCATCCAGC
TCACTTAAGCTCTTGGTTGCATh TestOligo-04
bhGAGATACGTTGACCTCGTTGAANNNNNNTCTTGAACTATGAATCGTC
TCACTTAAGCTCTTGGTTGCATh TestOligo-05
bhGAGATACGTTGACCTCGTTGAANNNNNNTCTATAGGTGTCTACTACC
TCACTTAAGCTCTTGGTTGCATh TestOligo-06
bhGAGATACGTTGACCTCGTTGAANNNNNNTCTTTATTGGAGAGCACGC
TCACTTAAGCTCTTGGTTGCATh
'b' = Biotin-TEG 5' modification
'h' = HEG (terminal modifications)
```

Q-PCR probes for quantifying the amount of TestOligos 1-6:

+=locked nucleic acid (LNA) modified RNA nucleotide

LNA-3

8=FAM; 7=BHQ-1-plus TCT[+A][+T][+C]A[+T][+T]CC[+A][+T][+C]CAGC

LNA-4

8=FAM; 7=BHQ-1-plus TCT[+T][+G][+A]AC[+T][+A]TG[+A][+A][+T]CGTC

LNA-5

9=HEX; 7=BHQ-1-plus TCT[+A][+T][+A]GG[+T][+G]TC[+T][+A][+C]TACC

LNA-6

2=Cy5; 1=BHQ-2-plus TCT[+T][+T][+A]TT[+G][+G]AG[+A][+G][+C]ACGC

The stability of oligo-tags by Q-PCR was analyzed under conditions relevant for T cell isolation:

The testOligos 1-6 were incubated in anticoagulated EDTA blood, and following incubation the amount of each of the testOligos was determined using Q-PCR using the abovementioned primers and probes. The oligo tags were quantified by QPCR with SYBR® Green JumpStart™ Taq ReadyMix™ according to manufacturer's protocol in combination with any capillary QPCR instruments (e.g. Roche LightCycler or Agilent Mx3005P).

Because of the different termini of the testOligos 1-6, this also was a test of the stability of non-modified DNA oligo tag vs HEG modified 5' and HEG modified 5' and 3' (TestOligo-01, -02 and -03 respectively).

The results are shown in FIG. 8. It is concluded that the stability of the testOligos is appropriately high for all variants tested, to perform the invention.

Generation and screening of a 3 member DNA tagged MHC Dextramer library for screening of antigen specific T cells in a lymphoid cell sample This experiment involves the generation of 3 DNA-tagged Dextramers, each with a unique specificity, as follows:

Dextramer 1: Flu (HLA-A*0201/GILGFVFTL/MP/Influenza)

Dextramer 2: CMV (HLA-A*0201/NLVPMVATV/pp65/CMV)

Dextramer 3: Negative (HLA-A*0201/ALIAPVHAV/Neg.Control).

Each of these Dextramers thus have a unique pMHC specificity (i.e. the three Dextramers have different binding molecules), and each Dextramer carries a unique label (DNA oligonucleotide) specific for that one pMHC specificity.

The library of DNA-tagged Dextramers are screened in a preparation of lymphoid cells such as anticoagulated EDTA blood or preparations of peripheral blood mononucleated cells (PBMC's). Those Dextramers that bind to cells of the cell sample will be relatively more enriched than those that do not bind.

Finally, the MHC/antigen specificity of the enriched Dextramers is revealed by identification of their DNA tags by Q-PCR with DNA tag-specific probes or by sequencing of the DNA tags.

1. Production of 3 Different DNA Tamed Dextramers with HLA-A*0201-Peptide (pMHC) Complexes.

pMHC complexes are generated and attached to dextran, along with unique DNA tags identifying each of the individual pMHC complexes, as follows.

Generation of DNA tagged Dextramers with Flu (HLA-A*0201/GILGFVFTL/MP/Influenza), CMV (HLA-A*0201/NLVPMVATV/pp65/CMV) and Negative (HLA-A*0201/ALIAPVHAV/Neg.Control).

Dextramer stock is 160 nanomolar (nM), TestOligo stock is diluted to 500 nM. Mix 10 micro liter (uL) 160 nM dextramer stock with 10 uL 500 nM TestOligo stock. Incubate 10 min at r.t. Mix with 1.5 ug pMHC complex of desired specificity. Adjust volume to 50 uL with a neutral pH buffer such as PBS or Tris pH 7.4, and store at 4 degrees Celsius. This will produce a DNA tagged Dextramer with approximately 3 oligo tags and 12 pMHC complexes, respectively, per Dextramer.
   a. Dex-Oligo-03=Dextramer with TestOligo-03 and HLA-A*0201/NLVPMVATV/pp65/CMV.
   b. Dex-Oligo-04=Dextramer with TestOligo-04 and HLA-A*0201/GILGFVFTL/MP/Influenza.
   c. Dex-Oligo-05=Dextramer with TestOligo-05 and HLA-A*0201/ALIAPVHAV/Neg.Control.

2. Preparation of Cell Sample for Screening for Antigen-Specific T Cells.
   a. Appropriate cell samples for identification of antigen specific T cells are preparations of lymphoid cells such as preparations of peripheral blood mononucleated cells (PBMC's) or anticoagulated blood. Such preparations of cell samples are prepared by standard techniques known by a person having ordinary skill in the art.
   b. Transfer in the range of 1E7 lymphoid cells (from PBMC or EDTA anticoagulated blood) to a 12×75 mm polystyrene test tube.
   c. Add 2 ml PBS containing 5% fetal calf serum, pH 7.4. Centrifuge at 300×g for 5 min. Remove supernatant and resuspend cells in a total volume of 2.5 ml PBS containing 5% fetal calf serum, pH 7.4.

3. Preparation and Modification of Library of DNA Tagged Dextramers with Three MHC/Peptide Specificities (from 1).
   a. Mix 5 ul 10 uM biotin with 10 ul each of Dex-Oligo-03, Dex-Oligo-04 and Dex-Oligo-05.

4. Mixing of Preparations of Lymphoid Cells with a Library of DNA Tagged MHC Dextramers.
   a. Mix 1E7 lymphoid cells in 2.5 mL (from 2b) with 30 uL library of DNA tagged Dextramers (from 3a).
   b. Incubate 30 min at r.t.
   c. Centrifuge at 300×g for 5 min. and remove the supernatant.
   d. Resuspend pellet in 2.5 ml PBS containing 5% fetal calf serum, pH 7.4. Centrifuge at 300×g for 5 min. and remove the supernatant.
   e. Resuspend pellet in 2.5 ml PBS containing 5% fetal calf serum, pH 7.4

5. Capture of All CD8+ Antigen Specific T Cells by Magnet Assisted Cell Sorting, Performed According to Miltenyi Biotec Catalog nr 130-090.878, Whole Blood CD8 MicroBead Protocol.
   a. Add 100 uL Whole Blood CD8 MicroBeads (Miltenyi Biotec catalog nr 130-090.878) to resuspended lymphoid cells from 4e. Mix and allow capture of CD8+ T cells for 15 min at r.t.
   b. Place Whole Blood Column in the magnetic field of a suitable MACS Separator. For details see the Whole Blood Column Kit data sheet.
   c. Prepare column by rinsing with 3 mL separation buffer (autoMACS Running Buffer or PBS containing 5% fetal calf serum, pH 7.4).
   d. Apply magnetically labeled cell suspension (4e) onto the prepared Whole Blood Column. Collect flow-through containing unlabeled cells.
   e. Wash Whole Blood Column with 3×3 mL separation buffer (autoMACS Running Buffer or PBS containing 5% fetal calf serum, pH 7.4).
   f. Remove Whole Blood Column from the separator and place it on a new collection tube.
   g. Capture CD8+ T cells by pipetting 5 mL Whole Blood Column Elution Buffer or PBS containing 5% fetal calf serum, pH 7.4 onto the Whole Blood Column. Immediately flush out the magnetically labeled cells by firmly pushing the plunger into the column.
   h. Centrifuge at 300×g for 5 min. and remove the supernatant. Resuspend the collected CD8+ cells in 50 uL and store at minus 20 degrees Celsius for subsequent analysis.

6. Identification of Dextramers that Bound Significantly to Antigen Specific T Cells of the Lymphoid Cell Sample.
   a. Quantifying ratios of DNA oligo tags in input (3a) vs captured fraction (5h) by sequencing or alternatively quantifying by QPCR using the DNA tag specific probes LNA-3, LNA-4 and LNA-5 will reveal the relative abundance of antigen specific T cells in the lymphoid cell sample.
      i. Quantifying ratios of DNA oligo tags in input (3a) vs captured fraction (5h) by QPCR using the DNA tag specific probes LNA-3, LNA-4 and LNA-5.
         1. Make 25 uL QPCR reactions of
            a. input of library of DNA tagged Dextramers (3a)
            b. output of library of DNA tagged Dextramers (5h)
            c. Standard curves of 10 to 1E8 TestOligo-03, TestOligo-04 and TestOligo-05 respectively.

2. Mix 12.5 uL JumpStart Taq ReadyMix (Sigma-Aldrich #D7440) with 0.125 uL 100 uM primer each of Forward-01 and Reverse-01, 0.625 ul 10 uM of either probe LNA-3, LNA-4 or LNA-5, 0.025 ul Reference dye (Sigma-Aldrich #R4526) and 12.5 uL of either input of library of DNA tagged Dextramers (3a), output of library of DNA tagged Dextramers (5h) or Standard curves of 10 to 1E8 TestOligo-03, TestOligo-04 and TestOligo-05 respectively.
3. Run two step QPCR thermal profile Cycle 1=5 min at 95 degrees Celsius, Cycle 2-40=30 sec at 95 degrees Celsius and 1 min at 60 degrees Celsius.
4. Estimate the relative abundance of T cells with antigen specificity against one of the three MHC Dextramers by plotting the QPC cycle time (Ct) values of the input of library of DNA tagged Dextramers (3a), the output of library of DNA tagged Dextramers (5h) in a plot of Ct values of the QPCR standard curve of TestOligo-03, TestOligo-04 and TestOligo-05 respectively.

ii. Quantifying ratios of DNA oligo tags in input (3a) vs captured fraction (5h) by ultra-deep sequencing.
1. Make 25 uL PCR reactions of
    a. input of library of DNA tagged Dextramers (3a)
    b. output of library of DNA tagged Dextramers (5h)
2. Mix PCR reaction using any standard PCR master mix with 1.25 uL 10 uM primer each of Forward-01 and Reverse-01, and 12.5 uL of either input of library of DNA tagged Dextramers (3a) or output of library of DNA tagged Dextramers (5h). Top up to 25 uL with pure water. For example use 2× PCR Master Mix from Promega containing Taq DNA polymerase, dNTPs, MgCl2 and reaction buffers.
3. Ultra Deep Sequencing of the above PCR product can be provided by a number of commercial suppliers such as for example Eurofins Genomics, GATC Biotech or Beckman Coulter Genomics using well established Next Generation Sequencing technologies such as Roche 454, Ion Torrent, the Illumina technology or any other high throughput sequencing technique for PCR amplicon sequencing.
4. PCR amplicon analysis of the relative abundances of the input of library of DNA tagged Dextramers (3a), the output of library of DNA tagged Dextramers (5h) will reveal the relative abundance of T cells with antigen specificity against one of the three MHC Dextramers.

7. Predicted Results and Comments
a. It is expected that the relative abundance and ratios of DNA oligo tags in input of a library of DNA tagged Dextramers (3a) as estimated by QPCR or sequencing is primarily affected by three parameters namely i) the ratio in which the DNA oligo tags were supplied during the generation of the DNA tagged Dextramers (1.a.i.1), ii) how the library input was mixed (3a) and iii) how efficiently the individual DNA oligo tags are amplified in the PCR reactions.
    i. In an example, the relative ratios of DNA oligo tags in input of a library of DNA tagged Dextramers as generated in 3a and as measured by QPCR or sequencing would be between 1 to 10 fold of each other.

b. It is expected that the relative abundance and ratios of DNA oligo tags in the output of library of DNA tagged Dextramers (5h) as estimated by QPCR or sequencing, in addition to the three parameters mentioned in 7a, is primarily affected by three additional parameters namely i) the number of antigen specific T cells with specificity for one of the three MHC-peptide combinations ii) the affinity of the T cell receptor of the given T cell for the given MHC-peptide complex and finally iii) the efficiency of separating antigen-specific T cells and their associated DNA tagged MHC Dextramers from unbound DNA tagged MHC Dextramers by washing and cell capture.
    i. In an example, the relative ratios of DNA oligo tags in output of a library of DNA tagged Dextramers as generated in 5 h and as measured by QPCR or sequencing would be more than 10 fold in favor of those DNA oligo tags coupled to an MHC Dextramer with an MHC-peptide complex for which antigen-specific T cells are present in the lymphoid cell sample.
        1. In a lymphoid cell sample from an influenza positive and CMV positive HLA-A0201 donor with antigen-specific T cells against HLA-A*0201/NLVPMVATV/pp65/CMV and HLA-A*0201/GILGFVFTL/MP/Influenza and no antigen-specific T cells against HLA-A*0201/ALIAPVHAV/Neg.Control it is expected that the relative ratios of TestOligo-03 (Dex-Oligo-03=Dextramer with TestOligo-03 and HLA-A*0201/NLVPMVATV/pp65/CMV), TestOligo-04 (Dex-Oligo-04=Dextramer with TestOligo-04 and HLA-A*0201/GILGFVFTL/MP/Influenza) and TestOligo-05 (Dex-Oligo-05=Dextramer with TestOligo-05 and HLA-A*0201/ALIAPVHAV/Neg.Control) will be more than 10 fold in the favor of TestOligo-03 and TestOligo-04 over TestOligo-05. That is TestOligo-03 and TestOligo-04 is expected to be more than 10 fold more abundant or frequent than TestOligo-05 as measured by sequencing or QPCR of the output of library of DNA tagged Dextramers (5h) if they were supplied in equal amounts in the input of library of DNA tagged Dextramers (3a).

Example B

FIG. 7 shows results that act as proof-of-principle for the claimed invention. FIG. 7A, Flow cytometry data of peripheral blood mononuclear cells (PBMCs) from healthy donors.

Materials and Methods

PBMCs were stained with CMV specific peptide-MHC multimers coupled to a specific nucleotide-barcode. In addition to CMV peptide-MHC reagents the cells were stained in the presence of negative control reagents i.e. HIV-peptide MHC multimers coupled to another specific barcode label and the additional negative control peptide-MHC reagents (p*) not holding a barcode—all multimers were additionally labeled with a PE-fluorescence label. The amounts of MHC multimers used for staining of PBMCs were equivalent to the required amount for staining of 1000 different peptide-MHC specificities i.e. 1× oligo-labeled CMV specific MHC multimers, 1× oligo-labeled HIV specific MHC multimers and 998× non-labeled p*MHC multimers, so as to give an impression whether background staining will interfere with the true positive signal. Prolonged washing steps were included (either 0 min (A), 30 min (B) or 60 min (C)) after removing the MHC multimers, and data from all experiments are shown. The PE-MHC-multimer positive cells were sorted by fluorescence activated cell sorting (FACS) FIG. 7B, Cross threshold (Ct) values from multiplex qPCR of the sorted PE-MHC-multimer positive cells. QPCR was used to assess the feasibility of detecting certain cell specificity through barcode-labeled peptide-MHC-multimers. Reagents associated with a positive control (CMV) barcode and a negative control (HIV) barcode were present during staining, but negative control (HIV) barcode-peptide-MHC multimers should be washed out.

Examples of nucleic acid sequences are:

DNA-barcode oligo for CMV MHC multimer attachment:

```
5GAGATACGTTGACCTCGTTGAANNNNNNNTCTATCCATTCCATCCAGCT
CACTTAAGCTCTTGGTTGCAT
```

DNA-barcode oligo for HIV MHC multimer attachment:

```
5GAGATACGTTGACCTCGTTGAANNNNNNNTCTATAGGTGTCTACTACCT
CACTTAAGCTCTTGGTTGCAT
5 = Biotin-TEG
```

Results

Results shows Ct value only detectable to the CMV peptide-MHC multimer associated barcode, whereas the HIV-peptide MHC multimer associated barcode was not detected Conclusion This experiment is a representative example of several similar experiment performed with other antigen specificities. Overall these data show that it is feasible to 1) stain with at least 1000 different MHC-multimers in a single sample while still maintain a specific signal,
2) attach a DNA-barcode to an MHC multimer,
3) amplify the DNA-barcode after cellular selection steps,
4) read the barcode with QPCR, using barcode specific probes,
5) obtain a specific signal corresponding to the antigen specific T cell population present in the sample, while non-specific MHC multimer barcodes are non-detectable.

Figure 3:
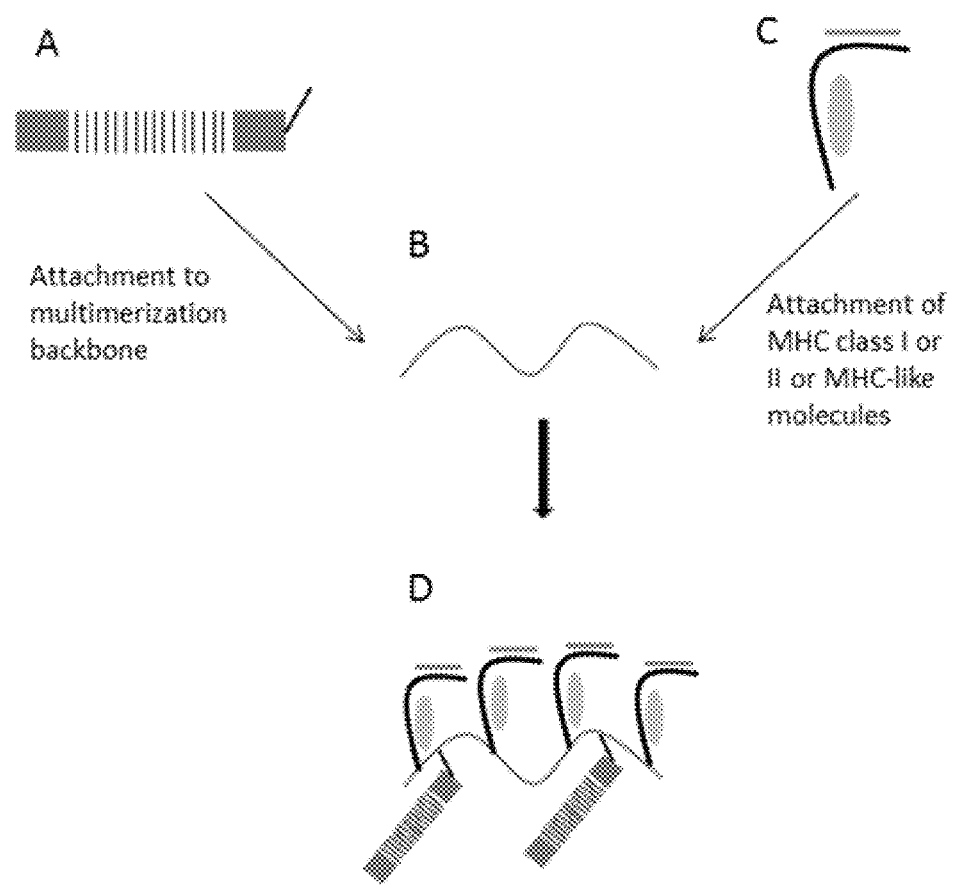
FIG. 3. Generation of barcode-labeled MHC multimers.
Figure 4:
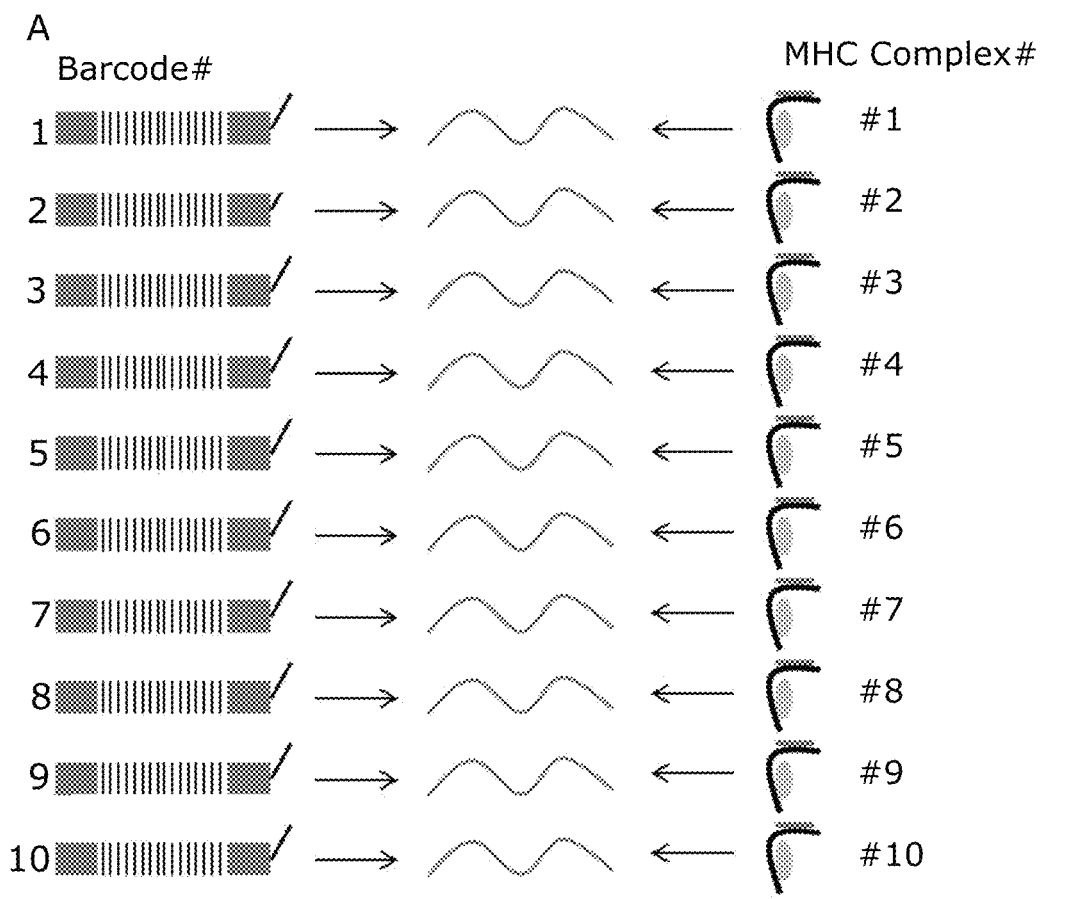
FIG. 4. Generation of a library of barcode labelled MHC multimers (Composition).
Figure 4:
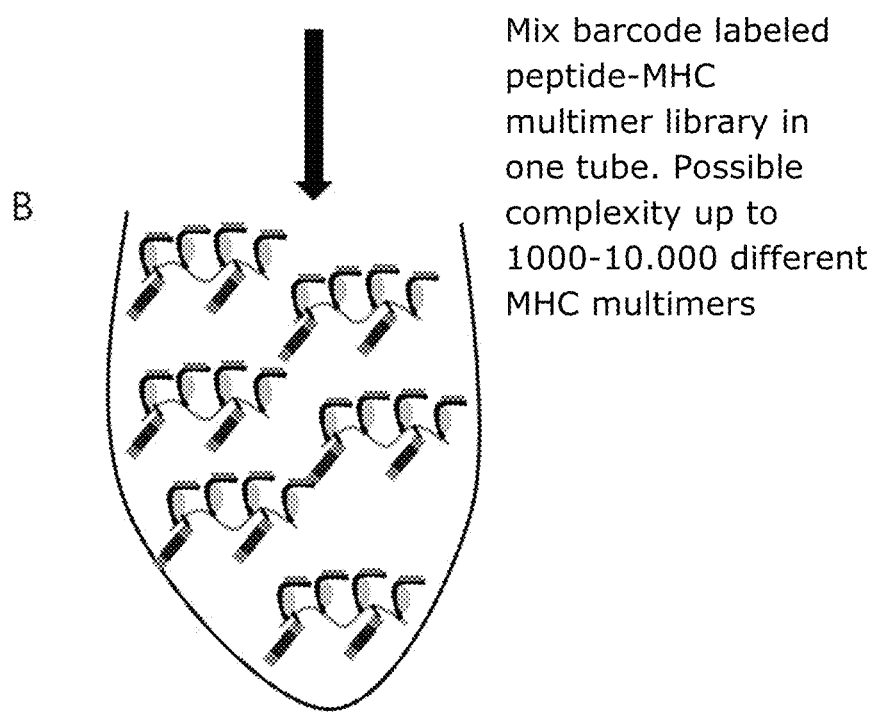
Figure 5:
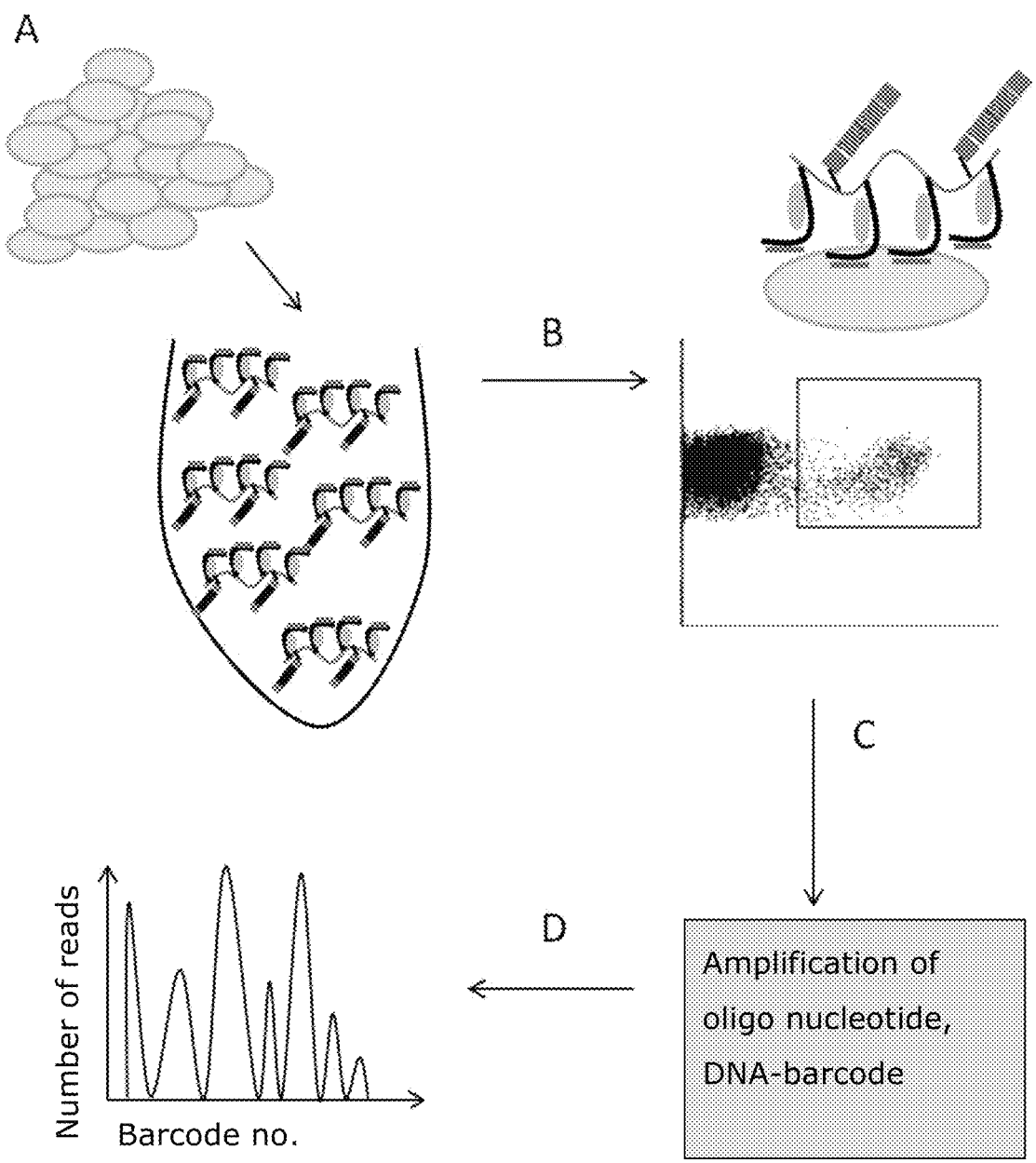
FIG. 5. Detection of antigen responsive cells in a single sample.

Together these (and similar data available) provide proof of feasibility for the steps described in FIGS. 3, 4 and 5.

EXAMPLES 1-12, 20-21, 60-61, 79-82 and 120-124

In the following examples, the experimental methods comprise one or more of the following steps
1. Sample preparation.
   a. Acquiring sample
   b. Modifying sample
2. Linker preparation.
3. Binding molecules preparation
   a. Synthesis
   b. Modification
   c. Purification
4. Label preparation
   a. Synthesis
   b. Modification
   c. Purification
5. Detection molecules preparation
   a. Synthesis
   b. Modification
   c. Purification
6. Incubation of sample and detection molecules
   a. Amount of sample
   b. Amount of detection molecule
   c. Conditions
7. Enrichment of detection molecules with desired characteristics
   a. Apply
   b. Wash
   c. Separate
8. Identification of enriched detection molecule
   a. Apply
   b. Analysis Example 1

In this example the binding molecules are pMHC complexes, the linker is a dextran-streptavidin-fluorochrome conjugate, and the label is a DNA oligonucleotide.

The sample is a HPBMC from humans, the isolating and/or detecting is done by flow cytometry (FACS), and the determining of the identity of the label is done by quantitative PCR (QPCR).

Example 1 Explained

This is an example where the Sample (1) was blood from one CMV positive and HIV negative donor which was modified (1b) to generate Peripheral blood mononuclear cells (PBMCs).

The Linker (2) was a dextran conjugate with streptavidin and fluorochrome (Dextramer backbone from Immudex).

The binding molecules (3) were peptide-MHC (pMHC) complexes displaying either CMV (positive antigen) or HIV (negative antigen) derived peptide-antigens. The binding molecules were modified (3b) by biotinylation to provide a biotin capture-tag for the Linker. The binding molecules were purified (2c) by HPLC and quality controlled in terms of the formation of functional pMHC multimers for staining of a control T-cell population.

The Labels (4) were oligonucleotides applied as DNA-barcodes. The oligonucleotides were synthetized (4a) by DNA Technology A/S (Denmark) and were synthetically modified (4b) with a terminal biotin capture-tag. The labels were combined oligonucleotide labels arising by annealing an A oligonucleotide (modified with biotin) to a partially complimentary B oligonucleotide label followed by enzymatic DNA polymerase extension of Oligo A and Oligo B to create a fully double stranded label. The detection molecule (5) was synthetized (5a) by attaching binding molecules in the form of biotinylated pMHC and labels in the form of biotin-modified double stranded oligonucleotides onto a streptavidin-modified dextran linker. The detection molecule further contained a modification (5b) in the form of a fluorochrome. Two different detection molecules were generated wherein the two individual detection molecules containing different pMHC were encoded by corresponding individual oligonucleotide labels.

An amount of sample, PBMC's (1b) was incubated with an amount of mixed detection molecules (5) under conditions (6c) that allowed binding of detection molecules to T cells in the sample.

The cell-bound detection molecules were separated from the non-cell bound detection molecules (7) by first a few rounds of washing the PBMC's through centrifugation sedimentation of cells and resuspension in wash buffer followed by Fluorescence Activated Cell Sorting (FACS) of fluorochrome labeled cells. T cells that can efficiently bind detection molecules will fluoresce because of the fluorochrome comprised within the detection molecules; T cells that cannot bind detection molecules will not fluoresce. FACS-sorting leads to enrichment of fluorescent cells, and hence, enrichment of the detection molecules along with the associated labels that bind T cells of the PBMC sample.

FACS isolated cells were subjected to quantitative PCR analysis of the oligonucleotide label associated with the detection molecules bound to the isolated cells to reveal the identity of the detection molecules that bound to the T cells present in the sample. This example thus revealed the presence of T cells in the blood expressing a T cell receptor that binds to peptide-MHC molecules represented within the library of Detection Molecules. It also revealed the feasibility of enriching for Detection Molecules based on the presence of T cells specific for the positive peptide-antigen (CMV) over the negative peptide-antigen (HIV) antigens.

Example 1 in Detail

1. Sample preparation. The cell sample used in this example was obtained by preparing PBMC's from blood drawn from a donor that was CMV positive as well as HIV negative as determined by conventional MHC-multimer staining.
   a. Acquiring sample: Blood was obtained from the Danish Blood Bank, in the form of buffy coats (BC). A peripheral blood mononuclear cell preparation obtained following standard donor blood preparations.
   b. Modifying sample: Peripheral blood mononuclear cells (PBMCs) were isolated from whole blood by density gradient centrifugation. The density gradient medium, Lymphoprep (Axis-Shield), which consists of carbohydrate polymers and a dense iodine compound, facilitate separation of the individual constituents of blood. Blood samples were diluted 1:1 in RPMI (RPMI 1640, GlutaMAX, 25 mM Hepes; gibco-Life technologies) and carefully layered onto the Lymphoprep. After centrifugation, 30 min, 490 g, PBMCs together with platelets were harvested from the middle layer of cells. The isolated cells, the buffy coat (BC), was washed twice in RPMI and cryopreserved at −150° C. in fetal calf serum (FCS; gibco-Life technologies) containing 10% dimethyl sulfoxide (DMSO; Sigma-Aldrich). BC's used in this example are listed in table 1 along with peptide-antigen specific T cells identified within these samples by conventional MHC multimer staining.
2. Linker preparation: The linker used in this example was a dextran molecule, to which was attached streptavidin and fluorochromes. The streptavidin served as attachment sites for biotinylated oligonucleotides (Label) and biotinylated peptide-MHC complexes (Binding Molecules). The fluorochrome allowed separation of cells bound to detection molecules from cells not bound to detection molecules.
   i. In this example linkers were linear and branched dextran molecules with covalently attached streptavidin (5-10 per linker) and fluorochromes (2-20 per linker) in the form of PE. Linkers were essentially Dextramer backbone as described by Immudex.
3. Binding molecules preparation: The binding molecules used in this example were two different class I MHC-peptide complexes. MHC heavy chains (HLA-A0201 and HLA-B0702) and B2M were expressed in *E. coli* as previously described (Hadrup et al. 2009) and each MHC-I complex generated with two peptide antigens. The individual specificities (allele and peptide combination) were generated in the following way:
   a. Synthesis: Binding molecules in this example were specific pMHC monomers that were produced from UV-exchange of selected HLA-I monomers carrying a photolabile 9-residue peptide-ligand (p*). When exposed to UV-light (366 nm) the photolabile ligand will be cleaved and leave the binding groove empty. Due to the instability of empty MHC-I molecules, the complexes will quickly degrade if they are not rescued by replacement with another peptide that match that HLA-type. In this way specific pMHC monomers were produced by mixing excess of desired HLA ligands with p*MHC monomers. p*MHC monomers were refolded, biotinylated and purified as previously described (Hadrup et al. 2009).
      i. HIV derived peptide ILKEPVHGV from antigen HIV polymerase and CMV derived peptide TPRVTGGGAM from antigen pp65 TPR (Pepscan Presto, NL) were diluted in phosphate buffered saline (DPBS; Lonza) and mixed to final concentrations 100 µg/ml: 200 µM (HLA-A0201: ILKEPVHGV and HLA-B0702:TPRVTGG-GAM). The mixtures were exposed to 366 nm UV light (UV cabinet; CAMAG) for one hour and optionally stored for up to 24 h at 4° C.
   b. Modification: No further modifications
   c. Purification: Before applying the peptide exchanged HLA monomer Binding Molecules for preparation of detection molecules these were centrifuged 5 min, 3300 g, to sediment any aggregated MHC molecules.
4. Label preparation: In this example, two different double stranded oligonucleotides, DNA barcodes, of the same length but partially different sequence, were generated. Each of the DNA barcodes would become attached to a specific pMHC, and thus functioned as a Label for this specific Binding Molecule. The oligonucleotides were biotinylated, allowing easy attachment to the dextran-streptavidin conjugate linker.
   a. Synthesis: The Labels were generated from partially complementary oligonucleotides which were purchased from DNA Technology (Denmark) and delivered as lyophilized powder. Stock dilutions of 100 µM oligonucleotides were made in nuclease free water and stored at −20° C.
      i. The Label system used in this example was named 2OS and was developed to increase the complexity of a limited number of oligonucleotide sequences. This was enabled by applying a combinatorial strategy where two partially complementary oligonucleotides (an A oligonucleotide with a 5' biotin tag and a B oligonucleotide) where annealed and then elongated to produce new unique oligonucleotide-sequences (AxBy) which were applied as a DNA-barcodes (Labels) (see FIG. 9 for design of the DNA-barcodes). By combining 2 unique oligonucleotide-sequences (A label precursor) that were partly complementary to 2 other unique oligonucleotide sequences (B label precursor) a combinatorial library of 4 different (AxBy) Labels were produced. Only 2 of these Labels were used in this example (A1B1 and A2B2). Refer to table 2 for an overview of the different 2OS A and B nucleotide sequences. Briefly:

Partly complementary A and B oligonucleotides were annealed to produce two combined A+B DNA barcodes (A1+B1 to produce A1B1 and A2+B2 to produce A2B2). The respective A and B oligonucleotides were mixed as stated in table 3, heated to 65° C. for 2 min and cooled slowly to <35° C. in 15-30 min. The annealed A and B oligonucleotides were then elongated as stated in table 3. Elongation reagents were mixed <15 min before use. After mixing, the reactions were incubated 5 min, RT, to allow elongation of the annealed oligonucleotides. The reagents used for annealing (left) and elongation (right) of partly complementary oligonucleotides is described in table 3. Reagents marked in italic were from the Sequenase Version 2.0 DNA Sequencing Kit (Affymetrix #70770).
  b. Modification: All labels were diluted to working concentrations (2.17 uM) in nuclease free water with 0.1% Tween and stored at −20° C.
  c. Purification: Labels were not purified further.
5. Detection Molecules preparation: The Binding Molecules (pMHCs) and Labels (DNA-barcodes) were attached to the Linker (dextran-streptavidin-PE conjugate), to form Detection Molecules, in such a way that a given pMHC was always attached to a given DNA-barcode.
  a. Synthesis: For preparation of Detection Molecules the 2OS DNA-barcodes were attached to the dextramer prior to addition of pMHC. 1 ul dextramer was used for every 3 ul of prepared Detection Molecule. Briefly, for generation of Detection Molecules:
    i. The Label:linker conjugate were generated by addition of label in two fold excess over linker (label:linker, 2:1) i.e. 1×0.16 uM linker (dex), were mixed with 0.15×2.17 uM label (2OS DNA-barcode) and incubated at least 30 min, 4° C.
    ii. Binding molecules, in the form of biotinylated UV-exchanged peptide-MHC monomer, were added to the label:linker conjugate to reach a concentration of 44 ug/ml of the given pMHC in 3 ul, and incubated 30 min, RT. The final volume was reached by addition of 0.02% $NaN_2$ in PBS together with D-biotin (Avidity Bio200) in a final concentration of $12.6 \times 10^{-6}$ M. The detection molecule preparation was incubated 30 min, 4° C., and optionally stored for up to 4 weeks at 4° C. (overview of the amounts used can be found in table 4). Two sets of two detection molecules were generated. Each set with the two specificities individually labeled. The label was inverted between the two sets as described below.
      1. 1×CMV specific pMHCs (HLA-A0201: ILKEPVHGV) coupled to 2OS-A1 B1, 1×HIV specific pMHCs (HLA-B0702:TPRVTGG-GAM) coupled to 2OS-A2B2.
      2. 1×CMV specific pMHCs (HLA-A0201: ILKEPVHGV) coupled to 2OS-A2B2, 1×HIV specific pMHCs (HLA-B0702:TPRVTGG-GAM) coupled to 2OS-A1B1.
  b. Modification: No further modifications were performed
  c. Purification: The Detection Molecules were centrifuged 5 min, 3300 g, to sediment any aggregates before being added to the cell sample,
6. Incubation of sample and Detection Molecules: The cell sample and the Detection Molecules were mixed in one container to allow Detection Molecules to bind to T cells.
  a. Amount of sample: 1×10E6-2×10E6 cells in the form of BC's, were used.
  b. Amount of detection molecule: According to table 4. for staining in 100 ul 1.32 ug/ml calculated in relation to each binding molecule (specific peptide-MHC) on the Detection Molecule was required per incubation, i.e. 3 ul of each Detection Molecule.
  c. Conditions: BCs were thawed in 10 ml, 37° C., RPMI with 10% fetal bovine serum (FBS), centrifuged 5 min, 490 g, and washed twice in 10 ml RPMI with 10% FBS. All washing of cells refer to centrifugation 5 min, 490 g, with subsequent removal of supernatant. 1×10E6-2×10E6 cells were washed in 200 ul barcode-buffer (PBS/0.5% BSA/2 mM EDTA/100 μg/ml herring DNA) and resuspended in this buffer to approximately 20 μl per sample. The barcode buffer is optimized to increase the stability of the oligonucleotides associated with the Detection molecules. The cells were incubated with 50 nM dasatinib, 30 min, 37° C., prior to incubation of cells with Detection Molecules.
    i. The Detection molecules were added in the required amount. If necessary barcode-buffer was added to reach a total volume of 100 ul and cells were incubated 15 min, 37° C. 20 ul antibody mixture containing PerCP-conjugated anti-CD8 antibody and dump channel FITC-conjugated antibodies (table 5) along with 0.1 μl near-IR-viability dye (Invitrogen L10119) was added for every 100 ul of PBMC:detection molecule sample. The samples were incubated 30 min, 4° C., and cells were washed twice in 200 ul barcode-buffer. Optionally cells were fixed in 1% paraformaldehyde in DPBS overnight, 4° C., and washed twice in barcode-buffer. Fixed cells were stored for up to a week at 4° C.
7. Enrichment of detection molecules with desired characteristics: The Detection Molecules were enriched by using flow cytometry, more specifically, Fluorescence-Activated-Cell-Sorting (FACS). Since all Detection Molecules carried a PE-fluorescent label, the cells that bound to Detection Molecules would fluoresce according to this fluorochromes emission peak. By applying a FACS sorter this feature could be used to separate cells that bound to detection molecules from cells that did not bind Detection Molecules i.e. to separate those cells that did fluoresce from those cells that did not fluoresce. As a result the Detection Molecules that bound to cells, and hence the associated Labels, were enriched for.
  a. Apply: Cells were sorted on a BD FACSAria, equipped with three lasers (488 nm blue, 633 nm red and 405 nm violet). The flow cytometry data analyses were performed using the BD FACSDiva software version 6.1.2. The following gating strategy was applied: Lymphocytes were identified in a FSC/SSC plot. Additional gating on single cells (FSC-A/FSC-H), live cells (near-IR-viability dye negative), and CD4, CD14, CD16, CD19, CD40 negative (FITC)/CD8 positive cells (PerCP) were used to define the CD8 T cell population (table 5). The PE positive population, i.e. the cells that bound to detection molecules, were defined within the PerCP positive population b. Wash: not applied c. Separate: The PE positive cells were sorted by FACS, as described in 7a, into tubes that contained 200 μl barcode-buffer and that had been pre-saturated for 2h-O.N. in 2% BSA. The sorted cells were centrifuged 5 min, 5000 g, to allow removal of excess buffer (<10 ul should reside in the container). Cells were stored at −80° C.

8. Identification of enriched Detection Molecules: Since the Detection Molecules were enriched based on specific binding of the Binding Molecule (the pMHC) to cells, the identification of the associated Labels (oligonucleotide barcodes) amongst the sorted cells would also reveal the pMHCs that had bound to cells in the PBMC sample. In this example the enriched Detection Molecules were identified by quantitative PCR (QPCR) using Label-specific fluorescent reporter probes.

a. Apply: Labels derived from sorted cells were analyzed by QPCR with the Brilliant II QRT-PCR Low ROX Master Mix Kit (Agilent technologies, #600837) according to table 6. PCR was run on the thermal cycler: Mx3000P qPCR system (Agilent Technologies). The thermal profile is listed in table 7 and the label-specific fluorescent reporter probes were: Probe123: 5'6-FAM/GCCTGTAGTCC-CACGCGATCTAACA/3'BHQ_1 for detection of label 2OS-A1B1 and Probe124: 5'HEX/CAACCAT-TGATTGGGGACAACTGGG/3'BHQ_1 for detection of label 2OS-A2B2. The label specific reporter probes were purchased from DNA Technology (Denmark) and delivered as lyophilized powder. Stock dilutions of 100 μM oligonucleotides were made in nuclease free water and stored at −20° C. Primers used for amplification in this experiment forward: GAAGTTCCAGCCAGCGTC, and reverse: CTGTGACTATGTGAGGCTTTC.

b. Analysis: combined with the above.

Example 1—Results and Conclusions

After sorting of PE labeled cells and QPCR the resultant Ct values confirmed that Detection Molecules were enriched, i.e. 2OS DNA-barcode Labels were successfully recovered, only when associated with the CMV epitope, while they were not detected when associated with the HIV epitope (FIG. 10). This was observed even when labels were inverted between the two Binding Molecules, implying that the recovery was not Label specific, but truly specific for the Binding molecule.

It was verified that the 2OS labels were recovered after cellular interaction, sorting and QPCR only if they were associated with positive control Detection molecules, and not if they were associated with negative control Detection molecules.

Example 2

In this example the binding molecules are pMHC complexes, the linker is a dextran-streptavidin-fluorochrome conjugate, and the label is a DNA oligonucleotide.

The sample is a HPBMC, the isolating and/or detecting is by FACS, and the determining of the identity of the label is by QPCR.

Example 2 Explained

This is an example where the Sample (1) was blood from one CMV positive and HIV negative donor which was modified (1b) to generate Peripheral blood mononuclear cells (PBMCs).

The Linker (2) was a dextran conjugate with streptavidin and fluorochrome (Dextramer backbone from Immudex).

The example is similar to example 1 except that a 1000 fold excess of Detection Molecules with irrelevant Binding Molecules but without label were included. The Binding Molecules used (3) are peptide-MHC (pMHC) complexes displaying either CMV (positive antigen) or HIV (negative antigen) derived peptide-antigens or pMHC complexes displaying irrelevant peptide antigen. The Binding Molecules were modified (3b) by biotinylation to provide a biotin capture-tag for the Linker. The binding Molecules were purified (2c) by HPLC.

The Labels (4) were single stranded oligonucleotides applied as DNA-barcodes. The oligonucleotides were synthetized (4a) by DNA Technology A/S (Denmark) and were synthetically modified (4b) with a terminal biotin capture-tag.

The Detection Molecule (5) was synthetized (5a) by attaching binding molecules in the form of biotinylated pMHC and Labels in the form of biotin-modified oligonucleotides, DNA-barcodes, onto a streptavidin-modified dextran linker. The detection molecule further contained a modification (5b) in the form of a fluorochrome. Three different detection molecules were generated wherein the two of these individual detection molecules containing CMV- and HIV-directed pMHC were encoded for by corresponding individual DNA-barcodes. Detection Molecules with irrelevant Binding Molecules (p*MHC) were not encoded for with a DNA-barcode.

An amount of sample, PBMC's (1b) was incubated with an amount of mixed detection molecules (5) in a ratio of 1:1:998 (Labeled-CMV:Labeled-HIV:unlabeled-irrelevant directed Binding Molecules) under conditions (6c) that allowed binding of detection molecules to T cells in the sample.

The cell-bound detection molecules were separated from the non-cell bound detection molecules (7) by first a few rounds of washing the PBMC's through centrifugation sedimentation of cells and resuspension in wash buffer followed by Fluorescence Activated Cell Sorting (FACS) of fluorochrome labeled cells. T cells that can efficiently bind detection molecules will fluoresce because of the fluorochrome comprised within the detection molecules; T cells that cannot bind detection molecules will not fluoresce. FACS-sorting leads to enrichment of fluorescent cells, and hence, enrichment of the detection molecules along with the associated labels that bind T cells of the PBMC sample.

FACS isolated cells were subjected to quantitative PCR analysis of the oligonucleotide label associated with the detection molecules bound to the isolated cells to reveal the identity of the detection molecules that bound to the T cells present in the sample. This example thus revealed the presence of T cells in the blood expressing a T cell receptor that binds to peptide-MHC molecules represented within the library of Detection Molecules. It also revealed the feasibility of enriching for Detection Molecules based on the presence of T cells specific for the positive peptide-antigen (CMV) over the negative peptide-antigen (HIV) antigens. In this setting, it was proved that it was possible to specifically enrich Detection Molecules associated with positive peptide-antigen when excess of irrelevant Detection Molecule was included in the sample incubation.

Example 2 in Detail

1. Sample preparation. The cell sample used in this example was obtained in the same way as described in example 1

2. Linker preparation: The linker used in this example was prepared as in example 1
3. Binding Molecules preparation: The binding molecules used in this example were two different class I MHC-peptide complexes. MHC heavy chains (HLA-A02 and HLA-B07) and B2M were expressed in *E. coli* as previously described (Hadrup et al. 2009) and each MHC-I complex generated with two peptide antigens or left with an irrelevant photolabile 9-mer peptide. The individual specificities (allele and peptide combination) were generated in the following way:
   a. Synthesis: As in example 1.
      i. HIV derived peptide ILKEPVHGV from antigen HIV polymerase and CMV derived peptide TPRVTGGGAM from antigen pp65 TPR (Pepscan Presto, NL) were diluted in phosphate buffered saline (DPBS; Lonza) and mixed to final concentrations 100 µg/ml:200 µM (HLA-A0201: ILKEPVHGV and HLA-B0702:TPRVTGGGAM). The mixtures were exposed to 366 nm UV light (UV cabinet; CAMAG) for one hour and optionally stored for up to 24 h at 4° C. The irrelevant Binding Molecules, p*HLA-A0201 and p*HLA-B0702 were mixed in equal amounts (µg/ml) and diluted to 100 µg/ml in DPBS.
   b. Modification: No further modifications
   c. Purification: Before applying the peptide exchanged HLA monomer Binding Molecules for preparation of detection molecules these were centrifuged 5 min, 3300 g, to sediment any aggregated MHC molecules. The p*MHC monomers were not purified further.
4. Label preparation: In this example Labels were synthetic oligonucleotides modified with biotin for coupling to the Linker.
   a. Synthesis: The Labels were oligonucleotides, DNA barcodes, which were purchased from DNA Technology (Denmark) and delivered as lyophilized powder. Stock dilutions of 100 µM oligonucleotide were made in nuclease free water and stored at −20° C.
      i. The Label system used in this example was named 1OS and comprised of single stranded oligonucleotides which were applied as a DNA barcodes (Oligo 4: 5GAGATACGTTGACCTCGTT-GAANNNNNNTCTTGAACTATGA ATCGTCT-CACTTAAGCTCTTGGTTGCAT and Oligo 5: 5GAGATACGTTGACCTCGTT-GAANNNNNNTCTATAGGTGTC TACTACCT-CACTTAAGCTCTTGGTTGCAT were used in this experiment, 5 indicates a 5' biotin modification).
   b. Modification: All Labels were diluted to working concentrations (2.17 uM) in nuclease free water with 0.1% Tween and stored at −20° C.
   c. Purification: Labels were not purified further.
5. Detection Molecules preparation: The Binding Molecules (pMHCs) and Labels (oligonucleotides) were attached to the Linker (dextran-streptavidin-PE conjugate), to form Detection Molecules, in such a way that a given pMHC was always attached to a given DNA-barcode.
   a. Synthesis: In this example the Detection Molecules were prepared by attaching 1OS DNA-barcodes prior to addition of pMHC. Detection Molecules were essentially generated in the same way as described in example 1, with the difference that two different sets of two detection molecules were generated.

Each set had two specificities individually labeled. The Labels were inverted between the two sets as described below. Moreover a third Detection Molecule was generated without any Label, but comprised of the Linker and a Binding Molecule (p*MHC), this detection molecule was included in both sets of Detection Molecules as described below in the indicated stoichiometry:
   1. 1×CMV specific pMHCs (HLA-A0201: ILKEPVHGV) coupled to Oligo4, 1×HIV specific pMHCs (HLA-B0702:TPRVTGGGAM) coupled to Oligo5 and 998× non-labeled p*MHC (HLA-A0201:p* and HLA-B0702:p*).
   2. 1×CMV specific pMHCs (HLA-A0201: ILKEPVHGV) coupled to Oligo5, 1×HIV specific pMHCs (HLA-B0702:TPRVTGGGAM) coupled to Oligo4 and 998× non-labeled p*MHC (HLA-A0201:p* and HLA-B0702:p*).
   b. Modification: Since the total volume of each set of Detection Molecules exceeded 100 µl this volume was reduced to reach a desired concentration of specific Binding Molecules in the pooled solution of Detection Molecules.
      i. Size exclusion spin columns (Nanosep 300K Omega, Pall Corporation) with a cut-off at 300 kDa were saturated by adding 500 µl 2% BSA/DPBS and centrifuging 5000 g, until the volume had passed through. Subsequently, the columns were washed twice by adding 500 µl DPBS and centrifuging 5000 g until no volume was left in the columns. Each pooled set of detection molecules were added to a spin column and centrifuged 5000 g, 4° C., until the desired volume resided in the column (80 µl per incubation with sample). The reduced volume of each set of Detection Molecules was moved to new containers.
   c. Purification: The Detection Molecules were centrifuged 5 min, 3300 g, to sediment any aggregates before being added to the sample.
6. Incubation of sample and Detection Molecules: The cell sample and the Detection Molecules were incubated in the same way as described in example 1.
7. Enrichment of Detection Molecules with desired characteristics: The Detection Molecules were enriched for in the same way as described in example 1.
8. Identification of enriched Detection Molecules: Enriched Detection Molecules were essentially identified in the same way as described in example 1, with the difference that two different label-specific fluorescent reporter probes were applied: LNA-4: 5'6-FAM/TCT[+T][+G][+A]AC[+T][+A]TG[+A][+A][+T]CGTC/3'BHQ-1-plus for detection of Oligo4 and LNA-5: 5'HEX/TCT[+A][+T][+A]GG[+T][+G]TC[+T][+A][+C]TACC/3'BHQ-1-plus for detection of Oligo5 ([+X] indicating locked nucleic acids (LNAs)).

Primers used for amplification of Oligo 4 and Oligo 5, forward: GAGATACGTTGACCTCGTTG and reverse: ATGCAACCAAGAGCTTAAGT.

Example 2—Results and Conclusions

After sorting of PE labeled cells and QPCR the resultant Ct values confirmed that Detection Molecules were enriched, i.e. 1OS DNA-barcode Labels were successfully recovered, only when associated with the CMV epitope, while they were not detected when associated with the HIV epitope (FIGS. 11A-11B). This was observed even when labels were inverted between the two Binding Molecules, implying that the recovery was not Label specific, but truly specific for the Binding molecule. Moreover the example demonstrated that a great amount of irrelevant Detection molecule equipped with the same fluorescent label as all Detection molecules in the incubation would not be detrimental for enrichment of cells that would fluoresce due to specific binding with a Detection molecule.

It was verified that the 1OS Labels were recovered after cellular interaction, sorting and QPCR only if they were associated with positive control Detection molecules, and not if they were associated with negative control Detection molecules, even in the presence of a high amount of irrelevant Detection molecule.

Example 3

In this example the binding molecules are pMHC representing 6 different HLA-alleles, the linker is dextran-streptavidin-PE conjugate and the label is a DNA oligonucleotide.

The sample is HPBMC, the isolating and/or detecting is by FACS, and the determining of the identity of the label is by sequencing.

Example 3 Explained

This is an example where the Samples (1) were blood from one donor that were HLA-B0702:CMV pp65 TPR positive and another donor that were HLA-B0702 negative which were modified (1*b*) to generate Peripheral blood mononuclear cells (PBMCs). These samples were mixed in different ratios to generate new samples with different but known frequencies of T cells specific toward the HLA-B0702:CMV epitope.

The Linker (2) was a dextran conjugate with streptavidin and fluorochrome (Dextramer backbone from Immudex).

The Binding Molecules (3) were peptide-MHC (pMHC) complexes displaying one out of 110 different peptide-antigens comprised within 6 different HLA-types. The MHC molecules were modified (3*b*) by biotinylation to provide a biotin capture-tag for the Linker. The binding molecules were purified (2*c*) by HPLC and quality controlled in terms of the formation of functional pMHC multimers for staining of control T-cell populations.

The Labels (4) were single stranded oligonucleotide applied as DNA-barcodes. The oligonucleotides were synthetized (4*a*) by DNA Technology A/S (Denmark) and were synthetically modified (4*b*) with a terminal biotin capture-tag.

The Detection Molecule (5) was synthetized (5*a*) by attaching Binding Molecules in the form of biotinylated pMHC and Labels in the form of biotin-modified oligonucleotides (DNA-barcodes) onto a streptavidin-modified dextran linker. The detection molecule further contained a modification (5*b*) in the form of a fluorochrome. A library of 110 different Detection Molecules were generated wherein individual Binding Molecules, comprised of different pMHC, were encoded for by corresponding individual Labels, comprised of different DNA-barcodes.

An amount of sample, PBMC's (1*b*) was incubated with an amount of mixed Detection Molecules (5) under conditions (6*c*) allowing binding of Detection Molecules to T cells in the sample.

The cell-bound Detection Molecules were separated from the non-cell bound Detection Molecules (7) by first a few rounds of washing the PBMC's through centrifugation sedimentation of cells and resuspension in wash buffer followed by Fluorescence Activated Cell Sorting (FACS) of fluorochrome labeled cells. T cells that can efficiently bind Detection Molecules will fluoresce because of the fluorochrome comprised within the detection molecules; T cells that cannot bind detection molecules will not fluoresce. FACS-sorting leads to enrichment of fluorescent cells, and hence, enrichment of the detection molecules along with the associated labels that bind T cells of the PBMC sample.

FACS isolated cells were subjected to PCR for specific amplification of the DNA-barcode Label associated with the Detection Molecules bound to the isolated cells. High throughput sequencing of the resultant PCR product revealed the identity of Detection Molecules that bound to T cells present in the sample.

This example thus revealed the presence of T cells in the blood expressing a T cell receptor that binds to pMHC molecules represented within the library of Detection Molecules. The number of sequencing reads mapped to a given DNA-barcode and its corresponding Binding Molecule would mirror the frequency of the T cells found by conventional MHC multimer stainings using the same Binding Molecule.

Example 3 in Detail

1. Sample preparation. The cell samples used in this example was obtained by preparing PBMC's from blood drawn from one donor that were HLA-B0702: CMV pp65 TPR positive and from another donor that were HLA-B0702 negative, as determined by conventional pMHC-multimer and antibody stainings.
   a. Acquiring sample: As in example 1
   b. Modifying sample: PBMCs were isolated from whole blood as described in example 1.
      i. Mixing of PBMCs from the two donors provided a titration of the HLA-B0702 CMV pp65 TPR responses in a B0702 negative donor sample. 5 fold dilutions of BC260 into BC262 were applied to generate seven samples with: 100, 20, 4, 0.8, 0.16, 0.032 and 0.0064% of cells derived from BC260. This corresponded to theoretical frequencies of HLA-B0702 CMV pp65 TPR specific T cells of 5%, 1%, 0.2%, 0.04%, 0.008%, 0.0016% and 0.00032%. The samples were in turn applied to evaluate the sensitivity of the Detection Molecules for detecting antigen-specific T cells in a sample. The relevance of the results obtained after applying the Detection Molecules could be evaluated by comparison of results obtained by conventional pMHC-multimer staining when applying a corresponding sample.
2. Linker preparation: The linker used in this example was prepared as in example 1-2.
3. Binding Molecules preparation: The Binding Molecules used in this example were class I MHC-peptide complexes. The individual specificities (allele and peptide combination) were generated as described in example 1. A library of 110 different pMHCs, comprised of 6 different HLA-types, were generated, these are listed in table 9.
   a. Synthesis: As described in example 1-2
   b. Modification: No further modifications
   c. Purification: As described in example 1-2
4. Label preparation: In this example Labels were synthetic oligonucleotides modified with biotin for coupling to the Linker. 110 different Labels from the 1OS system were applied (table 8).

a. Synthesis: As described in example 2
   i. The Label system used in this example were named 1OS and comprised of single stranded oligonucleotides which were applied as a DNA barcodes.
b. Modification: As described in example 1-2.
c. Purification: As described in example 1-2.
5. Detection Molecules preparation: 110 different Detection Molecules were generated, each with a different Binding Molecule encoded by a unique Label. The Binding Molecules (pMHCs) and Labels (1OS DNA-barcodes) were attached to the Linker (dextran-streptavidin-PE conjugate), to form Detection Molecules, in such a way that a given pMHC was always attached to a given DNA-barcode.
   a. Detection Molecules were essentially generated in the same way as described in example 2, with the difference that 110 different Detection Molecules were generated. The given combination of Label (DNA-barcode) and Binding Molecule (pMHC) of each Detection Molecule are presented in table 9.
   b. Modification: Since the total volume of 110 pooled Detection Molecules exceeded 100 μl this volume was reduced to reach a desired concentration of specific Binding Molecules. This was done as described in example 2
   c. Purification: As described in example 1-2.
6. Incubation of sample and Detection Molecules: The cell sample and the Detection Molecules were mixed in one container to allow Detection Molecules to bind to T cells.
   a. Amount of sample: Duplicates of seven samples each comprised of 2×10E6 cells in the form of BC's, i.e. 2×(1×100% BC260 and 6× five-fold dilutions of BC260 into BC262) (as described in 1.b)
   b. Amount of Detection Molecule: As described in example 1
   c. Conditions: BC260 and BC262 were thawed individually in 10 ml, 37° C., RPMI with 10% fetal bovine serum (FBS), centrifuged 5 min, 490 g, and washed twice in 10 ml RPMI with 10% FBS. All washing of cells refer to centrifugation 5 min, 490 g, with subsequent removal of supernatant. BC's were incubated individually in 50 nM dasatinib, 30 min, 37° C. and resuspended in 10 ml per 2×10E6 cells of the respective BC. Five-fold dilutions of BC260 were produced by adding 2.5 ml (0.5×10E6) of the former cell sample into 10 ml (2×10E6 cells) of the BC262 sample. The mixed cellular samples were washed in 200 ul barcode-buffer (PBS/0.5% BSA/2 mM EDTA/100 μg/ml herring DNA) and resuspended in this buffer to approximately 20 μl per sample prior to incubation of cells with Detection Molecules.
      i. The Detection molecules were added in the required amount and samples were incubated as described in example 1-2.
7. Enrichment of Detection Molecules with desired characteristics: The Detection Molecules were enriched for in the same way as described in example 1-2.
8. Identification of enriched Detection Molecules: Because the Detection Molecules were enriched based on specific binding of the Binding Molecule (the pMHC) to cells, the identification of the associated Labels (DNA-barcodes) amongst the sorted cells would also reveal the pMHCs that had bound to cells in the PBMC sample. In this example the DNA-barcodes associated with the enriched Detection Molecules, were amplified by PCR and identified by high-throughput sequencing.
   a. Apply. The sorted cell sample which contained DNA-barcodes derived from the enriched Detection Molecules were amplified by PCR. See table 10 for composition of the PCR and table 11 for the thermal profile. The Taq PCR Master Mix Kit (Qiagen, #201443) was applied and PCR was run on the thermal cycler: GeneAmp, PCR System 9700 (Applied Biosystem). PCR products were visualized after gel electrophoresis on a Bio-Rad Gel Doc EZ Imager. DNA was sequenced using the Ion Torrent PGM platform (Life Technologies)
      i. Primers were purchased from DNA Technology (Denmark) and delivered as lyophilized powder. Stock dilutions of 100 μM were made in nuclease free water and stored at −20° C. The primers included adaptors for Ion Torrent sequencing, i.e. an A-key and a P1-key on the forward and reverse primer respectively. Additionally the forward primers had unique DNA sequences besides the primer region and the A-key (the primer sequences are listed in table 12). These primers were used to assign DNA-barcodes derived from the same sample with a sample-identification sequence (Sample-ID barcode) (see FIG. 9 for a schematic presentation of this design). This enabled distribution of DNA-barcode sequence reads according to their originating sample, when DNA-barcodes from multiple samples were sequenced in the same sequencing reaction. The non-enriched library of the 110 different Detection Molecules (diluted 100.000× after being reduced in volume) were also assigned with a sample-ID barcode through PCR (referred to as the Detection Molecule input). Information about the distribution of Labels within the library of Detection Molecules before enrichment would allow normalization of the sequence output. Pooled PCR products derived from the sample input and from multiple incubations of Detection Molecule and sample were purified with the MinElute PCR purification Kit (Qiagen, #28006) according to standard procedure.
      ii. Purified DNA was sequenced by GeneDx (U.S.A) on an Ion Torrent PGM 314 chip.
   b. Analysis. Positive sequence reads were aligned to sequences that read from the sample-barcode-identity at the 5'-end all the way through the DNA-barcode-identity. The number of reads was normalized according to the total number of reads that mapped to the same sample-ID barcode and according to the Detection Molecule input reads.
      i. Mapping sequencing reads to 1OS DNA-barcodes: A sequence database was created consisting of the possible combinations of 15 sample-identification barcodes and 110 1OS DNA-barcodes together with the primer sequences from the 1OS system. This accumulated to 1650 sequences that could be expected from a sequencing run. Each sequencing read was then used to search the database for alignments, using the nucleotide BLAST algorithm, with a match reward of 1, mismatch reward of −2 and a gap cost of 2 for both opening and extending a gap. In this way sequencing errors were penalized equally, whether a base was miscalled or inserted/deleted in the sequencing read compared to the actual sequence. Alignments were discarded by the following criteria:
1. E-value>1e-12; insufficient length of alignment (should be greater than 60 for the 1OS barcodes).
2. Start position in subject sequence larger than 2, i.e. fewer than 5 out of 6 bases in the unique part of the sample-identification barcode was included in the alignment.

ii. If multiple alignments could still be found for any sequencing read, only the alignment with the best percent identity was kept. Finally, the number of reads mapping to each DNA barcode in the database was counted.

iii. Identifying overrepresented DNA barcodes: Relative read counts were calculated by normalizing each read to the total read count mapping to the same sample-ID barcode. The relative read counts were then used to calculate the fold change per DNA-barcode compared to the control DNA-barcode Detection Molecule input (the non-enriched Detection Molecule library). Significantly overrepresented DNA-barcodes were identified using a 2-sample test for equality of proportions on the raw read counts in a sample versus the DNA-barcode input-sample, and p-values were corrected for multiple testing using the Benjamini-Hochberg FDR method.

Example 3—Results and Conclusions

FACS sorting of fluorescent labeled cells, specific amplification of DNA-barcode Labels and high-throughput sequencing verified that it was possible to enrich and detect 1OS barcodes from a library of multiple different Detection molecules composed of 110 different 2OS DNA-barcode Labels encoding for 110 different antigen specificities distributed on 6 different HLA-types (FIG. 12). Moreover the number of sequence reads recovered from a given 1OS barcode was sensitive to the frequency of antigen specific T cells in the sample.

This example demonstrates that it is possible to detect antigen specific T cell responses of different frequencies in a panel of 110 different 1OS labeled Detection Molecules.

Example 4

In this example the binding molecules are class I pMHC complexes comprising 6 different HLA alleles, the linker is dextran-streptavidin-PE conjugate and the label is a DNA oligonucleotide.

The sample is HPBMC, the isolating and/or detecting is by FACS, and the determining of the identity of the label is by sequencing.

Example 4 Explained

This example was essentially the same as example 3 only another Label system was applied.

This is an example where the Samples (1) were blood from one donor that were HLA-B0702:CMV pp65 TPR positive and another donor that were HLA-B0702 negative which were modified (1b) to generate Peripheral blood mononuclear cells (PBMCs). These samples were mixed in different ratios to generate new samples with different but known frequencies of T cells specific toward the HLA-B0702:CMV epitope.

The Linker (2) was a dextran conjugate with streptavidin and fluorochrome (Dextramer backbone from Immudex).

The Binding Molecules (3) were peptide-MHC (pMHC) complexes displaying one out of 110 different peptide-antigens comprised within 6 different HLA-types. The MHC molecules were modified (3b) by biotinylation to provide a biotin capture-tag for the Linker. The binding molecules were purified (2c) by HPLC and quality controlled in terms of the formation of functional pMHC multimers for staining of control T-cell populations.

The Labels (4) were oligonucleotides applied as DNA-barcodes. The oligonucleotides were synthetized (4a) by DNA Technology A/S (Denmark) and were synthetically modified (4b) with a terminal biotin capture-tag. The labels were combined oligonucleotide labels arising by annealing an A oligonucleotide (modified with biotin) to a partially complimentary B oligonucleotide label followed by enzymatic DNA polymerase extension of Oligo A and Oligo B to create a fully double stranded label. The Detection Molecule (5) was synthetized (5a) by attaching Binding Molecules (3) in the form of biotinylated pMHC and Labels in the form of biotin-modified oligonucleotides (DNA-barcodes) onto a streptavidin-modified dextran linker. The detection molecule further contained a modification (5b) in the form of a fluorochrome. A library of 110 different Detection Molecules were generated wherein individual Binding Molecules, comprised of different pMHC, were encoded for by corresponding individual Labels, comprised of different DNA-barcodes.

An amount of sample, PBMC's (1b) was incubated with an amount of mixed Detection Molecules (5) under conditions (6c) allowing binding of Detection Molecules to T cells in the sample.

The cell-bound Detection Molecules were separated from the non-cell bound Detection Molecules (7) by first a few rounds of washing the PBMC's through centrifugation sedimentation of cells and resuspension in wash buffer followed by Fluorescence Activated Cell Sorting (FACS) of fluorochrome labeled cells. T cells that can efficiently bind Detection Molecules will fluoresce because of the fluorochrome comprised within the detection molecules; T cells that cannot bind detection molecules will not fluoresce. FACS-sorting leads to enrichment of fluorescent cells, and hence, enrichment of the detection molecules along with the associated labels that bind T cells of the PBMC sample.

FACS isolated cells were subjected to PCR for specific amplification of the DNA-barcode associated with the Detection Molecules bound to the isolated cells. High throughput sequencing of the resultant PCR product revealed the identity of Detection Molecules that bound to T cells present in the sample.

This example thus revealed the presence of T cells in the blood expressing a T cell receptor that binds to pMHC molecules represented within the library of Detection Molecules. The number of sequencing reads mapped to a given DNA-barcode and its corresponding Binding Molecule would mirror the frequency of the T cells found by conventional MHC multimer stainings using the same Binding Molecule. Moreover it revealed that Labels, i.e. Detection Molecules, associated with T cells in a sample would be sufficiently enriched to reveal the presence of low frequent T cells binding such Detection Molecules.

Example 4 in Detail

1. Sample preparation. The cell samples used in this example were obtained by preparing PBMC's from blood drawn from one donor that were HLA-B0702:CMV pp65 TPR positive and from another donor that were HLA-B0702 negative, as determined by conventional pMHC-multimer and antibody staining. They were acquired (a.) and modified (b.) in the same way as described in example 3.
2. Linker preparation: The linker used in this example was prepared as in example 1-3.
3. Binding Molecules preparation: The Binding Molecules used in this example were class I MHC-peptide complexes. The individual specificities (allele and peptide combination) were generated as described in example 1-3. A library of 110 different pMHCs were generated, comprised of 6 different HLA-types, these are listed in table 9.
   a. Synthesis: As described in example 1-3
   b. Modification: No further modifications
   c. Purification: As described in example 1-3
4. Label preparation: In this example Labels were synthetic oligonucleotides modified with biotin for coupling to the Linker. 110 different Labels from the 2OS system were applied (table 2).
   a. Synthesis: As described in example 1.
      i. The Label system used in this example was named 2OS and was developed to increase the complexity of a limited number of oligonucleotide sequences. This was enabled by applying a combinatorial strategy where two partially complementary oligonucleotides (an A oligonucleotide with a 5' biotin tag and a B oligonucleotide) where annealed and then elongated to produce new unique oligonucleotide-sequences (AxBy) which were applied as a DNA-barcodes (Labels) (FIG. 9). By combining 6 unique oligonucleotide-sequences (A label precursor) that were all partly complementary to 20 other unique oligonucleotide sequences (B label precursor) a combinatorial library of 120 different (AxBy) Labels were produced. Only 110 of these Labels were used in this example (table 9).
   b. Modification: As described in example 1-3.
   c. Purification: As described in example 1-3.
5. Detection Molecules preparation: 110 different Detection Molecules were generated, each with a different Binding Molecule encoded by a unique Label. The Binding Molecules (pMHCs) and Labels (2OS DNA-barcodes) were attached to the Linker (dextran-streptavidin-PE conjugate), to form Detection Molecules, in such a way that a given pMHC was always attached to a given DNA-barcode.
   a. Detection Molecules were essentially generated in the same way as described in example 3. The given combination of Label (2OS DNA-barcode) and Binding Molecule (pMHC) of each Detection Molecule are presented in table 9.
   b. Modification: Since the total volume of 110 pooled Detection Molecules exceeded 100 µl this volume was reduced to reach a desired concentration of specific Binding Molecules. This was done as described in example 2-3.
   c. Purification: As described in example 1-3.
6. Incubation of sample and Detection Molecules: The cell sample and the Detection Molecules were mixed in one container to allow Detection Molecules to bind to T cells.
   a. Amount of sample: Samples were equivalent to those used in example 3.
   b. Amount of Detection Molecule: As described in example 1-3
   c. Conditions: Samples and Detection Molecules were treated under the same conditions as described in example 3.
7. Enrichment of MHC molecules with desired characteristics: The Detection Molecules were enriched for in the same way as described in example 1-3.
8. Identification of enriched Detection Molecules: Because the Detection Molecules were enriched based on specific interaction of the Binding Molecule (the pMHC) with cells, the identification of the associated Labels (DNA-barcodes) amongst the sorted cells would also reveal the pMHCs that had bound to cells in the PBMC sample. In this example the DNA-barcodes associated with the enriched Detection Molecules, were amplified by PCR and identified by high-throughput sequencing.
   a. Apply. The sorted cell sample which contained DNA-barcodes derived from the enriched Detection Molecules were amplified by PCR. See table 10 for composition of the PCR and table 11 for the thermal profile. The Taq PCR Master Mix Kit (Qiagen, #201443) was applied and PCR was run on the thermal cycler: GeneAmp, PCR System 9700 (Applied Biosystem). PCR products were visualized after gel electrophoresis on a Bio-Rad Gel Doc EZ Imager. DNA was sequenced using the Ion Torrent PGM platform (Life Technologies)
      i. Primers were purchased from DNA Technology (Denmark) and delivered as lyophilized powder. Stock dilutions of 100 µM were made in nuclease free water and stored at −20° C. The primers included adaptors for Ion Torrent sequencing, i.e. an A-key and a P1-key on the forward and reverse primer respectively. Additionally the forward primers had unique DNA sequences besides the primer region and the A-key. These primers were used to assign DNA-barcodes derived from the same sample with a sample-identification sequence (Sample-ID barcode) (the primer sequences are listed in table 13). This enabled distribution of DNA-barcode sequence reads according to their originating sample, when DNA-barcodes from multiple samples were sequenced in the same sequencing reaction. The non-enriched library of the 110 different Detection Molecules (diluted 100.000× after being reduced in volume) were also assigned with a sample-ID barcode through PCR (referred to as the Detection Molecule input)(see FIG. 9 for a schematic overview of the primer design). Information about the distribution of Labels within the library of Detection Molecules before enrichment would allow normalization of the sequence output. Pooled PCR products derived from the sample input and from multiple incubations of Detection Molecule and sample were purified with the MinElute PCR purification Kit (Qiagen, #28006) according to standard procedure.
      ii. The purified DNA was sequenced by GeneDx (U.S.A) on an Ion Torrent PGM 314 chip.
   b. Analysis. Positive sequence reads were aligned to sequences that read from the sample-barcode-identity at the 5'-end all the way through the DNA-barcode-identity. The number of reads was normalized according to the total number of reads that mapped to the same sample-ID barcode and according to the Detection Molecule input reads. The Analysis was essentially as in example 3 except that another database of 2OS sequences was generated and sequences were mapped according to corresponding 2OS DNA-barcodes.

i. Mapping sequencing reads to 2OS DNA-barcodes: A sequence database was created consisting of the possible combinations of 15 sample-identification barcodes and 120 2OS DNA barcodes (together with the primer and annealing sequences from the 2OS system). This accumulated to 1800 sequences that could be expected from a sequencing run. Each sequencing read was then used to search the database for alignments, using the nucleotide BLAST algorithm, with a match reward of 1, mismatch reward of −2 and a gap cost of 2 for both opening and extending a gap. In this way sequencing errors were penalized equally, whether a base was miscalled or inserted/deleted in the sequencing read compared to the actual sequence. Alignments were discarded by the following criteria:
  1. E-value>1e-12; insufficient length of alignment (should be greater than 102 for the 2OS barcodes).
  2. Start position in subject sequence larger than 2, i.e. fewer than 5 out of 6 bases in the unique part of the sample-identification barcode was included in the alignment.

ii. If multiple alignments could still be found for any sequencing read, only the alignment with the best percent identity was kept. Finally, the number of reads mapping to each DNA barcode in the database was counted.

iii. Identifying overrepresented DNA barcodes: Relative read counts were calculated by normalizing each read to the total read count mapping to the same sample-ID barcode. The relative read counts were then used to calculate the fold change per DNA-barcode compared to the control DNA-barcode Detection Molecule input (the non-enriched Detection Molecule library). Significantly overrepresented DNA-barcodes were identified using a 2-sample test for equality of proportions on the raw read counts in a sample versus the DNA-barcode input-sample, and p-values were corrected for multiple testing using the Benjamini-Hochberg FDR method.

Example 4—Results and Conclusions

FACS sorting of fluorescent labeled cells, specific amplification of DNA-barcode Labels and high-throughput sequencing verified that it was possible to enrich and detect 2OS barcodes from a library of multiple different Detection molecules composed of 110 different 2OS DNA-barcode Labels encoding for 110 different antigen specificities distributed on 6 different HLA-types (FIG. 13). Moreover the number of sequence reads recovered from a given 2OS barcode was sensitive to the frequency of antigen specific T cells in the sample, also indicating that it will be possible to detect Labels associated with responses of very low frequency (<0.002).

This example demonstrates that it is possible to detect antigen specific T cell responses of different and of low frequencies in a panel of 110 different 2OS labeled Detection Molecules.

Example 5

In this example the binding molecules are class I pMHCs, the linker is streptavidin conjugate and the label is DNA.

The isolating and/or detecting is by FACS, and the determining of the identity of the label is by sequencing.

Example 5 Explained

This is an example where the Samples (1) were blood from six different donors with different HLA-types which were modified (1b) to generate Peripheral blood mononuclear cells (PBMCs).

The Linker (2) was a dextran conjugate with streptavidin and fluorochrome (Dextramer backbone from Immudex).

The Binding Molecules (3) were peptide-MHC (pMHC) complexes displaying one out of 110 different peptide-antigens comprised within 6 different HLA-types. The MHC molecules were modified (3b) by biotinylation to provide a biotin capture-tag for the Linker. The binding molecules were purified (2c) by HPLC and quality controlled in terms of the formation of functional pMHC multimers for staining of control T-cell populations.

The Labels (4) were single stranded oligonucleotide applied as DNA-barcodes. The oligonucleotides were synthetized (4a) by DNA Technology A/S (Denmark) and were synthetically modified (4b) with a terminal biotin capture-tag.

The Detection Molecule (5) was synthetized (5a) by attaching Binding Molecules in the form of biotinylated pMHC and Labels in the form of biotin-modified oligonucleotides (DNA-barcodes) onto a streptavidin-modified dextran linker. The detection molecule further contained a modification (5b) in the form of a fluorochrome. A library of 110 different Detection Molecules were generated wherein individual Binding Molecules, comprised of different pMHC, were encoded for by corresponding individual Labels, comprised of different DNA-barcodes.

An amount of sample, PBMC's (1b) was incubated with an amount of mixed Detection Molecules (5) under conditions (6c) allowing binding of Detection Molecules to T cells in the sample.

The cell-bound Detection Molecules were separated from the non-cell bound Detection Molecules (7) by first a few rounds of washing the PBMC's through centrifugation sedimentation of cells and resuspension in wash buffer followed by Fluorescence Activated Cell Sorting (FACS) of fluorochrome labeled cells. T cells that can efficiently bind Detection Molecules will fluoresce because of the fluorochrome comprised within the detection molecules; T cells that cannot bind detection molecules will not fluoresce. FACS-sorting leads to enrichment of fluorescent cells, and hence, enrichment of the detection molecules along with the associated labels that bind T cells of the PBMC sample.

FACS isolated cells were subjected to PCR for specific amplification of the DNA-barcode associated with the Detection Molecules bound to the isolated cells. High throughput sequencing of the resultant PCR product revealed the identity of Detection Molecules that bound to T cells present in the sample.

This example thus revealed the presence of T cells in the blood expressing a T cell receptor that binds to pMHC molecules represented within the library of Detection Molecules. The application of multiple (110) Detection Molecules in one sample enabled detection of T cells with different T cell receptor specificities in parallel.

Example 5 in Detail

1. Sample preparation. The cell samples used in this example were obtained by preparing PBMC's from blood drawn from six different donors with a number of different peptide-antigen responsive T cells, as determined by conventional pMHC-multimer staining.
   a. Acquiring sample: Blood was obtained from the Danish Blood Bank, as example 1-4
   b. Modifying sample: PBMCs were isolated from whole blood as described in example 1-4.
2. Linker preparation: The linker used in this example was prepared as in example 1-4.
3. Binding Molecules preparation: The Binding Molecules used in this example were class I MHC-peptide complexes. The individual specificities (allele and peptide combination) were generated as described in example 1. A library of 110 different pMHCs, comprised of 6 different HLA-types, were generated, these are listed in table 9.
   a. Synthesis: As described in example 1-4
   b. Modification: No further modifications
   c. Purification: As described in example 1-4
4. Label preparation: In this example Labels were synthetic oligonucleotides modified with biotin for coupling to the Linker. 110 different Labels from the 1OS system were applied (table 8).
   a. Synthesis: As described in example 2-3.
      i. The Label system used in this example were named 1OS and comprised of single stranded oligonucleotides which were applied as a DNA barcodes.
   b. Modification: As described in example 1-4.
   c. Purification: As described in example 1-4.
5. Detection Molecules preparation: 110 different Detection Molecules were generated, each with a different Binding Molecule encoded by a unique Label. The Binding Molecules (pMHCs) and Labels (1OS DNA-barcodes) were attached to the Linker (dextran-streptavidin-PE conjugate) to form Detection Molecules, in such a way that a given pMHC was always attached to a given DNA-barcode.
   a. Detection Molecules were generated in the same way as described in example 3. The given combination of Label (DNA-barcode) and Binding Molecule (pMHC) of each Detection Molecule are presented in table 9.
   b. Modification: Since the total volume of 110 pooled Detection Molecules exceeded 100 µl this volume was reduced to reach a desired concentration of specific Binding Molecules. This was done as described in example 2-4.
   c. Purification: As described in example 1-4.
6. Incubation of sample and Detection Molecules: The cell sample and the Detection Molecules were incubated in the same way as described in example 1-2.
7. Enrichment of MHC molecules with desired characteristics: The Detection Molecules were enriched for in the same way as described in example 1-6.
8. Identification of enriched Detection Molecules: Because the Detection Molecules were enriched based on specific interaction of the Binding Molecule (the pMHC) with cells, the identification of the associated Labels (DNA-barcodes) amongst the sorted cells would also reveal the pMHCs that had bound to cells in the PBMC sample. In this example the DNA-barcodes associated with the enriched Detection Molecules, were amplified by PCR and identified by high-throughput sequencing. The enriched Labels, of the 1OS DNA-barcode system, were identified as in example 3.

Example 5—Results and Conclusions

FACS sorting of fluorescent labeled cells, specific amplification of DNA-barcode Labels and high-throughput sequencing verified that it was possible to enrich and detect 1OS barcodes from a library of multiple different Detection molecules composed of 110 different 1OS DNA-barcode Labels encoding for 110 different antigen specificities distributed on 6 different HLA-types (FIG. 14). It was verified that several DNA-barcodes, encoding different antigen specificities on different HLA-types, could be enriched for and detected in parallel, indicative for the presence of multiple antigen-specific T cell responses in that sample.

This example demonstrates that it is possible to detect several antigen-specific T cell responses in parallel when applying a library of Detection molecules of increasing complexity.

Example 6

In this example 110 different binding molecules are used, the linker is dextran for all of the detection molecules and 110 different labels are used.

Example 6 Explained

This example was essentially the same as example 5 only another Label system was applied.

This is an example where the Samples (1) were blood from six different donors with different HLA-types which were modified (1b) to generate Peripheral blood mononuclear cells (PBMCs).

The Linker (2) was a dextran conjugate with streptavidin and fluorochrome (Dextramer backbone from Immudex).

The Binding Molecules (3) were peptide-MHC (pMHC) complexes displaying one out of 110 different peptide-antigens comprised within 6 different HLA-types. The MHC molecules were modified (3b) by biotinylation to provide a biotin capture-tag for the Linker. The binding molecules were purified (2c) by HPLC and quality controlled in terms of the formation of functional pMHC multimers for staining of control T cell populations.

The Labels (4) were oligonucleotides applied as DNA-barcodes. The oligonucleotides were synthetized (4a) by DNA Technology A/S (Denmark) and were synthetically modified (4b) with a terminal biotin capture-tag. The labels were combined oligonucleotide labels arising by annealing an A oligonucleotide (modified with biotin) to a partially complimentary B oligonucleotide label followed by enzymatic DNA polymerase extension of Oligo A and Oligo B to create a fully double stranded label. The Detection Molecule (5) was synthetized (5a) by attaching Binding Molecules in the form of biotinylated pMHC and Labels in the form of biotin-modified oligonucleotides (DNA-barcodes) onto a streptavidin-modified dextran linker. The detection molecule further contained a modification (5b) in the form of a fluorochrome. A library of 110 different Detection Molecules were generated wherein individual Binding Molecules, comprised of different pMHC, were encoded for by corresponding individual Labels, comprised of different DNA-barcodes.

An amount of sample, PBMC's (1b) was incubated with an amount of mixed Detection Molecules (5) under conditions (6c) allowing binding of Detection Molecules to T cells in the sample.

The cell-bound Detection Molecules were separated from the non-cell bound Detection Molecules (7) by first a few rounds of washing the PBMC's through centrifugation sedimentation of cells and resuspension in wash buffer followed by Fluorescence Activated Cell Sorting (FACS) of fluorochrome labeled cells. T cells that can efficiently bind Detection Molecules will fluoresce because of the fluorochrome comprised within the detection molecules; T cells that cannot bind detection molecules will not fluoresce. FACS-sorting leads to enrichment of fluorescent cells, and hence, enrichment of the detection molecules along with the associated labels that bind T cells of the PBMC sample.

FACS isolated cells were subjected to PCR for specific amplification of the DNA-barcode associated with the Detection Molecules bound to the isolated cells. High throughput sequencing of the resultant PCR product revealed the identity of Detection Molecules that bound to T cells present in the sample.

This example thus revealed the presence of T cells in the blood expressing a T cell receptor that binds to pMHC molecules represented within the library of Detection Molecules. The application of multiple (110) Detection Molecules in one sample enabled detection of T cells with different T cell receptor specificities in parallel.

Example 6 in Detail

1. Sample preparation. The cell samples used in this example were obtained by preparing PBMC's from blood drawn from six different donors with a number of different peptide-antigen responsive T cells, as determined by conventional pMHC-multimer.
   a. Acquiring sample: Blood was obtained from the Danish Blood Bank.
   b. Modifying sample: PBMCs were isolated from whole blood as described in example 1-2, 5.
2. Linker preparation: The linker used in this example was prepared as in example 1-5.
3. Binding Molecules preparation: The Binding Molecules used in this example were class I MHC-peptide complexes. The individual specificities (allele and peptide combination) were generated as described in example 1-5. A library of 110 different pMHCs, comprised of 6 different HLA-types, were generated, these are listed in table 9.
   a. Synthesis: As described in example 1-5.
   b. Modification: No further modifications
   c. Purification: As described in example 1-5
4. Label preparation: In this example Labels were synthetic oligonucleotides modified with biotin for coupling to the Linker. 110 different Labels from the 2OS system were applied (table 2).
   a. Synthesis: As described in example 1, 4.
      i. The Label system used in this example was named 2OS and was developed to increase the complexity of a limited number of oligonucleotide sequences. This was enabled by applying a combinatorial strategy where two partially complementary oligonucleotides (an A oligonucleotide with a 5' biotin tag and a B oligonucleotide) where annealed and then elongated to produce new unique oligonucleotide-sequences (AxBy) which were applied as a molecular barcodes (Labels) (FIG. 9). By combining 6 unique oligonucleotide-sequences (A label precursor) that were all partly complementary to 20 other unique oligonucleotide sequences (B label precursor) a combinatorial library of 120 different (AxBy) Labels were produced. Only 110 of these Labels were used in this example (table 9).
   b. Modification: As described in example 1-5.
   c. Purification: As described in example 1-5.
5. Detection Molecules preparation: 110 different Detection Molecules were generated, each with a different Binding Molecule encoded by a unique Label. The Binding Molecules (pMHCs) and Labels (2OS DNA-barcodes) were attached to the Linker (dextran-streptavidin-PE conjugate) to form Detection Molecules, in such a way that a given pMHC was always attached to a given DNA-barcode.
   a. Detection Molecules were generated in the same way as described in example 3, 4, 5. The given combination of Label (2OS DNA-barcode) and Binding Molecule (pMHC) of each Detection Molecule are presented in table 9.
   b. Modification: Since the total volume of 110 pooled Detection Molecules exceeded 100 µl this volume was reduced to reach a desired concentration of specific Binding Molecules (done as described in example 2-5).
   c. Purification: As described in example 1-5.
6. Incubation of sample and Detection Molecules: The cell sample and the Detection Molecules were incubated in the same way as described in example 1-2, 5.
7. Enrichment of MHC molecules with desired characteristics: The Detection Molecules were enriched for in the same way as described in example 1-5.
8. Identification of enriched Detection Molecules: Because the Detection Molecules were enriched based on specific binding of the Binding Molecule (the pMHC) to cells, the identification of the associated Labels (DNA-barcodes) amongst the sorted cells would also reveal the pMHCs that had bound to cells in the PBMC sample. In this example the DNA-barcodes associated with the enriched Detection Molecules, were amplified by PCR and identified by high-throughput sequencing. The enriched Labels, of the 2OS DNA-barcode system, were identified as in example 4.

Example 6—Results and Conclusions

FACS sorting of fluorescent labeled cells, specific amplification of DNA-barcode Labels and high-throughput sequencing verified that it was possible to enrich and detect 2OS barcodes from a library of multiple different Detection molecules composed of 110 different 2OS DNA-barcode Labels encoding for 110 different antigen specificities distributed on 6 different HLA-types (FIG. 15). It was verified that several DNA-barcodes, encoding different antigen specificities of different HLA-types, could be enriched for and detected in parallel, indicative for the presence of multiple antigen-specific T cell responses in that sample.

This example demonstrates that it is possible to detect several antigen-specific T cell responses in parallel when applying a library of Detection molecules of increasing complexity.

Example 7

In this example 175 different pMHC complexes are used as binding molecules. The sample is tumor infiltrating Lymphocytes from a resected tumor lesion of a human being.

Example 7 Explained

This is an example where the Samples (1) were resected tumor lesions from 11 HLA-A0201 positive patients with malignant melanoma. The samples were modified (1b) to generate Tumor Infiltrating Lymphocytes (TILs).

The Linker (2) was a dextran conjugate with streptavidin and fluorochrome (Dextramer backbone from Immudex).

The Binding Molecules (3) were peptide-MHC (pMHC) complexes displaying one out of 175 different peptide-antigens. The MHC molecules were modified (3b) by biotinylation to provide a biotin capture-tag for the Linker. The binding molecules were purified (2c) by HPLC and quality controlled in terms of the formation of functional pMHC multimers for staining of control T-cell populations.

The Labels (4) were oligonucleotides applied as DNA-barcodes. The oligonucleotides were synthetized (4a) by DNA Technology A/S (Denmark) and were synthetically modified (4b) with a terminal biotin capture-tag. The labels were combined oligonucleotide labels arising by annealing an A oligonucleotide (modified with biotin) to a partially complimentary B oligonucleotide label followed by enzymatic DNA polymerase extension of Oligo A and Oligo B to create a fully double stranded label. The Detection Molecule (5) was synthetized (5a) by attaching Binding Molecules in the form of biotinylated pMHC and Labels in the form of biotin-modified oligonucleotides (DNA-barcodes) onto a streptavidin-modified dextran linker. The detection molecule further contained a modification (5b) in the form of a fluorochrome. A library of 175 different Detection Molecules were generated wherein individual Binding Molecules, comprised of different pMHC, were encoded for by corresponding individual Labels, comprised of different DNA-barcodes.

An amount of sample, TILs (1b), was incubated with an amount of mixed Detection Molecules (5) under conditions (6c) allowing binding of Detection Molecules to T cells in the sample.

The cell-bound Detection Molecules were separated from the non-cell bound Detection Molecules (7) by first a few rounds of washing the TIL's through centrifugation sedimentation of cells and resuspension in wash buffer followed by Fluorescence Activated Cell Sorting (FACS) of fluorochrome labeled cells. T cells that can efficiently bind Detection Molecules will fluoresce because of the fluorochrome comprised within the detection molecules; T cells that cannot bind detection molecules will not fluoresce. FACS-sorting leads to enrichment of fluorescent cells, and hence, enrichment of the detection molecules along with the associated labels that bind T cells of the TIL sample.

FACS isolated cells were subjected to PCR for specific amplification of the DNA-barcode Label associated with the Detection Molecules bound to the isolated cells. High throughput sequencing of the resultant PCR product revealed the identity of Detection Molecules that bound to T cells present in the sample.

This example thus revealed the presence of T cells among the TIL's expressing a T cell receptor that binds to pMHC molecules represented within the library of Detection Molecules. The number of sequencing reads mapped to a given DNA-barcode and its corresponding Binding Molecule would mirror the frequency of the T cells found by conventional MHC multimer stainings using the same Binding Molecules. The application of multiple (175) Detection Molecules in one sample enabled detection of T cells with different T cell receptor specificities in parallel. This is feasible also when the sample, as in present example is TILs that on average basis has a lower avidity of their TCR to their pMHC antigen. Consequently they are more challenging to detect than virus-responsive T cells using traditional fluorescence labelled MHC multimers.

Example 7 in Detail

1. Sample preparation. The 11 cell samples used in this example were obtained from resected tumor lesions obtained from patients with malignant melanoma.
   a. Acquiring sample. TILs were derived from tumor fragments from melanoma patients. Tumor lesion were resected following surgical removal of the given tumor lesion.
   b. Modifying sample. Tumor fragments (1-3 mm3) were cultured individually in complete medium (RPMI with 10% human serum, 100 U/ml penicillin, 100 µg/ml streptomycin, 1.25 µg/ml fungizone [Bristol-Myers Squibb] and 6000 U/ml IL-2) at 37° C. and 5% CO2, allowing TILs to migrate to the medium. TILs were expanded to reach >50×10$^6$ total cells originated from approximately 24 fragments, which had expanded to confluent growth in 2-ml wells and eliminated adherent tumor cells (average of approximately 2×10$^6$ cells per well from each tumor fragment). TIL cultures were expanded on a clinical scale using a standard rapid expansion protocol (REP). Briefly, TILs were stimulated with 30 ng/ml anti-CD3 antibody (OKT-3; Ortho Biotech) and 6000 U/ml IL-2 in the presence of irradiated (40 Gy) allogenic feeder cells (PBMCs from a healthy donor) at a feeder:TIL ratio of 200:1. Initially, TILs were rapidly expanded in a 1:1 mix of complete medium and REP medium (AIM-V [Invitrogen] with 10% human serum, 1.25 µg/ml fungizone and 6000 U/ml IL-2), but after seven days complete medium and serum were removed stepwise from the culture by adding REP medium without serum to maintain cell densities around 1-2×10$^6$ cells/ml. TIL cultures were cryopreserved at −150° C. in human serum containing 10% DMSO. All patients were HLA-A0201 positive.
2. Linker preparation: The linker used in this example was prepared as in example 1-6.
3. Binding Molecules preparation: The Binding Molecules used in this example were class I MHC-peptide complexes (peptide-HLA-A0201). The individual specificities (allele and peptide combination) were generated as described in example 1-6. A library of 175 different pMHCs were generated, these are listed in table 2.
   a. Synthesis: As described in example 1-6
   b. Modification: No further modifications
   c. Purification: As described in example 1-6
4. Label preparation: In this example Labels were synthetic oligonucleotides modified with biotin for coupling to the Linker. 175 different Labels from the 2OS system were applied (table 14).

a. Synthesis: As described in example 1.
   i. The Label system used in this example was named 2OS and was developed to increase the complexity of a limited number of oligonucleotide sequences. This was enabled by applying a combinatorial strategy where two partially complementary oligonucleotides (an A oligonucleotide with a 5' biotin tag and a B oligonucleotide) where annealed and then elongated to produce new unique oligonucleotide-sequences (AxBy) which were applied as a DNA-barcodes (Labels) (FIG. 9). By combining 22 unique oligonucleotide-sequences (A label precursor) that are all partly complementary to 55 other unique oligonucleotide sequences (B label precursor) a combinatorial library of 1,210 different (AxBy) Labels were produced. Only 175 of these Labels were used in this example (table 14). Refer to table 2 for an overview of the different 2OS A and B nucleotide sequences.
b. Modification: As described in example 1-6.
c. Purification: As described in example 1-6.
5. Detection Molecules preparation: 175 different Detection Molecules were generated, each with a different Binding Molecule encoded by a unique Label. The Binding Molecules (pMHCs) and Labels (2OS DNA-barcodes) were attached to the Linker (dextran-streptavidin-PE conjugate), to form Detection Molecules, in such a way that a given pMHC was always attached to a given DNA-barcode.
   a. Detection Molecules were essentially generated in the same way as described in example 1-6. The given combination of Label (2OS DNA-barcode) and Binding Molecule (pMHC) of each Detection Molecule are presented in table 14.
   b. Modification: Since the total volume of 175 pooled Detection Molecules exceeded 100 μl this volume was reduced to reach a desired concentration of specific Binding Molecules. This was done as described in example 2-6.
   c. Purification: As described in example 1-6.
6. Incubation of sample and Detection Molecules: The cell sample and the Detection Molecules were mixed in one container to allow Detection Molecules to bind to T cells.
   a. Amount of sample: Between 0.2×10E6-2.3×10E6 cells in the form of TILs, were used.
   b. Amount of Detection Molecule: As described in example 1-6
   c. Conditions: Samples and Detection Molecules were treated as described in example 1-2 and 5-6.
7. Enrichment of MHC molecules with desired characteristics: The Detection Molecules were enriched for in the same way as described in example 1-6.
8. Identification of enriched Detection Molecules: Because the Detection Molecules were enriched based on specific interaction of the Binding Molecule (the pMHC) with cells, the identification of the associated Labels (DNA-barcodes) amongst the sorted cells would also reveal the pMHCs that had bound to cells in the TIL sample. In this example the DNA-barcodes associated with the enriched Detection Molecules, were amplified by PCR and identified by high-throughput sequencing.
   a. Apply. The sorted cell samples which contained DNA-barcodes derived from the enriched Detection Molecules were amplified by PCR. See table 10 for composition of the PCR and table 11 for the thermal profile. The Taq PCR Master Mix Kit (Qiagen, #201443) was applied and PCR was run on the thermal cycler: GeneAmp, PCR System 9700 (Applied Biosystem). PCR products were visualized after gel electrophoresis on a Bio-Rad Gel Doc EZ Imager. DNA was sequenced using the Ion Torrent PGM platform (Life Technologies)
   i. Primers were purchased from DNA Technology (Denmark) and delivered as lyophilized powder. Stock dilutions of 100 μM were made in nuclease free water and stored at −20° C. The primers included adaptors for Ion Torrent sequencing, i.e. an A-key and a P1-key on the forward and reverse primer respectively. Additionally the forward primers had unique DNA sequences besides the primer region and the A-key. These primers were used to assign DNA-barcodes derived from the same sample with a sample-identification sequence (Sample-ID barcode) (refer to table 13 for primer sequences). This enabled distribution of DNA-barcode sequence reads according to their originating sample, when DNA-barcodes from multiple samples were sequenced in the same sequencing reaction (see FIG. 9 for a schematic presentation of the primer design). If >10.000 cells were sorted in the enrichment step, only a volume corresponding to 10.000 cells were applied as template in the PCR. To further examine the potential impact on the number of cells selected with associated Detection molecules, we included Enriched Detection Molecules derived from one sample (sample 8) multiple times, so that triplicate PCRs were run with equivalent to 10.000 sorted cells and 100 sorted cells respectively. Moreover a single PCR was run with 1000 cells from the same sample. The non-enriched library of the 175 different Detection Molecules (diluted 10.000× after being reduced in volume) were also assigned with a sample-ID barcode through PCR (referred to as the Detection Molecule-input). Triplicate PCRs were run with the Detection Molecule-input. Information about the distribution of Labels within the library of Detection Molecules before enrichment would allow normalization of the sequence output. Pooled PCR products derived from the Detection Molecule-input and from multiple incubations of Detection Molecule and sample were separated according to size, by gel-electrophoresis, and the excised gel-fragment containing DNA-fragments of ~200 bp were purified with the QIAquick PCR Purification Kit (Qiagen, #28104) according to standard procedure.
   ii. The purified DNA was sequenced by Amplexa (Denmark) on an Ion Torrent PGM 314 chip.
   b. Analysis. Positive sequence reads were aligned to sequences that read from the sample-barcode-identity at the 5'-end all the way through the DNA-barcode-identity. The number of reads was normalized according to the total number of reads that mapped to the same sample-ID barcode and according to the Detection Molecule input reads. The Analysis was essentially as in example 4 and 6 except that the database of 2OS sequences was expanded to include the new 175 Labels and sequences were mapped according to corresponding 2OS DNA-barcodes.

i. Mapping sequencing reads to 2OS DNA-barcodes: A sequence database was created consisting of the possible combinations of 20 sample-identification barcodes and 192 2OS DNA barcodes (together with the primer and annealing sequences from the 2OS system). This accumulated to 3840 sequences that could be expected from a sequencing run. Each sequencing read was then used to search the database for alignments, using the nucleotide BLAST algorithm, with a match reward of 1, mismatch reward of −2 and a gap cost of 2 for both opening and extending a gap. In this way sequencing errors were penalized equally, whether a base was miscalled or inserted/deleted in the sequencing read compared to the actual sequence. Alignments were discarded by the following criteria:
   1. E-value>1e-12; insufficient length of alignment (should be greater than 102 for the 2OS barcodes).
   2. Start position in subject sequence larger than 2, i.e. fewer than 5 out of 6 bases in the unique part of the sample-identification barcode was included in the alignment.
ii. If multiple alignments could still be found for any sequencing read, only the alignment with the best percent identity was kept. Finally, the number of reads mapping to each DNA barcode in the database was counted.
iii. Identifying overrepresented DNA barcodes: Two amendments of the analysis performed in example 4 and 6 (as well as 3 and 5 in respect to the 1OS label system) were introduced:
   a. The N6 sequence (FIG. 9) were applied to reduce the clonality of the amplification product to avoid potential biases derived from amplification of enriched 2OS sequence Labels.
      i. Any repetitive reads that would share a N6 and map to a given sample-ID all through the 2OS barcode region were virtually removed ensuring that this sequence was only accounted for once.
   b. The sequencing data was reanalyzed after virtual removal of the most high-frequent sequences. This ensured that potential biases derived from high-percentage enrichment of a given Detection Molecule, resulting in large read counts from the associated 2OS sequence Label, would not mask the presence of lower percentages yet enriched Detection Molecules. Collectively this strategy is termed clonality reduction. Relative read counts were calculated by normalizing each read to the total read count mapping to the same sample-ID barcode. The relative read counts were then used to calculate the fold change per DNA-barcode compared to the control DNA-barcode Detection Molecule input (the non-enriched Detection Molecule library). Significantly overrepresented DNA-barcodes were identified using a 2-sample test for equality of proportions on the raw read counts in a sample versus the DNA-barcode input-sample, and p-values were corrected for multiple testing using the Benjamini-Hochberg FDR method. The algorithm applied for this analysis is available at: www.cbs.dtu.dk/services/Barracoda/

Example 7—Results and Conclusions

FACS sorting of fluorescent labeled cells, specific amplification of DNA-barcode Labels and high-throughput sequencing verified that it was possible to enrich and detect 2OS barcodes from a library of multiple different Detection molecules composed of 175 different 2OS DNA-barcode Labels encoding for 175 different cancer-specificities (FIG. 16). It implied that several DNA-barcodes, encoding different antigen specificities, could be enriched for and detected in parallel, also when the samples, as in the present example, were TILs that on average has a lower avidity of their TCR to their pMHC antigen. The results indicated that the presence of multiple cancer-specific T cell responses could be detected in parallel in a sample.

This example implies that it is possible to detect several cancer-specific T cell responses in parallel when applying a library of Detection molecules of increasing complexity.

Example 8

In this example 1025 different binding molecules are used in the form of pMHC complexes (each with DNA labels). The sample is a mixture of two different blood samples, the isolating and/or detecting is done by flow cytometry and the determining of the identity of the label is done by sequencing the DNA label.

Example 8 Explained

This example is essentially the same as example 4 but will apply a larger Detection Molecule library (1025) and will include a greater number of different HLA-types (11) to analyze the same samples.

This is an example where the Samples (1) are blood from one donor that is HLA-B0702:CMV pp65 TPR positive and another donor that is HLA-B0702 negative which are modified (1b) to generate Peripheral blood mononuclear cells (PBMCs). These samples are mixed in different ratios to generate new samples with different but known frequencies of T cells specific toward the HLA-B0702:CMV epitope.

The Linker (2) is a dextran conjugate with streptavidin and fluorochrome (Dextramer backbone from Immudex).

The Binding Molecules (3) are peptide-MHC (pMHC) complexes displaying one out of 1025 different peptide-antigens. The MHC molecules are modified (3b) by biotinylation to provide a biotin capture-tag for the Linker. The binding molecules are purified (2c) by HPLC and quality controlled in terms of the formation of functional pMHC multimers for staining of control T-cell populations.

The Labels (4) are oligonucleotides applied as DNA-barcodes. The oligonucleotides are synthetized (4a) by DNA Technology A/S (Denmark) and are synthetically modified (4b) with a terminal biotin capture-tag. The labels are combined oligonucleotide labels arising by annealing an A oligonucleotide (modified with biotin) to a partially complimentary B oligonucleotide label followed by enzymatic DNA polymerase extension of Oligo A and Oligo B to create a fully double stranded label.

The Detection Molecule (5) is synthetized (5a) by attaching Binding Molecules in the form of biotinylated pMHC and Labels in the form of biotin-modified oligonucleotides (DNA-barcodes) onto a streptavidin-modified dextran linker. The detection molecule further contains a modification (5b) in the form of a fluorochrome. A library of 1025 different Detection Molecules are generated wherein individual Binding Molecules, comprised of different pMHC, are encoded for by corresponding individual Labels, comprised of different DNA-barcodes.

An amount of sample, PBMC's (1b) is incubated with an amount of mixed Detection Molecules (5) under conditions (6c) allowing binding of Detection Molecules to T cells in the sample.

The cell-bound Detection Molecules are separated from the non-cell bound Detection Molecules (7) by first a few rounds of washing the PBMC's through centrifugation sedimentation of cells and resuspension in wash buffer followed by Fluorescence Activated Cell Sorting (FACS) of fluorochrome labeled cells. T cells that can efficiently bind Detection Molecules will fluoresce because of the fluorochrome comprised within the detection molecules; T cells that cannot bind detection molecules will not fluoresce. FACS-sorting leads to enrichment of fluorescent cells, and hence, enrichment of the detection molecules along with the associated labels that bind T cells of the PBMC sample.

FACS isolated cells are subjected to PCR for specific amplification of the DNA-barcode associated with the Detection Molecules bound to the isolated cells. High throughput sequencing of the resultant PCR product will reveal the identity of Detection Molecules that binds to T cells present in the sample.

This example will reveal the presence of T cells in the blood expressing a T cell receptor that binds to pMHC molecules represented within the library of 1025 Detection Molecules. The number of sequencing reads that will map to a given DNA-barcode and its corresponding Binding Molecule will mirror the frequency of the T cells found by conventional MHC multimer stainings using the same Binding Molecules. The increased complexity of the Detection Molecule library, in terms of the number of different Binding Molecules and Labels, will reflect positively upon the sensitivity for detecting a given Label, i.e. a Detection Molecule, associated with low frequencies of T cells binding such Detection Molecules.

Example 8 in Detail

Figure 2:
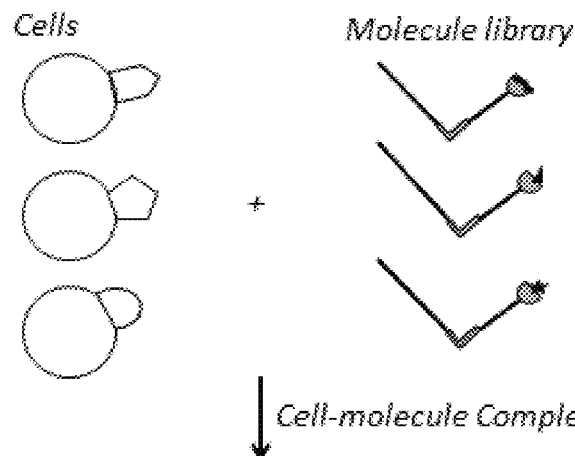
FIG. 2. Isolation and detection of detection molecules capable of binding to cells. The different steps of the method is outlined. In the depicted method the label of the detection molecule is an oligonucleotide. In Step 1 cells and "molecule library" (2-1015 detection molecules) is mixed. In Step 2 the cells and detection molecules are incubated, allowing none, some or all of the detection molecules to bind cells, and vice versa, allowing none, some or all of the cells to bind detection molecules. In step 3 the cell-detection molecule complexes are isolated, enriched for or detected. In the depicted approach, cells are spun down, having the effect of spinning detection molecules bound to the cells down as well. In Step 4 the detection molecules that bound to cells in step 3 (and therefore were co-precipitated with the cells) are identified. In the example the label consists of an oligonucleotide. Therefore, by PCR amplification of the oligonucleotide labels, followed by e.g. polyacrylamide gel electrophoresis to distinguish labels with different migration in the gel, the labels may be identified and thereby the detection molecules (and the identity of the corresponding binding molecules) can be identified. Alternatively, the oligonucleotide labels are identified by sequencing, directly from the precipitate of step 3, or following amplification of the oligonucleotides in the precipitate by e.g. PCR.
Figure 2:
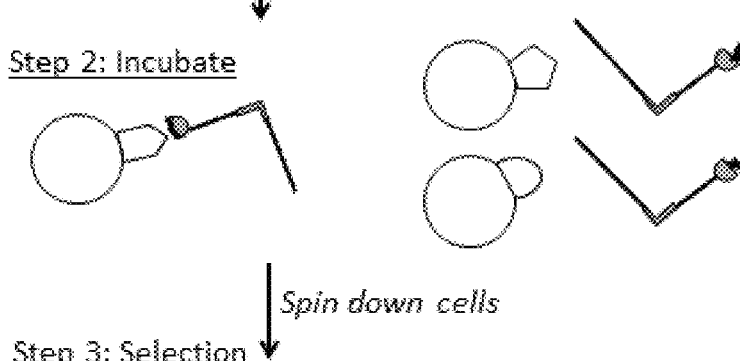
Figure 2:
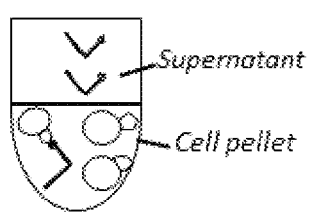
Figure 2:
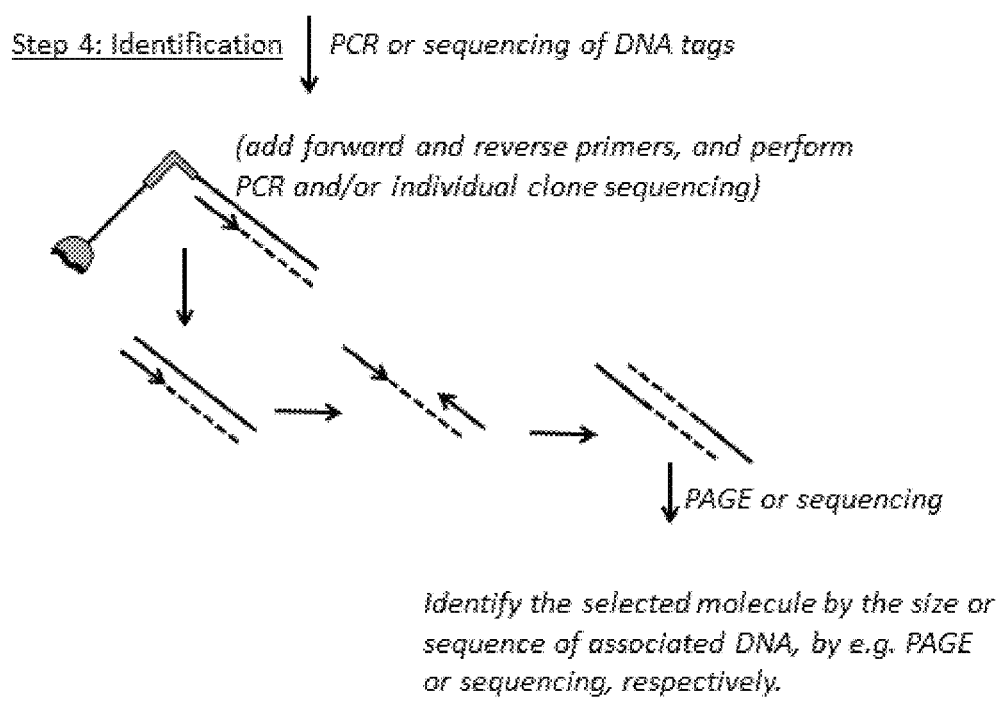

1. Sample preparation. The cell samples used in this example are obtained by preparing PBMC's from blood drawn from one donor that is HLA-B0702:CMV pp65 TPR positive and from another donor that is HLA-B0702 negative, as determined by conventional pMHC-multimer and antibody staining. They are acquired (a.) and modified (b.) in the same way as described in example 3-4.
2. Linker preparation: The linker used in this example is prepared as in example 1-7.
3. Binding Molecules preparation: The Binding Molecules used in this example are class I MHC-peptide complexes. The individual specificities (allele and peptide combination) are generated as described in example 1-7. A library of 1025 different pMHCs are generated including 11 different HLA-types.
   a. Synthesis: As described in example 1-7
   b. Modification: No further modifications
   c. Purification: As described in example 1-7
4. Label preparation: In this example Labels are synthetic oligonucleotides modified with biotin for coupling to the Linker. 1025 different Labels from the 2OS system were applied (table 2).
   a. Synthesis: As described in example 1.
      i. The Label system used in this example is named 2OS and was developed to increase the complexity of a limited number of oligonucleotide sequences. This is enabled by applying a combinatorial strategy where two partially complementary oligonucleotides (an A oligonucleotide with a 5' biotin tag and a B oligonucleotide) are annealed and then elongated to produce new unique oligonucleotide-sequences (AxBy) which are applied as a DNA-barcodes (Labels) (FIG. 2). By combining 22 unique oligonucleotide-sequences (A label precursor) that are all partly complementary to 55 other unique oligonucleotide sequences (B label precursor) a combinatorial library of 1210 different (AxBy) Labels are produced. Only 1025 of these Labels are used in this example.
   b. Modification: As described in example 1-7.
   c. Purification: As described in example 1-7.
5. Detection Molecules preparation: 1025 different Detection Molecules are generated, each with a different Binding Molecule encoded by a unique Label. The Binding Molecules (pMHCs) and Labels (2OS DNA-barcodes) are attached to the Linker (dextran-streptavidin-PE conjugate), to form Detection Molecules, in such a way that a given pMHC is always attached to a given DNA-barcode.
   a. Detection Molecules are essentially generated in the same way as described in example 1-7. The given combination of Label (2OS DNA-barcode) and Binding Molecule (pMHC) of each Detection Molecule are registered.
   b. Modification: Since the total volume of 1025 pooled Detection Molecules exceeds 100 µl this volume is reduced to reach a desired concentration of specific Binding Molecules. This is done as described in example 2-7.
   c. Purification: As described in example 1-7.
6. Incubation of sample and Detection Molecules: The cell sample and the Detection Molecules are mixed in one container to allow Detection Molecules to bind to T cells.
   a. Amount of sample: Samples are equivalent to those used in example 3-4.
   b. Amount of Detection Molecule: As described in example 1-7
   c. Conditions: Samples and Detection Molecules are treated under the same conditions as described in example 3-4.
7. Enrichment of MHC molecules with desired characteristics: The Detection Molecules are enriched for in the same way as described in example 1-7.
8. Identification of enriched Detection Molecules: Because the Detection Molecules are enriched based on specific interaction of the Binding Molecule (the pMHC) with cells, the identification of the associated Labels (DNA-barcodes) amongst the sorted cells will also reveal the pMHCs that bind to cells in the PBMC sample. In this example the DNA-barcodes associated with the enriched Detection Molecules, are amplified by PCR and identified by high-throughput sequencing.
   a. Apply. The sorted cell samples which contain DNA-barcodes derived from the enriched Detection Molecules are amplified by PCR. See table table 10 for composition of the PCR and table 11 for the thermal profile. The Taq PCR Master Mix Kit (Qiagen, #201443) is applied and PCR is run on the thermal cycler: GeneAmp, PCR System 9700 (Applied Biosystem). PCR products are visualized after gel electrophoresis on a Bio-Rad Gel Doc EZ Imager. DNA is sequenced using the Ion Torrent PGM platform (Life Technologies)
i. Primers are purchased from DNA Technology (Denmark) and delivered as lyophilized powder. Stock dilutions of 100 µM are made in nuclease free water and stored at −20° C. The primers include adaptors for Ion Torrent sequencing, i.e. an A-key and a P1-key on the forward and reverse primer respectively. Additionally the forward primers have unique DNA sequences besides the primer region and the A-key. These primers are used to assign DNA-barcodes derived from the same sample with a sample-identification sequence (Sample-ID barcode) (refer to table 13 for primer sequences). This enables distribution of DNA-barcode sequence reads according to their originating sample, when DNA-barcodes from multiple samples are sequenced in the same sequencing reaction (see FIG. 9 for a schematic presentation of the primer design). The non-enriched library of the 1025 different Detection Molecules (diluted 100.000× after being reduced in volume) are also assigned with a sample-ID barcode through PCR (referred to as the Detection Molecule input). Triplicate PCRs are run with the Detection Molecule-input. Information about the distribution of Labels within the library of Detection Molecules before enrichment will allow normalization of the sequence output. Pooled PCR products derived from the sample input and from multiple incubations of Detection Molecule and sample are separated according to size, by gel-electrophoresis, and the excised gel-fragment containing DNA-fragments of ~200 bp are purified with the QIAquick PCR Purification Kit (Qiagen, #28104) according to standard procedure.
ii. The purified DNA was sequenced on an Ion Torrent PGM 314 chip.

b. Analysis. Positive sequence reads are aligned to sequences that read from the sample-barcode-identity at the 5'-end all the way through the DNA-barcode-identity. The number of reads is normalized according to the total number of reads that maps to the same sample-ID barcode and according to the Detection Molecule input reads. The Analysis is essentially as in example 7 except that the database of 2OS sequences now includes 1025 Labels and sequences are mapped according to corresponding 2OS DNA-barcodes.
i. Mapping sequencing reads to 2OS DNA-barcodes: A sequence database is created consisting of the possible combinations of 10 sample-identification barcodes and 1025 2OS DNA barcodes (together with the primer and annealing sequences from the 2OS system). This accumulates to 10250 sequences that can be expected from a sequencing run. Each sequencing read is then used to search the database for alignments, using the nucleotide BLAST algorithm, with a match reward of 1, mismatch reward of −2 and a gap cost of 2 for both opening and extending a gap. In this way sequencing errors are penalized equally, whether a base was miscalled or inserted/deleted in the sequencing read compared to the actual sequence. Alignments are discarded by the following criteria:
1. E-value>1e-12; insufficient length of alignment (should be greater than 102 for the 2OS barcodes).
2. Start position in subject sequence larger than 2, i.e. fewer than 5 out of 6 bases in the unique part of the sample-identification barcode was included in the alignment.
If multiple alignments can still be found for any sequencing read, only the alignment with the best percent identity is kept. Finally, the number of reads mapping to each DNA barcode in the database is counted.
ii. Identifying overrepresented DNA barcodes: Is essentially performed as described in example 7 with the strategy of applying clonality reduction. Relative read counts are calculated by normalizing each read to the total read count mapping to the same sample-ID barcode. The relative read counts are then used to calculate the fold change per DNA-barcode compared to the control DNA-barcode Detection Molecule input (the non-enriched Detection Molecule library). Significantly overrepresented DNA-barcodes are identified using a 2-sample test for equality of proportions on the raw read counts in a sample versus the DNA-barcode input-sample, and p-values are corrected for multiple testing using the Benjamini-Hochberg FDR method. The algorithm applied for this analysis is available at: www.cbs.dtu.dk/services/Barracoda/

Example 8—Results and Conclusions

The expected outcome of this example is knowledge on the sensitivity for detecting antigen-specific T cell responses of decreasing frequency (<0.002% of CD8 T cells) in a number of similar samples. The sensitivity will expectantly increase with increasing numbers of Detection molecules incubated with a given sample, because any sequencing reads that are caused by background will be distributed on a greater number of Labels, in this example 1025.

Example 9

In this example 1025 different pMHC complexes, comprising 11 different HLA-alleles, are used as binding molecules. The sample is a mixture of blood from 10 different donors.

Example 9 Explained

This example is essentially the same as example 6 but a greater number of samples (10) will be analyzed with a larger Detection Molecule library (1025), which will include a greater number of different HLA-types (11).
This is an example where the Samples (1) are blood from 10 different donors with different HLA-types which are modified (1b) to generate Peripheral blood mononuclear cells (PBMCs).
The Linker (2) is a dextran conjugate with streptavidin and fluorochrome (Dextramer backbone from Immudex).
The Binding Molecules (3) are peptide-MHC (pMHC) complexes displaying one out of 1025 different peptide-antigens. The MHC molecules are modified (3b) by biotinylation to provide a biotin capture-tag for the Linker. The binding molecules are purified (2c) by HPLC and quality controlled in terms of the formation of functional pMHC multimers for staining of control T-cell populations.

The Labels (4) are oligonucleotides applied as DNA-barcodes. The oligonucleotides are synthetized (4a) by DNA Technology A/S (Denmark) and are synthetically modified (4b) with a terminal biotin capture-tag. The labels are combined oligonucleotide labels arising by annealing an A oligonucleotide (modified with biotin) to a partially complimentary B oligonucleotide label followed by enzymatic DNA polymerase extension of Oligo A and Oligo B to create a fully double stranded label.

The Detection Molecule (5) is synthetized (5a) by attaching Binding Molecules in the form of biotinylated pMHC and Labels in the form of biotin-modified oligonucleotides (DNA-barcodes) onto a streptavidin-modified dextran linker. The detection molecule further contains a modification (5b) in the form of a fluorochrome. A library of 1025 different Detection Molecules are generated wherein individual Binding Molecules, comprised of different pMHC, are encoded for by corresponding individual Labels, comprised of different DNA-barcodes.

An amount of sample, PBMC's (1b) is incubated with an amount of mixed Detection Molecules (5) under conditions (6c) allowing binding of Detection Molecules to T cells in the sample.

The cell-bound Detection Molecules are separated from the non-cell bound Detection Molecules (7) by first a few rounds of washing the PBMC's through centrifugation sedimentation of cells and resuspension in wash buffer followed by Fluorescence Activated Cell Sorting (FACS) of fluorochrome labeled cells. T cells that can efficiently bind Detection Molecules will fluoresce because of the fluorochrome comprised within the detection molecules; T cells that cannot bind detection molecules will not fluoresce. FACS-sorting leads to enrichment of fluorescent cells, and hence, enrichment of the detection molecules along with the associated labels that bind T cells of the PBMC sample.

FACS isolated cells are subjected to PCR for specific amplification of the DNA-barcode associated with the Detection Molecules bound to the isolated cells. High throughput sequencing of the resultant PCR product will reveal the identity of Detection Molecules that binds to T cells present in the sample.

This example will reveal the presence of T cells in the blood expressing a T cell receptor that binds to pMHC molecules represented within the library of 1025 Detection Molecules. The number of sequencing reads that will map to a given DNA-barcode and its corresponding Binding Molecule will mirror the frequency of the T cells found by conventional MHC multimer stainings using the same Binding Molecules. The increased complexity of the Detection Molecule library, in terms of the number of different Binding Molecules and Labels, will enable detection of T cells of 1025 different T cell receptor specificities in parallel and will reflect positively upon the sensitivity for detecting a given Label, i.e. a Detection Molecule, associated with low frequencies of T cells binding such Detection Molecules.

Example 9 in Detail

1. Sample preparation. The cell samples used in this example are obtained by preparing PBMC's from blood drawn from 10 different donors with a number of different peptide-antigen responsive T cells, as determined by conventional pMHC-multimer.
   a. Acquiring sample: Blood is obtained from the Danish Blood Bank.
   b. Modifying sample: PBMCs are isolated from whole blood as described in example 1-2, 5-6.
2. Linker preparation: The linker used in this example is prepared as in example 1-7 and example 8.
3. Binding Molecules preparation: The Binding Molecules used in this example are class I MHC-peptide complexes. The individual specificities (allele and peptide combination) are generated as described in example 1-7 and example 8. A library of 1025 different pMHCs are generated including 10 different HLA-types.
   a. Synthesis: As described in example 1-7 and example 8.
   b. Modification: No further modifications
   c. Purification: As described in example 1-7 and example 8.
4. Label preparation: In this example Labels are synthetic oligonucleotides modified with biotin for coupling to the Linker. 1025 different Labels from the 2OS system were applied (table 2).
   a. Synthesis: As described in example 1.
      i. The Label system used in this example is named 2OS and was developed to increase the complexity of a limited number of oligonucleotide sequences. This is enabled by applying a combinatorial strategy where two partially complementary oligonucleotides (an A oligonucleotide with a 5' biotin tag and a B oligonucleotide) are annealed and then elongated to produce new unique oligonucleotide-sequences (AxBy) which are applied as a DNA-barcodes (Labels) (FIG. 9). By combining 22 unique oligonucleotide-sequences (A label precursor) that are all partly complementary to 55 other unique oligonucleotide sequences (B label precursor) a combinatorial library of 1210 different (AxBy) Labels are produced. Only 1025 of these Labels are used in this example.
   b. Modification: As described in example 1-7 and example 8.
   c. Purification: As described in example 1-7 and example 8.
5. Detection Molecules preparation: 1025 different Detection Molecules are generated, each with a different Binding Molecule encoded by a unique Label. The Binding Molecules (pMHCs) and Labels (2OS DNA-barcodes) are attached to the Linker (dextran-streptavidin-PE conjugate), to form Detection Molecules, in such a way that a given pMHC is always attached to a given DNA-barcode.
   a. Detection Molecules are essentially generated in the same way as described in example 1-7 and example 8. The given combination of Label (2OS DNA-barcode) and Binding Molecule (pMHC) of each Detection Molecule are registered.
   b. Modification: Since the total volume of 1025 pooled Detection Molecules exceeds 100 µl this volume is reduced to reach a desired concentration of specific Binding Molecules. This is done as described in example 2-7 and example 8.
   c. Purification: As described in example 1-7 and example 8.
6. Incubation of sample and Detection Molecules: The cell sample and the Detection Molecules are incubated in the same way as described in example 1-2, 5-7.The cell sample and the Detection Molecules are mixed in one container to allow Detection Molecules to bind to T cells.

7. Enrichment of MHC molecules with desired characteristics: The Detection Molecules are enriched for in the same way as described in example 1-7 and example 8.
8. Identification of enriched Detection Molecules: Because the Detection Molecules are enriched based on specific interaction of the Binding Molecule (the pMHC) with cells, the identification of the associated Labels (DNA-barcodes) amongst the sorted cells will also reveal the pMHCs that bind to cells in the PBMC sample. In this example the DNA-barcodes associated with the enriched Detection Molecules, are amplified by PCR and identified by high-throughput sequencing. The enriched Labels, of the 2OS DNA-barcode system, are identified as in example 8.

Example 9—Results and Conclusions

The expected outcome of this example is knowledge of the potential complexity for detecting multiple antigen-specific T cell responses in parallel in a single sample. Since the sensitivity is expected to increase with increasing numbers of Detection molecules incubated with a given sample (as described in example 8) it is expected that multiple more T cell responses will also be detected in parallel when using a Detection molecule library of the said complexity. The example will thus prove that it is possible to detect multiple antigen-specific T cell responses in parallel when applying a Detection molecule library comprised of 1025 different 2OS Labels encoding 1025 different Binding molecules distributed on 11 HLA-types.

Example 10

In this example it is shown how multiple, single-cell analyses can be rapidly performed using the present invention. The isolating and/or detecting is done by FACS, leading to the identification of a T cell and its TCR, as well as the pMHC complex that recognizes the T cell by binding to the TCR.

Example 10 Explained

This example will describe how the detection of Binding Molecules can be linked to the T cell receptor (TCR) sequence following single cell sorting of T-cells associated with Detection Molecules.

This is an example where the Sample (1) will be a mixture of T cells comprising TCRs of interest. This could e.g. be tumor infiltrating lymphocytes from a cancer patient. The Linker (2) is a dextran conjugate with streptavidin and fluorochrome (Dextramer backbone from Immudex).

The Binding Molecules (3) is peptide-MHC (pMHC) complexes displaying a of library peptides that are potentially recognized by the T cells in the Sample. This could be a library of melanoma-associated peptides, as used in example 7, or it could be a library of personally-defined potential epitope sequences based on the characteristics of the given patient's tumor. This could e.g. be mutation-derived T cell epitopes and/or epitopes selected based on the expression pattern in the individual tumor. The Binding Molecules will be modified (3b) by biotinylation and quality controlled as described in example 1-6.

The Labels (4) are oligonucleotides as in example 7-9.
The detection molecule (5) will be synthetized (5a) and modified (5b) as in example 7-9.

An amount of Sample, Tumor infiltrating lymphocytes (1b) will be mixed with detection molecules (5) under conditions (6c) that allow binding of detection molecules to T cells in the sample.

Cells will be FACS sorted based on the attachment of Detection Molecules, transferred to a FLUIDIGM C1 unit (or similar device) for single-cell amplification of nucleotide labels and T cell receptor genes.

This example thus reveals the possibility to identify, on a single-cell level, both the antigen-specificity and the T cell receptor sequence. This being done in a mixture of multiple different Binding Molecules (potentially, but not exclusively, >1000). This technology provides a mean for high-throughput identification of TCRs combined with a description of the antigen specificity of the TCR.

Example 10 in Detail

1. Sample preparation. The cell sample to be used in this example is a collection of T cells with a recognition profile of interest for determining the sequences of the TCRs associated with this recognition. The sample could e.g. be tumor infiltration lymphocytes from a cancer patient. As described in example 7.
    c. Acquiring sample: As in example 7.
    d. Modifying sample: As in example 7.
2. Linker preparation: The linker used in this example is prepared as in example 1-10. The fluorochrome co-attachment is important for the selection process in the example.
3. Binding molecule preparation: The binding molecules used in this example will be a collection of peptide-MHC molecules, designed to match the T cell reactivity in the sample. This could be a library of melanoma-associated peptides, as used in example 7, or it could be a library of personally-defined potential epitope sequences based on the characteristics of the given patient's tumor. This could e.g. be mutation-derived T cell epitopes and/or epitopes selected based on the expression pattern if the individual tumor.
    a. Synthesis: as in example 7-9.
    b. Modification: No further modifications
    c. Purification: as in example 7-9.
4. Label preparation: as in example 7-9.
5. Detection Molecules preparation: multiple (<1000) different Detection Molecules are generated, each with a different Binding Molecule encoded by a unique Label. The Binding Molecules (pMHCs) and Labels (2OS DNA-barcodes) are attached to the Linker (dextran-streptavidin-PE conjugate), to form Detection Molecules, in such a way that a given pMHC is always attached to a given DNA-barcode.
    a. Detection Molecules are essentially generated in the same way as described in example 1-8.
    b. Modification: Since the total volume of >1000 pooled Detection Molecules exceeds 100 µl this volume is reduced to reach a desired concentration of specific Binding Molecules. This is done as described in example 2-8.
    c. Purification: As described in example 1-8.
6. Incubation of sample and Detection Molecules: The cell sample and the Detection Molecules are incubated in the same way as described in example 1-2, 5-7. The cell sample and the Detection Molecules are mixed in one container to allow Detection Molecules to bind to T cells 7. Enrichment of MHC molecules with desired characteristics: The Detection Molecules are enriched for in the same way as described in example 1-7. Cells associated with Detection Molecules are sorted by FACS, through means of the PE-fluorescence signal. The population of cells holding Detection Molecules are following injected to the FLUIDIGM C1 unit allowing for single cell distribution in a micro-well system. Other similar devices or platforms for single cell amplification can also be used.
8. Identification of enriched Detection Molecules: For each cell in the FLUIDIGM C1 unit we will amplify a) the label (=DNA oligonucleotide barcode) and b) the TCR V-alpha and -beta chains. In each well specific primers holding cell identification keys, will be used to amplify DNA oligonucleotide Label. Likewise specific primers holding cell identification keys will be used to amplify the TCR-associate genes, the TCR V-alpha and Beta chains. The complete sequence of the TCR chains will allow the assembly of a fully functional TCR sequence. In parallel knowledge about the Binding Molecules associated with the given T cell, will provide insight o the antigen recognition of the given TCR. Thus we can obtain paired samples of TCR sequences and antigen specificities, using the strategy explained in this example.

Example 10—Results and Conclusions

The expected outcome of this example is knowledge of the TCR receptor coupled to the knowledge of the recognition of Binding Molecules of this given TCR. Single-cell sorting will enable the generation of a correctly paired and fully functional TCR. The association of the labels will explain the recognition motif of this T cell receptor and provide valuable information in this regard. The technique described here will allow the parallel assessment of multiple different T cells while enabling the capture of specific T cells receptor sequences and have paired knowledge about the Binding molecules associated to this. The overall principle of example 10 is schematized in FIG. 6C.

Example 11

In this example all cells carry the same TCR (T cell receptor). A large number of different pMHC complexes (binding molecules) are employed, in order to examine the recognition breadth and affinity of a given T cell receptor (TCR).

Example 11 Explained

This example describes how the detection of Binding Molecules can be used to determine the recognition breadth and affinity of a given T cell receptor (TCR).
This is an example where the Sample (1) is a T cell clone or a culture of T cell receptor transduced T cells. Importantly for this example all cells will hold the same T cell receptor.
The Linker (2) was a dextran conjugate with streptavidin and fluorochrome (Dextramer backbone from Immudex).
The Binding Molecules (3) will be peptide-MHC (pMHC) complexes displaying a library of peptides that are potentially recognized by the T cell receptor in question. This could ideally be a set of alanine-scanning substituted peptides modified based on the known recognition sequence of the T cell receptor in question. The Binding Molecules will be modified (3b) by biotinylation and quality controlled as described in example 1-6.
The Labels (4) are oligonucleotides as in example 7-9.
The detection molecule (5) will be synthetized (5a) and modified (5b) as in example 7-9. Multiple different detection molecules will be generated wherein the individual detection molecules containing different pMHC were encoded by corresponding individual oligonucleotide labels, as in example 7-9.
An amount of Sample, T cell clone (1b) will be mixed with detection molecules (5) under conditions (6c) that allow binding of detection molecules to the T cells in the sample.
Cells will be washed to remove excess Detection Molecules, and following the identity of the Binding Molecules will be revealed through sequencing of the Label.
This example thus reveals the possibility to identify the specificity and breadth of specificity of a given T cell receptor. This knowledge is essential for the development of T cell receptor gene therapy strategies, and adoptive transfer of T cell population carrying specific T cell receptors.

Example 11 in Detail

1. Sample preparation. The cell sample to be used in this example is a T cell clone (carrying a single, defined T cell receptor) or a culture of T cells transduced with a given T cell receptor.
   e. Acquiring sample: Any PBMC sample can be used as a source to transduce the T cells with a characterized T cell receptor (TCR), expressed in a retroviral vector.
   f. Modifying sample: PBMCs modified to express a given TCR following retroviral transduction using a vector expressing the selected TCR.
2. Linker preparation: The linker used in this example is prepared as in example 1-10. The fluorochrome has no particular use in this example. Consequently, the fluorochrome attachment is not needed.
3. Binding molecule preparation: The binding molecules used in this example will be a collection of peptide-MHC molecules, designed to assess the breadth to recognition of the given TCR. The peptide library could be alanine substitution libraries of the known peptide-epitope recognized by the given TCR. Alanine substitution is used to assess the essential amino acids in given positions important for TCR recognition.
   a. Synthesis: as in example 7-9.
   b. Modification: No further modifications
   c. Purification: as in example 7-9.
4. Label preparation: as in example 7-9.
5. Detection molecules preparation: as in example 7-9.
6. Incubation of sample and detection molecules: The cell sample and the Detection Molecules were mixed in one container, to allow the Detection Molecules to bind the T cells that they recognize.
   a. Amount of sample: 100.000 cells expressing a given TCR
   b. Amount of detection molecule: as in example 7-9.
   c. Conditions: The 100.000 cells will be mixed with different quantities of Detection Molecules. This being the standard amount of detection molecules as given in example 7-9, but with parallel detection analysis using e.g. 5× excess for Detection molecules, as well as 5×, 25×, 125× fold less Detection Molecules. Such titration is done to assess the avidity of the selected TCR towards the Binding Molecule library used.
7. Enrichment of detection molecules with desired characteristics: In this example, excess Detection molecules are separated from Sample through centrifugation. All cells are expected to bind Detection molecules to some extent, and consequently all cells are used for characterization of Binding Molecules.
8. Identification of enriched Detection Molecules: The identification of Detection Molecules and analyses of sequencing results is conducted as described in example 7.

Example 11—Results and Conclusions

The expected outcome of this example is knowledge related to the Detection molecules associated with a given T cell receptor. Through this technology we can gain knowledge on the breadth and the avidity of a given TCR towards a large library of similar, overlapping and/or alanine substituted peptide-epitope sequences. The technique can be used to understand both avidity and 'fine-specificity' of a given TCR. This will be of crucial importance for development of TCR receptor-associated therapies, such as TCR gene therapy in cancer treatment. The overall principle of example 11 is schematized in FIG. 6D.

Example 12

In this example it is described how the present invention can be used to identify the specificity of the stimuli that lead to a functional response of certain cells. In the example, the external stimulus is the addition of tumor cells, and the functional response measured is the release of INF-γ.

Example 12 Explained

This example will describe how the detection of Binding Molecules can be associated to a functional response to a given stimuli provided to the Sample in vitro.

This is an example where the Sample (1) will be tumor infiltrating lymphocytes (TIL) from cancer patients which are modified to determine the reactivity toward tumor cells (1b). The Sample is mixed with tumor cells to allow cytokine release from responding T cells in the Sample. The cytokines are trapped intracellular following Golgi-transport blockade and cellular fixation.

The Linker (2) was a dextran conjugate with streptavidin and fluorochrome (Dextramer backbone from Immudex).

The Binding Molecules (3) will be peptide-MHC (pMHC) complexes displaying a library of melanoma-associated peptides (as described in Andersen et al. Dissection of T cell antigen specificity in human melanoma. *Cancer Research* 2012 Apr. 1; 72(7):1642-50), and used in example 7. The Binding Molecules will be modified (3b) by biotinylation and quality controlled as described in example 1-6.

The Labels (4) were oligonucleotides as in example 7-9.

The detection molecule (5) will be synthetized (5a) and modified (5b) as in example 7-9. 175 different detection molecules were generated wherein the individual detection molecules containing different pMHC were encoded by corresponding individual oligonucleotide labels, as in example 7.

An amount of Sample, TILs (1b) will mixed with detection molecules (5) under conditions (6c) that allow binding of detection molecules to T cells in the sample. Cells will be selected by FACS based on their cytokine release upon stimulation with the tumor cells. After cellular selection, cells encompassing different cytokine profiles will be analyzed for their binding to the Detection Molecules, consequently describing the T cell receptor specificity of the responding T cells, i.e. T cells recognizing tumor cells.

This example thus reveal the possibility to identify potential differences in T cell specificity among cells responding differently to a given stimuli, here provided be the mixture of T-cells with tumor cells.

Example 12 in Detail

1. Sample preparation. The cell sample to be used in this example is tumor infiltrating lymphocytes (TILs) obtained from melanoma patients (as example 7).
   a. Acquiring sample: as in example 7.
   b. Modifying sample: TILs will be purified and expanded as in example 7. Following, TILs will be mixed with tumor cell to assess cytokine release upon T-cell mediated tumor cell recognition, using the following protocol for intracellular cytokine staining: Tumor cells will be thawed, washed twice in culture media (RPMI), and cultured in RPMI+10% FCS (R10) until they had expanded to a sufficient amount of cells. TILs will be thawed in 10 ml RPMI+2.5 ul DNase and 50 ul MgCl2, washed twice in RPMI and rested overnight or at least 4 hr in X-vivo+5% HS+100 U/ml IL-2. Following rest, the cells will be washed, counted and resuspended in X-vivo+5% HS obtaining a concentration of $3*10^6$ cells/ml. 100 ul of the cell suspension will then be added to at least two wells in a 96 well plate—more replicates will be made if enough cells are available. Thus $3*10^5$ cells will added to each well. Tumor cells will be trypsinated, washed in R10, counted and resuspended in RPMI+10% HS to a concentration of $2*10^6$ cells/ml. 50 ul of cell suspension containing $1*10^5$ cells will be added to the TILs. To every well, 50 ul of Golgi medium, containing 45 ul RPMI+10% HS, 5 ul BV421 conjugated CD107a antibody (BD pharmingen) and 0.2 ul Golgi Plug (BD Bioscience 555029) was added. The cells were then incubated 4-5 hours in 37° C. All samples were cultured in a ratio of 3:1 TIL:tumor cells, with a total of $4*10^5$ cells per well. After end incubation, the cells were spun and all replicates were collected into one well. Cell will be washed in PBS+2% FCS (FACS buffer) and resuspended in 50 uL barcode-buffer (PBS/0.5% BSA/2 mM EDTA/100 µg/ml herring DNA).
2. Linker preparation: The linker used in this example is prepared as in example 1-8. The fluorochrome has no particular use in this example. Consequently, the fluorochrome attachment is not needed.
3. Binding molecule preparation: The binding molecules used in this example will be 175 different class I MHC-peptide complexes, as in example 7.
   a. Synthesis: as in example 7.
   b. Modification: No further modifications
   c. Purification: as in example 7.
4. Label preparation: as in example 7.
5. Detection molecules preparation: as in example 7.
6. Incubation of sample and detection molecules: The cell sample and the Detection Molecules were mixed in one container, to allow the Detection Molecules to bind the T cells that they recognize.

a. Amount of sample: 50 uL cell suspension as described in 1 b.
b. Amount of detection molecule: as in example 7.
c. Conditions: The Detection molecules were added in the required amount. If necessary barcode-buffer was added to reach a total volume of 100 ul and cells were incubated 15 min, 37° C. Following incubation, cells were and stained with the following surface antibodies: anti-CD3 antibody, anti-CD8 antibody, anti-CD4 antibody and near-IR-viability dye (Invitrogen L10119). The cells were then incubated for 30 min at 4° C., after which they were washed twice in barcode-buffer and incubated in 200 ul fixation buffer (1:4 concentrate, eBioscience 00-5123-43, to diluent eBioscience 00-5223-56) overnight at 4° C. The following day, cells were washed twice in permeabilization buffer (1:10 buffer to water, eBioscience 00-8333-56), resuspended in 50 ul permeabilization buffer and stained with intracellular antibodies: FITC-conjugated anti-TNF antibody (BD pharmingen 562082), APC-conjugated anti-IFN antibody (BD 341117). After incubating for 30 min at 4° C. with the antibodies, the cells were washed twice in permeabilization buffer, resuspended in 50 ul barcode-buffer.

7. Enrichment of detection molecules with desired characteristics: In this Example, the Sample is selected based on the cytokine secretion mediated following incubation with tumor cells. Cytokines are visualized through intracellular cytokine staining (ICS). The Sample is following stained with the Detection Molecules. Cytokine producing cells will be selected by Fluorescence-Activated-Cell-Sorting (FACS), and the Detection Molecules carried along with a given cytokine profile of a given cell population will be assessed through sequencing of the co-attached oligonucleotide barcodes
   a. Apply: Cells were sorted on a BD FACSAria, equipped with three lasers (488 nm blue, 633 nm red and 405 violet). The flow cytometry data analyses will be performed using the BD FACSDiva software version 6.1.2. The following gating strategy will be applied. Lymphocytes were identified in a FSC/SSC plot. Additional gating on single cells (FSC-A/FSC-H), live cells (near-IR-viability dye negative), and CD8, CD3 positive cells, and CD4 negative.
      From this defined cell population two separate subsets will be sorted based ion the cytokine secretion in relation to tumor-cell stimulation. T cells positive for any of the detected cytokines 'ICS positive' is sorted in one tube, and T cells negative for any of the detected cytokines 'ICS negative' is sorted in another tube.
   b. Wash: not applicable.
   c. Separate: Optionally cells were acquired up to one week after fixation in 1% paraformaldehyde. The 'ICS positive' and 'ICS negative' cells were sorted by FACS, as described in 7a, into tubes that had been pre-saturated for 2h-O.N. in 2% BSA and contained 200 µl barcode-buffer to increase the stability of the oligonucleotides that followed with the sorted cells. The sorted cells were centrifuged 5 min, 5000 g, to allow removal of all excess buffer. Cells were stored at −80° C.

8. Identification of enriched Detection Molecules: The identification of Detection Molecules and analyses of sequencing results is conducted as described in example 7. The 'ICS positive' and 'ICS negative' cells are treated as two independents samples. Following these two samples are compared for the association with Binding Molecules.

Example 12—Results and Conclusions

The expected outcome of this examples is knowledge related to the Detection molecules associated with tumor cell recognition (='ICS positive') as oppose to no recognition (='ICS negative'). In other terms, we will gain knowledge on the T cell recognition elements associated with tumor cell recognition, among a large pool of different Detection Molecules, here peptide-MHC molecules. Knowledge of T cell mediated recognition of tumor cells has major impact on the design and development of immunotherapeutic strategies for cancer. The overall principle of example 12 is schematized in FIG. 6A.

Figure 6:
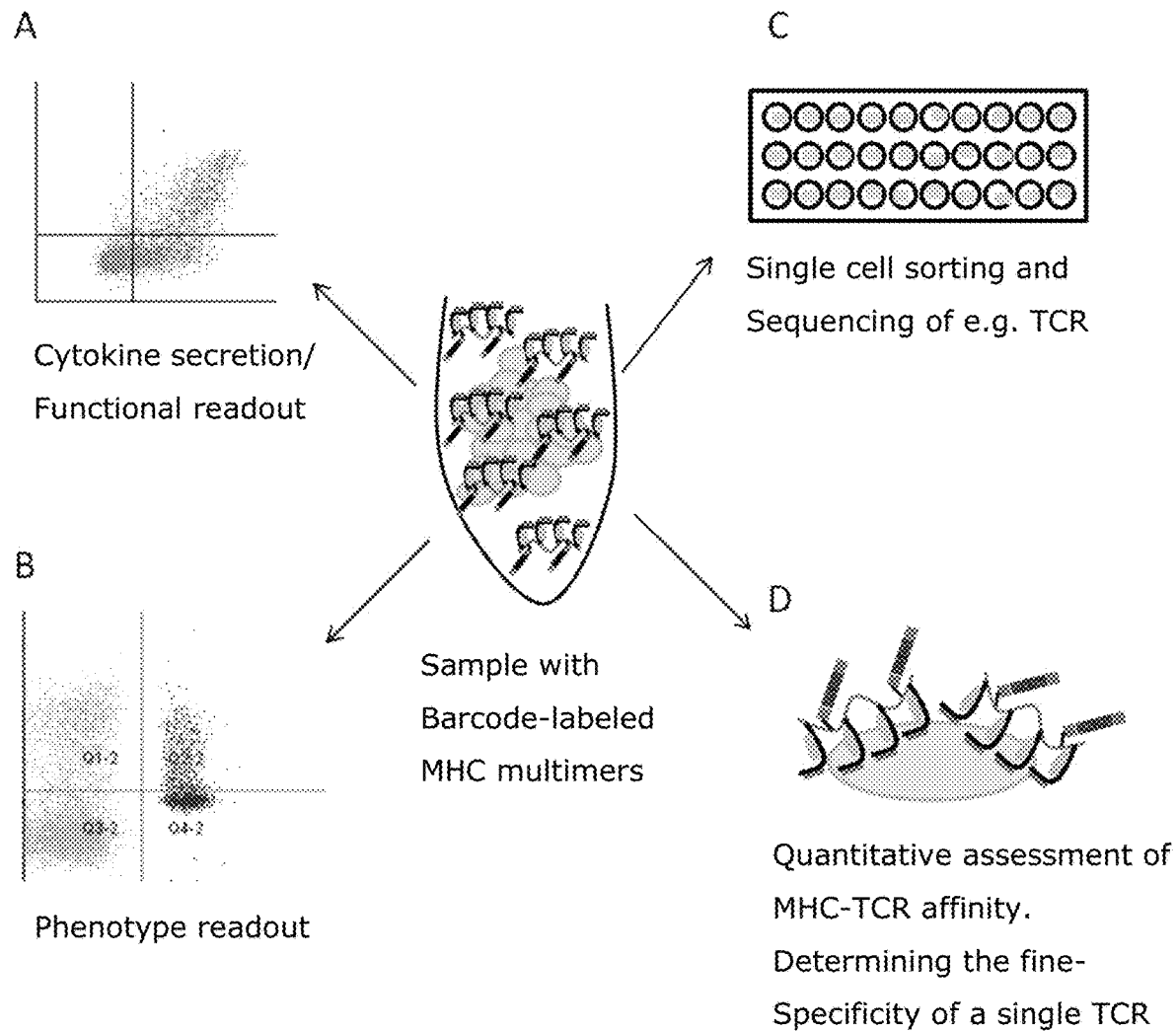
FIG. 6. Describes the possibility of linking the antigen specificity (tracked by the barcode) to other properties. Use of a multimeric major histocompatibility complex.

Cell could likewise be selected based on e.g. phenotypic characteristics, to assess what T specificities are associated with selected phenotypic characteristics as schematized in FIG. 6B.

Tables for Examples 1-12:

TABLE 1

BCs used in Examples 1-7 with indicated frequencies of peptide-antigen specific T cells as identified by conventional MHC multimer staining:

| | Epitope | Freq. (%) |
|---|---|---|
| BC171 | A11 EBV-EBNA4 | 0.32 |
| | A3 CMV pp150 TVY | 0.015 |
| BC254 | A2 FLU MP 58-66 GIL | 0.0522 |
| | A2 EBV LMP2 FLY | 0.014 |
| | A2 CMV pp65 NLV | 1.128 |
| BC261 | A2 FLU MP 58-66 GIL | 0.125 |
| | A3 EBV EBNA 3a RLR | 0.0258 |
| | A2 EBV LMP2 FLY | 0.0075 |
| BC266 | A1 CMV pp65 YSE | 0.0859 |
| | A1 FLU BP-VSD | 0.0628 |
| BC268 | A2 FLU MP 58-66 GIL | 0.2523 |
| | A2 CMV pp65 NLV | 0.5445 |
| BC260 | A2 FLU MP 58-66 GIL | 0.0456 |
| | A2 CMV pp65 NLV | 0.134 |
| | B7 CMV pp65 TPR | 4.5395 |
| BC262 | A11 EBV-EBNA4 | 0.0872 |

TABLE 2

Structure and sequences of 20S A oligonucleotides and 20S B oligonucleotides, used to produce 20S DNA-barcodes:

| Oligo name | 5' modification | Forward primer region | 6xN region | Coding region | Annealing region |
|---|---|---|---|---|---|
| 20S-1-Oligo-A1 | Biotin-C6- | GAAGTTCCAGCCAGCGTCACAGTTT | NNNNNN | CGAGGGCAATGGTTAACTGACACGT | GGTCAGCATCATTTCC |
| 20S-1-Oligo-A2 | Biotin-C6- | GAAGTTCCAGCCAGCGTCACAGTTT | NNNNNN | CAGAAAGCAGTCTCGTCGGTTCGAA | GGTCAGCATCATTTCC |

TABLE 2-continued

Structure and sequences of 20S A oligonucleotides and 20S B oligonucleotides, used to produce 20S DNA-barcodes:

| | | | | | |
|---|---|---|---|---|---|
| 20S-1-Oligo-A3 | Biotin-C6- | GAAGTTCCAGCCAGCGTCACAGTTT | NNNNNN | TAAGTAGCGGGCATAATGTACGCTC | GGTCAGCATCATTTCC |
| 20S-1-Oligo-A4 | Biotin-C6- | GAAGTTCCAGCCAGCGTCACAGTTT | NNNNNN | GGATCCAGTAAGCTACTGCGTTTAT | GGTCAGCATCATTTCC |
| 20S-1-Oligo-A5 | Biotin-C6- | GAAGTTCCAGCCAGCGTCACAGTTT | NNNNNN | GGGCTGCGGAGCGTTTACTCTGTAT | GGTCAGCATCATTTCC |
| 20S-1-Oligo-A6 | Biotin-C6- | GAAGTTCCAGCCAGCGTCACAGTTT | NNNNNN | AAACGTATGTGCTTTGTCGGATGCC | GGTCAGCATCATTTCC |
| 20S-1-Oligo-A7 | Biotin-C6- | GAAGTTCCAGCCAGCGTCACAGTTT | NNNNNN | ATATCATCATAGGCTTAGCGACGTA | GGTCAGCATCATTTCC |
| 20S-1-Oligo-A8 | Biotin-C6- | GAAGTTCCAGCCAGCGTCACAGTTT | NNNNNN | AGGAAAATCTGCTACCGCCAATGAT | GGTCAGCATCATTTCC |
| 20S-1-Oligo-A9 | Biotin-C6- | GAAGTTCCAGCCAGCGTCACAGTTT | NNNNNN | CTGATTGACTGCATGGAGGCTATAC | GGTCAGCATCATTTCC |
| 20S-1-Oligo-A10 | Biotin-C6- | GAAGTTCCAGCCAGCGTCACAGTTT | NNNNNN | GTGGCGACTTCACGATTATCTGAAC | GGTCAGCATCATTTCC |
| 20S-1-Oligo-A11 | Biotin-C6- | GAAGTTCCAGCCAGCGTCACAGTTT | NNNNNN | CCTGTATTGAAGGTTCAGTCCTGTT | GGTCAGCATCATTTCC |
| 20S-1-Oligo-A12 | Biotin-C6- | GAAGTTCCAGCCAGCGTCACAGTTT | NNNNNN | GGCTCTATAAGGTTTCCTCAAAGGT | GGTCAGCATCATTTCC |
| 20S-1-Oligo-A13 | Biotin-C6- | GAAGTTCCAGCCAGCGTCACAGTTT | NNNNNN | TTGGGAGCTTTCCTATGTACAGTCC | GGTCAGCATCATTTCC |
| 20S-1-Oligo-A14 | Biotin-C6- | GAAGTTCCAGCCAGCGTCACAGTTT | NNNNNN | AGAGAATATGTCGCTCCCGTTATGT | GGTCAGCATCATTTCC |
| 20S-1-Oligo-A15 | Biotin-C6- | GAAGTTCCAGCCAGCGTCACAGTTT | NNNNNN | GCAGTTAGATATGCAGTTACCTGAC | GGTCAGCATCATTTCC |
| 20S-1-Oligo-A16 | Biotin-C6- | GAAGTTCCAGCCAGCGTCACAGTTT | NNNNNN | CTTCACCCGAACATGCAGTGTTATT | GGTCAGCATCATTTCC |
| 20S-1-Oligo-A17 | Biotin-C6- | GAAGTTCCAGCCAGCGTCACAGTTT | NNNNNN | AAAGCCGTTGCAGTATCGTCTGAGC | GGTCAGCATCATTTCC |
| 20S-1-Oligo-A18 | Biotin-C6- | GAAGTTCCAGCCAGCGTCACAGTTT | NNNNNN | GCTGGATGTTAATAACTGCGGTCCG | GGTCAGCATCATTTCC |
| 20S-1-Oligo-A19 | Biotin-C6- | GAAGTTCCAGCCAGCGTCACAGTTT | NNNNNN | ACGAGTTGACATGGACGGATCCCTC | GGTCAGCATCATTTCC |
| 20S-1-Oligo-A20 | Biotin-C6- | GAAGTTCCAGCCAGCGTCACAGTTT | NNNNNN | TTCATCACTCATTGTTCTGAGTAGG | GGTCAGCATCATTTCC |
| 20S-1-Oligo-A21 | Biotin-C6- | GAAGTTCCAGCCAGCGTCACAGTTT | NNNNNN | ATGTTTAATCTAACTTGATGCCTCC | GGTCAGCATCATTTCC |
| 20S-1-Oligo-A22 | Biotin-C6- | GAAGTTCCAGCCAGCGTCACAGTTT | NNNNNN | TAATACGCCTGAGGTGTTGGGTTGC | GGTCAGCATCATTTCC |

| Oligo name | 5' modification | Forward (20S-R) primer region | 6xN region | Coding region | Annealing region |
|---|---|---|---|---|---|
| 20S-1-Oligo-B1 | | CTGTGACTATGTGAGGCTTTCTCGA | NNNNNN | GCCTGTAGTCCCACGCGATCTAACA | GGAAATGATGCTGACC |
| 20S-1-Oligo-B2 | | CTGTGACTATGTGAGGCTTTCTCGA | NNNNNN | CAACCATTGATTGGGGACAACTGGG | GGAAATGATGCTGACC |
| 20S-1-Oligo-B3 | | CTGTGACTATGTGAGGCTTTCTCGA | NNNNNN | ACGTTTAAGCATCTGTACTCCAGAT | GGAAATGATGCTGACC |
| 20S-1-Oligo-B4 | | CTGTGACTATGTGAGGCTTTCTCGA | NNNNNN | GAATTGAAGCCATCGTTTCGCGCAA | GGAAATGATGCTGACC |
| 20S-1-Oligo-B5 | | CTGTGACTATGTGAGGCTTTCTCGA | NNNNNN | CGTAGCTTTTGTAGCGTCTGAGGGC | GGAAATGATGCTGACC |
| 20S-1-Oligo-B6 | | CTGTGACTATGTGAGGCTTTCTCGA | NNNNNN | AATCGTCAGTCCCTGTTTCGACATC | GGAAATGATGCTGACC |
| 20S-1-Oligo-B7 | | CTGTGACTATGTGAGGCTTTCTCGA | NNNNNN | CGGTGGTAGGTGATACTTCTGTACC | GGAAATGATGCTGACC |

TABLE 2-continued

Structure and sequences of 20S A oligonucleotides and 20S B
oligonucleotides, used to produce 20S DNA-barcodes:

| | | | | |
|---|---|---|---|---|
| 20S-1-Oligo-B8 | CTGTGACTATGTGAGGCTTTCTCGA | NNNNNN | TGACTATCGGGGCGTGACATGAGCT | GGAAATGATGCTGACC |
| 20S-1-Oligo-B9 | CTGTGACTATGTGAGGCTTTCTCGA | NNNNNN | GTTGGTGAAACTACCGACGCTTTAC | GGAAATGATGCTGACC |
| 20S-1-Oligo-B10 | CTGTGACTATGTGAGGCTTTCTCGA | NNNNNN | AATGGAGGTGCAGGAATACTCTCGT | GGAAATGATGCTGACC |
| 20S-1-Oligo-B11 | CTGTGACTATGTGAGGCTTTCTCGA | NNNNNN | AAAACGCACCACAACTCGGACGTGA | GGAAATGATGCTGACC |
| 20S-1-Oligo-B12 | CTGTGACTATGTGAGGCTTTCTCGA | NNNNNN | GCCATATAAGCACAGCACGCAATCC | GGAAATGATGCTGACC |
| 20S-1-Oligo-B13 | CTGTGACTATGTGAGGCTTTCTCGA | NNNNNN | CCTATGCGAACTTGGTTTATCCTGC | GGAAATGATGCTGACC |
| 20S-1-Oligo-B14 | CTGTGACTATGTGAGGCTTTCTCGA | NNNNNN | AAGCTGCGTATCCTCGAACTAGCAG | GGAAATGATGCTGACC |
| 20S-1-Oligo-B15 | CTGTGACTATGTGAGGCTTTCTCGA | NNNNNN | ATGGCGCAGACATTCTGTAGTCGCA | GGAAATGATGCTGACC |
| 20S-1-Oligo-B16 | CTGTGACTATGTGAGGCTTTCTCGA | NNNNNN | CTTATGGACTGGTTGGGACAATCC | GGAAATGATGCTGACC |
| 20S-1-Oligo-B17 | CTGTGACTATGTGAGGCTTTCTCGA | NNNNNN | TGTCCTTCCTTACGAAATATTGGTC | GGAAATGATGCTGACC |
| 20S-1-Oligo-B18 | CTGTGACTATGTGAGGCTTTCTCGA | NNNNNN | TGATGAACCAATCCTCCGATTTCTT | GGAAATGATGCTGACC |
| 20S-1-Oligo-B19 | CTGTGACTATGTGAGGCTTTCTCGA | NNNNNN | ACCGAATGTGGGCCACGAGTCATTC | GGAAATGATGCTGACC |
| 20S-1-Oligo-B20 | CTGTGACTATGTGAGGCTTTCTCGA | NNNNNN | CGGGTGAGCATATAACTTGCAATTC | GGAAATGATGCTGACC |
| 20S-1-Oligo-821 | CTGTGACTATGTGAGGCTTTCTCGA | NNNNNN | AGAATTGTGCTTGGGGCGATTCATA | GGAAATGATGCTGACC |
| 20S-1-Oligo-822 | CTGTGACTATGTGAGGCTTTCTCGA | NNNNNN | AATTGGTGACATGCTTAACTACCGT | GGAAATGATGCTGACC |
| 20S-1-Oligo-823 | CTGTGACTATGTGAGGCTTTCTCGA | NNNNNN | GAGACGCCTAGAAAGTGATTAACTC | GGAAATGATGCTGACC |
| 20S-1-Oligo-824 | CTGTGACTATGTGAGGCTTTCTCGA | NNNNNN | ATTACAGTTACAGTGCTGGTCGCAG | GGAAATGATGCTGACC |
| 20S-1-Oligo-825 | CTGTGACTATGTGAGGCTTTCTCGA | NNNNNN | CGTTACGTTGGTGGGCTCTTGGTAC | GGAAATGATGCTGACC |
| 20S-1-Oligo-826 | CTGTGACTATGTGAGGCTTTCTCGA | NNNNNN | GTTATTATCGGTGTCCCGACTAGTT | GGAAATGATGCTGACC |
| 20S-1-Oligo-827 | CTGTGACTATGTGAGGCTTTCTCGA | NNNNNN | AGAAATGATTCCCGAGTCGCCTTTT | GGAAATGATGCTGACC |
| 20S-1-Oligo-828 | CTGTGACTATGTGAGGCTTTCTCGA | NNNNNN | TGCTCTCGGATGTGGTTCTATGGAT | GGAAATGATGCTGACC |
| 20S-1-Oligo-829 | CTGTGACTATGTGAGGCTTTCTCGA | NNNNNN | GAGTTAAAACCGTCGCCGTAGCACT | GGAAATGATGCTGACC |
| 20S-1-Oligo-830 | CTGTGACTATGTGAGGCTTTCTCGA | NNNNNN | TGTACGCGATAGTACTCGGGTCCTG | GGAAATGATGCTGACC |
| 20S-1-Oligo-831 | CTGTGACTATGTGAGGCTTTCTCGA | NNNNNN | AACTTACGCCCAGCAAGGCATTCAT | GGAAATGATGCTGACC |
| 20S-1-Oligo-832 | CTGTGACTATGTGAGGCTTTCTCGA | NNNNNN | AGCATGGCACAAGAGGAGCACTTCA | GGAAATGATGCTGACC |
| 20S-1-Oligo-833 | CTGTGACTATGTGAGGCTTTCTCGA | NNNNNN | CGATCGTGAGTTTGCAGCGTGACGA | GGAAATGATGCTGACC |
| 20S-1-Oligo-834 | CTGTGACTATGTGAGGCTTTCTCGA | NNNNNN | ACAGCTCCAGCCTCCCTTTGTTTGT | GGAAATGATGCTGACC |
| 20S-1-Oligo-835 | CTGTGACTATGTGAGGCTTTCTCGA | NNNNNN | AAACCTTTGTTCGGGCGTCTACCAT | GGAAATGATGCTGACC |
| 20S-1-Oligo-836 | CTGTGACTATGTGAGGCTTTCTCGA | NNNNNN | TCTTTCAAAACAGCGGGAGTCATCG | GGAAATGATGCTGACC |
| 20S-1-Oligo-837 | CTGTGACTATGTGAGGCTTTCTCGA | NNNNNN | GCGGTTTATCCGAATCTCACGCTAA | GGAAATGATGCTGACC |
| 20S-1-Oligo-838 | CTGTGACTATGTGAGGCTTTCTCGA | NNNNNN | GCATATGCTACAGGCTGGGGTGAAC | GGAAATGATGCTGACC |
| 20S-1-Oligo-839 | CTGTGACTATGTGAGGCTTTCTCGA | NNNNNN | GGAGGTCTAAACGTCCGGAGCTATT | GGAAATGATGCTGACC |
| 20S-1-Oligo-840 | CTGTGACTATGTGAGGCTTTCTCGA | NNNNNN | AAGAATAAGATTGCGTGCGCCTTAA | GGAAATGATGCTGACC |
| 20S-1-Oligo-B41 | CTGTGACTATGTGAGGCTTTCTCGA | NNNNNN | CATCATCGTCGTCCAAATATGTGAT | GGAAATGATGCTGACC |
| 20S-1-Oligo-B42 | CTGTGACTATGTGAGGCTTTCTCGA | NNNNNN | CACGTGTAGCTGTGGGCCAAGTCTA | GGAAATGATGCTGACC |
| 20S-1-Oligo-B43 | CTGTGACTATGTGAGGCTTTCTCGA | NNNNNN | CAGTTGTCAAATCTCCGCATTGGTA | GGAAATGATGCTGACC |
| 20S-1-Oligo-B44 | CTGTGACTATGTGAGGCTTTCTCGA | NNNNNN | ACTGGTAATGCCATTGGTCTAAATG | GGAAATGATGCTGACC |
| 20S-1-Oligo-B45 | CTGTGACTATGTGAGGCTTTCTCGA | NNNNNN | GTCTTTGGTCGTAACGAATCTCCGT | GGAAATGATGCTGACC |

TABLE 2-continued

Structure and sequences of 20S A oligonucleotides and 20S B oligonucleotides, used to produce 20S DNA-barcodes:

| | | | | |
|---|---|---|---|---|
| 20S-1-Oligo-B46 | CTGTGACTATGTGAGGCTTTCTCGA | NNNNNN | CTTAGGCATGACGGGGTTGTCCATG | GGAAATGATGCTGACC |
| 20S-1-Oligo-B47 | CTGTGACTATGTGAGGCTTTCTCGA | NNNNNN | CCGGTGAATTTTGGGTGTCCATGTA | GGAAATGATGCTGACC |
| 20S-1-Oligo-B48 | CTGTGACTATGTGAGGCTTTCTCGA | NNNNNN | CCTTTATCTCCTCCACCTATAAGGT | GGAAATGATGCTGACC |
| 20S-1-Oligo-B49 | CTGTGACTATGTGAGGCTTTCTCGA | NNNNNN | GATACTATATGACGGCCTGTAATCG | GGAAATGATGCTGACC |
| 20S-1-Oligo-B50 | CTGTGACTATGTGAGGCTTTCTCGA | NNNNNN | ATTGGTTGGCCGAAAGACTACATCT | GGAAATGATGCTGACC |
| 20S-1-Oligo-B51 | CTGTGACTATGTGAGGCTTTCTCGA | NNNNNN | CGTAGTTATGGGTGGGTCACCTGC | GGAAATGATGCTGACC |
| 20S-1-Oligo-B52 | CTGTGACTATGTGAGGCTTTCTCGA | NNNNNN | AAGTTTCCAGGCACTGATTCGTTCC | GGAAATGATGCTGACC |
| 20S-1-Oligo-B53 | CTGTGACTATGTGAGGCTTTCTCGA | NNNNNN | TTCCTTATTTCCCGGTTGAGATACA | GGAAATGATGCTGACC |
| 20S-1-Oligo-B54 | CTGTGACTATGTGAGGCTTTCTCGA | NNNNNN | AGGTATCATGCGGGCCGAATCTTGG | GGAAATGATGCTGACC |
| 20S-1-Oligo-B55 | CTGTGACTATGTGAGGCTTTCTCGA | NNNNNN | ATACCCGTAGGCCAGTACCCTCTCC | GGAAATGATGCTGACC |

TABLE 3

The reagents used for annealing (left) and elongation (right) of partly complementary oligonucleotides. Reagents marked in italic are from the Sequenase Version 2.0 DNA

| Annealing reaction | (μl) | Elongation reaction | (μl) |
|---|---|---|---|
| Oligo A (100 μM) | 2.6 | Annealing reaction | 10 μl |
| Oligo B (100 μM) | 5.4 | 0.1M DTT | 1 μl |
| *Sequenase reaction buffer* | 2 | H₂O | 0.5 μl |
| Total | 10 | 8x diluted *Sequenase polymerase* | 2 μl |
| | | 5x diluted *Sequence extension mixture* | 2 μl |
| | | Total | 15.5 |

TABLE 4

Overview of reagents required for production of Binding Molecules produced from 100 μg/ml pMHC exchange reaction. The amounts of Detection Molecule used for staining 1 × 10⁶-2 × 10⁶ cells in 100 μl are also specified.

| | Exchanged pMHC/ul SA conjugate | D-biotin | End: pMHC | Amount per staining |
|---|---|---|---|---|
| PE dex | 1.32 μl | 12.6 μM | 44 ug/ml | 3 ul |

TABLE 5

The components of the antibody mixture added while Detection Molecules are incubated with sample. The amount listed is for incubation of 1 × 10⁶-2 × 10⁶ cells in 100 ul.

| Target | Conjugate | Amount (μl) | Source |
|---|---|---|---|
| CD8 | PerCP | 2 | Invitrogen MHCD0831 |
| CD4 | FITC | 1.25 | BD bioscience 345768 |
| CD14 | FITC | 3.13 | BD bioscience 345784 |
| CD16 | FITC | 6.25 | BD bioscience 335035 |

TABLE 5-continued

The components of the antibody mixture added while Detection Molecules are incubated with sample. The amount listed is for incubation of 1 × 10⁶-2 × 10⁶ cells in 100 ul.

| Target | Conjugate | Amount (μl) | Source |
|---|---|---|---|
| CD19 | FITC | 2.50 | BD bioscience 345776 |
| CD40 | FITC | 1.56 | Serotec MCA1590F |

TABLE 6

The Master mix applied for recovery of DNA-barcodes by QPCR. The template was drawn from the residual fluid (5-9.25 ul) containing the sorted cells. Nuclease free H₂O was added to a final volume of 25 ul per PCR

| Component | Volume per sample (μl) |
|---|---|
| Master mix | 12.5 |
| Probe/SYBR (10 uM/100x) | 0.25 (0.1 uM/1x) |
| Forward primer (5 uM) | 1.5 (300 nM) |
| Reverse primer (5 uM) | 1.5 (300 nM) |
| Template | 5-9.25 |
| Nuclease free H₂O | 0-4.25 |
| Total | 25 |

TABLE 7

The thermal profile applied for qPCR amplification of barcodes associated with sorted cells.

| Temperature (° C.) | Time | No. of cycles |
|---|---|---|
| −95 | 10 min | 1 |
| −95 | 30 s | |
| −60 | 60 s | 40 |

TABLE 8

Structure and sequences of 10S oligonucleotides applied as DNA barcodes (10S-1-Oligo-1 to 10S-1-Oligo-110)

| Oligo name | 5' modif | Forward primer region | 6xN |
| --- | --- | --- | --- |
| 10S-1-Oligo-1 | Biotin-C6- | AGATTCTATAAACTGTGCGGTCCTT | NNNNNN |
| 10S-1-Oligo-2 | Biotin-C6- | AGATTCTATAAACTGTGCGGTCCTT | NNNNNN |
| 10S-1-Oligo-3 | Biotin-C6- | AGATTCTATAAACTGTGCGGTCCTT | NNNNNN |
| 10S-1-Oligo-4 | Biotin-C6- | AGATTCTATAAACTGTGCGGTCCTT | NNNNNN |
| 10S-1-Oligo-5 | Biotin-C6- | AGATTCTATAAACTGTGCGGTCCTT | NNNNNN |
| 10S-1-Oligo-6 | Biotin-C6- | AGATTCTATAAACTGTGCGGTCCTT | NNNNNN |
| 10S-1-Oligo-7 | Biotin-C6- | AGATTCTATAAACTGTGCGGTCCTT | NNNNNN |
| 10S-1-Oligo-8 | Biotin-C6- | AGATTCTATAAACTGTGCGGTCCTT | NNNNNN |
| 10S-1-Oligo-9 | Biotin-C6- | AGATTCTATAAACTGTGCGGTCCTT | NNNNNN |
| 10S-1-Oligo-10 | Biotin-C6- | AGATTCTATAAACTGTGCGGTCCTT | NNNNNN |
| 10S-1-Oligo-11 | Biotin-C6- | AGATTCTATAAACTGTGCGGTCCTT | NNNNNN |
| 10S-1-Oligo-12 | Biotin-C6- | AGATTCTATAAACTGTGCGGTCCTT | NNNNNN |
| 10S-1-Oligo-13 | Biotin-C6- | AGATTCTATAAACTGTGCGGTCCTT | NNNNNN |
| 10S-1-Oligo-14 | Biotin-C6- | AGATTCTATAAACTGTGCGGTCCTT | NNNNNN |
| 10S-1-Oligo-15 | Biotin-C6- | AGATTCTATAAACTGTGCGGTCCTT | NNNNNN |
| 10S-1-Oligo-16 | Biotin-C6- | AGATTCTATAAACTGTGCGGTCCTT | NNNNNN |
| 10S-1-Oligo-17 | Biotin-C6- | AGATTCTATAAACTGTGCGGTCCTT | NNNNNN |
| 10S-1-Oligo-18 | Biotin-C6- | AGATTCTATAAACTGTGCGGTCCTT | NNNNNN |
| 10S-1-Oligo-19 | Biotin-C6- | AGATTCTATAAACTGTGCGGTCCTT | NNNNNN |
| 10S-1-Oligo-20 | Biotin-C6- | AGATTCTATAAACTGTGCGGTCCTT | NNNNNN |
| 10S-1-Oligo-21 | Biotin-C6- | AGATTCTATAAACTGTGCGGTCCTT | NNNNNN |
| 10S-1-Oligo-22 | Biotin-C6- | AGATTCTATAAACTGTGCGGTCCTT | NNNNNN |
| 10S-1-Oligo-23 | Biotin-C6- | AGATTCTATAAACTGTGCGGTCCTT | NNNNNN |
| 10S-1-Oligo-24 | Biotin-C6- | AGATTCTATAAACTGTGCGGTCCTT | NNNNNN |
| 10S-1-Oligo-25 | Biotin-C6- | AGATTCTATAAACTGTGCGGTCCTT | NNNNNN |
| 10S-1-Oligo-26 | Biotin-C6- | AGATTCTATAAACTGTGCGGTCCTT | NNNNNN |
| 10S-1-Oligo-27 | Biotin-C6- | AGATTCTATAAACTGTGCGGTCCTT | NNNNNN |
| 10S-1-Oligo-28 | Biotin-C6- | AGATTCTATAAACTGTGCGGTCCTT | NNNNNN |
| 10S-1-Oligo-29 | Biotin-C6- | AGATTCTATAAACTGTGCGGTCCTT | NNNNNN |
| 10S-1-Oligo-30 | Biotin-C6- | AGATTCTATAAACTGTGCGGTCCTT | NNNNNN |
| 10S-1-Oligo-31 | Biotin-C6- | AGATTCTATAAACTGTGCGGTCCTT | NNNNNN |
| 10S-1-Oligo-32 | Biotin-C6- | AGATTCTATAAACTGTGCGGTCCTT | NNNNNN |
| 10S-1-Oligo-33 | Biotin-C6- | AGATTCTATAAACTGTGCGGTCCTT | NNNNNN |
| 10S-1-Oligo-34 | Biotin-C6- | AGATTCTATAAACTGTGCGGTCCTT | NNNNNN |
| 10S-1-Oligo-35 | Biotin-C6- | AGATTCTATAAACTGTGCGGTCCTT | NNNNNN |
| 10S-1-Oligo-36 | Biotin-C6- | AGATTCTATAAACTGTGCGGTCCTT | NNNNNN |
| 10S-1-Oligo-37 | Biotin-C6- | AGATTCTATAAACTGTGCGGTCCTT | NNNNNN |
| 10S-1-Oligo-38 | Biotin-C6- | AGATTCTATAAACTGTGCGGTCCTT | NNNNNN |

TABLE 8-continued

Structure and sequences of 10S oligonucleotides applied as DNA barcodes (10S-1-Oligo-1 to 10S-1-Oligo-110)

| | | | |
|---|---|---|---|
| 10S-1-Oligo-39 | Biotin-C6- | AGATTCTATAAACTGTGCGGTCCTT | NNNNNN |
| 10S-1-Oligo-40 | Biotin-C6- | AGATTCTATAAACTGTGCGGTCCTT | NNNNNN |
| 10S-1-Oligo-41 | Biotin-C6- | AGATTCTATAAACTGTGCGGTCCTT | NNNNNN |
| 10S-1-Oligo-42 | Biotin-C6- | AGATTCTATAAACTGTGCGGTCCTT | NNNNNN |
| 10S-1-Oligo-43 | Biotin-C6- | AGATTCTATAAACTGTGCGGTCCTT | NNNNNN |
| 10S-1-Oligo-44 | Biotin-C6- | AGATTCTATAAACTGTGCGGTCCTT | NNNNNN |
| 10S-1-Oligo-45 | Biotin-C6- | AGATTCTATAAACTGTGCGGTCCTT | NNNNNN |
| 10S-1-Oligo-46 | Biotin-C6- | AGATTCTATAAACTGTGCGGTCCTT | NNNNNN |
| 10S-1-Oligo-47 | Biotin-C6- | AGATTCTATAAACTGTGCGGTCCTT | NNNNNN |
| 10S-1-Oligo-48 | Biotin-C6- | AGATTCTATAAACTGTGCGGTCCTT | NNNNNN |
| 10S-1-Oligo-49 | Biotin-C6- | AGATTCTATAAACTGTGCGGTCCTT | NNNNNN |
| 10S-1-Oligo-50 | Biotin-C6- | AGATTCTATAAACTGTGCGGTCCTT | NNNNNN |
| 10S-1-Oligo-51 | Biotin-C6- | AGATTCTATAAACTGTGCGGTCCTT | NNNNNN |
| 10S-1-Oligo-52 | Biotin-C6- | AGATTCTATAAACTGTGCGGTCCTT | NNNNNN |
| 10S-1-Oligo-53 | Biotin-C6- | AGATTCTATAAACTGTGCGGTCCTT | NNNNNN |
| 10S-1-Oligo-54 | Biotin-C6- | AGATTCTATAAACTGTGCGGTCCTT | NNNNNN |
| 10S-1-Oligo-55 | Biotin-C6- | AGATTCTATAAACTGTGCGGTCCTT | NNNNNN |
| 10S-1-Oligo-56 | Biotin-C6- | AGATTCTATAAACTGTGCGGTCCTT | NNNNNN |
| 10S-1-Oligo-57 | Biotin-C6- | AGATTCTATAAACTGTGCGGTCCTT | NNNNNN |
| 10S-1-Oligo-58 | Biotin-C6- | AGATTCTATAAACTGTGCGGTCCTT | NNNNNN |
| 10S-1-Oligo-59 | Biotin-C6- | AGATTCTATAAACTGTGCGGTCCTT | NNNNNN |
| 10S-1-Oligo-60 | Biotin-C6- | AGATTCTATAAACTGTGCGGTCCTT | NNNNNN |
| 10S-1-Oligo-61 | Biotin-C6- | AGATTCTATAAACTGTGCGGTCCTT | NNNNNN |
| 10S-1-Oligo-62 | Biotin-C6- | AGATTCTATAAACTGTGCGGTCCTT | NNNNNN |
| 10S-1-Oligo-63 | Biotin-C6- | AGATTCTATAAACTGTGCGGTCCTT | NNNNNN |
| 10S-1-Oligo-64 | Biotin-C6- | AGATTCTATAAACTGTGCGGTCCTT | NNNNNN |
| 10S-1-Oligo-65 | Biotin-C6- | AGATTCTATAAACTGTGCGGTCCTT | NNNNNN |
| 10S-1-Oligo-66 | Biotin-C6- | AGATTCTATAAACTGTGCGGTCCTT | NNNNNN |
| 10S-1-Oligo-67 | Biotin-C6- | AGATTCTATAAACTGTGCGGTCCTT | NNNNNN |
| 10S-1-Oligo-68 | Biotin-C6- | AGATTCTATAAACTGTGCGGTCCTT | NNNNNN |
| 10S-1-Oligo-69 | Biotin-C6- | AGATTCTATAAACTGTGCGGTCCTT | NNNNNN |
| 10S-1-Oligo-70 | Biotin-C6- | AGATTCTATAAACTGTGCGGTCCTT | NNNNNN |
| 10S-1-Oligo-71 | Biotin-C6- | AGATTCTATAAACTGTGCGGTCCTT | NNNNNN |
| 10S-1-Oligo-72 | Biotin-C6- | AGATTCTATAAACTGTGCGGTCCTT | NNNNNN |
| 10S-1-Oligo-73 | Biotin-C6- | AGATTCTATAAACTGTGCGGTCCTT | NNNNNN |
| 10S-1-Oligo-74 | Biotin-C6- | AGATTCTATAAACTGTGCGGTCCTT | NNNNNN |
| 10S-1-Oligo-75 | Biotin-C6- | AGATTCTATAAACTGTGCGGTCCTT | NNNNNN |
| 10S-1-Oligo-76 | Biotin-C6- | AGATTCTATAAACTGTGCGGTCCTT | NNNNNN |

TABLE 8-continued

Structure and sequences of 10S oligonucleotides applied as DNA barcodes (10S-1-Oligo-1 to 10S-1-Oligo-110)

| | | | |
|---|---|---|---|
| 10S-1-Oligo-77 | Biotin-C6- | AGATTCTATAAACTGTGCGGTCCTT | NNNNNN |
| 10S-1-Oligo-78 | Biotin-C6- | AGATTCTATAAACTGTGCGGTCCTT | NNNNNN |
| 10S-1-Oligo-79 | Biotin-C6- | AGATTCTATAAACTGTGCGGTCCTT | NNNNNN |
| 10S-1-Oligo-80 | Biotin-C6- | AGATTCTATAAACTGTGCGGTCCTT | NNNNNN |
| 10S-1-Oligo-81 | Biotin-C6- | AGATTCTATAAACTGTGCGGTCCTT | NNNNNN |
| 10S-1-Oligo-82 | Biotin-C6- | AGATTCTATAAACTGTGCGGTCCTT | NNNNNN |
| 10S-1-Oligo-83 | Biotin-C6- | AGATTCTATAAACTGTGCGGTCCTT | NNNNNN |
| 10S-1-Oligo-84 | Biotin-C6- | AGATTCTATAAACTGTGCGGTCCTT | NNNNNN |
| 10S-1-Oligo-85 | Biotin-C6- | AGATTCTATAAACTGTGCGGTCCTT | NNNNNN |
| 10S-1-Oligo-86 | Biotin-C6- | AGATTCTATAAACTGTGCGGTCCTT | NNNNNN |
| 10S-1-Oligo-87 | Biotin-C6- | AGATTCTATAAACTGTGCGGTCCTT | NNNNNN |
| 10S-1-Oligo-88 | Biotin-C6- | AGATTCTATAAACTGTGCGGTCCTT | NNNNNN |
| 10S-1-Oligo-89 | Biotin-C6- | AGATTCTATAAACTGTGCGGTCCTT | NNNNNN |
| 10S-1-Oligo-90 | Biotin-C6- | AGATTCTATAAACTGTGCGGTCCTT | NNNNNN |
| 10S-1-Oligo-91 | Biotin-C6- | AGATTCTATAAACTGTGCGGTCCTT | NNNNNN |
| 10S-1-Oligo-92 | Biotin-C6- | AGATTCTATAAACTGTGCGGTCCTT | NNNNNN |
| 10S-1-Oligo-93 | Biotin-C6- | AGATTCTATAAACTGTGCGGTCCTT | NNNNNN |
| 10S-1-Oligo-94 | Biotin-C6- | AGATTCTATAAACTGTGCGGTCCTT | NNNNNN |
| 10S-1-Oligo-95 | Biotin-C6- | AGATTCTATAAACTGTGCGGTCCTT | NNNNNN |
| 10S-1-Oligo-96 | Biotin-C6- | AGATTCTATAAACTGTGCGGTCCTT | NNNNNN |
| 10S-1-Oligo-97 | Biotin-C6- | AGATTCTATAAACTGTGCGGTCCTT | NNNNNN |
| 10S-1-Oligo-98 | Biotin-C6- | AGATTCTATAAACTGTGCGGTCCTT | NNNNNN |
| 10S-1-Oligo-99 | Biotin-C6- | AGATTCTATAAACTGTGCGGTCCTT | NNNNNN |
| 10S-1-Oligo-100 | Biotin-C6- | AGATTCTATAAACTGTGCGGTCCTT | NNNNNN |
| 10S-1-Oligo-101 | Biotin-C6- | AGATTCTATAAACTGTGCGGTCCTT | NNNNNN |
| 10S-1-Oligo-102 | Biotin-C6- | AGATTCTATAAACTGTGCGGTCCTT | NNNNNN |
| 10S-1-Oligo-103 | Biotin-C6- | AGATTCTATAAACTGTGCGGTCCTT | NNNNNN |
| 10S-1-Oligo-104 | Biotin-C6- | AGATTCTATAAACTGTGCGGTCCTT | NNNNNN |
| 10S-1-Oligo-105 | Biotin-C6- | AGATTCTATAAACTGTGCGGTCCTT | NNNNNN |
| 10S-1-Oligo-106 | Biotin-C6- | AGATTCTATAAACTGTGCGGTCCTT | NNNNNN |
| 10S-1-Oligo-107 | Biotin-C6- | AGATTCTATAAACTGTGCGGTCCTT | NNNNNN |
| 10S-1-Oligo-108 | Biotin-C6- | AGATTCTATAAACTGTGCGGTCCTT | NNNNNN |
| 10S-1-Oligo-109 | Biotin-C6- | AGATTCTATAAACTGTGCGGTCCTT | NNNNNN |
| 10S-1-Oligo-110 | Biotin-C6- | AGATTCTATAAACTGTGCGGTCCTT | NNNNNN |

| Oligo name | Coding region | Reverse primer region |
|---|---|---|
| 10S-1-Oligo-1 | TATGAGGACGAATCTCCCGCTTATA | GGTACGGCGCTATCATGTACTCATG |
| 10S-1-Oligo-2 | GGTCTTGACAAACGTGTGCTTGTAC | GGTACGGCGCTATCATGTACTCATG |
| 10S-1-Oligo-3 | GTTTATCGGGCGTGGTGCTCGCATA | GGTACGGCGCTATCATGTACTCATG |
| 10S-1-Oligo-4 | CCGATGTTGACGGACTAATCCTGAC | GGTACGGCGCTATCATGTACTCATG |

TABLE 8-continued

Structure and sequences of 10S oligonucleotides applied as DNA barcodes (10S-1-Oligo-1 to 10S-1-Oligo-110)

| | | |
|---|---|---|
| 10S-1-Oligo-5 | TAGTAGTTCAGACGCCGTTAAGCGC | GGTACGGCGCTATCATGTACTCATG |
| 10S-1-Oligo-6 | CCGTACCTAGATACACTCAATTTGT | GGTACGGCGCTATCATGTACTCATG |
| 10S-1-Oligo-7 | GGGGTTCCGTTTTACATTCCAGGAA | GGTACGGCGCTATCATGTACTCATG |
| 10S-1-Oligo-8 | TATCCCGTGAAGCTTGAGTGGAATC | GGTACGGCGCTATCATGTACTCATG |
| 10S-1-Oligo-9 | CTGACGTGTGAGGCGCTAGAGCATA | GGTACGGCGCTATCATGTACTCATG |
| 10S-1-Oligo-10 | GGTATGGCACGCCTAATCTGGACAC | GGTACGGCGCTATCATGTACTCATG |
| 10S-1-Oligo-11 | GGATGCATGATCTAGGGCCTCGTCT | GGTACGGCGCTATCATGTACTCATG |
| 10S-1-Oligo-12 | GAGGTCTTTCATGCGTATAGTCACA | GGTACGGCGCTATCATGTACTCATG |
| 10S-1-Oligo-13 | GATTCAATATGTGTCGTCTATCCTC | GGTACGGCGCTATCATGTACTCATG |
| 10S-1-Oligo-14 | GGTAACTGCGCATAGTTGGCTCTAT | GGTACGGCGCTATCATGTACTCATG |
| 10S-1-Oligo-15 | GCGTTTAAGGTCACATCGCATGAAT | GGTACGGCGCTATCATGTACTCATG |
| 10S-1-Oligo-16 | GCCCGGGAAGTGTGAGGATATACCC | GGTACGGCGCTATCATGTACTCATG |
| 10S-1-Oligo-17 | GCTCTTAAAACTGGTATCACCTGAC | GGTACGGCGCTATCATGTACTCATG |
| 10S-1-Oligo-18 | GGGTGGTTAGTGATTTGCCCGTCAC | GGTACGGCGCTATCATGTACTCATG |
| 10S-1-Oligo-19 | TAGTTGGTGGGTTTCCCTACCGTGT | GGTACGGCGCTATCATGTACTCATG |
| 10S-1-Oligo-20 | GGTACAGTAAGTGAGAATCCTCTCT | GGTACGGCGCTATCATGTACTCATG |
| 10S-1-Oligo-21 | GGTTCTAAGTTTAGCGTAGCCGGTT | GGTACGGCGCTATCATGTACTCATG |
| 10S-1-Oligo-22 | CTTTAGGTGGGTGCGATTGCCAGTT | GGTACGGCGCTATCATGTACTCATG |
| 10S-1-Oligo-23 | GCCACCTTAACACGCGATGATATTG | GGTACGGCGCTATCATGTACTCATG |
| 10S-1-Oligo-24 | GCTATTACGAGCGCTTGGATCCCGT | GGTACGGCGCTATCATGTACTCATG |
| 10S-1-Oligo-25 | TATGTTGTGCCTTACGCCTCGATTA | GGTACGGCGCTATCATGTACTCATG |
| 10S-1-Oligo-26 | TTAACCGAACTGACGGCCATCAAGG | GGTACGGCGCTATCATGTACTCATG |
| 10S-1-Oligo-27 | GGGTACATGCGCCTTACTCCTTGTG | GGTACGGCGCTATCATGTACTCATG |
| 10S-1-Oligo-28 | TTCTATTCTAAGCCGGCGGTCATAT | GGTACGGCGCTATCATGTACTCATG |
| 10S-1-Oligo-29 | GCTTGATGCTTTACAAGATCGCGTT | GGTACGGCGCTATCATGTACTCATG |
| 10S-1-Oligo-30 | TCCAAGTTAGCTTACTCCATGCCCC | GGTACGGCGCTATCATGTACTCATG |
| 10S-1-Oligo-31 | AGAACTATTTCCTGGCTGTTACGCG | GGTACGGCGCTATCATGTACTCATG |
| 10S-1-Oligo-32 | TCGGTTTCAAGGATGATCCGCGCTT | GGTACGGCGCTATCATGTACTCATG |
| 10S-1-Oligo-33 | AGAGACTGCCCGACACATCTTAGTG | GGTACGGCGCTATCATGTACTCATG |
| 10S-1-Oligo-34 | CTGTTAATTAGGCTCGGTCGGCCTA | GGTACGGCGCTATCATGTACTCATG |
| 10S-1-Oligo-35 | AGGTAGTCCTATGCGGGCTTTCTCT | GGTACGGCGCTATCATGTACTCATG |
| 10S-1-Oligo-36 | GGCTTGGACTATAGTCATCGCGTTT | GGTACGGCGCTATCATGTACTCATG |
| 10S-1-Oligo-37 | CACTGTTTAACAAGCCCGTCAGTAG | GGTACGGCGCTATCATGTACTCATG |
| 10S-1-Oligo-38 | ACGTCGTATTATACCCGCCATGGAA | GGTACGGCGCTATCATGTACTCATG |
| 10S-1-Oligo-39 | TGCTTAATTTACGACCGATGCTGCG | GGTACGGCGCTATCATGTACTCATG |
| 10S-1-Oligo-40 | TCCATAGATTTCTCCGTGAGTCTTT | GGTACGGCGCTATCATGTACTCATG |
| 10S-1-Oligo-41 | GTGCCGCAGACATTGCATACGATAT | GGTACGGCGCTATCATGTACTCATG |
| 10S-1-Oligo-42 | GCAGGTCCTAACCCGCAACCATTTA | GGTACGGCGCTATCATGTACTCATG |

TABLE 8-continued

Structure and sequences of 10S oligonucleotides applied as DNA barcodes (10S-1-Oligo-1 to 10S-1-Oligo-110)

| | | |
|---|---|---|
| 10S-1-Oligo-43 | TGCACCGTTCATATGTTATCGGGAC | GGTACGGCGCTATCATGTACTCATG |
| 10S-1-Oligo-44 | AGAGACTTACACCCGTAGACGTCGG | GGTACGGCGCTATCATGTACTCATG |
| 10S-1-Oligo-45 | ATAAAAGAAACCCTCCGCATTGTGT | GGTACGGCGCTATCATGTACTCATG |
| 10S-1-Oligo-46 | GGTCCCATCCGAGCAGATTTGACTC | GGTACGGCGCTATCATGTACTCATG |
| 10S-1-Oligo-47 | ATGAGCTGTCTCGAACCGAAGGCAC | GGTACGGCGCTATCATGTACTCATG |
| 10S-1-Oligo-48 | TCGGGCGGTTCAACTTACTGGTAGA | GGTACGGCGCTATCATGTACTCATG |
| 10S-1-Oligo-49 | GGGGAAATAACGGATGCGCTCTTGA | GGTACGGCGCTATCATGTACTCATG |
| 10S-1-Oligo-50 | ACTTCTTCTCGGTCGCATGAGGCTG | GGTACGGCGCTATCATGTACTCATG |
| 10S-1-Oligo-51 | GGATACATATACGCTCGTCGGGACT | GGTACGGCGCTATCATGTACTCATG |
| 10S-1-Oligo-52 | CCGGGAAGTGTCATAACTTGAAGCG | GGTACGGCGCTATCATGTACTCATG |
| 10S-1-Oligo-53 | CTCAGCCTGCCTCGCTTCTGATATT | GGTACGGCGCTATCATGTACTCATG |
| 10S-1-Oligo-54 | AGGGCCAAGTCGACCTAGATGGCTA | GGTACGGCGCTATCATGTACTCATG |
| 10S-1-Oligo-55 | GGTAGGGCTACTGTTATCCTCCGTC | GGTACGGCGCTATCATGTACTCATG |
| 10S-1-Oligo-56 | CGTACGGCTGGAGAGCTGTATGTGG | GGTACGGCGCTATCATGTACTCATG |
| 10S-1-Oligo-57 | ACAGGTTGTATTACTTCGCGCCTTG | GGTACGGCGCTATCATGTACTCATG |
| 10S-1-Oligo-58 | CTGGGCTCATTACAAGTGTTGCATA | GGTACGGCGCTATCATGTACTCATG |
| 10S-1-Oligo-59 | CTAAGTGGCGCCGATTGTTTGTCCA | GGTACGGCGCTATCATGTACTCATG |
| 10S-1-Oligo-60 | GTATATTTTGCTCCCGGCGACGAGA | GGTACGGCGCTATCATGTACTCATG |
| 10S-1-Oligo-61 | GCAATTTGCGCTTGTTCGGCATAGC | GGTACGGCGCTATCATGTACTCATG |
| 10S-1-Oligo-62 | GAGTCGAATATCCACCACCGTATGG | GGTACGGCGCTATCATGTACTCATG |
| 10S-1-Oligo-63 | TTGTGGTTTGGGTCCTCAGAGGAGA | GGTACGGCGCTATCATGTACTCATG |
| 10S-1-Oligo-64 | GGTACCTAGTCTCGTAATCATAGGA | GGTACGGCGCTATCATGTACTCATG |
| 10S-1-Oligo-65 | GCGGCATGATCTACCTTAAAGCTTG | GGTACGGCGCTATCATGTACTCATG |
| 10S-1-Oligo-66 | CCGGCGCAGAAGTTTGAACGAAAAG | GGTACGGCGCTATCATGTACTCATG |
| 10S-1-Oligo-67 | ATGCACTATTTTACGTATCCCGTGC | GGTACGGCGCTATCATGTACTCATG |
| 10S-1-Oligo-68 | GATAGGGTGACTGCTTTCGCGTACA | GGTACGGCGCTATCATGTACTCATG |
| 10S-1-Oligo-69 | TATCTGGTAGACATCTCGGCACAGA | GGTACGGCGCTATCATGTACTCATG |
| 10S-1-Oligo-70 | TCGGGGTGCAATAATCACTAGTGCT | GGTACGGCGCTATCATGTACTCATG |
| 10S-1-Oligo-71 | TAGTTCTGGCTATACACACTTCGGG | GGTACGGCGCTATCATGTACTCATG |
| 10S-1-Oligo-72 | GCATAGAGTTACCCGATGGATTCGA | GGTACGGCGCTATCATGTACTCATG |
| 10S-1-Oligo-73 | GTTCATGGTACAGGCTTCTTTACGG | GGTACGGCGCTATCATGTACTCATG |
| 10S-1-Oligo-74 | CGATCTCGGGCCTGGGTTTTGAGTA | GGTACGGCGCTATCATGTACTCATG |
| 10S-1-Oligo-75 | ATTATTCGTGACCCAACTCATCAGG | GGTACGGCGCTATCATGTACTCATG |
| 10S-1-Oligo-76 | CTGAATGGTGAATAATGCGTTCGCC | GGTACGGCGCTATCATGTACTCATG |
| 10S-1-Oligo-77 | GCTATTAGTTGCTACCCCAAGAATC | GGTACGGCGCTATCATGTACTCATG |
| 10S-1-Oligo-78 | AGAAAGTCTTGGATACACGGCCGGG | GGTACGGCGCTATCATGTACTCATG |
| 10S-1-Oligo-79 | GTGTGTTCCTATGCACAATTTCATA | GGTACGGCGCTATCATGTACTCATG |
| 10S-1-Oligo-80 | TACATGGTAGGGGTCTCCGAACCGT | GGTACGGCGCTATCATGTACTCATG |
| 10S-1-Oligo-81 | TAGGGATAACTTTCCTCCCACTTGG | GGTACGGCGCTATCATGTACTCATG |

TABLE 8-continued

Structure and sequences of 10S oligonucleotides applied as DNA barcodes (10S-1-Oligo-1 to 10S-1-Oligo-110)

| | | |
|---|---|---|
| 10S-1-Oligo-82 | TCTGGTGTCTCACCCATGGGATGTC | GGTACGGCGCTATCATGTACTCATG |
| 10S-1-Oligo-83 | TAACGATTTTCTCGCGGGAGTTTCG | GGTACGGCGCTATCATGTACTCATG |
| 10S-1-Oligo-84 | CGAGCCTGGTTAGCGCCTACAAGAG | GGTACGGCGCTATCATGTACTCATG |
| 10S-1-Oligo-85 | CGTAGTAAGATATGTAGTCCACGTC | GGTACGGCGCTATCATGTACTCATG |
| 10S-1-Oligo-86 | TGTTAGTTGCCCCATATCTTTACGC | GGTACGGCGCTATCATGTACTCATG |
| 10S-1-Oligo-87 | GCTGGATTGTGATTGTCCGGATCCG | GGTACGGCGCTATCATGTACTCATG |
| 10S-1-Oligo-88 | GGGAGGACTGCGGTTCAGCTTACAA | GGTACGGCGCTATCATGTACTCATG |
| 10S-1-Oligo-89 | GCGTAGGTCTAGTTCAGATTCTATA | GGTACGGCGCTATCATGTACTCATG |
| 10S-1-Oligo-90 | GTCTACGTGGTTCTATACCATTCGG | GGTACGGCGCTATCATGTACTCATG |
| 10S-1-Oligo-91 | AGGCTTTACTACAATGCGTGGGCTC | GGTACGGCGCTATCATGTACTCATG |
| 10S-1-Oligo-92 | AGCTTGCTGTATGGGTCATGTTCCT | GGTACGGCGCTATCATGTACTCATG |
| 10S-1-Oligo-93 | TGCTCTAAAGACGCGAGGACTACCT | GGTACGGCGCTATCATGTACTCATG |
| 10S-1-Oligo-94 | TGTACATGTCATACTCAAGGCTTTA | GGTACGGCGCTATCATGTACTCATG |
| 10S-1-Oligo-95 | TTGACATGTACGCCATTTGGGTCGC | GGTACGGCGCTATCATGTACTCATG |
| 10S-1-Oligo-96 | GCAATTCAGTACGATCGTGTAGCGG | GGTACGGCGCTATCATGTACTCATG |
| 10S-1-Oligo-97 | CGCTGTCCAAAGGTTCTTCGTAACG | GGTACGGCGCTATCATGTACTCATG |
| 10S-1-Oligo-98 | TTAGACGAGCAGGTTTCTTGCCTAT | GGTACGGCGCTATCATGTACTCATG |
| 10S-1-Oligo-99 | TCGTTTGGAGCCGTTCACACATGAA | GGTACGGCGCTATCATGTACTCATG |
| 10S-1-Oligo-100 | CTGATCAACTTGCGCCCAGCGTTAT | GGTACGGCGCTATCATGTACTCATG |
| 10S-1-Oligo-101 | GACGATGTTGCCTGTTTTGATACGA | GGTACGGCGCTATCATGTACTCATG |
| 10S-1-Oligo-102 | GGGTAGTCGTGAGGTGAACTCTTCC | GGTACGGCGCTATCATGTACTCATG |
| 10S-1-Oligo-103 | AGCCATTTTACGATTCTATTCGATG | GGTACGGCGCTATCATGTACTCATG |
| 10S-1-Oligo-104 | GTGGTTTATATAATCCCACCTCCTA | GGTACGGCGCTATCATGTACTCATG |
| 10S-1-Oligo-105 | GCGAAGAACATCCCGGCATTTCATG | GGTACGGCGCTATCATGTACTCATG |
| 10S-1-Oligo-106 | GCTGGGACAATGCCGAAAACTCTTC | GGTACGGCGCTATCATGTACTCATG |
| 10S-1-Oligo-107 | ATTCCGTACCAACCCGCGTCTTAGA | GGTACGGCGCTATCATGTACTCATG |
| 10S-1-Oligo-108 | CTGCAGGAGGCTCTAATGCACTCAA | GGTACGGCGCTATCATGTACTCATG |
| 10S-1-Oligo-109 | GCGTTCAGCATTCATTACGTCTCAC | GGTACGGCGCTATCATGTACTCATG |
| 10S-1-Oligo-110 | GCTGAGGAAGCCCAATGTTCAGTAC | GGTACGGCGCTATCATGTACTCATG |

TABLE 9

Listing of the 110 combinations of peptide-HLA Binding Molecules and the respective Labels, 1OS and 2OS DNA-barcodes, that were used to encode the given specificity of all Detection Molecules applied in experiments 3-6. In the table, HLA code 'A1' refers to HLA-A0101. HLA code 'A2' refers to HLA-A0201. HLA code 'A3' refers to HLA-A0301. HLA code 'A11'+10' refers to HLA-A1101. HLA code 'A24' refers to HLA-A2402. HLA code 'B7' refers to HLA-B0702.

| 1OS Barcode | 2OS Barcode | HLA code | Peptide | Sequence |
|---|---|---|---|---|
| 1 | A1B1 | A1 | CMV pp65 YSE | YSEHPTFTSQY |
| 2 | A1B2 | A1 | CMV pp50 VTE | VTEHDTLLY |
| 3 | A1B3 | A1 | FLU BP-VSD | VSDGGPNLY |
| 4 | A1B4 | A11 | EBV-EBNA4 | AVFDRKSDAK |
| 5 | A1B5 | A11 | HCMV pp65 | GPISGHVLK |
| 6 | A1B6 | A11 | VP1 | DLQGLVLDY |
| 7 | A1B7 | A11 | VP1 | VLGRKMTPK |
| 8 | A1B8 | A11 | VP1 | VTLRKRVVVK |
| 9 | A1B9 | A11 | VP1 | LVLDYQTEY |
| 10 | A1B10 | A11 | VP1 | GQEKTVYPK |
| 11 | A2B1 | A11 | VP1 | VTFQSNQQDK |
| 12 | A2B2 | A11 | VP1 | LKGPQKASQK |
| 13 | A2B3 | A11 | VP1 | NVASVPKLLVK |
| 14 | A2B4 | A11 | VP1 | TSNWYTYTY |
| 15 | A2B5 | A11 | VP1 | LVLDYQTEYPK |
| 16 | A2B6 | A11 | VP1 | TLRKRWVKNPY |
| 17 | A2B7 | A11 | VP1 | AVTFQSNQQDK |
| 18 | A2B8 | A11 | VP1 | PLKGPQKASQK |
| 19 | A2B9 | A2 | VP1 | RIYEGSEQL |
| 20 | A2B10 | A11 | VP1 | SLFSNLMPK |
| 21 | A3B1 | A2 | VP1 | KLLVKGGVEV |
| 22 | A3B2 | A11 | VP1 | SLINVHYWDMK |
| 23 | A3B3 | A2 | HPV E6 29-38 | TIHDIILECV |
| 24 | A3B4 | A2 | FLU MP 58-66 GIL | GILGFVFTL |
| 25 | A3B5 | A2 | EBV LMP2 CLG | CLGGLLTMV |
| 26 | A3B6 | A2 | EBV BMF1 GLC | GLCTLVAML |
| 27 | A3B7 | A2 | EBV LMP2 FLY | FLYALALLL |
| 28 | A3B8 | A2 | CMV pp65 NLV | NLVPMVATV |
| 29 | A3B9 | A2 | EBV BRLF1 YVL | YVLDHLIVV |
| 30 | A3B10 | A2 | HPV E7 11-20 | YMLDLQPETT |
| 31 | A4B1 | A2 | CMV IE1 VLE | VLEETSVML |
| 32 | A4B2 | A2 | VP1 | GCCPNVASV |
| 33 | A4B3 | A2 | VP1 | SITQIELYL |
| 34 | A4B4 | A2 | VP1 | LQMWEAISV |

TABLE 9-continued

Listing of the 110 combinations of peptide-HLA Binding Molecules and the respective Labels, 10S and 20S DNA-barcodes, that were used to encode the given specificity of all Detection Molecules applied in experiments 3-6. In the table, HLA code 'A1' refers to HLA-A0101. HLA code 'A2' refers to HLA-A0201. HLA code 'A3' refers to HLA-A0301. HLA code 'A11'+10' refers to HLA-A1101. HLA code 'A24' refers to HLA-A2402. HLA code 'B7' refers to HLA-B0702.

| 10S Barcode | 20S Barcode | HLA code | Peptide | Sequence |
|---|---|---|---|---|
| 35 | A4B5 | A2 | VP1 | AISVKTEVV |
| 36 | A4B6 | A2 | VP1 | KMTPKNQGL |
| 37 | A4B7 | A2 | VP1 | TVLQFSNTL |
| 38 | A4B8 | A2 | VP1 | GLFISCADI |
| 39 | A4B9 | A2 | VP1 | LLVKGGVEVL |
| 40 | A4B10 | A2 | VP1 | ELYLNPRMGV |
| 41 | A5B1 | A2 | VP1 | NLPAYSVARV |
| 42 | A5B2 | A2 | VP1 | TLQMWEAISV |
| 43 | A5B3 | A2 | VP1 | QMWEAISVKT |
| 44 | A5B4 | A2 | VP1 | VVGISSLINV |
| 45 | A5B5 | A2 | VP1 | SLINVHYWDM |
| 46 | A5B6 | A2 | VP1 | HMFAIGGEPL |
| 47 | A5B7 | A2 | VP1 | FAIGGEPLDL |
| 48 | A5B8 | A2 | VP1 | NLINSLFSNL |
| 49 | A5B9 | A2 | VP1 | FLFKTSGKMAL |
| 50 | A5B10 | A2 | VP1 | ALHGLPRYFNV |
| 51 | A6B1 | A2 | VP1 | NLINSLFSNLM |
| 52 | A6B2 | A2 | VP1 | FLDKFGQEKTV |
| 53 | A6B3 | A2 | VP1 | VKGGVEVLSV |
| 54 | A6B4 | A24 | HCMV 248-256 | AYAQKIFKIL |
| 55 | A6B5 | A24 | EBV LM P2 | IYVLVMLVL |
| 56 | A6B6 | A24 | EBV BRLF1 | TYPVLEEMF |
| 57 | A6B7 | A24 | EBV BMLF1 | DYNFVKQLF |
| 58 | A6B8 | A3 | CMV pp150 TTV | TTVYPPSSTAK |
| 59 | A6B9 | A3 | FLU NP 265-273 ILR | ILRGSVAHK |
| 60 | A6B10 | A3 | EBV EBNA 3a RLR | RLRAEAQVK |
| 61 | A1B11 | A3 | CMV pp150 TVY | TVYPPSSTAK |
| 62 | A1B12 | A3 | EBV BRLF1 148-56 RVR | RVRAYTYSK |
| 63 | A1B13 | A3 | VP1 | ASVPKLLVK |
| 64 | A1B14 | A3 | VP1 | CCPNVASVPK |
| 65 | A1B15 | A3 | VP1 | ITIETVLGR |
| 66 | A1B16 | A3 | VP1 | NTLTTVLLD |
| 67 | A1B17 | A3 | VP1 | ALHGLPRYF |

TABLE 9-continued

Listing of the 110 combinations of peptide-HLA Binding Molecules and the respective Labels, 1OS and 2OS DNA-barcodes, that were used to encode the given specificity of all Detection Molecules applied in experiments 3-6. In the table, HLA code 'A1' refers to HLA-A0101. HLA code 'A2' refers to HLA-A0201. HLA code 'A3' refers to HLA-A0301. HLA code 'A11'+10' refers to HLA-A1101. HLA code 'A24' refers to HLA-A2402. HLA code 'B7' refers to HLA-B0702.

| 1OS Barcode | 2OS Barcode | HLA code | Peptide | Sequence |
|---|---|---|---|---|
| 68 | A1B18 | A3 | VP1 | VASVPKLLVK |
| 69 | A1B19 | A3 | VP1 | VSGQPMEGK |
| 70 | A1B20 | A3 | VP1 | KASSTCKTPK |
| 71 | A2B11 | A3 | VP1 | KTPKRQCIPK |
| 72 | A2B12 | A3 | VP1 | YTYTYDLQPK |
| 73 | A2B13 | A3 | VP1 | PITIETVLGR |
| 74 | A2B14 | B7 | VP1 | SVARVSLPM |
| 75 | A2B15 | A3 | VP1 | NSLFSNLMPK |
| 76 | A2B16 | A3 | VP1 | KVSGQPMEGK |
| 77 | A2B17 | A3 | VP1 | TVYPKPSVAP |
| 78 | A2B18 | A3 | VP1 | SLINVHYWDMK |
| 79 | A2B19 | A3 | VP1 | GVEVLSVVT |
| 80 | A2B20 | A3 | VP1 | PLDLQGLVL |
| 81 | A3B11 | A3 | VP1 | GLDPQAKAK |
| 82 | A3B12 | A3 | VP1 | EVWCPDPSK |
| 83 | A3B13 | A3 | VP1 | ADIVGFLFK |
| 84 | A3B14 | A3 | VP1 | KTSGKMALH |
| 85 | A3B15 | A3 | VP1 | KMALHGLPR |
| 86 | A3B16 | A3 | VP1 | RYFNVTLRK |
| 87 | A3B17 | A3 | VP1 | TLRKRWVKN |
| 88 | A3B18 | B7 | CMV pp65 TPR | TPRVTGGGAM |
| 89 | A3B19 | B7 | CMV pp65 RPH-L | RPHERNGFTV |
| 90 | A3B20 | B7 | EBV EBNA RPP | RPPIFIRLL |
| 91 | A4B11 | B7 | VP1 | KPGCCPNVA |
| 92 | A4B12 | B7 | VP1 | QPIKENLPA |
| 93 | A4B13 | B7 | VP1 | LPRYFNVTL |
| 94 | A4B14 | B7 | VP1 | MPKVSGQPM |
| 95 | A4B15 | B7 | VP1 | YPKPSVAPA |
| 96 | A4B16 | B7 | VP1 | KPSVAPAAV |
| 97 | A4B17 | B7 | VP1 | APLKGPQKA |
| 98 | A4B18 | B7 | VP1 | APKRKASSTC |
| 99 | A4B19 | B7 | VP1 | SVARVSLPML |
| 100 | A4B20 | B7 | VP1 | YPKTTNGGPI |
| 101 | A5B11 | B7 | VP1 | YPKPSVAPAA |

TABLE 9-continued

Listing of the 110 combinations of peptide-HLA Binding Molecules and the respective Labels, 10S and 20S DNA-barcodes, that were used to encode the given specificity of all Detection Molecules applied in experiments 3-6. In the table, HLA code 'A1' refers to HLA-A0101. HLA code 'A2' refers to HLA-A0201. HLA code 'A3' refers to HLA-A0301. HLA code 'A11'+10' refers to HLA-A1101. HLA code 'A24' refers to HLA-A2402. HLA code 'B7' refers to HLA-B0702.

| 10S Barcode | 20S Barcode | HLA code | Peptide | Sequence |
|---|---|---|---|---|
| 102 | A5B12 | B7 | VP1 | KPGCCPNVASV |
| 103 | A5B13 | B7 | VP1 | NPRMGVNSPDL |
| 104 | A5B14 | B7 | VP1 | LPAYSVARVSL |
| 105 | A5B15 | B7 | VP1 | TPTVLQFSNTL |
| 106 | A5B16 | B7 | VP1 | LPRYFNVTLRK |
| 107 | A5B17 | B7 | VP1 | YPVVNLINSLF |
| 108 | A5B18 | B7 | VP1 | YPKPSVAPAAV |
| 109 | A5B19 | B7 | VP1 | KPSVAPAAVTF |
| 110 | A5B20 | B7 | VP1 | APKRKASST |

TABLE 10

The PCR Master mix applied prior to sequencing of DNA-barcodes associated with sorted cells. The forward and reverse primer included adaptors for the sequencing reaction (A-key and P1-key respectively). Moreover the forward primer carried a sample-identification barcode (table 12 and 13). The template was drawn from the residual fluid (10-19 ul) containing the sorted cells. Nuclease free H2O was added to a final volume of 50 ul per PCR

| Component | Volume per sample (μl) |
|---|---|
| Master mix | 25 |
| Forward primer (5 μM) | 3 (300 nM) |
| Reverse primer (5 μM) | 3 (300 nM) |
| Template | 10-19 |
| Nuclease free H$_2$O | 0-9 |
| Total | 50 |

TABLE 11

The thermal profile applied for amplification of DNA-barcodes associated with sorted cells. 36 cycles were applied if >1,000 cells were sorted while 38 cycles were applied if <1,000 cells were sorted.

| Temperature (° C.) | Time | No. of cycles |
|---|---|---|
| ~95 | 10 min | 1 |
| ~95 | 30 s | |
| ~60 | 45 s | 36-38 |
| ~72 | 30 s | |
| ~72 | 4 min | 1 |
| 4 | ∞ | |

TABLE 12

Forward and reverse primers applied for amplification of enriched Detection Molecules prior to sequencing. Primers carry Ion Torrent adaptors, A-key and P1-key. Moreover the forward primer encodes a unique sample-ID barcode (6xN). Compatible with the 10S Label system (F1 = forward primer, R1 = reverse primer)

| Primer name | Forward primer region | 6xN | Ion Torrent region (A Key) |
|---|---|---|---|
| A-Key 10S-F1-1 | GATTCTATAAACTGTGCGGTCC | GAAGAT | CCATCTCATCCCTGCGTGTCTCCGACTCAG |
| A-Key 10S-F1-2 | GATTCTATAAACTGTGCGGTCC | TCCTGA | CCATCTCATCCCTGCGTGTCTCCGACTCAG |
| A-Key 10S-F1-3 | GATTCTATAAACTGTGCGGTCC | TGTGGA | CCATCTCATCCCTGCGTGTCTCCGACTCAG |
| A-Key 10S-F1-4 | GATTCTATAAACTGTGCGGTCC | CATTTA | CCATCTCATCCCTGCGTGTCTCCGACTCAG |
| A-Key 10S-F1-5 | GATTCTATAAACTGTGCGGTCC | TTACCC | CCATCTCATCCCTGCGTGTCTCCGACTCAG |
| A-Key 10S-F1-6 | GATTCTATAAACTGTGCGGTCC | ATTCTC | CCATCTCATCCCTGCGTGTCTCCGACTCAG |
| A-Key 10S-F1-7 | GATTCTATAAACTGTGCGGTCC | AGACCC | CCATCTCATCCCTGCGTGTCTCCGACTCAG |

TABLE 12-continued

Forward and reverse primers applied for amplification of enriched
Detection Molecules prior to sequencing. Primers carry Ion Torrent adaptors,
A-key and P1-key. Moreover the forward primer encodes a unique sample-ID
barcode (6xN). Compatible with the 10S Label system (F1 = forward primer,
R1 = reverse primer)

| | | | |
|---|---|---|---|
| A-Key 10S-F1-8 | GATTCTATAAACTGTGCGGTCC | CGCATG | CCATCTCATCCCTGCGTGTCTCCGACTCAG |
| A-Key 10S-F1-9 | GATTCTATAAACTGTGCGGTCC | TCCTCG | CCATCTCATCCCTGCGTGTCTCCGACTCAG |
| A-Key 10S-F1-10 | GATTCTATAAACTGTGCGGTCC | ATTCCT | CCATCTCATCCCTGCGTGTCTCCGACTCAG |
| A-Key 10S-F1-11 | GATTCTATAAACTGTGCGGTCC | CGTCGA | CCATCTCATCCCTGCGTGTCTCCGACTCAG |
| A-Key 10S-F1-12 | GATTCTATAAACTGTGCGGTCC | GCCAAT | CCATCTCATCCCTGCGTGTCTCCGACTCAG |
| A-Key 10S-F1-13 | GATTCTATAAACTGTGCGGTCC | ATACGG | CCATCTCATCCCTGCGTGTCTCCGACTCAG |
| A-Key 10S-F1-14 | GATTCTATAAACTGTGCGGTCC | GTCAGA | CCATCTCATCCCTGCGTGTCTCCGACTCAG |
| A-Key 10S-F1-15 | GATTCTATAAACTGTGCGGTCC | CGAGTT | CCATCTCATCCCTGCGTGTCTCCGACTCAG |

| Primer name | Ion Torrent (P1 Key) | Reverse primer region |
|---|---|---|
| P1-key 10S-R1 | CCTCTCTATGGGCAGTCGGTGAT | GAGTACATGATAGCGCCGTAC |

TABLE 13

Forward and reverse primers applied for amplification of enriched Detection
Molecules prior to sequencing. Primers carry Ion Torrent adaptors, A-key and P1-key.
Moreover the forward primer encodes a unique sample-ID barcode. A-key 20S-F1-1-15
have a 6xN sample-ID barcode region (applied in experiment 4 and 6) while A-key
20S-F1-16-40 have a 8xN sample-ID and a 2xN spacer (used in all other experiments
applying the 20S system). Compatible with the 20S Label system (F1 = forward primer,
R1 = reverse primer)

| Primer name | Forward primer region | 6N region | 8N region | 2N spacer | Ion Torrent region (A Key) |
|---|---|---|---|---|---|
| A-Key 20S-F1-1 | GAAGTTCCAGCCAGCGTC | CTGGGG | | | CCATCTCATCCCTGCGTGTCTCCGACTCAG |
| A-Key 20S-F1-2 | GAAGTTCCAGCCAGCGTC | CTCCAC | | | CCATCTCATCCCTGCGTGTCTCCGACTCAG |
| A-Key 20S-F1-3 | GAAGTTCCAGCCAGCGTC | CTTACC | | | CCATCTCATCCCTGCGTGTCTCCGACTCAG |
| A-Key 20S-F1-4 | GAAGTTCCAGCCAGCGTC | TGGCAG | | | CCATCTCATCCCTGCGTGTCTCCGACTCAG |
| A-Key 20S-F1-5 | GAAGTTCCAGCCAGCGTC | TGAGTA | | | CCATCTCATCCCTGCGTGTCTCCGACTCAG |
| A-Key 20S-F1-6 | GAAGTTCCAGCCAGCGTC | ATTCAG | | | CCATCTCATCCCTGCGTGTCTCCGACTCAG |
| A-Key 20S-F1-7 | GAAGTTCCAGCCAGCGTC | TGAGCT | | | CCATCTCATCCCTGCGTGTCTCCGACTCAG |
| A-Key 20S-F1-8 | GAAGTTCCAGCCAGCGTC | GGCGTG | | | CCATCTCATCCCTGCGTGTCTCCGACTCAG |
| A-Key 20S-F1-9 | GAAGTTCCAGCCAGCGTC | AAATTG | | | CCATCTCATCCCTGCGTGTCTCCGACTCAG |
| A-Key 20S-F1-10 | GAAGTTCCAGCCAGCGTC | GCTGAC | | | CCATCTCATCCCTGCGTGTCTCCGACTCAG |
| A-Key 20S-F1-11 | GAAGTTCCAGCCAGCGTC | TTCTTA | | | CCATCTCATCCCTGCGTGTCTCCGACTCAG |
| A-Key 20S-F1-12 | GAAGTTCCAGCCAGCGTC | TGGTGG | | | CCATCTCATCCCTGCGTGTCTCCGACTCAG |
| A-Key 20S-F1-13 | GAAGTTCCAGCCAGCGTC | GCAGTC | | | CCATCTCATCCCTGCGTGTCTCCGACTCAG |
| A-Key 20S-F1-14 | GAAGTTCCAGCCAGCGTC | TCGTGA | | | CCATCTCATCCCTGCGTGTCTCCGACTCAG |
| A-Key 20S-F1-15 | GAAGTTCCAGCCAGCGTC | TACAGT | | | CCATCTCATCCCTGCGTGTCTCCGACTCAG |
| A-Key 20S-F1-16 | GAAGTTCCAGCCAGCGTC | | TTGCGTTA | TG | CCATCTCATCCCTGCGTGTCTCCGACTCAG |
| A-Key 20S-F1-17 | GAAGTTCCAGCCAGCGTC | | CGAGCGAG | TG | CCATCTCATCCCTGCGTGTCTCCGACTCAG |
| A-Key 20S-F1-18 | GAAGTTCCAGCCAGCGTC | | CGACTCTG | TG | CCATCTCATCCCTGCGTGTCTCCGACTCAG |
| A-Key 20S-F1-19 | GAAGTTCCAGCCAGCGTC | | ATCCGTCC | TG | CCATCTCATCCCTGCGTGTCTCCGACTCAG |

TABLE 13-continued

Forward and reverse primers applied for amplification of enriched Detection Molecules prior to sequencing. Primers carry Ion Torrent adaptors, A-key and P1-key. Moreover the forward primer encodes a unique sample-ID barcode. A-key 20S-F1-1-15 have a 6xN sample-ID barcode region (applied in experiment 4 and 6) while A-key 20S-F1-16-40 have a 8xN sample-ID and a 2xN spacer (used in all other experiments applying the 20S system). Compatible with the 20S Label system (F1 = forward primer, R1 = reverse primer)

| Primer name | Forward primer region | 6N region | 8N region | 2N spacer | Ion Torrent region (A Key) |
|---|---|---|---|---|---|
| A-Key 20S-F1-20 | GAAGTTCCAGCCAGCGTC | | TTAAACGA | TG | CCATCTCATCCCTGCGTGTCTCCGACTCAG |
| A-Key 20S-F1-21 | GAAGTTCCAGCCAGCGTC | | TAGCTTTT | TG | CCATCTCATCCCTGCGTGTCTCCGACTCAG |
| A-Key 20S-F1-22 | GAAGTTCCAGCCAGCGTC | | CACATGTA | TG | CCATCTCATCCCTGCGTGTCTCCGACTCAG |
| A-Key 20S-F1-23 | GAAGTTCCAGCCAGCGTC | | GATAGCCA | TG | CCATCTCATCCCTGCGTGTCTCCGACTCAG |
| A-Key 20S-F1-24 | GAAGTTCCAGCCAGCGTC | | ACCTGTTA | TG | CCATCTCATCCCTGCGTGTCTCCGACTCAG |
| A-Key 20S-F1-25 | GAAGTTCCAGCCAGCGTC | | TGCGAATT | TG | CCATCTCATCCCTGCGTGTCTCCGACTCAG |
| A-Key 20S-F1-26 | GAAGTTCCAGCCAGCGTC | | GTACATTT | TG | CCATCTCATCCCTGCGTGTCTCCGACTCAG |
| A-Key 20S-F1-27 | GAAGTTCCAGCCAGCGTC | | CTATTGCA | TG | CCATCTCATCCCTGCGTGTCTCCGACTCAG |
| A-Key 20S-F1-28 | GAAGTTCCAGCCAGCGTC | | ACGATACA | TG | CCATCTCATCCCTGCGTGTCTCCGACTCAG |
| A-Key 20S-F1-29 | GAAGTTCCAGCCAGCGTC | | CTTAGCGC | TG | CCATCTCATCCCTGCGTGTCTCCGACTCAG |
| A-Key 20S-F1-30 | GAAGTTCCAGCCAGCGTC | | CGGAAACC | TG | CCATCTCATCCCTGCGTGTCTCCGACTCAG |
| A-Key 20S-F1-31 | GAAGTTCCAGCCAGCGTC | | GATGTTGG | TG | CCATCTCATCCCTGCGTGTCTCCGACTCAG |
| A-Key 20S-F1-32 | GAAGTTCCAGCCAGCGTC | | ATCGGCGT | TG | CCATCTCATCCCTGCGTGTCTCCGACTCAG |
| A-Key 20S-F1-33 | GAAGTTCCAGCCAGCGTC | | TAGTACGA | TG | CCATCTCATCCCTGCGTGTCTCCGACTCAG |
| A-Key 20S-F1-34 | GAAGTTCCAGCCAGCGTC | | GACGTGAT | TG | CCATCTCATCCCTGCGTGTCTCCGACTCAG |
| A-Key 20S-F1-35 | GAAGTTCCAGCCAGCGTC | | TGAGCCAA | TG | CCATCTCATCCCTGCGTGTCTCCGACTCAG |
| A-Key 20S-F1-36 | GAAGTTCCAGCCAGCGTC | | CCTCGCAG | TG | CCATCTCATCCCTGCGTGTCTCCGACTCAG |
| A-Key 20S-F1-37 | GAAGTTCCAGCCAGCGTC | | AGATCCAG | TG | CCATCTCATCCCTGCGTGTCTCCGACTCAG |
| A-Key 20S-F1-38 | GAAGTTCCAGCCAGCGTC | | TTGGCTGA | TG | CCATCTCATCCCTGCGTGTCTCCGACTCAG |
| A-Key 20S-F1-39 | GAAGTTCCAGCCAGCGTC | | GACCGCTA | TG | CCATCTCATCCCTGCGTGTCTCCGACTCAG |
| A-Key 20S-F1-40 | GAAGTTCCAGCCAGCGTC | | GAGCTTAA | TG | CCATCTCATCCCTGCGTGTCTCCGACTCAG |
| A-Key 20S-F1-41 | GAAGTTCCAGCCAGCGTC | | GGACTGGT | TG | CCATCTCATCCCTGCGTGTCTCCGACTCAG |
| A-Key 20S-F1-42 | GAAGTTCCAGCCAGCGTC | | TGGGAGTC | TG | CCATCTCATCCCTGCGTGTCTCCGACTCAG |
| A-Key 20S-F1-43 | GAAGTTCCAGCCAGCGTC | | GCGATGGC | TG | CCATCTCATCCCTGCGTGTCTCCGACTCAG |
| A-Key 20S-F1-44 | GAAGTTCCAGCCAGCGTC | | ACTTGGTT | TG | CCATCTCATCCCTGCGTGTCTCCGACTCAG |
| A-Key 20S-F1-45 | GAAGTTCCAGCCAGCGTC | | ATACTCAT | TG | CCATCTCATCCCTGCGTGTCTCCGACTCAG |
| A-Key 20S-F1-46 | GAAGTTCCAGCCAGCGTC | | TAGTGTCC | TG | CCATCTCATCCCTGCGTGTCTCCGACTCAG |
| A-Key 20S-F1-47 | GAAGTTCCAGCCAGCGTC | | GCATATAA | TG | CCATCTCATCCCTGCGTGTCTCCGACTCAG |
| A-Key 20S-F1-48 | GAAGTTCCAGCCAGCGTC | | GGCGATTG | TG | CCATCTCATCCCTGCGTGTCTCCGACTCAG |
| A-Key 20S-F1-49 | GAAGTTCCAGCCAGCGTC | | GGGCTGTA | TG | CCATCTCATCCCTGCGTGTCTCCGACTCAG |
| A-Key 20S-F1-50 | GAAGTTCCAGCCAGCGTC | | CGCTATTT | TG | CCATCTCATCCCTGCGTGTCTCCGACTCAG |
| A-Key 20S-F1-51 | GAAGTTCCAGCCAGCGTC | | GTACTGCA | TG | CCATCTCATCCCTGCGTGTCTCCGACTCAG |
| A-Key 20S-F1-52 | GAAGTTCCAGCCAGCGTC | | TGTCTATG | TG | CCATCTCATCCCTGCGTGTCTCCGACTCAG |
| A-Key 20S-F1-53 | GAAGTTCCAGCCAGCGTC | | CGAATCAC | TG | CCATCTCATCCCTGCGTGTCTCCGACTCAG |

TABLE 13-continued

Forward and reverse primers applied for amplification of enriched Detection Molecules prior to sequencing. Primers carry Ion Torrent adaptors, A-key and P1-key. Moreover the forward primer encodes a unique sample-ID barcode. A-key 2OS-F1-1-15 have a 6xN sample-ID barcode region (applied in experiment 4 and 6) while A-key 2OS-F1-16-40 have a 8xN sample-ID and a 2xN spacer (used in all other experiments applying the 2OS system). Compatible with the 2OS Label system (F1 = forward primer, R1 = reverse primer)

| Primer name | Forward primer region | 6N region | 8N region | 2N spacer | Ion Torrent region (A Key) |
|---|---|---|---|---|---|
| A-Key 2OS-F1-54 | GAAGTTCCAGCCAGCGTC | | CGTCCTAA | TG | CCATCTCATCCCTGCGTGTCTCCGACTCAG |
| A-Key 2OS-F1-55 | GAAGTTCCAGCCAGCGTC | | ACAAATGG | TG | CCATCTCATCCCTGCGTGTCTCCGACTCAG |
| A-Key 2OS-F1-56 | GAAGTTCCAGCCAGCGTC | | TCTACTTT | TG | CCATCTCATCCCTGCGTGTCTCCGACTCAG |
| A-Key 2OS-F1-57 | GAAGTTCCAGCCAGCGTC | | AATTCGAG | TG | CCATCTCATCCCTGCGTGTCTCCGACTCAG |
| A-Key 2OS-F1-58 | GAAGTTCCAGCCAGCGTC | | GAACTCGG | TG | CCATCTCATCCCTGCGTGTCTCCGACTCAG |
| A-Key 2OS-F1-59 | GAAGTTCCAGCCAGCGTC | | GCGGACGC | TG | CCATCTCATCCCTGCGTGTCTCCGACTCAG |
| A-Key 2OS-F1-60 | GAAGTTCCAGCCAGCGTC | | CTTGTCCA | TG | CCATCTCATCCCTGCGTGTCTCCGACTCAG |
| A-Key 2OS-F1-61 | GAAGTTCCAGCCAGCGTC | | GTCGCGGT | TG | CCATCTCATCCCTGCGTGTCTCCGACTCAG |
| A-Key 2OS-F1-62 | GAAGTTCCAGCCAGCGTC | | CAGGTCGT | TG | CCATCTCATCCCTGCGTGTCTCCGACTCAG |
| A-Key 2OS-F1-63 | GAAGTTCCAGCCAGCGTC | | TCTCATCC | TG | CCATCTCATCCCTGCGTGTCTCCGACTCAG |
| A-Key 2OS-F1-64 | GAAGTTCCAGCCAGCGTC | | GCTTCGTG | TG | CCATCTCATCCCTGCGTGTCTCCGACTCAG |
| A-Key 2OS-F1-65 | GAAGTTCCAGCCAGCGTC | | CGTGATAA | TG | CCATCTCATCCCTGCGTGTCTCCGACTCAG |
| A-Key 2OS-F1-66 | GAAGTTCCAGCCAGCGTC | | TTGCTCAC | TG | CCATCTCATCCCTGCGTGTCTCCGACTCAG |
| A-Key 2OS-F1-67 | GAAGTTCCAGCCAGCGTC | | CGCTCTCC | TG | CCATCTCATCCCTGCGTGTCTCCGACTCAG |
| A-Key 2OS-F1-68 | GAAGTTCCAGCCAGCGTC | | ATTCTACT | TG | CCATCTCATCCCTGCGTGTCTCCGACTCAG |
| A-Key 2OS-F1-69 | GAAGTTCCAGCCAGCGTC | | AAGGCGTT | TG | CCATCTCATCCCTGCGTGTCTCCGACTCAG |
| A-Key 2OS-F1-70 | GAAGTTCCAGCCAGCGTC | | GCGGGATT | TG | CCATCTCATCCCTGCGTGTCTCCGACTCAG |

TABLE 14

Listing of the 175 combinations of peptide-HLA Binding Molecules and the respective 2OS DNA-barcodes that were used to encode the given specificity of all Detection Molecules applied in experiments 7. 168 of the peptide-ligands are associated with melanoma while the remaining 7 are different virus specific peptides. All are HLA-A0201 peptide antigens.

| Barcode 2OS | HLA allele | Peptide | Sequence |
|---|---|---|---|
| A7B1 | HLA-A0201 | 707-AP | RVAALARDAP |
| A7B2 | HLA-A0201 | ATIC (AICRT) | RLDFNLIRV |
| A7B3 | HLA-A0201 | ATIC (AICRT) | MVYDLYKTL |
| A7B4 | HLA-A0201 | BA46 (MFGE8) | NLFETPVEA |
| A7B5 | HLA-A0201 | BA46 (MFGE8) | GLQHWVPEL |
| A7B6 | HLA-A0201 | Bcl-2 | PLFDFSWLSL |
| A7B7 | HLA-A0201 | Bcl-2 | WLSLKTLLSL |
| A7B8 | HLA-A0201 | Bcl-xL | YLNDHLEPWI |
| A7B9 | HLA-A0201 | BING-4 | CQWGRLWQL |
| A7B10 | HLA-A0201 | B-RAF | LATEKSRWSG |
| A7B11 | HLA-A0201 | cyclophilin B (Cyp-B) | VLEGMEVV |
| A7B12 | HLA-A0201 | Cadherin 3/P-cadherin | FILPVLGAV |
| A7B13 | HLA-A0201 | Cadherin 3/P-cadherin | FIIENLKAA |
| A7B14 | HLA-A0201 | CDCA1/NUF2 | YMMPVNSEV |
| A7B15 | HLA-A0201 | CDCA1/NUF2 | KLATAQFKI |
| A7B16 | HLA-A0201 | CDK4 | ACDPHSGHFV |
| A7B17 | HLA-A0201 | CML28 (EXOSC5) | ALVDAGVPM |
| A7B18 | HLA-A0201 | COA-1 (UBXN11) | FMTRKLWDL |

TABLE 14-continued

Listing of the 175 combinations of peptide-HLA Binding Molecules and the respective 20S DNA-barcodes that were used to encode the given specificity of all Detection Molecules applied in experiments 7. 168 of the peptide-ligands are associated with melanoma while the remaining 7 are different virus specific peptides. All are HLA-A0201 peptide antigens.

| Barcode 20S | HLA allele | Peptide | Sequence |
|---|---|---|---|
| A7B19 | HLA-A0201 | COA-1 (UBXN11) | RLLASLQDL |
| A7B20 | HLA-A0201 | CPSF | KVHPVIWSL |
| A7B21 | HLA-A0201 | CPSF | LMLQNALTTM |
| A7B22 | HLA-A0201 | Cyclin I | LLDRFLATV |
| A7B23 | HLA-A0201 | cyclin B1 | AGYLMELCC |
| A7B24 | HLA-A0201 | cyclin B1 | AKYLMELTM |
| A8B1 | HLA-A0201 | B-RAF | LATEKSRWS |
| A8B2 | HLA-A0201 | cyclophilin B (Cyp-B) | KLKHYGPGWV |
| A8B3 | HLA-A0201 | DAM-6, -10 (MAGE-B1, -B2) | FLWGPRAYA |
| A8B4 | HLA-A0201 | EphA2 | IMNDMPIYM |
| A8B5 | HLA-A0201 | EphA2 | VLAGVGFFI |
| A8B6 | HLA-A0201 | EphA2 | VLLLVLAGV |
| A8B7 | HLA-A0201 | EphA2 | TLADFDPRV |
| A8B8 | HLA-A0201 | EZH2 | FINDEIFVEL |
| A8B9 | HLA-A0201 | EZH2 | FMVEDETVL |
| A8B10 | HLA-A020 1 | GnTV | VLPDVFIRCV |
| A8B11 | HLA-A0201 | gp100/Pmel17 | YLEPGPVTA |
| A8B12 | HLA-A0201 | gp100/Pmel17 | LLDGTATLRL |
| A8B13 | HLA-A0201 | gp100/Pmel17 | ITDQVPFSV |
| A8B14 | HLA-A0201 | gp100/Pmel17 | VLYRGSFSV |
| A8B15 | HLA-A0201 | gp100/Pmel17 | RLMKQDFSV |
| A8B16 | HLA-A0201 | gp100/Pmel17 | RLPRIFCSC |
| A8B17 | HLA-A0201 | gp100/Pmel17 | AMLGTHTMEV |
| A8B18 | HLA-A0201 | gp100/Pmel17 | SLADTNSLAV |
| A8B19 | HLA-A0201 | gp100/Pmel17 | KTWGQYWQV |
| A8B20 | HLA-A0201 | HERV-K-MEL | MLAVISCAV |
| A8B21 | HLA-A0201 | hsp70 | LLLLDVAPL |
| A8B22 | HLA-A0201 | IDO1 | ALLEIASCL |
| A8B23 | HLA-A0201 | LAGE-1 | MLMAQEALAFL |
| A8B24 | HLA-A0201 | Livin (ML-IAP) | RLASFYDVVLP |
| A9B1 | HLA-A0201 | Livin (ML-IAP) | SLGSPVLGL |
| A9B2 | HLA-A0201 | Livin (ML-IAP) | QLCPICRAPV |
| A9B3 | HLA-A0201 | M2BP | RIDITLSSV |
| A9B4 | HLA-A0201 | MAGE-A1 | KVLEYVIKV |
| A9B5 | HLA-A0201 | GnTV | VLPDVFIRC |
| A9B6 | HLA-A0201 | gp100/Pmel17 | IMDQVPFSV |
| A9B7 | HLA-A0201 | gp100/Pmel17 | MLGTHTMEV |
| A9B8 | HLA-A0201 | hsp70 | LLDVAPLSL |
| A9B9 | HLA-A0201 | MAGE-A10 | GLYDGMEHL |
| A9B10 | HLA-A0201 | MAGE-A2 | LVHFLLLKY |
| A9B11 | HLA-A0201 | MAGE-A2 | LVQENYLEY |
| A9B12 | HLA-A0201 | MAGE-A2 | YLQLVFGIEV |
| A9B13 | HLA-A0201 | MAGE-A2 | KMVELVHFL |
| A9B14 | HLA-A0201 | MAGE-A3 | LVFGIELMEV |
| A9B15 | HLA-A0201 | MAGE-A4 | GVYDGREHTV |
| A9B16 | HLA-A0201 | MAGE-A1 | YLEYRQVPV |
| A9B17 | HLA-A0201 | MAGE-A8 | GLMDVQIPT |
| A9B18 | HLA-A0201 | MAGE-A8 | KVAELVRFL |
| A9B19 | HLA-A0201 | MAGE-A9 | ALSVMGVYV |
| A9B20 | HLA-A0201 | MAGE-C2 | ALKDVEERV |
| A9B21 | HLA-A0201 | MAGE-C2 | LLFGLALIEV |
| A9B22 | HLA-A0201 | MAGE-C2 | VIWEVLNAV |
| A9B23 | HLA-A0201 | MAGE-C2 | TLDEKVAELV |
| A9B24 | HLA-A0201 | MAGE-C2 | KVLEFLAKL |
| A10B1 | HLA-A0201 | MAGE-A3 | KVAELVHFL |
| A10B2 | HLA-A0201 | MC1R | TILLGIFFL |
| A10B3 | HLA-A0201 | Melan-A/MART-1 | ELAGIGILTV |
| A10B4 | HLA-A0201 | Melan-A/MART-1 | ILTVILGVL |
| A10B5 | HLA-A0201 | Meloe-1 | TLNDECWPA |
| A10B6 | HLA-A0201 | MG50 | CMHLLLEAV |
| A10B7 | HLA-A0201 | MG50 | VLSVNVPDV |
| A10B8 | HLA-A0201 | NY-ESO-1/LAGE-2 | QLSLLMWIT |
| A10B9 | HLA-A0201 | NY-ESO-1/LAGE-2 | SLLMWITQCFL |
| A10B10 | HLA-A0201 | P Polypeptide | IMLCLIAAV |
| A10B11 | HLA-A0201 | p53 | VVPCEPPEV |
| A10B12 | HLA-A0201 | p53 | KTCPVQLWV |
| A10B13 | HLA-A0201 | p53 | RMPEAAPPV |
| A10B14 | HLA-A0201 | p53 | LLPENNVLSPV |

TABLE 14-continued

Listing of the 175 combinations of peptide-HLA Binding Molecules and the respective 20S DNA-barcodes that were used to encode the given specificity of all Detection Molecules applied in experiments 7. 168 of the peptide-ligands are associated with melanoma while the remaining 7 are different virus specific peptides. All are HLA-A0201 peptide antigens.

| Barcode 20S | HLA allele | Peptide | Sequence |
|---|---|---|---|
| A10B15 | HLA-A0201 | p53 | KLCPVQLVVV |
| A10B16 | HLA-A0201 | p53 | SMPPPGTRV |
| A10B17 | HLA-A0201 | p53 | LLGRNSFEV |
| A10B18 | HLA-A0201 | p53 | GLAPPQHLIRV |
| A10B19 | HLA-A0201 | p53 | SLPPPGTRV |
| A10B20 | HLA-A0201 | p53 | YLGSYGFRL |
| A10B21 | HLA-A0201 | PGK1 | IIGGGMAFT |
| A10B22 | HLA-A0201 | PRAME | ALYVDSLFFL |
| A10B23 | HLA-A0201 | PRAME | SLLQHLIGL |
| A10B24 | HLA-A0201 | SOX10 | SAWISKPPGV |
| A11B1 | HLA-A0201 | PRAME | SLYSFPEPEA |
| A11B2 | HLA-A0201 | PRAME | VLDGLDVLL |
| A11B3 | HLA-A0201 | PRDX5 | LLLDDLLVSI |
| A11B4 | HLA-A0201 | NY-ESO-1/LAGE-2 | SLLMWITQC |
| A11B5 | HLA-A0201 | RAB38/NY-MEL-1 | VLHWDPETV |
| A11B6 | HLA-A0201 | RAGE-1 | LKLSGVVRL |
| A11B7 | HLA-A0201 | RAGE-1 | PLPPARNGGL |
| A11B8 | HLA-A0201 | Replication protein A | YLMDTSGKV |
| A11B9 | HLA-A0201 | SART-3 | LLQAEAPRL |
| A11B10 | HLA-A0201 | SART-3 | RLAEYQAYI |
| A11B11 | HLA-A0201 | secernin 1 | KMDAEHPEL |
| A11B12 | HLA-A0201 | SOX10 | AWISKPPGV |
| A11B13 | HLA-A0201 | SSX-2 | RLQGISPKI |
| A11B14 | HLA-A0201 | SSX-2 | KASEKIFYV |
| A11B15 | HLA-A0201 | STAT1-alpha/β | KLQELNYNL |
| A11B16 | HLA-A0201 | STEAP1 | FLYTLLREV |
| A11B17 | HLA-A0201 | STEAP1 | LLLGTIHAL |
| A11B18 | HLA-A0201 | STEAP1 | MIAVFLPIV |
| A11B19 | HLA-A0201 | Survivin | LMLGEFLKL |
| A11B20 | HLA-A0201 | Survivin | ELTLGEFLKL |
| A11B21 | HLA-A0201 | Survivin | TLPPAWQPFL |
| A11B22 | HLA-A0201 | TAG-1 | SLGWLFLLL |
| A11B23 | HLA-A0201 | Telomerase | RLFFYRKSV |
| A11B24 | HLA-A0201 | TRP-2 | VYDFFVWLHY |
| A12B1 | HLA-A0201 | NY-ESO-1/LAGE-2 | SLLMWITQA |
| A12B2 | HLA-A0201 | Telomerase | RLVDDFLLV |
| A12B3 | HLA-A0201 | Telomerase | ILAKFLHWL |
| A12B4 | HLA-A0201 | Topoisomerase II | FLYDDNQRV |
| A12B5 | HLA-A0201 | TRAG-3 | ILLRDAGLV |
| A12B6 | HLA-A0201 | TRP-2 | FVWLHYYSV |
| A12B7 | HLA-A0201 | TRP-2 | SLDDYNHLV |
| A12B8 | HLA-A0201 | TRP-2 | TLDSQVMSL |
| A12B9 | HLA-A0201 | TRP-2 | SVYDFFVVVL |
| A12B10 | HLA-A0201 | TRP2-6b | ATTNILEHY |
| A12B11 | HLA-A0201 | tyrosinase | CLLWSFQTSA |
| A12B12 | HLA-A0201 | tyrosinase | MLLAVLYCL |
| A12B13 | HLA-A0201 | tyrosinase | YMDGTMSQV |
| A12B14 | HLA-A0201 | XBP-1 | LLSGQPASA |
| A12B15 | HLA-A0201 | MG50 | LLLEAVPAV |
| A12B16 | HLA-A0201 | MG50 | TLKCDCEIL |
| A12B17 | HLA-A0201 | MG50 | WLPKILGEV |
| A12B18 | HLA-A0201 | MG50 | RLGPTLMCL |
| A12B19 | HLA-A0201 | Meloe-2 | RCPPKPPLA |
| A12B20 | HLA-A0201 | PRDX5 | AMAPIKVRL |
| A12B21 | HLA-A0201 | cyclin B1 | ILIDWLVQV |
| A12B22 | HLA-A0201 | Melan-A/MART-1 | EAAGIGILTV |
| A12B23 | HLA-A0201 | adipophilin | SVASTITGV |
| A12B24 | HLA-A0201 | alpha-actinin-4 | FIASNGVKLV |
| A13B1 | HLA-A0201 | Meloe-2 | RLPPKPPLA |
| A13B2 | HLA-A0201 | CDKN1A | LMAGCIQEA |
| A13B3 | HLA-A0201 | CDKN1A | GLGLPKLYL |
| A13B4 | HLA-A0201 | CDKN1A | FAWERVRGL |
| A13B5 | HLA-A0201 | CLP (coactosin-like protein) | NLVRDDGSAV |
| A13B6 | HLA-A0201 | CLP (coactosin-like protein) | RLFAFVRFT |
| A13B7 | HLA-A0201 | CLP (coactosin-like protein) | VVQNFAKEFV |

TABLE 14-continued

Listing of the 175 combinations of peptide-HLA Binding Molecules and the respective 20S DNA-barcodes that were used to encode the given specificity of all Detection Molecules applied in experiments 7. 168 of the peptide-ligands are associated with melanoma while the remaining 7 are different virus specific peptides. All are HLA-A0201 peptide antigens.

| Barcode 20S | HLA allele | Peptide | Sequence |
|---|---|---|---|
| A13B8 | HLA-A0201 | c-MET | YVDPVITSI |
| A13B9 | HLA-A0201 | CYP1B1 | WLQYFPNPV |
| A13B10 | HLA-A0201 | IMP-3 | NLSSAEVVV |
| A13B11 | HLA-A0201 | IMP-3 | RLLVPTQFV |
| A13B12 | HLA-A0201 | KIF20A | LLSDDDVVV |
| A13B13 | HLA-A0201 | KIF20A | CIAEQYHTV |
| A13B14 | HLA-A0201 | KIF20A | AQPDTAPLPV |
| A13B15 | HLA-A0201 | MAGE-A10 | SLLKFLAKV |
| A13B16 | HLA-A0201 | MAGE-A12 | FLWGPRALV |
| A13B17 | HLA-A0201 | MAGE-C2 | FLAKLNNTV |
| A13B18 | HLA-A0201 | Melan-A/MART-1 | AAGIGILTV |
| A13B19 | HLA-A0201 | Survivin | QMFFCFKEL |
| A13B20 | HLA-A0201 | Telomerase | LLTSRLRFI |
| A13B21 | HLA-A0201 | TYMS | LMALPPCHAL |
| A13B22 | HLA-A0201 | FLU MP 58-66 GIL | GILGFVFTL |
| A13B23 | HLA-A0201 | EBV LMP2 CLG | CLGGLLTMV |
| A13B24 | HLA-A0201 | EBV BMF1 GLC | GLCTLVAML |
| A14B1 | HLA-A0201 | cyclin D1 | LLGATCMFV |
| A14B2 | HLA-A0201 | HIV pol | TPRVTGGGAM |
| A14B3 | HLA-A0201 | EBV LMP2 FLY | FLYALALLL |
| A14B4 | HLA-A0201 | CMV pp65 NLV | NLVPMVATV |
| A14B5 | HLA-A0201 | EBV BRLF1 YVL | YVLDHLIVV |
| A14B6 | HLA-A0201 | BAP31 | KLDVGNAEV |
| A14B7 | HLA-A0201 | CMV IE1 VLE | VLEETSVML |

Example 20

This is an example where the Sample is a whole blood sample. Instead of being a mix of two PBMC donor materials as described in e.g. example 3 it is a mix of two whole blood samples. Except for the sample preparation the example is performed as example 3

Thus, the Linker is a dextrane conjugate with streptavidin and fluorochrome (PE Dextramer backbone from Immudex ApS).

The Binding Molecules are peptide-MHC (pMHC) complexes. In this example a panel of 110 labeled pMHC-multimers, constituting a library of Detection Molecules, are tested. Apart from 26 virus epitopes that are commonly found in healthy donors (derived from EBV, CMV, FLU and HPV), is included a number of polyomavirus capsid protein (VP1)-derived epitopes that has previously led to detection of T cells in healthy donors.

110 different Labels are generated as example 3. Detection Molecules are synthetized as in example 3.

Sample, whole blood, was incubated with an amount of a library of detection molecules as described in example 3.

The cell-bound detection molecules are separated from the non-cell bound detection molecules as described in example 3.

FACS isolated cells were subjected to PCR amplification of the oligonucleotide label associated with the detection molecules bound to cells. Subsequent extensive sequencing of PCR products revealed the identity of Detection Molecules that bound to the T cells present in the sample.

1. Sample preparation. The cell samples used in this experiment are obtained by mixing whole blood from two different donors to obtain a cell sample where a number of T-cell specificities are known prior to the experiment. Thus, the sensitivity of the method as well as the relevance of the results obtained in the experiment can be evaluated at the end of the experiment, by comparison with data obtained previously, using other methods but cell samples prepared from the same donors.
   a. Acquiring sample: Blood is obtained from the Danish Blood Bank.
   b. Modifying sample:
      i. Blood is drawn into BD Vacutainer® Plus Plastic K2EDTA Tubes according to manufacturer's protocol.
      ii. Anti-coagulated blood samples are diluted 1:1 in RPMI (RPMI 1640, GlutaMAX, 25 mM Hepes; gibco-Life technologies).
      iii. The samples used in the experiment are obtained by mixing blood from a donor (e.g. BC260) with 5% of the T cells specific for HLA-B7/CMV pp65 TPR into blood from a donor (e.g. BC262) without HLA-B7/CMV pp65 TPR specific T cells in five-fold dilutions, creating seven samples (with 5%, 1%, 0.2%, 0.04%, 0.008%, 0.0016% and 0.00032% HLA-B7/CMV pp65 TPR-specific T cells). The CMV pp65 TPR negative sample preparation instead has a population of HLA-A11/EBV-EBNA4 specific T cells.
      iv. The remaining of the example is as for example 3.
2. Linker preparation: The linker used in this example is dextrane conjugate with streptavidin and fluorochrome (PE Dextramer backbone from Immudex) as described in 1.
3. Binding molecules preparation: The 110 different Binding Molecules are prepared as in example 3.
4. Label preparation: The 110 different DNA oligo Labels are prepared as in example 3.
5. Detection molecules preparation: 110 different Detection Molecules are prepared as in example 3.
6. Incubation of sample and detection molecules:
   a. Amount of sample: 0.2 mL anti-coagulated blood diluted 1:1 in RPMI.
   b. Amount of detection molecule: As for e.g. example 3.
   c. Conditions: Sample is incubated with dasatinib (50 nM final concentration), 30 min, 37° C. Subsequently, sample and Detection Molecule is mixed and incubated as e.g. example 3.

7. Enrichment of detection molecules with desired characteristics: Detection Molecules are isolated with their associated cells by FACS as described in example 3.
8. Identification of enriched detection molecule: By identifying the Label (in this Example, the oligonucleotide label), the pMHCs that bound separated cells can be identified. Therefore, the oligonucleotide labels that were comprised within the Detection Molecule that were recovered with the cells, were sequenced. This allowed the identification of pMHCs that bound cells of the cell sample. Labels associated with FACS isolated cells are sequenced as described in example 3.

Example 21

This is an example where the Sample is mononuclear cells derived from bone marrow (BM MNCs). Instead of being a mix of two PBMC donor materials as described in example 3 it is a mix of two whole blood samples. Except for the sample preparation the example is performed as example 3.

Thus, the Linker is a dextrane conjugate with streptavidin and fluorochrome (PE Dextramer backbone from Immudex).

The Binding Molecules are peptide-MHC (pMHC) complexes. In this example a panel of 110 labeled pMHC-multimers, constituting a library of Detection Molecules, are tested. Apart from 26 virus epitopes that are commonly found in healthy donors (derived from EBV, CMV, FLU and HPV), is included a number of polyomavirus capsid protein (VP1)-derived epitopes that has previously led to detection of T cells in healthy donors.

110 different Labels are generated as in example 3. Detection Molecules are synthetized as in example 3.

Sample, whole blood, was incubated with an amount of a library of detection molecules as described in example 3.

The cell-bound detection molecules are separated from the non-cell bound detection molecules as described in example 3.

FACS isolated cells were subjected to PCR amplification of the oligonucleotide label associated with the detection molecules bound to cells. Subsequent extensive sequencing of PCR products revealed the identity of Detection Molecules that bound to the T cells present in the sample.

1. Sample preparation. The cell samples used in this experiment was obtained by mixing bone marrow from two different donors to obtain a cell sample where a number of T-cell specificities were known prior to the experiment. Thus, the sensitivity of the method as well as the relevance of the results obtained in the experiment could be evaluated at the end of the experiment, by comparison with data obtained previously, using other methods but cell samples prepared from the same donors.
   a. Acquiring sample: Collect bone marrow from the upper iliac crest or the sternum by using an aspiration needle.
   b. Modifying sample:
      i. Dilute aspirated human bone marrow at a ratio of 7:1 with buffer (phosphate buffered saline (PBS), pH 7.2, and 2 mM EDTA), e.g., dilute 30 mL of bone marrow with 5 mL of buffer to a final volume of 35 mL.
      ii. Pass cells through a 100 μm filter to remove bone fragments and cell clumps.
      iii. Carefully layer 35 mL of diluted cell suspension over 15 mL of Ficoll-Paque in a 50 mL conical tube. Centrifuge at 445×g for 35 minutes at 20° C. in a swinging bucket rotor without brake. Aspirate the upper layer leaving the mononuclear cell layer undisturbed at the interphase. Carefully transfer the BM MNCs at the interphase to a new 50 mL conical tube. Wash cells by adding up to 40 mL of buffer, mix gently and centrifuge at 300×g for 10 minutes at 20° C. Carefully remove supernatant completely. For removal of platelets, resuspend the cell pellet in 50 mL of buffer and centrifuge at 200×g for 10-15 minutes at 20° C. Carefully remove the supernatant completely. Resuspend cell pellet in 5 mL buffer for downstream applications.
      iv. The samples used in the experiment is obtained by mixing BM MNCs from a donor (e.g. BC260) with 5% of the T cells specific for HLA-B7/CMV pp65 TPR into BM MNCs from a donor (e.g. BC262) without HLA-B7/CMV pp65 TPR specific T cells in fivefold dilutions, creating seven samples (with 5%, 1%, 0.2%, 0.04%, 0.008%, 0.0016% and 0.00032% HLA-B7/CMV pp65 TPR-specific T cells). The CMV pp65 TPR negative BM MNC preparation instead has a population of HLA-A11/EBV-EBNA4 specific T cells.
      v. The remaining of the example is as for example 3.
2. Linker preparation: The linker used in this example is dextrane conjugate with streptavidin and fluorochrome (PE Dextramer backbone from Immudex) as described in 1.
3. Binding molecules preparation: The 110 different Binding Molecules are prepared as in example 3.
4. Label preparation: The 110 different DNA oligo Labels are prepared as in example 3.
5. Detection molecules preparation: 110 different Detection Molecules are prepared as in example 3.
6. Incubation of sample and detection molecules:
   a. Amount of sample: 0.2 mL anti-coagulated blood diluted 1:1 in RPMI.
   b. Amount of detection molecule: As for example 3.
   c. Conditions: Sample is incubated with dasatinib (50 nM final concentration), 30 min, 37° C. Subsequently, sample and Detection Molecule is mixed and incubated as e.g. example 3.
7. Enrichment of detection molecules with desired characteristics: Detection Molecules are isolated with their associated cells by FACS as described in example 3.
8. Identification of enriched detection molecule: By identifying the Label (in this Example, the oligonucleotide label), the pMHCs that bound separated cells can be identified. Therefore, the oligonucleotide labels that were comprised within the Detection Molecule that were recovered with the cells, were sequenced. This allowed the identification of pMHCs that bound cells of the cell sample. Labels associated with FACS isolated cells are sequenced as described in example 3.

Example 60

This is an example where the binding molecules (BM) are MHC-like antigen-presenting molecules such as e.g. CD1a, CD1b, CD1c and CD1d.

The Linker used in this example is dextran conjugate with streptavidin and fluorochrome (PE Dextramer backbone from Immudex), the label used is a DNA oligonucleotide and the Sample is PBMC's.

Isolation and identification of detection molecules capable of binding to cells of the cell sample is done by FACS of cells with PE labeled dextran conjugate, and the identity and amount of associated labels are determined by DNA sequencing.

1. Sample preparation.

The sample used in this example can be any type of cell sample, for example one PBMC sample from a human being, as described in Example 1.

2. Linker preparation:

The linker used in this experiment is a dextran molecule, prepared as described in Example 1.

3. Binding molecules preparation
   a. Synthesis: CD1a, CD1b, CD1c and CD1d is produced as described by Khurana A, et. al, J Vis Exp. 2007; (10): 556. and as performed by a person skilled in the art.
   b. Modification: CD1a, CD1b, CD1c and CD1d is loaded with 15 potential lipid antigens (GMM, glucose monomycolate; Sulfolipid, diacylated sulfoglycolipid; PIM's, phosphatidylinositol mannosides; Man-LAM, mannosylated lipoarabinomannan; MPM, mannosyl-b1-phosphomycoketide; MPP, mannosyl-b1-phosphoheptaprenol; DDM, dideoxymycobactin; GSL-1, a-glucoronsylceramide; GalDAG, a-galactosyldiacylglycerol; LPG, lipophosphoglycan; PI, phosphatidylinositol; PG, phosphatidylglycerol; PE, phosphatidylethanolamine; iGb3, isoglobotrihexosylceramide; Alpha-GC, a-galactosylceramide). Lipids are dissolved to 2 mg/mL in DMSO, heated to 50° C. for 2 min and diluted further 1:10 in PBS+0.1% Tween20. Lipids are mixed individually with the four different CD1 molecules giving rise to 4×15=60 combinations. Briefly 10 uL 1 ug/uL CD1 protein is mixed with 2 uL 0.2 mg mL lipid in PBS+0.1% Tween20+10% DMSO. Load lipids into CD1 4 h at 30° C.
   c. Purification: The CD1a-lipid, CD1b-lipid, CD1c-lipid and CD1d-lipid complexes are not purified further.

4. Label preparation: Labels as described in example 3 are used.
   a. Synthesis: The first 60 Labels in table 8 are used.
   b. Modification: no further
   c. Purification: no further 5. Detection molecules preparation
   a. Synthesis: The detection molecules are prepared as in example 3 except that the 60 different CD1 and lipid combinations are mixed with 60 individual DNA oligonucleotide labels (labels 1-60 from table 8).
   b. Modification: no further modifications
   c. Purification: no further 6. Incubation of sample and detection molecules The sample and detection molecules of step 1 and 5, respectively, are mixed and incubated as described in Example 3.

7. Enrichment of detection molecules with desired characteristic: Cells positive for PE fluorochrome on the Linker is isolated by FACS as described in example 3.

8. Identification of enriched detection molecule: The detection molecules recovered in step 7 are identified by sequencing, as described in Example 3.

Example 61

This is an example where the binding molecules (BM) are MHC class II proteins.

The Linker used in this example is dextran conjugate with streptavidin and fluorochrome (PE Dextramer backbone from Immudex), the label used is a DNA oligonucleotide and the Sample is PBMC's.

Isolation and identification of detection molecules capable of binding to cells of the cell sample is done by FACS of cells with PE labeled dextran conjugate, and the identity and amount of associated labels are determined by DNA sequencing.

1. Sample preparation: The sample used in this example can be any type of cell sample, for example one PBMC sample from a human being, as described in Example 1.

2. Linker preparation: The linker used in this experiment is a dextran molecule, prepared as described in Example 1.

3. Binding molecules preparation
   a. Synthesis: MHC class II protein in the form of biotinylated monomers are obtained from The NIH Tetramer Core Facility, at Emory University, US. The following eight MHC Class II monomers are used (DPB1*04:01 C. tetani TT 948-968 FNNFTVSFWLRVPKVSASHLE, DPB1*04:01 human MAGE3 243-258 KKLLTQHFVQENYLEY, DPB1*04:01 human oxytocinase 272-284 KKYFAATQFEPLA, DPB1*04:01 human CLIP 87-101 PVSKMRMATPLLMQA, DPB1*04:01 human CTAG1 157-170 SLLMWITQCFLPVF, DPB1*04:01 HIV env 31-45 TEKLWVTVYYGVPVW, DQB1*03:02 human CLIP 87-101 PVSKMRMATPLLMQA, DQB1*03:02 human FcR2 104-119 QDLELSWNLNGLQADL
   b. Modification: Monomers are obtained ready folded and biotinylated from The NIH Tetramer Core Facility.
   c. Purification: No further modification 4. Label preparation
   a. Synthesis: The first 8 labels from Table 8 are used
   b. Modification: No further
   c. Purification: No further 5. Detection molecules preparation
   a. Synthesis: The detection molecules are prepared as in example 3 except that the 8 different MHC class II molecules are combined with 8 different DNA oligonucleotide labels as described in example 3.
   b. Modification: No further
   c. Purification: No further 6. Incubation of sample and detection molecules: The sample and detection molecules of step 1 and 5, respectively, are mixed and incubated as described in Example 3.

7. Enrichment of detection molecules with desired characteristics: Cells positive for PE fluorochrome on the Linker is isolated by FACS as described in example 5.

8. Identification of enriched detection molecule: The detection molecules recovered in step 7 are identified by sequencing, as described in Example 3.

Example 79

In this example, 20 different pMHC complexes (e.g. corresponding to 20 known cancer epitopes) are used as binding molecules, the linker is dextran-streptavidin-PE conjugate, and 20 different DNA oligonucleotides are used as labels.

The detection of detection molecules capable of binding to cells of the sample, is by immobilization on an array of anti-sense DNA oligonucleotides.

20 different pMHC complexes (all A*02-01, but each of the 20 complexes carrying one specific peptide epitope commonly found in cancer patients) (e.g epitopes from antigens such as WT-1, survivin, and NY-ESO-1) are prepared using standard procedures, and as described in other examples above. The pMHC complexes are preferably mono-biotinylated.

Dextran-streptavidin-PE conjugate is used as linker, as described in several examples above. PE is a strong fluorochrome, and a given conjugate carries e.g. 1-3 PE molecules.

The labels are 20 different DNA oligonucleotides of different sequences, of approximately 50 nt in length. The oligonucleotides are biotinylated at one terminus. Detection molecules are generated by mixing the dextran-streptavidin-PE conjugate with the 20 different biotinylated pMHC complexes and the 20 different biotinylated DNA oligonucleotides from above, using standard conditions, as described in several examples above. This leads to generation of 20 detection molecules, each of which carries a specific pMHC complex and a specific DNA label.

Whole blood from e.g. a cancer patient is then mixed with the detection molecules generated immediately above, and incubated for 15 minutes. Then the cells are spun down and supernatant removed, and the centrifugation and resuspension repeated 0-3 times. Finally, the cells are resuspended in an appropriate binding buffer that allows specific hybridization of complementary DNA strands.

After incubation and washing the solution of cells and detection molecules is applied to an array, comprising 20 different anti-sense DNA oligos, each of which is confined to a specific area in the array. In other words, each of the 20 different anti-sense DNA oligonucleotides are located in a small area of the array—the array therefore consists of 20 areas each of which comprise antisense oligonucleotides of a given sequence. Each of these 20 anti-sense DNA oligonucleotides comprise a sequence of 10-15 nt that is complementary to the DNA label of one of the 20 detection molecules. Therefore, cells that are bound by a certain detection molecule will become immobilized to the array, through hybridization between the DNA oligonucleotide label of said certain detection molecule and the anti-sense DNA oligonucleotide of the array at that position. The hybridization conditions may be adjusted so that hybridization between just one detection molecule and one anti-sense DNA leads to inefficient immobilization of the corresponding cell, whereas hybridization of several detection molecules to several anti-sense DNA leads to efficient immobilization of the corresponding cell.

As a result, the cells bound by a certain kind of detection molecules (i.e. bound to a certain specificity of detection molecule) will become immobilized to one of the 20 areas of the array, defined by the sequence of the detection molecule bound to the cell and the position in the array of the antisense DNA oligonucleotide that is complementary to said detection molecule's label. Several cells, each bound by a large number of detection molecules, may become immobilized in a certain area of the array. Because of the fluorescent PE molecules attached to the detection molecule, this will give rise to a fluorescent signal from this area of the array. Moreover, at higher resolution (using a microscope) it will be possible to count the number of cells immobilized in the specific area of the array, and finally, the fluorescence of each cell and therefore the relative number of detection molecules bound to each cell, may be determined.

In this example, the fluid cell sample could be of any kind (e.g. synovial fluid, blood, bone marrow, environmental sample (e.g. comprising bacterial cells, in which case the binding molecules could be antibodies binding to proteins of different bacterial surfaces), etc.

The number of different detection molecules could be expanded to much larger numbers, e.g. 100, 1.000 or 10.000.

Rather than having the detection molecules carry the fluorescent molecules directly, a system of primary and secondary antibodies and a corresponding staining system could be used, like standard secondary labelling systems, in order to increase the signal strength.

Example 80

In this example, the labels used are DNA oligonucleotides of different length. The identity of the individual label is based on its mass, by either mass spectrometry or differential migration in a gel electrophoresis analysis.

1. Sample Preparation.

Blood comprising different kinds of blood cells is drawn from a person, and used directly in the incubation, step E below. Alternatively, any type of sample described in the examples above can be used.

3. Binding Molecules Preparation

The binding molecules used in this study are 10 different antibodies, recognizing 10 different cell differentiation markers (CDs) respectively, namely CD3, CD4, CD8, CD16, CD56, . . . **. Each of these are commercially available.

4. Label Preparation

10 DNA oligonucleotides of length 50 nt, 100 nt, 150 nt, 200 nt, 250 nt, 300 nt, 350 nt, 400 nt, 450 nt, and 500 nt, respectively, with a terminal N-succinimidyl ester moiety are prepared by standard means.

5. Detection Molecules Preparation

Each of the 10 antibodies mentioned under (B) are incubated in appropriate buffer (e.g. PBS pH 8) together with one of the 10 oligonucleotides mentioned in step (C) above, allowing the N-succinimidyl ester to react with free amines on the surface of the antibody, to form a covalent link between the antibody and the oligonucleotide. In this way, 10 detection molecules are generated, each of which comprise one specific antibody (e.g. anti-CD3 antibody) and one specific oligonucleotide (e.g. 50 nt DNA oligo).

6. Incubation of Sample and Detection Molecules

The sample of step (A) is incubated with the 10 detection molecules under appropriate conditions (e.g. appropriate buffer, e.g. Tris pH 7.5 is added, or the oligonucleotides from step (D) in e.g. PBS pH 8 is simply mixed with sample without further addition of buffer. Incubation can be at 0, 4, 10, 20, 30, or 40 degrees celcius.

7. Isolating Bound and Unbound Detection Molecules

The incubation mixture of step (E) is centrifuged, to recover all cells of the sample. Supernatant is removed, the cells resuspended and buffer added. Centrifugation is repeated 1-3 times, and the cells finally resuspended. The suspension of cells will contain detection molecules that are capable of binding to one or more cells. Thus, the detection molecules of the suspension are representative of the distribution of receptors on the cell surface of the cells of the original sample.

8. Determining the Identity and Amount of the Recovered Detection Molecules.

1 µL of the mixture of cells and bound detection molecules are transferred to a 100 µL PCR reaction comprising forward and reverse primers that can anneal to each of the 10 oligonucleotide labels described in step (C) above, and comprising all other components for an efficient PCR reaction. The PCR reaction is performed under standard conditions, and aliquots are taken out after 25, 30 and 35 cycles are performed.

The PCR product is applied to a gel capable of resolving the individual oligonucleotide fragments (e.g. a 2.5% agarose gel), and electrophoresis is performed. Once the fastest moving product (corresponding to the 50 nt oligonucleotide) has migrated about ¾ of the gel length, eletrophoresis is terminated. The position of a band in the gel reflects its size and therefore identifies the corresponding oligonucleotide label; the uppermost band represents the largest fragment (500 nt), and the lowermost band represents the smallest fragment (50 nt). The intensity of each of the 10 bands, corresponding to each of the 10 different oligonucleotide fragments, is indicative of the relative amount recovered of each oligonucleotide label and therefore, of each detection molecule.

Example 81

This example is as example 80, except that the labels used here are PNA fragments rather than DNA oligonucleotides, and the identity of the labels of the recovered detection molecules are determined by mass spectrometry analysis rather than gel electrophoresis.

Sample and binding molecules are as described in example 80.

Labels are prepared as follows. 10 different PNAs are prepared, of different size (e.g. comprising 5, 7, 9, 11, 13, 15, 17, 19, 21, and 23 bases). During synthesis, N-succinimidyl ester is introduced at one of the PNA fragment. Further, also during its synthesis, a disulfide bond (S—S) is introduced between the ester and the rest of the PNA fragment. Thus, in the label a disulfide bond links the N-succinimidyl ester with the remainder of the PNA fragment.

Detection molecules are prepared as in example 80, except that the PNA labels are used instead of the DNA oligonucleotide labels of example 80. Each of the resulting 10 detection molecules therefore consists of a specific binding molecule (a specific antibody, e.g. CD3) and a specific PNA label (e.g. PNA comprising 5 bases). Isolation of detection molecules capable of binding to cells of the sample is done by centrifugation as described in example 80, and the final cell suspension thus contains cells plus detection molecules capable of binding to cells of the sample.

Finally, the identity and amount of the recovered detection molecules is determined in the following way: First, the PNA labels are cleaved off from the detection molecules (and therefore, released from the cells that the detection molecule is bound to) by addition of DTT, which cleaves the disulfide bond. The cells are spun down by centrifugation, and the supernatant (comprising the released PNA labels but not the cells) is then subjected to a mass spectrometry analysis.

The mass spectrometry analysis will reveal the relative amount of each of the 10 PNA labels (corresponding to the relative amount of each of the 10 detection molecules recovered by centrifugation of the cells).

Example 82

This example is as example 81, except that the labels used here are peptide fragments rather than PNA fragments Labels are prepared as follows. 10 different peptides are prepared, of different size (e.g. comprising 5, 7, 9, 11, 13, 15, 17, 19, 21, and 23 amino acids). During synthesis, N-succinimidyl ester is introduced at one of the peptide fragment. Further, also during its synthesis, a disulfide bond (S—S) is introduced between the ester and the rest of the peptide fragment. Thus, in the label a disulfide bond links the N-succinimidyl ester with the remainder of the peptide fragment.

Detection molecules are prepared as in example 81, except that the peptide labels are used instead of the PNA labels of example 81. Each of the resulting 10 detection molecules therefore consist of a specific binding molecule (a specific antibody, e.g. CD3) and a specific peptide label (e.g. peptide comprising 5 amino acids).

The mass spectrometry analysis will reveal the relative amount of each of the 10 peptide labels (corresponding to the relative amount of each of the 10 detection molecules recovered by centrifugation of the cells).

Example 120

This is an example where the samples are three buffy coats (BC's), the Linker is PE and streptavidin conjugated dextran, and the Binding Molecules are biotinylated peptide-MHC (pMHC) complexes. The Labels are synthetic oligonucleotides modified with a terminal biotin capture-tag. The labels are combined oligonucleotide label arising by annealing an A oligonucleotide (modified with biotin) to a partially complimentary B oligonucleotide label followed by enzymatic DNA polymerase extension of Oligo A and Oligo B to create a fully double stranded label.

The Detection Molecules are created by combining biotinylated pMHC and labels in the form of biotin-modified oligonucleotide onto a streptavidin-modified dextran linker. The detection molecule further contained a fluorochrome (PE). 30 different Detection Molecules are generated wherein the individual detection molecules containing different pMHC are encoded by corresponding individual oligonucleotide labels. Two versions (Set 1 and Set 2, see table x) of each of the 30 different Detection Molecules are created in the way that all Detection molecules are generated in two forms with different labels. Three samples, PBMC's, were incubated with an amount of mixed Detection Molecules.

In this example CD8+ T cell-bound Detection Molecules are separated from the non-cell bound Detection Molecules by capture of CD8+ T cells using anti CD8-coated magnetic Dynabeads. Magnetic bead-isolated CD8-positive T cells are subjected to PCR amplification of associated Label and the PCR product is analyzed as a read of the oligonucleotide label associated with the detection molecules bound to the isolated cells thus revealing the identity of detection molecules bound to the T cells present in the sample.

1. Sample preparation.
   a. Acquiring sample: The cell sample used in this experiment is obtained by preparing PBMC's from blood drawn from three donors (D131, D149 and D158) that, by conventional MHC-multimer staining, are characterized for their specific T cells towards a number of virus antigens.
   b. Modifying sample: The PBMC's are prepared as described in example 1.
2. Linker preparation: The Linker is PE and streptavidin conjugated dextran (Dextramer from Immudex) which is prepared as in example 1.

3. Binding molecules preparation: Binding Molecules are biotinylated pMHC complexes with peptide/HLA combination as described in table below

| Labels set 1 | Labels set 2 | HLA | Antigen | Peptide |
|---|---|---|---|---|
| 2OS-A1-B2 | 2OS-A1-B12 | A2 | CMV pp65 | NLVPMVATV |
| 2OS-A1-B3 | 2OS-A1-B13 | A2 | EBV-E3B | LLDFVRFMGV |
| 2OS-A1-B4 | 2OS-A1-B14 | A2 | HPV E6 | TIHDIILECV |
| 2OS-A1-B5 | 2OS-A1-B15 | A2 | HSV-1gB | RMLGDVMAV |
| 2OS-Ai-B6 | 2OS-A1-B16 | A2 | Neg Control | ALIAPVHAV |
| 2OS-A2-B2 | 2OS-A2-B12 | A2 | CMV-IE1 | VLEETSVML |
| 2OS-A2-B3 | 2OS-A2-B13 | A2 | EBV-BALF4 | FLDKGTYTL |
| 2OS-A2-B4 | 2OS-A2-B14 | A2 | FLU | GILGFVFTL |
| 2OS-A2-B5 | 2OS-A2-B15 | A2 | MART-1 | ELAGIGILTV |
| 2OS-A2-B6 | 2OS-A2-B16 | A3 | Cancer-gp100 | ALLAVGATK |
| 2OS-A3-B2 | 2OS-A3-B12 | A2 | EBV-EBMAC3 | CLGGLLTMV |
| 2OS-A3-B3 | 2OS-A3-B13 | A2 | EBV-BMRF1 | TLDYKPLSV |
| 2OS-A3-B4 | 2OS-A3-B14 | A2 | FLU-BNP | KLGEFYNQMM |
| 2OS-A3-B5 | 2OS-A3-B15 | A2 | HIV-gag | SLYNTVATL |
| 2OS-A3-B6 | 2OS-A3-B16 | B07 | Neg Control | GPAESAAGL |
| 2OS-A4-B2 | 2OS-A4-B12 | A2 | EBV-BMLF1 | GLCTLVAML |
| 2OS-A4-B3 | 2OS-A4-B13 | A2 | EBV-BRLF1 | YVLDHLIVV |
| 2OS-A4-B4 | 2OS-A4-B14 | A2 | HSV1gB | GIFEDRAPV |
| 2OS-A4-B5 | 2OS-A4-B15 | A2 | HIV | ILKEPVHGV |
| 2OS-A4-B6 | 2OS-A4-B16 | B08 | Neg Control | AAKGRGAAL |
| 2OS-A5-B2 | 2OS-A5-B12 | A2 | EBV-LMP1 | YLLEMLWRL |
| 2OS-A5-B3 | 2OS-A5-B13 | A2 | HPV-E7 | YMLDLQPETT |
| 2OS-A5-B4 | 2OS-A5-B14 | A2 | Hsv1gB | YLANGGFLI |
| 2OS-A5-B5 | 2OS-A5-B15 | A2 | HIV | FLGKIWPS |
| 2OS-A5-B6 | 2OS-A5-B16 | H2Kb | Neg Control | AYAGSAGSI |
| 2OS-A6-B2 | 2OS-A6-B12 | A2 | EBV-LMP1 | YLQQNWWTL |
| 2OS-A6-B3 | 2OS-A6-B13 | A2 | HPV-E7 | LLMGTLGIVC |
| 2OS-A6-B4 | 2OS-A6-B14 | A2 | HSV-UI25 | FLWEDQTLL |
| 2OS-A6-B5 | 2OS-A6-B15 | A1 | Neg Control | STEGGGLAY |
| 2OS-A6-B6 | 2OS-A6-B16 |  | Neg Control | no peptide |

4. Label preparation: Label is generated as described in example 4 except that in this example only 2×60 labels are used (See table above)
5. Detection molecules preparation
   a. Synthesis
      i. According to table below transfer the required volume Dextran conjugate to an Eppendorf tube. Centrifuge (10.000 g, 10 min, 4° C.).
      ii. Transfer the supernatant containing dextrane conjugate without precipitates to 2*30 wells on two plates.
      iii. In a 96 well format add the 2×30 Label oligos in 2:1 molar concentration to PE-Dextramer conjugate.
      iv. Mix well and incubate 30 min, 4° C.
      v. Thaw pMHC binding molecules on ice, dilute to 100 μg/mL in PBS and centrifuge (2000 g, 5 minutes, 18° C.).
      vi. Transfer the pMHC monomers to wells of the 96 well plate according to the above table to allow the combination of pMHC with labeled linker.
      vii. Mix well and incubate 30 minutes at r.t. and PBS subsequently.

| Detection molecule preparation | Concentration | |
|---|---|---|
| Dextran conjugate | 16 | *10^ − 8M |
| Oligo lable | 54.25 | *10^ − 8M |

| | Detection molecules/samples |
|---|---|
| Number of Detection molecules | 30 |
| Number of samples | 20 |

| Assembling Label and Linker | Volumes needed | |
|---|---|---|
| 1: Transfer Dextran to Eppendorf tube and centrifuge 10000 g, 5 min, 4 C. | 630 | μl |
| 2: Transfer the supernatant to wells on a plate according to setup | 20 | μl/well |
| 3: Add oligo labels to wells according to setup, Mix and incubate 30 min, 4 C. Preparation of binding molecules: | 11.8 | μl/well |
| 1: Thaw pMHC monomers on ice 2: Dilute monomers in PBS to 100 μg/ml = 2 μM Vtotal needed per pMHC per plate Preparation of Detection Molecules | 40 | μl/pMHC |
| 1: Centrifuge pMHC monomers 2000 g, 10 min 18 C. 2: Transfer supernatant to the 96well plate (To the Dextran -MHC control is an equal volume of PBS added) 3: Mix well and incubate 30 min at RT 4: Add PBS 5: Store at 4 C. | 26.4 | μl/well |
| | 1.8 | μl/well |
| Vtotal in each well | 60.0 | | a. Modification: No further
   b. Purification: No further
6. Incubation of sample and detection molecules
   a. Amount of sample: 2 million PBMC's per sample
   b. Amount of detection molecule: According to table below. Each donor sample is incubated with 4 different amounts of Detection Molecule
   c. Conditions:
      i. PBMC's are thawed in 10 ml RPMI-10% FCS and washed twice in 2 mL RPMI-10% FCS. Cells are then washed in 2 mL PBS w. 0.5% BSA, 100 μg/ml Herring DNA, 2 mM EDTA. (All washing of cells in this experiment refers to centrifuge for 5 min at 800 g to collect cells followed by discarding of wash buffer)
      ii. Resuspend cells in 500 μl PBS w. 0.5% BSA, 100 μg/ml Herring DNA, 2 mM EDTA to a concentration 20 million/ml.
      iii. Add 25 μl 1 μM Dasatinib and incubate 30 min at 37° C. (Final Dasatinib conc. 50 nM).

iv. Centrifuge Detection Molecules (2000 g, 5 minutes, 18° C.)
v. Add 166.5 µl 10 µM biotin to an Eppendorf tube.
vi. Pool 25 µl of each Detection Molecule from each of the two sets into the Eppendorf tube (Detection Molecule library) Vtot=1666.5 µl which is enough for 3 donors in 4 concentrations.
vii. Centrifuge the library of Detection Molecules (10000 g, 10 min) and transfer 1550 µl to a new tube avoiding aggregates.
viii. Transfer from new tube to 5 ml tubes according to setup/volumes below.
ix. To all twelve tubes add 100 µl cells (2 million cells) of the respective donors, to a VTot in each sample of 300 µl. Incubate 15 minutes at 37° C.
x. Wash cells twice in 2 ml PBS w. 0.5% BSA, 100 µg/ml Herring DNA, 2 mM EDTA (Centrifuge 5 min at 800 g)

|  | Detect Mol | | | |
| --- | --- | --- | --- | --- |
| Sample | 3 µl | 1.5 µl | 0.75 µl | 0.375 µl |
| D131 | S1: 200 µl | S2: 100 µl | S3: 50 µl | S4: 25 µl |
| D149 | S5: 200 µl | S6: 100 µl | S7: 50 µl | S8: 25 µl |
| D158 | S9: 200 µl | S10: 100 µl | S11: 50 µl | S12: 25 µl |
| PBS w. 0.5% BSA, 100 µg/ml Herring DNA, 2 mM EDTA | | | | |
| D131 | S1: 0 µl | S2: 100 µl | S3: 150 µl | S4: 175 µl |
| D149 | S5: 0 µl | S6: 100 µl | S7: 150 µl | S8: 175 µl |
| D158 | S9: 0 µl | S10: 100 µl | S11: 150 µl | S12: 175 µl |

7. Enrichment of detection molecules with desired characteristics
   a. Apply: In this example Detection Molecules are isolated by capturing CD8+ cells using anti CD8 antibody coated magnetic beads (DYNABEADS CD8, #11147D, Life Technologies). Detection molecules associated with captured CD8+ cells are isolated. Dynabeads used according to manufacturer's protocol.
      i. Briefly; Dynabeads are vortex >30 sec and transfer 50 µl/sample=600 µl to a 5 ml tube and add 1 ml PBS+0.1% BSA+2 mM EDTA. Re-suspended dynabeads are placed in magnet 1 min, supernatant is discarded and dynabeads are re-suspended in 600 µl PBS+0.1% BSA+2 mM EDTA.
      ii. To all samples add 50 µl washed beads+950 µl Isolation buffer=>Vtot=1 ml. Incubate 20 min 4 C on a tilting plate.
   b. Wash:
      i. Place tubes in magnet (Dynal, Life Technologies) for 2 min and carefully remove supernatant
      ii. Wash twice: Add 2 ml PBS+0.1% BSA+2 mM EDTA, vortex, place in magnet 2 min, remove supernatant.
      iii. Re-suspend beads in 500 µl PBS w. 0.5% BSA, 100 µg/ml Herring DNA, 2 mM EDTA, transfer to Eppendorf tubes.
      iv. Centrifuge tubes 5 min at 5000 g, remove supernatant final volume app. 20 µl→Store at −80 C or store on ice at 4 C O.N for PCR
   c. Separate: Is done during washing.

8. Identification of enriched detection molecule: Separated Detection Molecules are analyzed by PCR amplification of the attached labels followed by sequencing of the PCR products to reveal the identity of isolated detection molecules and thus the identity of those antigens for which specific T cells were present in the sample. The PCR amplification and sequencing of PCR product is done as for example 3 using the same sets of primers and the same sequencing service and sequencing de-convolution service.

Example 121

This is an example where the samples are PBMC's prepared as three buffy coats (BC's), the Linker is PE and streptavidin conjugated dextran, and the Binding Molecules are biotinylated peptide-MHC (pMHC) complexes. The Labels are synthetic oligonucleotides modified with a terminal biotin capture-tag.

In this example CD8+ T cell-bound Detection Molecules are separated from non-cell bound Detection Molecules by capture of CD8+ T cells by magnetic labeling of CD8+ cells with CD8 MicroBeads (CD8 MicroBeads, human, #130-045-201, Miltenyi, Germany). Magnetic bead-isolated CD8-positive T cells are subjected to PCR amplification of associated Label (as described in example 3) and the PCR product is analyzed as a read of the oligonucleotide label associated with the detection molecules bound to the isolated cells thus revealing the identity of detection molecules bound to the T cells present in the sample (as example 3).

1. Sample preparation. The samples are PBMC's from three donor materials prepared as described in example 3.
2. Linker preparation: The Linker is PE and streptavidin conjugated dextran (Dextramer from Immudex) which is prepared as in example 1.
3. Binding molecules preparation: Binding Molecules are biotinylated pMHC complexes with peptide/HLA combination as described in example 3.
4. Label preparation: Labels are biotin modified DNA oligonucleotides as described in example 3.
5. Detection molecules preparation: Detection Molecules are prepared by combining 110 aliquots of Linker with individual Labels followed by adding pMHC Binding Molecules as described in Example 3.
6. Incubation of sample and detection molecules: PBMC's are mixed with the 110 member library of Detection Molecules as described in example 3.
7. Enrichment of detection molecules with desired characteristics:
   a. Apply: In this example Detection Molecules are isolated by capturing CD8+ cells using anti CD8 antibody coated magnetic beads (CD8 MicroBeads, human, #130-045-201, Miltenyi, Germany). Detection molecules associated with captured CD8+ cells are isolated. CD8 MicroBeads are used according to manufacturer's protocol. Briefly;
      i. Centrifuge cell suspensions at 300×g for 10 minutes. Aspirate supernatant completely.
      ii. Resuspend cell pellets in 80 µL of buffer (phosphate-buffered saline (PBS), pH 7.2, 0.5% bovine serum albumin (BSA), and 2 mM EDTA).
      iii. Add 20 µL of CD8 MicroBeads. Mix well and incubate for 15 minutes in the refrigerator (2-8 iv. Wash cells by adding 1-2 mL of buffer and centrifuge at 300×g for 10 minutes. Aspirate supernatant completely. Resuspend cells in 500 µL of buffer.
v. Place an MS column (Miltenyi, Germany) in the magnetic field of a OctoMACS column stand Separator. Prepare column by rinsing with 500 µL of buffer:
vi. Apply cell suspension onto the column. Collect unlabeled cells that pass through and wash column with 500 µL of buffer. Collect total effluent; this is the unlabeled cell fraction. Perform washing steps by adding buffer three times. Only add new buffer when the column reservoir is empty.
vii. Remove column from the separator and place it on a suitable collection tube.
viii. Pipette 1 mL of buffer onto the column.
ix. Immediately flush out the magnetically labeled cells by firmly pushing the plunger into the column.
x. Centrifuge tubes 5 min at 500 g, remove supernatant. The final volume of app. 20 µl containing collected CD8+ cells and their associated Detection Molecules are store at −80 C for later analysis.
8. Identification of enriched detection molecule: Separated cells and their associated Detection Molecules are analyzed by PCR amplification of the attached labels followed by sequencing of the PCR products to reveal the identity of isolated Detection Molecules and thus the identity of those antigens for which specific T cells were present in the sample. The identification is done as for example 3.

Example 122

This is an example where the samples are PBMC's prepared as three buffy coats (BC's), the Linker is PE and streptavidin conjugated dextran, and the Binding Molecules are biotinylated peptide-MHC (pMHC) complexes. The Labels are synthetic oligonucleotides modified with a terminal biotin capture-tag.

In this example, though, all cells and their bound Detection Molecules are first separated, by centrifugation, from the supernatant containing Detection Molecules not bound to cells. Secondly, remaining Detection Molecules are captured by their PE modification on the Linker using anti PE MicroBeads (anti PE MicroBeads, #130-048-801, Miltenyi, Germany). Magnetic bead-isolated cells are subjected to PCR amplification of Detection-Molecule associated Labels (as described in example 3) and the PCR product is analyzed as a read of the oligonucleotide label associated with the detection molecules bound to the isolated cells thus revealing the identity of detection molecules bound to the T cells present in the sample as in example 3.
1. Sample preparation. The samples are PBMC's from three donor materials prepared as described in example 3.
2. Linker preparation: The Linker is PE and streptavidin conjugated dextran (Dextramer from Immudex) which is prepared as in example 1.
3. Binding molecules preparation: Binding Molecules are biotinylated pMHC complexes with peptide/HLA combination as described in example 3.
4. Label preparation: Labels are biotin modified DNA oligonucleotides as described in example 3.
5. Detection molecules preparation: Detection Molecules are prepared by combining 110 aliquots of Linker with individual Labels followed by adding pMHC Binding Molecules as described in Example 3.
6. Incubation of sample and detection molecules: PBMC's are mixed with the 110 member library of Detection Molecules as described in example 3.
7. Enrichment of detection molecules with desired characteristics
   a. Apply: In this example Detection Molecules are isolated by centrifugation separation of cells and their bound Detection Molecules from the supernatant containing Detection Molecules not bound to cells followed by magnetic capture of cells with bound PE-labeled Detection Molecules thereby separating from cells without bound PE-labeled Detection Molecules using anti PE MicroBeads (anti PE MicroBeads, #130-048-801, Miltenyi, Germany). MicroBeads are used according to manufacturer's protocol. Briefly;
      i. Centrifuge cell suspensions at 300×g for 10 minutes. Aspirate supernatant completely.
      ii. Wash cells twice by adding 2 mL of buffer (phosphate-buffered saline (PBS), pH 7.2, 0.5% bovine serum albumin (BSA), and 2 mM EDTA) and centrifuge at 300×g for 10 minutes. Aspirate supernatant completely.
      iii. Resuspend cell pellets in 80 µL of buffer.
      iv. Add 20 µL of anti PE MicroBeads. Mix well and incubate for 15 minutes in the refrigerator (2-8)
      v. Wash cells by adding 1-2 mL of buffer and centrifuge at 300×g for 10 minutes. Aspirate supernatant completely. Resuspend cells in 500 µL of buffer.
      vi. Place an MS column (Miltenyi, Germany) in the magnetic field of a OctoMACS column stand Separator. Prepare column by rinsing with 500 µL of buffer:
      vii. Apply cell suspension onto the column. Collect unlabeled cells that pass through and wash column with 500 µL of buffer. Collect total effluent; this is the unlabeled cell fraction. Perform washing steps by adding buffer three times. Only add new buffer when the column reservoir is empty.
      viii. Remove column from the separator and place it on a suitable collection tube.
      ix. Pipette 1 mL of buffer onto the column.
      x. Immediately flush out the magnetically labeled cells by firmly pushing the plunger into the column.
      xi. Centrifuge tubes 5 min at 500 g, remove supernatant. The final volume of app. 20 µl containing collected CD8+ cells and their associated Detection Molecules are store at −80 C for later analysis.
8. Identification of enriched detection molecule: Separated cells and their associated Detection Molecules are analyzed by PCR amplification of the attached labels followed by sequencing of the PCR products to reveal the identity of isolated Detection Molecules and thus the identity of those antigens for which specific T cells were present in the sample. The identification is done as for e.g. example 6.

Example 123

This is an example where the samples are PBMC's prepared as three buffy coats (BC's), the Linker is PE and streptavidin conjugated dextran, and the Binding Molecules are biotinylated peptide-MHC (pMHC) complexes. The Labels are synthetic oligonucleotides modified with a terminal biotin capture-tag.

In this example, cells and their bound Detection Molecules are separated, by centrifugation, from the supernatant containing Detection Molecules not bound to cells. The DNA oligonucleotide Labels on Detection Molecules associated with captured cells are subjected to PCR amplification (as example 3) and the PCR product is analyzed as a read of the oligonucleotide label associated with the detection molecules bound to the isolated cells thus revealing the identity of detection molecules bound to the T cells present in the sample (as example 3).

1. Sample preparation. The samples are PBMC's from three donor materials prepared as described in example 3.
2. Linker preparation: The Linker is PE and streptavidin conjugated dextran (Dextramer from Immudex) which is prepared as in example 1.
3. Binding molecules preparation: Binding Molecules are biotinylated pMHC complexes with peptide/HLA combination as described in example 3.
4. Label preparation: Labels are biotin modified DNA oligonucleotides as described in example 3.
5. Detection molecules preparation: Detection Molecules are prepared by combining 110 aliquots of Linker with individual Labels followed by adding pMHC Binding Molecules as described in Example 3.
6. Incubation of sample and detection molecules: PBMC's are mixed with the 110 member library of Detection Molecules as described in example 3.
7. Enrichment of detection molecules with desired characteristics
   b. Apply: Detection Molecules are isolated by centrifugation-separation of cells and their bound Detection Molecules from the supernatant containing Detection Molecules not bound to cells. Briefly;
      i. Centrifuge cell suspensions at 300×g for 10 minutes. Aspirate supernatant completely.
      ii. Wash cells twice by adding 2 mL of buffer (phosphate-buffered saline (PBS), pH 7.2, 0.5% bovine serum albumin (BSA), and 2 mM EDTA) and centrifuge at 300×g for 10 minutes.
      iii. Aspirate supernatant completely. The final volume of app. 20 μl containing collected cells and their associated Detection Molecules are store at −80 C for later analysis.
8. Identification of enriched Detection Molecule: Separated cells and their associated Detection Molecules are analyzed by PCR amplification of the attached labels followed by sequencing of the PCR products to reveal the identity of isolated Detection Molecules and thus the identity of those antigens for which specific T cells were present in the sample. The identification is done as for example 3.

Example 124

This is an example where the samples are PBMC's prepared as three buffy coats (BC's), the Linker is PE and streptavidin conjugated dextran, and the Binding Molecules are biotinylated peptide-MHC (pMHC) complexes. The Labels are synthetic oligonucleotides modified with a terminal biotin capture-tag.

In this example, INFγ producing cells and their bound Detection Molecules are separated from Detection Molecules not bound to INFγ producing cells by magnetic labeling and capture of INFγ producing cells using the MicroBead based INFγ Secretion Assay (INFγ Secretion Assay, #130-054-201, Miltenyi, Germany). Magnetic bead-isolated INFg producing cells are subjected to PCR amplification of associated DNA oligonucleotide Label (as described in example 3) and the PCR product is analyzed as a read of the oligonucleotide label associated with the detection molecules bound to the isolated cells thus revealing the identity of detection molecules bound to the INFγ producing cells present in the sample (as example 3).

1. Sample preparation. The samples are PBMC's from three donor materials prepared as described in example 3.
2. Linker preparation: The Linker is PE and streptavidin conjugated dextran (Dextramer from Immudex) which is prepared as in example 1.
3. Binding molecules preparation: Binding Molecules are biotinylated pMHC complexes with peptide/HLA combination as described in example 3.
4. Label preparation: Labels are biotin modified DNA oligonucleotides as described in example 3.
5. Detection molecules preparation: Detection Molecules are prepared by combining 110 aliquots of Linker with individual Labels followed by adding pMHC Binding Molecules as described in Example 3.
6. Incubation of sample and detection molecules: PBMC's are mixed with the 110 member library of Detection Molecules as described in example 3.
7. Enrichment of detection molecules with desired characteristics
   i. Apply: In this example Detection Molecules are isolated by capturing INFγ producing cells using anti INFγ catch antibody in combination with anti INFγ detection antibody. All reagents and procedures as described by Miltenyi (INF γ Secretion Assay, #130-054-201, Miltenyi, Germany). Finally INFγ producing cells are captured using anti PE Microbeads.
   ii. Centrifuge tubes 5 min at 500 g, remove supernatant. The final volume of app. 20 μl containing collected INFγ producing cells and their associated Detection Molecules are store at −80 C for later analysis.
8. Identification of enriched detection molecule: Separated cells and their associated Detection Molecules are analyzed by PCR amplification of the attached labels followed by sequencing of the PCR products to reveal the identity of isolated Detection Molecules and thus the identity of those antigens for which specific T cells were present in the sample. The identification is done as for example 3.

All patent and non-patent references cited in the present application are hereby incorporated by reference in their entirety.

Items Set #1

1. A method comprising the following steps:
   a. Combining at least one cell with at least one detection molecule, where the detection molecule comprises a binding molecule (BM), a linker (Li), and a label (La);
   b. Allowing the detection molecules to recognize and bind cells through their binding molecule entity;
   c. Detecting or isolating pairs of cell-detection molecule complexes formed in step (b);
   d. Identifying detection molecules capable of binding to a cell in step (b).
2. The method of item 1 where the binding molecule (BM) is a peptide-MHC complex, an antibody or an oligonucleotide.

3. The method of item 1 or 2 where the label (La) is an antibody, a nucleic acid, a particle comprising an electronic or electromagnetic signal, or a particle comprising a radio signal.

4. The method of any of items 1-3 where the linker (Li) is a streptavidin, polysaccharide, dextran, peptide, or carbon-based polymer.

5. The method of any of items 1-4 where step c is carried out by immobilization of the cell-detection molecule pairs 6. The method of item 5 where said immobilization is by precipitating cells by centrifugation, immunoprecipitation of the cells optionally involving centrifugation, or any other means that precipitates the cells, leading to co-precipitation of detection molecules bound to cells.

7. The method of item 6 where said immobilization is by binding one or more cells to a bead, particle or surface, or any other means that immobilizes said one or more cells, leading to co-immobilization of the detection molecules bound to said one or more cells.

8. The method of any of items 5-7 where said immobilization involves the use of an antibody or other molecule, capable of specifically binding a subset of cells 9. The method of item 8 where said antibody or other molecule specifically recognizes the T cell receptor (TCR) or the CD4 or CD8 proteins of T cells.

10. The method of any of the preceding items where a label uniquely identifies individual detection molecules or identifies specific subsets of detection molecules 11. The method of any of the preceding items where the Label is an oligonucleotide.

12. The method of any of the preceding items where the binding molecule is a pMHC complex, an antibody or an oligonucleotide aptamer.

13. The method of any of the preceding items where the linker is a dextran molecule, polysaccharide, oligonucleotide, streptavidin, peptide, carbon-based molecule, carbohydrate or an organic molecule.

14. A multimeric major histocompatibility complex (MHC) comprising
   a. two or more MHC's linked by a backbone molecule; and
   b. at least one nucleic acid molecule linked to said backbone, wherein said nucleic acid molecule comprises a central stretch of nucleic acids (barcode region) designed to be amplified by e.g. PCR.

15. The multimeric major histocompatibility complex according to item 14, wherein the backbone molecule is selected from the group consisting of polysaccharides, such as glucans such as dextran, a streptavidin or a streptavidin multimer.

16. The multimeric major histocompatibility complex according to item 14 or 15, wherein the MHC's are coupled to the backbone through a streptavidin-biotin binding, streptavidin-avidin.

17. The multimeric major histocompatibility complex according to any of the preceding items, wherein the MHC's are linked to the backbone via the MHC heavy chain.

18. The multimeric major histocompatibility complex (MHC) according to any of the preceding items, wherein the MHC is artificially assembled.

19. The multimeric major histocompatibility complex (MHC) according to any of the preceding items, composed of at least four MHC's, such as at least eight, such as at least ten, 2-30, 2-20, such as 2-10 or such as 4-10 MHC's.

20. The multimeric major histocompatibility complex (MHC) according to any of the preceding items, wherein the at least one nucleic acid molecule is composed of at least a 5' first primer region, a central region (barcode region), and a 3' second primer region.

21. The multimeric major histocompatibility complex (MHC) according to any of the preceding items, wherein the at least one nucleic acid molecule has a length in the range 20-100 nucleotides, such as 30-100, such as 30-80, such as 30-50 nucleotides.

22. The multimeric major histocompatibility complex (MHC) according to any of the preceding items, wherein the at least one nucleic acid molecule is linked to said backbone via a streptavidin-biotin binding and/or streptavidina-avidin binding.

23. The multimeric major histocompatibility complex (MHC) according to any of the preceding items, wherein the at least one nucleic acid molecule comprises or consists of DNA, RNA, and/or artificial nucleotides such as PLA or LNA.

24. The multimeric major histocompatibility complex (MHC) according to any of the preceding items, wherein the MHC is selected from the group consisting of class I MHC, a class II MHC, a CD1, or a MHC-like molecule.

25. The multimeric major histocompatibility complex (MHC) according to any of the preceding items, wherein the backbone further comprises one or more linked fluorescent labels.

26. A composition comprising a subset of multimeric major histocompatibility complexes (MHC's) according to any of items 14-25, wherein each set of MHC's has a different peptide decisive for T cell recognition and a unique "barcode" region in the DNA molecule.

27. The composition according to item 26, wherein the primer regions in the DNA molecule are identical for each set of MHC's.

28. A) The composition according to item 26 or 27, comprising at least 10 different sets of MHC's such as at least 100, such as at least 500, at least 1000, at least 5000, such as in the range 10-50000, such as 10-1000 or such as 50-500 sets of MHC's.

28. B) A kit of parts comprising
   a. a composition according to any of items 26 to 28; and
   b. one or more sets of primers for amplifying the nucleic acid molecules.

29. A method for detecting antigen responsive cells in a sample comprising:
   i) providing one or more multimeric major histocompatibility complexes (MHC's) according to any of items 1-12 or a composition according to any of items 14-16;
   ii) contacting said multimeric MHC's with said sample; and detecting binding of the multimeric MHC's to said antigen responsive cells, thereby detecting cells responsive to an antigen present in a set of MHC's, wherein said binding is detected by amplifying the barcode region of said nucleic acid molecule linked to the one or more MHC's.

30. The method according to item 29, wherein unbound MHC's are removed before amplification, e.g. by washing and/or spinning.

31. The method according to item 29 or 30, wherein the sample is a blood sample, such as an peripheral blood sample, a blood derived sample, a tissue biopsy or another body fluid, such as spinal fluid, or saliva.

32. The method according to any of items 29-31, wherein said sample has been obtained from a mammal, such as a human, mouse, pigs, and/or horses.

33. The method according to any of item 30-32, wherein the method further comprises cell sorting by e.g. flow cytometry such as FACS.

34. The method according to any of items 29-33, wherein said binding detection includes comparing measured values to a reference level, e.g. a negative control and/or total level of response.

35. The method according to any of item 29-34, wherein said amplification is PCR such as QPCR.

36. The method according to any of items 29-35, wherein the detection of barcode regions includes sequencing of said region such as deep sequencing or next generation sequencing.

37. Use of a multimeric major histocompatibility complex (MHC) according to any of items 14-25 or a composition according to any of items 26-29 for the detecting of antigen responsive cells in a sample.

38. Use of a multimeric major histocompatibility complex (MHC) according to any of items 14-25 or a composition according to any of items 26-29 in the diagnosis of diseases or conditions, preferably cancer and/or infectious diseases.

39. Use of a multimeric major histocompatibility complex (MHC) according to any of items 14-25 or a composition according to any of items 26-29 in the development of immune-therapeutics.

40. Use of a multimeric major histocompatibility complex (MHC) according to any of items 14-25 or a composition according to any of items 26-29 in the development of vaccines.

41. Use of a multimeric major histocompatibility complex (MHC) according to any of items 14-25 or a composition according to any of items 26-29 for the identification of epitopes.

REFERENCES

1. Altman J D, Moss P A, Goulder P J, Barouch D H, McHeyzer-Williams M G, Bell J I, et al. Phenotypic analysis of antigen-specific T lymphocytes. Science. 1996; 274:94-6.
2. Davis M M, Bjorkman P J. T-cell antigen receptor genes and T-cell recognition. Nature. 1988; 334:395-402.
3. Robins H S, Campregher P V, Srivastava S K, Wacher A, Turtle C J, Kahsai O, et al. Comprehensive assessment of T-cell receptor beta-chain diversity in alphabeta T cells. Blood. 2009; 114:4099-107.
4. Hadrup S R, Bakker A H, Shu C J, Andersen R S, van V J, Hombrink P, et al. Parallel detection of antigen-specific T-cell responses by multidimensional encoding of MHC multimers. Nature Methods. 2009; 6:520-6.
5. Andersen R S, Kvistborg P, Mørch T F, Pedersen N W, Lyngaa R, Bakker A H, et al. Parallel detection of antigen-specific T-cell responses by combinatorial encoding of MHC multimers. NatProtoc. 2012
6. Newell E W, Sigal N, Nair N, Kidd B a, Greenberg H B, Davis M M. Combinatorial tetramer staining and mass cytometry analysis facilitate T-cell epitope mapping and characterization. Nat Biotechnol. 2013; 1-9.
7. Soen Y, Chen D S, Kraft D L, Davis M M, Brown P O. Detection and characterization of cellular immune responses using peptide-MHC microarrays. PLoSBiol. 2003; 1:429-38.
8. Stone J D, Demkowicz Jr. W E, Stern L J. HLA-restricted epitope identification and detection of functional T cell responses by using MHC-peptide and costimulatory microarrays. ProcNatlAcadSciUSA. 2005; 102:3744-9.
9. Newell E W, Davis M M. Beyond model antigens: high-dimensional methods for the analysis of antigen-specific T cells. Nat Biotechnol. 2014; 32.
10. Dossinger G, Bunse M, Bet J, Albrecht J, Paszkiewicz P J, Weißbrich B, et al. MHC multimer-guided and cell culture-independent isolation of functional T cell receptors from single cells facilitates TCR identification for immunotherapy. PLoS One. 2013; 8:e61384.
11. Cha E, Klinger M, Hou Y, Cummings C, Ribas A, Faham M, et al. Improved Survival with T Cell Clonotype Stability After Anti-CTLA-4 Treatment in Cancer Patients. Sci Transl Med. 2014; 6:238ra70.
12. Robert L, Tsoi J, Wang X, Emerson R O, Homet B, Chodon T, et al. CTLA4 blockade broadens the peripheral T cell receptor repertoire. Clin Cancer Res. 2014
13. Morgan R A, Dudley M E, Wunderlich J R, Hughes M S, Yang J C, Sherry R M, et al. Cancer Regression in Patients After Transfer of Genetically Engineered Lymphocytes. Science. 2006.
14. Pannetier C, Even J, Kourilsky P. T-cell repertoire diversity and clonal expansions in normal and clinical samples. ImmunolToday. 1995; 16:176-81.
15. Cameron B J, Gerry A B, Dukes J, Harper J V, Kannan V, Bianchi F C, et al. Identification of a Titin-derived HLA-A1-presented peptide as a cross-reactive target for engineered MAGE A3-directed T cells. Sci Transl Med. 2013; 5:197ra103.
16. Linette G P, Stadtmauer E a, Maus M V, Rapoport A P, Levine B L, Emery L, et al. Cardiovascular toxicity and titin cross-reactivity of affinity-enhanced T cells in myeloma and melanoma. Blood. 2013; 122:863-71.

ITEMS SET #2

1. A detection molecule comprising
   a. at least one binding molecule (BM),
   b. at least one linker (Li), and
   c. at least one label (La).
2. A cell-detection molecule complex comprising
   a. At least one detection molecule comprising a binding molecule (BM), a linker (Li) and a label (La), and
   b. at least one cell.
3. A composition comprising two or more different detection molecules, or two or more sets of different detection molecules, each detection molecule comprising at least one binding molecule (BM), at least one linker (Li) and at least one label (La),
   wherein each of the two or more detection molecules, or two or more sets of detection molecules, comprises a label which is unique to and specific for the binding molecule of each of said two or more different detection molecules.
4. The composition according to item 3, said composition comprising 2 to 1,000,000 different detection molecules, such as 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 different detection molecules or sets of different detection molecules; for example 1-3, 3-5, 5-10, 10-15, 15-20, 20-25, 25-30, 30-35, 35-40, 40-50, 50-60, 60-70, 70-80, 80-90, 90-100, 100-110, 110-120, 120-130, 130-140, 140-150, 150-175, 175-200, 200-250, 250-300, 300-400, 400-500, 500-600, 600-700, 700-800, 800-900, 900-1000, 1000-1500, 1500-2000, 2000-3000, 3000-4000, 4000-5000, 5000-7500, 7500-10,000, 10,000-20,000, 20,000-50,000, 50,000-100,000, 100,000-200,000, 200,000-500,000, 500,000-1,000,000 different detection molecules, or sets of different detection molecules.

5. The detection molecule according to any of the preceding items, wherein said binding molecule is capable of specifically associating with, recognizing and/or binding to a structure belonging to or associated with an entity in a sample, such as a target structure.
6. The detection molecule according to any of the preceding items, wherein said binding molecule associates with, recognizes and/or binds to a marker molecule specific for a given cell or cell type.
7. The detection molecule according to any of the preceding items, wherein said binding molecule is capable of specifically associating with, recognizing and/or binding to a specific cell type, such as selected from the group consisting of immune cells, lymphocytes, monocytes, dendritic cells, T-cells, B-cells, NK cells, CD4+ T cells, CD8+ T cells, αβ T cells, invariant γδ T cells, antigen-specific T-cells, cells comprising TCRs, cells comprising BCRs, a specific cancer cell
8. The detection molecule according to any of the preceding items, wherein said binding molecule is capable of specifically associating with, recognizing and/or binding to a target specifically associated with an organ selected from the group consisting of lymph nodes, kidney, liver, skin, brain, heart, muscles, bone marrow, skin, skeleton, lungs, the respiratory tract, spleen, thymus, pancreas, exocrine glands, bladder, endocrine glands, reproduction organs including the fallopian tubes, eye, ear, vascular system, the gastroinstestinal tract including small intestines, colon, rectum, canalis analis and prostate gland.
9. The detection molecule according to any of the preceding items, wherein said binding molecule is peptide-based or protein-based.
10. The detection molecule according to any of the preceding items, wherein said binding molecule is an anti-target molecule capable of specifically associating with, recognizing and/or binding to a predetermined target structure.
11. The detection molecule according to any of the preceding items, wherein said binding molecule is an anti-target-molecule.
12. The detection molecule according to any of the preceding items, wherein said binding molecule is selected from the group consisting of an antibody, an antibody mimetic, an antibody-like molecule, a peptide, an oligonucleotide, a peptide aptamer, a nucleic acid aptamer, a DNA aptamer, an RNA aptamer, an XNA aptamer, a ligand, a natural ligand, a variant or fragment of a natural ligands, a synthetic ligand and a small organic molecule.
13. The detection molecule according to any of the preceding items, wherein said antibody mimetic is selected from the group consisting of affibody molecules, affilins, affimers, affitins, alphabodies, anticalins, avimers, DARPins, fynomers, Kunitz domain peptides and monobodies.
14. The detection molecule according to any of the preceding items, wherein said binding molecule is an antibody selected from the group consisting of a monoclonal antibody, a polyclonal antibody, a bi-specific antibody, an antibody-like molecule, a Fc-molecule, a KIR-molecule, a ScFv and a Fab.
15. The detection molecule according to any of the preceding items, wherein said binding molecule is a peptide of 1-100 amino acid residues without tertiary structure.
16. The detection molecule according to any of the preceding items, wherein said binding molecule is a MHC molecule or MHC complex.
17. The detection molecule according to any of the preceding items, wherein said binding molecule is a MHC class I complex.
18. The detection molecule according to any of the preceding items, wherein said binding molecule is a MHC class II complex.
19. The detection molecule according to any of the preceding items, wherein said binding molecule is a MHC-like molecule.
20. The detection molecule according to any of the preceding items, wherein said binding molecule is CD1, wherein said CD1 is selected from the group consisting of CD1 CD1a, CD1b, CD1c, CD1d and CD1e.
21. The detection molecule according to any of the preceding items, wherein said binding molecule is a MHC Class I-like proteins; including MICA, MIC B, CD1d, HLA E, HLA F, HLA G, HLA H, ULBP-1, ULBP-2, and ULBP-3.
22. The detection molecule according to any of the preceding items, wherein the target of the binding molecule is a cell-surface target.
23. The detection molecule according to any of the preceding items, wherein the target of the binding molecule is an intracellular target.
24. The detection molecule according to any of the preceding items, wherein the target of the binding molecule is a receptor, such as a cell-surface receptor, an intracellular receptor, a soluble receptor or an extracellular receptor.
25. The detection molecule according to any of the preceding items, wherein the target of the binding molecule is a T-cell receptor.
26. The detection molecule according to any of the preceding items, wherein the target of the binding molecule is a B-cell receptor.
27. The detection molecule according to any of the preceding items, wherein the target of the binding molecule is CD4 of T cells.
28. The detection molecule according to any of the preceding items, wherein the target of the binding molecule is CD8 of T cells.
29. The detection molecule according to any of the preceding items, wherein the target of the binding molecule is CD20 of B cells.
30. The detection molecule according to any of the preceding items, wherein the target of the binding molecule is selected from the group consisting of cancer cell markers, developmental markers, cell cycle markers, proliferation markers, activation markers, hormones, hormone receptors, intracellular markers, cluster of differentiation (CD), cell surface markers, cytokines and cytokine receptors.
31. The detection molecule according to any of the preceding items, wherein the target of the binding molecule is selected from the group consisting of CD2, CD3, CD4, CD5, CD8, CD9, CD27, CD28, CD30, CD69, CD134 (OX40), CD137 (4-1BB), CD147, CDw150 (SLAM), CD152 (CTLA-4), CD153 (CD30L), CD40L (CD154), NKG2D, ICOS, HVEM, HLA Class II, PD-1, Fas (CD95), FasL, CD40, CD48, CD58, CD70, CD72, B7.1 (CD80), B7.2 (CD86), B7RP-1, B7-H3, PD-L1, PD-L2, CD134L, CD137L, ICOSL, LIGHT CD16, NKp30, NKp44, NKp46, NKp80, 2B4, KIR, LIR, CD94/NKG2A, CD94/NKG2C, LFA-1, CD11a/18, CD54 (ICAM-1), CD106 (VCAM), CD49a,b,c,d,e,f/CD29 (VLA-4), CD11a, CD14, CD15, CD19, CD25, CD30, CD37, CD49a, CD49e, CD56, CD27, CD28, CD45, CD45RA, CD45RO, CD45RB, CCR7, CCR5, CD62L, CD75, CD94, CD99, CD107b, CD109, CD152, CD153, CD154, CD160, CD161, CD178, CDw197, CDw217, Cd229, CD245, CD247 and Foxp3.

32. The detection molecule according to any of the preceding items, wherein the target of the binding molecule is a cytokine selected from the group consisting of TNFα, TNFβ, TNF, IFNα, IFNβ, IFNγ, IL-1, IL-2, IL-3, IL-4, IL-5, IL-6, IL-7, IL-8, IL-9, IL-10, IL-10-20, IL-20-30, IL-30, IL-31, IL-32, IL-33, IL-34, IL-35, IL-36, IL-37, IL-38, IL-39, IL-40, NFκB, chemokines including CC chemokines (CCL1 to CCL-28), CXC chemokines (CXCL1 to CXCL17) C chemokines (XCL-1 and -2) and CX3X chemokines (CX3CL1).

33. The detection molecule according to any of the preceding items, wherein the target of the binding molecule is a cancer cell marker selected from the group consisting of HER2, CA125, Tyrosinase, Melanoma-associated antigen (MAGE), abnormal products of Ras or p53, Carcinoembryonic antigen, Muc-1, Epithelial tumor antigen, Carbonic Anhydrase, VEGFR, EGFR, TRAIL and RANKL.

34. The detection molecule according to any of the preceding items, wherein the target of the binding molecule is a stem cell marker selected from the group consisting of Stro-1, CD146, CD105, CD44, c-kit, Oct4, Sox-2, Klf4, EphB, Nestin and TWIST-1.

35. The detection molecule according to any of the preceding items, wherein the target of the binding molecule is a developmental marker selected from the group consisting of Nanog, Oct4, Sox2, TEKT-1, NANOS, c-kit, Sox9, Notch, Msx1, Msx2 and Col1.

36. The detection molecule according to any of the preceding items, wherein the target of the binding molecule is a proliferation marker selected from the group consisting of CyclinA, CyclinB, PCNA, PC10, p53, Mdm2, Cyclin D, Cyclin E, Rb, ARF and HDM2.

37. The detection molecule according to any of the preceding items, wherein the target of the binding molecule is an activation marker selected from the group consisting of CD28, Tbet, Eomes, Blimp, Bcl-6, CD27, MHC-II, TNF, IFN, Fizz1, ARG1 and CCL22R.

38. The detection molecule according to any of the preceding items, wherein the target of the binding molecule is an hormone selected from the group consisting of estrogen, PTH, ADH, T3, ANP, Epinephrine, Norepinephrine, Cortisol, Corticosterone, Aldosterone, Progestin, EPO, Leptin, Insulin, Glucagon, T4, ACTH, FSH, oxytocin and Calcitriol.

39. The detection molecule according to any of the preceding items, wherein the target of the binding molecule is an hormone receptor selected from the group consisting of EstrogenR (ER), GLP-1R, Thyroid receptor, Leptin receptor, Epinephrine receptor, Insulin receptor and Glucagon receptor.

40. The detection molecule according to any of the preceding items, wherein the target of the binding molecule is a cluster of differentiation (CD) molecule selected from the group consisting of CD1-10, CD10-20, CD20-30, CD30-40, CD40-50, CD50-100, CD100-200, CD200-300 and CD300-364.

41. The detection molecule according to any of the preceding items, wherein the target of the binding molecule is an intracellular marker selected from the group consisting of Cyclins, Cytokines and organelle markers (for example Apg12, Syntaxin, PAF-46, Histones, Early endosome antigen, clathrin, tubulins, PAF49, FTCD).

42. The detection molecule according to any of the preceding items, wherein the target of the binding molecule is selected from the group consisting of CD1, CD1a, CD1b, CD1c, CD1d, and MR1.

43. The detection molecule according to any of the preceding items, wherein the target of the binding molecule is selected from the group consisting of targets included in Table 4 of the examples.

44. The detection molecule according to any of the preceding items, wherein said binding molecule is a surface-molecule receptor to a cytokine receptor selected from the group consisting of interleukins and TNF-like molecules.

45. The detection molecule according to any of the preceding items, wherein said label is any molecule, atom or signal the identity of which can be determined.

46. The detection molecule according to any of the preceding items, wherein said label is unique to and/or specifies the binding molecule or a group of binding molecules.

47. The detection molecule according to any of the preceding items, wherein said detection molecule comprises one label.

48. The detection molecule according to any of the preceding items, wherein said detection molecule comprises more than one label.

49. The detection molecule according to any of the preceding items, wherein said detection molecule comprises two or more labels, such as 3 labels, 4 labels, 5 labels, 6 labels, 7 labels, 8 labels, 9 labels, 10 labels, 11, 12, 13, 14, 15, 16, 17, 18, 19, 20, 20-25, 25-30, 30-40, 40-50, 50-75, 75-100 labels.

50. The detection molecule according to any of the preceding items, wherein said detection molecule comprises two or more labels and each of said labels are identical to each other.

51. The detection molecule according to any of the preceding items, wherein said detection molecule comprises two or more labels and at least two of said labels are different.

52. The detection molecule according to any of the preceding items, wherein said label is attached to the linker of the detection molecule.

53. The detection molecule according to any of the preceding items, wherein said label is attached to the binding molecule of the detection molecule.

54. The detection molecule according to any of the preceding items, wherein said label comprises a connector molecule (attachment molecule) for attachment to the detection molecule.

55. The detection molecule according to any of the preceding items, wherein said label is a nucleic acid label.

56. The detection molecule according to any of the preceding items, wherein said label is a nucleic acid label selected from the group consisting of a DNA label, an RNA label, and an artificial nucleic acid label.

57. The detection molecule according to any of the preceding items, wherein said label is a nucleic acid label comprising one or more nucleotides individually derived from one or more of DNA, RNA, and an artificial nucleic acid.

58. The detection molecule according to any of the preceding items, wherein said artificial nucleic acid is selected from the group consisting of XNA, LNA, PNA, GNA, TNA, HNA, CeNA, and morpholino-nucleic acids.

59. The detection molecule according to any of the preceding items, wherein said label is a DNA label.

60. The detection molecule according to any of the preceding items, wherein said nucleic acid label comprises 1 to 1,000,000 nucleic acids, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleic acids; for example 1-3, 3-5, 5-10, 10-15, 15-20, 20-25, 25-30, 30-35, 35-40, 40-50, 50-60, 60-70, 70-80, 80-90, 90-100, 100-110, 110-120, 120-130, 130-140, 140-150, 150-175, 175-200, 200-250, 250-300, 300-400, 400-500, 500-600, 600-700, 700-800, 800-900, 900-1000, 1000-1500, 1500-2000, 2000-3000, 3000-4000, 4000-5000, 5000-7500, 7500-10,000, 10,000-100,000, 100,000-1,000,000 nucleic acids.

61. The detection molecule according to any of the preceding items, wherein said label is a nucleic acid label comprising one or more of
   a. barcode region,
   b. 5' first primer region (forward)
   c. 3' second primer region (reverse),
   d. random nucleotide region,
   e. connector molecule
   f. stability-increasing components
   g. short nucleotide linkers in between any of the above-mentioned components
   h. adaptors for sequencing
   i. annealing region 62. The detection molecule according to any of the preceding items, wherein said label is a nucleic acid label comprising at least a barcode region.

63. The detection molecule according to any of the preceding items, wherein said label is a nucleic acid label comprising at least a barcode region, wherein said barcode region comprises a sequence of consecutive nucleic acids.

64. The detection molecule according to any of the preceding items, wherein the barcode region of said nucleic acid comprises 1-3, 3-5, 5-10, 10-15, 15-20, 20-25, 25-30, 30-35, 35-40, 40-50, 50-60, 60-70, 70-80, 80-90, 90-100, 100-110, 110-120, 120-130, 130-140, 140-150, 150-175, 175-200, 200-250, 250-300, 300-400, 400-500, 500-600, 600-700, 700-800, 800-900, 900-1000 nucleic acids.

65. The detection molecule according to any of the preceding items, wherein said barcode region comprises or consists of 5-10, 10-15, 15-20, 20-25, 25-30, 30-40, 40-45, 45-50 nucleic acids.

66. The detection molecule according to any of the preceding items, wherein said label is a nucleic acid label comprising at least a 3' primer region, a barcode region, and a 5' primer region.

67. The detection molecule according to any of the preceding items, wherein said label is a nucleic acid label comprising at least a 3' primer region, a barcode region, and a 5' primer region, wherein said barcode region is designed to be amplified by e.g. PCR and identified by e.g. sequencing.

68. The detection molecule according to any of the preceding items, wherein the primer regions of said nucleic acid label are identical for subsets of detection molecules comprising different labels.

69. The detection molecule according to any of the preceding items, wherein said label is a nucleic acid label comprising a connector molecule which is able to interact with a component on the linker and/or binding molecule of the detection molecule.

70. The detection molecule according to any of the preceding items, wherein said nucleic acid label comprises a connector molecule which is biotin.

71. The detection molecule according to any of the preceding items, wherein said nucleic acid label comprises a random nucleotide region comprising 3-20 nucleotides, such as 3, 4, 5, 6, 7, 8, 9, 10, 11, 12, 13, 1 4, 1 5, 16, 17, 18, 19 or 20 nt.

72. The detection molecule according to any of the preceding items, wherein said nucleic acid label comprises one or more stability-increasing components, such as HEG or TEG.

73. The detection molecule according to any of the preceding items, wherein a sample identifying sequence is attached to the nucleic acid label such as by attachment to one of the primers capable of binding to the primer regions of the nucleic acid label.

74. The detection molecule according to any of the preceding items, wherein said label is a peptide label.

75. The detection molecule according to any of the preceding items, wherein said peptide label comprises a stretch of consecutive amino acid residues (coding region).

76. The detection molecule according to any of the preceding items, wherein said peptide label comprises a stretch of consecutive amino acid residues (coding region) and a protease cleavage site.

77. The detection molecule according to any of the preceding items, wherein said peptide label comprises a stretch of consecutive amino acid residues (coding region) and a protease cleavage site.

78. The detection molecule according to any of the preceding items, wherein said protease cleavage site in said peptide label is located proximal to the linker that connects the label to the binding molecule.

79. The detection molecule according to any of the preceding items, wherein said peptide label comprising a protease cleavage site allows for cleavage of the stretch of consecutive amino acid residues (coding region) and release thereof from the detection molecule.

80. The detection molecule according to any of the preceding items, wherein said label is a peptide label comprising 2 or more consecutive amino acids, such as 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, 20-21, 21-22, 22-23, 23-24, 24-25, 25-26, 26-27, 27-28, 28-29, 29-30, 30-31, 31-32, 32-33, 33-34, 34-35, 35-36, 36-37, 37-38, 38-39, 39-40, 40-45, 45-50, 50-55, 55-60, 60-65, 65-70, 70-75, 75-80, 80-85, 85-90, 90-95, 95-100, 100-110, 110-120, 120-130, 130-140, 140-150, 150-160, 160-170, 170-180, 180-190, 190-200, 200-225, 225-250, 250-275, 275-300, 300-350, 350-400, 400-450, 450-500, 500-600, 600-700, 700-800, 800-900, 900-1000, 1000-1500, 1500-2000, or more than 2000, consecutive amino acids.

81. The detection molecule according to any of the preceding items, wherein said peptide label comprises proteinogenic and/or non-proteinogenic amino acids.
82. The detection molecule according to any of the preceding items, wherein said label is a fluorescent label (fluorophore label).
83. The detection molecule according to any of the preceding items, wherein said label is a fluorescent label selected from the group consisting of fluorescein isothiocyanate (FITC), fluorescein (Flu) derivates, rhodamine, tetramethylrhodamine, phycoerythrin, R-phycoerythrin (RPE), allophycoerythrin, phycocyanin, allophycocyanin, o-phthaldehyde, fluorescamine; 2-(4'-maleimidylanilino)naphthalene-6-sulfonic acid; 5-((((2-iodoacetyl)amino)ethyl)amino)naphthalene-1-sulfonic acid; Pyrene-1-butanoic acid; AlexaFluor 350 (7-amino-6-sulfonic acid-4-methyl coumarin-3-acetic acid); AMCA (7-amino-4-methyl coumarin-3-acetic acid); 7-hydroxy-4-methyl coumarin-3-acetic acid; Marina Blue (6,8-difluoro-7-hydroxy-4-methyl coumarin-3-acetic acid); 7-dimethylamino-coumarin-4-acetic acid; Fluorescamin-N-butyl amine adduct; 7-hydroxy-coumarine-3-carboxylic acid; CascadeBlue (pyrene-trisulphonic acid acetyl azide); Cascade Yellow; Pacific Blue (6,8 difluoro-7-hydroxy coumarin-3-carboxylic acid); 7-diethylamino-coumarin-3-carboxylic acid; N-(((4-azidobenzoyl)amino)ethyl)-4-amino-3,6-disulfo-1,8-naphthalimide; Alexa Fluor 430; 3-perylenedodecanoic acid; 8-hydroxypyrene-1,3,6-trisulfonic acid; 12-(N-(7-nitrobenz-2-oxa-1,3-diazol-4-yl)amino)dodecanoic acid; N,N'-dimethyl-N-(iodoacetyl)-N'-(7-nitrobenz-2-oxa-1,3-diazol-4-yl) ethylenediamine; Oregon Green 488 (difluoro carboxy fluorescein); 5-iodoacetamidofluorescein; propidium iodide-DNA adduct; Carboxy fluorescein; 5- or 6-carboxyfluorescein; 6-(fluorescein)-5-(and 6)-carboxamido hexanoic acid; Texas Red, Princeton Red, Green fluorescent protein (GFP) and analogues thereof; PerCP; AlexaFluor® (AF), AF405, AF488, AF500, AF514, AF532, AF546, AF555, AF568, AF594, AF610, AF633, AF635, AF647, AF680, AF700, AF710, AF750, AF800; Quantum Dot based dyes, Qdot®525, Qdot®565, Qdot®585, Qdot®605, Qdot®655, Qdot®705, Qdot®800; DyLight™ Dyes (Pierce) (DL); DL549, DL649, DL680, DL800; Cy-Dyes, Cy2, Cy3, Cy3.5, Cy5, Cy5.5, Cy7; Fluorescent Proteins, RPE, PerCp, APC, Green fluorescent proteins; GFP and GFP derivated mutant proteins; BFP, CFP, YFP, DsRed, T1, Dimer2, mRFP1, MBanana, mOrange, dTomato, tdTomato, mTangerine, mStrawberry, mCherry; Tandem dyes, RPE-Cy5, RPE-Cy5.5, RPE-Cy7, RPE-AlexaFluor® tandem conjugates; RPE-Alexa610, RPE-TxRed, APC-Aleca600, APC-Alexa610, APC-Alexa750, APC-Cy5 and APC-Cy5.5.
84. The detection molecule according to any of the preceding items, wherein said label is a phosphorescence label.
85. The detection molecule according to any of the preceding items, wherein said label is a bioluminescence label or chemoluminescence label.
86. The detection molecule according to any of the preceding items, wherein said chemoluminiscence label is selected from luminol, isoluminol, acridinium esters, acridinium salt, theromatic acridinium ester, 1,2-dioxetanes, oxalate ester, imidazole and pyridopyridazines.
87. The detection molecule according to any of the preceding items, wherein said bioluminescence label is selected from the group luciferin, luciferase and aequorin.
88. The detection molecule according to any of the preceding items, wherein said label is an enzymatic label.
89. The detection molecule according to any of the preceding items, wherein said label is an enzymatic label, wherein the enzyme catalyze a reaction between chemicals in the near environment of the labeling molecules, which results in one or more of producing a light signal (chemi-luminescence) and precipitation of chromophor dyes.
90. The detection molecule according to any of the preceding items, wherein said label is an enzymatic label selected from peroxidases, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase.
91. The detection molecule according to any of the preceding items, wherein said label is an enzymatic label selected from horse radish peroxidase (HRP), alkaline phosphatase (AP), beta-galactosidase (GAL), glucose-6-phosphate dehydrogenase, beta-N-acetylglucosaminidase, β-glucuronidase, invertase, Xanthine Oxidase, firefly luciferase and glucose oxidase (GO).
92. The detection molecule according to any of the preceding items, wherein said label is capable of reflection of light, such as gold, plastic, glass, polystyrene and pollen.
93. The detection molecule according to any of the preceding items, wherein said label is capable of capable of absorption of light, such as a chromophore or a dye.
94. The detection molecule according to any of the preceding items, wherein said label is capable of emission of light after excitation, such as a fluorochrome.
95. The detection molecule according to any of the preceding items, wherein said label is a nanoparticle label.
96. The detection molecule according to any of the preceding items, wherein said label is an element.
97. The detection molecule according to any of the preceding items, wherein said label is selected from the group consisting of heavy metal labels, isotope labels, radiolabels, radionuclide, stable isotopes, chains of isotopes and single atoms.
98. The detection molecule according to any of the preceding items, wherein said label is a single atom selected from the group consisting of zinc (Zn), iron (Fe), magnesium (Mg), any of the lanthanides (Ln) including La, Ce, Pr, Nd, Pm, Sm, Eu, Gd, Tb, Dy, Ho, Er, Tm, Yb and Lu; scandium (Sc) and yttrium (Y).
99. The detection molecule according to any of the preceding items, wherein said radioactivity labels comprises incorporated isotopes of iodide, cobalt, selenium, tritium and/or phosphor.
100. The detection molecule according to any of the preceding items, wherein said label is a DNA fluorescing stain, such as Propidium iodide, Hoechst stain, DAPI, DraQ5 or Acridine orange.

101. The detection molecule according to any of the preceding items, wherein said label comprises a nucleic acid label and at least a second label.
102. The detection molecule according to any of the preceding items, wherein said label comprises a nucleic acid label and at least a second label according to any of the preceding items.
103. The detection molecule according to any of the preceding items, wherein said label comprises a nucleic acid label and a fluorophore label.
104. The detection molecule according to any of the preceding items, wherein said label comprises one type of label.
105. The detection molecule according to any of the preceding items, wherein said label comprises more than one type of label, such as comprising 2 types of labels, for example comprising 3 types of labels, such as comprising 4 types of labels, for example comprising 5 types of labels.
106. The detection molecule according to any of the preceding items, wherein said linker is a molecular entity and/or bond that connects the binding molecule and the label.
107. The detection molecule according to any of the preceding items, wherein one or more of the binding molecules are covalently associated with the one or more linkers.
108. The detection molecule according to any of the preceding items, wherein one or more of the binding molecules are non-covalently associated with the one or more linkers.
109. The detection molecule according to any of the preceding items, wherein one or more labels are covalently associated with the one or more linkers.
110. The detection molecule according to any of the preceding items, wherein one or more of labels are non-covalently associated with the one or more linkers.
111. The detection molecule according to any of the preceding items, wherein the one or more labels and/or one or more binding molecules are associated with a molecule in the one or more linkers, such as a connector molecule, a sugar residue, a protein, an antibody, a DNA, an aptamer, reactive groups, nucleophilic group, electrophilic groups, radicals, or conjugated double bonds.
112. The detection molecule according to any of the preceding items, wherein the one or more linkers comprises one or more multimerization domains.
113. The detection molecule according to any of the preceding items, wherein the one or more linkers comprises one or more scaffolds.
114. The detection molecule according to any of the preceding items, wherein the one or more linkers comprises one or more connectors.
115. The detection molecule according to any of the preceding items, wherein the one or more multimerization domains comprises at least one scaffold and at least one connector.
116. The detection molecule according to any of the preceding items, wherein the binding molecule and/or the label is attached to the linker via a streptavidin-biotin linkage.
117. The detection molecule according to any of the preceding items, wherein the one or more linkers comprise one or more optionally substituted organic molecules.
118. The detection molecule according to any of the preceding items, wherein the optionally substituted organic molecule comprises one or more functionalized cyclic structures.
119. The detection molecule according to any of the preceding items, wherein the one or more functionalized cyclic structures comprises one or more benzene rings.
120. The detection molecule according to any of the preceding items, wherein the optionally substituted organic molecule comprises a scaffold molecule comprising at least three reactive groups, or at least three sites suitable for non-covalent attachment.
121. The detection molecule according to any of the preceding items, wherein the one or more linkers comprises one or more biological cells and/or cell-like structures, such as antigen presenting cells or dendritic cells.
122. The detection molecule according to any of the preceding items, wherein the one or more linkers comprises one or more membranes.
123. The detection molecule according to any of the preceding items, wherein the one or more membranes comprises liposomes or micelles.
124. The detection molecule according to any of the preceding items, wherein the one or more linkers comprises one or more polymers such as one or more synthetic polymers.
125. The detection molecule according to any of the preceding items, wherein reactive groups involved in forming an association between the multimerization domain and the binding molecule are located on glutamate or aspartate residues, or on a vinyl sulfone activated dextran.
126. The detection molecule according to any of the preceding items, wherein the one or more linker polymers are selected from the group consisting of polysaccharides.
127. The detection molecule according to any of the preceding items, wherein the linker comprises one or more dextran moieties.
128. The detection molecule according to any of the preceding items, wherein the one or more dextran moieties are covalently attached to one or more binding molecules.
129. The detection molecule according to any of the preceding items, wherein the one or more dextran moieties are non-covalently attached to one or more binding molecules.
130. The detection molecule according to any of the preceding items, wherein the one or more dextran moieties are covalently attached to one or more labels.
131. The detection molecule according to any of the preceding items, wherein the one or more dextran moieties are non-covalently attached to one or more labels.
132. The detection molecule according to any of the preceding items, wherein reactive groups of the multimerization domains include hydroxyls of polysaccharides such as dextrans.
133. The detection molecule according to any of the preceding items, wherein the one or more linker dextran moieties are modified.
134. The detection molecule according to any of the preceding items, wherein the one or more linker dextran moieties are activated.

135. The detection molecule according to any of the preceding items, wherein the one or more linker dextran moieties are activated by reaction of the dextran hydroxyls with divinyl sulfon.
136. The detection molecule according to any of the preceding items, wherein dextran is activated by a multistep reaction that results in the decoration of the dextran with maleimide groups.
137. The detection molecule according to any of the preceding items, wherein the one or more linker dextran moieties comprises one or more amino-dextrans.
138. The detection molecule according to any of the preceding items, wherein the one or more linker dextran moieties comprises one or more amino-dextrans modified with divinyl sulfone.
139. The detection molecule according to any of the preceding items, wherein the one or more linker dextran moieties comprises one or more dextrans with a molecular weight of from 1,000 to 50,000, such as from 1,000 to 5,000, for example 5,000 to 10,000, such as from 10,000 to 15,000, for example 15,000 to 20,000, such as from 20,000 to 25,000, for example 25,000 to 30,000, such as from 30,000 to 35,000, for example 35,000 to 40,000, such as from 40,000 to 45,000, for example 45,000 to 50,000.
140. The detection molecule according to any of the preceding items, wherein the one or more linker dextran moieties comprises one or more dextrans with a molecular weight of from 50,000 to 150,000, such as from 50,000 to 60,000, for example 60,000 to 70,000, such as from 70,000 to 80,000, for example 80,000 to 90,000, such as from 90,000 to 100,000, for example 100,000 to 110,000, such as from 110,000 to 120,000, for example 120,000 to 130,000, such as from 130,000 to 140,000, for example 140,000 to 150,000.
141. The detection molecule according to any of the preceding items, wherein the one or more linker dextran moieties comprises one or more dextrans with a molecular weight of from 150,000-270,000 such as from 150,000 to 160,000, for example 160,000 to 170,000, such as from 170,000 to 180,000, for example 180,000 to 190,000, such as from 190,000 to 200,000, for example 200,000 to 210,000, such as from 210,000 to 220,000, for example 220,000 to 230,000, such as from 230,000 to 240,000, for example 240,000 to 250,000, such as from 250,000 to 260,000, for example 260,000 to 270,000, such as from 270,000 to 280,000, for example 280,000 to 290,000, such as from 290,000 to 300,000, for example 300,000 to 310,000 such as from 310,000 to 320,000, for example 320,000 to 330,000 such as from 330,000 to 340,000, for example 340,000 to 350,000 such as from 350,000 to 360,000, for example 360,000 to 370,000 such as from 370,000 to 380,000, for example 380,000 to 390,000, such as from 390,000 to 400,000.
142. The detection molecule according to any of the preceding items, wherein the one or more linker dextran moieties are linear.
143. The detection molecule according to any of the preceding items, wherein the one or more linker dextran moieties are branched.
144. The detection molecule according to any of the preceding items, wherein the one or more linkers comprises a carboxy methyl dextran and/or a dextran polyaldehyde and/or a carboxymethyl dextran lactone and/or a cyclodextrin.
145. The detection molecule according to any of the preceding items, wherein the one or more linker synthetic polymers are selected from the group consisting of PNA, polyamide and PEG.
146. The detection molecule according to any of the preceding items, wherein the one or more linkers comprises one or more entities selected from the group consisting of an IgG domain, a coiled-coil polypeptide structure, a DNA duplex, a nucleic acid duplex, PNA-PNA, PNA-DNA, DNA-RNA.
147. The detection molecule according to any of the preceding items, wherein the one or more linkers, such as one or more multimerization domains, comprises one or more avidins, such as one or more streptavidins.
148. The detection molecule according to any of the preceding items, wherein the one or more streptavidins comprises one or more tetrameric streptavidin variants.
149. The detection molecule according to any of the preceding items, wherein the one or more streptavidins comprises one or more monomeric streptavidin variants.
150. The detection molecule according to any of the preceding items, wherein the one or more linkers comprises an antibody.
151. The detection molecule according to any of the preceding items, wherein the linker antibody is selected from the group consisting of polyclonal antibody, monoclonal antibody, IgA, IgG, IgM, IgD, IgE, IgG1, IgG2, IgG3, IgG4, IgA1, IgA2, IgM1, IgM2, humanized antibody, humanized monoclonal antibody, chimeric antibody, mouse antibody, rat antibody, rabbit antibody, human antibody, camel antibody, sheep antibody, engineered human antibody, epitope-focused antibody, agonist antibody, antagonist antibody, neutralizing antibody, naturally-occurring antibody, isolated antibody, monovalent antibody, bispecific antibody, trispecific antibody, multispecific antibody, heteroconjugate antibody, immunoconjugates, immunoliposomes, labeled antibody, antibody fragment, domain antibody, nanobody, minibody, maxibody, diabody, fusion antibody.
152. The detection molecule according to any of the preceding items, wherein the detection molecule comprises one or more organic molecules selected from the group consisting of small organic scaffold molecules, small organic molecules, steroids, peptides, aromatic organic molecules, monocyclic structures, functionalized or substituted benzene rings, dicyclic structures, polycyclic structures, aliphatic molecules, monocyclic molecules, dicyclic molecules, polycyclic molecules.
153. The detection molecule according to any of the preceding items, wherein the detection molecule comprises one or more monomeric molecules able to polymerize; one or more biological polymers such as one or more proteins; one or more small molecule scaffolds; one or more supramolecular structure(s) such as one or more nanoclusters; and/or one or more protein complexes.
154. The detection molecule according to any of the preceding items, wherein the linker of the detection molecule comprises one or more beads.
155. The detection molecule according to any of the preceding items, wherein the linker is a bead coated with streptavidin, such as streptavidin monomers or tetramers, and the one or more binding molecules are biotinylated.

156. The detection molecule according to any of the preceding items, wherein the linker is a bead coated with polysaccharide, such as a polysaccharide comprising dextran moieties.

157. The detection molecule according to any of the preceding items, wherein the one or more beads are selected from the groups consisting of beads that carry electrophilic groups e.g. divinyl sulfone activated polysaccharide, polystyrene beads that have been functionalized with tosyl-activated esters, magnetic polystyrene beads functionalized with tosyl-activated esters, and beads where binding molecules have been covalently immobilized to these by reaction of nucleophiles comprised within the binding molecules with the electrophiles of the beads.

158. The detection molecule according to any of the preceding items, wherein the one or more beads is selected from the groups consisting of sepharose beads, sephacryl beads, polystyrene beads, agarose beads, polysaccharide beads, polycarbamate beads and any other kind of beads that can be suspended in an aqueous buffer.

159. The detection molecule according to any of the preceding items, wherein the linker comprises one or more compounds selected from the group consisting of agarose, sepharose, resin beads, glass beads, pore-glass beads, glass particles coated with a hydrophobic polymer, chitosan-coated beads, SH beads, latex beads, spherical latex beads, allele-type beads, SPA bead, PEG-based resins, PEG-coated bead, PEG-encapsulated bead, polystyrene beads, magnetic polystyrene beads, glutathione agarose beads, magnetic bead, paramagnetic beads, protein A and/or protein G sepharose beads, activated carboxylic acid bead, macroscopic beads, microscopic beads, insoluble resin beads, silica-based resins, cellulosic resins, cross-linked agarose beads, polystyrene beads, cross-linked polyacrylamide resins, beads with iron cores, metal beads, dynabeads, Polymethylmethacrylate beads activated with NHS, streptavidin-agarose beads, polypropylene, polyethylene, dextran, nylon, amylases, natural and modified celluloses, nitrocellulose, polyacrylamides, gabbros, magnetite, polymers, oligomers, non-repeating moieties, polyethylene glycol (PEG), monomethoxy-PEG, mono-($C_1$-$C_{10}$)alkoxy-PEG, aryloxy-PEG, poly-(N-vinyl pyrrolidone)PEG, tresyl monomethoxy PEG, PEG propionaldehyde, bis-succinimidyl carbonate PEG, polystyrene bead crosslinked with divinylbenzene, propylene glycol homopolymers, a polypropylene oxide/ethylene oxide co-polymer, polyoxyethylated polyols (e.g., glycerol), polyvinyl alcohol, dextran, aminodextran, carbohydrate-based polymers, cross-linked dextran beads, polysaccharide beads, polycarbamate beads, divinyl sulfone activated polysaccharide, polystyrene beads that have been functionalized with tosyl-activated esters, magnetic polystyrene beads functionalized with tosyl-activated esters, streptavidin beads, streptaivdin-monomer coated beads, streptaivdin-tetramer coated beads, Streptavidin Coated Compel Magnetic beads, avidin coated beads, dextramer coated beads, divinyl sulfone-activated dextran, Carboxylate-modified bead, amine-modified beads, antibody coated beads, cellulose beads, grafted co-poly beads, polyacrylamide beads, dimethylacrylamide beads optionally crosslinked with N-N'-bis-acryloylethylenediamine, hollow fiber membranes, fluorescent beads, collagen-agarose beads, gelatin beads, collagen-gelatin beads, collagen-fibronectin-gelatin beads, collagen beads, chitosan beads, collagen-chitosan beads, protein-based beads, hydrogel beads, hemicellulose, alkyl cellulose, hydroxyalkyl cellulose, carboxymethylcellulose, sulfoethylcellulose, starch, xylan, amylopectine, chondroitin, hyarulonate, heparin, guar, xanthan, mannan, galactomannan, chitin and chitosan.

160. The detection molecule according to any of the preceding items, wherein the multimerization domain comprises one or more beads further comprises a linker moiety.

161. The detection molecule according to any of the preceding items, wherein the multimerization domain comprises one or more beads comprising a linker moiety which is a flexible linker, a rigid linker, a water-soluble linker or a cleavable linker.

162. The detection molecule according to any of the preceding items, wherein the one or more linkers comprises a dimerization domain.

163. The detection molecule according to any of the preceding items, wherein the one or more linkers comprises a trimerization domain.

164. The detection molecule according to any of the preceding items, wherein the one or more linkers comprises a tetramerization domain.

165. The detection molecule according to any of the preceding items, wherein the one or more linkers comprises a pentamerization domain.

166. The detection molecule according to any of the preceding items, wherein the pentamerization domain comprises a coiled-coil polypeptide structure.

167. The detection molecule according to any of the preceding items, wherein the one or more linkers comprises a hexamerization domain, such as a hexamerization domain comprises three IgG domains.

168. The detection molecule according to any of the preceding items, wherein the one or more linkers comprises a polyamide and/or a polyethylene glycol and/or a polysaccharide and/or a sepharose.

169. The detection molecule according to any of the preceding items, wherein the one or more linkers have a molecular weight of less than 1,000 Da.

170. The detection molecule according to any of the preceding items, wherein the one or more linkers have a molecular weight of from 1,000 Da to preferably less than 10,000 Da.

171. The detection molecule according to any of the preceding items, wherein the one or more linkers have a molecular weight of from 10,000 Da to preferably less than 100,000 Da.

172. The detection molecule according to any of the preceding items, wherein the one or more linkers have a molecular weight of from 100,000 Da to preferably less than 1,000,000 Da.

173. The detection molecule according to any of the preceding items, wherein the one or more linkers have a molecular weight of more than 1,000,000 Da.

174. The detection molecule according to any of the preceding items further comprising one or more scaffolds, carriers, connectors and/or linkers selected from the group consisting of streptavidin (SA) and avidin and derivatives thereof, biotin, immunoglobulins, antibodies (monoclonal, polyclonal, and recombinant), antibody fragments and derivatives thereof, leucine zipper domain of AP-1 (Jun and fos), hexa-his (metal chelate moiety), hexa-hat GST (glutathione S-tranferase) glutathione affinity, Calmodulin-binding peptide (CBP), Strep-tag, Cellulose Binding Domain, Maltose Binding Protein, S-Peptide Tag, Chitin Binding Tag, Immuno-reactive Epitopes, Epitope Tags, E2Tag, HA Epitope Tag, Myc Epitope, FLAG Epitope, AU1 and AU5 Epitopes, Glu-Glu Epitope, KT3 Epitope, IRS Epitope, Btag Epitope, Protein Kinase-C Epitope, VSV Epitope, lectins that mediate binding to a diversity of compounds, including carbohydrates, lipids and proteins, e.g. Con A (*Canavalia ensiformis*) or WGA (wheat germ agglutinin) and tetranectin or Protein A or G (antibody affinity).

175. The detection molecule according to any of the preceding items, wherein the binding molecule and/or the label comprises a connector molecule, such as biotin, and the linker comprises a connector such as streptavidin or another avidin connector.
176. The detection molecule according to any of the preceding items, wherein the binding molecule is linked to at least one of the one or more multimerization domains by a non-covalent linker moiety, such as natural dimerization or protein-protein interactions.
177. The detection molecule according to any of the preceding items, wherein the binding molecule is linked to at least one of the one or more multimerization domains by a protein-protein interaction selected from the group consisting of Fos/Jun interactions, Acid/Base coiled coil structure based interactions, antibody/antigen interactions, polynucleotide-polynucleotide interactions, synthetic molecule-synthetic molecule interactions and protein-small molecule interactions.
178. The detection molecule according to any of the preceding items, wherein the binding molecule is linked to at least one of the one or more multimerization domains by natural dimerization selected from the group consisting of antigen-antibody pairs, DNA-DNA interactions, natural interactions, biotin and streptavidin.
179. The detection molecule according to any of the preceding items, wherein the detection molecule further comprises an enzyme capable of catalysing the transfer of a cell surface moiety (e.g. a peptide fragment or 'peptide tag') from a cell surface protein to the binding molecule of the detection molecule, when said surface moiety binds to the binding molecule.
180. The detection molecule according to any of the preceding items, comprising
    a. a monomeric or a multimeric major histocompatibility complex (MHC) molecule, such as a monomeric or multimeric peptide MHC complex,
    b. a linker comprising a multimerization domain and optionally one or more connectors, and
    c. a nucleic acid label.
181. The detection molecule according to any of the preceding items, comprising
    a. a monomeric or a multimeric major histocompatibility complex (MHC) molecule, such as a monomeric or multimeric peptide MHC complex,
    b. a linker comprising a multimerization domain and optionally one or more connectors, and
    c. a peptide label.
182. The detection molecule according to any of the preceding items, comprising
    a. CD1, wherein said CD1 is selected from the group consisting of CD1 CD1a, CD1b, CD1c, CD1d and CD1e,
    b. a linker comprising a multimerization domain and optionally one or more connectors, and
    c. a nucleic acid label.
183. The detection molecule according to any of the preceding items, comprising
    a. an anti-target molecule capable of associating with, recognizing and/or binding to a predetermined marker molecule (or target) on a cell type, wherein said marker molecule is specific for a certain cell type
    b. a linker (Li) comprising a multimerization domain and optionally one or more connectors, and
    c. a nucleic acid label.
184. The detection molecule according to any of the preceding items, wherein said linker comprising a multimerization domain and optionally one or more connectors is a dextran optionally comprising streptavidin or avidin, and said binding molecule and/or label optionally comprises biotin.
185. A kit of parts comprising
    a. One or more detection molecules according to any of the preceding items, and
    b. one or more additional components.
186. The kit of parts according to any of the preceding items, wherein said one or more additional components comprise reagents for detecting and/or amplifying the label of the detection molecule.
187. The kit of parts according to any of the preceding items, wherein said one or more additional components comprise reagents for detecting and/or amplifying the nucleic acid label of the detection molecule.
188. The kit of parts according to any of the preceding items, wherein said reagents for detecting the nucleic acid label of the detection molecule comprises one or more primer sets capable of amplifying the nucleic acid label.
189. A detection method comprising the steps of
    a. Combining a sample with at least one detection molecule; wherein the detection molecule comprises a binding molecule (BM), a linker (Li), and a label (La) according to any of the preceding items; and wherein said sample comprises at least one cell and/or entity,
    b. Incubating the at least one detection molecule and the sample;
    c. Isolating and/or detecting the at least one detection molecule of step b), and
    d. Optionally determining the identity of the at least one detection molecule of step c).
190. The detection method according to any of the preceding items, wherein in step b) the one or more detection molecules are allowed to associate with, recognize, and/or bind to said at least one cell and/or entity through their binding molecule.
191. The detection method according to any of the preceding items, wherein in step c) and d) said detection molecule is comprised in a cell-detection molecule complex or an entity-detection molecule complex.
192. The detection method according to any of the preceding items, wherein in step c) and d) said detection molecule is not comprised in a cell-detection molecule complex or an entity-detection molecule complex.
193. The detection method according to any of the preceding items, wherein in step c) and d) said detection molecule is no longer comprised in a cell-detection molecule complex or an entity-detection molecule complex, wherein said detection molecule has previously interacted with a cell-detection molecule complex or an entity-detection molecule complex.
194. The detection method according to any of the preceding items, wherein said cell-detection molecule complexes comprises a cell, such as an immune cell, associated with or bound to a detection molecule having a binding molecule specific for the immune cell.
195. The detection method according to any of the preceding items, wherein step c) comprises isolating and detecting the at least one detection molecule.
196. The detection method according to any of the preceding items, wherein step c) comprises first isolating and then detecting the at least one detection molecule.
197. The detection method according to any of the preceding items, wherein step c) comprises detecting the at least one detection molecule.
198. The detection method according to any of the preceding items, wherein step c) comprises isolating the at least one detection molecule.
199. The detection method according to any of the preceding items, wherein step c) comprises first detecting and then isolating the at least one detection molecule.
200. The detection method according to any of the preceding items, wherein in step c) isolating comprises flow cytometry and/or FACS sorting
201. The detection method according to any of the preceding items, wherein in step c) isolating comprises one or more steps of washing, centrifugation and/or precipitation.
202. The detection method according to any of the preceding items, wherein in step c) isolating comprises one or more steps of filtration.
203. The detection method according to any of the preceding items, wherein in step c) isolating comprises one or more steps of application on an affinity column.
204. The detection method according to any of the preceding items, wherein in step c) isolating comprises sorting of cell populations based on the functional response to a stimuli (responsive or non-responsive population), such as cytokine secretion, phosphorylation, calcium release.
205. The detection method according to any of the preceding items, wherein in step c) isolating comprises sorting of cell populations based on phenotype, such as by linking a certain set of phenotypic characteristics to the antigen-responsiveness.
206. The detection method according to any of the preceding items, wherein in step c) isolating comprises immobilization of the detection molecule and/or cell-detection molecule complexes.
207. The detection method according to any of the preceding items, wherein said immobilization of the cell-detection molecule complexes comprises precipitating cells, such as by centrifugation, by immunoprecipitation, or any other means that precipitates the cells.
208. The detection method according to any of the preceding items, wherein said immobilization of the cell-detection molecule complexes comprises binding the cell-detection molecule complexes to a bead, a particle, another surface, an antibody or an MHC complex.
209. The detection method according to any of the preceding items, wherein said immobilization of the detection molecule and/or cell-detection molecule complexes comprises hybridization onto an array.
210. The detection method according to any of the preceding items, wherein said immobilization of the detection molecule and/or cell-detection molecule complexes by hybridization onto an array comprises a nucleic acid/nucleic acid-interaction between the nucleic acid label of the detection molecule and an antisense nucleic acid sequence in the array.
211. The detection method according to any of the preceding items, wherein said immobilization of the detection molecule and/or cell-detection molecule complexes by hybridization onto an array comprises a DNA/DNA-interaction between the DNA label of the detection molecule and an antisense DNA in the array.
212. The detection method according to any of the preceding items, wherein said detecting in step c) and/or determining the identity in step d) comprises one or more steps of adding primary antibodies that bind to the immobilized detection molecule and/or cell-detection molecule complexes and detecting said primary antibodies directly wherein the primary antibody is labelled, or indirectly by adding labelled secondary antibodies.
213. The detection method according to any of the preceding items, wherein said detecting in step c) and/or determining the identity in step d) comprises one or more steps of detecting the immobilized detection molecule and/or cell-detection molecule complexes by monitoring read-out from a second label such as a fluorophore.
214. The detection method according to any of the preceding items, wherein said detecting in step c) and/or determining the identity in step d) comprises one or more steps of determining the identity of said label.
215. The detection method according to any of the preceding items, wherein said detecting in step c) and/or determining the identity in step d) comprises interaction between 'coating DNA' on the cell surface and the DNA label of the detection molecule.
216. The detection method according to any of the preceding items, wherein said detecting in step c) and/or determining the identity in step d) comprises protease cleavage of the peptide label of the detection molecule.
217. The detection method according to any of the preceding items, wherein said detecting in step c) and/or determining the identity in step d) comprises transfer of a cell surface moiety to the detection molecule (e.g. a 'peptide tag').
218. The detection method according to any of the preceding items, wherein said detecting in step c) and/or determining the identity in step d) comprises detection of the label based on the physical characteristics of the label, including mass, sequence, charge, volume, size, dimensions, fluorescence, absorption, emission, NMR spectra and others.
219. The detection method according to any of the preceding items, wherein said detecting in step c) and/or determining the identity in step d) comprises amplification of the label.
220. The detection method according to any of the preceding items, wherein said detecting in step c) and/or determining the identity in step d) comprises sequencing of the label (e.g. DNA sequencing, peptide sequencing).
221. The detection method according to any of the preceding items, wherein said detecting in step c) and/or determining the identity in step d) comprises amplification of the barcode sequence of a nucleic acid label by PCR and/or sequencing of the barcode sequence.

222. The detection method according to any of the preceding items, wherein said sequencing comprises deep sequencing or next generation sequencing.
223. The detection method according to any of the preceding items, wherein said detecting in step c) and/or determining the identity in step d) comprises mass spectrometry.
224. The detection method according to any of the preceding items, wherein said detecting in step c) and/or determining the identity in step d) comprises one or more of gel electrophoresis, gel filtration, PAGE, column fractionation, PCR and QPCR.
225. The detection method according to any of the preceding items, said method further comprising one or more steps of providing a sample, preferably a sample comprising at least one entity and/or at least one cell.
226. The detection method according to any of the preceding items, said method further comprising one or more steps of pre-treatment of the sample, and/or pre-treatment of cells of the sample.
227. The detection method according to any of the preceding items, said method further comprising one or more steps of separating unbound detection molecules from cell- or entity-detection molecule complexes.
228. The detection method according to any of the preceding items, said method further comprising one or more steps of removing unbound detection molecules by washing and/or centrifuging.
229. The detection method according to any of the preceding items, said method further comprising one or more steps of single-cell sorting and sequencing.
230. The detection method according to any of the preceding items, said method further comprising one or more steps of single-cell T cell sorting of and single-cell TCR sequencing.
231. The detection method according to any of the preceding items, wherein said sample comprises one or more cells.
232. The detection method according to any of the preceding items, wherein said sample comprises at least one cell and/or entity to which the binding molecule of the detection molecule is able to associate with, recognize and/or bind.
233. The detection method according to any of the preceding items, wherein said sample is selected from the group consisting of a solid sample, a fluid sample, a semifluid sample, a liquid sample, a solubilised sample and a sample comprising dissociated cells of a solid sample.
234. The detection method according to any of the preceding items, wherein said sample is selected from the group consisting of a biofilm, a biopsy, a surgical sample, a tissue sample, a microarray-fixed sample, a section such as a fresh section, a frozen section and a FFPE section.
235. The detection method according to any of the previous items, wherein said sample is selected from the group consisting of blood, whole blood, plasma, serum, Peripheral blood mononuclear cells (PBMC), human PBMN (HPBMC), buffy coat, synovial fluid, bone marrow, cerebrospinal fluid, saliva, lymph fluid, seminal fluid, urine, stool, exudate, transdermal exudates, pharyngeal exudates, nasal secretions, sputum, sweat, bronchoalveolar lavage, tracheal aspirations, fluid from joints, vitreous fluid, vaginal or urethral secretions or semen.
236. The detection method according to any of the previous items, wherein said sample comprises cell populations isolated from a fluid, a semifluid sample or a solid sample.
237. The detection method according to any of the previous items, wherein said cell is selected from the group consisting of immune cells, lymphocytes, monocytes, dendritic cells, T-cells, B-cells and NK cells
238. The detection method according to any of the previous items, wherein said cell is a T-cell, such as a T cell selected from the group consisting of CD4+ T cells, CD8+ T cells, $\alpha\beta$ T cells and invariant $\gamma\delta$ T cells.
239. The detection method according to any of the previous items, wherein said cell is an antigen-specific T-cell or antigen-responsive T cell.
240. The detection method according to any of the previous items, wherein said cell comprises T-cell receptors.
241. The detection method according to any of the previous items, wherein said cell is a cancer cell.
242. The detection method according to any of the previous items, wherein said sample is derived from an organ selected from the group consisting of lymph nodes, kidney, liver, skin, brain, heart, muscles, bone marrow, skin, skeleton, lungs, the respiratory tract, spleen, thymus, pancreas, exocrine glands, bladder, endocrine glands, reproduction organs including the fallopian tubes, eye, ear, vascular system, the gastroinstestinal tract including small intestines, colon, rectum, canalis analis and prostate gland.
243. The detection method according to any of the previous items, wherein the surface of sample cells is coated with proteases capable of cleaving a peptide label, for example by adding antibody-protease conjugates where the antibody recognizes a particular cell surface structure.
244. The detection method according to any of the previous items, wherein the surface of sample cells is coated with DNA oligonucleotides ("coating DNA"), for example by adding antibody-DNA conjugates where the antibody recognizes a particular cell surface structure.
245. A method for detecting antigen-specific T cells in a sample, said method comprising providing a detection molecule and a detection method according to any of the preceding items.
246. A method for detecting specific cells in a sample, said method comprising providing a detection molecule and a detection method according to any of the preceding items.
247. A method for diagnosing a disease, said method comprising providing a detection molecule and a detection method according to any of the preceding items.
248. A method for diagnosing a disease according to the previous items, wherein said disease is selected from the group consisting of cancer, Cancerous diseases, infectious diseases, Infectious diseases caused by virus, Infectious diseases caused by bacteria, Infectious diseases caused by fungus, Parasitic diseases, Allergic diseases, Transplantation-related diseases and Autoimmune and inflammatory diseases.
249. A method for detecting the presence and/or abundance of a certain cell or cell type in a sample, said method comprising providing a detection molecule and a detection method according to any of the preceding items, wherein said detection molecule comprises a binding molecule capable of associating specifically with the cell or cell type in said sample 250. A method for investigating the binding characteristics of a certain cell or cell type in a sample, said method comprising providing a detection molecule and a detection method according to any of the preceding items, wherein said detection molecule comprises a binding molecule capable of associating specifically with a known target.

251. A method for the identification of epitopes comprising providing a detection molecule and a detection method according to any of the preceding items 252. A method for vaccine development comprising providing a detection molecule and a detection method according to any of the preceding items.

253. A method for measuring immune reactivity after vaccination comprising providing a detection molecule and a detection method according to any of the preceding items.

254. A method for development of immune-therapeutics comprising providing a detection molecule and a detection method according to any of the preceding items.

The invention claimed is:

1. A B-cell detection method comprising the steps of
   a. combining a sample comprising cells with a composition comprising two or more different sets of detection molecules to form a mixture;
   wherein each detection molecule comprises
      i) at least two identical binding molecules, wherein each of said binding molecules is a protein or an anti-target molecule capable of binding to a B-cell receptor,
      ii) at least one nucleic acid label, wherein said nucleic acid label comprises a 5' first primer region (forward), a barcode region, a 3' second primer region (reverse), and a random nucleotide region between the 5' first primer region and the 3' second primer region, wherein said random nucleotide region comprises 7 to 20 nucleotides, wherein the barcode region is unique to and specific for the binding molecules of a set, and wherein the detection molecules in a set have identical binding molecules and identical barcodes, and
      iii) a multimerization domain associated with the at least two identical binding molecules and the at least one nucleic acid label, optionally via one or more connector molecules, wherein the multimerization domain is selected from the group consisting of a peptide, a protein, streptactin, a polysaccharide, a dextran, an avidin and a streptavidin;
   wherein said barcode region serves as an identification tag for the at least two identical binding molecules of a set, wherein said random nucleotide region is unique for each detection molecule, and
   wherein the primer regions of said nucleic acid label are identical for all detection molecules in the composition;
   b. incubating the mixture, whereby said detection molecules bind to B-cells from the sample to form labeled B-cells;
   c. isolating the labeled B-cells from step b and detecting one or more labels bound to the labeled B-cells, and
   d. determining an identity of the detected labeled B-cells of step c.

2. The B-cell detection method according to claim 1, wherein in step c isolating comprises one or more methods selected from the group consisting of flow cytometry, fluorescence activated cell sorting (FACS), washing, centrifugation, precipitation, filtration, affinity column, sorting of cell populations based on the functional response to a stimulus, sorting of cell populations based on phenotype, and immobilization of one or more detection molecules and/or cell-detection molecule complexes.

3. The B-cell detection method according to claim 1, wherein said detecting in step c and/or determining the identity in step d comprises one or more steps of amplification of the label, sequencing of the label, DNA sequencing, mass spectrometry, gel electrophoresis, gel filtration, polyacrylamide gel electrophoresis, column fractionation, polymerase chain reaction (PCR), quantitative polymerase chain reaction (QPCR); adding primary antibodies that bind to the immobilized detection molecule and/or cell-detection molecule complexes and detecting said primary antibodies directly wherein the primary antibody is labelled, or indirectly by adding labelled secondary antibodies; and single-cell sorting and sequencing.

4. The B-cell detection method according to claim 2, wherein in step c isolating comprises flow cytometry and/or FACS.

5. The B-cell detection method according to claim 3, wherein said detecting in step c and/or determining the identity in step d comprises one or more steps of amplification of the label and sequencing of the label.

6. The B-cell detection method according to claim 1,
   wherein isolating in step c comprises flow cytometry and/or FACS,
   wherein detecting in step c comprises one or more steps of amplification of the label by PCR and
   wherein determining the identity in step d comprises sequencing of the label.

7. The B-cell detection method according to claim 1,
   wherein isolating in step c comprises flow cytometry and/or FACS, wherein detecting in step c comprises and/or determining the identity in step d comprises QPCR.

8. The B-cell detection method according to claim 1, wherein said detecting in step c and/or determining the identity in step d comprises one or more steps of single-cell sorting and sequencing.

9. The B-cell detection method according to claim 1, comprising one or more steps of single-cell B-cell sorting and single-cell B-cell receptor sequencing.

10. The B-cell detection method according to claim 1, wherein said detection molecules further comprise a fluorescent label.

11. The B-cell detection method according to claim 10, wherein the fluorescent label is suitable for use in flow cytometry and/or FACS.

12. The B-cell detection method according to claim 10, wherein said fluorescent label is used for the isolating in step c, and wherein the isolating in step c comprises flow cytometry and/or FACS.

13. The B-cell detection method according to claim 1, wherein the protein or the anti-target molecules of at least one of said sets are capable of binding a B cell receptor on a B-cell.

14. The B-cell detection method according to claim 1, wherein the anti-target molecules of at least one of said sets are selected from the group consisting of antibodies, antibody mimetics, DNA aptamers, RNA aptamers, and peptide aptamers.

15. The B-cell detection method according to claim 1, wherein the anti-target molecules of at least one of said sets are selected from natural ligands, and synthetic ligands.

16. The B-cell detection method according to claim 1, wherein the anti-target molecules of at least one of said sets are peptides.

17. The B-cell detection method according to claim 1, wherein the sample is a blood sample, a peripheral blood sample, a blood-derived sample, a tissue biopsy, a body fluid, spinal fluid or saliva.

18. The B-cell detection method according to claim 1, wherein said label comprises more than one random nucleotide region between the 5' first primer region and the 3' second primer region.

19. The B-cell detection method according to claim 1, wherein the sample comprises B-cells, and B-cells are detected in step c and identified in step d.

* * * * *

SEQUENCE LISTING

```
<160> NUMBER OF SEQ ID NOS: 606

<210> SEQ ID NO 1
<211> LENGTH: 69
<212> TYPE: DNA
<213> ORGANISM: Artificial sequence
<220> FEATURE:
<223> OTHER INFORMATION: Barcode for CMV, Biotin-TEG at 5' end
<220> FEATURE:
<221> NAME/KEY: misc_feature
<222> LOCATION: (1)..(69)
<223> OTHER INFORMATION: Barcode for CMV
<220> FEATURE:
<221> NAME/KEY: misc_feature
<222> LOCATION: (13)..(18)
<223> OTHER INFORMATION: n: any of A, T, G, C independently

<400> SEQUENCE: 1
gagatacgtt gacctcgttg aannnnnntc tatccattcc atccagctca cttaagctct    60
tggttgcat                                                             69

<210> SEQ ID NO 2
<211> LENGTH: 69
<212> TYPE: DNA
<213> ORGANISM: Artificial sequence
<220> FEATURE:
<223> OTHER INFORMATION: Barcode for HIV, Biotin-TEG at 5' end
<220> FEATURE:
<221> NAME/KEY: misc_feature
<222> LOCATION: (1)..(69)
<223> OTHER INFORMATION: Barcode for HIV
<220> FEATURE:
<221> NAME/KEY: misc_feature
<222> LOCATION: (13)..(18)
<223> OTHER INFORMATION: n: any of A, T, G, C independently

<400> SEQUENCE: 2
gagatacgtt gacctcgttg aannnnnntc tataggtgtc tactacctca cttaagctct    60
tggttgcat                                                             69

<210> SEQ ID NO 3
<211> LENGTH: 20
<212> TYPE: DNA
<213> ORGANISM: Artificial sequence
<220> FEATURE:
<223> OTHER INFORMATION: Forward-01 primer
<220> FEATURE:
<221> NAME/KEY: primer_bind
<222> LOCATION: (1)..(20)
<223> OTHER INFORMATION: Forward-01 primer

<400> SEQUENCE: 3
gagatacgtt gacctcgttg                                                 20

<210> SEQ ID NO 4
```

```
<211> LENGTH: 20
<212> TYPE: DNA
<213> ORGANISM: Artificial sequence
<220> FEATURE:
<223> OTHER INFORMATION: Reverse-01 primer
<220> FEATURE:
<221> NAME/KEY: primer_bind
<222> LOCATION: (1)..(20)
<223> OTHER INFORMATION: Reverse-01 primer

<400> SEQUENCE: 4
atgcaaccaa gagcttaagt                                              20

<210> SEQ ID NO 5
<211> LENGTH: 69
<212> TYPE: DNA
<213> ORGANISM: Artificial sequence
<220> FEATURE:
<223> OTHER INFORMATION: TestOligo-01, biotin-TEG at 5' end
<220> FEATURE:
<221> NAME/KEY: misc_feature
<222> LOCATION: (1)..(69)
<223> OTHER INFORMATION: TestOligo-01
<220> FEATURE:
<221> NAME/KEY: misc_feature
<222> LOCATION: (13)..(18)
<223> OTHER INFORMATION: n: any of A, T, G, C independently

<400> SEQUENCE: 5
gagatacgtt gacctcgttg aannnnnntc tatccattcc atccagctca cttaagctct   60
tggttgcat                                                          69

<210> SEQ ID NO 6
<211> LENGTH: 69
<212> TYPE: DNA
<213> ORGANISM: Artificial sequence
<220> FEATURE:
<223> OTHER INFORMATION: TestOligo-02, biotin-TEG at 5' end followed by
      HEG (terminal modifications)
<220> FEATURE:
<221> NAME/KEY: misc_feature
<222> LOCATION: (1)..(69)
<223> OTHER INFORMATION: TestOligo-02
<220> FEATURE:
<221> NAME/KEY: misc_feature
<222> LOCATION: (13)..(18)
<223> OTHER INFORMATION: n: any of A, T, G, C independently

<400> SEQUENCE: 6
gagatacgtt gacctcgttg aannnnnntc tatccattcc atccagctca cttaagctct   60
tggttgcat                                                          69

<210> SEQ ID NO 7
<211> LENGTH: 69
<212> TYPE: DNA
<213> ORGANISM: Artificial sequence
<220> FEATURE:
<223> OTHER INFORMATION: TestOligo-03, biotin-TEG at 5' end followed by
      HEG (terminal modifications) and HEG at 3' end
<220> FEATURE:
<221> NAME/KEY: misc_feature
<222> LOCATION: (1)..(69)
<223> OTHER INFORMATION: TestOligo-03
<220> FEATURE:
<221> NAME/KEY: misc_feature
<222> LOCATION: (13)..(18)
<223> OTHER INFORMATION: n: any of A, T, G, C independently

<400> SEQUENCE: 7
gagatacgtt gacctcgttg aannnnnntc tatccattcc atccagctca cttaagctct   60
``` tggttgcat                                                            69

<210> SEQ ID NO 8
<211> LENGTH: 69
<212> TYPE: DNA
<213> ORGANISM: Artificial sequence
<220> FEATURE:
<223> OTHER INFORMATION: TestOligo-04, biotin-TEG at 5' end followed by
      HEG (terminal modifications) and HEG at 3' end
<220> FEATURE:
<221> NAME/KEY: misc_feature
<222> LOCATION: (1)..(69)
<223> OTHER INFORMATION: TestOligo-04
<220> FEATURE:
<221> NAME/KEY: misc_feature
<222> LOCATION: (13)..(18)
<223> OTHER INFORMATION: n: any of A, T, G, C independently

<400> SEQUENCE: 8
gagatacgtt gacctcgttg aannnnnntc ttgaactatg aatcgtctca cttaagctct    60
tggttgcat                                                            69

<210> SEQ ID NO 9
<211> LENGTH: 69
<212> TYPE: DNA
<213> ORGANISM: Artificial sequence
<220> FEATURE:
<223> OTHER INFORMATION: TestOligo-05, biotin-TEG at 5' end followed by
      HEG (terminal modifications) and HEG at 3' end
<220> FEATURE:
<221> NAME/KEY: misc_feature
<222> LOCATION: (1)..(69)
<223> OTHER INFORMATION: TestOligo-05
<220> FEATURE:
<221> NAME/KEY: misc_feature
<222> LOCATION: (13)..(18)
<223> OTHER INFORMATION: n: any of A, T, G, C

<400> SEQUENCE: 9
gagatacgtt gacctcgttg aannnnnntc tataggtgtc tactacctca cttaagctct    60
tggttgcat                                                            69

<210> SEQ ID NO 10
<211> LENGTH: 69
<212> TYPE: DNA
<213> ORGANISM: Artificial sequence
<220> FEATURE:
<223> OTHER INFORMATION: TestOligo-06, biotin-TEG at 5' end followed by
      HEG (terminal modifications) and HEG at 3' end
<220> FEATURE:
<221> NAME/KEY: misc_feature
<222> LOCATION: (1)..(69)
<223> OTHER INFORMATION: TestOligo-06
<220> FEATURE:
<221> NAME/KEY: misc_feature
<222> LOCATION: (13)..(18)
<223> OTHER INFORMATION: n: any of A, T, G, C independently

<400> SEQUENCE: 10
gagatacgtt gacctcgttg aannnnnntc tttattggag agcacgctca cttaagctct    60
tggttgcat                                                            69

<210> SEQ ID NO 11
<211> LENGTH: 19
<212> TYPE: DNA
<213> ORGANISM: Artificial sequence
<220> FEATURE:
<223> OTHER INFORMATION: LNA-3, 6FAM in 5', BHQ-1-plus in 3'

```
<220> FEATURE:
<221> NAME/KEY: misc_feature
<222> LOCATION: (1)..(19)
<223> OTHER INFORMATION: LNA-3
<220> FEATURE:
<221> NAME/KEY: misc_feature
<222> LOCATION: (4)..(6)
<223> OTHER INFORMATION: LNA modified RNA nucleotides
<220> FEATURE:
<221> NAME/KEY: misc_feature
<222> LOCATION: (9)..(10)
<223> OTHER INFORMATION: LNA modified RNA nucleotides
<220> FEATURE:
<221> NAME/KEY: misc_feature
<222> LOCATION: (13)..(15)
<223> OTHER INFORMATION: LNA modified RNA nucleotides

<400> SEQUENCE: 11
tctatccatt ccatccagc                                              19

<210> SEQ ID NO 12
<211> LENGTH: 19
<212> TYPE: DNA
<213> ORGANISM: Artificial sequence
<220> FEATURE:
<223> OTHER INFORMATION: LNA-4, 6FAM in 5'. BHQ-1-plus in 3'
<220> FEATURE:
<221> NAME/KEY: misc_feature
<222> LOCATION: (1)..(19)
<223> OTHER INFORMATION: LNA-4
<220> FEATURE:
<221> NAME/KEY: misc_feature
<222> LOCATION: (4)..(6)
<223> OTHER INFORMATION: LNA modified RNA nucleotides
<220> FEATURE:
<221> NAME/KEY: misc_feature
<222> LOCATION: (9)..(10)
<223> OTHER INFORMATION: LNA modified RNA nucleotides
<220> FEATURE:
<221> NAME/KEY: misc_feature
<222> LOCATION: (13)..(15)
<223> OTHER INFORMATION: LNA modified RNA nucleotides

<400> SEQUENCE: 12
tcttgaacta tgaatcgtc                                              19

<210> SEQ ID NO 13
<211> LENGTH: 19
<212> TYPE: DNA
<213> ORGANISM: Artificial sequence
<220> FEATURE:
<223> OTHER INFORMATION: LNA-5, HEX in 5', BHQ-1-plus in 3'
<220> FEATURE:
<221> NAME/KEY: misc_feature
<222> LOCATION: (1)..(19)
<223> OTHER INFORMATION: LNA-5
<220> FEATURE:
<221> NAME/KEY: misc_feature
<222> LOCATION: (4)..(6)
<223> OTHER INFORMATION: LNA modified RNA nucleotides
<220> FEATURE:
<221> NAME/KEY: misc_feature
<222> LOCATION: (9)..(10)
<223> OTHER INFORMATION: LNA modified RNA nucleotides
<220> FEATURE:
<221> NAME/KEY: misc_feature
<222> LOCATION: (13)..(15)
<223> OTHER INFORMATION: LNA modified RNA nucleotides

<400> SEQUENCE: 13
tctataggtg tctactacc                                              19

<210> SEQ ID NO 14
```

-continued

```
<211> LENGTH: 19
<212> TYPE: DNA
<213> ORGANISM: Artificial sequence
<220> FEATURE:
<223> OTHER INFORMATION: LNA-6, cyanine 5 in 5'-end; bhq-2-plus in 3'
      end
<220> FEATURE:
<221> NAME/KEY: misc_feature
<222> LOCATION: (1)..(19)
<223> OTHER INFORMATION: LNA-6
<220> FEATURE:
<221> NAME/KEY: misc_feature
<222> LOCATION: (4)..(6)
<223> OTHER INFORMATION: LNA modified RNA nucleotides
<220> FEATURE:
<221> NAME/KEY: misc_feature
<222> LOCATION: (9)..(10)
<223> OTHER INFORMATION: LNA modified RNA nucleotides
<220> FEATURE:
<221> NAME/KEY: misc_feature
<222> LOCATION: (13)..(15)
<223> OTHER INFORMATION: LNA modified RNA nucleotides

<400> SEQUENCE: 14
tctttattgg agagcacgc                                                   19

<210> SEQ ID NO 15
<211> LENGTH: 9
<212> TYPE: PRT
<213> ORGANISM: Artificial sequence
<220> FEATURE:
<223> OTHER INFORMATION: Negative control
<220> FEATURE:
<221> NAME/KEY: PEPTIDE
<222> LOCATION: (1)..(9)
<223> OTHER INFORMATION: Dextramer 3, Negative
      (HLA-A*0201/ALIAPVHAV/Neg.Control).

<400> SEQUENCE: 15

Ala Leu Ile Ala Pro Val His Ala Val
1               5

<210> SEQ ID NO 16
<211> LENGTH: 58
<212> TYPE: DNA
<213> ORGANISM: Artificial sequence
<220> FEATURE:
<223> OTHER INFORMATION: A-key 1OS-F1-1
<220> FEATURE:
<221> NAME/KEY: misc_feature
<222> LOCATION: (1)..(58)
<223> OTHER INFORMATION: A-key 1OS-F1-1

<400> SEQUENCE: 16
ccatctcatc cctgcgtgtc tccgactcag gaagatgatt ctataaactg tgcggtcc       58

<210> SEQ ID NO 17
<211> LENGTH: 58
<212> TYPE: DNA
<213> ORGANISM: Artificial sequence
<220> FEATURE:
<223> OTHER INFORMATION: A-key 1OS-F1-2
<220> FEATURE:
<221> NAME/KEY: misc_feature
<222> LOCATION: (1)..(58)
<223> OTHER INFORMATION: A-key 1OS-F1-2

<400> SEQUENCE: 17
ccatctcatc cctgcgtgtc tccgactcag tcctgagatt ctataaactg tgcggtcc       58

<210> SEQ ID NO 18
```

```
<211> LENGTH: 58
<212> TYPE: DNA
<213> ORGANISM: Artificial sequence
<220> FEATURE:
<223> OTHER INFORMATION: A-key 1OS-F1-3
<220> FEATURE:
<221> NAME/KEY: misc_feature
<222> LOCATION: (1)..(58)
<223> OTHER INFORMATION: A-key 1OS-F1-3

<400> SEQUENCE: 18
ccatctcatc cctgcgtgtc tccgactcag tgtggagatt ctataaactg tgcggtcc       58

<210> SEQ ID NO 19
<211> LENGTH: 58
<212> TYPE: DNA
<213> ORGANISM: Artificial sequence
<220> FEATURE:
<223> OTHER INFORMATION: A-key 1OS-F1-4
<220> FEATURE:
<221> NAME/KEY: misc_feature
<222> LOCATION: (1)..(58)
<223> OTHER INFORMATION: A-key 1OS-F1-4

<400> SEQUENCE: 19
ccatctcatc cctgcgtgtc tccgactcag catttagatt ctataaactg tgcggtcc       58

<210> SEQ ID NO 20
<211> LENGTH: 58
<212> TYPE: DNA
<213> ORGANISM: Artificial sequence
<220> FEATURE:
<223> OTHER INFORMATION: A-key 1OS-F1-5
<220> FEATURE:
<221> NAME/KEY: misc_feature
<222> LOCATION: (1)..(58)
<223> OTHER INFORMATION: A-key 1OS-F1-5

<400> SEQUENCE: 20
ccatctcatc cctgcgtgtc tccgactcag ttacccgatt ctataaactg tgcggtcc       58

<210> SEQ ID NO 21
<211> LENGTH: 58
<212> TYPE: DNA
<213> ORGANISM: Artificial sequence
<220> FEATURE:
<223> OTHER INFORMATION: A-key 1OS-F1-6
<220> FEATURE:
<221> NAME/KEY: misc_feature
<222> LOCATION: (1)..(58)
<223> OTHER INFORMATION: A-key 1OS-F1-6

<400> SEQUENCE: 21
ccatctcatc cctgcgtgtc tccgactcag attctcgatt ctataaactg tgcggtcc       58

<210> SEQ ID NO 22
<211> LENGTH: 58
<212> TYPE: DNA
<213> ORGANISM: Artificial sequence
<220> FEATURE:
<223> OTHER INFORMATION: A-key 1OS-F1-7
<220> FEATURE:
<221> NAME/KEY: misc_feature
<222> LOCATION: (1)..(58)
<223> OTHER INFORMATION: A-key 1OS-F1-7

<400> SEQUENCE: 22
ccatctcatc cctgcgtgtc tccgactcag agacccgatt ctataaactg tgcggtcc       58
```

```
<210> SEQ ID NO 23
<211> LENGTH: 58
<212> TYPE: DNA
<213> ORGANISM: Artificial sequence
<220> FEATURE:
<223> OTHER INFORMATION: A-key 1OS-F1-8
<220> FEATURE:
<221> NAME/KEY: misc_feature
<222> LOCATION: (1)..(58)
<223> OTHER INFORMATION: A-key 1OS-F1-8

<400> SEQUENCE: 23
ccatctcatc cctgcgtgtc tccgactcag cgcatggatt ctataaactg tgcggtcc      58

<210> SEQ ID NO 24
<211> LENGTH: 58
<212> TYPE: DNA
<213> ORGANISM: Artificial sequence
<220> FEATURE:
<223> OTHER INFORMATION: A-key 1OS-F1-9
<220> FEATURE:
<221> NAME/KEY: misc_feature
<222> LOCATION: (1)..(58)
<223> OTHER INFORMATION: A-key 1OS-F1-9

<400> SEQUENCE: 24
ccatctcatc cctgcgtgtc tccgactcag tcctcggatt ctataaactg tgcggtcc      58

<210> SEQ ID NO 25
<211> LENGTH: 58
<212> TYPE: DNA
<213> ORGANISM: Artificial sequence
<220> FEATURE:
<223> OTHER INFORMATION: A-key 1OS-F1-10
<220> FEATURE:
<221> NAME/KEY: misc_feature
<222> LOCATION: (1)..(58)
<223> OTHER INFORMATION: A-key 1OS-F1-10

<400> SEQUENCE: 25
ccatctcatc cctgcgtgtc tccgactcag attcctgatt ctataaactg tgcggtcc      58

<210> SEQ ID NO 26
<211> LENGTH: 58
<212> TYPE: DNA
<213> ORGANISM: Artificial sequence
<220> FEATURE:
<223> OTHER INFORMATION: A-key 1OS-F1-11
<220> FEATURE:
<221> NAME/KEY: misc_feature
<222> LOCATION: (1)..(58)
<223> OTHER INFORMATION: A-key 1OS-F1-11

<400> SEQUENCE: 26
ccatctcatc cctgcgtgtc tccgactcag cgtcgagatt ctataaactg tgcggtcc      58

<210> SEQ ID NO 27
<211> LENGTH: 58
<212> TYPE: DNA
<213> ORGANISM: Artificial sequence
<220> FEATURE:
<223> OTHER INFORMATION: A-key 1OS-F1-12
<220> FEATURE:
<221> NAME/KEY: misc_feature
<222> LOCATION: (1)..(58)
<223> OTHER INFORMATION: A-key 1OS-F1-12

<400> SEQUENCE: 27
ccatctcatc cctgcgtgtc tccgactcag gccaatgatt ctataaactg tgcggtcc      58
```

<210> SEQ ID NO 28
<211> LENGTH: 58
<212> TYPE: DNA
<213> ORGANISM: Artificial sequence
<220> FEATURE:
<223> OTHER INFORMATION: A-key 1OS-F1-13
<220> FEATURE:
<221> NAME/KEY: misc_feature
<222> LOCATION: (1)..(58)
<223> OTHER INFORMATION: A-key 1OS-F1-13

<400> SEQUENCE: 28
ccatctcatc cctgcgtgtc tccgactcag atacgggatt ctataaactg tgcggtcc        58

<210> SEQ ID NO 29
<211> LENGTH: 58
<212> TYPE: DNA
<213> ORGANISM: Artificial sequence
<220> FEATURE:
<223> OTHER INFORMATION: A-key 1OS-F1-14
<220> FEATURE:
<221> NAME/KEY: misc_feature
<222> LOCATION: (1)..(58)
<223> OTHER INFORMATION: A-key 1OS-F1-14

<400> SEQUENCE: 29
ccatctcatc cctgcgtgtc tccgactcag gtcagagatt ctataaactg tgcggtcc        58

<210> SEQ ID NO 30
<211> LENGTH: 58
<212> TYPE: DNA
<213> ORGANISM: Artificial sequence
<220> FEATURE:
<223> OTHER INFORMATION: A-key 1OS-F1-15
<220> FEATURE:
<221> NAME/KEY: misc_feature
<222> LOCATION: (1)..(58)
<223> OTHER INFORMATION: A-key 1OS-F1-15

<400> SEQUENCE: 30
ccatctcatc cctgcgtgtc tccgactcag cgagttgatt ctataaactg tgcggtcc        58

<210> SEQ ID NO 31
<211> LENGTH: 54
<212> TYPE: DNA
<213> ORGANISM: Artificial sequence
<220> FEATURE:
<223> OTHER INFORMATION: A-key 2OS-F1-1
<220> FEATURE:
<221> NAME/KEY: misc_feature
<222> LOCATION: (1)..(54)
<223> OTHER INFORMATION: A-key 2OS-F1-1

<400> SEQUENCE: 31
ccatctcatc cctgcgtgtc tccgactcag ctgggggaag ttccagccag cgtc        54

<210> SEQ ID NO 32
<211> LENGTH: 54
<212> TYPE: DNA
<213> ORGANISM: Artificial sequence
<220> FEATURE:
<223> OTHER INFORMATION: A-key 2OS-F1-2
<220> FEATURE:
<221> NAME/KEY: misc_feature
<222> LOCATION: (1)..(54)
<223> OTHER INFORMATION: A-key 2OS-F1-2

<400> SEQUENCE: 32
ccatctcatc cctgcgtgtc tccgactcag ctccacgaag ttccagccag cgtc        54

<210> SEQ ID NO 33
<211> LENGTH: 54
<212> TYPE: DNA
<213> ORGANISM: Artificial sequence
<220> FEATURE:
<223> OTHER INFORMATION: A-key 2OS-F1-3
<220> FEATURE:
<221> NAME/KEY: misc_feature
<222> LOCATION: (1)..(54)
<223> OTHER INFORMATION: A-key 2OS-F1-3

<400> SEQUENCE: 33
ccatctcatc cctgcgtgtc tccgactcag cttaccgaag ttccagccag cgtc    54

<210> SEQ ID NO 34
<211> LENGTH: 54
<212> TYPE: DNA
<213> ORGANISM: Artificial sequence
<220> FEATURE:
<223> OTHER INFORMATION: A-key 2OS-F1-4
<220> FEATURE:
<221> NAME/KEY: misc_feature
<222> LOCATION: (1)..(54)
<223> OTHER INFORMATION: A-key 2OS-F1-4

<400> SEQUENCE: 34
ccatctcatc cctgcgtgtc tccgactcag tggcaggaag ttccagccag cgtc    54

<210> SEQ ID NO 35
<211> LENGTH: 54
<212> TYPE: DNA
<213> ORGANISM: Artificial sequence
<220> FEATURE:
<223> OTHER INFORMATION: A-key 2OS-F1-5
<220> FEATURE:
<221> NAME/KEY: misc_feature
<222> LOCATION: (1)..(54)
<223> OTHER INFORMATION: A-key 2OS-F1-5

<400> SEQUENCE: 35
ccatctcatc cctgcgtgtc tccgactcag tgagtagaag ttccagccag cgtc    54

<210> SEQ ID NO 36
<211> LENGTH: 54
<212> TYPE: DNA
<213> ORGANISM: Artificial sequence
<220> FEATURE:
<223> OTHER INFORMATION: A-key 2OS-F1-6
<220> FEATURE:
<221> NAME/KEY: misc_feature
<222> LOCATION: (1)..(54)
<223> OTHER INFORMATION: A-key 2OS-F1-6

<400> SEQUENCE: 36
ccatctcatc cctgcgtgtc tccgactcag attcaggaag ttccagccag cgtc    54

<210> SEQ ID NO 37
<211> LENGTH: 54
<212> TYPE: DNA
<213> ORGANISM: Artificial sequence
<220> FEATURE:
<223> OTHER INFORMATION: A-key 2OS-F1-7
<220> FEATURE:
<221> NAME/KEY: misc_feature
<222> LOCATION: (1)..(54)
<223> OTHER INFORMATION: A-key 2OS-F1-7

<400> SEQUENCE: 37

```
ccatctcatc cctgcgtgtc tccgactcag tgagctgaag ttccagccag cgtc          54
```

<210> SEQ ID NO 38
<211> LENGTH: 54
<212> TYPE: DNA
<213> ORGANISM: Artificial sequence
<220> FEATURE:
<223> OTHER INFORMATION: A-key 20S-F1-8
<220> FEATURE:
<221> NAME/KEY: misc_feature
<222> LOCATION: (1)..(54)
<223> OTHER INFORMATION: A-key 20S-F1-8

<400> SEQUENCE: 38

```
ccatctcatc cctgcgtgtc tccgactcag ggcgtggaag ttccagccag cgtc          54
```

<210> SEQ ID NO 39
<211> LENGTH: 54
<212> TYPE: DNA
<213> ORGANISM: Artificial sequence
<220> FEATURE:
<223> OTHER INFORMATION: A-key 20S-F1-9
<220> FEATURE:
<221> NAME/KEY: misc_feature
<222> LOCATION: (1)..(54)
<223> OTHER INFORMATION: A-key 20S-F1-9

<400> SEQUENCE: 39

```
ccatctcatc cctgcgtgtc tccgactcag aaattggaag ttccagccag cgtc          54
```

<210> SEQ ID NO 40
<211> LENGTH: 54
<212> TYPE: DNA
<213> ORGANISM: Artificial sequence
<220> FEATURE:
<223> OTHER INFORMATION: A-key 20S-F1-10
<220> FEATURE:
<221> NAME/KEY: misc_feature
<222> LOCATION: (1)..(54)
<223> OTHER INFORMATION: A-key 20S-F1-10

<400> SEQUENCE: 40

```
ccatctcatc cctgcgtgtc tccgactcag gctgacgaag ttccagccag cgtc          54
```

<210> SEQ ID NO 41
<211> LENGTH: 54
<212> TYPE: DNA
<213> ORGANISM: Artificial sequence
<220> FEATURE:
<223> OTHER INFORMATION: A-key 20S-F1-11
<220> FEATURE:
<221> NAME/KEY: misc_feature
<222> LOCATION: (1)..(54)
<223> OTHER INFORMATION: A-key 20S-F1-11

<400> SEQUENCE: 41

```
ccatctcatc cctgcgtgtc tccgactcag ttcttagaag ttccagccag cgtc          54
```

<210> SEQ ID NO 42
<211> LENGTH: 54
<212> TYPE: DNA
<213> ORGANISM: Artificial sequence
<220> FEATURE:
<223> OTHER INFORMATION: A-key 20S-F1-12
<220> FEATURE:
<221> NAME/KEY: misc_feature
<222> LOCATION: (1)..(54)
<223> OTHER INFORMATION: A-key 20S-F1-12

<400> SEQUENCE: 42
ccatctcatc cctgcgtgtc tccgactcag tggtgggaag ttccagccag cgtc        54

<210> SEQ ID NO 43
<211> LENGTH: 54
<212> TYPE: DNA
<213> ORGANISM: Artificial sequence
<220> FEATURE:
<223> OTHER INFORMATION: A-key 2OS-F1-13
<220> FEATURE:
<221> NAME/KEY: misc_feature
<222> LOCATION: (1)..(54)
<223> OTHER INFORMATION: A-key 2OS-F1-13

<400> SEQUENCE: 43
ccatctcatc cctgcgtgtc tccgactcag gcagtcgaag ttccagccag cgtc        54

<210> SEQ ID NO 44
<211> LENGTH: 54
<212> TYPE: DNA
<213> ORGANISM: Artificial sequence
<220> FEATURE:
<223> OTHER INFORMATION: A-key 2OS-F1-14
<220> FEATURE:
<221> NAME/KEY: misc_feature
<222> LOCATION: (1)..(54)
<223> OTHER INFORMATION: A-key 2OS-F1-14

<400> SEQUENCE: 44
ccatctcatc cctgcgtgtc tccgactcag tcgtgagaag ttccagccag cgtc        54

<210> SEQ ID NO 45
<211> LENGTH: 54
<212> TYPE: DNA
<213> ORGANISM: Artificial sequence
<220> FEATURE:
<223> OTHER INFORMATION: A-key 2OS-F1-15
<220> FEATURE:
<221> NAME/KEY: misc_feature
<222> LOCATION: (1)..(54)
<223> OTHER INFORMATION: A-key 2OS-F1-15

<400> SEQUENCE: 45
ccatctcatc cctgcgtgtc tccgactcag tacagtgaag ttccagccag cgtc        54

<210> SEQ ID NO 46
<211> LENGTH: 44
<212> TYPE: DNA
<213> ORGANISM: Artificial sequence
<220> FEATURE:
<223> OTHER INFORMATION: P1-key 1OS-R1
<220> FEATURE:
<221> NAME/KEY: misc_feature
<222> LOCATION: (1)..(44)
<223> OTHER INFORMATION: P1-key 1OS-R1

<400> SEQUENCE: 46
cctctctatg ggcagtcggt gatgagtaca tgatagcgcc gtac                  44

<210> SEQ ID NO 47
<211> LENGTH: 25
<212> TYPE: DNA
<213> ORGANISM: Artificial sequence
<220> FEATURE:
<223> OTHER INFORMATION: Probe123 6-FAM in 5', BHQ-1 in 3'
<220> FEATURE:
<221> NAME/KEY: misc_feature
<222> LOCATION: (1)..(25)
<223> OTHER INFORMATION: Probe123

<400> SEQUENCE: 47
gcctgtagtc ccacgcgatc taaca                                    25

<210> SEQ ID NO 48
<211> LENGTH: 25
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(25)
<223> OTHER INFORMATION: Probe124, HEX in 5', BHQ-1 in 3'

<400> SEQUENCE: 48
caaccattga ttggggacaa ctggg                                    25

<210> SEQ ID NO 49
<211> LENGTH: 18
<212> TYPE: DNA
<213> ORGANISM: Artificial sequence
<220> FEATURE:
<223> OTHER INFORMATION: Forward primer
<220> FEATURE:
<221> NAME/KEY: primer_bind
<222> LOCATION: (1)..(18)
<223> OTHER INFORMATION: Forward primer

<400> SEQUENCE: 49
gaagttccag ccagcgtc                                            18

<210> SEQ ID NO 50
<211> LENGTH: 21
<212> TYPE: DNA
<213> ORGANISM: Artificial sequence
<220> FEATURE:
<223> OTHER INFORMATION: Reverse primer
<220> FEATURE:
<221> NAME/KEY: primer_bind
<222> LOCATION: (1)..(21)
<223> OTHER INFORMATION: Reverse primer

<400> SEQUENCE: 50
ctgtgactat gtgaggcttt c                                        21

<210> SEQ ID NO 51
<211> LENGTH: 72
<212> TYPE: DNA
<213> ORGANISM: Artificial sequence
<220> FEATURE:
<223> OTHER INFORMATION: 2OS-1-Oligo-A1, Biotin-C6 in 5'
<220> FEATURE:
<221> NAME/KEY: misc_feature
<222> LOCATION: (1)..(72)
<223> OTHER INFORMATION: 2OS-1-Oligo-A1
<220> FEATURE:
<221> NAME/KEY: misc_feature
<222> LOCATION: (26)..(31)
<223> OTHER INFORMATION: n: any of A, T, G, C independently

<400> SEQUENCE: 51
gaagttccag ccagcgtcac agtttnnnnn ncgagggcaa tggttaactg acacgtggtc    60
agcatcattt cc                                                      72

<210> SEQ ID NO 52
<211> LENGTH: 72
<212> TYPE: DNA
<213> ORGANISM: Artificial sequence

```
<220> FEATURE:
<223> OTHER INFORMATION: 2OS-1-Oligo-A2, Biotin-C6 in 5'
<220> FEATURE:
<221> NAME/KEY: misc_feature
<222> LOCATION: (1)..(72)
<223> OTHER INFORMATION: 2OS-1-Oligo-A1
<220> FEATURE:
<221> NAME/KEY: misc_feature
<222> LOCATION: (26)..(31)
<223> OTHER INFORMATION: n: any of A, T, G, C independently

<400> SEQUENCE: 52
gaagttccag ccagcgtcac agtttnnnnn ncagaaagca gtctcgtcgg ttcgaaggtc    60
agcatcattt cc                                                       72

<210> SEQ ID NO 53
<211> LENGTH: 72
<212> TYPE: DNA
<213> ORGANISM: Artificial sequence
<220> FEATURE:
<223> OTHER INFORMATION: 2OS-1-Oligo-A3, Biotin-C6 in 5'
<220> FEATURE:
<221> NAME/KEY: misc_feature
<222> LOCATION: (1)..(72)
<223> OTHER INFORMATION: 2OS-1-Oligo-A3
<220> FEATURE:
<221> NAME/KEY: misc_feature
<222> LOCATION: (26)..(31)
<223> OTHER INFORMATION: n: any of A, T, G, C independently

<400> SEQUENCE: 53
gaagttccag ccagcgtcac agtttnnnnn ntaagtagcg ggcataatgt acgctcggtc    60
agcatcattt cc                                                       72

<210> SEQ ID NO 54
<211> LENGTH: 72
<212> TYPE: DNA
<213> ORGANISM: Artificial sequence
<220> FEATURE:
<223> OTHER INFORMATION: 2OS-1-Oligo-A4, Biotin-C6 in 5'
<220> FEATURE:
<221> NAME/KEY: misc_feature
<222> LOCATION: (1)..(72)
<223> OTHER INFORMATION: 2OS-1-Oligo-A4, Biotin-C6 in 5'
<220> FEATURE:
<221> NAME/KEY: misc_feature
<222> LOCATION: (26)..(31)
<223> OTHER INFORMATION: n: any of A, T, G, C independently

<400> SEQUENCE: 54
gaagttccag ccagcgtcac agtttnnnnn nggatccagt aagctactgc gtttatggtc    60
agcatcattt cc                                                       72

<210> SEQ ID NO 55
<211> LENGTH: 72
<212> TYPE: DNA
<213> ORGANISM: Artificial sequence
<220> FEATURE:
<223> OTHER INFORMATION: 2OS-1-Oligo-A5, Biotin-C6 in 5'
<220> FEATURE:
<221> NAME/KEY: misc_feature
<222> LOCATION: (1)..(72)
<223> OTHER INFORMATION: 2OS-1-Oligo-A5
<220> FEATURE:
<221> NAME/KEY: misc_feature
<222> LOCATION: (26)..(31)
<223> OTHER INFORMATION: n: any of A, T, G, C independently

<400> SEQUENCE: 55
```

```
gaagttccag ccagcgtcac agtttnnnnn ngggctgcgg agcgtttact ctgtatggtc    60
agcatcattt cc                                                       72
```

<210> SEQ ID NO 56
<211> LENGTH: 72
<212> TYPE: DNA
<213> ORGANISM: Artificial sequence
<220> FEATURE:
<223> OTHER INFORMATION: 2OS-1-Oligo-A6, Biotin-C6 in 5'
<220> FEATURE:
<221> NAME/KEY: misc_feature
<222> LOCATION: (1)..(72)
<223> OTHER INFORMATION: 2OS-1-Oligo-A6
<220> FEATURE:
<221> NAME/KEY: misc_feature
<222> LOCATION: (26)..(31)
<223> OTHER INFORMATION: n: any of A, T, G, C independently

<400> SEQUENCE: 56

```
gaagttccag ccagcgtcac agtttnnnnn naaacgtatg tgctttgtcg gatgccggtc    60
agcatcattt cc                                                       72
```

<210> SEQ ID NO 57
<211> LENGTH: 72
<212> TYPE: DNA
<213> ORGANISM: Artificial sequence
<220> FEATURE:
<223> OTHER INFORMATION: 2OS-1-Oligo-A7, Biotin-C6 in 5'
<220> FEATURE:
<221> NAME/KEY: misc_feature
<222> LOCATION: (1)..(72)
<223> OTHER INFORMATION: 2OS-1-Oligo-A7
<220> FEATURE:
<221> NAME/KEY: misc_feature
<222> LOCATION: (26)..(31)
<223> OTHER INFORMATION: n: any of A, T, G, C independently

<400> SEQUENCE: 57

```
gaagttccag ccagcgtcac agtttnnnnn natatcatca taggcttagc gacgtaggtc    60
agcatcattt cc                                                       72
```

<210> SEQ ID NO 58
<211> LENGTH: 72
<212> TYPE: DNA
<213> ORGANISM: Artificial sequence
<220> FEATURE:
<223> OTHER INFORMATION: 2OS-1-Oligo-A8, Biotin-C6 in 5'
<220> FEATURE:
<221> NAME/KEY: misc_feature
<222> LOCATION: (1)..(72)
<223> OTHER INFORMATION: 2OS-1-Oligo-A8
<220> FEATURE:
<221> NAME/KEY: misc_feature
<222> LOCATION: (26)..(31)
<223> OTHER INFORMATION: n: any of A, T, G, C

<400> SEQUENCE: 58

```
gaagttccag ccagcgtcac agtttnnnnn naggaaaatc tgctaccgcc aatgatggtc    60
agcatcattt cc                                                       72
```

<210> SEQ ID NO 59
<211> LENGTH: 72
<212> TYPE: DNA
<213> ORGANISM: Artificial sequence
<220> FEATURE:
<223> OTHER INFORMATION: 2OS-1-Oligo-A9, Biotin-C6 in 5'
<220> FEATURE:
<221> NAME/KEY: misc_feature

```
<222> LOCATION: (1)..(72)
<223> OTHER INFORMATION: 2OS-1-Oligo-A9
<220> FEATURE:
<221> NAME/KEY: misc_feature
<222> LOCATION: (26)..(31)
<223> OTHER INFORMATION: n: any of A, T, G, C independently

<400> SEQUENCE: 59
gaagttccag ccagcgtcac agtttnnnnn nctgattgac tgcatggagg ctatacggtc      60
agcatcattt cc                                                          72

<210> SEQ ID NO 60
<211> LENGTH: 72
<212> TYPE: DNA
<213> ORGANISM: Artificial sequence
<220> FEATURE:
<223> OTHER INFORMATION: 2OS-1-Oligo-A10, Biotin-C6 in 5'
<220> FEATURE:
<221> NAME/KEY: misc_feature
<222> LOCATION: (1)..(72)
<223> OTHER INFORMATION: 2OS-1-Oligo-A10, Biotin-C6 in 5'
<220> FEATURE:
<221> NAME/KEY: misc_feature
<222> LOCATION: (26)..(31)
<223> OTHER INFORMATION: n: any of A, T, G, C independently

<400> SEQUENCE: 60
gaagttccag ccagcgtcac agtttnnnnn ngtggcgact tcacgattat ctgaacggtc      60
agcatcattt cc                                                          72

<210> SEQ ID NO 61
<211> LENGTH: 72
<212> TYPE: DNA
<213> ORGANISM: Artificial sequence
<220> FEATURE:
<223> OTHER INFORMATION: 2OS-1-Oligo-A11 Biotin-C6 in 5'
<220> FEATURE:
<221> NAME/KEY: misc_feature
<222> LOCATION: (1)..(72)
<223> OTHER INFORMATION: 2OS-1-Oligo-A11 Biotin-C6 in 5'
<220> FEATURE:
<221> NAME/KEY: misc_feature
<222> LOCATION: (26)..(31)
<223> OTHER INFORMATION: n: any of A, T, G, C independently

<400> SEQUENCE: 61
gaagttccag ccagcgtcac agtttnnnnn ncctgtattg aaggttcagt cctgttggtc      60
agcatcattt cc                                                          72

<210> SEQ ID NO 62
<211> LENGTH: 72
<212> TYPE: DNA
<213> ORGANISM: Artificial sequence
<220> FEATURE:
<223> OTHER INFORMATION: 2OS-1-Oligo-A12 Biotin-C6 in 5'
<220> FEATURE:
<221> NAME/KEY: misc_feature
<222> LOCATION: (1)..(72)
<223> OTHER INFORMATION: 2OS-1-Oligo-A12, Biotin-C6 in 5', n: any of A,
      T, G, C independently

<400> SEQUENCE: 62
gaagttccag ccagcgtcac agtttnnnnn nggctctata aggtttcctc aaaggtggtc      60
agcatcattt cc                                                          72

<210> SEQ ID NO 63
<211> LENGTH: 72
```

```
<212> TYPE: DNA
<213> ORGANISM: Artificial sequence
<220> FEATURE:
<223> OTHER INFORMATION: 2OS-1-Oligo-A13 Biotin-C6 in 5'
<220> FEATURE:
<221> NAME/KEY: misc_feature
<222> LOCATION: (1)..(72)
<223> OTHER INFORMATION: 2OS-1-Oligo-A13 Biotin-C6 in 5', n: any of A,
      T, G, C independently

<400> SEQUENCE: 63
gaagttccag ccagcgtcac agtttnnnnn nttgggagct ttcctatgta cagtccggtc    60
agcatcattt cc                                                        72

<210> SEQ ID NO 64
<211> LENGTH: 72
<212> TYPE: DNA
<213> ORGANISM: Artificial sequence
<220> FEATURE:
<223> OTHER INFORMATION: 2OS-1-Oligo-A14, Biotin-C6 in 5'
<220> FEATURE:
<221> NAME/KEY: misc_feature
<222> LOCATION: (1)..(72)
<223> OTHER INFORMATION: 2OS-1-Oligo-A14; Biotin-C6 in 5'; n: any of A,
      T, G, C independently

<400> SEQUENCE: 64
gaagttccag ccagcgtcac agtttnnnnn nagagaatat gtcgctcccg ttatgtggtc    60
agcatcattt cc                                                        72

<210> SEQ ID NO 65
<211> LENGTH: 72
<212> TYPE: DNA
<213> ORGANISM: Artificial sequence
<220> FEATURE:
<223> OTHER INFORMATION: 2OS-1-Oligo-A15; Biotin-C6 in 5'
<220> FEATURE:
<221> NAME/KEY: misc_feature
<222> LOCATION: (1)..(72)
<223> OTHER INFORMATION: 2OS-1-Oligo-A15; Biotin-C6 in 5'; n: any of A,
      T, G, C independently

<400> SEQUENCE: 65
gaagttccag ccagcgtcac agtttnnnnn ngcagttaga tatgcagtta cctgacggtc    60
agcatcattt cc                                                        72

<210> SEQ ID NO 66
<211> LENGTH: 72
<212> TYPE: DNA
<213> ORGANISM: Artificial sequence
<220> FEATURE:
<223> OTHER INFORMATION: 2OS-1-Oligo-A16
<220> FEATURE:
<221> NAME/KEY: misc_feature
<222> LOCATION: (1)..(72)
<223> OTHER INFORMATION: 2OS-1-Oligo-A16; Biotin-C6 in 5'; n: any of A,
      T, G, C independently

<400> SEQUENCE: 66
gaagttccag ccagcgtcac agtttnnnnn ncttcacccg aacatgcagt gttattggtc    60
agcatcattt cc                                                        72

<210> SEQ ID NO 67
<211> LENGTH: 72
<212> TYPE: DNA
<213> ORGANISM: Artificial sequence
<220> FEATURE:
```

```
<223> OTHER INFORMATION: 2OS-1-Oligo-A17
<220> FEATURE:
<221> NAME/KEY: misc_feature
<222> LOCATION: (1)..(72)
<223> OTHER INFORMATION: 2OS-1-Oligo-A17; Biotin-C6 in 5'; n: any of A,
      T, G, C independently

<400> SEQUENCE: 67
gaagttccag ccagcgtcac agtttnnnnn naaagccgtt gcagtatcgt ctgagcggtc    60
agcatcattt cc                                                       72

<210> SEQ ID NO 68
<211> LENGTH: 72
<212> TYPE: DNA
<213> ORGANISM: Artificial sequence
<220> FEATURE:
<223> OTHER INFORMATION: 2OS-1-Oligo-A18
<220> FEATURE:
<221> NAME/KEY: misc_feature
<222> LOCATION: (1)..(72)
<223> OTHER INFORMATION: 2OS-1-Oligo-A18; Biotin-C6 in 5'; n: any of A,
      T, G, C independently

<400> SEQUENCE: 68
gaagttccag ccagcgtcac agtttnnnnn ngctggatgt taataactgc ggtccgggtc    60
agcatcattt cc                                                       72

<210> SEQ ID NO 69
<211> LENGTH: 72
<212> TYPE: DNA
<213> ORGANISM: Artificial sequence
<220> FEATURE:
<223> OTHER INFORMATION: 2OS-1-Oligo-A19
<220> FEATURE:
<221> NAME/KEY: misc_feature
<222> LOCATION: (1)..(72)
<223> OTHER INFORMATION: 2OS-1-Oligo-A19; Biotin-C6 in 5'; n: any of A,
      T, G, C independently

<400> SEQUENCE: 69
gaagttccag ccagcgtcac agtttnnnnn nacgagttga catggacgga tccctcggtc    60
agcatcattt cc                                                       72

<210> SEQ ID NO 70
<211> LENGTH: 72
<212> TYPE: DNA
<213> ORGANISM: Artificial sequence
<220> FEATURE:
<223> OTHER INFORMATION: 2OS-1-Oligo-A20
<220> FEATURE:
<221> NAME/KEY: misc_feature
<222> LOCATION: (1)..(72)
<223> OTHER INFORMATION: 2OS-1-Oligo-A20; Biotin-C6 in 5'; n: any of A,
      T, G, C independently

<400> SEQUENCE: 70
gaagttccag ccagcgtcac agtttnnnnn nttcatcact cattgttctg agtagggtc     60 agcatcattt cc                                                       72

<210> SEQ ID NO 71
<211> LENGTH: 72
<212> TYPE: DNA
<213> ORGANISM: Artificial sequence
<220> FEATURE:
<223> OTHER INFORMATION: 2OS-1-Oligo-A21
<220> FEATURE:
<221> NAME/KEY: misc_feature
```

```
<222> LOCATION: (1)..(72)
<223> OTHER INFORMATION: 2OS-1-Oligo-A21; Biotin-C6 in 5'; n: any of A,
      T, G, C independently

<400> SEQUENCE: 71
gaagttccag ccagcgtcac agtttnnnnn natgtttaat ctaacttgat gcctccggtc     60
agcatcattt cc                                                        72

<210> SEQ ID NO 72
<211> LENGTH: 72
<212> TYPE: DNA
<213> ORGANISM: Artificial sequence
<220> FEATURE:
<223> OTHER INFORMATION: 2OS-1-Oligo-A22
<220> FEATURE:
<221> NAME/KEY: misc_feature
<222> LOCATION: (1)..(72)
<223> OTHER INFORMATION: 2OS-1-Oligo-A22; Biotin-C6 in 5'; n: any of A,
      T, G, C independently

<400> SEQUENCE: 72
gaagttccag ccagcgtcac agtttnnnnn ntaatacgcc tgaggtgttg ggttgcggtc     60
agcatcattt cc                                                        72

<210> SEQ ID NO 73
<211> LENGTH: 72
<212> TYPE: DNA
<213> ORGANISM: Artificial sequence
<220> FEATURE:
<223> OTHER INFORMATION: 2OS-1-Oligo-B1
<220> FEATURE:
<221> NAME/KEY: misc_feature
<222> LOCATION: (1)..(72)
<223> OTHER INFORMATION: 2OS-1-Oligo-B1; n: any of A, T, G, C
      independently

<400> SEQUENCE: 73
ctgtgactat gtgaggcttt ctcgannnnn ngcctgtagt cccacgcgat ctaacaggaa     60
atgatgctga cc                                                        72

<210> SEQ ID NO 74
<211> LENGTH: 72
<212> TYPE: DNA
<213> ORGANISM: Artificial sequence
<220> FEATURE:
<223> OTHER INFORMATION: 2OS-1-Oligo-B2
<220> FEATURE:
<221> NAME/KEY: misc_feature
<222> LOCATION: (1)..(72)
<223> OTHER INFORMATION: 2OS-1-Oligo-B2; n: any of A, T, G, C
      independently

<400> SEQUENCE: 74
ctgtgactat gtgaggcttt ctcgannnnn ncaaccattg attggggaca actgggggaa     60
atgatgctga cc                                                        72

<210> SEQ ID NO 75
<211> LENGTH: 72
<212> TYPE: DNA
<213> ORGANISM: Artificial sequence
<220> FEATURE:
<223> OTHER INFORMATION: 2OS-1-Oligo-B3
<220> FEATURE:
<221> NAME/KEY: misc_feature
<222> LOCATION: (1)..(72)
<223> OTHER INFORMATION: 2OS-1-Oligo-B3; n: any of A, T, G, C
      independently
```

<400> SEQUENCE: 75
ctgtgactat gtgaggcttt ctcgannnnn nacgtttaag catctgtact ccagatggaa    60
atgatgctga cc    72

<210> SEQ ID NO 76
<211> LENGTH: 72
<212> TYPE: DNA
<213> ORGANISM: Artificial sequence
<220> FEATURE:
<223> OTHER INFORMATION: 2OS-1-Oligo-B4
<220> FEATURE:
<221> NAME/KEY: misc_feature
<222> LOCATION: (1)..(72)
<223> OTHER INFORMATION: 2OS-1-Oligo-B4; n: any of A, T, G, C
      independently

<400> SEQUENCE: 76
ctgtgactat gtgaggcttt ctcgannnnn ngaattgaag ccatcgtttc gcgcaaggaa    60
atgatgctga cc    72

<210> SEQ ID NO 77
<211> LENGTH: 72
<212> TYPE: DNA
<213> ORGANISM: Artificial sequence
<220> FEATURE:
<223> OTHER INFORMATION: 2OS-1-Oligo-B5
<220> FEATURE:
<221> NAME/KEY: misc_feature
<222> LOCATION: (1)..(72)
<223> OTHER INFORMATION: 2OS-1-Oligo-B5; n: any of A, T, G, C
      independently

<400> SEQUENCE: 77
ctgtgactat gtgaggcttt ctcgannnnn ncgtagcttt tgtagcgtct gagggcggaa    60
atgatgctga cc    72

<210> SEQ ID NO 78
<211> LENGTH: 72
<212> TYPE: DNA
<213> ORGANISM: Artificial sequence
<220> FEATURE:
<223> OTHER INFORMATION: 2OS-1-Oligo-B6
<220> FEATURE:
<221> NAME/KEY: misc_feature
<222> LOCATION: (1)..(72)
<223> OTHER INFORMATION: 2OS-1-Oligo-B6; n: any of A, T, G, C
      independently

<400> SEQUENCE: 78
ctgtgactat gtgaggcttt ctcgannnnn naatcgtcag tccctgtttc gacatcggaa    60
atgatgctga cc    72

<210> SEQ ID NO 79
<211> LENGTH: 72
<212> TYPE: DNA
<213> ORGANISM: Artificial sequence
<220> FEATURE:
<223> OTHER INFORMATION: 2OS-1-Oligo-B7
<220> FEATURE:
<221> NAME/KEY: misc_feature
<222> LOCATION: (1)..(72)
<223> OTHER INFORMATION: 2OS-1-Oligo-B7; n: any of A, T, G, C
      independently

<400> SEQUENCE: 79

```
ctgtgactat gtgaggcttt ctcgannnnn ncggtggtag gtgatacttc tgtaccggaa    60
atgatgctga cc                                                         72
```

<210> SEQ ID NO 80
<211> LENGTH: 72
<212> TYPE: DNA
<213> ORGANISM: Artificial sequence
<220> FEATURE:
<223> OTHER INFORMATION: 2OS-1-Oligo-B8
<220> FEATURE:
<221> NAME/KEY: misc_feature
<222> LOCATION: (1)..(72)
<223> OTHER INFORMATION: 2OS-1-Oligo-B8; n: any of A, T, G, C
      independently

<400> SEQUENCE: 80

```
ctgtgactat gtgaggcttt ctcgannnnn ntgactatcg ggcgtgaca tgagctggaa     60 atgatgctga cc                                                         72
```

<210> SEQ ID NO 81
<211> LENGTH: 72
<212> TYPE: DNA
<213> ORGANISM: Artificial sequence
<220> FEATURE:
<223> OTHER INFORMATION: 2OS-1-Oligo-B9
<220> FEATURE:
<221> NAME/KEY: misc_feature
<222> LOCATION: (1)..(72)
<223> OTHER INFORMATION: 2OS-1-Oligo-B9; n: any of A, T, G, C
      independently

<400> SEQUENCE: 81

```
ctgtgactat gtgaggcttt ctcgannnnn ngttggtgaa actaccgacg ctttacggaa    60
atgatgctga cc                                                         72
```

<210> SEQ ID NO 82
<211> LENGTH: 72
<212> TYPE: DNA
<213> ORGANISM: Artificial sequence
<220> FEATURE:
<223> OTHER INFORMATION: 2OS-1-Oligo-B10
<220> FEATURE:
<221> NAME/KEY: misc_feature
<222> LOCATION: (1)..(72)
<223> OTHER INFORMATION: 2OS-1-Oligo-B10; n: any of A, T, G, C
      independently

<400> SEQUENCE: 82

```
ctgtgactat gtgaggcttt ctcgannnnn naatggaggt gcaggaatac tctcgtggaa    60
atgatgctga cc                                                         72
```

<210> SEQ ID NO 83
<211> LENGTH: 72
<212> TYPE: DNA
<213> ORGANISM: Artificial sequence
<220> FEATURE:
<223> OTHER INFORMATION: 2OS-1-Oligo-B11
<220> FEATURE:
<221> NAME/KEY: misc_feature
<222> LOCATION: (1)..(72)
<223> OTHER INFORMATION: 2OS-1-Oligo-B11; n: any of A, T, G, C
      independently

<400> SEQUENCE: 83

```
ctgtgactat gtgaggcttt ctcgannnnn naaaacgcac cacaactcgg acgtgaggaa    60
atgatgctga cc                                                         72
```

<210> SEQ ID NO 84
<211> LENGTH: 72
<212> TYPE: DNA
<213> ORGANISM: Artificial sequence
<220> FEATURE:
<223> OTHER INFORMATION: 2OS-1-Oligo-B12
<220> FEATURE:
<221> NAME/KEY: misc_feature
<222> LOCATION: (1)..(72)
<223> OTHER INFORMATION: 2OS-1-Oligo-B12; n: any of A, T, G, C
      independently

<400> SEQUENCE: 84
ctgtgactat gtgaggcttt ctcgannnnn ngccatataa gcacagcacg caatccggaa    60
atgatgctga cc                                                        72

<210> SEQ ID NO 85
<211> LENGTH: 72
<212> TYPE: DNA
<213> ORGANISM: Artificial sequence
<220> FEATURE:
<223> OTHER INFORMATION: 2OS-1-Oligo-B13
<220> FEATURE:
<221> NAME/KEY: misc_feature
<222> LOCATION: (1)..(72)
<223> OTHER INFORMATION: 2OS-1-Oligo-B13; n: any of A, T, G, C
      independently

<400> SEQUENCE: 85
ctgtgactat gtgaggcttt ctcgannnnn ncctatgcga acttggttta tcctgcggaa    60
atgatgctga cc                                                        72

<210> SEQ ID NO 86
<211> LENGTH: 72
<212> TYPE: DNA
<213> ORGANISM: Artificial sequence
<220> FEATURE:
<223> OTHER INFORMATION: 2OS-1-Oligo-B14
<220> FEATURE:
<221> NAME/KEY: misc_feature
<222> LOCATION: (1)..(72)
<223> OTHER INFORMATION: 2OS-1-Oligo-B14; n: any of A, T, G, C
      independently

<400> SEQUENCE: 86
ctgtgactat gtgaggcttt ctcgannnnn naagctgcgt atcctcgaac tagcagggaa    60
atgatgctga cc                                                        72

<210> SEQ ID NO 87
<211> LENGTH: 72
<212> TYPE: DNA
<213> ORGANISM: Artificial sequence
<220> FEATURE:
<223> OTHER INFORMATION: 2OS-1-Oligo-B15
<220> FEATURE:
<221> NAME/KEY: misc_feature
<222> LOCATION: (1)..(72)
<223> OTHER INFORMATION: 2OS-1-Oligo-B15; n: any of A, T, G, C
      independently

<400> SEQUENCE: 87
ctgtgactat gtgaggcttt ctcgannnnn natggcgcag acattctgta gtcgcaggaa    60
atgatgctga cc                                                        72

<210> SEQ ID NO 88

```
<211> LENGTH: 72
<212> TYPE: DNA
<213> ORGANISM: Artificial sequence
<220> FEATURE:
<223> OTHER INFORMATION: 2OS-1-Oligo-B16
<220> FEATURE:
<221> NAME/KEY: misc_feature
<222> LOCATION: (1)..(72)
<223> OTHER INFORMATION: 2OS-1-Oligo-B16

<400> SEQUENCE: 88
ctgtgactat gtgaggcttt ctcgannnnn ncttatggac tggttgggga caatccggaa    60
atgatgctga cc                                                        72

<210> SEQ ID NO 89
<211> LENGTH: 72
<212> TYPE: DNA
<213> ORGANISM: Artificial sequence
<220> FEATURE:
<223> OTHER INFORMATION: 2OS-1-Oligo-B17
<220> FEATURE:
<221> NAME/KEY: misc_feature
<222> LOCATION: (1)..(72)
<223> OTHER INFORMATION: 2OS-1-Oligo-B17; n: any of A, T, G, C
      independently

<400> SEQUENCE: 89
ctgtgactat gtgaggcttt ctcgannnnn ntgtccttcc ttacgaaata ttggtcggaa    60
atgatgctga cc                                                        72

<210> SEQ ID NO 90
<211> LENGTH: 72
<212> TYPE: DNA
<213> ORGANISM: Artificial sequence
<220> FEATURE:
<223> OTHER INFORMATION: 2OS-1-Oligo-B18
<220> FEATURE:
<221> NAME/KEY: misc_feature
<222> LOCATION: (1)..(72)
<223> OTHER INFORMATION: 2OS-1-Oligo-B18; n: any of A, T, G, C
      independently

<400> SEQUENCE: 90
ctgtgactat gtgaggcttt ctcgannnnn ntgatgaacc aatcctccga tttcttggaa    60
atgatgctga cc                                                        72

<210> SEQ ID NO 91
<211> LENGTH: 72
<212> TYPE: DNA
<213> ORGANISM: Artificial sequence
<220> FEATURE:
<223> OTHER INFORMATION: 2OS-1-Oligo-B19
<220> FEATURE:
<221> NAME/KEY: misc_feature
<222> LOCATION: (1)..(72)
<223> OTHER INFORMATION: 2OS-1-Oligo-B19; n: any of A, T, G, C
      independently

<400> SEQUENCE: 91
ctgtgactat gtgaggcttt ctcgannnnn naccgaatgt gggccacgag tcattcggaa    60
atgatgctga cc                                                        72

<210> SEQ ID NO 92
<211> LENGTH: 72
<212> TYPE: DNA
<213> ORGANISM: Artificial sequence
<220> FEATURE:
```

```
<223> OTHER INFORMATION: 2OS-1-Oligo-B20
<220> FEATURE:
<221> NAME/KEY: misc_feature
<222> LOCATION: (1)..(72)
<223> OTHER INFORMATION: 2OS-1-Oligo-B20; n: any of A, T, G, C
      independently

<400> SEQUENCE: 92
ctgtgactat gtgaggcttt ctcgannnnn ncgggtgagc atataacttg caattcggaa    60
atgatgctga cc                                                       72

<210> SEQ ID NO 93
<211> LENGTH: 72
<212> TYPE: DNA
<213> ORGANISM: Artificial sequence
<220> FEATURE:
<223> OTHER INFORMATION: 2OS-1-Oligo-B21
<220> FEATURE:
<221> NAME/KEY: misc_feature
<222> LOCATION: (1)..(72)
<223> OTHER INFORMATION: 2OS-1-Oligo-B21; n: any of A, T, G, C
      independently

<400> SEQUENCE: 93
ctgtgactat gtgaggcttt ctcgannnnn nagaattgtg cttggggcga ttcataggaa    60
atgatgctga cc                                                       72

<210> SEQ ID NO 94
<211> LENGTH: 72
<212> TYPE: DNA
<213> ORGANISM: Artificial sequence
<220> FEATURE:
<223> OTHER INFORMATION: 2OS-1-Oligo-B22
<220> FEATURE:
<221> NAME/KEY: misc_feature
<222> LOCATION: (1)..(72)
<223> OTHER INFORMATION: 2OS-1-Oligo-B22; n: any of A, T, G, C
      independently

<400> SEQUENCE: 94
ctgtgactat gtgaggcttt ctcgannnnn naattggtga catgcttaac taccgtggaa    60
atgatgctga cc                                                       72

<210> SEQ ID NO 95
<211> LENGTH: 72
<212> TYPE: DNA
<213> ORGANISM: Artificial sequence
<220> FEATURE:
<223> OTHER INFORMATION: 2OS-1-Oligo-B23
<220> FEATURE:
<221> NAME/KEY: misc_feature
<222> LOCATION: (1)..(72)
<223> OTHER INFORMATION: 2OS-1-Oligo-B23; n: any of A, T, G, C
      independently

<400> SEQUENCE: 95
ctgtgactat gtgaggcttt ctcgannnnn ngagacgcct agaaagtgat taactcggaa    60
atgatgctga cc                                                       72

<210> SEQ ID NO 96
<211> LENGTH: 72
<212> TYPE: DNA
<213> ORGANISM: Artificial sequence
<220> FEATURE:
<223> OTHER INFORMATION: 2OS-1-Oligo-B24
<220> FEATURE:
<221> NAME/KEY: misc_feature
```

```
<222> LOCATION: (1)..(72)
<223> OTHER INFORMATION: 2OS-1-Oligo-B24; n: any of A, T, G, C
      independently

<400> SEQUENCE: 96
ctgtgactat gtgaggcttt ctcgannnnn nattacagtt acagtgctgg tcgcagggaa    60
atgatgctga cc                                                       72

<210> SEQ ID NO 97
<211> LENGTH: 72
<212> TYPE: DNA
<213> ORGANISM: Artificial sequence
<220> FEATURE:
<223> OTHER INFORMATION: 2OS-1-Oligo-B25
<220> FEATURE:
<221> NAME/KEY: misc_feature
<222> LOCATION: (1)..(72)
<223> OTHER INFORMATION: 2OS-1-Oligo-B25; n: any of A, T, G, C
      independently

<400> SEQUENCE: 97
ctgtgactat gtgaggcttt ctcgannnnn ncgttacgtt ggtgggctct tggtacggaa    60
atgatgctga cc                                                       72

<210> SEQ ID NO 98
<211> LENGTH: 72
<212> TYPE: DNA
<213> ORGANISM: Artificial sequence
<220> FEATURE:
<223> OTHER INFORMATION: 2OS-1-Oligo-B26
<220> FEATURE:
<221> NAME/KEY: misc_feature
<222> LOCATION: (1)..(72)
<223> OTHER INFORMATION: 2OS-1-Oligo-B26; n: any of A, T, G, C
      independently

<400> SEQUENCE: 98
ctgtgactat gtgaggcttt ctcgannnnn ngttattatc ggtgtcccga ctagttggaa    60
atgatgctga cc                                                       72

<210> SEQ ID NO 99
<211> LENGTH: 72
<212> TYPE: DNA
<213> ORGANISM: Artificial sequence
<220> FEATURE:
<223> OTHER INFORMATION: 2OS-1-Oligo-B27
<220> FEATURE:
<221> NAME/KEY: misc_feature
<222> LOCATION: (1)..(72)
<223> OTHER INFORMATION: 2OS-1-Oligo-B27; n: any of A, T, G, C
      independently

<400> SEQUENCE: 99
ctgtgactat gtgaggcttt ctcgannnnn nagaaatgat tcccgagtcg cctttttggaa   60 atgatgctga cc                                                       72

<210> SEQ ID NO 100
<211> LENGTH: 72
<212> TYPE: DNA
<213> ORGANISM: Artificial sequence
<220> FEATURE:
<223> OTHER INFORMATION: 2OS-1-Oligo-B28
<220> FEATURE:
<221> NAME/KEY: misc_feature
<222> LOCATION: (1)..(72)
<223> OTHER INFORMATION: 2OS-1-Oligo-B28; n: any of A, T, G, C
      independently
```

<400> SEQUENCE: 100
ctgtgactat gtgaggcttt ctcgannnnn ntgctctcgg atgtggttct atggatggaa    60
atgatgctga cc    72

<210> SEQ ID NO 101
<211> LENGTH: 72
<212> TYPE: DNA
<213> ORGANISM: Artificial sequence
<220> FEATURE:
<223> OTHER INFORMATION: 2OS-1-Oligo-B29
<220> FEATURE:
<221> NAME/KEY: misc_feature
<222> LOCATION: (1)..(72)
<223> OTHER INFORMATION: 2OS-1-Oligo-B29; n: any of A, T, G, C
      independently

<400> SEQUENCE: 101
ctgtgactat gtgaggcttt ctcgannnnn ngagttaaaa ccgtcgccgt agcactggaa    60
atgatgctga cc    72

<210> SEQ ID NO 102
<211> LENGTH: 72
<212> TYPE: DNA
<213> ORGANISM: Artificial sequence
<220> FEATURE:
<223> OTHER INFORMATION: 2OS-1-Oligo-B30
<220> FEATURE:
<221> NAME/KEY: misc_feature
<222> LOCATION: (1)..(72)
<223> OTHER INFORMATION: 2OS-1-Oligo-B30; n: any of A, T, G, C
      independently

<400> SEQUENCE: 102
ctgtgactat gtgaggcttt ctcgannnnn ntgtacgcga tagtactcgg gtcctgggaa    60
atgatgctga cc    72

<210> SEQ ID NO 103
<211> LENGTH: 72
<212> TYPE: DNA
<213> ORGANISM: Artificial sequence
<220> FEATURE:
<223> OTHER INFORMATION: 2OS-1-Oligo-B31
<220> FEATURE:
<221> NAME/KEY: misc_feature
<222> LOCATION: (1)..(72)
<223> OTHER INFORMATION: 2OS-1-Oligo-B31; n: any of A, T, G, C
      independently

<400> SEQUENCE: 103
ctgtgactat gtgaggcttt ctcgannnnn naacttacgc ccagcaaggc attcatggaa    60
atgatgctga cc    72

<210> SEQ ID NO 104
<211> LENGTH: 72
<212> TYPE: DNA
<213> ORGANISM: Artificial sequence
<220> FEATURE:
<223> OTHER INFORMATION: 2OS-1-Oligo-B32
<220> FEATURE:
<221> NAME/KEY: misc_feature
<222> LOCATION: (1)..(72)
<223> OTHER INFORMATION: 2OS-1-Oligo-B32; n: any of A, T, G, C
      independently

<400> SEQUENCE: 104
ctgtgactat gtgaggcttt ctcgannnnn nagcatggca caagaggagc acttcaggaa    60
atgatgctga cc                                                       72

<210> SEQ ID NO 105
<211> LENGTH: 72
<212> TYPE: DNA
<213> ORGANISM: Artificial sequence
<220> FEATURE:
<223> OTHER INFORMATION: 2OS-1-Oligo-B33
<220> FEATURE:
<221> NAME/KEY: misc_feature
<222> LOCATION: (1)..(72)
<223> OTHER INFORMATION: 2OS-1-Oligo-B33; n: any of A, T, G, C
      independently

<400> SEQUENCE: 105
ctgtgactat gtgaggcttt ctcgannnnn ncgatcgtga gtttgcagcg tgacgaggaa    60
atgatgctga cc                                                       72

<210> SEQ ID NO 106
<211> LENGTH: 72
<212> TYPE: DNA
<213> ORGANISM: Artificial sequence
<220> FEATURE:
<223> OTHER INFORMATION: 2OS-1-Oligo-B34
<220> FEATURE:
<221> NAME/KEY: misc_feature
<222> LOCATION: (1)..(72)
<223> OTHER INFORMATION: 2OS-1-Oligo-B34; n: any of A, T, G, C
      independently

<400> SEQUENCE: 106
ctgtgactat gtgaggcttt ctcgannnnn nacagctcca gcctcccttt gtttgtggaa    60
atgatgctga cc                                                       72

<210> SEQ ID NO 107
<211> LENGTH: 72
<212> TYPE: DNA
<213> ORGANISM: Artificial sequence
<220> FEATURE:
<223> OTHER INFORMATION: 2OS-1-Oligo-B35
<220> FEATURE:
<221> NAME/KEY: misc_feature
<222> LOCATION: (1)..(72)
<223> OTHER INFORMATION: 2OS-1-Oligo-B35; n: any of A, T, G, C
      independently

<400> SEQUENCE: 107
ctgtgactat gtgaggcttt ctcgannnnn naaacctttg ttcgggcgtc taccatggaa    60
atgatgctga cc                                                       72

<210> SEQ ID NO 108
<211> LENGTH: 72
<212> TYPE: DNA
<213> ORGANISM: Artificial sequence
<220> FEATURE:
<223> OTHER INFORMATION: 2OS-1-Oligo-B36
<220> FEATURE:
<221> NAME/KEY: misc_feature
<222> LOCATION: (1)..(72)
<223> OTHER INFORMATION: 2OS-1-Oligo-B36; n: any of A, T, G, C
      independently

<400> SEQUENCE: 108
ctgtgactat gtgaggcttt ctcgannnnn ntctttcaaa acagcgggag tcatcgggaa    60
atgatgctga cc                                                       72

<210> SEQ ID NO 109
<211> LENGTH: 72
<212> TYPE: DNA
<213> ORGANISM: Artificial sequence
<220> FEATURE:
<223> OTHER INFORMATION: 2OS-1-Oligo-B37
<220> FEATURE:
<221> NAME/KEY: misc_feature
<222> LOCATION: (1)..(72)
<223> OTHER INFORMATION: 2OS-1-Oligo-B37; n: any of A, T, G, C
      independently

<400> SEQUENCE: 109
ctgtgactat gtgaggcttt ctcgannnnn ngcggtttat ccgaatctca cgctaaggaa    60
atgatgctga cc                                                       72

<210> SEQ ID NO 110
<211> LENGTH: 72
<212> TYPE: DNA
<213> ORGANISM: Artificial sequence
<220> FEATURE:
<223> OTHER INFORMATION: 2OS-1-Oligo-B38
<220> FEATURE:
<221> NAME/KEY: misc_feature
<222> LOCATION: (1)..(72)
<223> OTHER INFORMATION: 2OS-1-Oligo-B38; n: any of A, T, G, C
      independently

<400> SEQUENCE: 110
ctgtgactat gtgaggcttt ctcgannnnn ngcatatgct acaggctggg gtgaacggaa    60
atgatgctga cc                                                       72

<210> SEQ ID NO 111
<211> LENGTH: 72
<212> TYPE: DNA
<213> ORGANISM: Artificial sequence
<220> FEATURE:
<223> OTHER INFORMATION: 2OS-1-Oligo-B39
<220> FEATURE:
<221> NAME/KEY: misc_feature
<222> LOCATION: (1)..(72)
<223> OTHER INFORMATION: 2OS-1-Oligo-B39; n: any of A, T, G, C
      independently

<400> SEQUENCE: 111
ctgtgactat gtgaggcttt ctcgannnnn nggaggtcta aacgtccgga gctattggaa    60
atgatgctga cc                                                       72

<210> SEQ ID NO 112
<211> LENGTH: 72
<212> TYPE: DNA
<213> ORGANISM: Artificial sequence
<220> FEATURE:
<223> OTHER INFORMATION: 2OS-1-Oligo-B40
<220> FEATURE:
<221> NAME/KEY: misc_feature
<222> LOCATION: (1)..(72)
<223> OTHER INFORMATION: 2OS-1-Oligo-B40; n: any of A, T, G, C
      independently

<400> SEQUENCE: 112
ctgtgactat gtgaggcttt ctcgannnnn naagaataag attgcgtgcg ccttaaggaa    60
atgatgctga cc                                                       72

<210> SEQ ID NO 113

```
<211> LENGTH: 72
<212> TYPE: DNA
<213> ORGANISM: Artificial sequence
<220> FEATURE:
<223> OTHER INFORMATION: 2OS-1-Oligo-B41
<220> FEATURE:
<221> NAME/KEY: misc_feature
<222> LOCATION: (1)..(72)
<223> OTHER INFORMATION: 2OS-1-Oligo-B41; n: any of A, T, G, C
      independently

<400> SEQUENCE: 113
ctgtgactat gtgaggcttt ctcgannnnn ncatcatcgt cgtccaaata tgtgatggaa     60
atgatgctga cc                                                        72

<210> SEQ ID NO 114
<211> LENGTH: 72
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(72)
<223> OTHER INFORMATION: 2OS-1-Oligo-B42; n: any of A, T, G, C
      independently

<400> SEQUENCE: 114
ctgtgactat gtgaggcttt ctcgannnnn ncacgtgtag ctgtgggcca agtctaggaa     60
atgatgctga cc                                                        72

<210> SEQ ID NO 115
<211> LENGTH: 72
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(72)
<223> OTHER INFORMATION: 2OS-1-Oligo-B43; n: any of A, T, G, C
      independently

<400> SEQUENCE: 115
ctgtgactat gtgaggcttt ctcgannnnn ncagttgtca aatctccgca ttggtaggaa     60
atgatgctga cc                                                        72

<210> SEQ ID NO 116
<211> LENGTH: 72
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(72)
<223> OTHER INFORMATION: 2OS-1-Oligo-B44; n: any of A, T, G, C
      independently

<400> SEQUENCE: 116
ctgtgactat gtgaggcttt ctcgannnnn nactggtaat gccattggtc taaatgggaa     60
atgatgctga cc                                                        72

<210> SEQ ID NO 117
<211> LENGTH: 72
<212> TYPE: DNA
<213> ORGANISM: Artificial sequence
```

```
<220> FEATURE:
<223> OTHER INFORMATION: Artificial sequence
<220> FEATURE:
<221> NAME/KEY: misc_feature
<222> LOCATION: (1)..(72)
<223> OTHER INFORMATION: 2OS-1-Oligo-B45; n: any of A, T, G, C
      independently

<400> SEQUENCE: 117
ctgtgactat gtgaggcttt ctcgannnnn ngtctttggt cgtaacgaat ctccgtggaa      60
atgatgctga cc                                                         72

<210> SEQ ID NO 118
<211> LENGTH: 72
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(72)
<223> OTHER INFORMATION: 2OS-1-Oligo-B46; n: any of A, T, G, C
      independently

<400> SEQUENCE: 118
ctgtgactat gtgaggcttt ctcgannnnn ncttaggcat gacggggttg tccatgggaa      60
atgatgctga cc                                                         72

<210> SEQ ID NO 119
<211> LENGTH: 72
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(72)
<223> OTHER INFORMATION: 2OS-1-Oligo-B47; n: any of A, T, G, C
      independently

<400> SEQUENCE: 119
ctgtgactat gtgaggcttt ctcgannnnn nccggtgaat tttgggtgtc catgtaggaa      60
atgatgctga cc                                                         72

<210> SEQ ID NO 120
<211> LENGTH: 72
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(72)
<223> OTHER INFORMATION: 2OS-1-Oligo-B48; n: any of A, T, G, C
      independently

<400> SEQUENCE: 120
ctgtgactat gtgaggcttt ctcgannnnn ncctttatct cctccaccta taaggtggaa      60
atgatgctga cc                                                         72

<210> SEQ ID NO 121
<211> LENGTH: 72
<212> TYPE: DNA
<213> ORGANISM: Artificial sequence
<220> FEATURE:
<223> OTHER INFORMATION: Artificial sequence
<220> FEATURE:
```

```
<221> NAME/KEY: misc_feature
<222> LOCATION: (1)..(72)
<223> OTHER INFORMATION: 2OS-1-Oligo-B49; n: any of A, T, G, C
      independently

<400> SEQUENCE: 121
ctgtgactat gtgaggcttt ctcgannnnn ngatactata tgacggcctg taatcgggaa     60
atgatgctga cc                                                         72

<210> SEQ ID NO 122
<211> LENGTH: 72
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(72)
<223> OTHER INFORMATION: 2OS-1-Oligo-B50; n: any of A, T, G, C
      independently

<400> SEQUENCE: 122
ctgtgactat gtgaggcttt ctcgannnnn nattggttgg ccgaaagact acatctggaa     60
atgatgctga cc                                                         72

<210> SEQ ID NO 123
<211> LENGTH: 72
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(72)
<223> OTHER INFORMATION: 2OS-1-Oligo-B51; n: any of A, T, G, C
      independently

<400> SEQUENCE: 123
ctgtgactat gtgaggcttt ctcgannnnn ncgtagttat ggggtgggtc acctgcggaa     60
atgatgctga cc                                                         72

<210> SEQ ID NO 124
<211> LENGTH: 72
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(72)
<223> OTHER INFORMATION: 2OS-1-Oligo-B52; n: any of A, T, G, C
      independently

<400> SEQUENCE: 124
ctgtgactat gtgaggcttt ctcgannnnn naagtttcca ggcactgatt cgttccggaa     60
atgatgctga cc                                                         72

<210> SEQ ID NO 125
<211> LENGTH: 72
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(72)
<223> OTHER INFORMATION: 2OS-1-Oligo-B53; n: any of A, T, G, C
``` independently

<400> SEQUENCE: 125
ctgtgactat gtgaggcttt ctcgannnnn nttccttatt tcccggttga gatacaggaa      60
atgatgctga cc                                                          72

<210> SEQ ID NO 126
<211> LENGTH: 72
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(72)
<223> OTHER INFORMATION: 2OS-1-Oligo-B54; n: any of A, T, G, C
      independently

<400> SEQUENCE: 126
ctgtgactat gtgaggcttt ctcgannnnn naggtatcat gcgggccgaa tcttggggaa      60
atgatgctga cc                                                          72

<210> SEQ ID NO 127
<211> LENGTH: 72
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(72)
<223> OTHER INFORMATION: 2OS-1-Oligo-B55; n: any of A, T, G, C
      independently

<400> SEQUENCE: 127
ctgtgactat gtgaggcttt ctcgannnnn natacccgta ggccagtacc ctctccggaa      60
atgatgctga cc                                                          72

<210> SEQ ID NO 128
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-1; Biotin-C6 in 5'; n: any of A, T,
      G, C independently

<400> SEQUENCE: 128
agattctata aactgtgcgg tccttnnnnn ntatgaggac gaatctcccg cttataggta      60
cggcgctatc atgtactcat g                                                81

<210> SEQ ID NO 129
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-2; Biotin-C6 in 5';  n: any of A,
      T, G, C independently

<400> SEQUENCE: 129
agattctata aactgtgcgg tccttnnnnn nggtcttgac aaacgtgtgc ttgtacggta    60
cggcgctatc atgtactcat g                                              81

<210> SEQ ID NO 130
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-3; Biotin-C6 in 5'; n: any of A, T,
      G, C independently

<400> SEQUENCE: 130
agattctata aactgtgcgg tccttnnnnn ngtttatcgg gcgtggtgct cgcataggta    60
cggcgctatc atgtactcat g                                              81

<210> SEQ ID NO 131
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-4; Biotin-C6 in 5'; n: any of A, T,
      G, C independently

<400> SEQUENCE: 131
agattctata aactgtgcgg tccttnnnnn nccgatgttg acggactaat cctgacggta    60
cggcgctatc atgtactcat g                                              81

<210> SEQ ID NO 132
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-5; Biotin-C6 in 5'; n: any of A, T,
      G, C independently

<400> SEQUENCE: 132
agattctata aactgtgcgg tccttnnnnn ntagtagttc agacgccgtt aagcgcggta    60
cggcgctatc atgtactcat g                                              81

<210> SEQ ID NO 133
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-6; Biotin-C6 in 5'; n: any of A, T,
      G, C independently

<400> SEQUENCE: 133
agattctata aactgtgcgg tccttnnnnn nccgtaccta gatacactca atttgtggta    60
cggcgctatc atgtactcat g                                          81

<210> SEQ ID NO 134
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 10S-1-Oligo-7; Biotin-C6 in 5'; n: any of A, T,
      G, C independently

<400> SEQUENCE: 134
agattctata aactgtgcgg tccttnnnnn ngggttccg ttttacattc caggaaggta    60
cggcgctatc atgtactcat g                                          81

<210> SEQ ID NO 135
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 10S-1-Oligo-8; Biotin-C6 in 5'; n: any of A, T,
      G, C independently

<400> SEQUENCE: 135
agattctata aactgtgcgg tccttnnnnn ntatcccgtg aagcttgagt ggaatcggta    60
cggcgctatc atgtactcat g                                          81

<210> SEQ ID NO 136
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 10S-1-Oligo-9; Biotin-C6 in 5'; n: any of A, T,
      G, C independently

<400> SEQUENCE: 136
agattctata aactgtgcgg tccttnnnnn nctgacgtgt gaggcgctag agcataggta    60
cggcgctatc atgtactcat g                                          81

<210> SEQ ID NO 137
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 10S-1-Oligo-10; Biotin-C6 in 5'; n: any of A,
      T, G, C independently

<400> SEQUENCE: 137
agattctata aactgtgcgg tccttnnnnn nggtatggca cgcctaatct ggacacggta    60
cggcgctatc atgtactcat g                                          81

```
<210> SEQ ID NO 138
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-11; Biotin-C6 in 5'; n: any of A,
      T, G, C independently

<400> SEQUENCE: 138
agattctata aactgtgcgg tccttnnnnn nggatgcatg atctagggcc tcgtctggta      60
cggcgctatc atgtactcat g                                               81

<210> SEQ ID NO 139
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-12; Biotin-C6 in 5'; n: any of A,
      T, G, C independently

<400> SEQUENCE: 139
agattctata aactgtgcgg tccttnnnnn ngaggtcttt catgcgtata gtcacaggta      60
cggcgctatc atgtactcat g                                               81

<210> SEQ ID NO 140
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-13; Biotin-C6 in 5'; n: any of A,
      T, G, C independently

<400> SEQUENCE: 140
agattctata aactgtgcgg tccttnnnnn ngattcaata tgtgtcgtct atcctcggta      60
cggcgctatc atgtactcat g                                               81

<210> SEQ ID NO 141
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-14; Biotin-C6 in 5'; n: any of A,
      T, G, C independently

<400> SEQUENCE: 141
agattctata aactgtgcgg tccttnnnnn nggtaactgc gcatagttgg ctctatggta      60
cggcgctatc atgtactcat g                                               81

<210> SEQ ID NO 142
<211> LENGTH: 81
<212> TYPE: DNA
```

<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-15; Biotin-C6 in 5'; n: any of A,
    T, G, C independently

<400> SEQUENCE: 142
agattctata aactgtgcgg tccttnnnnn ngcgtttaag gtcacatcgc atgaatggta    60
cggcgctatc atgtactcat g                                              81

<210> SEQ ID NO 143
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-16; Biotin-C6 in 5'; n: any of A,
    T, G, C independently

<400> SEQUENCE: 143
agattctata aactgtgcgg tccttnnnnn ngcccgggaa gtgtgaggat atacccggta    60
cggcgctatc atgtactcat g                                              81

<210> SEQ ID NO 144
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-17; Biotin-C6 in 5'; n: any of A,
    T, G, C independently

<400> SEQUENCE: 144
agattctata aactgtgcgg tccttnnnnn ngctcttaaa actggtatca cctgacggta    60
cggcgctatc atgtactcat g                                              81

<210> SEQ ID NO 145
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-18; Biotin-C6 in 5'; n: any of A,
    T, G, C independently

<400> SEQUENCE: 145
agattctata aactgtgcgg tccttnnnnn ngggtggtta gtgatttgcc cgtcacggta    60
cggcgctatc atgtactcat g                                              81

<210> SEQ ID NO 146
<211> LENGTH: 81
<212> TYPE: DNA
<213> ORGANISM: Artificial sequence
<220> FEATURE:
<223> OTHER INFORMATION: Artificial sequence

```
<220> FEATURE:
<221> NAME/KEY: misc_feature
<222> LOCATION: (1)..(81)
<223> OTHER INFORMATION: 1OS-1-Oligo-19; Biotin-C6 in 5'; n: any of A,
      T, G, C independently

<400> SEQUENCE: 146
agattctata aactgtgcgg tccttnnnnn ntagttggtg ggtttcccta ccgtgtggta    60
cggcgctatc atgtactcat g                                             81

<210> SEQ ID NO 147
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-20; Biotin-C6 in 5'; n: any of A,
      T, G, C independently

<400> SEQUENCE: 147
agattctata aactgtgcgg tccttnnnnn nggtacagta agtgagaatc ctctctggta    60
cggcgctatc atgtactcat g                                             81

<210> SEQ ID NO 148
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-21; Biotin-C6 in 5'; n: any of A,
      T, G, C independently

<400> SEQUENCE: 148
agattctata aactgtgcgg tccttnnnnn nggttctaag tttagcgtag ccggttggta    60
cggcgctatc atgtactcat g                                             81

<210> SEQ ID NO 149
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-22; Biotin-C6 in 5'; n: any of A,
      T, G, C independently

<400> SEQUENCE: 149
agattctata aactgtgcgg tccttnnnnn nctttaggtg ggtgcgattg ccagttggta    60
cggcgctatc atgtactcat g                                             81

<210> SEQ ID NO 150
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
```

```
<223> OTHER INFORMATION: 1OS-1-Oligo-23; Biotin-C6 in 5'; n: any of A,
      T, G, C independently

<400> SEQUENCE: 150
agattctata aactgtgcgg tccttnnnnn ngccaccttta acacgcgatg atattgggta    60
cggcgctatc atgtactcat g                                              81

<210> SEQ ID NO 151
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-24; Biotin-C6 in 5'; n: any of A,
      T, G, C independently

<400> SEQUENCE: 151
agattctata aactgtgcgg tccttnnnnn ngctattacg agcgcttgga tcccgtggta    60
cggcgctatc atgtactcat g                                              81

<210> SEQ ID NO 152
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-25; Biotin-C6 in 5'; n: any of A,
      T, G, C independently

<400> SEQUENCE: 152
agattctata aactgtgcgg tccttnnnnn ntatgttgtg ccttacgcct cgattaggta    60
cggcgctatc atgtactcat g                                              81

<210> SEQ ID NO 153
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-26; Biotin-C6 in 5'; n: any of A,
      T, G, C independently

<400> SEQUENCE: 153
agattctata aactgtgcgg tccttnnnnn nttaaccgaa ctgacggcca tcaaggggta    60
cggcgctatc atgtactcat g                                              81

<210> SEQ ID NO 154
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-27; Biotin-C6 in 5'; n: any of A,
      T, G, C independently
```

<400> SEQUENCE: 154
agattctata aactgtgcgg tccttnnnnn ngggtacatg cgccttactc cttgtgggta    60
cggcgctatc atgtactcat g    81

<210> SEQ ID NO 155
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-28; Biotin-C6 in 5'; n: any of A,
      T, G, C independently

<400> SEQUENCE: 155
agattctata aactgtgcgg tccttnnnnn nttctattct aagccggcgg tcatatggta    60
cggcgctatc atgtactcat g    81

<210> SEQ ID NO 156
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-29; Biotin-C6 in 5'; n: any of A,
      T, G, C independently

<400> SEQUENCE: 156
agattctata aactgtgcgg tccttnnnnn ngcttgatgc tttacaagat cgcgttggta    60
cggcgctatc atgtactcat g    81

<210> SEQ ID NO 157
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-30; Biotin-C6 in 5'; n: any of A,
      T, G, C independently

<400> SEQUENCE: 157
agattctata aactgtgcgg tccttnnnnn ntccaagtta gcttactcca tgccccggta    60
cggcgctatc atgtactcat g    81

<210> SEQ ID NO 158
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-31; Biotin-C6 in 5'; n: any of A,
      T, G, C independently

<400> SEQUENCE: 158
agattctata aactgtgcgg tccttnnnnn nagaactatt tcctggctgt tacgcgggta    60
cggcgctatc atgtactcat g                                            81

<210> SEQ ID NO 159
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-32; Biotin-C6 in 5'; n: any of A,
      T, G, C independently

<400> SEQUENCE: 159
agattctata aactgtgcgg tccttnnnnn ntcggtttca aggatgatcc gcgcttggta    60
cggcgctatc atgtactcat g                                            81

<210> SEQ ID NO 160
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-33; Biotin-C6 in 5'; n: any of A,
      T, G, C independently

<400> SEQUENCE: 160
agattctata aactgtgcgg tccttnnnnn nagagactgc ccgacacatc ttagtgggta    60
cggcgctatc atgtactcat g                                            81

<210> SEQ ID NO 161
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-34; Biotin-C6 in 5'; n: any of A,
      T, G, C independently

<400> SEQUENCE: 161
agattctata aactgtgcgg tccttnnnnn nctgttaatt aggctcggtc ggcctaggta    60
cggcgctatc atgtactcat g                                            81

<210> SEQ ID NO 162
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-35; Biotin-C6 in 5'; n: any of A,
      T, G, C independently

<400> SEQUENCE: 162
agattctata aactgtgcgg tccttnnnnn naggtagtcc tatgcgggct ttctctggta    60
cggcgctatc atgtactcat g                                            81

<210> SEQ ID NO 163
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-36; Biotin-C6 in 5'; n: any of A,
      T, G, C independently

<400> SEQUENCE: 163
agattctata aactgtgcgg tccttnnnnn nggcttggac tatagtcatc gcgtttggta      60
cggcgctatc atgtactcat g                                                81

<210> SEQ ID NO 164
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-37; Biotin-C6 in 5'; n: any of A,
      T, G, C independently

<400> SEQUENCE: 164
agattctata aactgtgcgg tccttnnnnn ncactgttta acaagcccgt cagtagggta      60
cggcgctatc atgtactcat g                                                81

<210> SEQ ID NO 165
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-38; Biotin-C6 in 5'; n: any of A,
      T, G, C independently

<400> SEQUENCE: 165
agattctata aactgtgcgg tccttnnnnn nacgtcgtat tatacccgcc atggaaggta      60
cggcgctatc atgtactcat g                                                81

<210> SEQ ID NO 166
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-39; Biotin-C6 in 5'; n: any of A,
      T, G, C independently

<400> SEQUENCE: 166
agattctata aactgtgcgg tccttnnnnn ntgcttaatt tacgaccgat gctgcgggta      60
cggcgctatc atgtactcat g                                                81

<210> SEQ ID NO 167
<211> LENGTH: 81

```
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-40; Biotin-C6 in 5'; n: any of A,
      T, G, C independently

<400> SEQUENCE: 167
agattctata aactgtgcgg tccttnnnnn ntccatagat ttctccgtga gtctttggta      60
cggcgctatc atgtactcat g                                                81

<210> SEQ ID NO 168
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-41; Biotin-C6 in 5'; n: any of A,
      T, G, C independently

<400> SEQUENCE: 168
agattctata aactgtgcgg tccttnnnnn ngtgccgcag acattgcata cgatatggta      60
cggcgctatc atgtactcat g                                                81

<210> SEQ ID NO 169
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-42; Biotin-C6 in 5'; n: any of A,
      T, G, C independently

<400> SEQUENCE: 169
agattctata aactgtgcgg tccttnnnnn ngcaggtcct aacccgcaac catttaggta      60
cggcgctatc atgtactcat g                                                81

<210> SEQ ID NO 170
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-43; Biotin-C6 in 5'; n: any of A,
      T, G, C independently

<400> SEQUENCE: 170
agattctata aactgtgcgg tccttnnnnn ntgcaccgtt catatgttat cgggacggta      60
cggcgctatc atgtactcat g                                                81

<210> SEQ ID NO 171
<211> LENGTH: 81
<212> TYPE: DNA
<213> ORGANISM: Artificial sequence
<220> FEATURE:
```

<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-44; Biotin-C6 in 5'; n: any of A,
      T, G, C independently

<400> SEQUENCE: 171
agattctata aactgtgcgg tccttnnnnn nagagactta cacccgtaga cgtcgggta      60 cggcgctatc atgtactcat g                                              81

<210> SEQ ID NO 172
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-45; Biotin-C6 in 5'; n: any of A,
      T, G, C independently

<400> SEQUENCE: 172
agattctata aactgtgcgg tccttnnnnn nataaaagaa accctccgca ttgtgtggta     60
cggcgctatc atgtactcat g                                              81

<210> SEQ ID NO 173
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-46; Biotin-C6 in 5'; n: any of A,
      T, G, C independently

<400> SEQUENCE: 173
agattctata aactgtgcgg tccttnnnnn nggtcccatc cgagcagatt tgactcggta     60
cggcgctatc atgtactcat g                                              81

<210> SEQ ID NO 174
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-47; Biotin-C6 in 5'; n: any of A,
      T, G, C independently

<400> SEQUENCE: 174
agattctata aactgtgcgg tccttnnnnn natgagctgt ctcgaaccga aggcacggta     60
cggcgctatc atgtactcat g                                              81

<210> SEQ ID NO 175
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature

```
<222> LOCATION: (1)..(81)
<223> OTHER INFORMATION: 1OS-1-Oligo-48; Biotin-C6 in 5'; n: any of A,
      T, G, C independently

<400> SEQUENCE: 175
agattctata aactgtgcgg tccttnnnnn ntcgggcggt tcaacttact ggtagaggta    60
cggcgctatc atgtactcat g                                             81

<210> SEQ ID NO 176
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-49; Biotin-C6 in 5'; n: any of A,
      T, G, C independently

<400> SEQUENCE: 176
agattctata aactgtgcgg tccttnnnnn ngggaaata acggatgcgc tcttgaggta     60
cggcgctatc atgtactcat g                                             81

<210> SEQ ID NO 177
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-50; Biotin-C6 in 5'; n: any of A,
      T, G, C independently

<400> SEQUENCE: 177
agattctata aactgtgcgg tccttnnnnn nacttcttct cggtcgcatg aggctgggta    60
cggcgctatc atgtactcat g                                             81

<210> SEQ ID NO 178
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-51; Biotin-C6 in 5'; n: any of A,
      T, G, C independently

<400> SEQUENCE: 178
agattctata aactgtgcgg tccttnnnnn nggatacata tacgctcgtc gggactggta    60
cggcgctatc atgtactcat g                                             81

<210> SEQ ID NO 179
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-52; Biotin-C6 in 5'; n: any of A,
      T, G, C independently
```

```
<400> SEQUENCE: 179
agattctata aactgtgcgg tccttnnnnn nccgggaagt gtcataactt gaagcgggta      60
cggcgctatc atgtactcat g                                               81

<210> SEQ ID NO 180
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-53; Biotin-C6 in 5'; n: any of A,
      T, G, C independently

<400> SEQUENCE: 180
agattctata aactgtgcgg tccttnnnnn nctcagcctg cctcgcttct gatattggta      60
cggcgctatc atgtactcat g                                               81

<210> SEQ ID NO 181
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-54; Biotin-C6 in 5'; n: any of A,
      T, G, C independently

<400> SEQUENCE: 181
agattctata aactgtgcgg tccttnnnnn nagggccaag tcgacctaga tggctaggta      60
cggcgctatc atgtactcat g                                               81

<210> SEQ ID NO 182
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-55; Biotin-C6 in 5'; n: any of A,
      T, G, C independently

<400> SEQUENCE: 182
agattctata aactgtgcgg tccttnnnnn nggtagggct actgttatcc tccgtcggta      60
cggcgctatc atgtactcat g                                               81

<210> SEQ ID NO 183
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-56; Biotin-C6 in 5'; n: any of A,
      T, G, C independently

<400> SEQUENCE: 183
```
agattctata aactgtgcgg tccttnnnnn ncgtacggct ggagagctgt atgtgggta    60 cggcgctatc atgtactcat g    81

<210> SEQ ID NO 184
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-57; Biotin-C6 in 5'; n: any of A,
      T, G, C independently

<400> SEQUENCE: 184
agattctata aactgtgcgg tccttnnnnn nacaggttgt attacttcgc gccttgggta    60
cggcgctatc atgtactcat g    81

<210> SEQ ID NO 185
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-58; Biotin-C6 in 5'; n: any of A,
      T, G, C independently

<400> SEQUENCE: 185
agattctata aactgtgcgg tccttnnnnn nctgggctca ttacaagtgt tgcataggta    60
cggcgctatc atgtactcat g    81

<210> SEQ ID NO 186
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-59; Biotin-C6 in 5'; n: any of A,
      T, G, C independently

<400> SEQUENCE: 186
agattctata aactgtgcgg tccttnnnnn nctaagtggc gccgattgtt tgtccaggta    60
cggcgctatc atgtactcat g    81

<210> SEQ ID NO 187
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-60; Biotin-C6 in 5'; n: any of A,
      T, G, C independently

<400> SEQUENCE: 187
agattctata aactgtgcgg tccttnnnnn ngtatatttt gctcccggcg acgagaggta    60
cggcgctatc atgtactcat g    81

<210> SEQ ID NO 188
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-61; Biotin-C6 in 5'; n: any of A,
      T, G, C independently

<400> SEQUENCE: 188
agattctata aactgtgcgg tccttnnnnn ngcaatttgc gcttgttcgg catagcggta      60
cggcgctatc atgtactcat g                                              81

<210> SEQ ID NO 189
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-62; Biotin-C6 in 5'; n: any of A,
      T, G, C independently

<400> SEQUENCE: 189
agattctata aactgtgcgg tccttnnnnn ngagtcgaat atccaccacc gtatggggta      60
cggcgctatc atgtactcat g                                              81

<210> SEQ ID NO 190
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-63; Biotin-C6 in 5'; n: any of A,
      T, G, C independently

<400> SEQUENCE: 190
agattctata aactgtgcgg tccttnnnnn nttgtggttt gggtcctcag aggagaggta      60
cggcgctatc atgtactcat g                                              81

<210> SEQ ID NO 191
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-64; Biotin-C6 in 5'; n: any of A,
      T, G, C independently

<400> SEQUENCE: 191
agattctata aactgtgcgg tccttnnnnn nggtacctag tctcgtaatc ataggaggta      60
cggcgctatc atgtactcat g                                              81

<210> SEQ ID NO 192

<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-65; Biotin-C6 in 5'; n: any of A,
      T, G, C independently

<400> SEQUENCE: 192
agattctata aactgtgcgg tccttnnnnn ngcggcatga tctaccttaa agcttgggta     60
cggcgctatc atgtactcat g                                              81

<210> SEQ ID NO 193
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-66; Biotin-C6 in 5'; n: any of A,
      T, G, C independently

<400> SEQUENCE: 193
agattctata aactgtgcgg tccttnnnnn nccggcgcag aagtttgaac gaaaagggta     60
cggcgctatc atgtactcat g                                              81

<210> SEQ ID NO 194
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-67; Biotin-C6 in 5'; n: any of A,
      T, G, C independently

<400> SEQUENCE: 194
agattctata aactgtgcgg tccttnnnnn natgcactat tttacgtatc ccgtgcggta     60
cggcgctatc atgtactcat g                                              81

<210> SEQ ID NO 195
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-68; Biotin-C6 in 5'; n: any of A,
      T, G, C independently

<400> SEQUENCE: 195
agattctata aactgtgcgg tccttnnnnn ngatagggtg actgctttcg cgtacaggta     60
cggcgctatc atgtactcat g                                              81

<210> SEQ ID NO 196
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-69; Biotin-C6 in 5'; n: any of A, T, G, C independently

<400> SEQUENCE: 196
agattctata aactgtgcgg tccttnnnnn ntatctggta gacatctcgg cacagaggta    60
cggcgctatc atgtactcat g                                              81

<210> SEQ ID NO 197
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-70; Biotin-C6 in 5'; n: any of A, T, G, C independently

<400> SEQUENCE: 197
agattctata aactgtgcgg tccttnnnnn ntcggggtgc ataatcact agtgctggta    60 cggcgctatc atgtactcat g                                              81

<210> SEQ ID NO 198
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-71; Biotin-C6 in 5'; n: any of A, T, G, C independently

<400> SEQUENCE: 198
agattctata aactgtgcgg tccttnnnnn ntagttctgg ctatacacac ttcggggta    60 cggcgctatc atgtactcat g                                              81

<210> SEQ ID NO 199
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-72; Biotin-C6 in 5'; n: any of A, T, G, C independently

<400> SEQUENCE: 199
agattctata aactgtgcgg tccttnnnnn ngcatagagt tacccgatgg attcgaggta    60
cggcgctatc atgtactcat g                                              81

<210> SEQ ID NO 200
<211> LENGTH: 81
<212> TYPE: DNA
<213> ORGANISM: Artificial sequence
<220> FEATURE:
<223> OTHER INFORMATION: Artificial sequence
<220> FEATURE:

```
<221> NAME/KEY: misc_feature
<222> LOCATION: (1)..(81)
<223> OTHER INFORMATION: 10S-1-Oligo-73; Biotin-C6 in 5'; n: any of A,
      T, G, C independently

<400> SEQUENCE: 200
agattctata aactgtgcgg tccttnnnnn ngttcatggt acaggcttct ttacggggta    60
cggcgctatc atgtactcat g                                             81

<210> SEQ ID NO 201
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 10S-1-Oligo-74; Biotin-C6 in 5'; n: any of A,
      T, G, C independently

<400> SEQUENCE: 201
agattctata aactgtgcgg tccttnnnnn ncgatctcgg gcctgggttt tgagtaggta    60
cggcgctatc atgtactcat g                                             81

<210> SEQ ID NO 202
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 10S-1-Oligo-75; Biotin-C6 in 5'; n: any of A,
      T, G, C independently

<400> SEQUENCE: 202
agattctata aactgtgcgg tccttnnnnn nattattcgt gacccaactc atcaggggta    60
cggcgctatc atgtactcat g                                             81

<210> SEQ ID NO 203
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 10S-1-Oligo-76; Biotin-C6 in 5'; n: any of A,
      T, G, C independently

<400> SEQUENCE: 203
agattctata aactgtgcgg tccttnnnnn nctgaatggt gaataatgcg ttcgccggta    60
cggcgctatc atgtactcat g                                             81

<210> SEQ ID NO 204
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 10S-1-Oligo-77; Biotin-C6 in 5'; n: any of A,
```

T, G, C independently

<400> SEQUENCE: 204
agattctata aactgtgcgg tccttnnnnn ngctattagt tgctacccca agaatcggta    60
cggcgctatc atgtactcat g    81

<210> SEQ ID NO 205
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-78; Biotin-C6 in 5'; n: any of A,
      T, G, C independently

<400> SEQUENCE: 205
agattctata aactgtgcgg tccttnnnnn nagaaagtct tggatacacg gccggggta    60 cggcgctatc atgtactcat g    81

<210> SEQ ID NO 206
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-79; Biotin-C6 in 5'; n: any of A,
      T, G, C independently

<400> SEQUENCE: 206
agattctata aactgtgcgg tccttnnnnn ngtgtgttcc tatgcacaat ttcataggta    60
cggcgctatc atgtactcat g    81

<210> SEQ ID NO 207
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-80; Biotin-C6 in 5'; n: any of A,
      T, G, C independently

<400> SEQUENCE: 207
agattctata aactgtgcgg tccttnnnnn ntacatggta ggggtctccg aaccgtggta    60
cggcgctatc atgtactcat g    81

<210> SEQ ID NO 208
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-81; Biotin-C6 in 5'; n: any of A,
      T, G, C independently

<400> SEQUENCE: 208
agattctata aactgtgcgg tccttnnnnn ntagggataa ctttcctccc acttggggta    60
cggcgctatc atgtactcat g                                              81

<210> SEQ ID NO 209
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-82; Biotin-C6 in 5'; n: any of A,
      T, G, C independently

<400> SEQUENCE: 209
agattctata aactgtgcgg tccttnnnnn ntctggtgtc tcacccatgg gatgtcggta    60
cggcgctatc atgtactcat g                                              81

<210> SEQ ID NO 210
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-83; Biotin-C6 in 5'; n: any of A,
      T, G, C independently

<400> SEQUENCE: 210
agattctata aactgtgcgg tccttnnnnn ntaacgattt tctcgcggga gtttcgggta    60
cggcgctatc atgtactcat g                                              81

<210> SEQ ID NO 211
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-84; Biotin-C6 in 5'; n: any of A,
      T, G, C independently

<400> SEQUENCE: 211
agattctata aactgtgcgg tccttnnnnn ncgagcctgg ttagcgccta caagagggta    60
cggcgctatc atgtactcat g                                              81

<210> SEQ ID NO 212
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-85; Biotin-C6 in 5'; n: any of A,
      T, G, C independently

<400> SEQUENCE: 212
agattctata aactgtgcgg tccttnnnnn ncgtagtaag atatgtagtc cacgtcggta    60

```
cggcgctatc atgtactcat g                                              81
```

<210> SEQ ID NO 213
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 10S-1-Oligo-86; Biotin-C6 in 5'; n: any of A, T, G, C independently

<400> SEQUENCE: 213

```
agattctata aactgtgcgg tccttnnnnn ntgttagttg ccccatatct ttacgcggta    60
cggcgctatc atgtactcat g                                              81
```

<210> SEQ ID NO 214
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 10S-1-Oligo-87; Biotin-C6 in 5'; n: any of A, T, G, C independently

<400> SEQUENCE: 214

```
agattctata aactgtgcgg tccttnnnnn ngctggattg tgattgtccg gatccgggta    60
cggcgctatc atgtactcat g                                              81
```

<210> SEQ ID NO 215
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 10S-1-Oligo-88; Biotin-C6 in 5'; n: any of A, T, G, C independently

<400> SEQUENCE: 215

```
agattctata aactgtgcgg tccttnnnnn ngggaggact gcggttcagc ttacaaggta    60
cggcgctatc atgtactcat g                                              81
```

<210> SEQ ID NO 216
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 10S-1-Oligo-89; Biotin-C6 in 5'; n: any of A, T, G, C independently

<400> SEQUENCE: 216

```
agattctata aactgtgcgg tccttnnnnn ngcgtaggtc tagttcagat tctataggta    60
cggcgctatc atgtactcat g                                              81
```

<210> SEQ ID NO 217
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-90; Biotin-C6 in 5'; n: any of A, T, G, C independently

<400> SEQUENCE: 217
agattctata aactgtgcgg tccttnnnnn ngtctacgtg gttctatacc attcgggta    60 cggcgctatc atgtactcat g                                             81

<210> SEQ ID NO 218
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-91; Biotin-C6 in 5'; n: any of A, T, G, C independently

<400> SEQUENCE: 218
agattctata aactgtgcgg tccttnnnnn naggctttac tacaatgcgt gggctcggta    60
cggcgctatc atgtactcat g                                             81

<210> SEQ ID NO 219
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-92; Biotin-C6 in 5'; n: any of A, T, G, C independently

<400> SEQUENCE: 219
agattctata aactgtgcgg tccttnnnnn nagcttgctg tatgggtcat gttcctggta    60
cggcgctatc atgtactcat g                                             81

<210> SEQ ID NO 220
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-93; Biotin-C6 in 5'; n: any of A, T, G, C independently

<400> SEQUENCE: 220
agattctata aactgtgcgg tccttnnnnn ntgctctaaa gacgcgagga ctacctggta    60
cggcgctatc atgtactcat g                                             81

<210> SEQ ID NO 221
<211> LENGTH: 81
<212> TYPE: DNA

<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-94; Biotin-C6 in 5'; n: any of A, T, G, C independently

<400> SEQUENCE: 221
agattctata aactgtgcgg tccttnnnnn ntgtacatgt catactcaag gctttaggta      60
cggcgctatc atgtactcat g                                                81

<210> SEQ ID NO 222
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-95; Biotin-C6 in 5'; n: any of A, T, G, C independently

<400> SEQUENCE: 222
agattctata aactgtgcgg tccttnnnnn nttgacatgt acgccatttg ggtcgcggta      60
cggcgctatc atgtactcat g                                                81

<210> SEQ ID NO 223
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-96; Biotin-C6 in 5'; n: any of A, T, G, C independently

<400> SEQUENCE: 223
agattctata aactgtgcgg tccttnnnnn ngcaattcag tacgatcgtg tagcggggta      60
cggcgctatc atgtactcat g                                                81

<210> SEQ ID NO 224
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-97; Biotin-C6 in 5'; n: any of A, T, G, C independently

<400> SEQUENCE: 224
agattctata aactgtgcgg tccttnnnnn ncgctgtcca aaggttcttc gtaacgggta      60
cggcgctatc atgtactcat g                                                81

<210> SEQ ID NO 225
<211> LENGTH: 81
<212> TYPE: DNA
<213> ORGANISM: Artificial sequence
<220> FEATURE:
<223> OTHER INFORMATION: Artificial sequence

```
<220> FEATURE:
<221> NAME/KEY: misc_feature
<222> LOCATION: (1)..(81)
<223> OTHER INFORMATION: 1OS-1-Oligo-98; Biotin-C6 in 5'; n: any of A,
      T, G, C independently

<400> SEQUENCE: 225
agattctata aactgtgcgg tccttnnnnn nttagacgag caggtttctt gcctatggta    60
cggcgctatc atgtactcat g                                              81

<210> SEQ ID NO 226
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-99; Biotin-C6 in 5'; n: any of A,
      T, G, C independently

<400> SEQUENCE: 226
agattctata aactgtgcgg tccttnnnnn ntcgtttgga gccgttcaca catgaaggta    60
cggcgctatc atgtactcat g                                              81

<210> SEQ ID NO 227
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-100; Biotin-C6 in 5'; n: any of A,
      T, G, C independently

<400> SEQUENCE: 227
agattctata aactgtgcgg tccttnnnnn nctgatcaac ttgcgcccag cgttatggta    60
cggcgctatc atgtactcat g                                              81

<210> SEQ ID NO 228
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-101; Biotin-C6 in 5'; n: any of A,
      T, G, C independently

<400> SEQUENCE: 228
agattctata aactgtgcgg tccttnnnnn ngacgatgtt gcctgttttg atacgaggta    60
cggcgctatc atgtactcat g                                              81

<210> SEQ ID NO 229
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
```

```
<223> OTHER INFORMATION: 1OS-1-Oligo-102; Biotin-C6 in 5'; n: any of A,
      T, G, C independently

<400> SEQUENCE: 229
agattctata aactgtgcgg tccttnnnnn ngggtagtcg tgaggtgaac tcttccggta    60
cggcgctatc atgtactcat g                                             81

<210> SEQ ID NO 230
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-102; Biotin-C6 in 5'; n: any of A,
      T, G, C independently

<400> SEQUENCE: 230
agattctata aactgtgcgg tccttnnnnn nagccatttt acgattctat tcgatgggta    60
cggcgctatc atgtactcat g                                             81

<210> SEQ ID NO 231
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-104; Biotin-C6 in 5'; n: any of A,
      T, G, C independently

<400> SEQUENCE: 231
agattctata aactgtgcgg tccttnnnnn ngtggtttat ataatcccac ctcctaggta    60
cggcgctatc atgtactcat g                                             81

<210> SEQ ID NO 232
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-105; Biotin-C6 in 5'; n: any of A,
      T, G, C independently

<400> SEQUENCE: 232
agattctata aactgtgcgg tccttnnnnn ngcgaagaac atcccggcat ttcatgggta    60
cggcgctatc atgtactcat g                                             81

<210> SEQ ID NO 233
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-106; Biotin-C6 in 5'; n: any of A,
      T, G, C independently
```

<400> SEQUENCE: 233
agattctata aactgtgcgg tccttnnnnn ngctgggaca atgccgaaaa ctcttcggta    60
cggcgctatc atgtactcat g    81

<210> SEQ ID NO 234
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-107; Biotin-C6 in 5'; n: any of A,
      T, G, C independently

<400> SEQUENCE: 234
agattctata aactgtgcgg tccttnnnnn nattccgtac caacccgcgt cttagaggta    60
cggcgctatc atgtactcat g    81

<210> SEQ ID NO 235
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-108; Biotin-C6 in 5'; n: any of A,
      T, G, C independently

<400> SEQUENCE: 235
agattctata aactgtgcgg tccttnnnnn nctgcaggag gctctaatgc actcaaggta    60
cggcgctatc atgtactcat g    81

<210> SEQ ID NO 236
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-109; Biotin-C6 in 5'; n: any of A,
      T, G, C independently

<400> SEQUENCE: 236
agattctata aactgtgcgg tccttnnnnn ngcgttcagc attcattacg tctcacggta    60
cggcgctatc atgtactcat g    81

<210> SEQ ID NO 237
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-110; Biotin-C6 in 5'; n: any of A,
      T, G, C independently

<400> SEQUENCE: 237
agattctata aactgtgcgg tccttnnnnn ngctgaggaa gcccaatgtt cagtacggta    60

```
cggcgctatc atgtactcat g                                           81
```

<210> SEQ ID NO 238
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-111; Biotin-C6 in 5'; n: any of A,
      T, G, C independently

<400> SEQUENCE: 238

```
agattctata aactgtgcgg tccttnnnnn ngtaaccttagcacgccgga gtggagggta   60 cggcgctatc atgtactcat g                                           81
```

<210> SEQ ID NO 239
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-112; Biotin-C6 in 5'; n: any of A,
      T, G, C independently

<400> SEQUENCE: 239

```
agattctata aactgtgcgg tccttnnnnn ngcgattagt tctgttgcta aaccagggta   60
cggcgctatc atgtactcat g                                           81
```

<210> SEQ ID NO 240
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-113; Biotin-C6 in 5'; n: any of A,
      T, G, C independently

<400> SEQUENCE: 240

```
agattctata aactgtgcgg tccttnnnnn nccttatgag agctcgttgt tcggtgggta   60
cggcgctatc atgtactcat g                                           81
```

<210> SEQ ID NO 241
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-114; Biotin-C6 in 5'; n: any of A,
      T, G, C independently

<400> SEQUENCE: 241

```
agattctata aactgtgcgg tccttnnnnn ncttaaaggt gattcacacg tgtgccggta   60
cggcgctatc atgtactcat g                                           81
```

<210> SEQ ID NO 242
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-115; Biotin-C6 in 5'; n: any of A,
    T, G, C independently

<400> SEQUENCE: 242
agattctata aactgtgcgg tccttnnnnn nttactgagt aacgttctac cccgaaggta    60
cggcgctatc atgtactcat g                                              81

<210> SEQ ID NO 243
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-116; Biotin-C6 in 5'; n: any of A,
    T, G, C independently

<400> SEQUENCE: 243
agattctata aactgtgcgg tccttnnnnn natacttatt ccgctcattg cacaggggta    60
cggcgctatc atgtactcat g                                              81

<210> SEQ ID NO 244
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-117; Biotin-C6 in 5'; n: any of A,
    T, G, C independently

<400> SEQUENCE: 244
agattctata aactgtgcgg tccttnnnnn ntgaaaccaa tttcacctca gcggcgggta    60
cggcgctatc atgtactcat g                                              81

<210> SEQ ID NO 245
<211> LENGTH: 81
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(81)
<223> OTHER INFORMATION: 1OS-1-Oligo-118; Biotin-C6 in 5'; n: any of A,
    T, G, C independently

<400> SEQUENCE: 245
agattctata aactgtgcgg tccttnnnnn ngcgatcggt aggtaccttt tcagtaggta    60
cggcgctatc atgtactcat g                                              81

<210> SEQ ID NO 246
<211> LENGTH: 58

<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-16

<400> SEQUENCE: 246
ccatctcatc cctgcgtgtc tccgactcag tgttgcgtta gaagttccag ccagcgtc     58

<210> SEQ ID NO 247
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-17

<400> SEQUENCE: 247
ccatctcatc cctgcgtgtc tccgactcag tgcgagcgag gaagttccag ccagcgtc     58

<210> SEQ ID NO 248
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-18

<400> SEQUENCE: 248
ccatctcatc cctgcgtgtc tccgactcag tgcgactctg gaagttccag ccagcgtc     58

<210> SEQ ID NO 249
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-19

<400> SEQUENCE: 249
ccatctcatc cctgcgtgtc tccgactcag tgatccgtcc gaagttccag ccagcgtc     58

<210> SEQ ID NO 250
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-20

<400> SEQUENCE: 250
ccatctcatc cctgcgtgtc tccgactcag tgttaaacga gaagttccag ccagcgtc     58

<210> SEQ ID NO 251

```
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-21

<400> SEQUENCE: 251
ccatctcatc cctgcgtgtc tccgactcag tgtagctttt gaagttccag ccagcgtc      58

<210> SEQ ID NO 252
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-22

<400> SEQUENCE: 252
ccatctcatc cctgcgtgtc tccgactcag tgcacatgta gaagttccag ccagcgtc      58

<210> SEQ ID NO 253
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-23

<400> SEQUENCE: 253
ccatctcatc cctgcgtgtc tccgactcag tggatagcca gaagttccag ccagcgtc      58

<210> SEQ ID NO 254
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-24

<400> SEQUENCE: 254
ccatctcatc cctgcgtgtc tccgactcag tgacctgtta gaagttccag ccagcgtc      58

<210> SEQ ID NO 255
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-25

<400> SEQUENCE: 255
ccatctcatc cctgcgtgtc tccgactcag tgtgcgaatt gaagttccag ccagcgtc      58
```

```
<210> SEQ ID NO 256
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-26

<400> SEQUENCE: 256
ccatctcatc cctgcgtgtc tccgactcag tggtacattt gaagttccag ccagcgtc        58

<210> SEQ ID NO 257
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-27

<400> SEQUENCE: 257
ccatctcatc cctgcgtgtc tccgactcag tgctattgca gaagttccag ccagcgtc        58

<210> SEQ ID NO 258
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-28

<400> SEQUENCE: 258
ccatctcatc cctgcgtgtc tccgactcag tgacgataca gaagttccag ccagcgtc        58

<210> SEQ ID NO 259
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-29

<400> SEQUENCE: 259
ccatctcatc cctgcgtgtc tccgactcag tgcttagcgc gaagttccag ccagcgtc        58

<210> SEQ ID NO 260
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-30

<400> SEQUENCE: 260
ccatctcatc cctgcgtgtc tccgactcag tgcggaaacc gaagttccag ccagcgtc        58
```

<210> SEQ ID NO 261
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-31

<400> SEQUENCE: 261
ccatctcatc cctgcgtgtc tccgactcag tggatgttgg gaagttccag ccagcgtc        58

<210> SEQ ID NO 262
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-32

<400> SEQUENCE: 262
ccatctcatc cctgcgtgtc tccgactcag tgatcggcgt gaagttccag ccagcgtc        58

<210> SEQ ID NO 263
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-33

<400> SEQUENCE: 263
ccatctcatc cctgcgtgtc tccgactcag tgtagtacga gaagttccag ccagcgtc        58

<210> SEQ ID NO 264
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-34

<400> SEQUENCE: 264
ccatctcatc cctgcgtgtc tccgactcag tggacgtgat gaagttccag ccagcgtc        58

<210> SEQ ID NO 265
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-35

<400> SEQUENCE: 265
ccatctcatc cctgcgtgtc tccgactcag tgtgagccaa gaagttccag ccagcgtc        58

<210> SEQ ID NO 266
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-36

<400> SEQUENCE: 266
ccatctcatc cctgcgtgtc tccgactcag tgcctcgcag gaagttccag ccagcgtc       58

<210> SEQ ID NO 267
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-37

<400> SEQUENCE: 267
ccatctcatc cctgcgtgtc tccgactcag tgagatccag gaagttccag ccagcgtc       58

<210> SEQ ID NO 268
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-38

<400> SEQUENCE: 268
ccatctcatc cctgcgtgtc tccgactcag tgttggctga gaagttccag ccagcgtc       58

<210> SEQ ID NO 269
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-39

<400> SEQUENCE: 269
ccatctcatc cctgcgtgtc tccgactcag tggaccgcta gaagttccag ccagcgtc       58

<210> SEQ ID NO 270
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-40

<400> SEQUENCE: 270
ccatctcatc cctgcgtgtc tccgactcag tggagcttaa gaagttccag ccagcgtc    58

<210> SEQ ID NO 271
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-41

<400> SEQUENCE: 271
ccatctcatc cctgcgtgtc tccgactcag tgggactggt gaagttccag ccagcgtc    58

<210> SEQ ID NO 272
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-42

<400> SEQUENCE: 272
ccatctcatc cctgcgtgtc tccgactcag tgtgggagtc gaagttccag ccagcgtc    58

<210> SEQ ID NO 273
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-43

<400> SEQUENCE: 273
ccatctcatc cctgcgtgtc tccgactcag tggcgatggc gaagttccag ccagcgtc    58

<210> SEQ ID NO 274
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-44

<400> SEQUENCE: 274
ccatctcatc cctgcgtgtc tccgactcag tgacttggtt gaagttccag ccagcgtc    58

<210> SEQ ID NO 275
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-45

<400> SEQUENCE: 275
ccatctcatc cctgcgtgtc tccgactcag tgatactcat gaagttccag ccagcgtc    58

<210> SEQ ID NO 276
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-46

<400> SEQUENCE: 276
ccatctcatc cctgcgtgtc tccgactcag tgtagtgtcc gaagttccag ccagcgtc    58

<210> SEQ ID NO 277
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-47

<400> SEQUENCE: 277
ccatctcatc cctgcgtgtc tccgactcag tggcatataa gaagttccag ccagcgtc    58

<210> SEQ ID NO 278
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-48

<400> SEQUENCE: 278
ccatctcatc cctgcgtgtc tccgactcag tgggcgattg gaagttccag ccagcgtc    58

<210> SEQ ID NO 279
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-49

<400> SEQUENCE: 279
ccatctcatc cctgcgtgtc tccgactcag tggggctgta gaagttccag ccagcgtc    58

<210> SEQ ID NO 280
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-50

```
<400> SEQUENCE: 280
ccatctcatc cctgcgtgtc tccgactcag tgcgctattt gaagttccag ccagcgtc        58

<210> SEQ ID NO 281
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-51

<400> SEQUENCE: 281
ccatctcatc cctgcgtgtc tccgactcag tggtactgca gaagttccag ccagcgtc        58

<210> SEQ ID NO 282
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-52

<400> SEQUENCE: 282
ccatctcatc cctgcgtgtc tccgactcag tgtgtctatg gaagttccag ccagcgtc        58

<210> SEQ ID NO 283
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-53

<400> SEQUENCE: 283
ccatctcatc cctgcgtgtc tccgactcag tgcgaatcac gaagttccag ccagcgtc        58

<210> SEQ ID NO 284
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-54

<400> SEQUENCE: 284
ccatctcatc cctgcgtgtc tccgactcag tgcgtcctaa gaagttccag ccagcgtc        58

<210> SEQ ID NO 285
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-55
```

<400> SEQUENCE: 285
ccatctcatc cctgcgtgtc tccgactcag tgacaaatgg gaagttccag ccagcgtc        58

<210> SEQ ID NO 286
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-56

<400> SEQUENCE: 286
ccatctcatc cctgcgtgtc tccgactcag tgtctacttt gaagttccag ccagcgtc        58

<210> SEQ ID NO 287
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-57

<400> SEQUENCE: 287
ccatctcatc cctgcgtgtc tccgactcag tgaattcgag gaagttccag ccagcgtc        58

<210> SEQ ID NO 288
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-58

<400> SEQUENCE: 288
ccatctcatc cctgcgtgtc tccgactcag tggaactcgg gaagttccag ccagcgtc        58

<210> SEQ ID NO 289
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-59

<400> SEQUENCE: 289
ccatctcatc cctgcgtgtc tccgactcag tggcggacgc gaagttccag ccagcgtc        58

<210> SEQ ID NO 290
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)

```
<223> OTHER INFORMATION: A-Key 2OS-F1-60

<400> SEQUENCE: 290
ccatctcatc cctgcgtgtc tccgactcag tgcttgtcca gaagttccag ccagcgtc        58

<210> SEQ ID NO 291
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-61

<400> SEQUENCE: 291
ccatctcatc cctgcgtgtc tccgactcag tggtcgcggt gaagttccag ccagcgtc        58

<210> SEQ ID NO 292
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-62

<400> SEQUENCE: 292
ccatctcatc cctgcgtgtc tccgactcag tgcaggtcgt gaagttccag ccagcgtc        58

<210> SEQ ID NO 293
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-63

<400> SEQUENCE: 293
ccatctcatc cctgcgtgtc tccgactcag tgtctcatcc gaagttccag ccagcgtc        58

<210> SEQ ID NO 294
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-64

<400> SEQUENCE: 294
ccatctcatc cctgcgtgtc tccgactcag tggcttcgtg gaagttccag ccagcgtc        58

<210> SEQ ID NO 295
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
```

-continued

```
<222> LOCATION: (1)..(58)
<223> OTHER INFORMATION: A-Key 2OS-F1-65

<400> SEQUENCE: 295
ccatctcatc cctgcgtgtc tccgactcag tgcgtgataa gaagttccag ccagcgtc      58

<210> SEQ ID NO 296
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-66

<400> SEQUENCE: 296
ccatctcatc cctgcgtgtc tccgactcag tgttgctcac gaagttccag ccagcgtc      58

<210> SEQ ID NO 297
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-67

<400> SEQUENCE: 297
ccatctcatc cctgcgtgtc tccgactcag tgcgctctcc gaagttccag ccagcgtc      58

<210> SEQ ID NO 298
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-68

<400> SEQUENCE: 298
ccatctcatc cctgcgtgtc tccgactcag tgattctact gaagttccag ccagcgtc      58

<210> SEQ ID NO 299
<211> LENGTH: 58
<212> TYPE: DNA
<213> ORGANISM: Artificial sequence
<220> FEATURE:
<223> OTHER INFORMATION: Artificial sequence
<220> FEATURE:
<221> NAME/KEY: misc_feature
<222> LOCATION: (1)..(58)
<223> OTHER INFORMATION: A-Key 2OS-F1-69

<400> SEQUENCE: 299
ccatctcatc cctgcgtgtc tccgactcag tgaaggcgtt gaagttccag ccagcgtc      58

<210> SEQ ID NO 300
<211> LENGTH: 58
<212> TYPE: DNA
<213> ORGANISM: Artificial sequence
<220> FEATURE:
<223> OTHER INFORMATION: Artificial sequence
<220> FEATURE:
```

```
<221> NAME/KEY: misc_feature
<222> LOCATION: (1)..(58)
<223> OTHER INFORMATION: A-Key 20S-F1-70

<400> SEQUENCE: 300
ccatctcatc cctgcgtgtc tccgactcag tggcgggatt gaagttccag ccagcgtc      58

<210> SEQ ID NO 301
<211> LENGTH: 9
<212> TYPE: PRT
<213> ORGANISM: Artificial sequence
<220> FEATURE:
<223> OTHER INFORMATION: Artificial sequence
<220> FEATURE:
<221> NAME/KEY: PEPTIDE
<222> LOCATION: (1)..(9)
<223> OTHER INFORMATION: Neg Control

<400> SEQUENCE: 301

Gly Pro Ala Glu Ser Ala Ala Gly Leu
1               5

<210> SEQ ID NO 302
<211> LENGTH: 9
<212> TYPE: PRT
<213> ORGANISM: Artificial sequence
<220> FEATURE:
<223> OTHER INFORMATION: Artificial sequence
<220> FEATURE:
<221> NAME/KEY: PEPTIDE
<222> LOCATION: (1)..(9)
<223> OTHER INFORMATION: Neg Control

<400> SEQUENCE: 302

Ala Ala Lys Gly Arg Gly Ala Ala Leu
1               5

<210> SEQ ID NO 303
<211> LENGTH: 9
<212> TYPE: PRT
<213> ORGANISM: Artificial sequence
<220> FEATURE:
<223> OTHER INFORMATION: Artificial sequence
<220> FEATURE:
<221> NAME/KEY: PEPTIDE
<222> LOCATION: (1)..(9)
<223> OTHER INFORMATION: Neg Control

<400> SEQUENCE: 303

Ala Tyr Ala Gly Ser Ala Gly Ser Ile
1               5

<210> SEQ ID NO 304
<211> LENGTH: 9
<212> TYPE: PRT
<213> ORGANISM: Artificial sequence
<220> FEATURE:
<223> OTHER INFORMATION: Artificial sequence
<220> FEATURE:
<221> NAME/KEY: PEPTIDE
<222> LOCATION: (1)..(9)
<223> OTHER INFORMATION: Neg Control

<400> SEQUENCE: 304

Ser Thr Glu Gly Gly Gly Leu Ala Tyr
1               5

<210> SEQ ID NO 305
<211> LENGTH: 21
```

```
<212> TYPE: PRT
<213> ORGANISM: Clostridium tetani
<220> FEATURE:
<221> NAME/KEY: PEPTIDE
<222> LOCATION: (1)..(21)
<223> OTHER INFORMATION: C. tetani TT 948-968

<400> SEQUENCE: 305

Phe Asn Asn Phe Thr Val Ser Phe Trp Leu Arg Val Pro Lys Val Ser
1               5                   10                  15

Ala Ser His Leu Glu
            20

<210> SEQ ID NO 306
<211> LENGTH: 9
<212> TYPE: PRT
<213> ORGANISM: Human cytomegalovirus
<220> FEATURE:
<221> NAME/KEY: PEPTIDE
<222> LOCATION: (1)..(9)
<223> OTHER INFORMATION: Dextramer 2

<400> SEQUENCE: 306

Asn Leu Val Pro Met Val Ala Thr Val
1               5

<210> SEQ ID NO 307
<211> LENGTH: 10
<212> TYPE: PRT
<213> ORGANISM: Human cytomegalovirus
<220> FEATURE:
<221> NAME/KEY: PEPTIDE
<222> LOCATION: (1)..(10)
<223> OTHER INFORMATION: CMV-derived peptide

<400> SEQUENCE: 307

Thr Pro Arg Val Thr Gly Gly Gly Ala Met
1               5                   10

<210> SEQ ID NO 308
<211> LENGTH: 11
<212> TYPE: PRT
<213> ORGANISM: Human cytomegalovirus
<220> FEATURE:
<221> NAME/KEY: PEPTIDE
<222> LOCATION: (1)..(11)
<223> OTHER INFORMATION: CMV pp65 YSE

<400> SEQUENCE: 308

Tyr Ser Glu His Pro Thr Phe Thr Ser Gln Tyr
1               5                   10

<210> SEQ ID NO 309
<211> LENGTH: 9
<212> TYPE: PRT
<213> ORGANISM: Human cytomegalovirus
<220> FEATURE:
<221> NAME/KEY: PEPTIDE
<222> LOCATION: (1)..(9)
<223> OTHER INFORMATION: CMV pp50 VTE

<400> SEQUENCE: 309

Val Thr Glu His Asp Thr Leu Leu Tyr
1               5

<210> SEQ ID NO 310
<211> LENGTH: 9
<212> TYPE: PRT
```

```
<213> ORGANISM: Human cytomegalovirus
<220> FEATURE:
<221> NAME/KEY: PEPTIDE
<222> LOCATION: (1)..(9)
<223> OTHER INFORMATION: CMV  IE1  VLE

<400> SEQUENCE: 310

Val Leu Glu Glu Thr Ser Val Met Leu
1               5

<210> SEQ ID NO 311
<211> LENGTH: 11
<212> TYPE: PRT
<213> ORGANISM: Human cytomegalovirus
<220> FEATURE:
<221> NAME/KEY: PEPTIDE
<222> LOCATION: (1)..(11)
<223> OTHER INFORMATION: CMV  pp150  TTV

<400> SEQUENCE: 311

Thr Thr Val Tyr Pro Pro Ser Ser Thr Ala Lys
1               5                   10

<210> SEQ ID NO 312
<211> LENGTH: 10
<212> TYPE: PRT
<213> ORGANISM: Human cytomegalovirus
<220> FEATURE:
<221> NAME/KEY: PEPTIDE
<222> LOCATION: (1)..(10)
<223> OTHER INFORMATION: CMV  pp150  TVY

<400> SEQUENCE: 312

Thr Val Tyr Pro Pro Ser Ser Thr Ala Lys
1               5                   10

<210> SEQ ID NO 313
<211> LENGTH: 10
<212> TYPE: PRT
<213> ORGANISM: Human cytomegalovirus
<220> FEATURE:
<221> NAME/KEY: PEPTIDE
<222> LOCATION: (1)..(10)
<223> OTHER INFORMATION: CMV  pp65  RPH-L

<400> SEQUENCE: 313

Arg Pro His Glu Arg Asn Gly Phe Thr Val
1               5                   10

<210> SEQ ID NO 314
<211> LENGTH: 9
<212> TYPE: PRT
<213> ORGANISM: Human cytomegalovirus
<220> FEATURE:
<221> NAME/KEY: PEPTIDE
<222> LOCATION: (1)..(9)
<223> OTHER INFORMATION: CMV  IE1  VLE

<400> SEQUENCE: 314

Val Leu Glu Glu Thr Ser Val Met Leu
1               5

<210> SEQ ID NO 315
<211> LENGTH: 10
<212> TYPE: PRT
<213> ORGANISM: Homo sapiens
<220> FEATURE:
<221> NAME/KEY: PEPTIDE
<222> LOCATION: (1)..(10)
```

```
<223> OTHER INFORMATION: 707-AP

<400> SEQUENCE: 315

Arg Val Ala Ala Leu Ala Arg Asp Ala Pro
1               5                   10

<210> SEQ ID NO 316
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: ATIC (AICRT)

<400> SEQUENCE: 316

Arg Leu Asp Phe Asn Leu Ile Arg Val
1               5

<210> SEQ ID NO 317
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: ATIC (AICRT)

<400> SEQUENCE: 317

Met Val Tyr Asp Leu Tyr Lys Thr Leu
1               5

<210> SEQ ID NO 318
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: BA46 (MFGE8)

<400> SEQUENCE: 318

Asn Leu Phe Glu Thr Pro Val Glu Ala
1               5

<210> SEQ ID NO 319
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: BA46 (MFGE8)

<400> SEQUENCE: 319

Gly Leu Gln His Trp Val Pro Glu Leu
1               5

<210> SEQ ID NO 320
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: Bcl-2

<400> SEQUENCE: 320
```

```
Pro Leu Phe Asp Phe Ser Trp Leu Ser Leu
1               5                   10

<210> SEQ ID NO 321
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: Bcl-2

<400> SEQUENCE: 321

Trp Leu Ser Leu Lys Thr Leu Leu Ser Leu
1               5                   10

<210> SEQ ID NO 322
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: Bcl-xL

<400> SEQUENCE: 322

Tyr Leu Asn Asp His Leu Glu Pro Trp Ile
1               5                   10

<210> SEQ ID NO 323
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: BING-4

<400> SEQUENCE: 323

Cys Gln Trp Gly Arg Leu Trp Gln Leu
1               5

<210> SEQ ID NO 324
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: B-RAF

<400> SEQUENCE: 324

Leu Ala Thr Glu Lys Ser Arg Trp Ser Gly
1               5                   10

<210> SEQ ID NO 325
<211> LENGTH: 8
<212> TYPE: PRT
<213> ORGANISM: Homo sapiens
<220> FEATURE:
<221> NAME/KEY: PEPTIDE
<222> LOCATION: (1)..(8)
<223> OTHER INFORMATION: cyclophilin B (Cyp-B)

<400> SEQUENCE: 325

Val Leu Glu Gly Met Glu Val Val
1               5
```

-continued

```
<210> SEQ ID NO 326
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Cadherin 3/P-cadherin

<400> SEQUENCE: 326

Phe Ile Leu Pro Val Leu Gly Ala Val
1               5

<210> SEQ ID NO 327
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Cadherin 3/P-cadherin

<400> SEQUENCE: 327

Phe Ile Ile Glu Asn Leu Lys Ala Ala
1               5

<210> SEQ ID NO 328
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: CDCA1/NUF2

<400> SEQUENCE: 328

Tyr Met Met Pro Val Asn Ser Glu Val
1               5

<210> SEQ ID NO 329
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: CDCA1/NUF2

<400> SEQUENCE: 329

Lys Leu Ala Thr Ala Gln Phe Lys Ile
1               5

<210> SEQ ID NO 330
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: CDK4

<400> SEQUENCE: 330

Ala Cys Asp Pro His Ser Gly His Phe Val
1               5                   10

<210> SEQ ID NO 331
<211> LENGTH: 9
<212> TYPE: PRT
<213> ORGANISM: Homo sapiens
```

```
<220> FEATURE:
<221> NAME/KEY: PEPTIDE
<222> LOCATION: (1)..(9)
<223> OTHER INFORMATION: CML28 (EXOSC5)

<400> SEQUENCE: 331

Ala Leu Val Asp Ala Gly Val Pro Met
1               5

<210> SEQ ID NO 332
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: COA-1 (UBXN11)

<400> SEQUENCE: 332

Phe Met Thr Arg Lys Leu Trp Asp Leu
1               5

<210> SEQ ID NO 333
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: COA-1 (UBXN11)

<400> SEQUENCE: 333

Arg Leu Leu Ala Ser Leu Gln Asp Leu
1               5

<210> SEQ ID NO 334
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: CPSF

<400> SEQUENCE: 334

Lys Val His Pro Val Ile Trp Ser Leu
1               5

<210> SEQ ID NO 335
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: CPSF

<400> SEQUENCE: 335

Leu Met Leu Gln Asn Ala Leu Thr Thr Met
1               5                   10

<210> SEQ ID NO 336
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Cyclin I
```

<400> SEQUENCE: 336

Leu Leu Asp Arg Phe Leu Ala Thr Val
1               5

<210> SEQ ID NO 337
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: cyclin B1

<400> SEQUENCE: 337

Ala Gly Tyr Leu Met Glu Leu Cys Cys
1               5

<210> SEQ ID NO 338
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: cyclin B1

<400> SEQUENCE: 338

Ala Lys Tyr Leu Met Glu Leu Thr Met
1               5

<210> SEQ ID NO 339
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: B-RAF

<400> SEQUENCE: 339

Leu Ala Thr Glu Lys Ser Arg Trp Ser
1               5

<210> SEQ ID NO 340
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: cyclophilin B (Cyp-B)

<400> SEQUENCE: 340

Lys Leu Lys His Tyr Gly Pro Gly Trp Val
1               5                   10

<210> SEQ ID NO 341
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: DAM-6, -10 (MAGE-B1, -B2)

<400> SEQUENCE: 341

Phe Leu Trp Gly Pro Arg Ala Tyr Ala

-continued

```
<210> SEQ ID NO 342
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: EphA2

<400> SEQUENCE: 342

Ile Met Asn Asp Met Pro Ile Tyr Met
1               5

<210> SEQ ID NO 343
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: EphA2

<400> SEQUENCE: 343

Val Leu Ala Gly Val Gly Phe Phe Ile
1               5

<210> SEQ ID NO 344
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: EphA2

<400> SEQUENCE: 344

Val Leu Leu Leu Val Leu Ala Gly Val
1               5

<210> SEQ ID NO 345
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: EphA2

<400> SEQUENCE: 345

Thr Leu Ala Asp Phe Asp Pro Arg Val
1               5

<210> SEQ ID NO 346
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: EZH2

<400> SEQUENCE: 346

Phe Ile Asn Asp Glu Ile Phe Val Glu Leu
1               5                   10

<210> SEQ ID NO 347
```

```
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: EZH2

<400> SEQUENCE: 347

Phe Met Val Glu Asp Glu Thr Val Leu
1               5

<210> SEQ ID NO 348
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: GnTV

<400> SEQUENCE: 348

Val Leu Pro Asp Val Phe Ile Arg Cys Val
1               5                   10

<210> SEQ ID NO 349
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: gp100 / Pmel17

<400> SEQUENCE: 349

Tyr Leu Glu Pro Gly Pro Val Thr Ala
1               5

<210> SEQ ID NO 350
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: gp100 / Pmel17

<400> SEQUENCE: 350

Leu Leu Asp Gly Thr Ala Thr Leu Arg Leu
1               5                   10

<210> SEQ ID NO 351
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: gp100 / Pmel17

<400> SEQUENCE: 351

Ile Thr Asp Gln Val Pro Phe Ser Val
1               5

<210> SEQ ID NO 352
<211> LENGTH: 10
<212> TYPE: PRT
<213> ORGANISM: Homo sapiens
<220> FEATURE:
```

```
<221> NAME/KEY: PEPTIDE
<222> LOCATION: (1)..(10)
<223> OTHER INFORMATION: gp100 / Pmel17

<400> SEQUENCE: 352

Val Leu Tyr Arg Tyr Gly Ser Phe Ser Val
1               5                   10

<210> SEQ ID NO 353
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: gp100 / Pmel17

<400> SEQUENCE: 353

Arg Leu Met Lys Gln Asp Phe Ser Val
1               5

<210> SEQ ID NO 354
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: gp100 / Pmel17

<400> SEQUENCE: 354

Arg Leu Pro Arg Ile Phe Cys Ser Cys
1               5

<210> SEQ ID NO 355
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: gp100 / Pmel17

<400> SEQUENCE: 355

Ala Met Leu Gly Thr His Thr Met Glu Val
1               5                   10

<210> SEQ ID NO 356
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: gp100 / Pmel17

<400> SEQUENCE: 356

Ser Leu Ala Asp Thr Asn Ser Leu Ala Val
1               5                   10

<210> SEQ ID NO 357
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: gp100 / Pmel17
```

-continued

```
<400> SEQUENCE: 357

Lys Thr Trp Gly Gln Tyr Trp Gln Val
1               5

<210> SEQ ID NO 358
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: HERV-K-MEL

<400> SEQUENCE: 358

Met Leu Ala Val Ile Ser Cys Ala Val
1               5

<210> SEQ ID NO 359
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: hsp70

<400> SEQUENCE: 359

Leu Leu Leu Leu Asp Val Ala Pro Leu
1               5

<210> SEQ ID NO 360
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: IDO1

<400> SEQUENCE: 360

Ala Leu Leu Glu Ile Ala Ser Cys Leu
1               5

<210> SEQ ID NO 361
<211> LENGTH: 11
<212> TYPE: PRT
<213> ORGANISM: Homo sapiens
<220> FEATURE:
<221> NAME/KEY: PEPTIDE
<222> LOCATION: (1)..(11)
<223> OTHER INFORMATION: LAGE-1

<400> SEQUENCE: 361

Met Leu Met Ala Gln Glu Ala Leu Ala Phe Leu
1               5                   10

<210> SEQ ID NO 362
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: Livin (ML-IAP)

<400> SEQUENCE: 362

Arg Leu Ala Ser Phe Tyr Asp Trp Leu Pro
1               5                   10
```

<210> SEQ ID NO 363
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Livin (ML-IAP)

<400> SEQUENCE: 363

Ser Leu Gly Ser Pro Val Leu Gly Leu
1               5

<210> SEQ ID NO 364
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: Livin (ML-IAP)

<400> SEQUENCE: 364

Gln Leu Cys Pro Ile Cys Arg Ala Pro Val
1               5                   10

<210> SEQ ID NO 365
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: M2BP

<400> SEQUENCE: 365

Arg Ile Asp Ile Thr Leu Ser Ser Val
1               5

<210> SEQ ID NO 366
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: MAGE-A1

<400> SEQUENCE: 366

Lys Val Leu Glu Tyr Val Ile Lys Val
1               5

<210> SEQ ID NO 367
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: GnTV

<400> SEQUENCE: 367

Val Leu Pro Asp Val Phe Ile Arg Cys
1               5

<210> SEQ ID NO 368
<211> LENGTH: 9

```
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: gp100 / Pmel17

<400> SEQUENCE: 368

Ile Met Asp Gln Val Pro Phe Ser Val
1               5

<210> SEQ ID NO 369
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: gp100 / Pmel17

<400> SEQUENCE: 369

Met Leu Gly Thr His Thr Met Glu Val
1               5

<210> SEQ ID NO 370
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: hsp70

<400> SEQUENCE: 370

Leu Leu Asp Val Ala Pro Leu Ser Leu
1               5

<210> SEQ ID NO 371
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: MAGE-A10

<400> SEQUENCE: 371

Gly Leu Tyr Asp Gly Met Glu His Leu
1               5

<210> SEQ ID NO 372
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: MAGE-A2

<400> SEQUENCE: 372

Leu Val His Phe Leu Leu Leu Lys Tyr
1               5

<210> SEQ ID NO 373
<211> LENGTH: 9
<212> TYPE: PRT
<213> ORGANISM: Homo sapiens
<220> FEATURE:
<221> NAME/KEY: PEPTIDE
```

```
<222> LOCATION: (1)..(9)
<223> OTHER INFORMATION: MAGE-A2

<400> SEQUENCE: 373

Leu Val Gln Glu Asn Tyr Leu Glu Tyr
1               5

<210> SEQ ID NO 374
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: MAGE-A2

<400> SEQUENCE: 374

Tyr Leu Gln Leu Val Phe Gly Ile Glu Val
1               5                   10

<210> SEQ ID NO 375
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: MAGE-A2

<400> SEQUENCE: 375

Lys Met Val Glu Leu Val His Phe Leu
1               5

<210> SEQ ID NO 376
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: MAGE-A3

<400> SEQUENCE: 376

Leu Val Phe Gly Ile Glu Leu Met Glu Val
1               5                   10

<210> SEQ ID NO 377
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: MAGE-A4

<400> SEQUENCE: 377

Gly Val Tyr Asp Gly Arg Glu His Thr Val
1               5                   10

<210> SEQ ID NO 378
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: MAGE-A1

<400> SEQUENCE: 378
```

```
Tyr Leu Glu Tyr Arg Gln Val Pro Val
1               5
```

<210> SEQ ID NO 379
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: MAGE-A8

<400> SEQUENCE: 379

```
Gly Leu Met Asp Val Gln Ile Pro Thr
1               5
```

<210> SEQ ID NO 380
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: MAGE-A8

<400> SEQUENCE: 380

```
Lys Val Ala Glu Leu Val Arg Phe Leu
1               5
```

<210> SEQ ID NO 381
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: MAGE-A9

<400> SEQUENCE: 381

```
Ala Leu Ser Val Met Gly Val Tyr Val
1               5
```

<210> SEQ ID NO 382
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: MAGE-C2

<400> SEQUENCE: 382

```
Ala Leu Lys Asp Val Glu Glu Arg Val
1               5
```

<210> SEQ ID NO 383
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: MAGE-C2

<400> SEQUENCE: 383

```
Leu Leu Phe Gly Leu Ala Leu Ile Glu Val
1               5                   10
```

```
<210> SEQ ID NO 384
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: MAGE-C2

<400> SEQUENCE: 384

Val Ile Trp Glu Val Leu Asn Ala Val
1               5

<210> SEQ ID NO 385
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: MAGE-C2

<400> SEQUENCE: 385

Thr Leu Asp Glu Lys Val Ala Glu Leu Val
1               5                   10

<210> SEQ ID NO 386
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: MAGE-C2

<400> SEQUENCE: 386

Lys Val Leu Glu Phe Leu Ala Lys Leu
1               5

<210> SEQ ID NO 387
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: MAGE-A3

<400> SEQUENCE: 387

Lys Val Ala Glu Leu Val His Phe Leu
1               5

<210> SEQ ID NO 388
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: MC1R

<400> SEQUENCE: 388

Thr Ile Leu Leu Gly Ile Phe Phe Leu
1               5

<210> SEQ ID NO 389
<211> LENGTH: 10
<212> TYPE: PRT
```

```
<213> ORGANISM: Homo sapiens
<220> FEATURE:
<221> NAME/KEY: PEPTIDE
<222> LOCATION: (1)..(10)
<223> OTHER INFORMATION: Melan-A / MART-1

<400> SEQUENCE: 389

Glu Leu Ala Gly Ile Gly Ile Leu Thr Val
1               5                   10

<210> SEQ ID NO 390
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Melan-A / MART-1

<400> SEQUENCE: 390

Ile Leu Thr Val Ile Leu Gly Val Leu
1               5

<210> SEQ ID NO 391
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Meloe-1

<400> SEQUENCE: 391

Thr Leu Asn Asp Glu Cys Trp Pro Ala
1               5

<210> SEQ ID NO 392
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: MG50

<400> SEQUENCE: 392

Cys Met His Leu Leu Leu Glu Ala Val
1               5

<210> SEQ ID NO 393
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: MG50

<400> SEQUENCE: 393

Val Leu Ser Val Asn Val Pro Asp Val
1               5

<210> SEQ ID NO 394
<211> LENGTH: 9
<212> TYPE: PRT
<213> ORGANISM: Homo sapiens
<220> FEATURE:
<221> NAME/KEY: PEPTIDE
<222> LOCATION: (1)..(9)
```

```
<223> OTHER INFORMATION: NY-ESO-1 / LAGE-2

<400> SEQUENCE: 394

Gln Leu Ser Leu Leu Met Trp Ile Thr
1               5

<210> SEQ ID NO 395
<211> LENGTH: 11
<212> TYPE: PRT
<213> ORGANISM: Homo sapiens
<220> FEATURE:
<221> NAME/KEY: PEPTIDE
<222> LOCATION: (1)..(11)
<223> OTHER INFORMATION: NY-ESO-1 / LAGE-2

<400> SEQUENCE: 395

Ser Leu Leu Met Trp Ile Thr Gln Cys Phe Leu
1               5                   10

<210> SEQ ID NO 396
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: P Polypeptide

<400> SEQUENCE: 396

Ile Met Leu Cys Leu Ile Ala Ala Val
1               5

<210> SEQ ID NO 397
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: p53

<400> SEQUENCE: 397

Val Val Pro Cys Glu Pro Pro Glu Val
1               5

<210> SEQ ID NO 398
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: p53

<400> SEQUENCE: 398

Lys Thr Cys Pro Val Gln Leu Trp Val
1               5

<210> SEQ ID NO 399
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: p53

<400> SEQUENCE: 399
```

```
Arg Met Pro Glu Ala Ala Pro Pro Val
1               5

<210> SEQ ID NO 400
<211> LENGTH: 11
<212> TYPE: PRT
<213> ORGANISM: Homo sapiens
<220> FEATURE:
<221> NAME/KEY: PEPTIDE
<222> LOCATION: (1)..(11)
<223> OTHER INFORMATION: p53

<400> SEQUENCE: 400

Leu Leu Pro Glu Asn Asn Val Leu Ser Pro Val
1               5                   10

<210> SEQ ID NO 401
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: p53

<400> SEQUENCE: 401

Lys Leu Cys Pro Val Gln Leu Trp Val
1               5

<210> SEQ ID NO 402
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: p53

<400> SEQUENCE: 402

Ser Met Pro Pro Pro Gly Thr Arg Val
1               5

<210> SEQ ID NO 403
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: p53

<400> SEQUENCE: 403

Leu Leu Gly Arg Asn Ser Phe Glu Val
1               5

<210> SEQ ID NO 404
<211> LENGTH: 11
<212> TYPE: PRT
<213> ORGANISM: Homo sapiens
<220> FEATURE:
<221> NAME/KEY: PEPTIDE
<222> LOCATION: (1)..(11)
<223> OTHER INFORMATION: p53

<400> SEQUENCE: 404

Gly Leu Ala Pro Pro Gln His Leu Ile Arg Val
1               5                   10
```

```
<210> SEQ ID NO 405
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: p53

<400> SEQUENCE: 405

Ser Leu Pro Pro Pro Gly Thr Arg Val
1               5

<210> SEQ ID NO 406
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: p53

<400> SEQUENCE: 406

Tyr Leu Gly Ser Tyr Gly Phe Arg Leu
1               5

<210> SEQ ID NO 407
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: PGK1

<400> SEQUENCE: 407

Ile Ile Gly Gly Gly Met Ala Phe Thr
1               5

<210> SEQ ID NO 408
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: PRAME

<400> SEQUENCE: 408

Ala Leu Tyr Val Asp Ser Leu Phe Phe Leu
1               5                   10

<210> SEQ ID NO 409
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: PRAME

<400> SEQUENCE: 409

Ser Leu Leu Gln His Leu Ile Gly Leu
1               5

<210> SEQ ID NO 410
<211> LENGTH: 10
<212> TYPE: PRT
<213> ORGANISM: Homo sapiens
```

-continued

```
<220> FEATURE:
<221> NAME/KEY: PEPTIDE
<222> LOCATION: (1)..(10)
<223> OTHER INFORMATION: SOX10

<400> SEQUENCE: 410

Ser Ala Trp Ile Ser Lys Pro Pro Gly Val
1               5                   10

<210> SEQ ID NO 411
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: PRAME

<400> SEQUENCE: 411

Ser Leu Tyr Ser Phe Pro Glu Pro Glu Ala
1               5                   10

<210> SEQ ID NO 412
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: PRAME

<400> SEQUENCE: 412

Val Leu Asp Gly Leu Asp Val Leu Leu
1               5

<210> SEQ ID NO 413
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: PRAME

<400> SEQUENCE: 413

Leu Leu Leu Asp Asp Leu Leu Val Ser Ile
1               5                   10

<210> SEQ ID NO 414
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: NY-ESO-1 / LAGE-2

<400> SEQUENCE: 414

Ser Leu Leu Met Trp Ile Thr Gln Cys
1               5

<210> SEQ ID NO 415
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: RAB38 / NY-MEL-1
```

-continued

```
<400> SEQUENCE: 415

Val Leu His Trp Asp Pro Glu Thr Val
1               5

<210> SEQ ID NO 416
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: RAGE-1

<400> SEQUENCE: 416

Leu Lys Leu Ser Gly Val Val Arg Leu
1               5

<210> SEQ ID NO 417
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: RAGE-1

<400> SEQUENCE: 417

Pro Leu Pro Pro Ala Arg Asn Gly Gly Leu
1               5                   10

<210> SEQ ID NO 418
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Replication protein A

<400> SEQUENCE: 418

Tyr Leu Met Asp Thr Ser Gly Lys Val
1               5

<210> SEQ ID NO 419
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: SART-3

<400> SEQUENCE: 419

Leu Leu Gln Ala Glu Ala Pro Arg Leu
1               5

<210> SEQ ID NO 420
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: SART-3

<400> SEQUENCE: 420

Arg Leu Ala Glu Tyr Gln Ala Tyr Ile
```

```
<210> SEQ ID NO 421
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: secernin 1

<400> SEQUENCE: 421

Lys Met Asp Ala Glu His Pro Glu Leu
1               5

<210> SEQ ID NO 422
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: SOX10

<400> SEQUENCE: 422

Ala Trp Ile Ser Lys Pro Pro Gly Val
1               5

<210> SEQ ID NO 423
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: SSX-2

<400> SEQUENCE: 423

Arg Leu Gln Gly Ile Ser Pro Lys Ile
1               5

<210> SEQ ID NO 424
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: SSX-2

<400> SEQUENCE: 424

Lys Ala Ser Glu Lys Ile Phe Tyr Val
1               5

<210> SEQ ID NO 425
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: STAT1-alpha/beta

<400> SEQUENCE: 425

Lys Leu Gln Glu Leu Asn Tyr Asn Leu
1               5

<210> SEQ ID NO 426
```

```
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: STEAP1

<400> SEQUENCE: 426

Phe Leu Tyr Thr Leu Leu Arg Glu Val
1               5

<210> SEQ ID NO 427
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: STEAP1

<400> SEQUENCE: 427

Leu Leu Leu Gly Thr Ile His Ala Leu
1               5

<210> SEQ ID NO 428
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: STEAP1

<400> SEQUENCE: 428

Met Ile Ala Val Phe Leu Pro Ile Val
1               5

<210> SEQ ID NO 429
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Survivin

<400> SEQUENCE: 429

Leu Met Leu Gly Glu Phe Leu Lys Leu
1               5

<210> SEQ ID NO 430
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: Survivin

<400> SEQUENCE: 430

Glu Leu Thr Leu Gly Glu Phe Leu Lys Leu
1               5                   10

<210> SEQ ID NO 431
<211> LENGTH: 10
<212> TYPE: PRT
<213> ORGANISM: Homo sapiens
<220> FEATURE:
```

```
<221> NAME/KEY: PEPTIDE
<222> LOCATION: (1)..(10)
<223> OTHER INFORMATION: Survivin

<400> SEQUENCE: 431

Thr Leu Pro Pro Ala Trp Gln Pro Phe Leu
1               5                   10

<210> SEQ ID NO 432
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: TAG-1

<400> SEQUENCE: 432

Ser Leu Gly Trp Leu Phe Leu Leu Leu
1               5

<210> SEQ ID NO 433
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Telomerase

<400> SEQUENCE: 433

Arg Leu Phe Phe Tyr Arg Lys Ser Val
1               5

<210> SEQ ID NO 434
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: TRP-2

<400> SEQUENCE: 434

Val Tyr Asp Phe Phe Val Trp Leu His Tyr
1               5                   10

<210> SEQ ID NO 435
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: NY-ESO-1 / LAGE-2

<400> SEQUENCE: 435

Ser Leu Leu Met Trp Ile Thr Gln Ala
1               5

<210> SEQ ID NO 436
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Telomerase
```

```
<400> SEQUENCE: 436

Arg Leu Val Asp Asp Phe Leu Leu Val
1               5

<210> SEQ ID NO 437
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Telomerase

<400> SEQUENCE: 437

Ile Leu Ala Lys Phe Leu His Trp Leu
1               5

<210> SEQ ID NO 438
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Topoisomerase II

<400> SEQUENCE: 438

Phe Leu Tyr Asp Asp Asn Gln Arg Val
1               5

<210> SEQ ID NO 439
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: TRAG-3

<400> SEQUENCE: 439

Ile Leu Leu Arg Asp Ala Gly Leu Val
1               5

<210> SEQ ID NO 440
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: TRP-2

<400> SEQUENCE: 440

Phe Val Trp Leu His Tyr Tyr Ser Val
1               5

<210> SEQ ID NO 441
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: TRP-2

<400> SEQUENCE: 441

Ser Leu Asp Asp Tyr Asn His Leu Val
1               5
```

<210> SEQ ID NO 442
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: TRP-2

<400> SEQUENCE: 442

Thr Leu Asp Ser Gln Val Met Ser Leu
1               5

<210> SEQ ID NO 443
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: TRP-2

<400> SEQUENCE: 443

Ser Val Tyr Asp Phe Phe Val Trp Leu
1               5

<210> SEQ ID NO 444
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: TRP2-6b

<400> SEQUENCE: 444

Ala Thr Thr Asn Ile Leu Glu His Tyr
1               5

<210> SEQ ID NO 445
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: tyrosinase

<400> SEQUENCE: 445

Cys Leu Leu Trp Ser Phe Gln Thr Ser Ala
1               5                   10

<210> SEQ ID NO 446
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: tyrosinase

<400> SEQUENCE: 446

Met Leu Leu Ala Val Leu Tyr Cys Leu
1               5

<210> SEQ ID NO 447
<211> LENGTH: 9

```
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: tyrosinase

<400> SEQUENCE: 447

Tyr Met Asp Gly Thr Met Ser Gln Val
1               5

<210> SEQ ID NO 448
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: XBP-1

<400> SEQUENCE: 448

Leu Leu Ser Gly Gln Pro Ala Ser Ala
1               5

<210> SEQ ID NO 449
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: MG50

<400> SEQUENCE: 449

Leu Leu Leu Glu Ala Val Pro Ala Val
1               5

<210> SEQ ID NO 450
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: MG50

<400> SEQUENCE: 450

Thr Leu Lys Cys Asp Cys Glu Ile Leu
1               5

<210> SEQ ID NO 451
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: MG50

<400> SEQUENCE: 451

Trp Leu Pro Lys Ile Leu Gly Glu Val
1               5

<210> SEQ ID NO 452
<211> LENGTH: 9
<212> TYPE: PRT
<213> ORGANISM: Homo sapiens
<220> FEATURE:
<221> NAME/KEY: PEPTIDE
```

```
<222> LOCATION: (1)..(9)
<223> OTHER INFORMATION: MG50

<400> SEQUENCE: 452

Arg Leu Gly Pro Thr Leu Met Cys Leu
1               5

<210> SEQ ID NO 453
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Meloe-2

<400> SEQUENCE: 453

Arg Cys Pro Pro Lys Pro Pro Leu Ala
1               5

<210> SEQ ID NO 454
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: PRDX5

<400> SEQUENCE: 454

Ala Met Ala Pro Ile Lys Val Arg Leu
1               5

<210> SEQ ID NO 455
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: cyclin B1

<400> SEQUENCE: 455

Ile Leu Ile Asp Trp Leu Val Gln Val
1               5

<210> SEQ ID NO 456
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: Melan-A / MART-1

<400> SEQUENCE: 456

Glu Ala Ala Gly Ile Gly Ile Leu Thr Val
1               5                   10

<210> SEQ ID NO 457
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: adipophilin

<400> SEQUENCE: 457
```

```
Ser Val Ala Ser Thr Ile Thr Gly Val
1               5

<210> SEQ ID NO 458
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: alpha-actinin-4

<400> SEQUENCE: 458

Phe Ile Ala Ser Asn Gly Val Lys Leu Val
1               5                   10

<210> SEQ ID NO 459
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Meloe-2

<400> SEQUENCE: 459

Arg Leu Pro Pro Lys Pro Pro Leu Ala
1               5

<210> SEQ ID NO 460
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: CDKN1A

<400> SEQUENCE: 460

Leu Met Ala Gly Cys Ile Gln Glu Ala
1               5

<210> SEQ ID NO 461
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: CDKN1A

<400> SEQUENCE: 461

Gly Leu Gly Leu Pro Lys Leu Tyr Leu
1               5

<210> SEQ ID NO 462
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: CDKN1A

<400> SEQUENCE: 462

Phe Ala Trp Glu Arg Val Arg Gly Leu
1               5
```

```
<210> SEQ ID NO 463
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: CLP (coactosin-like protein)

<400> SEQUENCE: 463

Asn Leu Val Arg Asp Asp Gly Ser Ala Val
1               5                   10

<210> SEQ ID NO 464
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: CLP (coactosin-like protein)

<400> SEQUENCE: 464

Arg Leu Phe Ala Phe Val Arg Phe Thr
1               5

<210> SEQ ID NO 465
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: CLP (coactosin-like protein)

<400> SEQUENCE: 465

Val Val Gln Asn Phe Ala Lys Glu Phe Val
1               5                   10

<210> SEQ ID NO 466
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: c-MET

<400> SEQUENCE: 466

Tyr Val Asp Pro Val Ile Thr Ser Ile
1               5

<210> SEQ ID NO 467
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: CYP1B1

<400> SEQUENCE: 467

Trp Leu Gln Tyr Phe Pro Asn Pro Val
1               5

<210> SEQ ID NO 468
<211> LENGTH: 9
<212> TYPE: PRT
```

<213> ORGANISM: Homo sapiens
<220> FEATURE:
<221> NAME/KEY: PEPTIDE
<222> LOCATION: (1)..(9)
<223> OTHER INFORMATION: IMP-3

<400> SEQUENCE: 468

Asn Leu Ser Ser Ala Glu Val Val Val
1               5

<210> SEQ ID NO 469
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: IMP-3

<400> SEQUENCE: 469

Arg Leu Leu Val Pro Thr Gln Phe Val
1               5

<210> SEQ ID NO 470
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: KIF20A

<400> SEQUENCE: 470

Leu Leu Ser Asp Asp Asp Val Val Val
1               5

<210> SEQ ID NO 471
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: KIF20A

<400> SEQUENCE: 471

Cys Ile Ala Glu Gln Tyr His Thr Val
1               5

<210> SEQ ID NO 472
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: KIF20A

<400> SEQUENCE: 472

Ala Gln Pro Asp Thr Ala Pro Leu Pro Val
1               5                   10

<210> SEQ ID NO 473
<211> LENGTH: 9
<212> TYPE: PRT
<213> ORGANISM: Homo sapiens
<220> FEATURE:
<221> NAME/KEY: PEPTIDE
<222> LOCATION: (1)..(9)

```
<223> OTHER INFORMATION: MAGE-A10

<400> SEQUENCE: 473

Ser Leu Leu Lys Phe Leu Ala Lys Val
1               5

<210> SEQ ID NO 474
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: MAGE-A12

<400> SEQUENCE: 474

Phe Leu Trp Gly Pro Arg Ala Leu Val
1               5

<210> SEQ ID NO 475
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: MAGE-C2

<400> SEQUENCE: 475

Phe Leu Ala Lys Leu Asn Asn Thr Val
1               5

<210> SEQ ID NO 476
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Melan-A / MART-1

<400> SEQUENCE: 476

Ala Ala Gly Ile Gly Ile Leu Thr Val
1               5

<210> SEQ ID NO 477
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Survivin

<400> SEQUENCE: 477

Gln Met Phe Phe Cys Phe Lys Glu Leu
1               5

<210> SEQ ID NO 478
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Telomerase

<400> SEQUENCE: 478
```

```
Leu Leu Thr Ser Arg Leu Arg Phe Ile
1               5
```

<210> SEQ ID NO 479
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: TYMS

<400> SEQUENCE: 479

```
Leu Met Ala Leu Pro Pro Cys His Ala Leu
1               5                   10
```

<210> SEQ ID NO 480
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: cyclin D1

<400> SEQUENCE: 480

```
Leu Leu Gly Ala Thr Cys Met Phe Val
1               5
```

<210> SEQ ID NO 481
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: BAP31

<400> SEQUENCE: 481

```
Lys Leu Asp Val Gly Asn Ala Glu Val
1               5
```

<210> SEQ ID NO 482
<211> LENGTH: 16
<212> TYPE: PRT
<213> ORGANISM: Homo sapiens
<220> FEATURE:
<221> NAME/KEY: PEPTIDE
<222> LOCATION: (1)..(16)
<223> OTHER INFORMATION: human MAGE3 243-258

<400> SEQUENCE: 482

```
Lys Lys Leu Leu Thr Gln His Phe Val Gln Glu Asn Tyr Leu Glu Tyr
1               5                   10                  15
```

<210> SEQ ID NO 483
<211> LENGTH: 13
<212> TYPE: PRT
<213> ORGANISM: Homo sapiens
<220> FEATURE:
<221> NAME/KEY: PEPTIDE
<222> LOCATION: (1)..(13)
<223> OTHER INFORMATION: human oxytocinase 272-284

<400> SEQUENCE: 483

```
Lys Lys Tyr Phe Ala Ala Thr Gln Phe Glu Pro Leu Ala
1               5                   10
```

```
<210> SEQ ID NO 484
<211> LENGTH: 15
<212> TYPE: PRT
<213> ORGANISM: Homo sapiens
<220> FEATURE:
<221> NAME/KEY: PEPTIDE
<222> LOCATION: (1)..(15)
<223> OTHER INFORMATION: human CLIP 87-101

<400> SEQUENCE: 484

Pro Val Ser Lys Met Arg Met Ala Thr Pro Leu Leu Met Gln Ala
1               5                   10                  15

<210> SEQ ID NO 485
<211> LENGTH: 14
<212> TYPE: PRT
<213> ORGANISM: Homo sapiens
<220> FEATURE:
<221> NAME/KEY: PEPTIDE
<222> LOCATION: (1)..(14)
<223> OTHER INFORMATION: human CTAG1 157-170

<400> SEQUENCE: 485

Ser Leu Leu Met Trp Ile Thr Gln Cys Phe Leu Pro Val Phe
1               5                   10

<210> SEQ ID NO 486
<211> LENGTH: 15
<212> TYPE: PRT
<213> ORGANISM: Homo sapiens
<220> FEATURE:
<221> NAME/KEY: PEPTIDE
<222> LOCATION: (1)..(15)
<223> OTHER INFORMATION: DQB1*03:02  human CLIP 87-101

<400> SEQUENCE: 486

Pro Val Ser Lys Met Arg Met Ala Thr Pro Leu Leu Met Gln Ala
1               5                   10                  15

<210> SEQ ID NO 487
<211> LENGTH: 16
<212> TYPE: PRT
<213> ORGANISM: Homo sapiens
<220> FEATURE:
<221> NAME/KEY: PEPTIDE
<222> LOCATION: (1)..(16)
<223> OTHER INFORMATION: human FcR2 104-119

<400> SEQUENCE: 487

Gln Asp Leu Glu Leu Ser Trp Asn Leu Asn Gly Leu Gln Ala Asp Leu
1               5                   10                  15

<210> SEQ ID NO 488
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Cancer-gp100

<400> SEQUENCE: 488

Ala Leu Leu Ala Val Gly Ala Thr Lys
1               5

<210> SEQ ID NO 489
<211> LENGTH: 9
<212> TYPE: PRT
<213> ORGANISM: Human cytomegalovirus
```

```
<220> FEATURE:
<221> NAME/KEY: PEPTIDE
<222> LOCATION: (1)..(9)
<223> OTHER INFORMATION: HCMV pp65

<400> SEQUENCE: 489

Gly Pro Ile Ser Gly His Val Leu Lys
1               5

<210> SEQ ID NO 490
<211> LENGTH: 10
<212> TYPE: PRT
<213> ORGANISM: Human cytomegalovirus
<220> FEATURE:
<221> NAME/KEY: PEPTIDE
<222> LOCATION: (1)..(10)
<223> OTHER INFORMATION: HCMV 248-256

<400> SEQUENCE: 490

Ala Tyr Ala Gln Lys Ile Phe Lys Ile Leu
1               5                   10

<210> SEQ ID NO 491
<211> LENGTH: 10
<212> TYPE: PRT
<213> ORGANISM: Human herpesvirus 4
<220> FEATURE:
<221> NAME/KEY: PEPTIDE
<222> LOCATION: (1)..(10)
<223> OTHER INFORMATION: EBV-EBNA4

<400> SEQUENCE: 491

Ala Val Phe Asp Arg Lys Ser Asp Ala Lys
1               5                   10

<210> SEQ ID NO 492
<211> LENGTH: 9
<212> TYPE: PRT
<213> ORGANISM: Human herpesvirus 4
<220> FEATURE:
<221> NAME/KEY: PEPTIDE
<222> LOCATION: (1)..(9)
<223> OTHER INFORMATION: EBV  LMP2  CLG

<400> SEQUENCE: 492

Cys Leu Gly Gly Leu Leu Thr Met Val
1               5

<210> SEQ ID NO 493
<211> LENGTH: 9
<212> TYPE: PRT
<213> ORGANISM: Human herpesvirus 4
<220> FEATURE:
<221> NAME/KEY: PEPTIDE
<222> LOCATION: (1)..(9)
<223> OTHER INFORMATION: EBV  BMF1  GLC

<400> SEQUENCE: 493

Gly Leu Cys Thr Leu Val Ala Met Leu
1               5

<210> SEQ ID NO 494
<211> LENGTH: 9
<212> TYPE: PRT
<213> ORGANISM: Human herpesvirus 4
<220> FEATURE:
<221> NAME/KEY: PEPTIDE
<222> LOCATION: (1)..(9)
<223> OTHER INFORMATION: EBV  LMP2  FLY
```

<400> SEQUENCE: 494

Phe Leu Tyr Ala Leu Ala Leu Leu Leu
1               5

<210> SEQ ID NO 495
<211> LENGTH: 9
<212> TYPE: PRT
<213> ORGANISM: Human herpesvirus 4
<220> FEATURE:
<221> NAME/KEY: PEPTIDE
<222> LOCATION: (1)..(9)
<223> OTHER INFORMATION: EBV BRLF1 YVL

<400> SEQUENCE: 495

Tyr Val Leu Asp His Leu Ile Val Val
1               5

<210> SEQ ID NO 496
<211> LENGTH: 9
<212> TYPE: PRT
<213> ORGANISM: Human herpesvirus 4
<220> FEATURE:
<221> NAME/KEY: PEPTIDE
<222> LOCATION: (1)..(9)
<223> OTHER INFORMATION: EBV LMP2

<400> SEQUENCE: 496

Ile Tyr Val Leu Val Met Leu Val Leu
1               5

<210> SEQ ID NO 497
<211> LENGTH: 9
<212> TYPE: PRT
<213> ORGANISM: Human herpesvirus 4
<220> FEATURE:
<221> NAME/KEY: PEPTIDE
<222> LOCATION: (1)..(9)
<223> OTHER INFORMATION: EBV BRLF1

<400> SEQUENCE: 497

Thr Tyr Pro Val Leu Glu Glu Met Phe
1               5

<210> SEQ ID NO 498
<211> LENGTH: 9
<212> TYPE: PRT
<213> ORGANISM: Human herpesvirus 4
<220> FEATURE:
<221> NAME/KEY: PEPTIDE
<222> LOCATION: (1)..(9)
<223> OTHER INFORMATION: EBV BMLF1

<400> SEQUENCE: 498

Asp Tyr Asn Phe Val Lys Gln Leu Phe
1               5

<210> SEQ ID NO 499
<211> LENGTH: 9
<212> TYPE: PRT
<213> ORGANISM: Human herpesvirus 4
<220> FEATURE:
<221> NAME/KEY: PEPTIDE
<222> LOCATION: (1)..(9)
<223> OTHER INFORMATION: EBV EBNA 3a RLR

<400> SEQUENCE: 499

Arg Leu Arg Ala Glu Ala Gln Val Lys

```
<210> SEQ ID NO 500
<211> LENGTH: 9
<212> TYPE: PRT
<213> ORGANISM: Human herpesvirus 4
<220> FEATURE:
<221> NAME/KEY: PEPTIDE
<222> LOCATION: (1)..(9)
<223> OTHER INFORMATION: EBV   BRLF1 148-56   RVR

<400> SEQUENCE: 500

Arg Val Arg Ala Tyr Thr Tyr Ser Lys
1               5

<210> SEQ ID NO 501
<211> LENGTH: 9
<212> TYPE: PRT
<213> ORGANISM: Human herpesvirus 4
<220> FEATURE:
<221> NAME/KEY: PEPTIDE
<222> LOCATION: (1)..(9)
<223> OTHER INFORMATION: EBV   EBNA   RPP

<400> SEQUENCE: 501

Arg Pro Pro Ile Phe Ile Arg Leu Leu
1               5

<210> SEQ ID NO 502
<211> LENGTH: 9
<212> TYPE: PRT
<213> ORGANISM: Human herpesvirus 4
<220> FEATURE:
<221> NAME/KEY: PEPTIDE
<222> LOCATION: (1)..(9)
<223> OTHER INFORMATION: EBV   LMP2   FLY

<400> SEQUENCE: 502

Phe Leu Tyr Ala Leu Ala Leu Leu Leu
1               5

<210> SEQ ID NO 503
<211> LENGTH: 10
<212> TYPE: PRT
<213> ORGANISM: Human herpesvirus 4
<220> FEATURE:
<221> NAME/KEY: PEPTIDE
<222> LOCATION: (1)..(10)
<223> OTHER INFORMATION: EBV-E3B

<400> SEQUENCE: 503

Leu Leu Asp Phe Val Arg Phe Met Gly Val
1               5                   10

<210> SEQ ID NO 504
<211> LENGTH: 9
<212> TYPE: PRT
<213> ORGANISM: Human herpesvirus 4
<220> FEATURE:
<221> NAME/KEY: PEPTIDE
<222> LOCATION: (1)..(9)
<223> OTHER INFORMATION: EBV-BALF4

<400> SEQUENCE: 504

Phe Leu Asp Lys Gly Thr Tyr Thr Leu
1               5

<210> SEQ ID NO 505
```

```
<211> LENGTH: 9
<212> TYPE: PRT
<213> ORGANISM: Human herpesvirus 4
<220> FEATURE:
<221> NAME/KEY: PEPTIDE
<222> LOCATION: (1)..(9)
<223> OTHER INFORMATION: EBV-BMRF1

<400> SEQUENCE: 505

Thr Leu Asp Tyr Lys Pro Leu Ser Val
1               5

<210> SEQ ID NO 506
<211> LENGTH: 9
<212> TYPE: PRT
<213> ORGANISM: Human herpesvirus 4
<220> FEATURE:
<221> NAME/KEY: PEPTIDE
<222> LOCATION: (1)..(9)
<223> OTHER INFORMATION: EBV-LMP1

<400> SEQUENCE: 506

Tyr Leu Leu Glu Met Leu Trp Arg Leu
1               5

<210> SEQ ID NO 507
<211> LENGTH: 9
<212> TYPE: PRT
<213> ORGANISM: Human herpesvirus 4
<220> FEATURE:
<221> NAME/KEY: PEPTIDE
<222> LOCATION: (1)..(9)
<223> OTHER INFORMATION: EBV-LMP1

<400> SEQUENCE: 507

Tyr Leu Gln Gln Asn Trp Trp Thr Leu
1               5

<210> SEQ ID NO 508
<211> LENGTH: 9
<212> TYPE: PRT
<213> ORGANISM: Human immunodeficiency virus
<220> FEATURE:
<221> NAME/KEY: PEPTIDE
<222> LOCATION: (1)..(9)
<223> OTHER INFORMATION: Peptide

<400> SEQUENCE: 508

Ile Leu Lys Glu Pro Val His Gly Val
1               5

<210> SEQ ID NO 509
<211> LENGTH: 10
<212> TYPE: PRT
<213> ORGANISM: Human immunodeficiency virus
<220> FEATURE:
<221> NAME/KEY: PEPTIDE
<222> LOCATION: (1)..(10)
<223> OTHER INFORMATION: HIV pol

<400> SEQUENCE: 509

Thr Pro Arg Val Thr Gly Gly Gly Ala Met
1               5                   10

<210> SEQ ID NO 510
<211> LENGTH: 15
<212> TYPE: PRT
<213> ORGANISM: Human immunodeficiency virus
<220> FEATURE:
```

```
<221> NAME/KEY: PEPTIDE
<222> LOCATION: (1)..(15)
<223> OTHER INFORMATION: HIV env 31-45

<400> SEQUENCE: 510

Thr Glu Lys Leu Trp Val Thr Val Tyr Tyr Gly Val Pro Val Trp
1               5                   10                  15

<210> SEQ ID NO 511
<211> LENGTH: 9
<212> TYPE: PRT
<213> ORGANISM: Human immunodeficiency virus
<220> FEATURE:
<221> NAME/KEY: PEPTIDE
<222> LOCATION: (1)..(9)
<223> OTHER INFORMATION: HIV-gag

<400> SEQUENCE: 511

Ser Leu Tyr Asn Thr Val Ala Thr Leu
1               5

<210> SEQ ID NO 512
<211> LENGTH: 8
<212> TYPE: PRT
<213> ORGANISM: Human immunodeficiency virus
<220> FEATURE:
<221> NAME/KEY: PEPTIDE
<222> LOCATION: (1)..(8)
<223> OTHER INFORMATION: HIV

<400> SEQUENCE: 512

Phe Leu Gly Lys Ile Trp Pro Ser
1               5

<210> SEQ ID NO 513
<211> LENGTH: 9
<212> TYPE: PRT
<213> ORGANISM: Influenza virus
<220> FEATURE:
<221> NAME/KEY: PEPTIDE
<222> LOCATION: (1)..(9)
<223> OTHER INFORMATION: Dextramer 1

<400> SEQUENCE: 513

Gly Ile Leu Gly Phe Val Phe Thr Leu
1               5

<210> SEQ ID NO 514
<211> LENGTH: 9
<212> TYPE: PRT
<213> ORGANISM: Influenza virus
<220> FEATURE:
<221> NAME/KEY: PEPTIDE
<222> LOCATION: (1)..(9)
<223> OTHER INFORMATION: FLU  BP-VSD

<400> SEQUENCE: 514

Val Ser Asp Gly Gly Pro Asn Leu Tyr
1               5

<210> SEQ ID NO 515
<211> LENGTH: 9
<212> TYPE: PRT
<213> ORGANISM: Influenza virus
<220> FEATURE:
<221> NAME/KEY: PEPTIDE
<222> LOCATION: (1)..(9)
<223> OTHER INFORMATION: FLU  NP 265-273  ILR
```

-continued

```
<400> SEQUENCE: 515

Ile Leu Arg Gly Ser Val Ala His Lys
1               5

<210> SEQ ID NO 516
<211> LENGTH: 10
<212> TYPE: PRT
<213> ORGANISM: Influenza virus
<220> FEATURE:
<221> NAME/KEY: PEPTIDE
<222> LOCATION: (1)..(10)
<223> OTHER INFORMATION: FLU-BNP

<400> SEQUENCE: 516

Lys Leu Gly Glu Phe Tyr Asn Gln Met Met
1               5                   10

<210> SEQ ID NO 517
<211> LENGTH: 9
<212> TYPE: PRT
<213> ORGANISM: Merkel Cell Polyoma Virus
<220> FEATURE:
<221> NAME/KEY: PEPTIDE
<222> LOCATION: (1)..(9)
<223> OTHER INFORMATION: VP1

<400> SEQUENCE: 517

Asp Leu Gln Gly Leu Val Leu Asp Tyr
1               5

<210> SEQ ID NO 518
<211> LENGTH: 9
<212> TYPE: PRT
<213> ORGANISM: Merkel Cell Polyoma Virus
<220> FEATURE:
<221> NAME/KEY: PEPTIDE
<222> LOCATION: (1)..(9)
<223> OTHER INFORMATION: VP1

<400> SEQUENCE: 518

Val Leu Gly Arg Lys Met Thr Pro Lys
1               5

<210> SEQ ID NO 519
<211> LENGTH: 9
<212> TYPE: PRT
<213> ORGANISM: Merkel Cell Polyoma Virus
<220> FEATURE:
<221> NAME/KEY: PEPTIDE
<222> LOCATION: (1)..(9)
<223> OTHER INFORMATION: VP1

<400> SEQUENCE: 519

Val Thr Leu Arg Lys Arg Trp Val Lys
1               5

<210> SEQ ID NO 520
<211> LENGTH: 9
<212> TYPE: PRT
<213> ORGANISM: Merkel Cell Polyoma Virus
<220> FEATURE:
<221> NAME/KEY: PEPTIDE
<222> LOCATION: (1)..(9)
<223> OTHER INFORMATION: VP1

<400> SEQUENCE: 520

Leu Val Leu Asp Tyr Gln Thr Glu Tyr
1               5
```

<210> SEQ ID NO 521
<211> LENGTH: 9
<212> TYPE: PRT
<213> ORGANISM: Merkel Cell Polyoma Virus
<220> FEATURE:
<221> NAME/KEY: PEPTIDE
<222> LOCATION: (1)..(9)
<223> OTHER INFORMATION: VP1

<400> SEQUENCE: 521

Gly Gln Glu Lys Thr Val Tyr Pro Lys
1               5

<210> SEQ ID NO 522
<211> LENGTH: 10
<212> TYPE: PRT
<213> ORGANISM: Merkel Cell Polyoma Virus
<220> FEATURE:
<221> NAME/KEY: PEPTIDE
<222> LOCATION: (1)..(10)
<223> OTHER INFORMATION: VP1

<400> SEQUENCE: 522

Val Thr Phe Gln Ser Asn Gln Gln Asp Lys
1               5                   10

<210> SEQ ID NO 523
<211> LENGTH: 10
<212> TYPE: PRT
<213> ORGANISM: Merkel Cell Polyoma Virus
<220> FEATURE:
<221> NAME/KEY: PEPTIDE
<222> LOCATION: (1)..(10)
<223> OTHER INFORMATION: VP1

<400> SEQUENCE: 523

Leu Lys Gly Pro Gln Lys Ala Ser Gln Lys
1               5                   10

<210> SEQ ID NO 524
<211> LENGTH: 11
<212> TYPE: PRT
<213> ORGANISM: Merkel Cell Polyoma Virus
<220> FEATURE:
<221> NAME/KEY: PEPTIDE
<222> LOCATION: (1)..(11)
<223> OTHER INFORMATION: VP1

<400> SEQUENCE: 524

Asn Val Ala Ser Val Pro Lys Leu Leu Val Lys
1               5                   10

<210> SEQ ID NO 525
<211> LENGTH: 9
<212> TYPE: PRT
<213> ORGANISM: Merkel Cell Polyoma Virus
<220> FEATURE:
<221> NAME/KEY: PEPTIDE
<222> LOCATION: (1)..(9)
<223> OTHER INFORMATION: VP1

<400> SEQUENCE: 525

Thr Ser Asn Trp Tyr Thr Tyr Thr Tyr
1               5

<210> SEQ ID NO 526
<211> LENGTH: 11

```
<212> TYPE: PRT
<213> ORGANISM: Merkel Cell Polyoma Virus
<220> FEATURE:
<221> NAME/KEY: PEPTIDE
<222> LOCATION: (1)..(11)
<223> OTHER INFORMATION: VP1

<400> SEQUENCE: 526

Leu Val Leu Asp Tyr Gln Thr Glu Tyr Pro Lys
1               5                   10

<210> SEQ ID NO 527
<211> LENGTH: 11
<212> TYPE: PRT
<213> ORGANISM: Merkel Cell Polyoma Virus
<220> FEATURE:
<221> NAME/KEY: PEPTIDE
<222> LOCATION: (1)..(11)
<223> OTHER INFORMATION: VP1

<400> SEQUENCE: 527

Thr Leu Arg Lys Arg Trp Val Lys Asn Pro Tyr
1               5                   10

<210> SEQ ID NO 528
<211> LENGTH: 11
<212> TYPE: PRT
<213> ORGANISM: Merkel Cell Polyoma Virus
<220> FEATURE:
<221> NAME/KEY: PEPTIDE
<222> LOCATION: (1)..(11)
<223> OTHER INFORMATION: VP1

<400> SEQUENCE: 528

Ala Val Thr Phe Gln Ser Asn Gln Gln Asp Lys
1               5                   10

<210> SEQ ID NO 529
<211> LENGTH: 11
<212> TYPE: PRT
<213> ORGANISM: Merkel Cell Polyoma Virus
<220> FEATURE:
<221> NAME/KEY: PEPTIDE
<222> LOCATION: (1)..(11)
<223> OTHER INFORMATION: VP1

<400> SEQUENCE: 529

Pro Leu Lys Gly Pro Gln Lys Ala Ser Gln Lys
1               5                   10

<210> SEQ ID NO 530
<211> LENGTH: 9
<212> TYPE: PRT
<213> ORGANISM: Merkel Cell Polyoma Virus
<220> FEATURE:
<221> NAME/KEY: PEPTIDE
<222> LOCATION: (1)..(9)
<223> OTHER INFORMATION: VP1

<400> SEQUENCE: 530

Arg Ile Tyr Glu Gly Ser Glu Gln Leu
1               5

<210> SEQ ID NO 531
<211> LENGTH: 9
<212> TYPE: PRT
<213> ORGANISM: Merkel Cell Polyoma Virus
<220> FEATURE:
<221> NAME/KEY: PEPTIDE
```

```
<222> LOCATION: (1)..(9)
<223> OTHER INFORMATION: VP1

<400> SEQUENCE: 531

Ser Leu Phe Ser Asn Leu Met Pro Lys
1               5

<210> SEQ ID NO 532
<211> LENGTH: 10
<212> TYPE: PRT
<213> ORGANISM: Merkel Cell Polyoma Virus
<220> FEATURE:
<221> NAME/KEY: PEPTIDE
<222> LOCATION: (1)..(10)
<223> OTHER INFORMATION: VP1

<400> SEQUENCE: 532

Lys Leu Leu Val Lys Gly Gly Val Glu Val
1               5                   10

<210> SEQ ID NO 533
<211> LENGTH: 11
<212> TYPE: PRT
<213> ORGANISM: Merkel Cell Polyoma Virus
<220> FEATURE:
<221> NAME/KEY: PEPTIDE
<222> LOCATION: (1)..(11)
<223> OTHER INFORMATION: VP1

<400> SEQUENCE: 533

Ser Leu Ile Asn Val His Tyr Trp Asp Met Lys
1               5                   10

<210> SEQ ID NO 534
<211> LENGTH: 10
<212> TYPE: PRT
<213> ORGANISM: Human papillomavirus
<220> FEATURE:
<221> NAME/KEY: PEPTIDE
<222> LOCATION: (1)..(10)
<223> OTHER INFORMATION: HPV E6 29-38

<400> SEQUENCE: 534

Thr Ile His Asp Ile Ile Leu Glu Cys Val
1               5                   10

<210> SEQ ID NO 535
<211> LENGTH: 10
<212> TYPE: PRT
<213> ORGANISM: Human papillomavirus
<220> FEATURE:
<221> NAME/KEY: PEPTIDE
<222> LOCATION: (1)..(10)
<223> OTHER INFORMATION: HPV E7 11-20

<400> SEQUENCE: 535

Tyr Met Leu Asp Leu Gln Pro Glu Thr Thr
1               5                   10

<210> SEQ ID NO 536
<211> LENGTH: 9
<212> TYPE: PRT
<213> ORGANISM: Merkel Cell Polyoma Virus
<220> FEATURE:
<221> NAME/KEY: PEPTIDE
<222> LOCATION: (1)..(9)
<223> OTHER INFORMATION: VP1

<400> SEQUENCE: 536
```

Gly Cys Cys Pro Asn Val Ala Ser Val
1               5

<210> SEQ ID NO 537
<211> LENGTH: 9
<212> TYPE: PRT
<213> ORGANISM: Merkel Cell Polyoma Virus
<220> FEATURE:
<221> NAME/KEY: PEPTIDE
<222> LOCATION: (1)..(9)
<223> OTHER INFORMATION: VP1

<400> SEQUENCE: 537

Ser Ile Thr Gln Ile Glu Leu Tyr Leu
1               5

<210> SEQ ID NO 538
<211> LENGTH: 9
<212> TYPE: PRT
<213> ORGANISM: Merkel Cell Polyoma Virus
<220> FEATURE:
<221> NAME/KEY: PEPTIDE
<222> LOCATION: (1)..(9)
<223> OTHER INFORMATION: VP1

<400> SEQUENCE: 538

Leu Gln Met Trp Glu Ala Ile Ser Val
1               5

<210> SEQ ID NO 539
<211> LENGTH: 9
<212> TYPE: PRT
<213> ORGANISM: Merkel Cell Polyoma Virus
<220> FEATURE:
<221> NAME/KEY: PEPTIDE
<222> LOCATION: (1)..(9)
<223> OTHER INFORMATION: VP1

<400> SEQUENCE: 539

Ala Ile Ser Val Lys Thr Glu Val Val
1               5

<210> SEQ ID NO 540
<211> LENGTH: 9
<212> TYPE: PRT
<213> ORGANISM: Merkel Cell Polyoma Virus
<220> FEATURE:
<221> NAME/KEY: PEPTIDE
<222> LOCATION: (1)..(9)
<223> OTHER INFORMATION: VP1

<400> SEQUENCE: 540

Lys Met Thr Pro Lys Asn Gln Gly Leu
1               5

<210> SEQ ID NO 541
<211> LENGTH: 9
<212> TYPE: PRT
<213> ORGANISM: Merkel Cell Polyoma Virus
<220> FEATURE:
<221> NAME/KEY: PEPTIDE
<222> LOCATION: (1)..(9)
<223> OTHER INFORMATION: VP1

<400> SEQUENCE: 541

Thr Val Leu Gln Phe Ser Asn Thr Leu
1               5

<210> SEQ ID NO 542
<211> LENGTH: 9
<212> TYPE: PRT
<213> ORGANISM: Merkel Cell Polyoma Virus
<220> FEATURE:
<221> NAME/KEY: PEPTIDE
<222> LOCATION: (1)..(9)
<223> OTHER INFORMATION: VP1

<400> SEQUENCE: 542

Gly Leu Phe Ile Ser Cys Ala Asp Ile
1               5

<210> SEQ ID NO 543
<211> LENGTH: 10
<212> TYPE: PRT
<213> ORGANISM: Merkel Cell Polyoma Virus
<220> FEATURE:
<221> NAME/KEY: PEPTIDE
<222> LOCATION: (1)..(10)
<223> OTHER INFORMATION: VP1

<400> SEQUENCE: 543

Leu Leu Val Lys Gly Gly Val Glu Val Leu
1               5                   10

<210> SEQ ID NO 544
<211> LENGTH: 10
<212> TYPE: PRT
<213> ORGANISM: Merkel Cell Polyoma Virus
<220> FEATURE:
<221> NAME/KEY: PEPTIDE
<222> LOCATION: (1)..(10)
<223> OTHER INFORMATION: VP1

<400> SEQUENCE: 544

Glu Leu Tyr Leu Asn Pro Arg Met Gly Val
1               5                   10

<210> SEQ ID NO 545
<211> LENGTH: 10
<212> TYPE: PRT
<213> ORGANISM: Merkel Cell Polyoma Virus
<220> FEATURE:
<221> NAME/KEY: PEPTIDE
<222> LOCATION: (1)..(10)
<223> OTHER INFORMATION: VP1

<400> SEQUENCE: 545

Asn Leu Pro Ala Tyr Ser Val Ala Arg Val
1               5                   10

<210> SEQ ID NO 546
<211> LENGTH: 10
<212> TYPE: PRT
<213> ORGANISM: Merkel Cell Polyoma Virus
<220> FEATURE:
<221> NAME/KEY: PEPTIDE
<222> LOCATION: (1)..(10)
<223> OTHER INFORMATION: VP1

<400> SEQUENCE: 546

Thr Leu Gln Met Trp Glu Ala Ile Ser Val
1               5                   10

<210> SEQ ID NO 547
<211> LENGTH: 10
<212> TYPE: PRT

```
<213> ORGANISM: Merkel Cell Polyoma Virus
<220> FEATURE:
<221> NAME/KEY: PEPTIDE
<222> LOCATION: (1)..(10)
<223> OTHER INFORMATION: VP1

<400> SEQUENCE: 547

Gln Met Trp Glu Ala Ile Ser Val Lys Thr
1               5                   10

<210> SEQ ID NO 548
<211> LENGTH: 10
<212> TYPE: PRT
<213> ORGANISM: Merkel Cell Polyoma Virus
<220> FEATURE:
<221> NAME/KEY: PEPTIDE
<222> LOCATION: (1)..(10)
<223> OTHER INFORMATION: VP1

<400> SEQUENCE: 548

Val Val Gly Ile Ser Ser Leu Ile Asn Val
1               5                   10

<210> SEQ ID NO 549
<211> LENGTH: 10
<212> TYPE: PRT
<213> ORGANISM: Merkel Cell Polyoma Virus
<220> FEATURE:
<221> NAME/KEY: PEPTIDE
<222> LOCATION: (1)..(10)
<223> OTHER INFORMATION: VP1

<400> SEQUENCE: 549

Ser Leu Ile Asn Val His Tyr Trp Asp Met
1               5                   10

<210> SEQ ID NO 550
<211> LENGTH: 10
<212> TYPE: PRT
<213> ORGANISM: Merkel Cell Polyoma Virus
<220> FEATURE:
<221> NAME/KEY: PEPTIDE
<222> LOCATION: (1)..(10)
<223> OTHER INFORMATION: VP1

<400> SEQUENCE: 550

His Met Phe Ala Ile Gly Gly Glu Pro Leu
1               5                   10

<210> SEQ ID NO 551
<211> LENGTH: 10
<212> TYPE: PRT
<213> ORGANISM: Merkel Cell Polyoma Virus
<220> FEATURE:
<221> NAME/KEY: PEPTIDE
<222> LOCATION: (1)..(10)
<223> OTHER INFORMATION: VP1

<400> SEQUENCE: 551

Phe Ala Ile Gly Gly Glu Pro Leu Asp Leu
1               5                   10

<210> SEQ ID NO 552
<211> LENGTH: 10
<212> TYPE: PRT
<213> ORGANISM: Merkel Cell Polyoma Virus
<220> FEATURE:
<221> NAME/KEY: PEPTIDE
<222> LOCATION: (1)..(10)
```

<223> OTHER INFORMATION: VP1

<400> SEQUENCE: 552

Asn Leu Ile Asn Ser Leu Phe Ser Asn Leu
1               5                   10

<210> SEQ ID NO 553
<211> LENGTH: 11
<212> TYPE: PRT
<213> ORGANISM: Merkel Cell Polyoma Virus
<220> FEATURE:
<221> NAME/KEY: PEPTIDE
<222> LOCATION: (1)..(11)
<223> OTHER INFORMATION: VP1

<400> SEQUENCE: 553

Phe Leu Phe Lys Thr Ser Gly Lys Met Ala Leu
1               5                   10

<210> SEQ ID NO 554
<211> LENGTH: 11
<212> TYPE: PRT
<213> ORGANISM: Merkel Cell Polyoma Virus
<220> FEATURE:
<221> NAME/KEY: PEPTIDE
<222> LOCATION: (1)..(11)
<223> OTHER INFORMATION: VP1

<400> SEQUENCE: 554

Ala Leu His Gly Leu Pro Arg Tyr Phe Asn Val
1               5                   10

<210> SEQ ID NO 555
<211> LENGTH: 11
<212> TYPE: PRT
<213> ORGANISM: Merkel Cell Polyoma Virus
<220> FEATURE:
<221> NAME/KEY: PEPTIDE
<222> LOCATION: (1)..(11)
<223> OTHER INFORMATION: VP1

<400> SEQUENCE: 555

Asn Leu Ile Asn Ser Leu Phe Ser Asn Leu Met
1               5                   10

<210> SEQ ID NO 556
<211> LENGTH: 11
<212> TYPE: PRT
<213> ORGANISM: Merkel Cell Polyoma Virus
<220> FEATURE:
<221> NAME/KEY: PEPTIDE
<222> LOCATION: (1)..(11)
<223> OTHER INFORMATION: VP1

<400> SEQUENCE: 556

Phe Leu Asp Lys Phe Gly Gln Glu Lys Thr Val
1               5                   10

<210> SEQ ID NO 557
<211> LENGTH: 10
<212> TYPE: PRT
<213> ORGANISM: Merkel Cell Polyoma Virus
<220> FEATURE:
<221> NAME/KEY: PEPTIDE
<222> LOCATION: (1)..(10)
<223> OTHER INFORMATION: VP1

<400> SEQUENCE: 557

-continued

Val Lys Gly Gly Val Glu Val Leu Ser Val
1               5                   10

<210> SEQ ID NO 558
<211> LENGTH: 9
<212> TYPE: PRT
<213> ORGANISM: Merkel Cell Polyoma Virus
<220> FEATURE:
<221> NAME/KEY: PEPTIDE
<222> LOCATION: (1)..(9)
<223> OTHER INFORMATION: VP1

<400> SEQUENCE: 558

Ala Ser Val Pro Lys Leu Leu Val Lys
1               5

<210> SEQ ID NO 559
<211> LENGTH: 10
<212> TYPE: PRT
<213> ORGANISM: Merkel Cell Polyoma Virus
<220> FEATURE:
<221> NAME/KEY: PEPTIDE
<222> LOCATION: (1)..(10)
<223> OTHER INFORMATION: VP1

<400> SEQUENCE: 559

Cys Cys Pro Asn Val Ala Ser Val Pro Lys
1               5                   10

<210> SEQ ID NO 560
<211> LENGTH: 9
<212> TYPE: PRT
<213> ORGANISM: Merkel Cell Polyoma Virus
<220> FEATURE:
<221> NAME/KEY: PEPTIDE
<222> LOCATION: (1)..(9)
<223> OTHER INFORMATION: VP1

<400> SEQUENCE: 560

Ile Thr Ile Glu Thr Val Leu Gly Arg
1               5

<210> SEQ ID NO 561
<211> LENGTH: 9
<212> TYPE: PRT
<213> ORGANISM: Merkel Cell Polyoma Virus
<220> FEATURE:
<221> NAME/KEY: PEPTIDE
<222> LOCATION: (1)..(9)
<223> OTHER INFORMATION: VP1

<400> SEQUENCE: 561

Asn Thr Leu Thr Thr Val Leu Leu Asp
1               5

<210> SEQ ID NO 562
<211> LENGTH: 9
<212> TYPE: PRT
<213> ORGANISM: Merkel Cell Polyoma Virus
<220> FEATURE:
<221> NAME/KEY: PEPTIDE
<222> LOCATION: (1)..(9)
<223> OTHER INFORMATION: VP1

<400> SEQUENCE: 562

Ala Leu His Gly Leu Pro Arg Tyr Phe
1               5

```
<210> SEQ ID NO 563
<211> LENGTH: 10
<212> TYPE: PRT
<213> ORGANISM: Merkel Cell Polyoma Virus
<220> FEATURE:
<221> NAME/KEY: PEPTIDE
<222> LOCATION: (1)..(10)
<223> OTHER INFORMATION: VP1

<400> SEQUENCE: 563

Val Ala Ser Val Pro Lys Leu Leu Val Lys
1               5                   10

<210> SEQ ID NO 564
<211> LENGTH: 9
<212> TYPE: PRT
<213> ORGANISM: Merkel Cell Polyoma Virus
<220> FEATURE:
<221> NAME/KEY: PEPTIDE
<222> LOCATION: (1)..(9)
<223> OTHER INFORMATION: VP1

<400> SEQUENCE: 564

Val Ser Gly Gln Pro Met Glu Gly Lys
1               5

<210> SEQ ID NO 565
<211> LENGTH: 10
<212> TYPE: PRT
<213> ORGANISM: Merkel Cell Polyoma Virus
<220> FEATURE:
<221> NAME/KEY: PEPTIDE
<222> LOCATION: (1)..(10)
<223> OTHER INFORMATION: VP1

<400> SEQUENCE: 565

Lys Ala Ser Ser Thr Cys Lys Thr Pro Lys
1               5                   10

<210> SEQ ID NO 566
<211> LENGTH: 10
<212> TYPE: PRT
<213> ORGANISM: Merkel Cell Polyoma Virus
<220> FEATURE:
<221> NAME/KEY: PEPTIDE
<222> LOCATION: (1)..(10)
<223> OTHER INFORMATION: VP1

<400> SEQUENCE: 566

Lys Thr Pro Lys Arg Gln Cys Ile Pro Lys
1               5                   10

<210> SEQ ID NO 567
<211> LENGTH: 10
<212> TYPE: PRT
<213> ORGANISM: Merkel Cell Polyoma Virus
<220> FEATURE:
<221> NAME/KEY: PEPTIDE
<222> LOCATION: (1)..(10)
<223> OTHER INFORMATION: VP1

<400> SEQUENCE: 567

Tyr Thr Tyr Thr Tyr Asp Leu Gln Pro Lys
1               5                   10

<210> SEQ ID NO 568
<211> LENGTH: 10
<212> TYPE: PRT
<213> ORGANISM: Merkel Cell Polyoma Virus
```

```
<220> FEATURE:
<221> NAME/KEY: PEPTIDE
<222> LOCATION: (1)..(10)
<223> OTHER INFORMATION: VP1

<400> SEQUENCE: 568

Pro Ile Thr Ile Glu Thr Val Leu Gly Arg
1               5                   10

<210> SEQ ID NO 569
<211> LENGTH: 9
<212> TYPE: PRT
<213> ORGANISM: Merkel Cell Polyoma Virus
<220> FEATURE:
<221> NAME/KEY: PEPTIDE
<222> LOCATION: (1)..(9)
<223> OTHER INFORMATION: VP1

<400> SEQUENCE: 569

Ser Val Ala Arg Val Ser Leu Pro Met
1               5

<210> SEQ ID NO 570
<211> LENGTH: 10
<212> TYPE: PRT
<213> ORGANISM: Merkel Cell Polyoma Virus
<220> FEATURE:
<221> NAME/KEY: PEPTIDE
<222> LOCATION: (1)..(10)
<223> OTHER INFORMATION: VP1

<400> SEQUENCE: 570

Asn Ser Leu Phe Ser Asn Leu Met Pro Lys
1               5                   10

<210> SEQ ID NO 571
<211> LENGTH: 10
<212> TYPE: PRT
<213> ORGANISM: Merkel Cell Polyoma Virus
<220> FEATURE:
<221> NAME/KEY: PEPTIDE
<222> LOCATION: (1)..(10)
<223> OTHER INFORMATION: VP1

<400> SEQUENCE: 571

Lys Val Ser Gly Gln Pro Met Glu Gly Lys
1               5                   10

<210> SEQ ID NO 572
<211> LENGTH: 10
<212> TYPE: PRT
<213> ORGANISM: Merkel Cell Polyoma Virus
<220> FEATURE:
<221> NAME/KEY: PEPTIDE
<222> LOCATION: (1)..(10)
<223> OTHER INFORMATION: VP1

<400> SEQUENCE: 572

Thr Val Tyr Pro Lys Pro Ser Val Ala Pro
1               5                   10

<210> SEQ ID NO 573
<211> LENGTH: 9
<212> TYPE: PRT
<213> ORGANISM: Merkel Cell Polyoma Virus
<220> FEATURE:
<221> NAME/KEY: PEPTIDE
<222> LOCATION: (1)..(9)
<223> OTHER INFORMATION: VP1
```

```
<400> SEQUENCE: 573

Gly Val Glu Val Leu Ser Val Val Thr
1               5

<210> SEQ ID NO 574
<211> LENGTH: 9
<212> TYPE: PRT
<213> ORGANISM: Merkel Cell Polyoma Virus
<220> FEATURE:
<221> NAME/KEY: PEPTIDE
<222> LOCATION: (1)..(9)
<223> OTHER INFORMATION: VP1

<400> SEQUENCE: 574

Pro Leu Asp Leu Gln Gly Leu Val Leu
1               5

<210> SEQ ID NO 575
<211> LENGTH: 9
<212> TYPE: PRT
<213> ORGANISM: Merkel Cell Polyoma Virus
<220> FEATURE:
<221> NAME/KEY: PEPTIDE
<222> LOCATION: (1)..(9)
<223> OTHER INFORMATION: VP1

<400> SEQUENCE: 575

Gly Leu Asp Pro Gln Ala Lys Ala Lys
1               5

<210> SEQ ID NO 576
<211> LENGTH: 9
<212> TYPE: PRT
<213> ORGANISM: Merkel Cell Polyoma Virus
<220> FEATURE:
<221> NAME/KEY: PEPTIDE
<222> LOCATION: (1)..(9)
<223> OTHER INFORMATION: VP1

<400> SEQUENCE: 576

Glu Val Trp Cys Pro Asp Pro Ser Lys
1               5

<210> SEQ ID NO 577
<211> LENGTH: 9
<212> TYPE: PRT
<213> ORGANISM: Merkel Cell Polyoma Virus
<220> FEATURE:
<221> NAME/KEY: PEPTIDE
<222> LOCATION: (1)..(9)
<223> OTHER INFORMATION: VP1

<400> SEQUENCE: 577

Ala Asp Ile Val Gly Phe Leu Phe Lys
1               5

<210> SEQ ID NO 578
<211> LENGTH: 9
<212> TYPE: PRT
<213> ORGANISM: Merkel Cell Polyoma Virus
<220> FEATURE:
<221> NAME/KEY: PEPTIDE
<222> LOCATION: (1)..(9)
<223> OTHER INFORMATION: VP1

<400> SEQUENCE: 578

Lys Thr Ser Gly Lys Met Ala Leu His
```

```
<210> SEQ ID NO 579
<211> LENGTH: 9
<212> TYPE: PRT
<213> ORGANISM: Merkel Cell Polyoma Virus
<220> FEATURE:
<221> NAME/KEY: PEPTIDE
<222> LOCATION: (1)..(9)
<223> OTHER INFORMATION: VP1

<400> SEQUENCE: 579

Lys Met Ala Leu His Gly Leu Pro Arg
1               5

<210> SEQ ID NO 580
<211> LENGTH: 9
<212> TYPE: PRT
<213> ORGANISM: Merkel Cell Polyoma Virus
<220> FEATURE:
<221> NAME/KEY: PEPTIDE
<222> LOCATION: (1)..(9)
<223> OTHER INFORMATION: VP1

<400> SEQUENCE: 580

Arg Tyr Phe Asn Val Thr Leu Arg Lys
1               5

<210> SEQ ID NO 581
<211> LENGTH: 9
<212> TYPE: PRT
<213> ORGANISM: Merkel Cell Polyoma Virus
<220> FEATURE:
<221> NAME/KEY: PEPTIDE
<222> LOCATION: (1)..(9)
<223> OTHER INFORMATION: VP1

<400> SEQUENCE: 581

Thr Leu Arg Lys Arg Trp Val Lys Asn
1               5

<210> SEQ ID NO 582
<211> LENGTH: 9
<212> TYPE: PRT
<213> ORGANISM: Merkel Cell Polyoma Virus
<220> FEATURE:
<221> NAME/KEY: PEPTIDE
<222> LOCATION: (1)..(9)
<223> OTHER INFORMATION: VP1

<400> SEQUENCE: 582

Lys Pro Gly Cys Cys Pro Asn Val Ala
1               5

<210> SEQ ID NO 583
<211> LENGTH: 9
<212> TYPE: PRT
<213> ORGANISM: Merkel Cell Polyoma Virus
<220> FEATURE:
<221> NAME/KEY: PEPTIDE
<222> LOCATION: (1)..(9)
<223> OTHER INFORMATION: VP1

<400> SEQUENCE: 583

Gln Pro Ile Lys Glu Asn Leu Pro Ala
1               5

<210> SEQ ID NO 584
```

```
<211> LENGTH: 9
<212> TYPE: PRT
<213> ORGANISM: Merkel Cell Polyoma Virus
<220> FEATURE:
<221> NAME/KEY: PEPTIDE
<222> LOCATION: (1)..(9)
<223> OTHER INFORMATION: VP1

<400> SEQUENCE: 584

Leu Pro Arg Tyr Phe Asn Val Thr Leu
1               5

<210> SEQ ID NO 585
<211> LENGTH: 9
<212> TYPE: PRT
<213> ORGANISM: Merkel Cell Polyoma Virus
<220> FEATURE:
<221> NAME/KEY: PEPTIDE
<222> LOCATION: (1)..(9)
<223> OTHER INFORMATION: VP1

<400> SEQUENCE: 585

Met Pro Lys Val Ser Gly Gln Pro Met
1               5

<210> SEQ ID NO 586
<211> LENGTH: 9
<212> TYPE: PRT
<213> ORGANISM: Merkel Cell Polyoma Virus
<220> FEATURE:
<221> NAME/KEY: PEPTIDE
<222> LOCATION: (1)..(9)
<223> OTHER INFORMATION: VP1

<400> SEQUENCE: 586

Tyr Pro Lys Pro Ser Val Ala Pro Ala
1               5

<210> SEQ ID NO 587
<211> LENGTH: 9
<212> TYPE: PRT
<213> ORGANISM: Merkel Cell Polyoma Virus
<220> FEATURE:
<221> NAME/KEY: PEPTIDE
<222> LOCATION: (1)..(9)
<223> OTHER INFORMATION: VP1

<400> SEQUENCE: 587

Lys Pro Ser Val Ala Pro Ala Ala Val
1               5

<210> SEQ ID NO 588
<211> LENGTH: 9
<212> TYPE: PRT
<213> ORGANISM: Merkel Cell Polyoma Virus
<220> FEATURE:
<221> NAME/KEY: PEPTIDE
<222> LOCATION: (1)..(9)
<223> OTHER INFORMATION: VP1

<400> SEQUENCE: 588

Ala Pro Leu Lys Gly Pro Gln Lys Ala
1               5

<210> SEQ ID NO 589
<211> LENGTH: 10
<212> TYPE: PRT
<213> ORGANISM: Merkel Cell Polyoma Virus
<220> FEATURE:
```

<221> NAME/KEY: PEPTIDE
<222> LOCATION: (1)..(10)
<223> OTHER INFORMATION: VP1

<400> SEQUENCE: 589

Ala Pro Lys Arg Lys Ala Ser Ser Thr Cys
1               5                   10

<210> SEQ ID NO 590
<211> LENGTH: 10
<212> TYPE: PRT
<213> ORGANISM: Merkel Cell Polyoma Virus
<220> FEATURE:
<221> NAME/KEY: PEPTIDE
<222> LOCATION: (1)..(10)
<223> OTHER INFORMATION: VP1

<400> SEQUENCE: 590

Ser Val Ala Arg Val Ser Leu Pro Met Leu
1               5                   10

<210> SEQ ID NO 591
<211> LENGTH: 10
<212> TYPE: PRT
<213> ORGANISM: Merkel Cell Polyoma Virus
<220> FEATURE:
<221> NAME/KEY: PEPTIDE
<222> LOCATION: (1)..(10)
<223> OTHER INFORMATION: VP1

<400> SEQUENCE: 591

Tyr Pro Lys Thr Thr Asn Gly Gly Pro Ile
1               5                   10

<210> SEQ ID NO 592
<211> LENGTH: 10
<212> TYPE: PRT
<213> ORGANISM: Merkel Cell Polyoma Virus
<220> FEATURE:
<221> NAME/KEY: PEPTIDE
<222> LOCATION: (1)..(10)
<223> OTHER INFORMATION: VP1

<400> SEQUENCE: 592

Tyr Pro Lys Pro Ser Val Ala Pro Ala Ala
1               5                   10

<210> SEQ ID NO 593
<211> LENGTH: 11
<212> TYPE: PRT
<213> ORGANISM: Merkel Cell Polyoma Virus
<220> FEATURE:
<221> NAME/KEY: PEPTIDE
<222> LOCATION: (1)..(11)
<223> OTHER INFORMATION: VP1

<400> SEQUENCE: 593

Lys Pro Gly Cys Cys Pro Asn Val Ala Ser Val
1               5                   10

<210> SEQ ID NO 594
<211> LENGTH: 11
<212> TYPE: PRT
<213> ORGANISM: Merkel Cell Polyoma Virus
<220> FEATURE:
<221> NAME/KEY: PEPTIDE
<222> LOCATION: (1)..(11)
<223> OTHER INFORMATION: VP1

```
<400> SEQUENCE: 594

Asn Pro Arg Met Gly Val Asn Ser Pro Asp Leu
1               5                   10

<210> SEQ ID NO 595
<211> LENGTH: 11
<212> TYPE: PRT
<213> ORGANISM: Merkel Cell Polyoma Virus
<220> FEATURE:
<221> NAME/KEY: PEPTIDE
<222> LOCATION: (1)..(11)
<223> OTHER INFORMATION: VP1

<400> SEQUENCE: 595

Leu Pro Ala Tyr Ser Val Ala Arg Val Ser Leu
1               5                   10

<210> SEQ ID NO 596
<211> LENGTH: 11
<212> TYPE: PRT
<213> ORGANISM: Merkel Cell Polyoma Virus
<220> FEATURE:
<221> NAME/KEY: PEPTIDE
<222> LOCATION: (1)..(11)
<223> OTHER INFORMATION: VP1

<400> SEQUENCE: 596

Thr Pro Thr Val Leu Gln Phe Ser Asn Thr Leu
1               5                   10

<210> SEQ ID NO 597
<211> LENGTH: 11
<212> TYPE: PRT
<213> ORGANISM: Merkel Cell Polyoma Virus
<220> FEATURE:
<221> NAME/KEY: PEPTIDE
<222> LOCATION: (1)..(11)
<223> OTHER INFORMATION: VP1

<400> SEQUENCE: 597

Leu Pro Arg Tyr Phe Asn Val Thr Leu Arg Lys
1               5                   10

<210> SEQ ID NO 598
<211> LENGTH: 11
<212> TYPE: PRT
<213> ORGANISM: Merkel Cell Polyoma Virus
<220> FEATURE:
<221> NAME/KEY: PEPTIDE
<222> LOCATION: (1)..(11)
<223> OTHER INFORMATION: VP1

<400> SEQUENCE: 598

Tyr Pro Val Val Asn Leu Ile Asn Ser Leu Phe
1               5                   10

<210> SEQ ID NO 599
<211> LENGTH: 11
<212> TYPE: PRT
<213> ORGANISM: Merkel Cell Polyoma Virus
<220> FEATURE:
<221> NAME/KEY: PEPTIDE
<222> LOCATION: (1)..(11)
<223> OTHER INFORMATION: VP1

<400> SEQUENCE: 599

Tyr Pro Lys Pro Ser Val Ala Pro Ala Ala Val
1               5                   10
```

<210> SEQ ID NO 600
<211> LENGTH: 11
<212> TYPE: PRT
<213> ORGANISM: Merkel Cell Polyoma Virus
<220> FEATURE:
<221> NAME/KEY: PEPTIDE
<222> LOCATION: (1)..(11)
<223> OTHER INFORMATION: VP1

<400> SEQUENCE: 600

Lys Pro Ser Val Ala Pro Ala Ala Val Thr Phe
1               5                   10

<210> SEQ ID NO 601
<211> LENGTH: 9
<212> TYPE: PRT
<213> ORGANISM: Merkel Cell Polyoma Virus
<220> FEATURE:
<221> NAME/KEY: PEPTIDE
<222> LOCATION: (1)..(9)
<223> OTHER INFORMATION: VP1

<400> SEQUENCE: 601

Ala Pro Lys Arg Lys Ala Ser Ser Thr
1               5

<210> SEQ ID NO 602
<211> LENGTH: 9
<212> TYPE: PRT
<213> ORGANISM: Herpes Simplex Virus
<220> FEATURE:
<221> NAME/KEY: PEPTIDE
<222> LOCATION: (1)..(9)
<223> OTHER INFORMATION: HSV-1gB

<400> SEQUENCE: 602

Arg Met Leu Gly Asp Val Met Ala Val
1               5

<210> SEQ ID NO 603
<211> LENGTH: 9
<212> TYPE: PRT
<213> ORGANISM: Herpes Simplex Virus
<220> FEATURE:
<221> NAME/KEY: PEPTIDE
<222> LOCATION: (1)..(9)
<223> OTHER INFORMATION: HSV1gB

<400> SEQUENCE: 603

Gly Ile Phe Glu Asp Arg Ala Pro Val
1               5

<210> SEQ ID NO 604
<211> LENGTH: 9
<212> TYPE: PRT
<213> ORGANISM: Herpes Simplex Virus
<220> FEATURE:
<221> NAME/KEY: PEPTIDE
<222> LOCATION: (1)..(9)
<223> OTHER INFORMATION: HSV1gB

<400> SEQUENCE: 604

Tyr Leu Ala Asn Gly Gly Phe Leu Ile
1               5

<210> SEQ ID NO 605
<211> LENGTH: 10

```
<212> TYPE: PRT
<213> ORGANISM: Herpes Simplex Virus
<220> FEATURE:
<221> NAME/KEY: PEPTIDE
<222> LOCATION: (1)..(10)
<223> OTHER INFORMATION: HPV-E7

<400> SEQUENCE: 605

Leu Leu Met Gly Thr Leu Gly Ile Val Cys
1               5                   10

<210> SEQ ID NO 606
<211> LENGTH: 9
<212> TYPE: PRT
<213> ORGANISM: Herpes Simplex Virus
<220> FEATURE:
<221> NAME/KEY: PEPTIDE
<222> LOCATION: (1)..(9)
<223> OTHER INFORMATION: HSV-U125

<400> SEQUENCE: 606

Phe Leu Trp Glu Asp Gln Thr Leu Leu
1               5
```